US009499553B2

United States Patent
Ohtake et al.

(10) Patent No.: US 9,499,553 B2
(45) Date of Patent: Nov. 22, 2016

(54) DIHYDROPYRIDAZINE-3,5-DIONE DERIVATIVE AND PHARMACEUTICALS CONTAINING THE SAME

(71) Applicant: CHUGAI SEIYAKU KABUSHIKI KAISHA, Tokyo (JP)

(72) Inventors: Yoshihito Ohtake, Shizuoka (JP); Naoki Okamoto, Shizuoka (JP); Yoshiyuki Ono, Shizuoka (JP); Hirotaka Kashiwagi, Shizuoka (JP); Atsushi Kimbara, Shizuoka (JP); Takeo Harada, Shizuoka (JP); Nobuyuki Hori, Shizuoka (JP); Yoshihisa Murata, Shizuoka (JP); Kazutaka Tachibana, Shizuoka (JP); Shota Tanaka, Shizuoka (JP); Kenichi Nomura, Shizuoka (JP); Mitsuaki Ide, Shizuoka (JP); Eisaku Mizuguchi, Shizuoka (JP); Yasuhiro Ichida, Shizuoka (JP); Shuichi Ohtomo, Shizuoka (JP); Naoshi Horiba, Shizuoka (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/852,738

(22) Filed: Sep. 14, 2015

(65) Prior Publication Data

US 2016/0002251 A1 Jan. 7, 2016

Related U.S. Application Data

(63) Continuation-in-part of application No. PCT/JP2014/056778, filed on Mar. 13, 2014.

(30) Foreign Application Priority Data

Mar. 13, 2013 (JP) .................. 2013-051082
Jun. 25, 2013 (JP) .................. 2013-132889
Sep. 12, 2014 (JP) .................. 2014-187048

(51) Int. Cl.

| | | |
|---|---|---|
| *C07D 487/04* | (2006.01) | |
| *A61K 31/5025* | (2006.01) | |
| *C07D 403/12* | (2006.01) | |
| *C07D 471/04* | (2006.01) | |
| *C07D 491/107* | (2006.01) | |
| *A61K 31/504* | (2006.01) | |
| *A61K 31/5377* | (2006.01) | |
| *A61K 31/506* | (2006.01) | |
| *C07D 401/12* | (2006.01) | |
| *A61K 31/503* | (2006.01) | |
| *C07D 401/14* | (2006.01) | |
| *C07D 491/08* | (2006.01) | |
| *A61K 45/06* | (2006.01) | |

(52) U.S. Cl.
CPC .......... *C07D 487/04* (2013.01); *A61K 31/503* (2013.01); *A61K 31/504* (2013.01); *A61K 31/506* (2013.01); *A61K 31/5025* (2013.01); *A61K 31/5377* (2013.01); *A61K 45/06* (2013.01); *C07D 401/12* (2013.01); *C07D 401/14* (2013.01); *C07D 403/12* (2013.01); *C07D 471/04* (2013.01); *C07D 491/08* (2013.01); *C07D 491/107* (2013.01)

(58) Field of Classification Search
None
See application file for complete search history.

(56) References Cited

U.S. PATENT DOCUMENTS

| | | |
|---|---|---|
| 2013/0029973 A1 | 1/2013 | Hachiya et al. |
| 2013/0053369 A1 | 2/2013 | Hachiya et al. |
| 2013/0336919 A1* | 12/2013 | Lewis ................. C07D 209/12 424/78.36 |
| 2014/0329802 A1 | 11/2014 | Hachiya et al. |
| 2015/0031727 A1 | 1/2015 | Miura et al. |

FOREIGN PATENT DOCUMENTS

| | | |
|---|---|---|
| WO | 2010009183 A1 | 1/2010 |
| WO | 2010022240 A1 | 2/2010 |
| WO | 2011048611 A1 | 4/2011 |
| WO | 2011136269 A1 | 11/2011 |
| WO | 2012006474 A2 | 1/2012 |
| WO | 2012006475 A1 | 1/2012 |
| WO | 2012054367 A1 | 4/2012 |
| WO | 2013062065 A1 | 5/2013 |

OTHER PUBLICATIONS

Ken-ichi Miyamoto, et al., J Pharm Sci. Sep. 2011;100(9):3719-30.
Y. Sabbagh, et al., J Am Soc Nephrol. Nov. 2009;20(11):2348-58.
H. Murer, et al., Pflugers Arch. Feb. 2004;447(5):763-7.
Akiko Ohi, et al., Am J Physiol Renal Physiol. Nov. 2011;301(5):F1105-13.
Mario Cozzolino, et al., Kidney Int. Nov. 2003;64(5):1653-61.

(Continued)

*Primary Examiner* — Michael G Hartley
*Assistant Examiner* — Lance Rider
(74) *Attorney, Agent, or Firm* — Browdy and Neimark, P.L.L.C.

(57) ABSTRACT

The present invention provides a dihydropyridazine-3,5-dione derivative or a salt thereof, or a solvate of the compound or the salt, a pharmaceutical drug, a pharmaceutical composition, a sodium-dependent phosphate transporter inhibitor, and a preventive and/or therapeutic agent for hyperphosphatemia, secondary hyperparathyroidism, chronic renal failure, chronic kidney disease, and arteriosclerosis associated with vascular calcification comprising the compound as an active ingredient, and a method for prevention and/or treatment.

47 Claims, No Drawings

(56) References Cited

OTHER PUBLICATIONS

Ian C. Foster, et al., Mol Aspects Med. Apr.-Jun. 2013;34(2-3):386-95.
Yu Zhang, et al., Org. Lett., vol. 14, No. 12, 2012, 3056-3059.
Masanori Kitamura, et al., Angew. Chem. Int. Ed. 2005, 44, 1549-1551.
Charlotte M. Haskins, et al., Chem. Commun. 2002, 2724-2725.
Charlotte M. Griffiths-Jones, et al., Tetrahedron 2010, 66, 4150-4166.
International Search Report in corresponding PCT/JP2014/056778 dated Mar. 28, 2014.
Supplementary European Search Report in corresponding European Appl. No. EP14765619 dated Jun. 30, 2016.

* cited by examiner

DIHYDROPYRIDAZINE-3,5-DIONE DERIVATIVE AND PHARMACEUTICALS CONTAINING THE SAME

This application is a continuation-in-part of international application No. PCT/JP2014/056778, filed on Mar. 13, 2014.

TECHNICAL FIELD

The present invention relates to a dihydropyridazine-3,5-dione derivative or a salt thereof, or a solvate of the compound or the salt. The present invention also relates to a pharmaceutical drug, a pharmaceutical composition, a sodium-dependent phosphate transporter inhibitor, and a preventive and/or therapeutic agent for hyperphosphatemia, secondary hyperparathyroidism, and chronic renal failure, containing the dihydropyridazine-3,5-dione derivative or the salt thereof, or the solvate of the compound or the salt as an active ingredient, and a method for prevention and/or treatment.

The present invention relates to a pharmaceutical composition containing a dihydropyridazine-3,5-dione derivative or a salt thereof, or a solvate of the compound or the salt. Further, this invention relates to a method for preventing or treating a disease selected from hyperphosphatemia, secondary hyperparathyroidism, chronic kidney disease, and arteriosclerosis associated with vascular calcification and to a method for preventing or suppressing ectopic calcification.

BACKGROUND ART

Phosphorus is found in every cell and makes up 1% of a person's body weight. This element plays an essential role in sustaining life, such as the energy metabolism of cells. The concentration of phosphorus in blood is determined by absorption from the gastrointestinal tract and excretion from the kidney as well as bone formation and bone resorption and adjusted to a constant level. The phosphorus absorption in the gastrointestinal tract is performed mainly by a sodium-dependent phosphate transporter NaPi-IIb (SLC34A2) (Non-Patent Documents 1 and 2). Phosphorus in blood is filtered by renal glomerulus and reabsorbed in necessary amounts mainly by NaPi-IIa (SLC34A1) and NaPi-IIc (SLC34A3) in the renal tubule (Non-Patent Documents 1 and 3). The kidney plays a very important role in regulating phosphorus in vivo. In end-stage renal failure patients and dialysis patients with impaired renal functions, phosphorus accumulates in the body, resulting in a rise in phosphorus concentration in blood, i.e., hyperphosphatemia.

Hyperphosphatemia brings about the calcification of soft tissues. Particularly, vascular calcification is considered responsible for the dysfunction of the heart, leading to the death of the patient. Hyperphosphatemia also brings about the hypersecretion of parathyroid hormones, i.e., secondary hyperparathyroidism, and causes bone lesions. Thus, hyperphosphatemia is viewed as a problematic factor that deteriorates the prognosis and QOL of end-stage renal failure patients and dialysis patients.

In the current treatment of hyperphosphatemia, phosphorus adsorbents are used for the purpose of suppressing phosphorus absorption in the gastrointestinal tract. Nonmetallic polymer adsorbents typified by sevelamer carbonate and sevelamer hydrochloride, calcium salt preparations typified by precipitated calcium carbonate, or metallic adsorbents typified by lanthanum carbonate are used as the phosphorus adsorbents. These adsorbents, however, have each been reported to have adverse reactions such as gastrointestinal disorders including constipation and diarrhea, hypercalcemia caused by a rise in serum calcium concentration, and in vivo metal accumulation. In addition, these adsorbents require a daily intake of a few grams and therefore present noncompliance problems. Accordingly, there is a strong demand for the development of novel hyperphosphatemia therapy improved in terms of these problems of the phosphorus adsorbents.

The inhibition of NaPi-IIb, which plays a major role in phosphorus absorption in the gastrointestinal tract, may suppress phosphorus absorption in the gastrointestinal tract, as with the phosphorus adsorbents, to decrease phosphorus concentration in blood (Non-Patent Documents 2 and 4). Also, PiT-1 (SLC20A1) and PiT-2 (SLC20A2), which are sodium-dependent phosphate transporters like NaPi-IIb, are partially responsible for phosphorus absorption in the gastrointestinal tract (Non-Patent Documents 1 and 6). Thus, a compound that inhibits NaPi-IIb, PiT-1, and PiT-2 can be expected to produce a stronger phosphorus absorption inhibitory effect and decrease phosphorus concentration in blood, compared with an inhibitor for only NaPi-IIb. Meanwhile, the suppression of phosphorus absorption by the inhibition of these sodium-dependent phosphate transporters is based on the mechanism of action different from that of the phosphorus adsorbents currently used. Thus, the sodium-dependent phosphate transporter inhibitor can be expected to serve as a novel preventive or therapeutic agent for hyperphosphatemia in place of the conventional phosphorus adsorbents. The sodium-dependent phosphate transporter inhibitor is further expected to exert preventive or therapeutic effects on secondary hyperparathyroidism and chronic kidney disease by decreasing phosphorus concentration in blood (Non-Patent Document 5). Chronic kidney disease (CKD) is a disease which brings about persistent kidney damage (e.g., proteinuria) or persistent deterioration in kidney function (a decrease in GFR: glomerular filtration rate). In 2012, the number of patients having the disease in Japan reached 13, 300, 000 (Non-Patent Document 7), and it has been desired to develop a new medicament for preventing or treating chronic kidney disease.

NTX1942 (Patent Document 1) and compounds described in Patent Documents 2 and 4 have been reported so far as NaPi-IIb inhibitors. Also, a compound having a pyridazine skeleton has been reported in Patent Document 3 which makes mention about the treatment of anemia, ischemia, and hypoxia by the HIF hydroxylase inhibitory activity of the compound.

CITATION LIST

Patent Documents

Patent Document 1: WO2012/006475
Patent Document 2: WO2011/136269
Patent Document 4: WO2013/062065

Non-Patent Documents

Non-Patent Document 1: J Pharm Sci. 2011 September; 100 (9): 3719-30;
Non-Patent Document 2: J Am Soc Nephrol. 2009 November; 20 (11): 2348-58;
Non-Patent Document 3: Pflugers Arch. 2004 February; 447(5): 763-7;
Non-Patent Document 4: Am J Physiol Renal Physiol. 2011 November; 301 (5): F1105-13;

Non-Patent Document 5: Kidney Int. 2003 November; 64 (5): 1653-61; and

Non-Patent Document 6: Mol Aspects Med. 2013 April-June; 34 (2-3): 386-95.

Non-Patent Document 7: Japanese Journal of Nephrology, 2012; 54 (8); 1031-1189

SUMMARY OF INVENTION

Technical Problem

There is a strong demand for the development of novel hyperphosphatemia therapy improved in terms of these problems of the existing phosphorus adsorbents. There is also a strong demand for the development of a method for preventing or treating hyperphosphatemia, secondary hyperparathyroidism, chronic kidney disease, and arteriosclerosis associated with vascular calcification, as well as for the development of a method for preventing or suppressing ectopic calcification, which are improved in terms of these problems of the existing phosphorus adsorbents.

Solution to Problem

The present inventors have conducted diligent studies in light of the problems described above and consequently completed the present invention by finding for the first time that a compound represented by the formula (I) shown below, which largely differ in chemical structure from NaPi-IIb inhibitors known in the art, has an excellent NaPi-IIb inhibitory effect, PiT-1 inhibitory effect, and/or PiT-2 inhibitory effect, is useful in the prevention and/or treatment of hyperphosphatemia, secondary hyperparathyroidism, and chronic renal failure, and has excellent drug efficacy on these diseases. Specifically, one aspect of the present invention provides compounds shown below or salts thereof, or solvates of the compounds or the salts.

One embodiment of the present invention provides the following compounds (1-1) to (1-55):

(1-1) A compound represented by the formula (I) or a salt thereof, or a solvate of the compound or the salt:

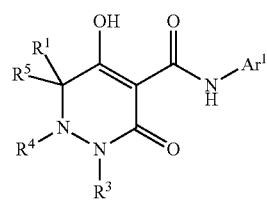

(I)

wherein $R^1$, $R^4$, and $R^5$ are as defined in any one of the following (1) to (3):

(1) $R^1$ is a hydrogen atom or $C_{1-10}$ alkyl;

$R^4$ is a hydrogen atom, $C_{1-4}$ alkyl optionally substituted with one or more substituents Rf, $C_{6-10}$ aryl optionally substituted with one or more substituents Rg, ($C_{1-6}$ alkyl) carbon ($C_{6-10}$ aryl)carbonyl, a group —C(O)NR$^{37}$R$^{38}$, $C_{3-7}$ cycloalkyl, or 5- to 8-membered heterocycloalkyl; and $R^5$ is a hydrogen atom or $C_{1-4}$ alkyl;

(2) $R^1$ and $R^5$ together with the carbon atom to which they are attached form a $C_{3-6}$ saturated carbocyclic ring; and $R^4$ is as defined above; and (3) $R^1$ is a hydrogen atom or linear $C_{1-10}$ alkyl;

$R^4$ and $R^5$ together with the carbon atom and the nitrogen atom to which they are attached form a 5- to 8-membered saturated heterocyclic ring, wherein the saturated heterocyclic ring is optionally substituted with one or more substituents $R^2$;

$R^3$ is $C_{1-10}$ alkyl optionally substituted with one or more substituents Rh, or $R^3$ is $C_{1-4}$ alkyl substituted with Re;

$R^{37}$ and $R^{38}$ are each independently selected from a hydrogen atom and $C_{1-3}$ alkyl;

each $R^2$ is independently selected from $C_{1-5}$ alkyl and a halogen atom; and/or two or more substituents $R^2$ on the 5- to 8-membered saturated heterocyclic ring may together form $C_{1-5}$ alkylene that links the ring atoms to which they are attached;

each Rh is independently selected from a halogen atom, ($C_{1-4}$ alkoxy)carbonyl, and a group —$(O(CH_2)_a)_b$—$C_{1-4}$ alkoxy, wherein a is an integer selected from 2 to 4, and b is an integer selected from 1 to 4;

Re is $C_{6-10}$ aryl optionally substituted with one or more substituents Ra, or 5- to 10-membered heteroaryl optionally substituted with one or more substituents Ra;

each Rf is independently selected from a halogen atom, hydroxy, cyano, carboxy, ($C_{1-6}$ alkoxy)carbonyl, $C_{1-6}$ alkoxy, and $C_{6-10}$ aryl optionally substituted with one or more substituents Rg;

each Rg is independently selected from a halogen atom, $C_{1-6}$ alkyl, $C_{2-6}$ alkynyl, and $C_{1-6}$ alkoxy, wherein the alkyl, alkynyl, and alkoxy groups are each optionally substituted with one or more substituents selected from hydroxy and cyano;

each Ra is independently selected from a halogen atom, hydroxy, nitro, cyano, ($C_{1-4}$ alkoxy)carbonyl, 3- to 10-membered heterocycloalkyloxy (the heterocycloalkyloxy group is optionally substituted with optionally $C_{1-4}$ alkoxy-substituted $C_{1-4}$ alkyl), $C_{1-10}$ alkyl optionally substituted with one or more substituents $R^{10}$, $C_{2-10}$ alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, $C_{1-4}$ alkylthio optionally substituted with one or more substituents $R^{13}$, a group —$(O(CH_2)_{q1})_{q2}$—NR$^{41}$R$^{42}$ (wherein q1 is an integer selected from 1 to 4, and q2 is an integer selected from 2 to 6), a group —$(O(CH_2)_{r1})_{r2}$—C(O)NR$^{43}$R$^{44}$ (wherein r1 is an integer selected from 1 to 4, and r2 is an integer selected from 1 to 4), a group —$(O(CH_2)_{s1})_{s2}$—NR$^{45}$—C(O)R$^{46}$ (wherein s1 and s2 are each independently an integer selected from 2 to 4), a group —C(O)NR$^{47}$R$^{48}$, pyridinyl, pyrrolyl, a group —NR$^{49}$R$^{50}$, and a group —$(O(CH_2)_{y1})_{y2}$—O—CH$_2$—C(O)NR$^{51}$R$^{52}$ (wherein y1 is an integer selected from 1 to 4, and y2 is an integer selected from 1 to 4);

$R^{10}$, $R^{11}$, $R^{12}$, $R^{13}$, and $R^{15}$ are each independently selected from a halogen atom, hydroxy, carboxy, $C_{1-6}$ alkoxy optionally substituted with one or more hydroxy groups, ($C_{1-4}$ alkoxy)$C_{1-6}$ alkoxy, ($C_{1-4}$ alkoxy)carbonyl, a group —$(O(CH_2)_o)_p$—OH (wherein o and p are each independently an integer selected from 2 to 4), $C_{3-6}$ cycloalkyl optionally substituted with one or more hydroxy groups, 3- to 10-membered heterocycloalkyl, 5- to 10-membered heteroaryl, and a group —NR$^{39}$R$^{40}$, wherein the 3- to 10-membered heterocycloalkyl group is optionally substituted with one or more substituents selected from oxo, a halogen atom, $C_{1-4}$ alkyl (wherein the alkyl group is optionally substituted with one or more hydroxy groups), ($C_{1-4}$ alkoxy)$C_{1-4}$ alkyl (wherein the alkoxy moiety is optionally substituted with one or more hydroxy groups), $C_{1-4}$ alkoxy, ($C_{1-4}$ alkoxy)carbonyl, $C_{1-4}$ alkylthio, morpholino, ($C_{1-3}$ alkyl)sulfonyl, and —C(O)NR$^{53}$R$^{54}$;

Ar$^1$ is $C_{6-10}$ aryl or 5- to 10-membered heteroaryl, wherein the aryl and heteroaryl groups are each optionally substituted with one to three substituents selected from Rb, Rc, and Rd;

Rb, Rc, and Rd are each independently selected from optionally $C_{1-4}$ alkoxy-substituted $C_{1-5}$ alkoxy, a halogen atom, $C_{1-10}$ alkyl optionally substituted with one or more halogen atoms, a group —SF$_5$, cyano, hydroxy, 5- to 10-membered heterocycloalkyl optionally substituted with one or more substituents R$^{14}$, $C_{6-10}$ aryl optionally substituted with one or more substituents R$^{14}$, and 5- to 10-membered heteroaryl optionally substituted with one or more substituents R$^{14}$;

each R$^{14}$ is independently selected from a halogen atom, oxo, cyano, nitro, $C_{1-4}$ alkyl optionally substituted with one or more halogen atoms, $C_{1-4}$ alkoxy optionally substituted with one or more halogen atoms, ($C_{1-6}$ alkoxy)carbonyl, a group —NR$^{27}$R$^{28}$, a group —SO$_2$NR$^{35}$R$^{36}$, $C_{1-4}$ alkylthio, and 5- to 10-membered heterocycloalkyl;

R$^{27}$ and R$^{28}$ are each independently selected from a hydrogen atom and $C_{1-4}$ alkyl optionally substituted with ($C_{1-4}$ alkoxy)carbonyl;

R$^{35}$ and R$^{36}$ are each independently selected from a hydrogen atom and $C_{1-4}$ alkyl;

R$^{39}$ is a hydrogen atom, or optionally $C_{1-6}$ alkoxy-substituted $C_{1-6}$ alkyl;

R$^{40}$ is a hydrogen atom, optionally $C_{1-6}$ alkoxy-substituted $C_{1-6}$ alkyl, (($C_{1-4}$ alkoxy)carbonyl)$C_{1-6}$ alkyl, hydroxy-substituted $C_{1-6}$ alkyl, a group —(CH$_2$)$_u$—NR$^{55}$R$^{56}$ (wherein u is an integer selected from 1 to 4), a group —CH((CH$_2$)$_{v1}$COOR$^{57}$)—(CH$_2$)$_{v2}$—COOR$^{57}$ (wherein v1 is an integer selected from 0 to 2, and v2 is an integer selected from 1 to 3), a group —(CH$_2$)$_w$—SO$_3$H (wherein w is an integer selected from 1 to 4), a group —(CH$_2$)$_{x1}$—CH(COOH)—(CH$_2$)$_{x2}$—SO$_3$H (wherein x1 is an integer selected from 0 to 2, and x2 is an integer selected from 1 to 3), 3- to 6-membered oxacycloalkyl, or a group —(CH$_2$)$_{t1}$—O—(CH$_2$)$_{t2}$—C(O)NR$^{58}$R$^{59}$ (wherein t1 and t2 are each independently an integer selected from 1 to 3);

R$^{41}$ is a hydrogen atom or $C_{1-3}$ alkyl;

R$^{42}$ is $C_{1-8}$ alkyl substituted with one or more hydroxy groups, or ($C_{1-3}$ alkoxy)$C_{1-4}$ alkyl;

R$^{43}$ is a hydrogen atom or $C_{1-3}$ alkyl;

R$^{44}$ is $C_{1-8}$ alkyl substituted with one or more hydroxy groups, or

R$^{43}$ and R$^{44}$ together with the nitrogen atom to which they are attached may form morpholino;

R$^{45}$ is a hydrogen atom or $C_{1-3}$ alkyl;

R$^{46}$ is $C_{1-6}$ alkyl substituted with one or more hydroxy groups;

R$^{47}$ is $C_{1-3}$ alkyl;

R$^{48}$ is ($C_{1-3}$ alkoxy)$C_{1-4}$ alkyl;

R$^{49}$ is a hydrogen atom and $C_{1-4}$ alkyl;

R$^{50}$ is —(CH$_2$)$_z$—NR$^{60}$R$^{61}$ (z is an integer selected from 1 to 4, R$^{60}$ is a hydrogen atom or $C_{1-4}$ alkyl, and R$^{61}$ is ($C_{1-3}$ alkoxy)$C_{1-4}$ alkyl, or R$^{60}$ and R$^{61}$ together with the nitrogen atom to which they are attached may form morpholino);

R$^{51}$ is a hydrogen atom or $C_{1-4}$ alkyl;

R$^{52}$ is $C_{1-8}$ alkyl substituted with one or more hydroxy groups;

R$^{53}$ and R$^{54}$ are each independently selected from a hydrogen atom and $C_{1-4}$ alkyl;

R$^{55}$ is a hydrogen atom or $C_{1-4}$ alkyl;

R$^{56}$ is ($C_{1-4}$ alkyl)carbonyl;

R$^{57}$ is a hydrogen atom or $C_{1-4}$ alkyl;

R$^{58}$ is a hydrogen atom or $C_{1-3}$ alkyl; and

R$^{59}$ is $C_{1-8}$ alkyl substituted with one or more hydroxy groups.

(1-2) The compound according to (1-1) or a salt thereof, or a solvate of the compound or the salt, wherein each Ra is independently selected from a halogen atom, hydroxy, nitro, cyano, ($C_{1-4}$ alkoxy)carbonyl, 3- to 10-membered heterocycloalkyloxy, $C_{1-10}$ alkyl optionally substituted with one or more substituents R$^{10}$, $C_{2-10}$ alkenyl optionally substituted with one or more substituents R$^{15}$, $C_{2-10}$ alkynyl optionally substituted with one or more substituents R$^{11}$, $C_{1-8}$ alkoxy optionally substituted with one or more substituents R$^{12}$, and $C_{1-4}$ alkylthio optionally substituted with one or more substituents R$^{13}$;

R$^{10}$, R$^{11}$, R$^{12}$, R$^{13}$, and R$^{15}$ are each independently selected from a halogen atom, hydroxy, carboxy, $C_{1-6}$ alkoxy optionally substituted with one or more hydroxy groups, ($C_{1-4}$ alkoxy)carbonyl, a group —(O(CH$_2$)$_o$)$_p$—OH (wherein o and p are each independently an integer selected from 2 to 4), $C_{3-6}$ cycloalkyl optionally substituted with one or more hydroxy groups, 3- to 10-membered heterocycloalkyl, 5- to 10-membered heteroaryl, and a group —NR$^{39}$R$^{40}$, wherein the 3- to 10-membered heterocycloalkyl group is optionally substituted with one or more substituents selected from oxo, a halogen atom, and $C_{1-4}$ alkyl (wherein the alkyl group is optionally substituted with one or more hydroxy groups); and R$^{39}$ and R$^{40}$ are each independently selected from a hydrogen atom and optionally $C_{1-6}$ alkoxy-substituted $C_{1-6}$ alkyl.

(1-3) The compound according to (1-1) or (1-2) or a salt thereof, or a solvate of the compound or the salt, wherein 3- to 10-membered heterocycloalkyloxy in the definition of Ra is 3- to 6-membered heterocycloalkyloxy;

3- to 10-membered heterocycloalkyl in the definition of R$^{10}$, R$^{11}$, R$^{12}$, R$^{13}$ and R$^{15}$ is 3- to 6-membered heterocycloalkyl; and 5- to 10-membered heteroaryl in the definition of R$^{10}$, R$^{11}$, R$^{12}$, R$^{13}$ and R$^{15}$ is 5- to 6-membered heteroaryl.

(1-4) The compound according to any of (1-1) to (1-3) or a salt thereof, or a solvate of the compound or the salt, wherein Rb is optionally $C_{1-4}$ alkoxy-substituted $C_{1-5}$ alkoxy or a halogen atom;

Rc is a halogen atom, $C_{1-10}$ alkyl optionally substituted with one or more halogen atoms, or a group —SF$_5$; and Rd is cyano, hydroxy, a halogen atom, $C_{1-4}$ alkyl optionally substituted with one or more halogen atoms, 5- to 10-membered heterocycloalkyl optionally substituted with one or more substituents R$^{14}$, $C_{6-10}$ aryl optionally substituted with one or more substituents R$^{14}$, or 5- to 10-membered heteroaryl optionally substituted with one or more substituents R$^{14}$.

(1-5) The compound according to any of (1-1) to (1-4) or a salt thereof, or a solvate of the compound or the salt, wherein each Ra is independently selected from a halogen atom, nitro, cyano, ($C_{1-4}$ alkoxy)carbonyl, 3- to 6-membered heterocycloalkyloxy (the heterocycloalkyloxy group is optionally substituted with optionally $C_{1-4}$ alkoxy-substituted $C_{1-4}$ alkyl), $C_{1-10}$ alkyl optionally substituted with one or more substituents R$^{10}$, $C_{2-10}$ alkynyl optionally substituted with one or more substituents R$^{11}$, $C_{1-8}$ alkoxy optionally substituted with one or more substituents R$^{12}$, $C_{1-4}$ alkylthio optionally substituted with one or more substituents R$^{13}$, a group —(O(CH$_2$)$_{q1}$)$_{q2}$—NR$^{41}$R$^{42}$, a group —(O (CH$_2$)$_{r1}$)$_{r2}$—C(O)NR$^{43}$R$^{44}$, a group —(O(CH$_2$)$_{s1}$)$_{s2}$—NR$^{45}$—C(O)R$^{46}$, a group —C(O)NR$^{47}$R$^{48}$, pyridinyl, pyrrolyl, a group —NR$^{49}$R$^{50}$, and a group —(O(CH$_2$)$_{y1}$)$_{y2}$—O—CH$_2$—NR$^{51}$R$^{52}$;

R$^{10}$ is carboxy, 3- to 6-membered heterocycloalkyl, C$_{1-6}$ alkoxy optionally substituted with one or more hydroxy groups, or a group —(O(CH$_2$)$_o$)$_p$—OH;

R$^{11}$ is hydroxy, carboxy, 5- or 6-membered heterocycloalkyl optionally substituted with one or more oxo groups, C$_{1-6}$ alkoxy optionally substituted with one or more hydroxy groups, a group —(O(CH$_2$)$_o$)$_p$—OH, C$_{3-6}$ cycloalkyl optionally substituted with one or more hydroxy groups or a group —NR$^{39}$R$^{40}$;

R$^{12}$ is a halogen atom, hydroxy, carboxy, C$_{1-6}$ alkoxy optionally substituted with one or more hydroxy groups, (C$_{1-4}$ alkoxy)C$_{1-6}$ alkoxy, (C$_{1-3}$ alkoxy)carbonyl, 3- to 6-membered heterocycloalkyl, 5- or 6-membered heteroaryl, or a group —NR$^{39}$R$^{40}$, wherein the 3- to 6-membered heterocycloalkyl group is optionally substituted with one or more substituents selected from oxo, a halogen atom, C$_{1-4}$ alkyl (wherein the alkyl group is optionally substituted with one or more hydroxy groups), (C$_{1-4}$ alkoxy)C$_{1-4}$ alkyl (wherein the alkoxy moiety is optionally substituted with one or more hydroxy groups), C$_{1-4}$ alkoxy, (C$_{1-4}$ alkoxy)carbonyl, C$_{1-4}$ alkylthio, morpholinyl, (C$_{1-3}$ alkyl)sulfonyl, and —C(O)NR$^{53}$R$^{54}$;

R$^{13}$ is 5- or 6-membered heterocycloalkyl; and o and p are each independently an integer selected from 2 to 4.

(1-6) The compound according to any of (1-1) to (1-5) or a salt thereof, or a solvate of the compound or the salt, wherein each Ra is independently selected from a halogen atom, nitro, cyano, (C$_{1-4}$ alkoxy)carbonyl, 3- to 6-membered heterocycloalkyloxy, C$_{1-10}$ alkyl optionally substituted with one or more substituents R$^{10}$, C$_{2-10}$ alkynyl optionally substituted with one or more substituents R$^{11}$, C$_{1-8}$ alkoxy optionally substituted with one or more substituents R$^{12}$, and C$_{1-4}$ alkylthio optionally substituted with one or more substituents R$^{13}$;

each R$^{10}$ is independently selected from carboxy, 3- to 6-membered heterocycloalkyl, C$_{1-6}$ alkoxy optionally substituted with one or more hydroxy groups, and a group —(O(CH$_2$)$_o$)$_p$—OH;

each R$^{11}$ is independently selected from hydroxy, carboxy, 5- or 6-membered heterocycloalkyl optionally substituted with one or more oxo groups, C$_{1-6}$ alkoxy optionally substituted with one or more hydroxy groups, a group —(O(CH$_2$)$_o$)$_p$—OH, and C$_{3-6}$ cycloalkyl optionally substituted with one or more hydroxy groups;

each R$^{12}$ is independently selected from a halogen atom, hydroxy, C$_{1-6}$ alkoxy optionally substituted with one or more hydroxy groups, (C$_{1-3}$ alkoxy)carbonyl, 3- to 6-membered heterocycloalkyl, 5- or 6-membered heteroaryl, and a group —NR$^{39}$R$^{40}$;

R$^{13}$ is 5- or 6-membered heterocycloalkyl; and o and p are each independently an integer selected from 2 to 4.

(1-7) The compound according to any of (1-1) to (1-5) or a salt thereof, or a solvate of the compound or the salt, wherein each Ra is independently selected from a halogen atom, hydroxy, nitro, cyano, C$_{1-6}$ alkyl, (carboxy)C$_{1-8}$ alkyl, (morpholino)C$_{1-4}$ alkyl, [HO—((CH$_2$)$_o$O)$_p$]C$_{1-6}$ alkyl, (C$_{1-6}$ alkoxy)C$_{1-8}$ alkyl optionally substituted with one or more hydroxy groups, C$_{1-6}$ alkoxy optionally substituted with one or more halogen atoms, [N—((C$_{1-3}$ alkoxy)C$_{1-4}$ alkyl)-N—(C$_{1-3}$ alkyl)amino]C$_{1-4}$ alkoxy, C$_{1-6}$ alkoxy substituted with one or more hydroxy groups, ((C$_{1-3}$ alkoxy)carbonyl)C$_{1-3}$ alkoxy, (C$_{1-6}$ alkoxy)C$_{1-8}$ alkoxy optionally substituted with one or more hydroxy groups, (C$_{1-3}$ alkoxy(C$_{1-4}$ alkoxy))C$_{1-4}$ alkoxy, (carboxy)C$_{1-8}$ alkoxy, (3- to 6-membered heterocycloalkyl)C$_{1-6}$ alkoxy (the heterocycloalkyl moiety is optionally substituted with one or more substituents selected from oxo, a halogen atom, C$_{1-4}$ alkyl optionally substituted with one or more hydroxy groups, (C$_{1-4}$ alkoxy)C$_{1-4}$ alkyl (the alkoxy moiety is optionally substituted with one or more hydroxy groups), C$_{1-4}$ alkoxy, (C$_{1-4}$ alkoxy)carbonyl, C$_{1-4}$ alkylthio, morpholino, (C$_{1-3}$ alkyl)sulfonyl, and (di(C$_{1-3}$ alkyl)amino)carbonyl), C$_{1-4}$ alkoxy substituted with a group —NH—CH((CH$_2$)$_{v1}$COOR$^{57}$)—(CH$_2$)$_{v2}$—COOR$^{57}$, [N-(3- to 6-membered oxacycloalkyl)-N—(C$_{1-3}$ alkyl)amino]C$_{1-4}$ alkoxy, [N,N-di((hydroxy)C$_{1-4}$ alkyl)-amino]C$_{1-4}$ alkoxy, [N—((C$_{1-3}$ alkoxy)carbonyl)C$_{1-3}$ alkyl-N—(C$_{1-3}$ alkyl)amino]C$_{1-4}$ alkoxy, (pyridinyl)C$_{1-4}$ alkoxy, (pyrimidinyl)C$_{1-4}$ alkoxy, (1,2,4-triazolyl)C$_{1-4}$alkoxy, [N-(hydroxy)C$_{1-4}$ alkyl-N—(C$_{1-3}$ alkyl)amino]C$_{1-4}$ alkoxy, [N,N-di((C$_{1-3}$ alkoxy)C$_{1-4}$ alkyl)amino]C$_{1-6}$ alkoxy, [N,N-di(C$_{1-3}$alkyl)amino]C$_{1-6}$ alkoxy, [N—[N—(C$_{1-4}$alkyl)carbonyl-N—(C$_{1-3}$alkyl)amino]C$_{1-4}$ alkyl-N—(C$_{1-3}$ alkyl)amino]C$_{1-4}$ alkoxy, [N—[N—(C$_{1-4}$alkyl)carbonyl-amino]C$_{1-4}$ alkyl-N—(C$_{1-3}$ alkyl)amino]C$_{1-4}$ alkoxy, a group —(O(CH$_2$)$_{r1}$)$_{r2}$—C(O)NR$^{43}$R$^{44}$, a group —(O(CH$_2$)$_{q1}$)$_{q2}$—NR$^{41}$R$^{42}$, C$_{1-4}$ alkoxy substituted with a group —NH—(CH$_2$)$_w$—SO$_3$H, C$_{1-4}$ alkoxy substituted with a group —NH—(CH$_2$)$_{x1}$—CH(COOH)—(CH$_2$)$_{x2}$—SO$_3$H, a group —(O(CH$_2$)$_{s1}$)$_{s2}$—NR$^{45}$—C(O)R$^{46}$, a group —C(O)NR$^{47}$R$^{48}$, pyridinyl, a group —NR$^{49}$R$^{50}$, a group —(O(CH$_2$)$_{y1}$)$_{y2}$—O—CH$_2$—C(O)NR$^{51}$R$^{52}$, (carboxy)C$_{2-6}$ alkynyl, (3- to 6-membered heterocycloalkyl)C$_{2-6}$ alkynyl optionally substituted with one or more oxo groups, C$_{2-8}$ alkynyl optionally substituted with one or more hydroxy groups, [HO—((CH$_2$)$_o$O)$_p$]C$_{2-8}$ alkynyl, (C$_{1-6}$ alkoxy)C$_{2-8}$ alkynyl optionally substituted with one or more hydroxy groups, (C$_{3-6}$ cycloalkyl)C$_{2-6}$ alkynyl optionally substituted with one or more hydroxy groups, [N—((C$_{1-3}$ alkoxy)C$_{1-4}$ alkyl)-N—(C$_{1-3}$ alkyl)amino]C$_{2-6}$ alkynyl, (C$_{1-3}$ alkoxy)carbonyl, (morpholino)C$_{1-4}$ alkylthio optionally substituted with one or more oxo groups, 3- to 6-membered oxacycloalkyloxy, or 4- to 6-membered nitrogen containing heterocycloalkyloxy (the nitrogen containing heterocycloalkyl moiety is optionally substituted with one substituent selected from (C$_{1-3}$ alkoxy)C$_{1-4}$ alkyl and C$_{1-3}$ alkyl).

(1-8) The compound according to any of (1-1) to (1-7) or a salt thereof, or a solvate of the compound or the salt, wherein each Ra is independently selected from a halogen atom, hydroxy, cyano, C$_{1-6}$ alkyl, (carboxy)C$_{1-8}$ alkyl, (morpholino)C$_{1-4}$ alkyl, (C$_{1-6}$ alkoxy)C$_{1-8}$ alkyl substituted with one or more hydroxy groups, C$_{1-6}$ alkoxy optionally substituted with one or more halogen atoms, [N—((C$_{1-3}$ alkoxy)C$_{1-4}$ alkyl)-N—(C$_{1-3}$ alkyl)amino]C$_{1-4}$ alkoxy, (morpholino)C$_{1-6}$ alkoxy (the morpholino moiety is optionally substituted with one or two substituent(s) selected from oxo and C$_{1-3}$ alkyl), (C$_{1-6}$ alkoxy)C$_{1-8}$ alkoxy optionally substituted with one or more hydroxy groups, (C$_{1-3}$ alkoxy(C$_{1-4}$ alkoxy))C$_{1-4}$ alkoxy, (carboxy)C$_{1-8}$ alkoxy, (pyrrolidinyl)C$_{1-4}$ alkoxy (the pyrrolidinyl moiety is optionally substituted with (C$_{1-3}$ alkyl)C$_{1-4}$ alkoxy), C$_{1-4}$ alkoxy substituted with a group —NH—CH((CH$_2$)$_{v1}$COOR$^{57}$)—(CH$_2$)$_{v2}$—COOR$^{57}$, [N-(oxetanyl)-N—(C$_{1-3}$ alkyl)amino]C$_{1-4}$ alkoxy, [N,N-di(C$_{1-3}$ alkyl)amino]C$_{1-6}$ alkoxy, a group —(O(CH$_2$)$_{r1}$)$_{r2}$—C(O)NR$^{43}$R$^{44}$, a group —(O(CH$_2$)$_{q1}$)$_{q2}$—NR$^{41}$R$^{42}$, C$_{1-4}$ alkoxy substituted with a group —NH—(CH$_2$)$_w$—SO$_3$H, C$_{1-4}$ alkoxy substituted with a group —NH—(CH$_2$)$_{x1}$—CH(COOH)—(CH$_2$)$_{x2}$—SO$_3$H, (carboxy)C$_{2-6}$ alkynyl, (morpholino)$C_{2-6}$ alkynyl, $C_{2-8}$ alkynyl optionally substituted with one or more hydroxy groups, [HO—$((CH_2)_oO)_p$]$C_{2-8}$ alkynyl, $(C_{1-6}$ alkoxy)$C_{2-8}$ alkynyl substituted with one or more hydroxy groups, or $(C_{1-3}$ alkoxy)carbonyl.

(1-9) The compound according to any of (1-1) to (1-8) or a salt thereof, or a solvate of the compound or the salt, wherein each Ra is independently selected from a halogen atom, hydroxy, cyano, $C_{1-3}$ alkyl, (carboxy)$C_{1-8}$ alkyl, $(C_{1-6}$ alkoxy)$C_{1-8}$ alkyl substituted with one or more hydroxy groups, $C_{1-3}$ alkoxy optionally substituted with one or more halogen atoms, [N—$((C_{1-3}$ alkoxy)$C_{1-4}$ alkyl)-N—$(C_{1-3}$ alkyl)amino]$C_{1-4}$ alkoxy, (morpholino)$C_{1-6}$ alkoxy, $(C_{1-6}$ alkoxy)$C_{1-8}$ alkoxy substituted with one or more hydroxy groups, (carboxy)$C_{2-6}$ alkynyl, (morpholino)$C_{2-6}$ alkynyl, $C_{2-8}$ alkynyl optionally substituted with one or more hydroxy groups, [HO—$((CH_2)_oO)_p$]$C_{2-8}$ alkynyl, $(C_{1-6}$ alkoxy)$C_{2-8}$ alkynyl substituted with one or more hydroxy groups, and $(C_{1-3}$ alkoxy)carbonyl.

(1-10) The compound according to any of (1-1) to (1-9) or a salt thereof, or a solvate of the compound or the salt, wherein $R^3$ is methyl substituted with Re.

(1-11) The compound according to any of (1-1) to (1-10) or a salt thereof, or a solvate of the compound or the salt, wherein $R^3$ is benzyl optionally substituted with one or more substituents Ra on the benzene ring.

(1-12) The compound according to any of (1-1) to (1-11) or a salt thereof, or a solvate of the compound or the salt, wherein $R^3$ is benzyl optionally substituted with one to three substituents Ra on the benzene ring.

(1-13) The compound according to any of (1-1) to (1-6), and (1-10) to (1-12) or a salt thereof, or a solvate of the compound or the salt, wherein Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri is a halogen atom or $C_{1-3}$ alkoxy;

Rj is a halogen atom, nitro, or cyano; and

Rk is hydroxy, a halogen atom, $(C_{1-4}$ alkoxy)carbonyl, 5- to 10-membered heterocycloalkyloxy (the heterocycloalkyloxy group is optionally substituted with optionally $C_{1-4}$ alkoxy-substituted $C_{1-4}$ alkyl), $C_{1-10}$ alkyl optionally substituted with one or more substituents $R^{10}$, $C_{2-10}$ alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, $C_{1-4}$ alkylthio optionally substituted with one or more substituents $R^{13}$, a group —O$(CH_2)_{q1})_{q2}$—$NR^{41}R^{42}$, a group —$(O(CH_2)_{r1})_{r2}$—$C(O)NR^{43}R^{44}$, a group —$(O(CH_2)_{s1})_{s2}$—$NR^{45}$—$C(O)R^{46}$, a group —$C(O)NR^{47}R^{48}$, pyridinyl, pyrrolyl, a group —$NR^{49}R^{50}$, or a group —$(O(CH_2)_{y1})_{y2}$—O—$CH_2$—$C(O)NR^{51}R^{52}$.

(1-14) The compound according to (1-13) or a salt thereof, or a solvate of the compound or the salt, wherein Rk is hydroxy, a halogen atom, $(C_{1-4}$ alkoxy)carbonyl, 3- to 6-membered heterocycloalkyloxy (the heterocycloalkyloxy group is optionally substituted with optionally $C_{1-4}$ alkoxy-substituted $C_{1-4}$ alkyl), $C_{1-10}$ alkyl optionally substituted with one or more substituents $R^{10}$, $C_{2-10}$ alkynyl optionally substituted with one or more substituents $R^{11}$, $C_{1-8}$ alkoxy optionally substituted with one or more substituents $R^{12}$, $C_{1-4}$ alkylthio optionally substituted with one or more substituents $R^{13}$, a group —$(O(CH_2)_{q1})_{q2}$—$NR^{41}R^{42}$, a group —$(O(CH_2)_{r1})_{r2}$—$C(O)NR^{43}R^{44}$, a group —$(O(CH_2)_{s1})_{s2}$—$NR^{45}$—$C(O)R^{46}$, a group —$C(O)NR^{47}R^{48}$, pyridinyl, pyrrolyl, a group —$NR^{49}R^{50}$, or a group —$(O(CH_2)_{y1})_{y2}$—O—$CH_2$—$C(O)NR^{51}R^{52}$;

each $R^{10}$ is independently carboxy, hydroxy, morpholinyl, $C_{1-6}$ alkoxy optionally substituted with one or more hydroxy groups, or a group —$(O(CH_2)_o)_p$—OH;

each $R^{11}$ is independently hydroxy, carboxy, morpholinyl optionally substituted with one or more oxo groups, $C_{1-6}$ alkoxy optionally substituted with one or more hydroxy groups, a group —$(O(CH_2)_o)_p$—OH, $C_{3-6}$ cycloalkyl optionally substituted with one or more hydroxy groups or a group —$NR^{39}R^{40}$;

$R^{12}$ is a halogen atom, hydroxy, carboxy, $C_{1-6}$ alkoxy optionally substituted with one or more hydroxy groups, $(C_{1-4}$ alkoxy)$C_{1-6}$ alkoxy, $(C_{1-3}$ alkoxy)carbonyl, 3- to 6-membered heterocycloalkyl, 5- or 6-membered heteroaryl containing one nitrogen atom, or a group —$NR^{39}R^{40}$, wherein the 3- to 6-membered heterocycloalkyl group is optionally substituted with one or more substituents selected from oxo, a halogen atom, $C_{1-4}$ alkyl (wherein the alkyl group is optionally substituted with one or more hydroxy groups), $(C_{1-4}$ alkoxy)$C_{1-4}$ alkyl (wherein the alkoxy moiety is optionally substituted with one or more hydroxy groups), $C_{1-4}$ alkoxy, $(C_{1-4}$ alkoxy)carbonyl, $C_{1-4}$ alkylthio, morpholinyl, $(C_{1-3}$ alkyl)sulfonyl, and —$C(O)NR^{53}R^{54}$;

$R^{13}$ is morpholinyl; and o and p are each independently an integer selected from 2 to 4.

(1-15) The compound according to any of (1-1) to (1-6) and (1-10) to (1-13) or a salt thereof, or a solvate of the compound or the salt, wherein Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri is a halogen atom or $C_{1-3}$ alkoxy;

Rj is a halogen atom, nitro, or cyano; and

Rk is hydroxy, a halogen atom, $(C_{1-4}$ alkoxy)carbonyl, 5- to 10-membered heterocycloalkyloxy, $C_{1-10}$ alkyl optionally substituted with one or more substituents $R^{10}$, $C_{2-10}$ alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, or $C_{1-4}$ alkylthio optionally substituted with one or more substituents $R^{13}$.

(1-16) The compound according to (1-14) or (1-15) or a salt thereof, or a solvate of the compound or the salt, wherein Rk is hydroxy, a halogen atom, $(C_{1-4}$ alkoxy)carbonyl, 3- to 6-membered heterocycloalkyloxy, $C_{1-10}$ alkyl optionally substituted with one or more substituents $R^{10}$, $C_{2-10}$ alkynyl optionally substituted with one or more substituents $R^1$, $C_{1-8}$ alkoxy optionally substituted with one or more substituents $R^{12}$, or $C_{1-4}$ alkylthio optionally substituted with one or more substituents $R^{13}$;

each $R^{10}$ is independently selected from hydroxy, carboxy, morpholinyl, $C_{1-6}$ alkoxy optionally substituted with one or more hydroxy groups, and a group —$(O(CH_2)_o)_p$—OH;

each $R^1$ is independently selected from hydroxy, carboxy, morpholinyl optionally substituted with one or more oxo groups, $C_{1-6}$ alkoxy optionally substituted with one or more hydroxy groups, a group —$(O(CH_2)_o)_p$—OH, and $C_{3-6}$ cycloalkyl optionally substituted with one or more hydroxy groups;

each $R^{12}$ is independently selected from a halogen atom, hydroxy, $C_{1-6}$ alkoxy optionally substituted with one or more hydroxy groups, ($C_{1-3}$ alkoxy)carbonyl, 3- to 6-membered heterocycloalkyl, pyridinyl, pyrroryl, and a group —$NR^{39}R^{40}$;

$R^{13}$ is morpholinyl; and o and p are each independently an integer selected from 2 to 4.

(1-17) The compound according to (1-13) or (1-14) or a salt thereof, or a solvate of the compound or the salt, wherein Rk is a halogen atom, hydroxy, $C_{1-6}$ alkyl, (carboxy)$C_{1-8}$ alkyl, (morpholino)$C_{1-4}$ alkyl, [HO—$((CH_2)_oO)_p$]$C_{1-6}$ alkyl, ($C_{1-6}$ alkoxy)$C_{1-8}$ alkyl optionally substituted with one or more hydroxy groups, $C_{1-6}$ alkoxy optionally substituted with one or more halogen atoms, [N—(($C_{1-3}$ alkoxy)$C_{1-4}$ alkyl)-N—($C_{1-3}$ alkyl)amino]$C_{1-4}$ alkoxy, $C_{1-6}$ alkoxy substituted with one or more hydroxy groups, (($C_{1-3}$ alkoxy) carbonyl)$C_{1-3}$ alkoxy, ($C_{1-6}$ alkoxy)$C_{1-8}$ alkoxy optionally substituted with one or more hydroxy groups, ($C_{1-3}$ alkoxy ($C_{1-4}$ alkoxy))$C_{1-4}$ alkoxy, (carboxy)$C_{1-8}$ alkoxy, (3- to 6-membered heterocycloalkyl)$C_{1-6}$ alkoxy (the heterocycloalkyl moiety contains one to three heteroatoms selected from O or N, and is optionally substituted with one or more substituents selected from oxo, a halogen atom, $C_{1-4}$ alkyl (wherein the alkyl moiety is optionally substituted with one or more hydroxy groups), ($C_{1-4}$ alkoxy)$C_{1-4}$ alkyl (the alkoxy moiety is optionally substituted with one or more hydroxy groups), $C_{1-4}$ alkoxy, ($C_{1-4}$ alkoxy)carbonyl, $C_{1-4}$ alkylthio, morpholino, ($C_{1-3}$ alkyl)sulfonyl, and (di($C_{1-3}$ alkyl)amino)carbonyl), $C_{1-4}$ alkoxy substituted with a group —NH—CH(($CH_2)_{v1}COOR^{57}$)—($CH_2)_{v2}$—COOR$^{57}$, [N-(3- to 6-membered oxacycloalkyl)-N—($C_{1-3}$ alkyl)amino]$C_{1-4}$ alkoxy, [N,N-di((hydroxy)$C_{1-4}$ alkyl)-amino]$C_{1-4}$ alkoxy, [N—(($C_{1-3}$ alkoxy)carbonyl)$C_{1-3}$ alkyl-N—($C_{1-3}$ alkyl) amino]$C_{1-4}$ alkoxy, (pyridinyl)$C_{1-4}$ alkoxy, (pyrimidinyl) $C_{1-4}$ alkoxy, (1,2,4-triazolyl)$C_{1-4}$ alkoxy, [N-(hydroxy)$C_{1-4}$ alkyl-N—($C_{1-3}$ alkyl)amino]$C_{1-4}$ alkoxy, [N,N-di($C_{1-3}$ alkoxy($C_{1-3}$ alkyl))amino]$C_{1-6}$ alkoxy, [N,N-di($C_{1-3}$alkyl) amino]$C_{1-6}$ alkoxy, [N—[N—($C_{1-4}$ alkyl)carbonyl-N—($C_{1-3}$ alkyl)amino]$C_{1-4}$ alkyl-N—($C_{1-3}$ alkyl)amino]$C_{1-4}$ alkoxy, [N—[N—($C_{1-4}$ alkyl)carbonyl-amino]$C_{1-4}$ alkyl-N—($C_{1-3}$ alkyl)amino]$C_{1-4}$ alkoxy, a group —(O($CH_2)_{r1})_{r2}$—C(O)NR$^{43}$R$^{44}$, a group —(O($CH_2)_{q1})_{q2}$—NR$^{41}$R$^{42}$, $C_{1-4}$ alkoxy substituted with a group —NH—($CH_2)_w$—SO$_3$H, $C_{1-4}$ alkoxy substituted with a group —NH—($CH_2)_{x1}$—CH(COOH)—($CH_2)_{x2}$—SO$_3$H, a group —(O($CH_2)_{s1})_{s2}$—NR$^{45}$—C(O)R$^{46}$, a group —C(O) NR$^{47}$R$^{48}$, pyridinyl, a group —NR$^{49}$R$^{50}$, a group —(O ($CH_2)_{v1})_{y2}$—O—$CH_2$—C(O)NR$^{51}$R$^{52}$, (carboxy)$C_{2-8}$ alkynyl, (3- to 6-membered heterocycloalkyl)$C_{2-6}$ alkynyl optionally substituted with one or more oxo groups, $C_{2-8}$ alkynyl optionally substituted with one or more hydroxy groups, [HO—$((CH_2)_oO)_p$]$C_{2-8}$ alkynyl, ($C_{1-6}$ alkoxy)$C_{2-8}$ alkynyl optionally substituted with one or more hydroxy groups, ($C_{3-6}$ cycloalkyl)$C_{2-6}$ alkynyl optionally substituted with one or more hydroxy groups, ($C_{1-3}$ alkoxy)carbonyl, (morpholino)$C_{1-4}$ alkylthio, 3- to 6-membered oxacycloalkyloxy, or 3- to 6-membered nitrogen containing heterocycloalkyloxy (the nitrogen containing heterocycloalkyl moiety is optionally substituted with one substituent selected from ($C_{1-3}$ alkoxy)$C_{1-4}$ alkyl and $C_{1-3}$ alkyl).

(1-18) The compound according to any of (1-13), (1-14) and (1-17) or a salt thereof, or a solvate of the compound or the salt, wherein Rk is hydroxy, a halogen atom, $C_{1-6}$ alkyl, (carboxy)$C_{1-8}$ alkyl, (morpholino)$C_{1-4}$ alkyl, ($C_{1-6}$ alkoxy) $C_{1-8}$ alkyl substituted with one or more hydroxy groups, $C_{1-6}$ alkoxy optionally substituted with one or more halogen atoms, [N—(($C_{1-3}$ alkoxy)$C_{1-4}$ alkyl)-N—($C_{1-3}$ alkyl) amino]$C_{1-4}$ alkoxy, (morpholino)$C_{1-6}$ alkoxy, ($C_{1-6}$ alkoxy) $C_{1-8}$ alkoxy optionally substituted with one or more hydroxy groups, ($C_{1-3}$ alkoxy($C_{1-4}$ alkoxy))$C_{1-4}$ alkoxy, (carboxy) $C_{1-8}$ alkoxy, (pyrrolidinyl)$C_{1-4}$ alkoxy (the pyrrolidinyl moiety is substituted with ($C_{1-3}$ alkyl)$C_{1-4}$ alkoxy), $C_{1-4}$ alkoxy substituted with a group —NH—CH(($CH_2)_{v1}COOR^{57}$)—($CH_2)_{v2}$—COOR$^{57}$, [N-(oxetanyl)-N—($C_{1-3}$ alkyl)amino] $C_{1-4}$ alkoxy, [N,N-di($C_{1-3}$ alkyl)amino]$C_{1-6}$ alkoxy, a group —(O($CH_2)_{r1})_{r2}$—C(O)NR$^{43}$R$^{44}$, a group —(O($CH_2)_{q1})_{q2}$—NR$^{41}$R$^{42}$, $C_{1-4}$ alkoxy substituted with a group —NH—($CH_2)_w$—SO$_3$H, $C_{1-4}$ alkoxy substituted with a group —NH—($CH_2)_{x1}$—CH(COOH)—($CH_2)_{x2}$—SO$_3$H, (carboxy)$C_{2-8}$ alkynyl, (morpholino)$C_{2-6}$ alkynyl, $C_{2-8}$ alkynyl optionally substituted with one or more hydroxy groups, [HO—$((CH_2)_oO)_p$]$C_{2-8}$ alkynyl, ($C_{1-6}$ alkoxy)$C_{2-8}$ alkynyl substituted with one or more hydroxy groups, or ($C_{1-3}$ alkoxy)carbonyl.

(1-19) The compound according to any of (1-13) to (1-18) or a salt thereof, or a solvate of the compound or the salt, wherein Rk is hydroxy, a halogen atom, $C_{1-6}$ alkyl, (carboxy)$C_{1-8}$ alkyl, ($C_{1-6}$ alkoxy)$C_{1-8}$ alkyl substituted with one or more hydroxy groups, $C_{1-3}$ alkoxy optionally substituted with one or more halogen atoms, [N—(($C_{1-3}$ alkoxy)$C_{1-4}$ alkyl)-N—($C_{1-3}$ alkyl)amino]$C_{1-4}$ alkoxy, (morpholino)$C_{1-6}$ alkoxy, ($C_{1-6}$ alkoxy)$C_{1-8}$ alkoxy substituted with one or more hydroxy groups, (carboxy)$C_{2-8}$ alkynyl, (morpholino) $C_{2-6}$ alkynyl, $C_{2-8}$ alkynyl optionally substituted with one or more hydroxy groups, [HO—$((CH_2)_oO)_p$]$C_{2-8}$ alkynyl, ($C_{1-6}$ alkoxy)$C_{2-8}$ alkynyl substituted with one or more hydroxy groups, or ($C_{1-3}$ alkoxy)carbonyl.

(1-20) The compound according to any of (1-1) to (1-19) or a salt thereof, or a solvate of the compound or the salt, wherein $R^1$, $R^4$, and $R^5$ are as defined in any one of the following (1) to (3):

(1) $R^1$ is a hydrogen atom or $C_{1-6}$ alkyl;

$R^4$ is $C_{1-4}$ alkyl optionally substituted with one or more halogen atom(s), or phenyl; and $R^5$ is a hydrogen atom or $C_{1-4}$ alkyl;

(2) $R^1$ and $R^5$ together with the carbon atom to which they are attached form a $C_{3-6}$ saturated carbocyclic ring; and $R^4$ is as defined above; and (3) $R^1$ is a hydrogen atom or linear $C_{1-6}$ alkyl;

$R^4$ and $R^5$ together with the carbon atom and the nitrogen atom to which they are attached form a 5- to 8-membered saturated heterocyclic ring.

(1-21) The compound according to any of (1-1) to (1-3), (1-10) to (1-12), and (1-20) or a salt thereof, or a solvate of the compound or the salt, wherein $R^1$, $R^4$, and $R^5$ are as defined in the following (1) or (2):

(1) $R^1$ is $C_{1-6}$ alkyl;

$R^4$ is optionally halogen atom-substituted $C_{1-4}$ alkyl or phenyl; and $R^5$ is a hydrogen atom or $C_{1-4}$ alkyl; or (2) $R^1$ and $R^5$ together with the carbon atom to which they are attached form a $C_{3-6}$ saturated carbocyclic ring; and $R^4$ is as defined above;

$R^3$ is $C_{1-4}$ alkyl substituted with Re;

Re is phenyl optionally substituted with one or more substituents Ra;

each Ra is independently selected from a halogen atom, $C_{2-6}$ alkynyl optionally substituted with one or more substituents $R^1$, $C_{1-6}$ alkoxy optionally substituted with one or more substituents $R^{12}$, 3- to 6-membered heterocycloalkyloxy (the heterocycloalkyloxy group is optionally substituted with optionally $C_{1-4}$ alkoxy-substituted $C_{1-4}$ alkyl), a group —(O($CH_2)_{q1})_{q2}$—NR$^{41}$R$^{42}$, a group —(O ($CH_2)_{r1})_{r2}$—C(O)NR$^{43}$R$^{44}$, a group —(O($CH_2)_{s1})_{s2}$—

NR$^{45}$—C(O)R$^{46}$, a group —C(O)NR$^{47}$R$^{48}$, pyridinyl, pyrrolyl, a group —NR$^{49}$R$^{50}$, and a group —(O(CH$_2$)$_{y1}$)$_{y2}$—O—CH$_2$—C(O)NR$^{51}$R$^{52}$;

R$^{11}$ and R$^{12}$ are each independently selected from halogen atom, hydroxy, carboxy, C$_{1-6}$ alkoxy optionally substituted with one or more hydroxy, (C$_{1-4}$ alkoxy)C$_{1-6}$ alkoxy, 3- to 6-membered heterocycloalkyl, 5- to 6-membered heteroaryl, and a group —NR$^{39}$R$^{40}$, wherein the 3- to 6-membered heterocycloalkyl group is optionally substituted with one or two substituents selected from oxo, a halogen atom, C$_{1-4}$ alkyl (wherein the alkyl group is optionally substituted with one or more hydroxy groups), (C$_{1-4}$ alkoxy)C$_{1-4}$ alkyl (wherein the alkoxy moiety is optionally substituted with one or more hydroxy groups), C$_{1-4}$ alkoxy, (C$_{1-4}$ alkoxy) carbonyl, C$_{1-4}$ alkylthio, morpholino, (C$_{1-3}$ alkyl)sulfonyl, and —C(O)NR$^{53}$R$^{54}$;

Ar$^1$ is phenyl or 5- or 6-membered heteroaryl, wherein the phenyl and heteroaryl groups are each optionally substituted with one to three substituents selected from Rb, Rc, and Rd;

Rb, Rc, and Rd are each independently selected from a halogen atom, C$_{1-4}$ alkyl optionally substituted with one or more halogen atoms, phenyl optionally substituted with one or more substituents R$^{14}$, and 5- or 6-membered heteroaryl optionally substituted with one or more substituents R$^{14}$; and each R$^{14}$ is independently selected from a halogen atom, cyano, C$_{1-4}$ alkyl optionally substituted with one or more halogen atoms, C$_{1-4}$ alkoxy, a group —SO$_2$NR$^{35}$R$^{36}$ (wherein R$^{35}$ and R$^{36}$ are each independently selected from C$_{1-4}$ alkyl), and C$_{1-4}$ alkylthio.

(1-22) The compound according to any of (1-1) to (1-3), (1-5) to (1-7), (1-10) to (1-12), (1-20), and (1-21) or a salt thereof, or a solvate of the compound or the salt, wherein each Ra is independently selected from a halogen atom, [N—((C$_{1-3}$ alkoxy)C$_{1-4}$ alkyl)-N—(C$_{1-3}$ alkyl)amino]C$_{1-4}$ alkoxy, (C$_{1-4}$ alkoxy)C$_{1-6}$ alkoxy (the C$_{1-4}$ alkoxy moiety is optionally substituted with one or more hydroxy groups), (C$_{1-3}$ alkoxy(C$_{1-4}$ alkoxy))C$_{1-4}$ alkoxy, (carboxy)C$_{1-6}$ alkoxy, (3- to 6-membered heterocycloalkyl)C$_{1-6}$ alkoxy (the heterocycloalkyl moiety is optionally substituted with one or two substituents selected from oxo, a halogen atom, C$_{1-4}$ alkyl optionally substituted with one or more hydroxy groups, (C$_{1-4}$ alkoxy)C$_{1-4}$ alkyl (the alkoxy moiety is optionally substituted with one or more hydroxy groups), C$_{1-4}$alkoxy, (C$_{1-4}$ alkoxy)carbonyl, C$_{1-4}$ alkylthio, morpholino, (C$_{1-3}$ alkyl)sulfonyl, and (di(C$_{1-3}$ alkyl)amino)carbonyl), C$_{1-4}$ alkoxy substituted with a group —NH—CH((CH$_2$)$_{v1}$COOR$^{57}$)—(CH$_2$)$_{v2}$—COOR$^{57}$, [N-(3- to 6-membered oxacycloalkyl)-N—(C$_{1-3}$ alkyl)amino]C$_{1-4}$ alkoxy, [N,N-di((hydroxy)C$_{1-4}$ alkyl)-amino]C$_{1-4}$ alkoxy, [N—((C$_{1-3}$ alkoxy)carbonyl)C$_{1-3}$ alkyl-N—(C$_{1-3}$ alkyl)amino]C$_{1-4}$ alkoxy, (1,2,4-triazolyl)C$_{1-4}$alkoxy, [N-(hydroxy)C$_{1-4}$ alkyl-N—(C$_{1-3}$ alkyl)amino]C$_{1-4}$ alkoxy, [N,N-di((C$_{1-3}$ alkoxy)C$_{1-4}$ alkyl)amino]C$_{1-6}$ alkoxy, [N,N-di(C$_{1-3}$alkyl)amino]C$_{1-6}$ alkoxy, [N—[N—(C$_{1-4}$alkyl)carbonyl-N—(C$_{1-3}$alkyl)amino]C$_{1-4}$ alkyl-N—(C$_{1-3}$ alkyl)amino]C$_{1-4}$ alkoxy, [N—[N—(C$_{1-4}$alkyl)carbonyl-amino]C$_{1-4}$ alkyl-N—(C$_{1-3}$ alkyl)amino]C$_{1-4}$ alkoxy, C$_{1-6}$ alkoxy optionally substituted with one or more halogen atoms, a group —(O(CH$_2$)$_{r1}$)$_{r2}$—C(O)NR$^{43}$R$^{44}$, a group —(O(CH$_2$)$_{q1}$)$_{q2}$—NR$^{41}$R$^{42}$, C$_{1-4}$ alkoxy substituted with a group —NH—(CH$_2$)$_w$—SO$_3$H, C$_{1-4}$ alkoxy substituted with a group —NH—(CH$_2$)$_{x1}$—CH(COOH)—(CH$_2$)$_{x2}$—SO$_3$H, a group —(O(CH$_2$)$_{s1}$)$_{s2}$—NR$^{45}$—C(O)R$^{46}$, a group —C(O)NR$^{47}$R$^{48}$, pyridinyl, a group —NR$^{49}$R$^{50}$, a group —(O(CH$_2$)$_{y1}$)$_{y2}$—O—CH$_2$—C(O)NR$^{51}$R$^{52}$, (3- to 6-membered heterocycloalkyl)C$_{2-6}$ alkynyl (the heterocycloalkyl moiety is optionally substituted with one or more oxo groups),

[N—((C$_{1-3}$alkoxy)C$_{1-4}$alkyl-N—(C$_{1-3}$alkyl)amino]C$_{2-6}$ alkynyl, C$_{2-8}$ alkynyl optionally substituted with one or more hydroxy groups, 3- to 6-membered oxacycloalkyloxy, or 4- to 6-membered nitrogen containing heterocycloalkyloxy (the heterocycloalkyl moiety is optionally substituted with one substituent selected from (C$_{1-3}$ alkoxy)C$_{1-4}$ alkyl and C$_{1-3}$ alkyl).

(1-23) The compound according to any of (1-1) to (1-3), (1-10) to (1-13), (1-20), and (1-21) or a salt thereof, or a solvate of the compound or the salt, wherein Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri is a halogen atom;

Rj is a halogen atom; and

Rk is a halogen atom, 3- to 6-membered heterocycloalkyloxy (the heterocycloalkyl moiety comprises one heteroatom selected from O and N and is optionally substituted with optionally C$_{1-4}$ alkoxy-substituted C$_{1-4}$ alkyl), optionally R$^{11}$-substituted C$_{2-6}$ alkynyl, optionally R$^{12}$-substituted C$_{1-6}$ alkoxy, a group —(O(CH$_2$)$_{q1}$)$_{q2}$—NR$^{41}$R$^{42}$, a group —(O(CH$_2$)$_{r1}$)$_{r2}$—C(O)NR$^{43}$R$^{44}$, a group —(O(CH$_2$)$_{s1}$)$_{s2}$—NR$^{45}$—C(O)R$^{46}$, a group —C(O)NR$^{47}$R$^{48}$, a group —NR$^{49}$R$^{50}$, or a group —(O(CH$_2$)$_{y1}$)$_{y2}$—O—CH$_2$—CH(O)NR$^{51}$R$^{52}$.

(1-24) The compound according to (1-21) or (1-23) or a salt thereof, or a solvate of the compound or the salt, wherein R$^{11}$ is morpholino;

R$^{12}$ is selected from 5- to 6-membered heterocycloalkyl which contains one or two hetero atoms selected from O and N, (C$_{1-4}$alkoxy)C$_{1-6}$alkoxy or a group —NR$^{39}$R$^{40}$.

(1-25) The compound according to any of (1-13), (1-14), (1-17) and (1-23) or a salt thereof, or a solvate of the compound or the salt, wherein Rk is [N—((C$_{1-3}$ alkoxy)C$_{1-4}$ alkyl)-N—(C$_{1-3}$ alkyl)amino]C$_{1-4}$ alkoxy, (C$_{1-4}$ alkoxy)C$_{1-6}$ alkoxy (the C$_{1-4}$ alkoxy moiety is optionally substituted with one or more hydroxy groups), (C$_{1-3}$ alkoxy(C$_{1-4}$ alkoxy))C$_{1-4}$ alkoxy, (carboxy)C$_{1-6}$ alkoxy, (3- to 6-membered heterocycloalkyl)C$_{1-6}$ alkoxy (the heterocycloalkyl moiety comprises one to three hetero atom(s) which is selected from O or N and is optionally substituted with one or two substituents selected from oxo, a halogen atom, C$_{1-4}$ alkyl (wherein the alkyl moiety is optionally substituted with one or more hydroxy groups), (C$_{1-4}$ alkoxy)C$_{1-4}$ alkyl (the alkoxy moiety is optionally substituted with one or more hydroxy groups), C$_{1-4}$ alkoxy, (C$_{1-4}$ alkoxy)carbonyl, C$_{1-4}$ alkylthio, morpholino, (C$_{1-3}$ alkyl)sulfonyl, and (di(C$_{1-3}$ alkyl)amino)carbonyl), C$_{1-4}$ alkoxy substituted with a group —NH—CH((CH$_2$)$_{v1}$COOR$^{57}$)—(CH$_2$)$_{v2}$—COOR$^{57}$, [N-(3- to 6-membered oxacycloalkyl)-N—(C$_{1-3}$ alkyl)amino]C$_{1-4}$ alkoxy, [N,N-di((hydroxy)C$_{1-4}$ alkyl)-amino]C$_{1-4}$ alkoxy, [N—((C$_{1-3}$ alkoxy)carbonyl)C$_{1-3}$ alkyl-N—(C$_{1-3}$ alkyl) amino]C$_{1-4}$ alkoxy, (1,2,4-triazolyl)C$_{1-4}$ alkoxy, [N-(hydroxy)C$_{1-4}$ alkyl-N—(C$_{1-3}$ alkyl)amino]C$_{1-4}$ alkoxy, [N,N-di(C$_{1-3}$ alkoxy(C$_{1-4}$ alkyl))amino]C$_{1-6}$ alkoxy, [N,N-di(C$_{1-3}$alkyl)amino]C$_{1-6}$ alkoxy, [N—[N—(C$_{1-4}$ alkyl)carbonyl-N—(C$_{1-3}$ alkyl)amino]C$_{1-4}$ alkyl-N—(C$_{1-3}$ alkyl) amino]C$_{1-4}$ alkoxy, [N—[N—(C$_{1-4}$ alkyl)carbonyl-amino]C$_{1-4}$ alkyl-N—(C$_{1-3}$ alkyl)amino]C$_{1-4}$ alkoxy, a group —(O(CH$_2$)$_{r1}$)$_{r2}$—C(O)NR$^{43}$R$^{44}$, a group —(O(CH$_2$)$_{q1}$)$_{q2}$—NR$^{41}$R$^{42}$, C$_{1-4}$ alkoxy substituted with a group —NH—(CH$_2$)$_w$—SO$_3$H, C$_{1-4}$ alkoxy substituted with a group —NH—(CH$_2$)$_{x1}$—CH(COOH)—(CH$_2$)$_{x2}$—SO$_3$H, a group —(O(CH$_2$)$_{s1}$)$_{s2}$—NR$^{45}$—C(O)R$^{46}$, a group —C(O)

$NR^{47}R^{48}$, pyridinyl, a group —$NR^{49}R^{50}$, a group —(O(CH$_2$)$_{y1}$)$_{y2}$—O—CH$_2$—C(O)NR$^{51}$R$^{52}$, (3- to 6-membered heterocycloalkyl)C$_{2-6}$ alkynyl optionally substituted with one or more oxo groups (the heterocycloalkyl moiety comprises one to three hetero atoms selected from O and N), [N—((C$_{1-3}$alkoxy)C$_{1-4}$alkyl-N—(C$_{1-3}$alkyl)amino]C$_{2-6}$ alkynyl, 3- to 6-membered oxacycloalkyloxy, or 4- to 6-membered nitrogen containing heterocycloalkyloxy (the nitrogen containing heterocycloalkyl moiety is optionally substituted with one substituent selected from (C$_{1-3}$ alkoxy) C$_{1-4}$ alkyl and C$_{1-3}$ alkyl).

(1-26) The compound according to any of (1-1) to (1-3), (1-5), (1-7), (1-8), (1-10) to (1-20), and (1-21) or a salt thereof, or a solvate of the compound or the salt, wherein $R^1$, $R^4$, and $R^5$ are as defined in the following (1) or (2):

(1) $R^1$ is C$_{1-6}$ alkyl;

$R^4$ is optionally halogen atom-substituted C$_{1-4}$ alkyl or phenyl; and $R^5$ is a hydrogen atom or C$_{1-4}$ alkyl; or (2) $R^1$ and $R^5$ together with the carbon atom to which they are attached form a C$_{3-6}$ saturated carbocyclic ring; and $R^4$ is as defined above;

$R^3$ is C$_{1-4}$ alkyl substituted with Re;

Re is phenyl optionally substituted with one or more substituents Ra;

each Ra is independently selected from a halogen atom, optionally $R^{11}$-substituted C$_{2-6}$ alkynyl, and optionally $R^{12}$-substituted C$_{1-6}$ alkoxy;

$R^{11}$ and $R^{12}$ are each independently selected from 5- or 6-membered heterocycloalkyl and —NR$^{39}$R$^{40}$;

$R^{39}$ and $R^{40}$ are each independently selected from hydrogen atom and optionally C$_{1-6}$ alkoxy-substituted C$_{1-6}$ alkyl;

Ar$^1$ is phenyl or 5- or 6-membered heteroaryl, wherein the phenyl and heteroaryl groups are each optionally substituted with one to three substituents selected from Rb, Rc, and Rd;

Rb, Rc, and Rd are each independently selected from a halogen atom, C$_{1-4}$ alkyl optionally substituted with one or more halogen atoms, phenyl optionally substituted with one or more substituents $R^{14}$, and 5- or 6-membered heteroaryl optionally substituted with one or more substituents $R^{14}$; and each $R^{14}$ is independently selected from a halogen atom, cyano, C$_{1-4}$ alkyl optionally substituted with one or more halogen atoms, C$_{1-4}$ alkoxy, a group —SO$_2$NR$^{35}$R$^{36}$ (wherein $R^{35}$ and $R^{36}$ are each independently selected from C$_{1-4}$ alkyl), and C$_{1-4}$ alkylthio.

(1-27) The compound according to any of (1-1) to (1-26) or a salt thereof, or a solvate of the compound or the salt, wherein Rb is a halogen atom;

Rc is a halogen atom or C$_{1-4}$ alkyl optionally substituted with one or more halogen atoms; and Rd is a halogen atom, C$_{1-4}$ alkyl optionally substituted with one or more halogen atoms, phenyl optionally substituted with one or more substituents $R^{14}$, or 5- or 6-membered heteroaryl optionally substituted with one or more substituents $R^{14}$.

(1-28) The compound according to any of (1-1) to (1-12), (1-20), (1-21), (1-23), (1-26) and (1-27) or a salt thereof, or a solvate of the compound or the salt, wherein Re is phenyl optionally substituted with one or more substituents Ra;

$R^{11}$ and $R^{12}$ are each independently selected from morpholinyl and a group —NR$^{39}$R$^{40}$;

$R^4$ is optionally halogen atom-substituted C$_{1-4}$ alkyl or phenyl;

Ar$^1$ is phenyl, pyridinyl, or pyrimidinyl, wherein the phenyl, pyridinyl, and pyrimidinyl groups are each optionally substituted with one to three substituents selected from Rb, Rc, and Rd;

Rb is a halogen atom;

Rc is a halogen atom or C$_{1-4}$ alkyl optionally substituted with one or more halogen atoms; and Rd is a halogen atom, C$_{1-4}$ alkyl optionally substituted with one or more halogen atoms, phenyl, pyridinyl, or pyrimidinyl, wherein the phenyl, pyridinyl, and pyrimidinyl groups are each optionally substituted with one or more substituents $R^{14}$.

(1-29) The compound according to any of (1-1) to (1-4), (1-10) to (1-17), (1-20), (1-21), (1-23), and (1-26) to (1-28) or a salt thereof, or a solvate of the compound or the salt, wherein Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri is a halogen atom;

Rj is a halogen atom; and

Rk is hydroxy, C$_{2-6}$ alkynyl optionally substituted with a substituent $R^{11}$, or C$_{1-6}$ alkoxy optionally substituted with a substituent $R^{12}$.

(1-30) The compound according to any of (1-26) to (1-29) or a salt thereof, or a solvate of the compound or the salt, wherein $R^{11}$ and $R^{12}$ are each independently selected from morpholinyl, [N—((C$_{1-3}$ alkoxy)C$_{1-4}$ alkyl)-N—(C$_{1-3}$ alkyl)amino] and [N,N-di(C$_{1-3}$alkyl)amino].

(1-31) The compound according to any of (1-26) to (1-30) or a salt thereof, or a solvate of the compound or the salt, wherein $R^{11}$ and $R^{12}$ are each independently selected from morpholinyl, and [N-((methoxy)ethyl)-N-(methyl)amino].

(1-32) The compound according to any of (1-1) to (1-31) or a salt thereof, or a solvate of the compound or the salt, wherein $R^1$ and $R^5$ together with the carbon atom to which they are attached form a C$_{3-6}$ saturated carbocyclic ring, and $R^4$ is C$_{1-4}$ alkyl.

(1-33) The compound according to any of (1-1) to (1-3), (1-5), (1-6), (1-10) to (1-12) and (1-20) or a salt thereof, or a solvate of the compound or the salt, wherein $R^1$ and $R^5$ together with the carbon atom to which they are attached form a C$_{3-6}$ saturated carbocyclic ring;

$R^4$ is C$_{1-4}$ alkyl;

$R^3$ is C$_{1-4}$ alkyl substituted with Re;

Re is phenyl optionally substituted with one or more substituents Ra;

each Ra is independently selected from a halogen atom and C$_{1-4}$ alkoxy optionally substituted with one or more substituents $R^{12}$;

each $R^{12}$ is independently selected from 5- or 6-membered heterocycloalkyl and —NR$^{39}$R$^{40}$;

$R^{39}$ and $R^{40}$ are each independently selected from a hydrogen atom and optionally C$_{1-4}$ alkoxy-substituted C$_{1-4}$ alkyl;

Ar$^1$ is phenyl or 5- or 6-membered heteroaryl, wherein the phenyl and heteroaryl groups are each optionally substituted with one to three substituents selected from Rb, Rc, and Rd;

Rb, Rc, and Rd are each independently selected from a halogen atom, C$_{1-4}$ alkyl optionally substituted with one or more halogen atoms, and 5- or 6-membered heteroaryl optionally substituted with one or more substituents $R^{14}$; and each $R^{14}$ is independently selected from a halogen atom, cyano, $C_{1-4}$ alkyl optionally substituted with one or more halogen atoms, and $C_{1-4}$ alkylthio.

(1-34) The compound according to any of (1-1) to (1-33) or a salt thereof, or a solvate of the compound or the salt, wherein Rb is a halogen atom;

Rc is a halogen atom or $C_{1-4}$ alkyl optionally substituted with one or more halogen atoms; and Rd is a halogen atom or 5- or 6-membered heteroaryl optionally substituted with one or more substituents $R^{14}$.

(1-35) The compound according to any of (1-1) to (1-34) or a salt thereof, or a solvate of the compound or the salt, wherein $R^3$ is benzyl optionally substituted with one to three substituents Ra on the benzene ring.

(1-36) The compound according to any of (1-1) to (1-35) or a salt thereof, or a solvate of the compound or the salt, wherein Ra is selected from a halogen atom, (morpholino)$C_{1-4}$alkoxy, [N—(($C_{1-3}$ alkoxy)$C_{1-4}$ alkyl)-N—($C_{1-3}$alkyl)amino]$C_{1-4}$ alkoxy, or [N,N-di($C_{1-3}$ alkyl)amino]$C_{1-4}$ alkoxy.

(1-37) The compound according to any of (1-1) to (1-5), (1-10) to (1-16), (1-20), and (1-33) to (1-36) or a salt thereof, or a solvate of the compound or the salt, wherein Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri and Rj are each independently a halogen atom; and

Rk is $C_{1-4}$ alkoxy optionally substituted with one or more substituents $R^{12}$.

(1-38) The compound according to any of (1-13) to (1-18), (1-20), (1-25), (1-29) and (1-37) or a salt thereof, or a solvate of the compound or the salt, wherein Rk is a halogen atom, (morpholino)$C_{1-4}$ alkoxy, [N—(($C_{1-3}$ alkoxy)$C_{1-4}$ alkyl)-N—($C_{1-3}$alkyl)amino]$C_{1-4}$ alkoxy, [N,N-di($C_{1-3}$ alkyl)amino]$C_{1-4}$ alkoxy.

(1-39) The compound according to any of (1-1) to (1-6), (1-10) to (1-16), (1-20) to (1-23), (1-26), (1-33) to (1-35), (1-37) and (1-38) or a salt thereof, or a solvate of the compound or the salt, wherein $Ar^1$ is phenyl or pyridinyl;

Rd is pyridinyl or pyrimidinyl;

$R^{12}$ is selected from morpholinyl, [N-(2-(methoxy)ethyl)-N-(methyl)amiono], [N,N-dimethylamino].

(1-40) The compound according to any of (1-1) to (1-39) or a salt thereof, or a solvate of the compound or the salt, wherein Rb is a halogen atom;

Rc is a halogen atom, methyl or trifluoromethyl;

Rd is a halogen atom, trifluoromethyl, phenyl optionally substituted with one to three substitutrents $R^{14}$ and 5- to 6-membered heteroaryl optionally substituted with one to three substitutrents $R^{14}$, wherein the heteroaryl comprises one to three hetero atoms selected from O, S, and N.

(1-41) The compound according to any of (1-1) to (1-40) or a salt thereof, or a solvate of the compound or the salt, wherein $R^{14}$ is each independently selected from methyl, trifluoromethyl, cyano, nitro, a halogen atom, methoxy, ethoxy, trifluoromethoxy, methylthio, methoxycarbonyl and dimethylaminosulfonyl.

(1-42) The compound according to any of (1-1) to (1-41) or a salt thereof, or a solvate of the compound or the salt, wherein $R^{14}$ is each independently selected from methyl, trifluoromethyl, cyano, a chlorine atom and methylthio.

(1-43) The compound according to any of (1-1) to (1-42) or a salt thereof, or a solvate of the compound or the salt, wherein $Ar^1$ is phenyl or 5- to 6-membered heteroaryl which comprises one to three hetero atoms selected from O, S, and N, wherein the phenyl and the heteroaryl is substituted with one to three substituents selected from Rb, Rc, and Rd.

(1-44) The compound, according to any of (1-1) to (1-11), (1-20) to (1-22), (1-24), (1-26) to (1-28), (1-30) to (1-36), and (1-39) to (1-43) or a salt thereof, or a solvate of the compound or the salt, wherein the compound is represented by the formula (I-c);

(I-c)

wherein, n1 is an interger selected from 1 to 4, n2 is an interger selected from 0 or more, $R^1$, $R^4$, $R^5$, $Ar^1$, Ra, Rb, Rc, Rd, Re are as defined in any of (1-1) to (1-11), (1-20) to (1-22), (1-24), (1-26) to (1-28), (1-30) to (1-36), and (1-39) to (1-43).

(1-45) The compound according to (1-44) or a salt thereof, or a solvate of the compound or the salt, wherein n1 is 1 and n2 is 3.

(1-46) The compound, according to any of (1-13) to (1-20), (1-23) to (1-25), (1-29) to (1-32) and (1-37) to (1-43) or a salt thereof, or a solvate of the compound or the salt, wherein the compound is represented by the formula (I-d);

(I-d)

wherein n1 is an interger selected from 1 to 4, n3, n4 and n5 is a interger independently selected from 0 or 1, provided that at least one of n3, n4 and n5 is 1, $R^1$, $R^4$, $R^5$, $Ar^1$, Ra, Rb, Rc, Rd, Re, Ri, Rj, and Rk are as defined in any of (1-13) to (1-20), (1-23) to (1-25), (1-29) to (1-32), and (1-37) to (1-43).

(1-47) The compound according to (1-46) or a salt thereof, or a solvate of the compound or the salt, wherein n1 is 1.

(1-48) The compound according to any of (1-1) to (1-47) or a salt thereof, or a solvate of the compound or the salt, wherein Ar$^1$ is 4-(trifluoromethyl)-2-(6-methylthiopyridin-3-yl)phenyl, 4-(trifluoromethyl)-2-(6-trifluoromethylpyridin-3-yl)phenyl, 4-(trifluoromethyl)-2-(4-trifluoromethylpyrimidin-5-yl)phenyl, 4-(trifluoromethyl)-2-(6-trifluoromethylpyrimidin-4-yl)phenyl, 4-(trifluoromethyl)-2-(6-cyano-5-methylpyrimidin-4-yl)phenyl, 4-(trifluoromethyl)-2-(2-cyanopyridin-4-yl)phenyl, 4-chloro-2-(6-methylthiopyridin-3-yl)phenyl, 4-chloro-2-(6-trifluoromethylpyridin-3-yl)phenyl, 4-chloro-2-(4-trifluoromethylpyrimidin-5-yl)phenyl, 4-chloro-2-(6-cyano-5-methylpyrimidin-4-yl)phenyl, 4-chloro-2-(6-trifluoromethylpyrimidin-4-yl)phenyl, or 4-chloro-2-(2-cyanopyridin-4-yl)phenyl.

(1-49) A compound selected from:
- (4aR)-1-[(2,3-difluorophenyl)methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide;
- (4aR)—N-[2-(6-cyano-5-methylpyrimidin-4-yl)-4-(trifluoromethyl)phenyl]-1-[[2,3-difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxamide;
- (4aR)—N-[2-(2-cyanopyridin-4-yl)-4-(trifluoromethyl)phenyl]-1-[[2,3-difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxamide;
- 6-[4-[[(4aR)-4-hydroxy-4a-methyl-2-oxo-3-[[4-(trifluoromethyl)-2-[6-(trifluoromethyl)pyrimidin-4-yl]phenyl]carbamoyl]-6,7-dihydro-5H-pyrrolo[1,2-b]pyridazin-1-yl]methyl]-2,3-difluorophenyl]hex-5-ynoic acid;
- (4aR)-1-[[2,3-difluoro-4-(3-morpholin-4-ylprop-1-ynyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;
- (4aR)-1-[[4-[3-[(2R)-2,3-dihydroxypropoxy]propoxy]-2,3-difluorophenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;
- (4aR)-1-[[4-[4-[(2R)-2,3-dihydroxypropoxy]butoxy]-2,3-difluorophenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide;
- (4aR)-1-[[4-[6-[(2R)-2,3-dihydroxypropoxy]hexoxy]-2,3-difluorophenyl]methyl]-4-hydroxy-4a-methyl-2-oxo-N-[2-(trifluoromethyl)-4-[6-(trifluoromethyl)pyridin-3-yl]pyrimidin-5-yl]-6,7-dihydro-5H-pyrrolo[1,2-b]pyridazine-3-carboxamide;
- (4aR)-1-[[2,3-difluoro-4-(2-morpholin-4-ylethoxy)phenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide;
- (4aR)-1-[[2,3-difluoro-4-(morpholin-4-ylmethyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;
- (4aR)—N-(4-bromo-3,5-difluorophenyl)-1-[(3-chloro-2-fluorophenyl)methyl]-4-hydroxy-4a-methyl-2-oxo-6,7-dihydro-5H-pyrrolo[1,2-b]pyridazine-3-carboxamide;
- (3S)-3-tert-butyl-1-[[2,3-difluoro-4-(2-morpholin-4-ylethoxy)phenyl]methyl]-4-hydroxy-2-methyl-6-oxo-N-[4-(trifluoromethyl)-2-[6-(trifluoromethyl)pyrimidin-4-yl]phenyl]-3H-pyridazine-5-carboxamide;
- (3S)-3-tert-butyl-N-[4-chloro-2-[6-(trifluoromethyl)pyrimidin-4-yl]phenyl]-1-[[2,3-difluoro-4-(2-morpholin-4-ylethoxy)phenyl]methyl]-4-hydroxy-2-methyl-6-oxo-3H-pyridazine-5-carboxamide;
- (3S)-3-tert-butyl-N-[4-chloro-2-[6-(trifluoromethyl)pyridin-3-yl]phenyl]-1-[[2,3-difluoro-4-(2-morpholin-4-ylethoxy)phenyl]methyl]-4-hydroxy-2-methyl-6-oxo-3H-pyridazine-5-carboxamide;
- (3S)-3-tert-butyl-N-[4-chloro-2-(6-methylsulfanylpyridin-3-yl)phenyl]-1-[[2,3-difluoro-4-(2-morpholin-4-ylethoxy)phenyl]methyl]-4-hydroxy-2-methyl-6-oxo-3H-pyridazine-5-carboxamide;
- (3S)-3-tert-butyl-N-[2-(6-cyano-5-methylpyrimidin-4-yl)-4-(trifluoromethyl)phenyl]-1-[[2,3-difluoro-4-(2-morpholin-4-ylethoxy)phenyl]methyl]-4-hydroxy-2-methyl-6-oxo-3H-pyridazine-5-carboxamide;
- 6-[[2,3-difluoro-4-(2-morpholin-4-ylethoxy)phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide;
- 7-[[2,3-difluoro-4-(2-morpholin-4-ylethoxy)phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;
- 6-[[2,3-difluoro-4-[2-[2-methoxyethyl(methyl)amino]ethoxy]phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide;
- 7-[[2,3-difluoro-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;
- 4-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]butanoic acid;
- 5-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]pentanoic acid;
- 6-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]hexanoic acid;
- 7-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]heptanoic acid;
- 7-[[2,3-difluoro-4-[2-[(2S)-2-(methoxymethyl)pyrrolidin-1-yl]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;
- (2S)-2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]butanedioic acid;
- 3-[2-[2,3-difluoro-4-[[1-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]pentanedioic acid;
- 6-(2,3-difluoro-4-(2-(methyl(oxetan-3-yl)amino)ethoxy)benzyl)-9-hydroxy-5-methyl-7-oxo-N-(4-(trifluoromethyl)-2-(6-(trifluoromethyl)pyrimidin-4-yl)phenyl)-5,6-diazaspiro[3.5]non-8-ene-8-carboxamide;

7-[[2,3-difluoro-4-[2-[methyl(oxetan-3-yl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

7-(2,3-difluoro-4-(2-(methyl(oxetan-3-yl)amino)ethoxy)benzyl)-1-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide;

7-(4-(3-(dimethylamino)-2,2-dimethylpropoxy)-2,3-difluorobenzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide;

6-[[2,3-difluoro-4-[1-(2-methoxyethyl)azetidin-3-yl]oxyphenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide;

7-[[2,3-difluoro-4-[4-methyl-[(2S,3R,4R,5R)-2,3,4,5,6-pentahydroxyhexyl]amino]-4-oxobutoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

7-[[2,3-difluoro-4-[2-[2-methyl-[(2S,3R,4R,5R)-2,3,4,5,6-pentahydroxyhexyl]amino]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

7-[[2,3-difluoro-4-[2-[2-[2-[2-[2-methoxyethyl(methyl)amino]ethoxy]ethoxy]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]ethanesulfonic acid; and 2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]ethanesulfonic acid or a salt thereof, or a solvate of the compound or the salt.

(1-50) The compound according to any of (1-1) to (1-49) or the salt thereof, or the solvate of the compound or the salt for use in the prevention and/or treatment of a disease selected from hyperphosphatemia, secondary hyperparathyroidism, and chronic renal failure.

(1-51) A NaPi-IIb inhibitor comprising a compound according to any of (1-1) to (1-49) or a salt thereof, or a solvate of the compound or the salt.

(1-52) A PiT-1 inhibitor comprising a compound according to any of (1-1) to (1-49) or a salt thereof, or a solvate of the compound or the salt.

(1-53) A PiT-2 inhibitor comprising a compound according to any of (1-1) to (1-49) or a salt thereof, or a solvate of the compound or the salt.

(1-54) A preventive and/or therapeutic agent for a disease selected from hyperphosphatemia, secondary hyperparathyroidism, and chronic renal failure, the agent comprising a compound according to any of (1-1) to (1-49) or a salt thereof, or a solvate of the compound or the salt as an active ingredient.

(1-55) A method for preventing and/or treating a disease selected from hyperphosphatemia, secondary hyperparathyroidism, and chronic renal failure, comprising administering a therapeutically effective amount of a compound according to any of (1-1) to (1-49) or a salt thereof, or a solvate of the compound or the salt to a patient.

Another embodiment of the present invention provides the following compounds (2-1) to (2-26):

(2-1) A compound represented by the formula (I) or a salt thereof, or a solvate of the compound or the salt:

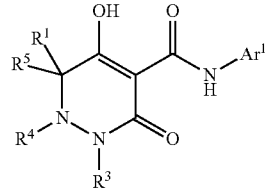

wherein $R^1$, $R^4$, and $R^5$ are as defined in any one of the following (1) to (3):

(1) $R^1$ is a hydrogen atom or $C_{1-10}$ alkyl;
$R^4$ is a hydrogen atom, $C_{1-4}$ alkyl optionally substituted with one or more substituents Rf, $C_{6-10}$ aryl optionally substituted with one or more substituents Rg, ($C_{1-6}$ alkyl)carbonyl, ($C_{6-10}$ aryl)carbonyl, a group $—C(O)NR^{37}R^{38}$, $C_{3-7}$ cycloalkyl, or 5- to 8-membered heterocycloalkyl; and
$R^5$ is a hydrogen atom or $C_{1-4}$ alkyl;

(2) $R^1$ and $R^5$ together with the carbon atom to which they are attached form a $C_{3-6}$ saturated carbocyclic ring; and
$R^4$ is as defined above; and (3) $R^1$ is a hydrogen atom or linear $C_{1-10}$ alkyl;
$R^4$ and $R^5$ together with the carbon atom and the nitrogen atom to which they are attached form a 5- to 8-membered saturated heterocyclic ring, wherein the saturated heterocyclic ring is optionally substituted with one or more substituents $R^2$;

$R^3$ is $C_{1-10}$ alkyl optionally substituted with one or more substituents Rh or $C_{1-4}$ alkyl substituted with Re;
$R^{37}$ and $R^{38}$ are each independently selected from a hydrogen atom and $C_{1-3}$ alkyl;
each $R^2$ is independently selected from $C_{1-5}$ alkyl and a halogen atom; and/or
two or more substituents $R^2$ on the 5- to 8-membered saturated heterocyclic ring may together form $C_{1-5}$ alkylene that links the ring atoms to which they are attached;
each Rh is independently selected from a halogen atom, ($C_{1-4}$ alkoxy)carbonyl, and a group $—(O(CH_2)_a)_b—C_{1-4}$ alkoxy (wherein a is an integer selected from 2 to 4, and b is an integer selected from 1 to 4);
Re is $C_{6-10}$ aryl optionally substituted with one or more substituents Ra or 5- to 10-membered heteroaryl optionally substituted with one or more substituents Ra;
each Rf is independently selected from a halogen atom, hydroxy, cyano, carboxy, ($C_{1-6}$ alkoxy)carbonyl, $C_{1-6}$ alkoxy, and $C_{6-10}$ aryl optionally substituted with one or more substituents Rg;
each Rg is independently selected from a halogen atom, $C_{1-6}$ alkyl, $C_{2-6}$ alkynyl, and $C_{1-6}$ alkoxy, wherein the alkyl, alkynyl, and alkoxy groups are each optionally substituted with one or more substituents selected from hydroxy and cyano;
each Ra is independently selected from a halogen atom, hydroxy, nitro, cyano, ($C_{1-4}$ alkoxy)carbonyl, 3- to 10-membered heterocycloalkyloxy, $C_{1-10}$ alkyl optionally substituted with one or more substituents $R^{10}$, $C_{2-10}$ alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, and $C_{1-4}$ alkylthio optionally substituted with one or more substituents $R^{13}$;

$R^{10}$, $R^{11}$, $R^{12}$, $R^{13}$, and $R^{15}$ are each independently selected from a halogen atom, hydroxy, carboxy, $C_{1-6}$ alkoxy optionally substituted with one or more hydroxy groups, ($C_{1-4}$ alkoxy)carbonyl, a group —$(O(CH_2)_o)_p$—OH (wherein o and p are each independently an integer selected from 2 to 4), $C_{3-6}$ cycloalkyl optionally substituted with one or more hydroxy groups, 3- to 10-membered heterocycloalkyl, 5- to 10-membered heteroaryl, and a group —$NR^{39}R^{40}$, wherein the 3- to 10-membered heterocycloalkyl group is optionally substituted with one or more substituents selected from oxo, a halogen atom, and $C_{1-4}$ alkyl (wherein the alkyl group is optionally substituted with one or more hydroxy groups);

$Ar^1$ is $C_{6-10}$ aryl or 5- to 10-membered heteroaryl, wherein the aryl and heteroaryl groups are each optionally substituted with one to three substituents selected from Rb, Rc, and Rd;

Rb, Rc, and Rd are each independently selected from optionally $C_{1-4}$ alkoxy-substituted $C_{1-5}$ alkoxy, a halogen atom, $C_{1-10}$ alkyl optionally substituted with one or more halogen atoms, a group —$SF_5$, cyano, hydroxy, 5- to 10-membered heterocycloalkyl optionally substituted with one or more substituents $R^{14}$, $C_{6-10}$ aryl optionally substituted with one or more substituents $R^{14}$, and 5- to 10-membered heteroaryl optionally substituted with one or more substituents $R^{14}$;

each $R^{14}$ is independently selected from a halogen atom, oxo, cyano, nitro, $C_{1-4}$ alkyl optionally substituted with one or more halogen atoms, $C_{1-4}$ alkoxy optionally substituted with one or more halogen atoms, ($C_{1-6}$ alkoxy)carbonyl, a group —$NR^{27}R^{28}$, a group —$SO_2NR^{35}R^{36}$, $C_{1-4}$ alkylthio, and 5- to 10-membered heterocycloalkyl;

$R^{27}$ and $R^{28}$ are each independently selected from a hydrogen atom and optionally ($C_{1-4}$ alkoxy)carbonyl-substituted $C_{1-4}$ alkyl;

$R^{35}$ and $R^{36}$ are each independently selected from a hydrogen atom and $C_{1-4}$ alkyl; and $R^{39}$ and $R^{40}$ are each independently selected from a hydrogen atom and optionally $C_{1-6}$ alkoxy-substituted $C_{1-6}$ alkyl.

(2-2) The compound according to (2-1) or a salt thereof, or a solvate of the compound or the salt, wherein Rb is optionally $C_{1-4}$ alkoxy-substituted $C_{1-5}$ alkoxy or a halogen atom;

Rc is a halogen atom, $C_{1-10}$ alkyl optionally substituted with one or more halogen atoms, or a group —$SF_5$; and Rd is cyano, hydroxy, a halogen atom, $C_{1-4}$ alkyl optionally substituted with one or more halogen atoms, 5- to 10-membered heterocycloalkyl optionally substituted with one or more substituents $R^{14}$, $C_{6-10}$ aryl optionally substituted with one or more substituents $R^{14}$, or 5- to 10-membered heteroaryl optionally substituted with one or more substituents $R^{14}$.

(2-3) The compound according to (2-1) or (2-2) or a salt thereof, or a solvate of the compound or the salt, wherein each Ra is independently selected from a halogen atom, nitro, cyano, ($C_{1-4}$ alkoxy)carbonyl, 3- to 6-membered heterocycloalkyloxy, $C_{1-10}$ alkyl optionally substituted with one or more substituents $R^{10}$, $C_{2-10}$ alkynyl optionally substituted with one or more substituents $R^{11}$, $C_{1-8}$ alkoxy optionally substituted with one or more substituents $R^{12}$, and $C_{1-4}$ alkylthio optionally substituted with one or more substituents $R^{13}$;

each $R^{10}$ is independently selected from carboxy, 3- to 6-membered heterocycloalkyl, $C_{1-6}$ alkoxy optionally substituted with one or more hydroxy groups, and a group —$(O(CH_2)_o)_p$—OH;

each $R^{11}$ is independently selected from hydroxy, carboxy, 5- or 6-membered heterocycloalkyl optionally substituted with one or more oxo groups, $C_{1-6}$ alkoxy optionally substituted with one or more hydroxy groups, a group —$(O(CH_2)_o)_p$—OH, and $C_{3-6}$ cycloalkyl optionally substituted with one or more hydroxy groups;

each $R^{12}$ is independently selected from a halogen atom, hydroxy, $C_{1-6}$ alkoxy optionally substituted with one or more hydroxy groups, ($C_{1-3}$ alkoxy)carbonyl, 3- to 6-membered heterocycloalkyl, 5- or 6-membered heteroaryl, and a group —$NR^{39}R^{40}$;

$R^{13}$ is 5- or 6-membered heterocycloalkyl; and o and p are each independently an integer selected from 2 to 4.

(2-4) The compound according to any of (2-1) to (2-3) or a salt thereof, or a solvate of the compound or the salt, wherein each Ra is independently selected from a halogen atom, hydroxy, nitro, cyano, $C_{1-6}$ alkyl, (carboxy)$C_{1-8}$ alkyl, (morpholino)$C_{1-4}$ alkyl, (oxetanyl)$C_{1-4}$ alkyl, [HO—$((CH_2)_oO)_p$]$C_{1-6}$ alkyl, ($C_{1-6}$ alkoxy)$C_{1-8}$ alkyl optionally substituted with one or more hydroxy groups, $C_{1-3}$ alkoxy substituted with one or more halogen atoms, [N—(($C_{1-3}$ alkoxy)$C_{1-4}$ alkyl)-N—($C_{1-3}$ alkyl)amino]$C_{1-4}$ alkoxy, $C_{1-6}$ alkoxy optionally substituted with one or more hydroxy groups, (($C_{1-3}$ alkoxy)carbonyl)$C_{1-3}$ alkoxy, (morpholino)$C_{1-6}$ alkoxy optionally substituted with one or more oxo groups, (3- to 6-membered oxacycloalkyl)$C_{1-4}$ alkoxy, (pyridinyl)$C_{1-4}$ alkoxy, (pyrimidinyl)$C_{1-4}$ alkoxy, ($C_{1-6}$ alkoxy)$C_{1-8}$ alkoxy optionally substituted with one or more hydroxy groups, (carboxy)$C_{2-6}$ alkynyl, (morpholino)$C_{2-6}$ alkynyl optionally substituted with one or more oxo groups, (3- to 6-membered oxacycloalkyl)$C_{2-6}$ alkynyl, (pyrrolidino)$C_{2-6}$ alkynyl optionally substituted with one or more oxo groups, $C_{2-8}$ alkynyl optionally substituted with one or more hydroxy groups, [HO—$((CH_2)_oO)_p$]$C_{2-8}$ alkynyl, ($C_{1-6}$ alkoxy)$C_{2-8}$ alkynyl optionally substituted with one or more hydroxy groups, ($C_{3-6}$ cycloalkyl)$C_{2-6}$ alkynyl optionally substituted with one or more hydroxy groups, ($C_{1-3}$ alkoxy)carbonyl, (morpholino)$C_{1-4}$ alkylthio optionally substituted with one or more oxo groups, and 3- to 6-membered oxacycloalkyloxy.

(2-5) The compound according to any of (2-1) to (2-4) or a salt thereof, or a solvate of the compound or the salt, wherein each Ra is independently selected from a halogen atom, hydroxy, cyano, $C_{1-3}$ alkyl, (carboxy)$C_{1-8}$ alkyl, ($C_{1-6}$ alkoxy)$C_{1-8}$ alkyl substituted with one or more hydroxy groups, $C_{1-3}$ alkoxy optionally substituted with one or more halogen atoms, [N—(($C_{1-3}$ alkoxy)$C_{1-4}$ alkyl)-N—($C_{1-3}$ alkyl)amino]$C_{1-4}$ alkoxy, (morpholino)$C_{1-6}$ alkoxy, ($C_{1-6}$ alkoxy)$C_{1-8}$ alkoxy substituted with one or more hydroxy groups, (carboxy)$C_{2-6}$ alkynyl, (morpholino)$C_{2-6}$ alkynyl, $C_{2-8}$ alkynyl optionally substituted with one or more hydroxy groups, [HO—$((CH_2)_oO)_p$]$C_{2-8}$ alkynyl, ($C_{1-6}$ alkoxy)$C_{2-8}$ alkynyl substituted with one or more hydroxy groups, and ($C_{1-3}$ alkoxy)carbonyl.

(2-6) The compound according to any of (2-1) to (2-5) or a salt thereof, or a solvate of the compound or the salt, wherein $R^3$ is methyl substituted with Re.

(2-7) The compound according to any of (2-1) to (2-6) or a salt thereof, or a solvate of the compound or the salt, wherein $R^3$ is benzyl optionally substituted with one or more substituents Ra on the benzene ring.

(2-8) The compound according to any of (2-1) to (2-7) or a salt thereof, or a solvate of the compound or the salt, wherein $R^3$ is benzyl optionally substituted with one to three substituents Ra on the benzene ring.

(2-9) The compound according to any of (2-1), (2-4) and (2-6) to (2-8) or a salt thereof, or a solvate of the compound or the salt, wherein Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri is a halogen atom or $C_{1-3}$ alkoxy;

Rj is a halogen atom, nitro, or cyano; and

Rk is hydroxy, a halogen atom, ($C_{1-4}$ alkoxy)carbonyl, 5- to 10-membered heterocycloalkyloxy, $C_{1-10}$ alkyl optionally substituted with one or more substituents $R^{10}$, $C_2$-10 alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, or $C_{1-4}$ alkylthio optionally substituted with one or more substituents $R^{13}$.

(2-10) The compound according to (2-9) or a salt thereof, or a solvate of the compound or the salt, wherein Rk is hydroxy, a halogen atom, $C_{1-6}$ alkyl, (carboxy)$C_{1-8}$ alkyl, ($C_{1-6}$ alkoxy)$C_{1-8}$ alkyl substituted with one or more hydroxy groups, $C_{1-3}$ alkoxy optionally substituted with one or more halogen atoms, [N—(($C_{1-3}$ alkoxy)$C_{1-4}$ alkyl)-N—($C_{1-3}$ alkyl)amino]$C_{1-4}$ alkoxy, (morpholino)$C_{1-6}$ alkoxy, ($C_{1-6}$ alkoxy)$C_{1-8}$ alkoxy substituted with one or more hydroxy groups, (carboxy)$C_{2-8}$ alkynyl, (morpholino)$C_{2-6}$ alkynyl, $C_{2-8}$ alkynyl optionally substituted with one or more hydroxy groups, [HO—(($CH_2)_oO)_p$]$C_{2-8}$ alkynyl, ($C_{1-6}$ alkoxy)$C_{2-8}$ alkynyl substituted with one or more hydroxy groups, or ($C_{1-3}$ alkoxy)carbonyl.

(2-11) The compound according to (2-1) or a salt thereof, or a solvate of the compound or the salt, wherein $R^1$, $R^4$, and $R^5$ are as defined in the following (1) or (2):

(1) $R^1$ is a hydrogen atom or $C_{1-6}$ alkyl;

$R^4$ is a hydrogen atom, $C_{1-4}$ alkyl optionally substituted with one or more substituents Rf, $C_{6-10}$ aryl optionally substituted with one or more substituents Rg, ($C_{1-6}$ alkyl)carbonyl, ($C_{6-10}$ aryl)carbonyl, —C(O)$NR^{37}R^{38}$, $C_{3-7}$ cycloalkyl, or 5- to 8-membered heterocycloalkyl; and $R^5$ is a hydrogen atom or $C_{1-4}$ alkyl; or (2) $R^1$ and $R^5$ together with the carbon atom to which they are attached form a $C_{3-6}$ saturated carbocyclic ring; and $R^4$ is as defined above;

$R^3$ is $C_{1-4}$ alkyl substituted with Re;

Re is $C_{6-10}$ aryl optionally substituted with one or more substituents Ra;

each Ra is independently selected from a halogen atom, cyano, hydroxy, $C_{1-6}$ alkyl optionally substituted with one or more substituents $R^{10}$, $C_{2-6}$ alkynyl optionally substituted with one or more substituents $R^1$, and $C_{1-6}$ alkoxy optionally substituted with one or more substituents $R^{12}$;

$R^{10}$, $R^{11}$, and $R^{12}$ are each independently selected from 4- to 10-membered heterocycloalkyl optionally substituted with one or more substituents and a group —$NR^{39}R^{40}$, wherein the substituents are each independently selected from oxo, a halogen atom, and $C_{1-4}$ alkyl (wherein the alkyl group is optionally substituted with one or more hydroxy groups);

$Ar^1$ is $C_{6-10}$ aryl or 5- to 10-membered heteroaryl, wherein the aryl and heteroaryl groups are each optionally substituted with one to three substituents selected from Rb, Rc, and Rd;

Rb, Rc, and Rd are each independently selected from a halogen atom, $C_{1-4}$ alkyl optionally substituted with one or more halogen atoms, optionally $C_{1-4}$ alkyl-substituted 5- to 10-membered heterocycloalkyl, $C_{6-10}$ aryl optionally substituted with one or more substituents $R^{14}$, and 5- to 10-membered heteroaryl optionally substituted with one or more substituents $R^{14}$; and each $R^{14}$ is independently selected from a halogen atom, cyano, $C_{1-4}$ alkyl optionally substituted with one or more halogen atoms, $C_{1-4}$ alkoxy, a group —$SO_2NR^{35}R^{36}$, and $C_{1-4}$ alkylthio.

(2-12) The compound according to (2-11) or a salt thereof, or a solvate of the compound or the salt, wherein $R^{10}$, $R^{11}$, and $R^{12}$ are each independently selected from 5- or 6-membered heterocycloalkyl optionally substituted with one or more substituents.

(2-13) The compound according to any of (2-1) and (2-11) or a salt thereof, or a solvate of the compound or the salt, wherein $R^1$, $R^4$, and $R^5$ are as defined in the following (1) or (2):

(1) $R^1$ is $C_{1-6}$ alkyl;

$R^4$ is optionally halogen atom-substituted $C_{1-4}$ alkyl or phenyl; and $R^5$ is a hydrogen atom or $C_{1-4}$ alkyl; or (2) $R^1$ and $R^5$ together with the carbon atom to which they are attached form a $C_{3-6}$ saturated carbocyclic ring; and $R^4$ is as defined above;

$R^3$ is $C_{1-4}$ alkyl substituted with Re;

Re is phenyl optionally substituted with one or more substituents Ra;

each Ra is independently selected from a halogen atom, optionally $R^{11}$-substituted $C_{2-6}$ alkynyl, and optionally $R^{12}$-substituted $C_{1-6}$ alkoxy;

$R^{11}$ and $R^{12}$ are each independently selected from 5- or 6-membered heterocycloalkyl and —$NR^{39}R^{40}$;

$Ar^1$ is phenyl or 5- or 6-membered heteroaryl, wherein the phenyl and heteroaryl groups are each optionally substituted with one to three substituents selected from Rb, Rc, and Rd;

Rb, Rc, and Rd are each independently selected from a halogen atom, $C_{1-4}$ alkyl optionally substituted with one or more halogen atoms, phenyl optionally substituted with one or more substituents $R^{14}$, and 5- or 6-membered heteroaryl optionally substituted with one or more substituents $R^{14}$; and each $R^{14}$ is independently selected from a halogen atom, cyano, $C_{1-4}$ alkyl optionally substituted with one or more halogen atoms, $C_{1-4}$ alkoxy, a group —$SO_2NR^{35}R^{36}$ (wherein $R^{35}$ and $R^{36}$ are each independently selected from $C_{1-4}$ alkyl), and $C_{1-4}$ alkylthio.

(2-14) The compound according to any of (2-11) to (2-13) or a salt thereof, or a solvate of the compound or the salt, wherein Rb is a halogen atom;

Rc is a halogen atom or $C_{1-4}$ alkyl optionally substituted with one or more halogen atoms; and Rd is a halogen atom, $C_{1-4}$ alkyl optionally substituted with one or more halogen atoms, phenyl optionally substituted with one or more substituents $R^{14}$, or 5- or 6-membered heteroaryl optionally substituted with one or more substituents $R^{14}$.

(2-15) The compound according to (2-13) or a salt thereof, or a solvate of the compound or the salt, wherein Re is phenyl optionally substituted with one or more substituents Ra;

$R^{11}$ and $R^{12}$ are each independently selected from morpholinyl and a group —$NR^{39}R^{40}$;

$R^4$ is optionally halogen atom-substituted $C_{1-4}$ alkyl or phenyl;

Ar¹ is phenyl, pyridinyl, or pyrimidinyl, wherein the phenyl, pyridinyl, and pyrimidinyl groups are each optionally substituted with one to three substituents selected from Rb, Rc, and Rd;

Rb is a halogen atom;

Rc is a halogen atom or $C_{1-4}$ alkyl optionally substituted with one or more halogen atoms; and Rd is a halogen atom, $C_{1-4}$ alkyl optionally substituted with one or more halogen atoms, phenyl, pyridinyl, or pyrimidinyl, wherein the phenyl, pyridinyl, and pyrimidinyl groups are each optionally substituted with one or more substituents $R^{14}$.

(2-16) The compound according to (2-15) or a salt thereof, or a solvate of the compound or the salt, wherein $R^{11}$ and $R^{12}$ are each independently selected from morpholinyl and [N-((methoxy)ethyl)-N-(methyl)amino].

(2-17) The compound according to (2-11) or (2-12) or a salt thereof, or a solvate of the compound or the salt, wherein $R^{10}$, $R^{11}$, and $R^{12}$ are each independently selected from morpholinyl, thiomorpholinyl, azetidinyl, pyrrolidinyl, 2-oxa-6-azaspiro[3.3]heptanyl, 3,7-dioxa-9-azabicyclo[3.3.1]nonanyl, piperazinyl, piperidyl, and [N-((methoxy)ethyl)-N-(methyl)amino].

(2-18) The compound according to any of (2-1) to (2-17) or a salt thereof, or a solvate of the compound or the salt, wherein $R^1$, $R^4$, and $R^5$ are as defined in any one of the following (1) to (3):

(1) $R^1$ is a hydrogen atom, and $R^4$ and $R^5$ are each independently selected from $C_{1-6}$ alkyl;

(2) $R^1$ and $R^5$ together with the carbon atom to which they are attached form a $C_{3-5}$ saturated carbocyclic ring, and $R^4$ is $C_{1-6}$ alkyl; and (3) $R^1$ is linear $C_{1-6}$ alkyl, and $R^4$ and $R^5$ together with the carbon atom to which they are attached form a pyrrolidine ring;

$R^3$ is benzyl substituted with one or more substituents Ra on the benzene ring;

each Ra is independently selected from a halogen atom, (morpholino)$C_{2-6}$ alkoxy, (morpholino)$C_{1-6}$ alkyl, (carboxy)$C_{2-6}$ alkynyl, ($C_{1-6}$ alkoxy)$C_{1-6}$ alkoxy optionally substituted with one or more hydroxy groups, and [N-((methoxy)ethyl)-N-(methyl)amino]ethoxy;

Ar¹ is phenyl or pyrimidyl, wherein these groups are each substituted with one to three groups each independently selected from a halogen atom, trifluoromethyl, pyridinyl substituted with one or more substituents $R^{14}$, and pyrimidyl substituted with one or more substituents $R^{14}$; and each $R^{14}$ is independently selected from methyl, cyano, trifluoromethyl, and methylthio.

(2-19) The compound according to any of (2-1) to (2-18) or a salt thereof, or a solvate of the compound or the salt, wherein Ar¹ is 4-(trifluoromethyl)-2-(6-methylthiopyridin-3-yl)phenyl, 4-(trifluoromethyl)-2-(6-trifluoromethylpyridin-3-yl)phenyl, 4-(trifluoromethyl)-2-(4-trifluoromethylpyrimidin-5-yl)phenyl, 4-(trifluoromethyl)-2-(6-trifluoromethylpyrimidin-4-yl)phenyl, 4-(trifluoromethyl)-2-(6-cyano-5-methylpyrimidin-4-yl)phenyl, 4-(trifluoromethyl)-2-(2-cyanopyridin-4-yl)phenyl, 4-chloro-2-(6-methylthiopyridin-3-yl)phenyl, 4-chloro-2-(6-trifluoromethylpyridin-3-yl)phenyl, 4-chloro-2-(4-trifluoromethylpyrimidin-5-yl)phenyl, 4-chloro-2-(6-cyano-5-methylpyrimidin-4-yl)phenyl, 4-chloro-2-(6-trifluoromethylpyrimidin-4-yl)phenyl, or 4-chloro-2-(2-cyanopyridin-4-yl)phenyl.

(2-20) The compound according to any of (2-1) to (2-19) or a salt thereof, or a solvate of the compound or the salt, wherein $R^1$ and $R^5$ together with the carbon atom to which they are attached form a $C_{3-6}$ saturated carbocyclic ring;

$R^4$ is $C_{1-4}$ alkyl;

$R^3$ is $C_{1-4}$ alkyl substituted with Re;

Re is phenyl optionally substituted with one or more substituents Ra;

each Ra is independently selected from a halogen atom and $C_{1-4}$ alkoxy optionally substituted with one or more substituents $R^{12}$;

each $R^{12}$ is independently selected from 5- or 6-membered heterocycloalkyl and a group —$NR^{39}R^{40}$;

$R^{39}$ and $R^{40}$ are each independently selected from a hydrogen atom and optionally $C_{1-4}$ alkoxy-substituted $C_{1-4}$ alkyl;

Ar¹ is phenyl or 5- or 6-membered heteroaryl, wherein the phenyl and heteroaryl groups are each optionally substituted with one to three substituents selected from Rb, Rc, and Rd;

Rb, Rc, and Rd are each independently selected from a halogen atom, $C_{1-4}$ alkyl optionally substituted with one or more halogen atoms, and 5- or 6-membered heteroaryl optionally substituted with one or more substituents $R^{14}$; and each $R^{14}$ is independently selected from a halogen atom, cyano, $C_{1-4}$ alkyl optionally substituted with one or more halogen atoms, and $C_{1-4}$ alkylthio.

(2-21) The compound according to (2-20) or a salt thereof, or a solvate of the compound or the salt, wherein Rb is a halogen atom;

Rc is a halogen atom or $C_{1-4}$ alkyl optionally substituted with one or more halogen atoms; and Rd is selected from a halogen atom and 5- or 6-membered heteroaryl optionally substituted with one or more substituents $R^{14}$.

(2-22) The compound according to any of (2-1), (2-20) and (2-21) or a salt thereof, or a solvate of the compound or the salt, wherein Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri and Rj are each independently a halogen atom; and

Rk is $C_{1-4}$ alkoxy optionally substituted with one or more substituents $R^{12}$.

(2-23) The compound according to any of (2-20) to (2-22) or a salt thereof, or a solvate of the compound or the salt, wherein $R^3$ is benzyl, wherein the benzyl group is optionally substituted with one to three substituents Ra.

(2-24) The compound according to any of (2-20) to (2-23) or a salt thereof, or a solvate of the compound or the salt, wherein Ar¹ is phenyl or pyridinyl;

Rd is pyridinyl or pyrimidinyl; and $R^{12}$ is morpholinyl or [N-((methoxy)ethyl)-N-(methyl)amino].

(2-25) The compound according to any of (2-1) to (2-24) or a salt thereof, or a solvate of the compound or the salt, wherein the compound is represented by the formula I-a:

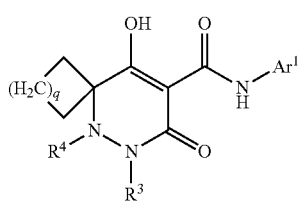

(I-a)

wherein q is an integer selected from 0 to 3, and $R^3$, $R^4$, and $Ar^1$ are as defined above in any of (2-1) to (2-24).

(2-26) A compound selected from:
(4aR)-1-[(2,3-difluorophenyl)methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrlo[1,2-b]pyridazine-3-carboxamide;
(4aR)—N-[2-(6-cyano-5-methylpyrimidin-4-yl)-4-(trifluoromethyl)phenyl]-1-[[2,3-difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxamide;
(4aR)—N-[2-(2-cyanopyridin-4-yl)-4-(trifluoromethyl)phenyl]-1-[[2,3-difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxamide;
6-[4-[[(4aR)-4-hydroxy-4a-methyl-2-oxo-3-[[4-(trifluoromethyl)-2-[6-(trifluoromethyl)pyrimidin-4-yl]phenyl]carbamoyl]-6,7-dihydro-5H-pyrrolo[1,2-b]pyridazin-1-yl]methyl]-2,3-difluorophenyl]hex-5-ynoic acid;
(4aR)-1-[[2,3-difluoro-4-(3-morpholin-4-ylprop-1-ynyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;
(4aR)-1-[[4-[3-[(2R)-2,3-dihydroxypropoxy]propoxy]-2,3-difluorophenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;
(4aR)-1-[[4-[4-[(2R)-2,3-dihydroxypropoxy]butoxy]-2,3-difluorophenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide;
(4aR)-1-[[4-[6-[(2R)-2,3-dihydroxypropoxy]hexoxy]-2,3-difluorophenyl]methyl]-4-hydroxy-4a-methyl-2-oxo-N-[2-(trifluoromethyl)-4-[6-(trifluoromethyl)pyridin-3-yl]pyrimidin-5-yl]-6,7-dihydro-5H-pyrrolo[1,2-b]pyridazine-3-carboxamide;
(4aR)-1-[[2,3-difluoro-4-(2-morpholin-4-ylethoxy)phenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide;
(4aR)-1-[[2,3-difluoro-4-(morpholin-4-ylmethyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;
(4aR)—N-(4-bromo-3,5-difluorophenyl)-1-[(3-chloro-2-fluorophenyl)methyl]-4-hydroxy-4a-methyl-2-oxo-6,7-dihydro-5H-pyrrolo[1,2-b]pyridazine-3-carboxamide;
(3S)-3-tert-butyl-1-[[2,3-difluoro-4-(2-morpholin-4-ylethoxy)phenyl]methyl]-4-hydroxy-2-methyl-6-oxo-N-[4-(trifluoromethyl)-2-[6-(trifluoromethyl)pyrimidin-4-yl]phenyl]-3H-pyridazine-5-carboxamide;
(3S)-3-tert-butyl-N-[4-chloro-2-[6-(trifluoromethyl)pyrimidin-4-yl]phenyl]-1-[[2,3-difluoro-4-(2-morpholin-4-ylethoxy)phenyl]methyl]-4-hydroxy-2-methyl-6-oxo-3H-pyridazine-5-carboxamide;
(3S)-3-tert-butyl-N-[4-chloro-2-[6-(trifluoromethyl)pyridin-3-yl]phenyl]-1-[[2,3-difluoro-4-(2-morpholin-4-ylethoxy)phenyl]methyl]-4-hydroxy-2-methyl-6-oxo-3H-pyridazine-5-carboxamide;
(3S)-3-tert-butyl-N-[4-chloro-2-(6-methylsulfanylpyridin-3-yl)phenyl]-1-[[2,3-difluoro-4-(2-morpholin-4-ylethoxy)phenyl]methyl]-4-hydroxy-2-methyl-6-oxo-3H-pyridazine-5-carboxamide;
(3S)-3-tert-butyl-N-[2-(6-cyano-5-methylpyrimidin-4-yl)-4-(trifluoromethyl)phenyl]-1-[[2,3-difluoro-4-(2-morpholin-4-ylethoxy)phenyl]methyl]-4-hydroxy-2-methyl-6-oxo-3H-pyridazine-5-carboxamide;
6-[[2,3-difluoro-4-(2-morpholin-4-ylethoxy)phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide;
7-[[2,3-difluoro-4-(2-morpholin-4-ylethoxy)phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;
6-[[2,3-difluoro-4-[2-[2-methoxyethyl(methyl)amino]ethoxy]phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide; and
7-[[2,3-difluoro-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide
or a salt thereof, or a solvate of the compound or the salt.

Another embodiment of the present invention provides the following compounds (3-1) to (3-13):

(3-1) A compound represented by the formula (I) or a salt thereof or a solvate of the compound or the salt:

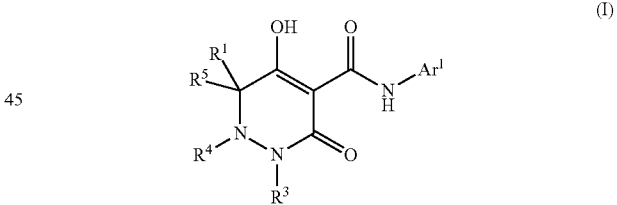

(I)

wherein
$R^1$ is a hydrogen atom or $C_{1-10}$ alkyl;
$R^4$ is a hydrogen atom, $C_{1-4}$ alkyl optionally substituted with one or more substituents Rf, $C_{6-10}$ aryl optionally substituted with one or more substituents Rg, ($C_{1-6}$ alkyl)carbonyl, ($C_{6-10}$ aryl)carbonyl, —C(O)NR$^{37}$R$^{38}$, $C_{3-7}$ cycloalkyl, or 5- to 8-membered heterocycloalkyl;
$R^5$ is a hydrogen atom or $C_{1-4}$ alkyl; or
$R^1$ and $R^5$ together with the carbon atom to which they are attached may form a $C_{3-6}$ saturated carbocyclic ring; or
$R^4$ and $R^5$ together with the carbon atom and the nitrogen atom to which they are attached may form a 5- to 8-membered saturated heterocyclic ring, wherein the 5- to 8-membered saturated heterocyclic ring is optionally substituted with one or more substituents $R^2$;
$R^3$ is $C_{1-10}$ alkyl optionally substituted with one or more substituents Rh, or $C_{1-4}$ alkyl substituted with Re;

$R^{37}$ and $R^{38}$ are each independently selected from a hydrogen atom and $C_{1-3}$ alkyl;

each $R^2$ is independently selected from $C_{1-5}$ alkyl and a halogen atom; and/or two or more substituents $R^2$ on the 5- to 8-membered saturated heterocyclic ring may together form $C_{1-5}$ alkylene that links the ring atoms to which they are attached;

each Rh is independently selected from a halogen atom, ($C_{1-4}$ alkoxy)carbonyl, and —(O(CH$_2$)$_a$)$_b$—$C_{1-4}$ alkoxy (wherein a is an integer selected from 2 to 4, and b is an integer selected from 1 to 4);

Re is $C_{6-10}$ aryl optionally substituted with one or more substituents Ra or 5- to 10-membered heteroaryl optionally substituted with one or more substituents Ra;

each Rf is independently selected from a halogen atom, hydroxy, cyano, carboxy, ($C_{1-6}$ alkoxy)carbonyl, $C_{1-6}$ alkoxy, and $C_{6-10}$ aryl optionally substituted with one or more substituents Rg;

each Rg is independently selected from a halogen atom, $C_{1-6}$ alkyl, $C_{2-6}$ alkynyl, and $C_{1-6}$ alkoxy, wherein the alkyl, alkynyl, and alkoxy groups are each optionally substituted with one or more substituents selected from hydroxy and cyano;

each Ra is independently selected from a halogen atom, hydroxy, nitro, cyano, ($C_{1-4}$ alkoxy)carbonyl, 5- to 10-membered heterocycloalkyloxy, $C_{1-10}$ alkyl optionally substituted with one or more substituents $R^{10}$, $C_{2-10}$ alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, and $C_{1-4}$ alkylthio optionally substituted with one or more substituents $R^{13}$;

the substituents $R^{10}$, $R^{11}$, $R^{12}$, $R^{13}$, and $R^{15}$ are each independently selected from a halogen atom, hydroxy, carboxy, $C_{1-6}$ alkoxy optionally substituted with one or more hydroxy groups, ($C_{1-4}$ alkoxy)carbonyl, a group —(O (CH$_2$)$_o$)$_p$—OH (wherein o and p are each independently an integer selected from 2 to 4), $C_{3-6}$ cycloalkyl optionally substituted with one or more hydroxy groups, 4- to 10-membered heterocycloalkyl, and 5- to 10-membered heteroaryl, wherein the 4- to 10-membered heterocycloalkyl is optionally substituted with one or more substituents selected from oxo, a halogen atom, and $C_{1-4}$ alkyl (wherein the alkyl group is optionally substituted with one or more hydroxy groups);

Ar$^1$ is $C_{6-10}$ aryl or 5- to 10-membered heteroaryl, wherein the aryl and heteroaryl groups are each optionally substituted with one to three substituents selected from Rb, Rc, and Rd;

Rb, Rc, and Rd are each independently selected from optionally $C_{1-4}$ alkoxy-substituted $C_{1-5}$ alkoxy, a halogen atom, $C_{1-10}$ alkyl optionally substituted with one or more halogen atoms, a group —SF$_5$, cyano, hydroxy, 5- to 10-membered heterocycloalkyl optionally substituted with one or more substituents $R^{14}$, $C_{6-10}$ aryl optionally substituted with one or more substituents $R^{14}$, and 5- to 10-membered heteroaryl optionally substituted with one or more substituents $R^{14}$;

each $R^{14}$ is independently selected from a halogen atom, oxo, cyano, nitro, $C_{1-4}$ alkyl optionally substituted with one or more halogen atoms, $C_{1-4}$ alkoxy optionally substituted with one or more halogen atoms, ($C_{1-6}$ alkoxy)carbonyl, —NR$^{27}$R$^{28}$, —SO$_2$NR$^{35}$R$^{36}$, $C_{1-4}$ alkylthio, and 5- to 10-membered heterocycloalkyl;

$R^{27}$ and $R^{28}$ are each independently selected from a hydrogen atom and optionally ($C_{1-4}$ alkoxy)carbonyl-substituted $C_{1-4}$ alkyl; and $R^{35}$ and $R^{36}$ are each independently selected from a hydrogen atom and $C_{1-4}$ alkyl.

(3-2) The compound according to (3-1) or a salt thereof, or a solvate of the compound or the salt, wherein $R^1$ is $C_{1-10}$ alkyl.

(3-3) The compound according to (3-1) or (3-2) or a salt thereof, or a solvate of the compound or the salt, wherein Rb is optionally $C_{1-4}$ alkoxy-substituted $C_{1-5}$ alkoxy or a halogen atom;

Rc is a halogen atom, $C_{1-10}$ alkyl optionally substituted with one or more halogen atoms, or a group —SF$_5$; and Rd is selected from cyano, hydroxy, a halogen atom, $C_{1-4}$ alkyl optionally substituted with one or more halogen atoms, 5- to 10-membered heterocycloalkyl optionally substituted with one or more substituents $R^{14}$, $C_{6-10}$ aryl optionally substituted with one or more substituents $R^{14}$, or 5- to 10-membered heteroaryl optionally substituted with one or more substituents $R^{14}$.

(3-4) The compound according to any of (3-1) to (3-3) or a salt thereof, or a solvate of the compound or the salt, wherein each Ra is independently selected from a halogen atom, nitro, cyano, ($C_{1-4}$ alkoxy)carbonyl, 5- or 6-membered heterocycloalkyloxy, $C_{1-10}$ alkyl optionally substituted with one or more substituents $R^{10}$, $C_{2-10}$ alkynyl optionally substituted with one or more substituents $R^{11}$, $C_{1-8}$ alkoxy optionally substituted with one or more substituents $R^{12}$, and $C_{1-4}$ alkylthio optionally substituted with one or more substituents $R^{13}$;

each $R^{10}$ is independently selected from carboxy, 5- or 6-membered heterocycloalkyl, $C_{1-6}$ alkoxy optionally substituted with one or more hydroxy groups, and a group —(O(CH$_2$)$_o$)$_p$—OH;

each $R^{11}$ is independently selected from hydroxy, carboxy, 5- or 6-membered heterocycloalkyl optionally substituted with one or more oxo groups, $C_{1-6}$ alkoxy optionally substituted with one or more hydroxy groups, a group —(O(CH$_2$)$_o$)$_p$—OH, and $C_{3-6}$ cycloalkyl optionally substituted with one or more hydroxy groups;

each $R^{12}$ is independently selected from a halogen atom, hydroxy, $C_{1-6}$ alkoxy optionally substituted with one or more hydroxy groups, ($C_{1-3}$ alkoxy)carbonyl, 5- or 6-membered heterocycloalkyl, and 5- or 6-membered heteroaryl;

each $R^{13}$ is independently selected from 5- or 6-membered heterocycloalkyl; and o and p are each independently an integer selected from 2 to 4.

(3-5) The compound according to any of (3-1) to (3-4) or a salt thereof, or a solvate of the compound or the salt, wherein $R^1$ is selected from $C_{1-4}$ alkyl;

$R^3$ is selected from $C_{1-4}$ alkyl substituted with Re;

Re is selected from $C_{6-10}$ aryl optionally substituted with one or more substituents Ra;

each Ra is independently selected from a halogen atom and optionally $R^{12}$-substituted $C_{1-6}$ alkoxy;

$R^4$ is selected from $C_{1-4}$ alkyl;

$R^5$ is selected from $C_{1-4}$ alkyl; or of $R^1$, $R^4$, and $R^5$, $R^1$ and $R^5$ together with the carbon atom to which they are attached form a $C_{3-6}$ saturated carbocyclic ring, or $R^4$ and $R^5$ together with the nitrogen atom and the carbon atom to which they are attached form a 5- to 8-membered saturated heterocyclic ring;

Ar$^1$ is $C_{6-10}$ aryl, wherein the aryl group is substituted with two substituents selected from Rc and Rd;

Rc is a halogen atom or $C_{1-4}$ alkyl optionally substituted with one or more halogen atoms;

Rd is 5- to 10-membered heterocycloalkyl optionally substituted with one or more $C_{1-4}$ alkyl groups and 5- to 10-membered heteroaryl optionally substituted with one or more substituents $R^{14}$;

$R^{12}$ is 5- to 10-membered heterocycloalkyl; and $R^{14}$ is $C_{1-4}$ alkyl optionally substituted with one or more halogen atoms.

(3-6) The compound according to (3-1) or (3-2) or a salt thereof, or a solvate of the compound or the salt, wherein $R^1$ is a hydrogen atom or $C_{1-6}$ alkyl;

$R^3$ is $C_{1-4}$ alkyl substituted with Re;

Re is $C_{6-10}$ aryl optionally substituted with one or more substituents Ra; each Ra is independently selected from a halogen atom, cyano, hydroxy, $C_{1-6}$ alkyl optionally substituted with one or more substituents $R^{10}$, $C_{2-6}$ alkynyl optionally substituted with one or more substituents $R^{11}$, and $C_{1-6}$ alkoxy optionally substituted with one or more substituents $R^{12}$;

$R^{10}$, $R^{11}$, and $R^{12}$ are each independently selected from 4- to 10-membered heterocycloalkyl optionally substituted with one or more substituents, wherein the substituents are each independently selected from oxo, a halogen atom, and $C_{1-4}$ alkyl (wherein the alkyl group is optionally substituted with one or more hydroxy groups);

$R^4$ is a hydrogen atom, $C_{1-4}$ alkyl optionally substituted with one or more substituents Rf, $C_{6-10}$ aryl optionally substituted with one or more substituents Rg, ($C_{1-6}$ alkyl)carbonyl, ($C_{6-10}$ aryl)carbonyl, —C(O)NR$^{37}$R$^{38}$, $C_{3-7}$ cycloalkyl, or 5- to 8-membered heterocycloalkyl;

$R^5$ is a hydrogen atom or $C_{1-4}$ alkyl; or $R^1$ and $R^5$ together with the carbon atom to which they are attached may form a $C_{3-6}$ saturated carbocyclic ring;

$Ar^1$ is $C_{6-10}$ aryl or 5- to 10-membered heteroaryl, wherein the aryl and heteroaryl groups are each optionally substituted with one to three substituents selected from Rb, Rc, and Rd;

Rb, Rc, and Rd are each independently selected from a halogen atom, $C_{1-4}$ alkyl optionally substituted with one or more halogen atoms, optionally $C_{1-4}$ alkyl-substituted 5- to 10-membered heterocycloalkyl, $C_{6-10}$ aryl optionally substituted with one or more substituents $R^{14}$, and 5- to 10-membered heteroaryl optionally substituted with one or more substituents $R^{14}$; and each $R^{14}$ is independently selected from a halogen atom, cyano, $C_{1-4}$ alkyl optionally substituted with one or more halogen atoms, $C_{1-4}$ alkoxy, —SO$_2$NR$^{35}$R$^{36}$, and $C_{1-4}$ alkylthio.

(3-7) The compound according to any of (3-1), (3-2), and (3-6) or a salt thereof, or a solvate of the compound or the salt, wherein $R^1$ is $C_{1-6}$ alkyl;

$R^3$ is $C_{1-4}$ alkyl substituted with Re;

Re is $C_{6-10}$ aryl optionally substituted with one or more substituents Ra;

each Ra is independently selected from a halogen atom, optionally $R^{11}$-substituted $C_{2-6}$ alkynyl, and optionally $R^{12}$-substituted $C_{1-6}$ alkoxy;

$R^{11}$ and $R^{12}$ are each selected from 5- to 10-membered heterocycloalkyl;

$R^4$ is optionally halogen atom-substituted $C_{1-4}$ alkyl or $C_{6-10}$ aryl;

$R^5$ is a hydrogen atom or $C_{1-4}$ alkyl; or $R^1$ and $R^5$ together with the carbon atom to which they are attached may form a $C_{3-6}$ saturated carbocyclic ring;

$Ar^1$ is $C_{6-10}$ aryl or 5- to 10-membered heteroaryl, wherein the aryl and heteroaryl groups are each optionally substituted with one to three substituents selected from Rb, Rc, and Rd;

Rb, Rc, and Rd are each independently selected from a halogen atom, $C_{1-4}$ alkyl optionally substituted with one or more halogen atoms, $C_{6-10}$ aryl optionally substituted with one or more substituents $R^{14}$, and 5- to 10-membered heteroaryl optionally substituted with one or more substituents $R^{14}$; and each $R^{14}$ is independently selected from a halogen atom, cyano, $C_{1-4}$ alkyl optionally substituted with one or more halogen atoms, $C_{1-4}$ alkoxy, —SO$_2$NR$^{35}$R$^{36}$ (wherein $R^{35}$ and $R^{36}$ are each independently selected from $C_{1-4}$ alkyl), and $C_{1-4}$ alkylthio.

(3-8) The compound according to (3-7) or a salt thereof, or a solvate of the compound or the salt, wherein Rb is a halogen atom;

Rc is a halogen atom or $C_{1-4}$ alkyl optionally substituted with one or more halogen atoms; and Rd is a halogen atom, $C_{1-4}$ alkyl optionally substituted with one or more halogen atoms, $C_{6-10}$ aryl optionally substituted with one or more substituents $R^{14}$, or 5- to 10-membered heteroaryl optionally substituted with one or more substituents $R^{14}$.

(3-9) The compound according to (3-7) or a salt thereof, or a solvate of the compound or the salt, wherein Re is phenyl optionally substituted with one or more substituents Ra;

$R^{11}$ and $R^{12}$ are each independently morpholinyl;

$R^4$ is optionally halogen atom-substituted $C_{1-4}$ alkyl or phenyl;

$Ar^1$ is phenyl, pyridinyl, or pyrimidinyl, wherein the phenyl, pyridinyl, and pyrimidinyl groups are each optionally substituted with one to three substituents selected from Rb, Rc, and Rd;

Rb is a halogen atom;

Rc is a halogen atom or $C_{1-4}$ alkyl optionally substituted with one or more halogen atoms; and Rd is a halogen atom, $C_{1-4}$ alkyl optionally substituted with one or more halogen atoms, phenyl, pyridinyl, or pyrimidinyl, wherein the phenyl, pyridinyl, and pyrimidinyl groups are each optionally substituted with one or more substituents $R^{14}$.

(3-10) The compound according to (3-6) or (3-7) or a salt thereof, or a solvate of the compound or the salt, wherein $R^{10}$, $R^{11}$, and $R^{12}$ are each independently selected from morpholinyl, thiomorpholinyl, azetidinyl, pyrrolidinyl, 2-oxa-6-azaspiro[3.3]heptanyl, 3,7-dioxa-9-azabicyclo[3.3.1]nonanyl, piperazinyl, and piperidyl.

(3-11) The compound according to any of (3-1) to (3-10) or a salt thereof, or a solvate of the compound or the salt, wherein $R^3$ is benzyl optionally substituted with one or more substituents Ra on the benzene ring.

(3-12) The compound according to (3-1) or a salt thereof, or a solvate of the compound or the salt, wherein $R^1$ is $C_{1-6}$ alkyl, and $R^4$ and $R^5$ together with the carbon atom to which they are attached form a pyrrolidine ring; or $R^1$ is a hydrogen atom, and $R^4$ and $R^5$ are each independently selected from $C_{1-6}$ alkyl; or $R^1$ and $R^5$ together with the carbon atom to which they are attached form a $C_{3-5}$ saturated carbocyclic ring, and $R^4$ is $C_{1-6}$ alkyl;

$R^3$ is benzyl substituted with one or more substituents Ra on the benzene ring;

each Ra is independently selected from a halogen atom, (morpholino)$C_{2-6}$ alkoxy, (morpholino)$C_{1-6}$ alkyl, (carboxy)

$C_{2-6}$ alkynyl, and $(C_{1-6}$ alkoxy$)C_{1-6}$ alkoxy optionally substituted with one or more hydroxy groups;

$Ar^1$ is phenyl or pyrimidyl, wherein these groups are each substituted with one to three groups each independently selected from a halogen atom, trifluoromethyl, pyridinyl substituted with one or more substituents $R^{14}$, and pyrimidyl substituted with one or more substituents $R^{14}$; and each $R^{14}$ is independently selected from methyl, cyano, trifluoromethyl, and methylthio.

(3-13) The compound according to any of (3-1) to (3-11) or a salt thereof, or a solvate of the compound or the salt, wherein $Ar^1$ is 4-(trifluoromethyl)-2-(6-methylthiopyridin-3-yl)phenyl, 4-(trifluoromethyl)-2-(6-trifluoromethylpyridin-3-yl)phenyl, 4-(trifluoromethyl)-2-(4-trifluoromethylpyrimidin-5-yl)phenyl, 4-(trifluoromethyl)-2-(6-trifluoromethylpyrimidin-4-yl)phenyl, 4-(trifluoromethyl)-2-(6-cyano-5-methylpyrimidin-4-yl)phenyl, 4-(trifluoromethyl)-2-(2-cyanopyridin-4-yl)phenyl, 4-chloro-2-(6-methylthiopyridin-3-yl)phenyl, 4-chloro-2-(6-trifluoromethylpyridin-3-yl)phenyl, 4-chloro-2-(4-trifluoromethylpyrimidin-5-yl)phenyl, 4-chloro-2-(6-cyano-5-methylpyrimidin-4-yl)phenyl, 4-chloro-2-(6-trifluoromethylpyrimidin-4-yl)phenyl, or 4-chloro-2-(2-cyanopyridin-4-yl)phenyl.

An alternative aspect of the present invention provides a pharmaceutical drug comprising a compound according to any of (2-1) to (2-26) and (3-1) to (3-13) or a salt thereof, or a solvate of the compound or the salt.

A further alternative aspect of the present invention provides a pharmaceutical composition comprising a compound according to any of (2-1) to (2-26) and (3-1) to (3-13) or a salt thereof, or a solvate of the compound or the salt.

A further alternative aspect of the present invention provides the compound according to any of (2-1) to (2-26) and (3-1) to (3-13) or the salt thereof, or the solvate of the compound or the salt for use in the prevention and/or treatment of a disease selected from hyperphosphatemia, secondary hyperparathyroidism, and chronic renal failure.

A further alternative aspect of the present invention provides a NaPi-IIb inhibitor comprising a compound according to any of (2-1) to (2-26) and (3-1) to (3-13) or a salt thereof, or a solvate of the compound or the salt.

A further alternative aspect of the present invention provides a preventive and/or therapeutic agent for a disease selected from hyperphosphatemia, secondary hyperparathyroidism, and chronic renal failure, the agent comprising a compound according to any of (2-1) to (2-26) and (3-1) to (3-13) or a salt thereof, or a solvate of the compound or the salt as an active ingredient.

A further alternative aspect of the present invention provides a method for preventing and/or treating a disease selected from hyperphosphatemia, secondary hyperparathyroidism, and chronic renal failure, comprising administering a therapeutically effective amount of a compound according to any of (2-1) to (2-26) and (3-1) to (3-13) or a salt thereof, or a solvate of the compound or the salt to a patient.

According to one embodiment of the compound represented by the formula (I) wherein $R^4$ and $R^5$ together with the carbon atom and the nitrogen atom to which they are attached form a 5- to 8-membered saturated heterocyclic ring, the following compound (4-1) is provided:

(4-1) A compound represented by the formula (II) or a salt thereof, or a solvate of the compound or the salt:

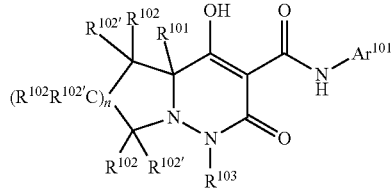

(II)

wherein $R^{10}$ is selected from a hydrogen atom and linear $C_{1-10}$ alkyl;

$R^{102}$ may be the same or different and are each independently selected from a hydrogen atom, $C_{1-5}$ alkyl, and a halogen atom; or two $R^{102}$ moieties bonded to different carbon atoms may together form $C_{1-5}$ alkylene that links the carbon atoms;

$R^{102'}$ may be the same or different and are each independently selected from a hydrogen atom, $C_{1-5}$ alkyl, and a halogen atom;

n is an integer selected from 1 to 4;

$R^{103}$ is $C_{1-10}$ alkyl optionally substituted with one or more substituents Rw or $C_{1-4}$ alkyl substituted with one or more substituents Rx;

each Rw is independently selected from a halogen atom, $(C_{1-4}$ alkoxy)carbonyl, and a group $—(O(CH_2)_a)_b—C_{1-4}$ alkoxy (wherein a is an integer selected from 2 to 4, and b is an integer selected from 1 to 4);

each Rx is independently selected from $C_{6-10}$ aryl optionally substituted with one or more substituents Ry and 5- to 10-membered heteroaryl optionally substituted with one or more substituents Ry;

each Ry is independently selected from a halogen atom, hydroxy, nitro, cyano, $(C_{1-4}$ alkoxy)carbonyl, 5- to 10-membered heterocycloalkyloxy, $C_{1-10}$ alkyl optionally substituted with one or more substituents $R^{110}$, $C_{2-10}$ alkenyl optionally substituted with one or more substituents $R^{115}$, $C_{2-10}$ alkynyl optionally substituted with one or more substituents $R^{111}$, $C_{1-8}$ alkoxy optionally substituted with one or more substituents $R^{112}$, and $C_{1-4}$ alkylthio optionally substituted with one or more substituents $R^{13}$;

$R^{110}$, $R^{111}$, $R^{112}$, $R^{113}$, and $R^{115}$ are each independently selected from a halogen atom, hydroxy, carboxy, $C_{1-6}$ alkoxy optionally substituted with one or more hydroxy groups, $(C_{1-4}$ alkoxy)carbonyl, a group $—(O(CH_2)_o)_p—OH$ (wherein o and p are each independently an integer selected from 2 to 4), $C_{3-6}$ cycloalkyl optionally substituted with one or more hydroxy groups, 5- to 10-membered heterocycloalkyl optionally substituted with one or more oxo groups, and 5- to 10-membered heteroaryl;

$Ar^{101}$ is $C_{6-10}$ aryl or 5- to 10-membered heteroaryl, wherein the $C_{6-10}$ aryl and 5- to 10-membered heteroaryl groups are each optionally substituted with one to three substituents selected from $Rz^1$, $Rz^2$, and $Rz^3$;

$Rz^1$, $Rz^2$, and $Rz^3$ are each independently selected from optionally $C_{1-4}$ alkoxy-substituted $C_{1-5}$ alkoxy, a halogen atom, $C_{1-10}$ alkyl optionally substituted with one or more halogen atoms, a group $—SF_5$, cyano, hydroxy, 5- to 10-membered heterocycloalkyl optionally substituted with one or more substituents $R^{114}$, $C_{6-10}$ aryl optionally substituted with one or more substituents $R^{114}$, and 5- to 10-membered heteroaryl optionally substituted with one or more substituents $R^{114}$; and each $R^{114}$ is independently selected from a halogen atom, cyano, nitro, $C_{1-4}$ alkyl optionally substituted with one or more halogen atoms, $C_{1-4}$ alkoxy optionally substituted with one or more halogen atoms, $C_{1-6}$ alkoxy)carbonyl, a group —NR$^{127}$R$^{128}$ (wherein R$^{127}$ and R$^{128}$ are each independently selected from a hydrogen atom and optionally ($C_{1-4}$ alkoxy)carbonyl-substituted $C_{1-4}$ alkyl), a group —SO$_2$NR$^{135}$R$^{136}$ (wherein R$^{135}$ and R$^{136}$ are each independently selected from a hydrogen atom and $C_{1-4}$ alkyl), $C_{1-4}$ alkylthio, and 5- to 10-membered heterocycloalkyl.

According to another embodiment, the present invention provides the following compounds (4-2) to (4-17) represented by the formula (II).

(4-2) The compound according to (4-1) or a salt thereof, or a solvate of the compound or the salt, wherein Rz$^1$ is optionally $C_{1-4}$ alkoxy-substituted $C_{1-5}$ alkoxy or a halogen atom;

Rz$^2$ is a halogen atom, $C_{1-10}$ alkyl optionally substituted with one or more halogen atoms, and a group —SF$_5$; and Rz$^3$ is cyano, hydroxy, a halogen atom, $C_{1-4}$ alkyl optionally substituted with one or more halogen atoms, 5- to 10-membered heterocycloalkyl optionally substituted with one or more substituents R$^{114}$, $C_{6-10}$ aryl optionally substituted with one or more substituents R$^{114}$ or 5- to 10-membered heteroaryl optionally substituted with one or more substituents R$^{114}$.

(4-3) The compound according to (4-1) or (4-2) or a salt thereof, or a solvate of the compound or the salt, wherein Rz$^3$ is cyano, hydroxy, a halogen atom, $C_{1-4}$ alkyl optionally substituted with one or more halogen atoms, phenyl, and 5- to 6-membered heteroaryl, wherein the pheny and 5- to 6-membered heteroaryl may be substituted with one or two substituents R$^{114}$.

(4-4) The compound according to any of (4-1) to (4-3) or a salt thereof, or a solvate of the compound or the salt, wherein R$^{101}$ is a hydrogen atom or linear $C_{1-6}$ alkyl;

R$^{102}$ may be the same or different and are each independently selected from a hydrogen atom, $C_{1-3}$ alkyl, and a halogen atom;

R$^{102'}$ may be the same or different and are each independently selected from a hydrogen atom, $C_{1-3}$ alkyl, and a halogen atom;

n is an integer selected from 1 to 3;

Rx is independently selected from $C_{6-10}$ aryl optionally substituted with one or more substituents Ry and 5- to 10-membered heteroaryl optionally substituted with one or more substituents Ry;

Ry is independently selected from a halogen atom, hydroxy, nitro, cyano, ($C_{1-3}$ alkoxy)carbonyl, 5- to 10-membered heterocycloalkyloxy, $C_{1-10}$ alkyl optionally substituted with one or more substituents R$^{110}$, $C_{2-10}$ alkynyl optionally substituted with one or more substituents R$^{111}$, $C_{1-8}$ alkoxy optionally substituted with one or more substituents R$^{112}$, and $C_{1-3}$ alkylthio optionally substituted with one or more substituents R$^{113}$;

R$^{110}$ is independently selected from carboxyl, 5- to 10-membered heterocycloalkyl, $C_{1-6}$ alkoxy optionally substituted with one or more hydroxy groups, and a group —(O(CH$_2$)$_o$)$_p$—OH (wherein o and p are each independently an integer selected from 2 to 4);

R$^{111}$ is independently selected from hydroxy, carboxy, 5- to 10-membered heterocycloalkyl optionally substituted with one or more oxo groups, $C_{1-6}$ alkoxy optionally substituted with one or more hydroxy groups, a group —(O(CH$_2$)$_o$)$_p$—OH (wherein o and p are each independently an integer selected from 2 to 4), and $C_{3-6}$ cycloalkyl optionally substituted with one or more hydroxy groups;

R$^{112}$ is independently selected from a halogen atom, hydroxy, $C_{1-6}$ alkoxy optionally substituted with one or more hydroxy groups, ($C_{1-3}$ alkoxy)carbonyl, 5- to 10-membered heterocycloalkyl, and 5- to 10-membered heteroaryl;

R$^{113}$ is independently selected from 5- to 10-membered heterocycloalkyl;

Rz$^1$ is selected from optionally $C_{1-3}$ alkoxy-substituted $C_{1-4}$ alkoxy and a halogen atom; and R$^{114}$ is independently selected from a halogen atom, cyano, nitro, $C_{1-4}$ alkyl optionally substituted with one or more halogen atoms, $C_{1-4}$ alkoxy optionally substituted with one or more halogen atoms, ($C_{1-6}$ alkoxy)carbonyl, a group —NR$^{127}$R$^{128}$ (wherein R$^{127}$ and R$^{128}$ are each independently selected from a hydrogen atom and optionally ($C_{1-3}$ alkoxy)carbonyl-substituted $C_{1-4}$ alkyl), a group —SO$_2$NR$^{135}$R$^{136}$ (wherein R$^{135}$ and R$^{136}$ are each independently selected from a hydrogen atom and $C_{1-3}$ alkyl), $C_{1-3}$ alkylthio, and 5- to 10-membered heterocycloalkyl.

(4-5) The compound according to any of (4-1) to (4-4) or a salt thereof, or a solvate of the compound or the salt, wherein Rx is $C_{6-10}$ aryl optionally substituted with one or more substituents Ry.

(4-6) The compound according to any of (4-1) to (4-5) or a salt thereof, or a solvate of the compound or the salt, wherein Ar$^{101}$ is phenyl or 5- or 6-membered heteroaryl, wherein the phenyl and heteroaryl groups are each optionally substituted with Rz$^1$, Rz$^2$, and/or Rz$^3$;

Rz$^1$ is a halogen atom or optionally $C_{1-3}$ alkoxy-substituted $C_{1-4}$ alkoxy;

Rz$^2$ is a halogen atom or $C_{1-10}$ alkyl optionally substituted with one or more halogen atoms; and Rz$^3$ is 5- or 6-membered heterocycloalkyl optionally substituted with one or more substituents R$^{114}$, phenyl optionally substituted with one or more substituents R$^{114}$, or 5- or 6-membered heteroaryl optionally substituted with one or more substituents R$^{114}$.

(4-7) The compound according to any of (4-1) to (4-6) or a salt thereof, or a solvate of the compound or the salt, wherein Ar$^{101}$ is phenyl or 5- or 6-membered heteroaryl, wherein the aryl and heteroaryl groups are each optionally substituted with one to three substituents selected from Rz$^1$, Rz$^2$, and Rz$^3$;

Rz$^1$ is a halogen atom;

Rz$^2$ is selected from a halogen atom, $C_{1-10}$ alkyl optionally substituted with one or more halogen atoms, and a group —SF$_5$; and Rz$^3$ is cyano, hydroxy, or a halogen atom.

(4-8) The compound according to any of (4-1) to (4-7) or a salt thereof, or a solvate of the compound or the salt, wherein Rz$^3$ is phenyl, thienyl, pyridinyl, pyrimidinyl, or quinolinyl, wherein these groups are each optionally substituted with one or more substituents R$^{114}$.

(4-9) The compound according to any of (4-1) to (4-8) or a salt thereof, or a solvate of the compound or the salt, wherein each R$^{114}$ is independently selected from a halogen atom, cyano, nitro, $C_{1-4}$ alkyl optionally substituted with one or more halogen atoms, $C_{1-4}$ alkoxy optionally substituted with one or more halogen atoms, ($C_{1-6}$ alkoxy)carbonyl, a group —NR$^{127}$R$^{128}$ (each R$^{127}$ and R$^{128}$ are independently selected from a hydrogen atom, and $C_{1-4}$ alkyl optionally substituted with ($C_{1-4}$ alkoxy)carbonyl), a group —SO$_2$NR$^{135}$R$^{136}$ (each R$^{135}$ and R$^{136}$ are independently selected from a hydrogen atom, and $C_{1-4}$ alkyl), and $C_{1-4}$ alkylthio.

(4-10) The compound according to any of (4-1) to (4-9) or a salt thereof, or a solvate of the compound or the salt, wherein R$^{101}$ is linear $C_{1-6}$ alkyl.

(4-11) The compound according to any of (4-1) to (4-10) or a salt thereof, or a solvate of the compound or the salt, wherein $R^{102}$ and $R^{102'}$ are a hydrogen atom.

(4-12) The compound according to any of (4-1) to (4-11) or a salt thereof, or a solvate of the compound or the salt, wherein $R^{101}$ is linear $C_{1-6}$ alkyl;

$R^{102}$ and $R^{102'}$ are a hydrogen atom;

$R^{103}$ is $C_{1-10}$ alkyl optionally substituted with Rx;

Rx is phenyl optionally substituted with one or more substituents Ry;

each Ry is independently selected from a halogen atom and $C_{1-8}$ alkoxy optionally substituted with $R^{112}$;

$R^{112}$ is 5- or 6-membered heterocycloalkyl;

$Ar^{101}$ is phenyl optionally substituted with one to three substituents selected from $Rz^1$, $Rz^2$, and $Rz^3$;

$Rz^1$ is optionally $C_{1-3}$ alkoxy-substituted $C_{1-4}$ alkoxy or a halogen atom;

$Rz^2$ is a halogen atom or $C_{1-10}$ alkyl optionally substituted with one or more halogen atoms;

$Rz^3$ is 5- or 6-membered heteroaryl optionally substituted with one or more substituents $R^{114}$; and each $R^{114}$ is selected independently from $C_{1-4}$ alkyl optionally substituted with one or more halogen atoms.

(4-13) The compound according to any of (4-1) to (4-12) or a salt thereof, or a solvate of the compound or the salt, wherein $Rz^3$ is substituted with one or two substituents $R^{114}$.

(4-14) The compound according to any of (4-1) to (4-13) or a salt thereof, or a solvate of the compound or the salt, wherein $R^{110}$, $R^{111}$, $R^{112}$, $R^{113}$, and $R^{115}$ are each independently selected from tetrahydrofuranyl, pyrrolidinyl, morpholinyl, cyclopentyl, and pyridinyl.

(4-15) The compound according to any of (4-1) to (4-14) or a salt thereof, or a solvate of the compound or the salt, wherein $R^{103}$ is benzyl optionally substituted with one or more substituents Ry on the benzene ring.

(4-16) The compound according to any of (4-1) to (4-15) or a salt thereof, or a solvate of the compound or the salt, wherein $R^{103}$ is benzyl optionally substituted with one to three substituents Ry on the benzene ring.

(4-17) The compound according to any of (4-1) to (4-16) or a salt thereof, or a solvate of the compound or the salt, wherein the one to three substituents Ry are one substituent selected from Ri', Rj', and Rk', two substituents selected from combinations of Ri' and Rj', R'i and Rk', and Rj' and Rk', or three substituents Ri', Rj', and Rk';

Ri' is a halogen atom or $C_{1-3}$ alkoxy;

Rj' is a halogen atom, nitro, or cyano; and

Rk' is hydroxy, a halogen atom, $C_{1-6}$ alkyl, (carboxy)$C_{1-8}$ alkyl, (morpholino)$C_{1-4}$ alkyl, ($C_{1-6}$ alkoxy)$C_{1-8}$ alkyl, (the alkoxy is optionally substituted with one or more hydrxy groups), (5- to 6-membered heterocycloalkyl)$C_{1-6}$ alkoxy, [HO—$((CH_2)_oO)_p$]$C_{1-6}$ alkyl, (carboxy)$C_{2-6}$ alkynyl, (3- to 6-membered heterocycloalkyl)$C_{2-6}$ alkynyl (the heterocycloalkyl moiety is optionally substituted with oxo), $C_{1-3}$ alkoxy optionally substituted with one or more halogen atoms, $C_{1-6}$ alkoxy substituted with one or more hydroxy groups, (($C_{1-3}$ alkoxy)carbonyl)$C_{1-3}$ alkoxy, (pyridinyl)$C_{1-4}$ alkoxy, ($C_{1-6}$ alkoxy)$C_{1-8}$ alkoxy (the $C_{1-6}$ alkoxy is optionally substituted with one or more hydroxy groups), optionally hydroxy-substituted $C_{2-8}$ alkynyl, ($C_{3-6}$ cycloalkyl)$C_{2-6}$ alkynyl (the cycloalkyl is optionally substituted with a hydroxy group), [HO—$((CH_2)_oO)_p$]$C_{2-8}$ alkynyl, ($C_{1-6}$ alkoxy)$C_{2-8}$ alkynyl (the alkoxy is optionally substituted with one or more hydroxy groups), (morpholino)$C_{1-4}$ alkylthio, 3- to 6-membered oxacycloalkyloxy, or ($C_{1-3}$ alkoxy)carbonyl.

An alternative embodiment of the present invention provides the following compounds (5-1) to (5-12) represented by the formula (I):

(5-1) The compound according to (1-1), (2-1) or (3-1) or a salt thereof, or a solvate of the compound or the salt, wherein $R^1$ is a hydrogen atom or linear $C_{1-10}$ alkyl; and $R^4$ and $R^5$ together with the carbon atom and the nitrogen atom to which they are attached form a 5- to 8-membered saturated heterocyclic ring, wherein the saturated heterocyclic ring is optionally substituted with one or more substituents $R^2$.

(5-2) The compound according to (5-1) or a salt thereof, or a solvate of the compound or the salt, wherein Rb is optionally $C_{1-4}$ alkoxy-substituted $C_{1-5}$ alkoxy or a halogen atom; and/or Rc is a halogen atom, $C_{1-10}$ alkyl optionally substituted with one or more halogen atoms, or a group —$SF_5$; and/or Rd is cyano, hydroxy, a halogen atom, $C_{1-4}$ alkyl optionally substituted with one or more halogen atoms, 5- to 10-membered heterocycloalkyl optionally substituted with one or more substituents $R^{14}$, $C_{6-10}$ aryl optionally substituted with one or more substituents $R^{14}$, or 5- to 10-membered heteroaryl optionally substituted with one or more substituents $R^{14}$.

(5-3) The compound according to (5-1) or (5-2) or a salt thereof, or a solvate of the compound or the salt, wherein $R^1$ is a hydrogen atom or linear $C_{1-6}$ alkyl;

$R^2$ may be the same or different and are each independently selected from $C_{1-3}$ alkyl and a halogen atom;

Re is $C_{6-10}$ aryl optionally substituted with one or more substituents Ra or 5- to 10-membered heteroaryl optionally substituted with one or more substituents Ra;

each Ra is independently selected from a halogen atom, hydroxy, nitro, cyano, ($C_{1-3}$ alkoxy)carbonyl, 5- to 10-membered heterocycloalkyloxy, $C_{1-10}$ alkyl optionally substituted with one or more substituents $R^{10}$, $C_{2-10}$ alkynyl optionally substituted with one or more substituents $R^1$, $C_{1-8}$ alkoxy optionally substituted with one or more substituents $R^{12}$, and $C_{1-3}$ alkylthio optionally substituted with one or more substituents $R^{13}$;

each $R^{10}$ is independently selected from carboxyl, 5- to 10-membered heterocycloalkyl, $C_{1-6}$ alkoxy optionally substituted with one or more hydroxy groups, and a group —$(O(CH_2)_o)_p$—OH (wherein o and p are each independently an integer selected from 2 to 4);

each $R^{11}$ is independently selected from hydroxy, carboxy, 5- to 10-membered heterocycloalkyl optionally substituted with one or more oxo groups, $C_{1-6}$ alkoxy optionally substituted with one or more hydroxy groups, a group —$(O(CH_2)_o)_p$—OH (wherein o and p are each independently an integer selected from 2 to 4), and $C_{3-6}$ cycloalkyl optionally substituted with one or more hydroxy groups;

each $R^{12}$ is selected from a halogen atom, hydroxy, $C_{1-6}$ alkoxy optionally substituted with one or more hydroxy groups, ($C_{1-3}$ alkoxy)carbonyl, 5- to 10-membered heterocycloalkyl, and 5- to 10-membered heteroaryl;

each $R^{13}$ is independently selected from 5- to 10-membered heterocycloalkyl;

Rb is optionally $C_{1-3}$ alkoxy-substituted $C_{1-4}$ alkoxy or a halogen atom; and each $R^{14}$ is independently selected from a halogen atom, cyano, nitro, $C_{1-4}$ alkyl optionally substituted with one or more halogen atoms, $C_{1-4}$ alkoxy optionally substituted with one or more halogen atoms, ($C_{1-6}$ alkoxy)carbonyl, a group —$NR^{27}R^{28}$ (wherein $R^{27}$ and $R^{28}$ are each independently selected from a hydrogen atom and optionally ($C_{1-3}$ alkoxy)

carbonyl-substituted $C_{1-4}$ alkyl), a group —$SO_2NR^{35}R^{36}$ (wherein $R^{35}$ and $R^{36}$ are each independently selected from a hydrogen atom and $C_{1-3}$ alkyl), $C_{1-3}$ alkylthio, and 5- to 10-membered heterocycloalkyl.

(5-4) The compound according to any of (5-1) to (5-3) or a salt thereof, or a solvate of the compound or the salt, wherein Re is selected from $C_{6-10}$ aryl optionally substituted with one or more substituents Ra.

(5-5) The compound according to any of (5-1) to (5-4) or a salt thereof, or a solvate of the compound or the salt, wherein
$Ar^1$ is phenyl or 5- or 6-membered heteroaryl, wherein the phenyl and heteroaryl groups are each optionally substituted with Rb, Rc, and/or Rd;
Rb is a halogen atom or optionally $C_{1-3}$ alkoxy-substituted $C_{1-4}$ alkoxy; and/or
Rc is a halogen atom or $C_{1-10}$ alkyl optionally substituted with one or more halogen atoms; and/or
Rd is 5- or 6-membered heterocycloalkyl optionally substituted with one or more substituents $R^{14}$, phenyl optionally substituted with one or more substituents $R^{14}$, or 5- or 6-membered heteroaryl optionally substituted with one or more substituents $R^{14}$.

(5-6) The compound according to any of (5-1) to (5-5) or a salt thereof, or a solvate of the compound or the salt, wherein
$Ar^1$ is phenyl or 5- or 6-membered heteroaryl, wherein the phenyl and heteroaryl groups are each optionally substituted with one to three substituents selected from Rb, Rc, and Rd;
Rb is a halogen atom;
Rc is a halogen atom, $C_{1-10}$ alkyl optionally substituted with one or more halogen atoms, or a group —$SF_5$; and
Rd is cyano, hydroxy, or a halogen atom.

(5-7) The compound according to any of (5-1) to (5-6) or a salt thereof, or a solvate of the compound or the salt, wherein Rd is phenyl, thienyl, pyridinyl, pyrimidinyl, or quinolinyl, wherein these groups are each optionally substituted with one or more substituents $R^{14}$.

(5-8) The compound according to any of (5-1) to (5-7) or a salt thereof, or a solvate of the compound or the salt, wherein $R^1$ is linear $C_{1-6}$ alkyl.

(5-9) The compound according to any of (5-1) to (5-8) or a salt thereof, or a solvate of the compound or the salt, wherein $R^2$ is a hydrogen atom.

(5-10) The compound according to any of (5-1) to (5-9) or a salt thereof, or a solvate of the compound or the salt, wherein
$R^1$ is linear $C_{1-6}$ alkyl;
$R^2$ is a hydrogen atom;
$R^3$ is $C_{1-4}$ alkyl substituted with Re;
Re is phenyl optionally substituted with one or more substituents Ra;
each Ra is independently selected from a halogen atom and optionally $R^{12}$-substituted $C_{1-8}$ alkoxy;
each $R^{12}$ is independently selected from 5- or 6-membered heterocycloalkyl;
$Ar^1$ is phenyl optionally substituted with one to three substituents selected from Rb, Rc, and Rd;
Rb is optionally $C_{1-3}$ alkoxy-substituted $C_{1-4}$ alkoxy and a halogen atom; and/or
Rc is a halogen atom or $C_{1-10}$ alkyl optionally substituted with one or more halogen atoms; and/or
Rd is 5- or 6-membered heteroaryl optionally substituted with one or more substituents $R^{14}$; and
each $R^{14}$ is independently selected from $C_{1-4}$ alkyl optionally substituted with one or more halogen atoms.

(5-11) The compound according to any of (5-1) to (5-10) or a salt thereof, or a solvate of the compound or the salt, wherein $R^{10}$, $R^{11}$, $R^{12}$, $R^{13}$, and $R^{15}$ are each independently selected from tetrahydrofuranyl, pyrrolidinyl, morpholinyl, cyclopentyl, and pyridinyl.

(5-12) The compound according to any of (5-1) to (5-11) or a salt thereof, or a solvate of the compound or the salt, wherein $R^3$ is benzyl optionally substituted with one or more substituents Ra on the benzene ring.

An alternative embodiment of the present invention provides the following compounds (6-1) to (6-10) represented by the formula (I):

(6-1) A compound represented by the formula I-b or a salt thereof, or a solvate of the compound or the salt:

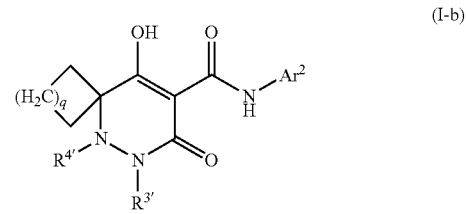

(I-b)

wherein
$R^{4'}$ is selected from $C_{1-4}$ alkyl;
q is an integer selected from 0 to 3;
$R^{3'}$ is selected from $C_{1-4}$ alkyl substituted with Re';
Re' is $C_{6-10}$ aryl, wherein the aryl group is optionally substituted with one to three substituents each independently selected from a halogen atom, $C_{1-4}$ alkoxy optionally substituted with one or more substituents $R^{12'}$, 4- to 6-membered heterocycloalkyloxy (the heterocycloalkyloxy group is optionally substituted with optionally $C_{1-4}$ alkoxy-substituted $C_{1-4}$ alkyl), a group —$(O(CH_2)_{q1})_{q2}$—$NR^{41'}R^{42'}$ (wherein q1 is an integer selected from 1 to 4, and q2 is an integer selected from 2 to 6), a group —$(O(CH_2)_{r1})_{r2}$—$C(O)NR^{43'}R^{44'}$ (wherein r1 is an integer selected from 1 to 4, and r2 is an integer selected from 1 to 4), a group —$(O(CH_2)_{s1})_{s2}$—$NR^{45'}$—$C(O)R^{46'}$ (wherein s1 and s2 are each independently an integer selected from 2 to 4), a group —$C(O)NR^{47'}R^{48'}$, pyridinyl, pyrrolyl, a group —$NR^{49'}R^{50'}$ and a group —$(O(CH_2)_{y1})_{y2}$—O—$CH_2$—$C(O)NR^{51'}R^{52'}$ (wherein y1 is an integer selected from 1 to 4, and y2 is an integer selected from 1 to 4);

each $R^{12'}$ is independently selected from ($C_{1-4}$ alkoxy) $C_{1-6}$ alkoxy, 5- or 6-membered heterocycloalkyl, and a group —$NR^{39'}R^{40'}$, wherein the 5- or 6-membered heterocycloalkyl group is optionally substituted with one or more substituents selected from oxo, a halogen atom, $C_{1-4}$ alkyl (wherein the alkyl group is optionally substituted with one or more hydroxy groups), ($C_{1-4}$ alkoxy)$C_{1-4}$ alkyl (wherein the alkoxy moiety is optionally substituted with one or more hydroxy groups), $C_{1-4}$ alkoxy, $C_{1-4}$ alkoxycarbonyl, $C_{1-4}$ alkylthio, morpholino, ($C_{1-3}$ alkyl)sulfonyl, and —$C(O)NR^{53'}R^{54'}$;

$R^{39'}$ is selected from a hydrogen and optionally $C_{1-6}$ alkoxy-substituted $C_{1-6}$ alkyl;

$R^{40'}$ is independently selected from a hydrogen atom, optionally $C_{1-6}$ alkoxy-substituted $C_{1-6}$ alkyl, (($C_{1-4}$ alkoxy) carbonyl)$C_{1-6}$ alkyl, hydroxy-substituted $C_{1-6}$ alkyl, a group —$(CH_2)_u$—$NR^{55'}R^{56'}$ (wherein u is an integer selected from 1 to 4), a group —$CH((CH_2)_{v1}COOR^{57'})$—$(CH_2)_{v2}$—$COOR^{57'}$ (wherein v1 is an integer selected from 0 to 2, and v2 is an integer selected from 1 to 3), a group —$(CH_2)_w$—

SO$_3$H (wherein w is an integer selected from 1 to 4), a group —(CH$_2$)$_{x1}$—CH(COOH)—(CH$_2$)$_{x2}$—SO$_3$H (wherein x1 is an integer selected from 0 to 2, and x2 is an integer selected from 1 to 3), 3- to 6-membered oxacycloalkyl, and a group —(CH$_2$)$_{t1}$—O—(CH$_2$)$_{t2}$—C(O)NR$^{58'}$R$^{59'}$ (wherein t1 and t2 are each independently an integer selected from 1 to 3);

R$^{41'}$ is a hydrogen atom or C$_{1-3}$ alkyl;

R$^{42'}$ is C$_{1-8}$ alkyl substituted with one or more hydroxy groups or (C$_{1-3}$ alkoxy)C$_{1-4}$ alkyl:

R$^{43'}$ is a hydrogen atom or C$_{1-3}$ alkyl;

R$^{44'}$ is C$_{1-8}$ alkyl substituted with one or more hydroxy groups, wherein R$^{43'}$ and R$^{44'}$ together with the nitrogen atom to which they are attached may form morpholino;

R$^{45'}$ is a hydrogen atom and C$_{1-3}$ alkyl;

R$^{46'}$ is C$_{1-6}$ alkyl substituted with one or more hydroxy groups;

R$^{47'}$ is C$_{1-3}$ alkyl;

R$^{48'}$ is (C$_{1-3}$ alkoxy)C$_{1-4}$ alkyl;

R$^{49'}$ is a hydrogen atom or C$_{1-4}$ alkyl;

R$^{50'}$ is —(CH$_2$)$_z$—NR$^{60'}$R$^{61'}$ (z is an integer selected from 1 to 4, R$^{60'}$ is a hydrogen atom and C$_{1-4}$ alkyl, and R$^{61'}$ is (C$_{1-3}$ alkoxy)C$_{1-4}$ alkyl, or R$^{60'}$ and R$^{61'}$ together with the nitrogen atom to which they are attached may form morpholino);

R$^{51'}$ is a hydrogen atom and C$_{1-4}$ alkyl;

R$^{52'}$ is C$_{1-8}$ alkyl substituted with one or more hydroxy groups;

R$^{53'}$ and R$^{54'}$ are each independently selected from a hydrogen atom and C$_{1-4}$ alkyl;

R$^{55'}$ is a hydrogen atom or C$_{1-4}$ alkyl;

R$^{56'}$ is (C$_{1-4}$ alkyl)carbonyl;

R$^{57'}$ is a hydrogen atom or C$_{1-4}$ alkyl;

R$^{58'}$ is a hydrogen atom or C$_{1-3}$ alkyl;

R$^{59'}$ is C$_{1-8}$ alkyl substituted with one or more hydroxy groups;

Ar$^2$ is phenyl or 5- or 6-membered heteroaryl, wherein the aryl and the heteroaryl groups are each optionally substituted with one to three substituents selected from Rb', Rc', and Rd';

Rb', Rc', and Rd' are each independently selected from optionally C$_{1-4}$ alkoxy-substituted C$_{1-5}$ alkoxy, a halogen atom, C$_{1-4}$ alkyl optionally substituted with one or more halogen atoms, and 5- or 6-membered heteroaryl optionally substituted with one or more substituents R$^{14'}$; and each R$^{14'}$ is independently selected from a halogen atom, cyano, C$_{1-4}$ alkyl optionally substituted with one or more halogen atoms, and C$_{1-4}$ alkylthio.

(6-2) The compound according to (6-1) or a salt thereof, or a solvate of the compound or the salt, wherein R$^{4'}$ is C$_{1-4}$ alkyl;

q is an integer selected from 0 to 3;

R$^{3'}$ is C$_{1-4}$ alkyl substituted with Re';

Re' is C$_{6-10}$ aryl, wherein the aryl group is optionally substituted with one to three substituents each independently selected from a halogen atom and C$_{1-4}$ alkoxy optionally substituted with one or more substituents R$^{12'}$;

each R$^{12'}$ is independently selected from 5- or 6-membered heterocycloalkyl and a group —NR$^{39'}$R$^{40'}$;

R$^{39'}$ and R$^{40'}$ are each independently selected from a hydrogen atom and optionally C$_{1-4}$ alkoxy-substituted C$_{1-4}$ alkyl;

Ar$^2$ is phenyl or 5- or 6-membered heteroaryl, wherein the phenyl and heteroaryl groups are each optionally substituted with one to three substituents selected from Rb', Rc', and Rd';

Rb', Rc', and Rd' are each independently selected from a halogen atom, C$_{1-4}$ alkyl optionally substituted with one or more halogen atoms, and 5- or 6-membered heteroaryl optionally substituted with one or more substituents R$^{14'}$; and each R$^{14'}$ is independently selected from a halogen atom, cyano, C$_{1-4}$ alkyl optionally substituted with one or more halogen atoms, and C$_{1-4}$ alkylthio.

(6-3) The compound according to (6-1) or (6-2) or a salt thereof, or a solvate of the compound or the salt, wherein Rb' is a halogen atom;

Rc' is a halogen atom or C$_{1-4}$ alkyl optionally substituted with one or more halogen atoms; and Rd' is a halogen atom or 5- or 6-membered heteroaryl optionally substituted with one or more substituents R$^{14'}$.

(6-4) The compound according to any of (6-1) to (6-3) or a salt thereof, or a solvate of the compound or the salt, wherein R$^{3'}$ is benzyl, wherein phenyl in the benzyl group is optionally substituted with one to three substituents each independently selected from a halogen atom and C$_{1-4}$ alkoxy optionally substituted with one or more substituents R$^{12'}$.

(6-5) The compound according to any of (6-1) to (6-4) or a salt thereof, or a solvate of the compound or the salt, wherein Re' is phenyl, wherein the phenyl group is optionally substituted with one substituent selected from Ri', Rj', and Rk', two substituents selected from combinations of Ri' and Rj', Ri' and Rk', and Rj' and Rk', or three substituents Ri', Rj', and Rk';

Ri' and Rj' are each independently a halogen atom; and

Rk' is C$_{1-4}$ alkoxy optionally substituted with one or more substituents R$^{12'}$.

(6-6) The compound according to any of (6-1) to (6-5) or a salt thereof, or a solvate of the compound or the salt, wherein Ar$^2$ is phenyl or pyridinyl;

Rd' is pyridinyl or pyrimidinyl; and

R$^{12'}$ is morpholinyl or —NR$^{39'}$R$^{40'}$.

(6-7) The compound according to any of (6-1) to (6-6) or a salt thereof, or a solvate of the compound or the salt, wherein R$^{12'}$ is selected from morpholinyl, [N—((C$_{1-3}$ alkoxy)C$_{1-4}$ alkyl)-N—(C$_{1-3}$alkyl)amino], and [N,N-di(C$_{1-3}$ alkyl)amino].

(6-8) The compound according to any of (6-1) to (6-3) or a salt thereof, or a solvate of the compound or the salt, wherein Ra is selected from a halogen atom, (morpholino)C$_{1-4}$alkoxy, [N—((C$_{1-3}$ alkoxy)C$_{1-4}$ alkyl)-N—(C$_{1-3}$alkyl)amino]C$_{1-4}$ alkoxy, and [N,N-di(C$_{1-3}$ alkyl)amino]C$_{1-4}$ alkoxy.

(6-9) The compound according to (6-5) or (6-6) or a salt thereof, or a solvate of the compound or the salt, wherein Rk is selected from (morpholino)C$_{1-4}$alkoxy, [N—((C$_{1-3}$ alkoxy)C$_{1-4}$ alkyl)-N—(C$_{1-3}$alkyl)amino]C$_{1-4}$ alkoxy, and [N,N-di(C$_{1-3}$ alkyl)amino]C$_{1-4}$alkoxy.

(6-10) The compound according to any of (6-1) to (6-6) or a salt thereof, or a solvate of the compound or the salt, wherein R$^{12'}$ is a group —NR$^{39'}$R$^{40'}$.

An alternative aspect of the present invention provides a pharmaceutical drug comprising a compound according to any of (4-1) to (4-17), (5-1) to (5-12), and (6-1) to (6-10) or a salt thereof, or a solvate of the compound or the salt.

A further alternative aspect of the present invention provides a pharmaceutical composition comprising a compound according to any of (4-1) to (4-17), (5-1) to (5-12), and (6-1) to (6-10) or a salt thereof, or a solvate of the compound or the salt.

A further alternative aspect of the present invention provides the compound according to any of (4-1) to (4-17), (5-1) to (5-12), and (6-1) to (6-10) or the salt thereof, or the solvate of the compound or the salt for use in the prevention and/or treatment of a disease selected from hyperphosphatemia, secondary hyperparathyroidism, and chronic renal failure.

A further alternative aspect of the present invention provides a NaPi-IIb inhibitor comprising a compound according to any of (4-1) to (4-17), (5-1) to (5-12), and (6-1) to (6-10) or a salt thereof, or a solvate of the compound or the salt.

A further alternative aspect of the present invention provides a preventive and/or therapeutic agent for a disease selected from hyperphosphatemia, secondary hyperparathyroidism, and chronic renal failure, the agent comprising a compound according to any of (4-1) to (4-17), (5-1) to (5-12), and (6-1) to (6-10) or a salt thereof, or a solvate of the compound or the salt as an active ingredient.

A further alternative aspect of the present invention provides a method for preventing and/or treating a disease selected from hyperphosphatemia, secondary hyperparathyroidism, and chronic renal failure, comprising administering a therapeutically effective amount of a compound according to any of (4-1) to (4-17), (5-1) to (5-12), and (6-1) to (6-10) or a salt thereof, or a solvate of the compound or the salt to a patient.

The present inventors have further found for the first time that a compound represented by the formula (I) has an excellent NaPi-IIb inhibitory effect, PiT-1 inhibitory effect, or PiT-2 inhibitory effect, that the compound is useful in the prevention or treatment of hyperphosphatemia, secondary hyperparathyroidism, chronic kidney disease, and arteriosclerosis associated with vascular calcification and in the prevention or suppression of ectipic calcification, and that the compound has excellent drug efficacy on these diseases.

Further, the inventors have found for the first time that inhibition of one or more transporters selected from PiT-1 and PiT-2 provides an excellent effect in the prevention or treatment of hyperphosphatemia, secondary hyperparathyroidism, chronic kidney disease, and arteriosclerosis associated with vascular calcification (herein after referred to as "hyperphosphatemia, etc.") and in the prevention or suppression of ectipic calcification.

Furthermore, the inventors have found that use of a substance that inhibits one or more transporters selected from NaPi-IIb, PiT-1, and PiT-2 in combination with a phosphorus adsorbent provides an excellent effect in the prevention or treatment of hyperphosphatemia, etc. and in the prevention or suppression of ectipic calcification, and completed the present invention.

One aspect of the present invention provides the following pharmaceutical compositions (7-1) to (7-60).

(7-1) A pharmaceutical composition comprising a compound represented by the formula (I) or a salt thereof, or a solvate of the compound or the salt:

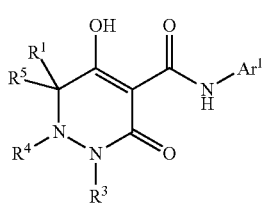

(I)

wherein $R^1$, $R^4$, and $R^5$ are as defined in any one of the following (1) to (3):

(1) $R^1$ is a hydrogen atom or $C_{1-10}$ alkyl;
$R^4$ is a hydrogen atom, $C_{1-4}$ alkyl optionally substituted with one or more substituents Rf, $C_{6-10}$ aryl optionally substituted with one or more substituents Rg, ($C_{1-6}$ alkyl)carbonyl, ($C_{6-10}$ aryl)carbonyl, a group —C(O)NR$^{37}$R$^{38}$, $C_{3-7}$ cycloalkyl, or 5- to 8-membered heterocycloalkyl; and
$R^5$ is a hydrogen atom or $C_{1-4}$ alkyl;

(2) $R^1$ and $R^5$ together with the carbon atom to which they are attached form a $C_{3-6}$ saturated carbocyclic ring; and
$R^4$ is as defined above; and (3) $R^1$ is a hydrogen atom or linear $C_{1-10}$ alkyl;
$R^4$ and $R^5$ together with the carbon atom and the nitrogen atom to which they are attached form a 5- to 8-membered saturated heterocyclic ring, wherein the saturated heterocyclic ring is optionally substituted with one or more substituents $R^2$;

$R^3$ is $C_{1-10}$ alkyl optionally substituted with one or more substituents Rh, or $R^3$ is $C_{1-4}$ alkyl substituted with Re;

$R^{37}$ and $R^{38}$ are each independently selected from a hydrogen atom and $C_{1-3}$ alkyl;

each $R^2$ is independently selected from $C_{1-5}$ alkyl and a halogen atom; and/or two or more substituents $R^2$ on the 5- to 8-membered saturated heterocyclic ring may together form $C_{1-5}$ alkylene that links the ring atoms to which they are attached;

each Rh is independently selected from a halogen atom, ($C_{1-4}$ alkoxy)carbonyl, and a group —(O(CH$_2$)$_a$)$_b$—C$_{1-4}$ alkoxy, wherein a is an integer selected from 2 to 4, and b is an integer selected from 1 to 4;

Re is $C_{6-10}$ aryl optionally substituted with one or more substituents Ra, or 5- to 10-membered heteroaryl optionally substituted with one or more substituents Ra;

each Rf is independently selected from a halogen atom, hydroxy, cyano, carboxy, ($C_{1-6}$ alkoxy)carbonyl, $C_{1-6}$ alkoxy, and $C_{6-10}$ aryl optionally substituted with one or more substituents Rg;

each Rg is independently selected from a halogen atom, $C_{1-6}$ alkyl, $C_{2-6}$ alkynyl, and $C_{1-6}$ alkoxy, wherein the alkyl, alkynyl, and alkoxy groups are each optionally substituted with one or more substituents selected from hydroxy and cyano;

each Ra is independently selected from a halogen atom, hydroxy, nitro, cyano, ($C_{1-4}$ alkoxy)carbonyl, 3- to 10-membered heterocycloalkyloxy (the heterocycloalkyloxy group is optionally substituted with optionally $C_{1-4}$ alkoxy-substituted $C_{1-4}$ alkyl), $C_{1-10}$ alkyl optionally substituted with one or more substituents $R^{10}$, $C_{2-10}$ alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, $C_{1-4}$ alkylthio optionally substituted with one or more substituents $R^{13}$, a group —(O(CH$_2$)$_{q1}$)$_{q2}$—NR$^{41}$R$^{42}$ (wherein q1 is an integer selected from 1 to 4, and q2 is an integer selected from 2 to 6), a group —(O(CH$_2$)$_{r1}$)$_{r2}$—C(O)NR$^{43}$R$^{44}$ (wherein r1 is an integer selected from 1 to 4, and r2 is an integer selected from 1 to 4), a group —(O(CH$_2$)$_{s1}$)$_{s2}$—NR$^{45}$—C(O)R$^{46}$ (wherein s1 and s2 are each independently an integer selected from 2 to 4), a group —C(O)NR$^{47}$R$^{48}$, pyridinyl, pyrrolyl, a group —NR$^{49}$R$^{50}$, and a group —(O(CH$_2$)$_{y1}$)$_{y2}$—O—CH$_2$—C(O)NR$^{51}$R$^{52}$ (wherein y1 is an integer selected from 1 to 4, and y2 is an integer selected from 1 to 4);

$R^{10}$, $R^{11}$, $R^{12}$, $R^{13}$, and $R^{15}$ are each independently selected from a halogen atom, hydroxy, carboxy, $C_{1-6}$ alkoxy optionally substituted with one or more hydroxy groups, ($C_{1-4}$ alkoxy)$C_{1-6}$ alkoxy, ($C_{1-4}$ alkoxy)carbonyl, a group —O($CH_2$)$_o$)$_p$—OH (wherein o and p are each independently an integer selected from 2 to 4), $C_{3-6}$ cycloalkyl optionally substituted with one or more hydroxy groups, 3- to 10-membered heterocycloalkyl, 5- to 10-membered heteroaryl, and a group —$NR^{39}R^{40}$, wherein the 3- to 10-membered heterocycloalkyl group is optionally substituted with one or more substituents selected from oxo, a halogen atom, $C_{1-4}$ alkyl (wherein the alkyl group is optionally substituted with one or more hydroxy groups), ($C_{1-4}$ alkoxy)$C_{1-4}$ alkyl (wherein the alkoxy moiety is optionally substituted with one or more hydroxy groups), $C_{1-4}$ alkoxy, ($C_{1-4}$ alkoxy)carbonyl, $C_{1-4}$ alkylthio, morpholino, ($C_{1-3}$ alkyl)sulfonyl, and —C(O)$NR^{53}R^{54}$;

$Ar^1$ is $C_{6-10}$ aryl or 5- to 10-membered heteroaryl, wherein the aryl and heteroaryl groups are each optionally substituted with one to three substituents selected from Rb, Rc, and Rd;

Rb, Rc, and Rd are each independently selected from optionally $C_{1-4}$ alkoxy-substituted $C_{1-5}$ alkoxy, a halogen atom, $C_{1-10}$ alkyl optionally substituted with one or more halogen atoms, a group —$SF_5$, cyano, hydroxy, 5- to 10-membered heterocycloalkyl optionally substituted with one or more substituents $R^{14}$, $C_{6-10}$ aryl optionally substituted with one or more substituents $R^{14}$, and 5- to 10-membered heteroaryl optionally substituted with one or more substituents $R^{14}$;

each $R^{14}$ is independently selected from a halogen atom, oxo, cyano, nitro, $C_{1-4}$ alkyl optionally substituted with one or more halogen atoms, $C_{1-4}$ alkoxy optionally substituted with one or more halogen atoms, ($C_{1-6}$ alkoxy)carbonyl, a group —$NR^{27}R^{28}$, a group —$SO_2NR^{35}R^{36}$, $C_{1-4}$ alkylthio, and 5- to 10-membered heterocycloalkyl;

$R^{27}$ and $R^{28}$ are each independently selected from a hydrogen atom and $C_{1-4}$ alkyl optionally substituted with ($C_{1-4}$ alkoxy)carbonyl;

$R^{35}$ and $R^{36}$ are each independently selected from a hydrogen atom and $C_{1-4}$ alkyl;

$R^{39}$ is a hydrogen atom or $C_{1-6}$ alkyl, wherein the alkyl is optionally substituted with hydroxy or $C_{1-6}$ alkoxy;

$R^{40}$ is a hydrogen atom, optionally $C_{1-6}$ alkoxy-substituted $C_{1-6}$ alkyl, (($C_{1-4}$ alkoxy)carbonyl)$C_{1-6}$ alkyl, hydroxy-substituted $C_{1-6}$ alkyl, $C_{1-4}$ alkyl substituted with a group —$NR^{55}R^{56}$, a group —CH(($CH_2$)$_{v1}$$COOR^{57}$)—($CH_2$)$_{v2}$—$COOR^{57}$ (wherein v1 is an integer selected from 0 to 2, and v2 is an integer selected from 1 to 3), a group —($CH_2$)$_w$—$SO_3H$ (wherein w is an integer selected from 1 to 4), a group —($CH_2$)$_{x1}$—CH(COOH)—($CH_2$)$_{x2}$—$SO_3H$ (wherein x1 is an integer selected from 0 to 2, and x2 is an integer selected from 1 to 3), 3- to 6-membered oxacycloalkyl, or a group —($CH_2$)$_{t1}$—O—($CH_2$)$_{t2}$—C(O)$NR^{58}R^{59}$ (wherein t1 and t2 are each independently an integer selected from 1 to 3);

$R^{41}$ is a hydrogen atom or $C_{1-3}$ alkyl;
$R^{42}$ is $C_{1-8}$ alkyl substituted with one or more hydroxy groups, or ($C_{1-3}$ alkoxy)$C_{1-4}$ alkyl;
$R^{43}$ is a hydrogen atom or $C_{1-3}$ alkyl;
$R^{44}$ is $C_{1-8}$ alkyl substituted with one or more hydroxy groups, or
$R^{43}$ and $R^{44}$ together with the nitrogen atom to which they are attached may form morpholino;
$R^{45}$ is a hydrogen atom or $C_{1-3}$ alkyl;
$R^{46}$ is $C_{1-6}$ alkyl substituted with one or more hydroxy groups;
$R^{47}$ is $C_{1-3}$ alkyl;
$R^{48}$ is ($C_{1-3}$ alkoxy)$C_{1-4}$ alkyl;
$R^{49}$ is a hydrogen atom and $C_{1-4}$ alkyl;

$R^{50}$ is —($CH_2$)$_z$—$NR^{60}R^{61}$ (wherein z is an integer selected from 1 to 4, $R^{60}$ is a hydrogen atom or $C_{1-4}$ alkyl, and $R^{61}$ is ($C_{1-3}$ alkoxy)$C_{1-4}$ alkyl, or $R^{60}$ and $R^{61}$ together with the nitrogen atom to which they are attached may form morpholino);
$R^{51}$ is a hydrogen atom or $C_{1-4}$ alkyl;
$R^{52}$ is $C_{1-8}$ alkyl substituted with one or more hydroxy groups;
$R^{53}$ and $R^{54}$ are each independently selected from a hydrogen atom and $C_{1-4}$ alkyl;
$R^{55}$ is a hydrogen atom or $C_{1-4}$ alkyl;
$R^{56}$ is ($C_{1-4}$ alkyl)carbonyl;
$R^{57}$ is a hydrogen atom or $C_{1-4}$ alkyl;
$R^{58}$ is a hydrogen atom or $C_{1-3}$ alkyl; and
$R^{59}$ is $C_{1-8}$ alkyl substituted with one or more hydroxy groups.

(7-2) The pharmaceutical composition of (7-1), wherein, in the compound represented by the formula (I), Rb is optionally $C_{1-4}$ alkoxy-substituted $C_{1-5}$ alkoxy or a halogen atom;

Rc is a halogen atom, $C_{1-10}$ alkyl optionally substituted with one or more halogen atoms, or a group —$SF_5$; and Rd is cyano, hydroxy, a halogen atom, $C_{1-4}$ alkyl optionally substituted with one or more halogen atoms, 5- to 10-membered heterocycloalkyl optionally substituted with one or more substituents $R^{14}$, $C_{6-10}$ aryl optionally substituted with one or more substituents $R^{14}$, or 5- to 10-membered heteroaryl optionally substituted with one or more substituents $R^{14}$.

(7-3) The pharmaceutical composition of (7-2) or (7-3), wherein, in the compound
represented by the formula (I), each Ra is independently selected from a halogen atom, hydroxy, nitro, cyano, ($C_{1-4}$ alkoxy)carbonyl, 3- to 10-membered heterocycloalkyloxy, $C_{1-10}$ alkyl optionally substituted with one or more substituents $R^{10}$, $C_{2-10}$ alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, and $C_{1-4}$ alkylthio optionally substituted with one or more substituents $R^{13}$;

$R^{10}$, $R^{11}$, $R^{12}$, $R^{13}$, and $R^{15}$ are each independently selected from a halogen atom, hydroxy, carboxy, $C_{1-6}$ alkoxy optionally substituted with one or more hydroxy groups, ($C_{1-4}$ alkoxy)carbonyl, a group —O($CH_2$)$_o$)$_p$—OH (wherein o and p are each independently an integer selected from 2 to 4), $C_{3-6}$ cycloalkyl optionally substituted with one or more hydroxy groups, 3- to 10-membered heterocycloalkyl, 5- to 10-membered heteroaryl, and a group —$NR^{39}R^{40}$, wherein the 3- to 10-membered heterocycloalkyl group is optionally substituted with one or more substituents selected from oxo, a halogen atom, and $C_{1-4}$ alkyl (wherein the alkyl group is optionally substituted with one or more hydroxy groups); and $R^{39}$ and $R^{40}$ are each independently selected from a hydrogen atom and optionally $C_{1-6}$ alkoxy-substituted $C_{1-6}$ alkyl.

(7-4) The pharmaceutical composition of any of (7-1) to (7-3), wherein, in the compound represented by the formula (I), 3- to 10-membered heterocycloalkyloxy in the definition of Ra is 3- to 6-membered heterocycloalkyloxy;

3- to 10-membered heterocycloalkyl in the definition of $R^{10}$, $R^{11}$, $R^{12}$, $R^{13}$ and $R^{15}$ is 3- to 6-membered heterocyloalkyl; and 5- to 10-membered heteroaryl in the definition of $R^{10}$, $R^{11}$, $R^{12}$, $R^{13}$ and $R^{15}$ is 5- to 6-membered heteroaryl.

(7-5) The pharmaceutical composition of any of (7-1), (7-2), and (7-4), wherein, in the compound represented by the formula (I), each Ra is independently selected from a halogen atom, hydroxy, nitro, cyano, ($C_{1-4}$ alkoxy)carbonyl, 3- to 6-membered heterocycloalkyloxy (the heterocycloalkyloxy group is optionally substituted with optionally $C_{1-4}$ alkoxy-substituted $C_{1-4}$ alkyl), $C_{1-10}$ alkyl optionally substituted with one or more substituents $R^{10}$, $C_{2-10}$ alkynyl optionally substituted with one or more substituents $R^{11}$, $C_{1-8}$ alkoxy optionally substituted with one or more substituents $R^{12}$, $C_{1-4}$ alkylthio optionally substituted with one or more substituents $R^{13}$, a group —$(O(CH_2)_{q1})_{q2}$—$NR^{41}R^{42}$, a group —$(O(CH_2)_{r1})_{r2}$—$C(O)NR^{43}R^{44}$, a group —$(O(CH_2)_{s1})_{s2}$—$NR^{45}$—$C(O)R^{46}$, a group —$C(O)NR^{47}R^{48}$ pyridinyl, pyrrolyl, a group —$NR^{49}R^{50}$, and a group —$(O(CH_2)_{y1})_{y2}$—O—$CH_2$—$NR_{51}R_{52}$;

$R^{10}$ is carboxy, 3- to 6-membered heterocycloalkyl, $C_{1-6}$ alkoxy optionally substituted with one or more hydroxy groups, or a group —$(O(CH_2)_o)_p$—OH;

$R^{11}$ is hydroxy, carboxy, 5- or 6-membered heterocycloalkyl optionally substituted with one or more oxo groups, $C_{1-6}$ alkoxy optionally substituted with one or more hydroxy groups, a group —$(O(CH_2)_o)_p$—OH, $C_{3-6}$ cycloalkyl optionally substituted with one or more hydroxy groups, or a group —$NR^{39}R^{40}$;

$R^{12}$ is a halogen atom, hydroxy, carboxy, $C_{1-6}$ alkoxy optionally substituted with one or more hydroxy groups, ($C_{1-4}$ alkoxy)$C_{1-6}$ alkoxy, ($C_{1-3}$ alkoxy)carbonyl, 3- to 6-membered heterocycloalkyl, 5- or 6-membered heteroaryl, or a group —$NR^{39}R^{40}$, wherein the 3- to 6-membered heterocycloalkyl group is optionally substituted with one or more substituents selected from oxo, a halogen atom, $C_{1-4}$ alkyl (wherein the alkyl group is optionally substituted with one or more hydroxy groups), ($C_{1-4}$ alkoxy)$C_{1-4}$ alkyl (wherein the alkoxy moiety is optionally substituted with one or more hydroxy groups), $C_{1-4}$ alkoxy, ($C_{1-4}$ alkoxy)carbonyl, $C_{1-4}$ alkylthio, morpholinyl, ($C_{1-3}$ alkyl)sulfonyl, and —$C(O)NR^{53}R^{54}$;

$R^{13}$ is 5- or 6-membered heterocycloalkyl; and o and p are each independently an integer selected from 2 to 4.

(7-6) The pharmaceutical composition of any of (7-1) to (7-5), wherein, in the compound represented by the formula (I), each Ra is independently selected from a halogen atom, hydroxy, nitro, cyano, ($C_{1-4}$ alkoxy)carbonyl, 3- to 6-membered heterocycloalkyloxy, $C_{1-10}$ alkyl optionally substituted with one or more substituents $R^{10}$, $C_{2-10}$ alkynyl optionally substituted with one or more substituents $R^1$, $C_{1-8}$ alkoxy optionally substituted with one or more substituents $R^{12}$, and $C_{1-4}$ alkylthio optionally substituted with one or more substituents $R^{13}$;

each $R^{10}$ is independently selected from carboxy, 3- to 6-membered heterocycloalkyl, $C_{1-6}$ alkoxy optionally substituted with one or more hydroxy groups, and a group —$(O(CH_2)_o)_p$—OH;

each $R^{11}$ is independently selected from hydroxy, carboxy, 5- or 6-membered heterocycloalkyl optionally substituted with one or more oxo groups, $C_{1-6}$ alkoxy optionally substituted with one or more hydroxy groups, a group —$(O(CH_2)_o)_p$—OH, and $C_{3-6}$ cycloalkyl optionally substituted with one or more hydroxy groups;

each $R^{12}$ is independently selected from a halogen atom, hydroxy, $C_{1-6}$ alkoxy optionally substituted with one or more hydroxy groups, ($C_{1-3}$ alkoxy)carbonyl, 3- to 6-membered heterocycloalkyl, 5- or 6-membered heteroaryl, and a group —$NR^{39}R^{40}$;

$R^{13}$ is 5- or 6-membered heterocycloalkyl; and o and p are each independently an integer selected from 2 to 4.

(7-7) The pharmaceutical composition of any of (7-1) (7-2), (7-4), and (7-5), wherein, in the compound represented by the formula (I), each Ra is independently selected from a halogen atom, hydroxy, nitro, cyano, $C_{1-6}$ alkyl, (carboxy)$C_{1-8}$ alkyl, (morpholino)$C_{1-4}$ alkyl, [HO—(($CH_2$)$_o$O)$_p$]$C_{1-6}$ alkyl, ($C_{1-6}$ alkoxy)$C_{1-8}$ alkyl (the $C_{1-6}$ alkoxy is optionally substituted with one or more hydroxy groups), $C_{1-6}$ alkoxy optionally substituted with one or more halogen atoms, [N—(($C_{1-3}$ alkoxy)$C_{1-4}$ alkyl)-N—($C_{1-3}$ alkyl)amino]$C_{1-4}$ alkoxy, $C_{1-6}$ alkoxy substituted with one or more hydroxy groups, (($C_{1-3}$ alkoxy)carbonyl)$C_{1-3}$ alkoxy, ($C_{1-6}$ alkoxy)$C_{1-8}$ alkoxy (the $C_{1-6}$ alkoxy is optionally substituted with one or more hydroxy groups), ($C_{1-3}$ alkoxy ($C_{1-4}$ alkoxy))$C_{1-4}$ alkoxy, (carboxy)$C_{1-8}$ alkoxy, (3- to 6-membered heterocycloalkyl)$C_{1-6}$ alkoxy (the heterocycloalkyl moiety is optionally substituted with one or more substituents selected from oxo, a halogen atom, $C_{1-4}$alkyl (wherein the alkyl is optionally substituted with one or more hydroxy groups), $C_{1-4}$ alkoxy$C_{1-4}$ alkyl (wherein the alkoxy moiety is optionally substituted with one or more hydroxyl groups), $C_{1-4}$ alkoxy, ($C_{1-4}$ alkoxy)carbonyl, $C_{1-4}$ alkylthio, morpholino, ($C_{1-3}$ alkyl)sulfonyl, and (di($C_{1-3}$ alkyl)amino) carbonyl), $C_{1-4}$ alkoxy substituted with a group —NH—CH(($CH_2$)$_{v1}$COOR$^{57}$)—($CH_2$)$_{v2}$—COOR$^{57}$, [N-(3- to 6-membered oxacycloalkyl)-N—($C_{1-3}$ alkyl)amino]$C_{1-4}$ alkoxy, [N,N-di((hydroxy)$C_{1-4}$ alkyl)-amino]$C_{1-4}$ alkoxy, [N—(($C_{1-3}$ alkoxy)carbonyl)$C_{1-3}$ alkyl-N—($C_{1-3}$ alkyl)amino] $C_{1-4}$ alkoxy, (pyridinyl)$C_{1-4}$ alkoxy, (pyrimidinyl)$C_{1-4}$ alkoxy, (1,2,4-triazolyl)$C_{1-4}$ alkoxy, [N-(hydroxy)$C_{1-4}$ alkyl-N—($C_{1-3}$ alkyl)amino]$C_{1-4}$ alkoxy, [N,N-di(($C_{1-3}$ alkoxy)$C_{1-4}$ alkyl)amino]$C_{1-6}$ alkoxy, [N,N-di($C_{1-3}$ alkyl)amino]$C_{1-6}$ alkoxy, [N—[N—($C_{1-4}$alkyl)carbonyl-N—($C_{1-3}$alkyl)amino]$C_{1-4}$ alkyl-N—($C_{1-3}$ alkyl)amino]$C_{1-4}$ alkoxy, [N—[N—($C_{1-4}$alkyl)carbonyl-amino]$C_{1-4}$ alkyl-N—($C_{1-3}$ alkyl)amino]$C_{1-4}$ alkoxy, a group —$(O(CH_2)_{r1})_{r2}$—$C(O)NR^{43}R^{44}$, a group —$(O(CH_2)_{q1})_{q2}$—$NR^{41}R^{42}$, $C_{1-4}$ alkoxy substituted with a group —NH—($CH_2$)$_w$—$SO_3$H, $C_{1-4}$ alkoxy substituted with a group —NH—($CH_2$)$_{x1}$—CH(COOH)—($CH_2$)$_{x2}$—$SO_3$H, a group —$(O(CH_2)_{s1})_{s2}$—$NR^{45}$—$C(O)R^{46}$, a group —$C(O)NR^{47}R^{48}$, pyridinyl, a group —$NR^{49}R^{50}$, a group —$(O(CH_2)_{y1})_{y2}$—O—$CH_2$—$C(O)NR^{51}R^{52}$, (carboxy)$C_{2-6}$ alkynyl, (5- to 6-membered heterocycloalkyl)$C_{2-6}$ alkynyl (the heterocycloalkyl is optionally substituted with one or more oxo groups), $C_{2-8}$ alkynyl optionally substituted with one or more hydroxy groups, [HO—(($CH_2$)$_o$O)$_p$]$C_{2-8}$ alkynyl, ($C_{1-6}$ alkoxy)$C_{2-8}$ alkynyl (the alkoxy is optionally substituted with one or more hydroxy groups), ($C_{3-6}$ cycloalkyl)$C_{2-6}$ alkynyl (the cycloalkyl is optionally substituted with one or more hydroxy groups), [N—(($C_{1-3}$ alkoxy)$C_{1-4}$ alkyl)-N—($C_{1-3}$ alkyl)amino]$C_{2-6}$ alkynyl, ($C_{1-3}$ alkoxy)carbonyl, (morpholino)$C_{1-4}$ alkylthio (the morpholino is optionally substituted with one or more oxo groups), 3- to 6-membered oxacycloalkyloxy, or 4- to 6-membered nitrogen containing heterocycloalkyloxy (the nitrogen containing heterocycloalkyl moiety is optionally substituted with one substituent selected from ($C_{1-3}$ alkoxy)$C_{1-4}$ alkyl and $C_{1-3}$ alkyl).

(7-8) The pharmaceutical composition of any of (7-1) (7-2), (7-4), (7-5), and (7-7), wherein, in the compound represented by the formula (I), each Ra is independently selected from a halogen atom, hydroxy, cyano, $C_{1-6}$ alkyl, (carboxy)$C_{1-8}$ alkyl, (morpholino)$C_{1-4}$ alkyl, ($C_{1-6}$ alkoxy)$C_{1-8}$ alkyl (the alkoxy is substituted with one or more hydroxy groups), $C_{1-6}$ alkoxy optionally substituted with one or more halogen atoms, [N—(($C_{1-3}$ alkoxy)$C_{1-4}$ alkyl)-

N—(C$_{1-3}$ alkyl)amino]C$_{1-4}$ alkoxy, (morpholino)C$_{1-6}$ alkoxy (the morpholino moiety may be substituted with one or two substituents selected from oxo and C$_{1-3}$ alkyl), (C$_{1-6}$ alkoxy)C$_{1-8}$ alkoxy (the C$_{1-6}$ alkoxy is optionally substituted with one or more hydroxy groups), (C$_{1-3}$ alkoxy(C$_{1-4}$ alkoxy))C$_{1-4}$ alkoxy, (carboxy)C$_{1-8}$ alkoxy, (pyrrolidinyl)C$_{1-4}$ alkoxy (the pyrrolidinyl moiety is optionally substituted with (C$_{1-4}$ alkoxy)C$_{1-3}$ alkyl, C$_{1-4}$ alkoxy substituted with a group —NH—CH((CH$_2$)$_{v1}$COOR$^{57}$)—(CH$_2$)$_{v2}$—COOR$^{57}$, [N-(oxetanyl)-N—(C$_{1-3}$ alkyl)amino]C$_{1-4}$ alkoxy, [N,N-di(C$_{1-3}$ alkyl)amino]C$_{1-6}$ alkoxy, a group —(O(CH$_2$)$_{r1}$)$_{r2}$—C(O)NR$^{43}$R$^{44}$, a group —(O(CH$_2$)$_{q1}$)$_{q2}$—NR$^{41}$R$^{42}$, C$_{1-4}$ alkoxy substituted with a group —NH—(CH$_2$)$_w$—SO$_3$H, C$_{1-4}$ alkoxy substituted with a group —NH—(CH$_2$)$_{x1}$—CH(COOH)—(CH$_2$)$_{x2}$—SO$_3$H, (carboxy)C$_{2-6}$ alkynyl, (morpholino)C$_{2-6}$ alkynyl, C$_{2-8}$ alkynyl optionally substituted with one or more hydroxy groups, [HO—((CH$_2$)$_o$O)$_p$]C$_{2-8}$ alkynyl, (C$_{1-6}$ alkoxy)C$_{2-8}$ alkynyl (the alkoxy is substituted with one or more hydroxy groups), and (C$_{1-3}$ alkoxy)carbonyl.

(7-9) The pharmaceutical composition of any of (7-1) to (7-8), wherein, in the compound represented by the formula (I), each Ra is independently selected from a halogen atom, hydroxy, cyano, C$_{1-3}$ alkyl, (carboxy)C$_{1-8}$ alkyl, (C$_{1-6}$ alkoxy)C$_{1-8}$ alkyl (the alkoxy is substituted with one or more hydroxy groups), C$_{1-3}$ alkoxy optionally substituted with one or more halogen atoms, [N—((C$_{1-3}$ alkoxy)C$_{1-4}$ alkyl)-N—(C$_{1-3}$ alkyl)amino]C$_{1-4}$ alkoxy, (morpholino)C$_{1-6}$ alkoxy, (C$_{1-6}$ alkoxy)C$_{1-8}$ alkoxy (the alkoxy is optionally substituted with one or more hydroxy groups), (carboxy)C$_{2-6}$ alkynyl, (morpholino)C$_{2-6}$ alkynyl, C$_{2-8}$ alkynyl optionally substituted with one or more hydroxy groups, [HO—((CH$_2$)$_o$O)$_p$]C$_{2-8}$ alkynyl, (C$_{1-6}$ alkoxy)C$_{2-8}$ alkynyl substituted with one or more hydroxy groups, and (C$_{1-3}$ alkoxy)carbonyl.

(7-10) The pharmaceutical composition of any of (7-1) to (7-9), wherein, in the compound represented by the formula (I), R$^3$ is methyl substituted with Re.

(7-11) The pharmaceutical composition of any of (7-1) to (7-10), wherein, in the compound represented by the formula (I), R$^3$ is benzyl optionally substituted with one or more substituents Ra on the benzene ring.

(7-12) The pharmaceutical composition of any of (7-1) to (7-11), wherein, in the compound represented by the formula (I), R$^3$ is benzyl optionally substituted with one to three substituents Ra on the benzene ring.

(7-13) The pharmaceutical composition of any of (7-1) to (7-6) and (7-10) to (7-12), wherein, in the compound represented by the formula (I), Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri is a halogen atom or C$_{1-3}$ alkoxy;

Rj is a halogen atom, nitro, or cyano; and

Rk is hydroxy, a halogen atom, (C$_{1-4}$ alkoxy)carbonyl, 5- to 10-membered heterocycloalkyloxy (the heterocycloalkyloxy is optionally substituted with optionally C$_{1-4}$ alkoxy-substituted C$_{1-4}$ alkyl), C$_{1-10}$ alkyl optionally substituted with one or more substituents R$^{10}$, C$_{2-10}$ alkenyl optionally substituted with one or more substituents R$^{15}$, C$_{2-10}$ alkynyl optionally substituted with one or more substituents R$^{11}$, C$_{1-8}$ alkoxy optionally substituted with one or more substituents R$^{12}$, or C$_{1-4}$ alkylthio optionally substituted with one or more substituents R$^{13}$, a group —(O(CH$_2$)$_{q1}$)$_{q2}$—NR$^{41}$R$^{42}$, a group —(O(CH$_2$)$_{r1}$)$_{r2}$—C(O)NR$^{43}$R$^{44}$, a group —(O(CH$_2$)$_{s1}$)$_{s2}$—NR$^{45}$—C(O)R$^{46}$, a group —C(O)NR$^{47}$R$^{48}$, pyridinyl, pyrrolyl, a group —NR$^{49}$R$^{50}$, or a group —(O(CH$_2$)$_{y1}$)$_{y2}$—O—CH$_2$—C(O)NR$^{51}$R$^{52}$.

(7-14) The pharmaceutical composition of any of (7-13), wherein, in the compound represented by the formula (I), Rk is hydroxy, a halogen atom, (C$_{1-4}$ alkoxy)carbonyl, 3- to 6-membered heterocycloalkyloxy (the heterocycloalkyloxy moiety is optionally substituted with optionally C$_{1-4}$ alkoxy-substituted C$_{1-4}$ alkyl), C$_{1-10}$ alkyl optionally substituted with one or more substituents R$^{10}$, C$_{2-10}$ alkynyl optionally substituted with one or more substituents R$^{11}$, C$_{1-8}$ alkoxy optionally substituted with one or more substituents R$^{12}$, and C$_{1-4}$ alkylthio optionally substituted with one or more substituents R$^{13}$, a group —(O(CH$_2$)$_{q1}$)$_{q2}$—NR$^{41}$R$^{42}$, a group —(O(CH$_2$)$_{r1}$)$_{r2}$—C(O)NR$^{43}$R$^{44}$, a group —(O(CH$_2$)$_{s1}$)$_{s2}$—NR$^{45}$—C(O)R$^{46}$, a group —C(O)NR$^{47}$R$^{48}$, pyridinyl, pyrrolyl, a group —NR$^{49}$R$^{50}$, or a group —(O(CH$_2$)$_{y1}$)$_{y2}$—O—CH$_2$—C(O)NR$^{51}$R$^{52}$;

each R$^{10}$ is independently carboxy, hydroxy, morpholinyl, C$_{1-6}$ alkoxy optionally substituted with one or more hydroxy groups, or a group —(O(CH$_2$)$_o$)$_p$—OH;

each R$^{11}$ is independently hydroxy, carboxy, morpholinyl optionally substituted with one or more oxo groups, C$_{1-6}$ alkoxy optionally substituted with one or more hydroxy groups, a group —(O(CH$_2$)$_o$)$_p$—OH, C$_{3-6}$ cycloalkyl optionally substituted with one or more hydroxy groups or a group —NR$^{39}$R$^{40}$;

R$^{12}$ is a halogen atom, hydroxy, carboxy, C$_{1-6}$ alkoxy optionally substituted with one or more hydroxy groups, (C$_{1-4}$ alkoxy)C$_{1-6}$ alkoxy, (C$_{1-3}$ alkoxy)carbonyl, 3- to 6-membered heterocycloalkyl, 5- or 6-membered heteroaryl containing one nitrogen atom, or a group —NR$^{39}$R$^{40}$, wherein the 3- to 6-membered heterocycloalkyl group is optionally substituted with one or more substituents selected from oxo, a halogen atom, C$_{1-4}$ alkyl (wherein the alkyl group is optionally substituted with one or more hydroxy groups), (C$_{1-4}$ alkoxy)C$_{1-4}$ alkyl (wherein the alkoxy moiety is optionally substituted with one or more hydroxy groups), C$_{1-4}$ alkoxy, (C$_{1-4}$ alkoxy)carbonyl, C$_{1-4}$ alkylthio, morpholinyl, (C$_{1-3}$ alkyl)sulfonyl, and —C(O)NR$^{53}$R$^{54}$;

R$^{13}$ is morpholinyl; and o and p are each independently an integer selected from 2 to 4.

(7-15) The pharmaceutical composition of any of (7-1) to (7-6) and (7-10) to (7-13), wherein, in the compound represented by the formula (I), Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri is a halogen atom or C$_{1-3}$ alkoxy;

Rj is a halogen atom, nitro, or cyano; and

Rk is hydroxy, a halogen atom, (C$_{1-4}$ alkoxy)carbonyl, 5- to 10-membered heterocycloalkyloxy, C$_{1-10}$ alkyl optionally substituted with one or more substituents R$^{10}$, C$_{2-10}$ alkenyl optionally substituted with one or more substituents R$^{15}$, C$_{2-10}$ alkynyl optionally substituted with one or more substituents R$^{11}$, C$_{1-8}$ alkoxy optionally substituted with one or more substituents R$^{12}$, or C$_{1-4}$ alkylthio optionally substituted with one or more substituents R$^{13}$.

(7-16) The pharmaceutical composition of any of (7-14) or (7-15), wherein, in the compound represented by the formula (I), Rk is hydroxy, a halogen atom, (C$_{1-4}$ alkoxy)carbonyl, 3- to 6-membered heterocycloalkyloxy, C$_{1-10}$ alkyl optionally substituted with one or more substituents R$^{10}$, C$_{2-10}$ alkynyl optionally substituted with one or more substituents $R^1$, $C_{1-8}$ alkoxy optionally substituted with one or more substituents $R^{12}$, or $C_{1-4}$ alkylthio optionally substituted with one or more substituents $R^{13}$;

each $R^{10}$ is independently selected from hydroxy, carboxy, morpholinyl, $C_{1-6}$ alkoxy optionally substituted with one or more hydroxy groups, and a group —$(O(CH_2)_o)_p$—OH;

each $R^{11}$ is independently selected from hydroxy, carboxy, morpholinyl optionally substituted with one or more oxo groups, $C_{1-6}$ alkoxy optionally substituted with one or more hydroxy groups, a group —$(O(CH_2)_o)_p$—OH, and $C_{3-6}$ cycloalkyl optionally substituted with one or more hydroxy groups;

each $R^{12}$ is independently selected from a halogen atom, hydroxy, $C_{1-6}$ alkoxy optionally substituted with one or more hydroxy groups, $(C_{1-3}$ alkoxy)carbonyl, 3- to 6-membered heterocycloalkyl, pyridinyl, pyrroryl, and a group —$NR^{39}R^{40}$;

$R^{13}$ is morpholinyl; and o and p are each independently an integer selected from 2 to 4.

(7-17) The pharmaceutical composition of (7-13) or (7-14), wherein, in the compound represented by the formula (I), Rk is a halogen atom, hydroxy, $C_{1-6}$ alkyl, (carboxy)$C_{1-8}$ alkyl, (morpholino)$C_{1-4}$ alkyl, [HO—$((CH_2)_oO)_p$]$C_{1-6}$ alkyl, $(C_{1-6}$ alkoxy)$C_{1-8}$ alkyl (the alkoxy is optionally substituted with one or more hydroxy groups), $C_{1-6}$ alkoxy optionally substituted with one or more halogen atoms, [N—$((C_{1-3}$ alkoxy)$C_{1-4}$ alkyl)-N—$(C_{1-3}$ alkyl)amino]$C_{1-4}$ alkoxy, $C_{1-6}$ alkoxy substituted with one or more hydroxy groups, $((C_{1-3}$ alkoxy)carbonyl)$C_{1-3}$ alkoxy, $(C_{1-6}$ alkoxy)$C_{1-8}$ alkoxy (the $C_{1-6}$ alkoxy is optionally substituted with one or more hydroxy groups), $(C_{1-3}$ alkoxy($C_{1-4}$ alkoxy))$C_{1-4}$ alkoxy, (carboxy)$C_{1-8}$ alkoxy, (3- to 6-membered heterocycloalkyl)$C_{1-6}$ alkoxy (the heterocycloalkyl moiety contains one to three heteroatoms selected from O or N, and is optionally substituted with one or more substituents selected from oxo, a halogen atom, $C_{1-4}$ alkyl (wherein the alkyl moiety is optionally substituted with one or more hydroxy groups), $(C_{1-4}$ alkoxy)$C_{1-4}$ alkyl (the alkoxy moiety is optionally substituted with one or more hydroxy groups), $C_{1-4}$ alkoxy, $(C_{1-4}$ alkoxy)carbonyl, $C_{1-4}$ alkylthio, morpholino, $(C_{1-3}$ alkyl)sulfonyl, and (di($C_{1-3}$ alkyl)amino)carbonyl), $C_{1-4}$ alkoxy substituted with a group —NH—CH$((CH_2)_{v1}COOR^{57})$—$(CH_2)_{v2}$—COOR$^{57}$, [N-(3- to 6-membered oxacycloalkyl)-N—$(C_{1-3}$ alkyl)amino]$C_{1-4}$ alkoxy, [N,N-di((hydroxy)$C_{1-4}$ alkyl)-amino]$C_{1-4}$ alkoxy, [N—$((C_{1-3}$ alkoxy)carbonyl)$C_{1-3}$ alkyl-N—$(C_{1-3}$ alkyl)amino]$C_{1-4}$ alkoxy, (pyridinyl)$C_{1-4}$ alkoxy, (pyrimidinyl)$C_{1-4}$ alkoxy, (1,2,4-triazolyl)$C_{1-4}$ alkoxy, [N-(hydroxy)$C_{1-4}$ alkyl-N—$(C_{1-3}$ alkyl)amino]$C_{1-4}$ alkoxy, [N,N-di($C_{1-3}$ alkoxy($C_{1-3}$ alkyl))amino]$C_{1-6}$ alkoxy, [N,N-di($C_{1-3}$alkyl)amino]$C_{1-6}$ alkoxy, [N—[N—$(C_{1-4}$ alkyl)carbonyl-N—$(C_{1-3}$ alkyl)amino]$C_{1-4}$ alkyl-N—$(C_{1-3}$ alkyl)amino]$C_{1-4}$ alkoxy, [N—[N—$(C_{1-4}$ alkyl)carbonyl-amino]$C_{1-4}$ alkyl-N—$(C_{1-3}$ alkyl)amino]$C_{1-4}$ alkoxy, a group —$(O(CH_2)_{r1})_{r2}$—C(O)NR$^{43}$R$^{44}$, a group —$(O(CH_2)_{q1})_{q2}$—NR$^{41}$R$^{42}$, $C_{1-4}$ alkoxy substituted with a group —NH—$(CH_2)_w$—SO$_3$H, $C_{1-4}$ alkoxy substituted with a group —NH—$(CH_2)_{x1}$—CH(COOH)—$(CH_2)_{x2}$—SO$_3$H, a group —$(O(CH_2)_{s1})_{s2}$—NR$^{45}$—C(O)R$^{46}$, a group —C(O)NR$^{47}$R$^{48}$, pyridinyl, a group —NR$^{49}$R$^{50}$, a group —$(O(CH_2)_{y1})_{y2}$—O—CH$_2$—C(O)NR$^{51}$R$^{52}$, (carboxy)$C_{2-8}$ alkynyl, (morpholino) $C_{2-6}$ alkynyl (the morpholino is optionally substituted with one or more oxo groups), $C_{2-8}$ alkynyl optionally substituted with one or more hydroxy groups, [HO—$((CH_2)_oO)_p$]$C_{2-8}$ alkynyl, $(C_{1-6}$ alkoxy)$C_{2-8}$ alkynyl (the alkoxy is optionally substituted with one or more hydroxy groups), $(C_{3-6}$ cycloalkyl)$C_{2-6}$ alkynyl (the cycloalkyl is optionally substituted with one or more hydroxy groups), $(C_{1-3}$ alkoxy)carbonyl, (morpholino)$C_{1-4}$ alkylthio, 3- to 6-membered oxacycloalkyloxy, or 3- to 6-membered nitrogen containing heterocycloalkyloxy (the nitrogen containing heterocycloalkyl moiety is optionally substituted with one substituent selected from $(C_{1-3}$ alkoxy)$C_{1-4}$ alkyl and $C_{1-3}$ alkyl).

(7-18) The pharmaceutical composition of (7-13), (7-14), or (7-17), wherein, in the compound represented by the formula (I), Rk is hydroxy, a halogen atom, $C_{1-6}$ alkyl, (carboxy)$C_{1-8}$ alkyl, (morpholino)$C_{1-4}$ alkyl, $(C_{1-6}$ alkoxy) $C_{1-8}$ alkyl (the alkoxy is substituted with one or more hydroxy groups), $C_{1-6}$ alkoxy optionally substituted with one or more halogen atoms, [N—$((C_{1-3}$ alkoxy)$C_{1-4}$ alkyl)-N—$(C_{1-3}$ alkyl)amino]$C_{1-4}$ alkoxy, (morpholino)$C_{1-6}$ alkoxy, $(C_{1-6}$ alkoxy)$C_{1-8}$ alkoxy (the $C_{1-6}$ alkoxy is optionally substituted with one or more hydroxy groups), $(C_{1-3}$ alkoxy($C_{1-4}$ alkoxy))$C_{1-4}$ alkoxy, (carboxy)$C_{1-8}$ alkoxy, (pyrrolidinyl)$C_{1-4}$ alkoxy (the pyrrolidinyl moiety is substituted with $(C_{1-4}$ alkoxy)$C_{1-3}$ alkyl), $C_{1-4}$ alkoxy substituted with a group —NH—CH$((CH_2)_{v1}COOR^{57})$—$(CH_2)_{v2}$—COOR$^{57}$, [N-(oxetanyl)-N—$(C_{1-3}$ alkyl)amino]$C_{1-4}$ alkoxy, [N,N-di($C_{1-3}$ alkyl)amino]$C_{1-6}$ alkoxy, a group —$(O(CH_2)_{r1})_{r2}$—C(O)NR$^{43}$R$^{44}$, a group —$(O(CH_2)_{q1})_{q2}$—NR$^{41}$R$^{42}$, $C_{1-4}$ alkoxy substituted with a group —NH—$(CH_2)_w$—SO$_3$H, $C_{1-4}$ alkoxy substituted with a group —NH—$(CH_2)_{x1}$—CH(COOH)—$(CH_2)_{x2}$—SO$_3$H, (carboxy)$C_{2-8}$ alkynyl, (morpholino)$C_{2-6}$ alkynyl, $C_{2-8}$ alkynyl optionally substituted with one or more hydroxy groups, [HO—$((CH_2)_oO)_p$]$C_{2-8}$ alkynyl, $(C_{1-6}$ alkoxy)$C_{2-8}$ alkynyl (the alkoxy is substituted with one or more hydroxy groups), or $(C_{1-3}$ alkoxy)carbonyl.

(7-19) The pharmaceutical composition of any of (7-13) to (7-18), wherein, in the compound represented by the formula (I), Rk is hydroxy, a halogen atom, $C_{1-6}$ alkyl, (carboxy)$C_{1-8}$ alkyl, $(C_{1-6}$ alkoxy)$C_{1-8}$ alkyl (the alkoxy is substituted with one or more hydroxy groups), $C_{1-3}$ alkoxy optionally substituted with one or more halogen atoms, [N—$((C_{1-3}$ alkoxy)$C_{1-4}$ alkyl)-N—$(C_{1-3}$ alkyl)amino]$C_{1-4}$ alkoxy, (morpholino)$C_{1-6}$ alkoxy, $(C_{1-6}$ alkoxy)$C_{1-8}$ alkoxy (the $C_{1-6}$ alkoxy is substituted with one or more hydroxy groups), (carboxy)$C_{2-8}$ alkynyl, (morpholino)$C_{2-6}$ alkynyl, $C_{2-8}$ alkynyl optionally substituted with one or more hydroxy groups, [HO—$((CH_2)_oO)_p$]$C_{2-8}$ alkynyl, $(C_{1-6}$ alkoxy)$C_{2-8}$ alkynyl (the alkoxy is substituted with one or more hydroxy groups), or $(C_{1-3}$ alkoxy)carbonyl.

(7-20) The pharmaceutical composition of any of (7-1) to (7-19), wherein, in the compound represented by the formula (I), $R^1$, $R^4$, and $R^5$ are as defined in any one of the following (1) to (3):

(1) $R^1$ is a hydrogen atom or $C_{1-6}$ alkyl;

$R^4$ is $C_{1-4}$ alkyl optionally substituted with one or more halogen atom(s), or phenyl; and $R^5$ is a hydrogen atom or $C_{1-4}$ alkyl;

(2) $R^1$ and $R^5$ together with the carbon atom to which they are attached form a $C_{3-6}$ saturated carbocyclic ring; and $R^4$ is as defined above; and (3) $R^1$ is a hydrogen atom or linear $C_{1-6}$ alkyl;

$R^4$ and $R^5$ together with the carbon atom and the nitrogen atom to which they are attached form a 5- to 8-membered saturated heterocyclic ring, wherein the saturated heterocyclic ring is optionally substituted with one or more substituents $R^2$.

(7-21) The pharmaceutical composition of any of (7-1) to (7-20), wherein, in the compound represented by the formula (I), $R^1$ is $C_{1-6}$ alkyl;

$R^4$ is $C_{1-4}$ alkyl, optionally substituted with one or more halogen atoms, or phenyl; and $R^5$ is a hydrogen atom or $C_{1-4}$ alkyl.

(7-22) The pharmaceutical composition of any of (7-1) to (7-20), wherein, in the compound represented by the formula (I), $R^1$ is a hydrogen atom or linear $C_{1-4}$ alkyl;

$R^4$ and $R^5$ together with the carbon atom and the nitrogen atom to which they are attached form a 5- to 8-membered saturated heterocyclic ring, wherein the saturated heterocyclic ring is optionally substituted with one or more substituents $R^2$.

(7-23) The pharmaceutical composition of any of (7-1) to (7-20), wherein, in the compound represented by the formula (I), $R^1$ and $R^5$ together with the carbon atom to which they are attached form a $C_{3-6}$ saturated carbocyclic ring; and $R^4$ is $C_{1-4}$ alkyl.

(7-24) The pharmaceutical composition of any of (7-1) to (7-4), (7-10) to (7-12) and (7-20), wherein, in the compound represented by the formula (I), $R^1$, $R^4$, and $R^5$ are as defined in the following (1) or (2):

(1) $R^1$ is $C_{1-6}$ alkyl;

$R^4$ is optionally halogen atom-substituted $C_{1-4}$ alkyl or phenyl; and $R^5$ is a hydrogen atom or $C_{1-4}$ alkyl; or (2) $R^1$ and $R^5$ together with the carbon atom to which they are attached form a $C_{3-6}$ saturated carbocyclic ring; and $R^4$ is as defined above;

$R^3$ is $C_{1-4}$ alkyl substituted with Re;

Re is phenyl optionally substituted with one or more substituents Ra;

each Ra is independently selected from a halogen atom, $C_{2-6}$ alkynyl optionally substituted with one or more substituents $R^{11}$, $C_{1-6}$ alkoxy optionally substituted with one or more substituents $R^{12}$, 3- to 6-membered heterocycloalkyloxy (the heterocycloalkyloxy group is optionally substituted with optionally $C_{1-4}$ alkoxy-substituted $C_{1-4}$ alkyl), a group —$O(CH_2)_{q1})_{q2}$—$NR^{41}R^{42}$, a group —$(O(CH_2)_{r1})_{r2}$—$C(O)NR^{43}R^{44}$, a group —$(O(CH_2)_{s1})_{s2}$—$NR^{45}$—$C(O)R^{46}$, a group —$C(O)NR^{47}R^{48}$, pyridinyl, pyrrolyl, a group —$NR^{49}R^{50}$, and a group —$(O(CH_2)_{y1})_{y2}$—O—$CH_2$—$C(O)NR^{51}R^{52}$;

$R^{11}$ and $R^{12}$ are each independently selected from halogen atom, hydroxy, carboxy, $C_{1-6}$ alkoxy optionally substituted with one or more hydroxy, $(C_{1-4}$ alkoxy)$C_{1-6}$ alkoxy, 3- to 6-membered heterocycloalkyl, 5- to 6-membered heteroaryl, and a group —$NR^{39}R^{40}$, wherein the 3- to 6-membered heterocycloalkyl group is optionally substituted with one or two substituents selected from oxo, a halogen atom, $C_{1-4}$ alkyl (wherein the alkyl group is optionally substituted with one or more hydroxy groups), $(C_{1-4}$ alkoxy)$C_{1-4}$ alkyl (wherein the alkoxy moiety is optionally substituted with one or more hydroxy groups), $C_{1-4}$ alkoxy, $(C_{1-4}$ alkoxy)carbonyl, $C_{1-4}$ alkylthio, morpholino, $(C_{1-3}$ alkyl)sulfonyl, and —$C(O)NR^{53}R^{54}$;

$Ar^1$ is phenyl or 5- or 6-membered heteroaryl, wherein the phenyl and heteroaryl groups are each optionally substituted with one to three substituents selected from Rb, Rc, and Rd;

Rb, Rc, and Rd are each independently selected from a halogen atom, $C_{1-4}$ alkyl optionally substituted with one or more halogen atoms, phenyl optionally substituted with one or more substituents $R^{14}$, and 5- or 6-membered heteroaryl optionally substituted with one or more substituents $R^{14}$; and each $R^{14}$ is independently selected from a halogen atom, cyano, $C_{1-4}$ alkyl optionally substituted with one or more halogen atoms, $C_{1-4}$ alkoxy, a group —$SO_2NR^{35}R^{36}$ (wherein $R^{35}$ and $R^{36}$ are each independently selected from $C_{1-4}$ alkyl), and $C_{1-4}$ alkylthio.

(7-25) The pharmaceutical composition of any of (7-1) to (7-7), (7-10) to (7-12), (7-20), and (7-24), wherein, in the compound represented by the formula (I), each Ra is independently selected from a halogen atom, [N—(($C_{1-3}$ alkoxy)$C_{1-4}$ alkyl)-N—($C_{1-3}$ alkyl)amino]$C_{1-4}$ alkoxy, $(C_{1-4}$ alkoxy)$C_{1-6}$ alkoxy (the $C_{1-4}$ alkoxy moiety is optionally substituted with one or more hydroxy groups), $(C_{1-3}$ alkoxy($C_{1-4}$ alkoxy))$C_{1-4}$ alkoxy, (carboxy)$C_{1-6}$ alkoxy, (3- to 6-membered heterocycloalkyl)$C_{1-6}$ alkoxy (the heterocycloalkyl moiety is optionally substituted with one or two substituents selected from oxo, a halogen atom, $C_{1-4}$ alkyl (the alkyl is optionally substituted with one or more hydroxy groups), $(C_{1-4}$ alkoxy)$C_{1-4}$ alkyl (the alkoxy moiety is optionally substituted with one or more hydroxy groups), $C_{1-4}$alkoxy, $(C_{1-4}$ alkoxy)carbonyl, $C_{1-4}$ alkylthio, morpholino, $(C_{1-3}$ alkyl)sulfonyl, and $(di(C_{1-3}$ alkyl)amino)carbonyl), $C_{1-4}$ alkoxy substituted with a group —NH—CH(($CH_2)_{v1}$COOR$^{57}$)—$(CH_2)_{v2}$—COOR$^{57}$, [N-(3- to 6-membered oxacycloalkyl)-N—$(C_{1-3}$ alkyl)amino]$C_{1-4}$ alkoxy, [N,N-di((hydroxy)$C_{1-4}$ alkyl)-amino]$C_{1-4}$ alkoxy, [N—(($C_{1-3}$ alkoxy)carbonyl)$C_{1-3}$ alkyl-N—$(C_{1-3}$ alkyl)amino]$C_{1-4}$ alkoxy, (1,2,4-triazolyl)$C_{1-4}$alkoxy, [N-(hydroxy)$C_{1-4}$ alkyl-N—$(C_{1-3}$ alkyl)amino]$C_{1-4}$ alkoxy, [N,N-di(($C_{1-3}$ alkoxy)$C_{1-4}$ alkyl)amino]$C_{1-6}$ alkoxy, [N,N-di($C_{1-3}$alkyl)amino]$C_{1-6}$ alkoxy, [N—[N—$(C_{1-4}$alkyl)carbonyl-N—$(C_{1-3}$alkyl)amino]$C_{1-4}$ alkyl-N—$(C_{1-3}$ alkyl)amino]$C_{1-4}$ alkoxy, [N—[N—$(C_{1-4}$alkyl)carbonyl-amino]$C_{1-4}$ alkyl-N—$(C_{1-3}$ alkyl)amino]$C_{1-4}$ alkoxy, $C_{1-6}$ alkoxy optionally substituted with one or more halogen atoms, a group —$(O(CH_2)_{r1})_{r2}$—$C(O)NR^{43}R^{44}$, a group —$(O(CH_2)_{q1})_{q2}$—$NR^{41}R^{42}$, $C_{1-4}$ alkoxy substituted with a group —NH—$(CH_2)_w$—$SO_3H$, $C_{1-4}$ alkoxy substituted with a group —NH—$(CH_2)_{x1}$—CH(COOH)—$(CH_2)_{x2}$—$SO_3H$, a group —$(O(CH_2)_{s1})_{s2}$—$NR^{45}$—$C(O)R^{46}$, a group —$C(O)NR^{47}R^{48}$, pyridinyl, a group —$NR^{49}R^{50}$, a group —$(O(CH_2)_{y1})_{y2}$—O—$CH_2$—$C(O)NR^{51}R^{52}$, (3- to 6-membered heterocycloalkyl)$C_{2-6}$ alkynyl (the heterocycloalkyl moiety is optionally substituted with one oxo group), [N—(($C_{1-3}$alkoxy)$C_{1-4}$alkyl-N—$(C_{1-3}$alkyl)amino]$C_{2-6}$alkynyl, $C_{2-8}$ alkynyl optionally substituted with one or more hydroxy groups, 3- to 6-membered oxacycloalkyloxy, or 4- to 6-membered nitrogen containing heterocycloalkyloxy (the heterocycloalkyl moiety is optionally substituted with one substituent selected from $(C_{1-3}$ alkoxy)$C_{1-4}$ alkyl and $C_{1-3}$ alkyl).

(7-26) The pharmaceutical composition of any of (7-1) to (7-4), (7-10) to (7-13), (7-20) to (7-25), wherein, in the compound represented by the formula (I), Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri is a halogen atom;

Rj is a halogen atom; and

Rk is a halogen atom, 3- to 6-membered heterocycloalkyloxy (the heterocycloalkyl moiety comprises one heteroatom selected from O and N and is optionally substituted with optionally $C_{1-4}$ alkoxy-substituted $C_{1-4}$ alkyl), optionally $R^{11}$-substituted $C_{2-6}$ alkynyl, optionally $R^{12}$-substituted $C_{1-6}$ alkoxy, a group —$(O(CH_2)_{q1})_{q2}$—$NR^{41}R^{42}$, a group —$(O(CH_2)_{r1})_{r2}$—$C(O)NR^{43}R^{44}$, a group —$(O(CH_2)_{s1})_{s2}$—$NR^{45}$—$C(O)R^{46}$, a group —$C(O)NR^{47}R^{48}$, a group —$NR^{49}R^{50}$, or a group —$(O(CH_2)_{y1})_{y2}$—O—$CH_2$—$CH(O)NR^{51}R^{52}$.

(7-27) The pharmaceutical composition of any of (7-24) to (7-26), wherein, in the compound represented by the formula (I), $R^{11}$ is morpholino;

$R^{12}$ is selected from 5- to 6-membered heterocycloalkyl which contains one or two hetero atoms selected from O and N, $(C_{1-4}$alkoxy$)C_{1-6}$alkoxy or a group $-NR^{39}R^{40}$.

(7-28) The pharmaceutical composition of any of (7-13), (7-14) (7-17) or (7-26), wherein, in the compound represented by the formula (I), Rk is [N—(($C_{1-3}$ alkoxy)$C_{1-4}$ alkyl)-N—($C_{1-3}$ alkyl)amino] $C_{1-4}$ alkoxy, ($C_{1-4}$ alkoxy)$C_{1-6}$ alkoxy (the $C_{1-4}$ alkoxy moiety is optionally substituted with one or more hydroxy groups), ($C_{1-3}$ alkoxy($C_{1-4}$ alkoxy))$C_{1-4}$ alkoxy, (carboxy)$C_{1-6}$ alkoxy, (3- to 6-membered heterocycloalkyl)$C_{1-6}$ alkoxy (the heterocycloalkyl moiety comprises one to three hetero atom(s) which is selected from O or N and is optionally substituted with one or two substituents selected from oxo, a halogen atom, $C_{1-4}$ alkyl (wherein the alkyl moiety is optionally substituted with one or more hydroxy groups), ($C_{1-4}$ alkoxy)$C_{1-4}$ alkyl (the alkoxy moiety is optionally substituted with one or more hydroxy groups), $C_{1-4}$ alkoxy, ($C_{1-4}$ alkoxy)carbonyl, $C_{1-4}$ alkylthio, morpholino, ($C_{1-3}$ alkyl)sulfonyl, and (di($C_{1-3}$ alkyl)amino)carbonyl), $C_{1-4}$ alkoxy substituted with a group $-NH-CH((CH_2)_{v1}COOR^{57})-(CH_2)_{v2}-COOR^{57}$, [N-(3- to 6-membered oxacycloalkyl)-N—($C_{1-3}$ alkyl)amino]$C_{1-4}$ alkoxy, [N,N-di((hydroxy)$C_{1-4}$ alkyl)-amino]$C_{1-4}$ alkoxy, [N—(($C_{1-3}$ alkoxy)carbonyl)$C_{1-3}$ alkyl-N—($C_{1-3}$ alkyl) amino]$C_{1-4}$ alkoxy, (1,2,4-triazolyl)$C_{1-4}$ alkoxy, [N-(hydroxy)$C_{1-4}$ alkyl-N—($C_{1-3}$ alkyl)amino]$C_{1-4}$ alkoxy, [N,N-di($C_{1-3}$ alkoxy($C_{1-4}$ alkyl))amino]$C_{1-6}$ alkoxy, [N,N-di($C_{1-3}$alkyl)amino]$C_{1-6}$ alkoxy, [N—[N—($C_{1-4}$ alkyl)carbonyl-N—($C_{1-3}$ alkyl)amino]$C_{1-4}$ alkyl-N—($C_{1-3}$ alkyl) amino]$C_{1-4}$ alkoxy, [N—[N—($C_{1-4}$ alkyl)carbonyl-amino] $C_{1-4}$ alkyl-N—($C_{1-3}$ alkyl)amino]$C_{1-4}$ alkoxy, a group $-(O(CH_2)_{r1})_{r2}-C(O)NR^{43}R^{44}$, a group $-(O(CH_2)_{q1})_{q2}-NR^{41}R^{42}$, $C_{1-4}$ alkoxy substituted with a group $-NH-(CH_2)_w-SO_3H$, $C_{1-4}$ alkoxy substituted with a group $-NH-(CH_2)_{x1}-CH(COOH)-(CH_2)_{x2}-SO_3H$, a group $-(O(CH_2)_{s1})_{s2}-NR^{45}-C(O)R^{46}$, a group $-C(O)NR^{47}R^{48}$, pyridinyl, a group $-NR^{49}R^{50}$, a group $-(O(CH_2)_{y1})_{y2}-O-CH_2-C(O)NR^{51}R^{52}$, (3- to 6-membered heterocycloalkyl)$C_{2-6}$ alkynyl (the heterocycloalkyl moiety comprises one to three hetero atoms selected from O and N and is optionally substituted with one oxo group), [N—(($C_{1-3}$alkoxy)$C_{1-4}$alkyl-N—($C_{1-3}$alkyl)amino]$C_{2-6}$alkynyl, 3- to 6-membered oxacycloalkyloxy, or 4- to 6-membered nitrogen containing heterocycloalkyloxy (the nitrogen containing heterocycloalkyl moiety is optionally substituted with one substituent selected from ($C_{1-3}$ alkoxy)$C_{1-4}$ alkyl and $C_{1-3}$ alkyl).

(7-29) The pharmaceutical composition of any of (7-1) to (7-8), (7-10) to (7-12), (7-20) and (7-24), wherein, in the compound represented by the formula (I), $R^1$, $R^4$, and $R^5$ are as defined in the following (1) or (2):

(1) $R^1$ is $C_{1-6}$ alkyl;

$R^4$ is optionally halogen atom-substituted $C_{1-4}$ alkyl or phenyl; and $R^5$ is a hydrogen atom or $C_{1-4}$ alkyl; or (2) $R^1$ and $R^5$ together with the carbon atom to which they are attached form a $C_{3-6}$ saturated carbocyclic ring; and $R^4$ is as defined above;

$R^3$ is $C_{1-4}$ alkyl substituted with Re;

Re is phenyl optionally substituted with one or more substituents Ra;

each Ra is independently selected from a halogen atom, optionally $R^{11}$-substituted $C_{2-6}$ alkynyl, and optionally $R^{12}$-substituted $C_{1-6}$ alkoxy;

$R^{11}$ and $R^{12}$ are each independently selected from 5- or 6-membered heterocycloalkyl and $-NR^{39}R^{40}$;

$R^{39}$ and $R^{40}$ are each independently selected from hydrogen atom and optionally $C_{1-6}$ alkoxy-substituted $C_{1-6}$ alkyl;

$Ar^1$ is phenyl or 5- or 6-membered heteroaryl, wherein the phenyl and heteroaryl groups are each optionally substituted with one to three substituents selected from Rb, Rc, and Rd;

Rb, Rc, and Rd are each independently selected from a halogen atom, $C_{1-4}$ alkyl optionally substituted with one or more halogen atoms, phenyl optionally substituted with one or more substituents $R^{14}$, and 5- or 6-membered heteroaryl optionally substituted with one or more substituents $R^{14}$; and each $R^{14}$ is independently selected from a halogen atom, cyano, $C_{1-4}$ alkyl optionally substituted with one or more halogen atoms, $C_{1-4}$ alkoxy, a group $-SO_2NR^{35}R^{36}$ (wherein $R^{35}$ and $R^{36}$ are each independently selected from $C_{1-4}$ alkyl), and $C_{1-4}$ alkylthio.

(7-30) The pharmaceutical composition of any of (7-1) to (7-29), wherein, in the compound represented by the formula (I), Rb is a halogen atom;

Rc is a halogen atom or $C_{1-4}$ alkyl optionally substituted with one or more halogen atoms; and Rd is a halogen atom, $C_{1-4}$ alkyl optionally substituted with one or more halogen atoms, phenyl optionally substituted with one or more substituents $R^{14}$, or 5- or 6-membered heteroaryl optionally substituted with one or more substituents $R^{14}$.

(7-31) The pharmaceutical composition of any of (7-1) to (7-12), (7-20) to (7-24), (7-29), and (7-30), wherein, in the compound represented by the formula (I), Re is phenyl optionally substituted with one or more substituents Ra;

$R^{11}$ and $R^{12}$ are each independently selected from morpholinyl and a group $-NR^{39}R^{40}$;

$R^4$ is optionally halogen atom-substituted $C_{1-4}$ alkyl or phenyl;

$Ar^1$ is phenyl, pyridinyl, or pyrimidinyl, wherein the phenyl, pyridinyl, and pyrimidinyl groups are each optionally substituted with one to three substituents selected from Rb, Rc, and Rd;

Rb is a halogen atom;

Rc is a halogen atom or $C_{1-4}$ alkyl optionally substituted with one or more halogen atoms; and Rd is a halogen atom, $C_{1-4}$ alkyl optionally substituted with one or more halogen atoms, phenyl, pyridinyl, or pyrimidinyl, wherein the phenyl, pyridinyl, and pyrimidinyl groups are each optionally substituted with one or more substituents $R^{14}$.

(7-32) The pharmaceutical composition of any of (7-1) to (7-4), (7-10) to (7-16), (7-20) to (7-24), (7-26) and (7-29) to (7-31), wherein, in the compound represented by the formula (I), Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri is a halogen atom;

Rj is a halogen atom; and

Rk is hydroxy, $C_{2-6}$ alkynyl optionally substituted with a substituent $R^{11}$, or $C_{1-6}$ alkoxy optionally substituted with a substituent $R^{12}$.

(7-33) The pharmaceutical composition of any of (7-29) to (7-32), wherein, in the compound represented by the formula (I), $R^{11}$ and $R^{12}$ are each independently selected from morpholinyl, [N—(($C_{1-3}$ alkoxy)$C_{1-4}$ alkyl)-N—($C_{1-3}$ alkyl)amino] and [N,N-di($C_{1-3}$alkyl)amino].

(7-34) The pharmaceutical composition of any of (7-29) to (7-33), wherein, in the compound represented by the formula (I), $R^{11}$ and $R^{12}$ are each independently selected from morpholinyl, and [N-((methoxy)ethyl)-N-(methyl)amino].

(7-35) The pharmaceutical composition of any of (7-1), (7-3) to (7-6), (7-10) to (7-12), (7-20), (7-23), (7-24), and (7-29), wherein, in the compound represented by the formula (I), $R^1$ and $R^5$ together with the carbon atom to which they are attached form a $C_{3-6}$ saturated carbocyclic ring;

$R^4$ is $C_{1-4}$ alkyl;

$R^3$ is $C_{1-4}$ alkyl substituted with Re;

Re is phenyl optionally substituted with one or more substituents Ra;

each Ra is independently selected from a halogen atom and $C_{1-4}$ alkoxy optionally substituted with one or more substituents $R^{12}$;

each $R^{12}$ is independently selected from 5- or 6-membered heterocycloalkyl and —$NR^{39}R^{40}$;

$R^{39}$ and $R^{40}$ are each independently selected from a hydrogen atom and optionally $C_{1-4}$ alkoxy-substituted $C_{1-4}$ alkyl;

$Ar^1$ is phenyl or 5- or 6-membered heteroaryl, wherein the phenyl and heteroaryl groups are each optionally substituted with one to three substituents selected from Rb, Rc, and Rd;

Rb, Rc, and Rd are each independently selected from a halogen atom, $C_{1-4}$ alkyl optionally substituted with one or more halogen atoms, and 5- or 6-membered heteroaryl optionally substituted with one or more substituents $R^{14}$; and each $R^{14}$ is independently selected from a halogen atom, cyano, $C_{1-4}$ alkyl optionally substituted with one or more halogen atoms, and $C_{1-4}$ alkylthio.

(7-36) The pharmaceutical composition of any of (7-1) to (7-35), wherein, in the compound represented by the formula (I), Rb is a halogen atom;

Rc is a halogen atom or $C_{1-4}$ alkyl optionally substituted with one or more halogen atoms; and Rd is a halogen atom or 5- or 6-membered heteroaryl optionally substituted with one or more substituents $R^{14}$.

(7-37) The pharmaceutical composition of any of (7-1) to (7-12), (7-20) to (7-25), (7-29) to (7-31), (7-35), and (7-36), wherein, in the compound represented by the formula (I), Ra is selected from a halogen atom, (morpholino)$C_{1-4}$alkoxy, [N—(($C_{1-3}$ alkoxy)$C_{1-4}$ alkyl)-N—($C_{1-3}$alkyl)amino]$C_{1-4}$ alkoxy, or [N,N-di($C_{1-3}$ alkyl)amino]$C_{1-4}$ alkoxy.

(7-38) The pharmaceutical composition of any of (7-1) to (7-5), (7-10) to (7-16), (7-20) to (7-23), (7-26) to (7-29), (7-32), (7-35), and (7-36), wherein, in the compound represented by the formula (I), Re is phenyl optionally substituted with one to three substituents Ra;

the one to three substituents Ra are one substituent selected from Ri, Rj, and Rk, two substituents selected from combinations of Ri and Rj, Ri and Rk, and Rj and Rk, or three substituents Ri, Rj, and Rk;

Ri and Rj are each independently a halogen atom; and

Rk is $C_{1-4}$ alkoxy optionally substituted with one or more substituents $R^{12}$.

(7-39) The pharmaceutical composition of any of (7-13) to (7-18), (7-20) to (7-23), (7-26) to (7-28), (7-32), (7-33), (7-34), and (7-38) wherein, in the compound represented by the formula (I), Rk is a halogen atom, (morpholino)$C_{1-4}$ alkoxy, [N—(($C_{1-3}$ alkoxy)$C_{1-4}$ alkyl)-N—($C_{1-3}$alkyl)amino]$C_{1-4}$ alkoxy, [N,N-di($C_{1-3}$ alkyl)amino]$C_{1-4}$ alkoxy.

(7-40) The pharmaceutical composition of any of (7-1) to (7-39), wherein, in the compound represented by the formula (I), Rb is a halogen atom;

Rc is a halogen atom, methyl or trifluoromethyl;

Rd is a halogen atom, trifluoromethyl, phenyl optionally substituted with one to three substitutrents $R^{14}$ and 5- to 6-membered heteroaryl optionally substituted with one to three substitutrents $R^{14}$, wherein the heteroaryl comprises one to three hetero atoms selected from O, S, and N.

(7-41) The pharmaceutical composition of any of (7-1) to (7-40), wherein, in the compound represented by the formula (I), $R^{14}$ is each independently selected from methyl, trifluoromethyl, cyano, nitro, a halogen atom, methoxy, ethoxy, trifluoromethoxy, methylthio, methoxycarbonyl and dimethylaminosulfonyl.

(7-42) The pharmaceutical composition of any of (7-1) to (7-41), wherein, in the compound represented by the formula (I), $R^{14}$ is each independently selected from methyl, trifluoromethyl, cyano, a chlorine atom and methylthio.

(7-43) The pharmaceutical composition of any of (7-1) to (7-42), wherein, in the compound represented by the formula (I), $Ar^1$ is phenyl or 5- to 6-membered heteroaryl which comprises one to three hetero atoms selected from O, S, and N, wherein the phenyl and the heteroaryl is substituted with one to three substituents selected from Rb, Rc, and Rd.

(7-44) The pharmaceutical composition of any of (7-1) to (7-11), (7-20) to (7-25), (7-29) to (7-31), (7-33) to (7-37), and (7-40) to (7-43), wherein, the compound represented by the formula (I) is represented by the formula (I-c);

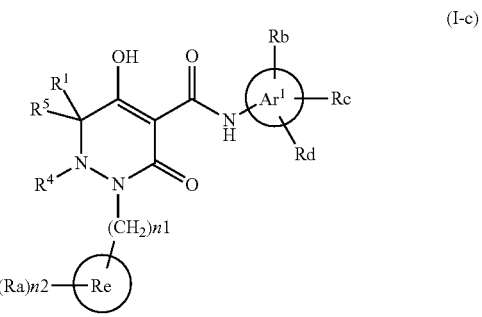

wherein, n1 is an interger selected from 1 to 4, n2 is an interger selected from 0 or more, $R^1$, $R^4$, $R^5$, $Ar^1$, Ra, Rb, Rc, Rd, Re are as defined in any of (7-1) to (7-11), (7-20) to (7-25), (7-29) to (7-31), (7-33) to (7-37), and (7-40) to (7-43).

(7-45) The pharmaceutical composition of (7-44), wherein, in the compound represented by the formula (I-c), n1 is 1 and n2 is 3.

(7-46) The pharmaceutical composition of any of (7-13) to (7-23), (7-26) to (7-28), (7-30), (7-32) to (7-34), (7-36), and (7-38) to (7-43), wherein, the compound represented by the formula (I) is represented by the formula (I-d);

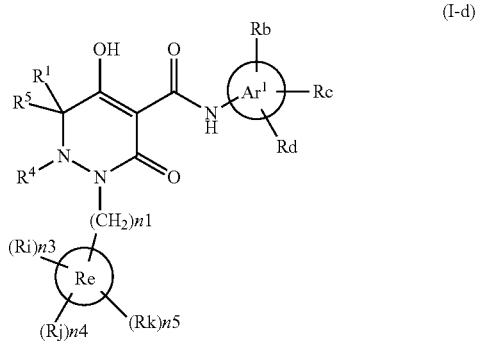

wherein n1 is an interger selected from 1 to 4, n3, n4 and n5 is a interger independently selected from 0 or 1, provided that at least one of n3, n4 and n5 is 1, $R^1$, $R^4$, $R^5$, $Ar^1$, Ra, Rb, Rc, Rd, Re, Ri, Rj, and Rk are as defined in any of (7-13) to (7-23), (7-26) to (7-28), (7-30), (7-32) to (7-34), (7-36), and (7-38) to (7-43).

(7-47) The pharmaceutical composition of (7-46), wherein, in the compound represented by the formula (I-d), n1 is 1.

(7-48) The pharmaceutical composition of any of (7-1) to (7-47), wherein, in the compound represented by the formula (I), $Ar^1$ is 4-(trifluoromethyl)-2-(6-methylthiopyridin-3-yl)phenyl, 4-(trifluoromethyl)-2-(6-trifluoromethylpyridin-3-yl)phenyl, 4-(trifluoromethyl)-2-(4-trifluoromethylpyrimidin-5-yl)phenyl, 4-(trifluoromethyl)-2-(6-trifluoromethylpyrimidin-4-yl)phenyl, 4-(trifluoromethyl)-2-(6-cyano-5-methylpyrimidin-4-yl)phenyl, 4-(trifluoromethyl)-2-(2-cyanopyridin-4-yl)phenyl, 4-chloro-2-(6-methylthiopyridin-3-yl)phenyl, 4-chloro-2-(6-trifluoromethylpyridin-3-yl)phenyl, 4-chloro-2-(4-trifluoromethylpyrimidin-5-yl)phenyl, 4-chloro-2-(6-cyano-5-methylpyrimidin-4-yl)phenyl, 4-chloro-2-(6-trifluoromethylpyrimidin-4-yl)phenyl, or 4-chloro-2-(2-cyanopyridin-4-yl)phenyl.

(7-49) The pharmaceutical composition of (7-1), which comprises a compound selected from:

(4aR)-1-[(2,3-difluorophenyl)methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide;

(4aR)—N-[2-(6-cyano-5-methylpyrimidin-4-yl)-4-(trifluoromethyl)phenyl]-1-[[2,3-difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxamide;

(4aR)—N-[2-(2-cyanopyridin-4-yl)-4-(trifluoromethyl)phenyl]-1-[[2,3-difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxamide;

6-[4-[[(4aR)-4-hydroxy-4a-methyl-2-oxo-3-[[4-(trifluoromethyl)-2-[6-(trifluoromethyl)pyrimidin-4-yl]phenyl]carbamoyl]-6,7-dihydro-5H-pyrrolo[1,2-b]pyridazin-1-yl]methyl]-2,3-difluorophenyl]hex-5-ynoic acid;

(4aR)-1-[[2,3-difluoro-4-(3-morpholin-4-ylprop-1-ynyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;

(4aR)-1-[[4-[3-[(2R)-2,3-dihydroxypropoxy]propoxy]-2,3-difluorophenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;

(4aR)-1-[[4-[4-[(2R)-2,3-dihydroxypropoxy]butoxy]-2,3-difluorophenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide;

(4aR)-1-[[4-[6-[(2R)-2,3-dihydroxypropoxy]hexoxy]-2,3-difluorophenyl]methyl]-4-hydroxy-4a-methyl-2-oxo-N-[2-(trifluoromethyl)-4-[6-(trifluoromethyl)pyridin-3-yl]pyrimidin-5-yl]-6,7-dihydro-5H-pyrrolo[1,2-b]pyridazine-3-carboxamide;

(4aR)-1-[[2,3-difluoro-4-(2-morpholin-4-ylethoxy)phenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide;

(4aR)-1-[[2,3-difluoro-4-(morpholin-4-ylmethyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;

(4aR)—N-(4-bromo-3,5-difluorophenyl)-1-[(3-chloro-2-fluorophenyl)methyl]-4-hydroxy-4a-methyl-2-oxo-6,7-dihydro-5H-pyrrolo[1,2-b]pyridazine-3-carboxamide;

(3S)-3-tert-butyl-1-[[2,3-difluoro-4-(2-morpholin-4-ylethoxy)phenyl]methyl]-4-hydroxy-2-methyl-6-oxo-N-[4-(trifluoromethyl)-2-[6-(trifluoromethyl)pyrimidin-4-yl]phenyl]-3H-pyridazine-5-carboxamide;

(3S)-3-tert-butyl-N-[4-chloro-2-[6-(trifluoromethyl)pyrimidin-4-yl]phenyl]-1-[[2,3-difluoro-4-(2-morpholin-4-ylethoxy)phenyl]methyl]-4-hydroxy-2-methyl-6-oxo-3H-pyridazine-5-carboxamide;

(3S)-3-tert-butyl-N-[4-chloro-2-[6-(trifluoromethyl)pyridin-3-yl]phenyl]-1-[[2,3-difluoro-4-(2-morpholin-4-ylethoxy)phenyl]methyl]-4-hydroxy-2-methyl-6-oxo-3H-pyridazine-5-carboxamide;

(3S)-3-tert-butyl-N-[4-chloro-2-(6-methylsulfanylpyridin-3-yl)phenyl]-1-[[2,3-difluoro-4-(2-morpholin-4-ylethoxy)phenyl]methyl]-4-hydroxy-2-methyl-6-oxo-3H-pyridazine-5-carboxamide;

(3S)-3-tert-butyl-N-[2-(6-cyano-5-methylpyrimidin-4-yl)-4-(trifluoromethyl)phenyl]-1-[[2,3-difluoro-4-(2-morpholin-4-ylethoxy)phenyl]methyl]-4-hydroxy-2-methyl-6-oxo-3H-pyridazine-5-carboxamide;

6-[[2,3-difluoro-4-(2-morpholin-4-ylethoxy)phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide;

7-[[2,3-difluoro-4-(2-morpholin-4-ylethoxy)phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

6-[[2,3-difluoro-4-[2-[2-methoxyethyl(methyl)amino]ethoxy]phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide;

7-[[2,3-difluoro-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

4-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]butanoic acid;

5-[2,3-[difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]pentanoic acid;

6-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]hexanoic acid;

7-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]heptanoic acid;

7-[[2,3-difluoro-4-[2-[(2S)-2-(methoxymethyl)pyrrolidin-1-yl]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

(2S)-2-[2-[2,3-difluoro-4-[[1-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]butanedioic acid;

3-[2-[2,3-difluoro-4-[[1-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]pentanedioic acid;

6-(2,3-difluoro-4-(2-(methyl(oxetan-3-yl)amino)ethoxy)benzyl)-9-hydroxy-5-methyl-7-oxo-N-(4-(trifluoromethyl)-2-(6-(trifluoromethyl)pyrimidin-4-yl)phenyl)-5,6-diazaspiro[3.5]non-8-ene-8-carboxamide;

7-[[2,3-difluoro-4-[2-[methyl(oxetan-3-yl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

7-(2,3-difluoro-4-(2-(methyl(oxetan-3-yl)amino)ethoxy)benzyl)-1-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide;

7-(4-(3-(dimethylamino)-2,2-dimethylpropoxy)-2,3-difluorobenzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide;

6-[[2,3-difluoro-4-[1-(2-methoxyethyl)azetidin-3-yl]oxyphenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide;

7-[[2,3-difluoro-4-[4-[methyl-[(2S,3R,4R,5R)-2,3,4,5,6-pentahydroxyhexyl]amino]-4-oxobutoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

7-[[2,3-difluoro-4-[2-[2-[methyl-[(2S,3R,4R,5R)-2,3,4,5,6-pentahydroxyhexyl]amino]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

7-[[2,3-difluoro-4-[2-[2-[2-[2-[2-methoxyethyl(methyl)amino]ethoxy]ethoxy]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]ethanesulfonic acid; and 2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]ethanesulfonic acid or a salt thereof, or a solvate of the compound or the salt.

(7-50) The pharmaceutical composition of any of (7-1) to (7-49) for use in the prevention or treatment of a disease selected from hyperphosphatemia, secondary hyperparathyroidism, chronic kidney disease, and arteriosclerosis associated with vascular calcification.

(7-51) The pharmaceutical composition of any of (7-1) to (7-49) for use in the prevention or treatment of a disease selected from hyperphosphatemia and chronic kidney disease.

(7-52) The pharmaceutical composition of (7-50) or (7-51), wherein the hyperphosphatemia is hyperphosphatemia in a patient with chronic kidney disease.

(7-53) The pharmaceutical composition of (7-50) or (7-51), wherein the chronic kidney disease is at stage 2 to 4 classified by GFR.

(7-54) The pharmaceutical composition of any of (7-1) to (7-49) for use in the prevention or suppression of ectopic calcification.

(7-55) The pharmaceutical composition of any of (7-1) to (7-49) for use in the inhibition of one or more transporters selected from NaPi-IIb, PiT-1, and PiT-2.

(7-56) A pharmaceutical composition comprising a substance that inhibits one or more transporters selected from PiT-1 and PiT-2 and used in the prevention or treatment of a disease selected from hyperphosphatemia, secondary hyperparathyroidism, chronic kidney disease, and arteriosclerosis associated with vascular calcification.

(7-57) A pharmaceutical composition comprising a substance that inhibits one or more transporters selected from PiT-1 and PiT-2 and used in the prevention or suppression of ectopic calcification.

(7-58) The pharmaceutical composition of (7-56) or (7-57), wherein the substance further inhibits NaPi-IIb.

(7-59) The pharmaceutical composition of any of (7-56) to (7-58), wherein the substance inhibits NaPi-IIb, PiT-1, and PiT-2.

(7-60) The pharmaceutical composition of any of (7-56) to (7-59), wherein the substance is a low-molecular compound.

One aspect of the present invention provides the following pharmaceutical compositions (8-1) to (8-24).

(8-1) A pharmaceutical composition comprising a substance that inhibits one or more transporters selected from NaPi-IIb, PiT-1, and PiT-2 and used in the prevention or treatment of a disease selected from hyperphosphatemia, secondary hyperparathyroidism, chronic kidney disease, and arteriosclerosis associated with vascular calcification, wherein the substance is administered in combination with a phosphorus adsorbent.

(8-2) A pharmaceutical composition for use in the prevention or suppression of ectopic calcification, comprising a substance that inhibits one or more transporters selected from NaPi-IIb, PiT-1, and PiT-2 wherein the composition is administered in combination with a phosphorus adsorbent.

(8-3) The pharmaceutical composition of (8-1) or (8-2) which is a combined drug comprising the substance that inhibits one or more transporters selected from NaPi-IIb, PiT-1, and PiT-2, and the phosphorus adsorbent.

(8-4) The pharmaceutical composition of (8-1) or (8-2), wherein the phosphorus adsorbent is administered as separate pharmaceutical compositions.

(8-5) The pharmaceutical composition of any of (8-1), (8-2), and (8-4), wherein the substance that inhibits the one or more transporters and the phosphorus adsorbent are administered simultaneously.

(8-6) The pharmaceutical composition of any of (8-1), (8-2), and (8-4), wherein the substance that inhibits the one or more transporters and the phosphorus adsorbent are administered sequentially.

(8-7) The pharmaceutical composition of any of (8-1), (8-2), (8-4) and (8-6), wherein the substance that inhibits the one or more transporters is administered before or after administration of the phosphorus adsorbent.

(8-8) A pharmaceutical composition comprising a phosphorus adsorbent, for use in the prevention or treatment of a disease selected from hyperphosphatemia, secondary hyperparathyroidism, chronic kidney disease, and arteriosclerosis associated with vascular calcification, wherein the composition is administered in combination with a substance that inhibits one or more transporters selected from NaPi-IIb, PiT-1, and PiT-2.

(8-9) A pharmaceutical composition comprising a phosphorus adsorbent, for use in the prevention or suppression of ectopic calcification, wherein the composition is administered in combination with a substance that inhibits one or more transporters selected from NaPi-IIb, PiT-1, and PiT-2.

(8-10) The pharmaceutical composition of (8-8) or (8-9), wherein the substance that inhibits the one or more transporters is administered simultaneously with the phosphorus adsorbent.

(8-11) The pharmaceutical composition of (8-8) or (8-9), wherein the substance that inhibits the one or more transporters is administered before or after administration of the phosphorus adsorbent.

(8-12) The pharmaceutical composition of any of (8-1) to (8-11), wherein the substance that inhibits one or more transporters selected from NaPi-IIb, PiT-1, and PiT-2 is a substance that inhibits one or more transporters selected from PiT-1 and PiT-2.

(8-13) The pharmaceutical composition of any of (8-1) to (8-12), wherein the substance further inhibits NaPi-IIb.

(8-14) A pharmaceutical composition comprising a substance that inhibits one or more transporters selected from NaPi-IIb, PiT-1, and PiT-2 and a phosphorus adsorbent.

(8-15) The pharmaceutical composition of (8-14) for use in the prevention or treatment of a disease selected from hyperphosphatemia, secondary hyperparathyroidism, chronic kidney disease, and arteriosclerosis associated with vascular calcification.

(8-16) The pharmaceutical composition of (8-14) for use in the prevention or suppression of ectopic calcification.

(8-17) The pharmaceutical composition of any of (8-1) to (8-16), wherein the substance that inhibits one or more transporters selected from NaPi-IIb, PiT-1, and PiT-2 is a substance that inhibits one or more of transporters selected from PiT-1 and PiT-2.

(8-18) The pharmaceutical composition of any of (8-1) to (8-16), wherein the substance further inhibits NaPi-IIb.

(8-19) The pharmaceutical composition of any of (8-1) to (8-18), wherein the substance that inhibits one or more transporters selected from NaPi-IIb, PiT-1, and PiT-2 is a compound of any of (7-1) to (7-49) or a salt thereof or a solvate of the compound or the salt.

(8-20) The pharmaceutical composition of any of (8-1) or (8-19), wherein the substance that inhibits one or more transporters selected from NaPi-IIb, PiT-1, and PiT-2 is a compound represented by any one of the following formulae (1) to (5):

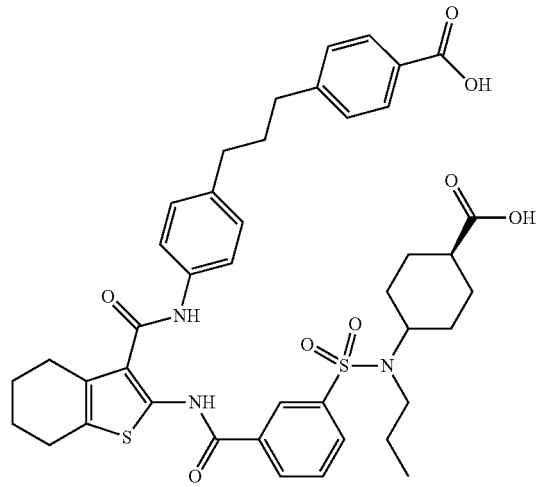

(1)

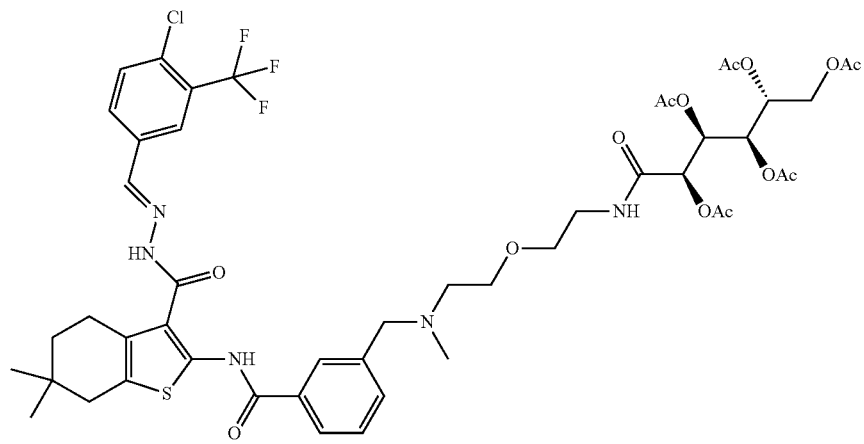
(2)
(wherein Ac is an acetyl group)
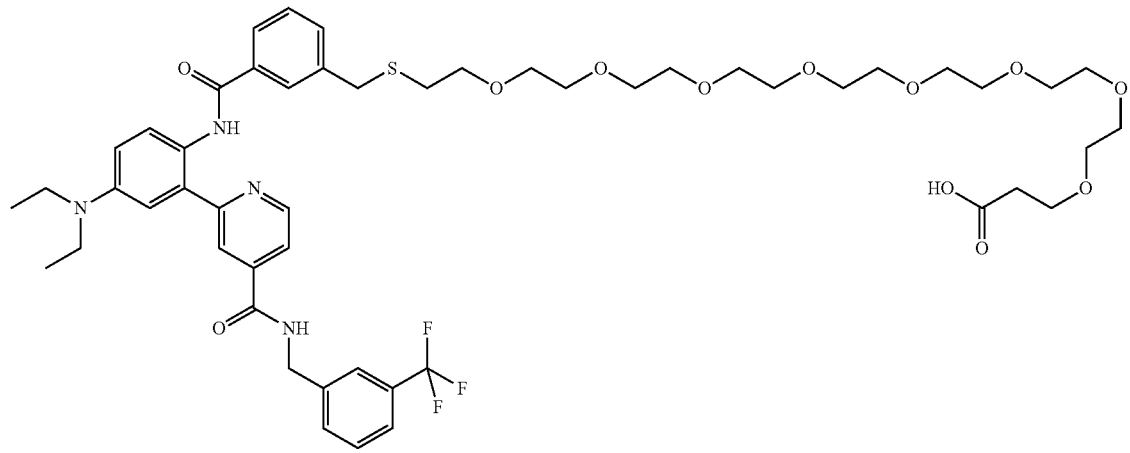
(3)
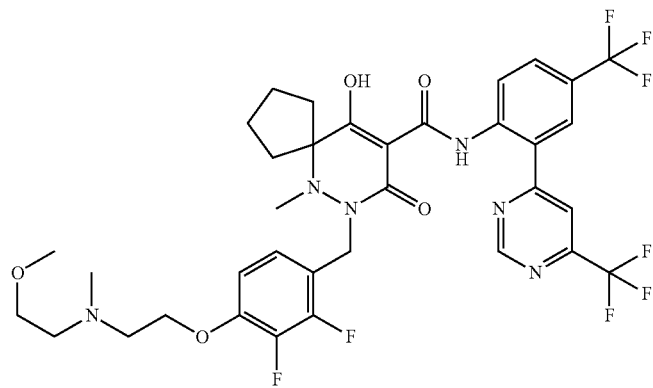
(4)

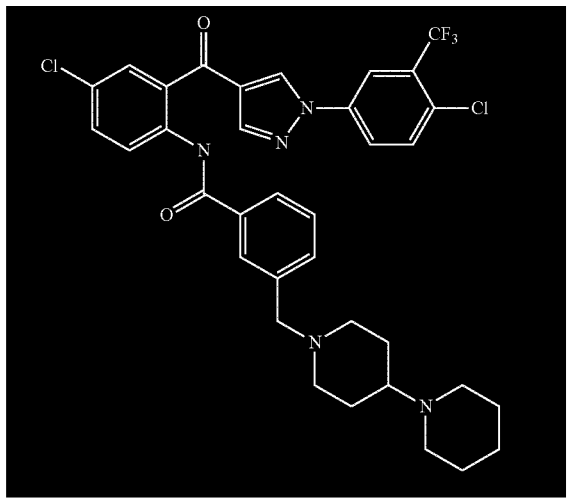

(5)

or a salt thereof or a solvate or the compound or the salt.

(8-21) The pharmaceutical composition of any of (8-1) or (8-20), wherein the substance that inhibits one or more transporters selected from NaPi-IIb, PiT-1, and PiT-2 is a compound represented by the following formula (4):

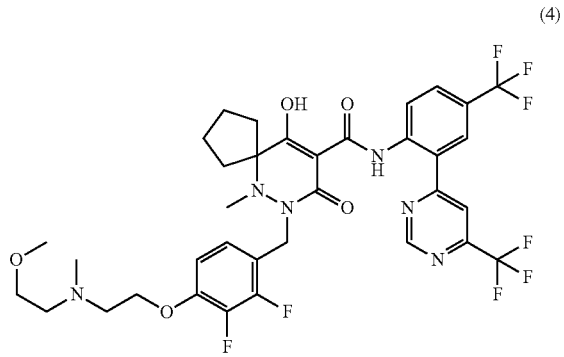 [SMILES: COCCN(C)CCOc1ccc(CN2C(=O)C(C(=O)Nc3ccc(C(F)(F)F)cc3-c3cc(C(F)(F)F)ncn3)=C(O)C3(CCCC3)N2C)c(F)c1F]

(4)

or a salt thereof or a solvate or the compound or the salt.

(8-22) The pharmaceutical composition of any of (8-1) to (8-21), wherein the phosphorus adsorbent is a nonmetallic polymer adsorbent, a calcium salt preparation, or a metallic salt preparation.

(8-23) The pharmaceutical composition of any of (8-1) to (8-22), wherein the phosphorus adsorbent is any one of medicaments selected from bixalomer, sevelamer carbonate, sevelamer hydrochloride, precipitated calcium carbonate, calcium acetate, calcium citrate, calcium alginate, calcium salt of keto-acid, lanthanum carbonate, aluminum hydroxide, sucroferric oxyhydroxide, Fermagate, and ferric citrate hydrate.

(8-24) The pharmaceutical composition of any of (8-1) to (8-23), wherein the phosphorus adsorbent is sevelamer carbonate.

One aspect of the present invention provides the following methods (9-1) to (9-6):

(9-1) A method for preventing or treating a disease selected from hyperphosphatemia, secondary hyperparathyroidism, chronic kidney disease, and arteriosclerosis associated with vascular calcification, comprising administering to a subject an effective amount of a substance that inhibits one or more transporters selected from NaPi-IIb, PiT-1, and PiT-2 in combination with an effective amount of a phosphorus adsorbent.

(9-2) A method for preventing or suppressing ectopic calcification, comprising administering to a subject an effective amount of a substance that inhibits one or more transporters selected from NaPi-IIb, PiT-1, and PiT-2 in combination with an effective amount of a phosphorus adsorbent.

(9-3) The method of (9-1) or (9-2), wherein the substance that inhibits the one or more transporters and the phosphorus adsorbent are administered as a combined drug.

(9-4) The method of (9-1) or (9-2), wherein the substance that inhibits the one or more transporters and the phosphorus adsorbent are administered as separate pharmaceutical compositions.

(9-5) The method of any of (9-1), (9-2) and (9-4), wherein the the substance that inhibits the one or more transporters and the phosphorus adsorbent are administered simultaneously.

(9-6) The method of any of (9-1), (9-2) and (9-4), wherein the substance that inhibits the one or more transporters is administered before or after administration of the phosphorus adsorbent.

One aspect of the present invention provides the following uses (10-1) to (10-10).

(10-1) A use of a substance that inhibits one or more transporters selected from NaPi-IIb, PiT-1, and PiT-2 in combination with a phosphorus adsorbent, for preventing or treating a disease selected from hyperphosphatemia, secondary hyperparathyroidism, chronic kidney disease, and arteriosclerosis associated with vascular calcification.

(10-2) A use of a substance that inhibits one or more transporters selected from NaPi-IIb, PiT-1, and PiT-2 in combination with a phosphorus adsorbent, for preventing or suppressing ectopic calcification.

(10-3) The use of (10-1) or (10-2), wherein the substance that inhibits the one or more transporters are administered to a subject as a pharmaceutical composition separately from the phosphorus adsorbent.

(10-4) The use of any of (10-1) or (10-3), wherein the substance that inhibits the one or more transporters are administered to the subject simultaneously with the phosphorus adsorbent.

(10-5) The use of any of (10-1) or (10-3), wherein the substance that inhibits the one or more transporters are administered to the subject before or after administration of the phosphorus adsorbent.

(10-6) A use of a phosphorus adsorbent administered in combination with a substance that inhibits one or more transporters selected from NaPi-IIb, PiT-1, and PiT-2, for use in the prevention or treatment of a disease selected from hyperphosphatemia, secondary hyperparathyroidism, chronic kidney disease, and arteriosclerosis associated with vascular calcification.

(10-7) A use of a phosphorus adsorbent administered in combination with a substance that inhibits one or more transporters selected from NaPi-IIb, PiT-1, and PiT-2, for use in the prevention or suppression of ectopic calcification.

(10-8) The use of (10-6) or (10-7), wherein the substance that inhibits the one or more transporters are administered to a subject as a pharmaceutical composition different from the phosphorus adsorbent.

(10-9) The use of any of (10-6) or (10-8), wherein the phosphorus adsorbent is administered to the subject simultaneously with the substance that inhibits the one or more transporters.

(10-10) The use of any of (10-6) or (10-8), wherein the phosphorus adsorbent is administered to the subject before or after administration of the substance that inhibits the one or more transporters.

ADVANTAGIOUS EFFECTS OF INVENTION

The compound, the salt thereof or the solvate of the compound or the salt has an excellent NaPi-IIb inhibitory effect, PiT-1 inhibitory effect, or PiT-2 inhibitory effect, and is useful as a prevention and/or treatment agent for hyperphosphatemia. Further, the compound, the salt thereof or the solvate of the compound or the salt is useful as a prevention and/or treatment agent for secondary hyperparathyroidism, or chronic renal failure. Further, the pharmaceutical composition of the present invention is useful as a prevention and/or treatment agent for a disease selected from hyperphosphatemia, secondary hyperparathyroidism, chronic kidney disease, and vascular calcification.

DESCRIPTION OF EMBODIMENTS

Hereinafter, a compound of the present invention or a salt thereof, or a solvate of the compound or the salt, a method for producing the same, and a pharmaceutical drug and a pharmaceutical composition each containing this compound will be described.

Definition

In the present invention, a "halogen atom" means a fluorine atom, a chlorine atom, a bromine atom, an iodine atom, and the like. In the present invention, preferred examples of the halogen atom used as a substituent for aryl, heteroaryl, etc. include a fluorine atom, a chlorine atom, and a bromine atom. In the present invention, preferred examples of the halogen atom used as a substituent for alkyl or a group partially containing alkyl (alkoxy, alkenyl, alkylthio, etc.) include a fluorine atom. Specific examples of groups having the halogen atom as a substituent include trifluoromethyl, pentafluoroethyl, trifluoromethoxy, pentafluoroethoxy, trifluoromethylthio, and pentafluoroethylthio.

In the present invention, "$C_{1-3}$ alkyl" refers to a monovalent group derived from a linear and branched saturated aliphatic hydrocarbon having 1 to 3 carbon atoms by the loss of one arbitrary hydrogen atom. Specific examples thereof include methyl, ethyl, n-propyl, and isopropyl.

In the present invention, "$C_{1-4}$ alkyl" refers to a monovalent group derived from a linear and branched saturated aliphatic hydrocarbon having 1 to 4 carbon atoms by the loss of one arbitrary hydrogen atom. Specific examples thereof include methyl, ethyl, n-propyl, isopropyl, n-butyl, isobutyl, sec-butyl, t-butyl, and 1-methylpropyl.

In the present invention, "$C_{1-5}$ alkyl" refers to a monovalent group derived from a linear and branched saturated aliphatic hydrocarbon having 1 to 5 carbon atoms by the loss of one arbitrary hydrogen atom. Specific examples thereof include methyl, ethyl, n-propyl, isopropyl, n-butyl, isobutyl, sec-butyl, t-butyl, 1-methylpropyl, n-pentyl, isopentyl, 2-methylbutyl, 1,1-dimethylpropyl, and 1-ethylpropyl.

In the present invention, "$C_{1-6}$ alkyl" refers to a monovalent group derived from a linear and branched saturated aliphatic hydrocarbon having 1 to 6 carbon atoms by the loss of one arbitrary hydrogen atom. Specific examples thereof include methyl, ethyl, n-propyl, isopropyl, n-butyl, isobutyl, sec-butyl, t-butyl, 1-methylpropyl, n-pentyl, isopentyl, 2-methylbutyl, 1,1-dimethylpropyl, 1-ethylpropyl, hexyl, 4-methylpentyl, and 2-ethylbutyl.

In the present invention, "$C_{1-8}$ alkyl" refers to a monovalent group derived from a linear and branched saturated aliphatic hydrocarbon having 1 to 8 carbon atoms by the loss of one arbitrary hydrogen atom. Specific examples thereof include the groups listed above in the definition of "$C_{1-6}$ alkyl" as well as n-heptyl, 5-methylhexyl, 1-propylbutyl, 2-ethyl-2-methylbutyl, n-octyl, 5-methylheptyl, 2,3-dimethylhexyl, 1-methyl-1-propylbutyl, and 2,2-diethylbutyl.

In the present invention, "$C_{1-10}$ alkyl" refers to a monovalent group derived from a linear and branched saturated aliphatic hydrocarbon having 1 to 10 carbon atoms by the loss of one arbitrary hydrogen atom. Specific examples thereof include the groups listed above in the definition of "$C_{1-8}$ alkyl" as well as 7-methyloctyl, 5-ethylheptyl, n-decyl, 8-methylnonyl, 5,5-dimethyloctyl, and 4-ethyl-6-methylheptyl.

In the present invention, "linear $C_{1-6}$ alkyl" refers to a monovalent group derived from a linear saturated aliphatic hydrocarbon having 1 to 6 carbon atoms by the loss of one arbitrary hydrogen atom. "Linear $C_{1-6}$ alkyl" specifically means methyl, ethyl, n-propyl, n-butyl, n-pentyl, and n-hexyl.

In the present invention, "linear $C_{1-10}$ alkyl" refers to a monovalent group derived from a linear saturated aliphatic hydrocarbon having 1 to 10 carbon atoms by the loss of one arbitrary hydrogen atom. "Linear $C_{1-10}$ alkyl" specifically means methyl, ethyl, n-propyl, n-butyl, n-pentyl, n-hexyl, n-heptyl, n-octyl, n-nonyl, and n-decyl.

In the present invention, "morpholino" means morpholin-4-yl.

In the present invention, "(morpholino)$C_{1-6}$ alkyl" means a $C_{1-6}$ alkyl group substituted with morpholino. "$C_{1-6}$ alkyl" is as defined above. Specific examples thereof include morpholinomethyl, morpholinoethyl, morpholino-n-propyl, morpholinoisopropyl, morpholino-n-butyl, morpholinoisobutyl, morpholino-sec-butyl, morpholino-t-butyl, morpholino-1-methylpropyl, morpholino-n-pentyl, morpholinoisopentyl, morpholino-2-methylbutyl, morpholino-1,1-dimethylpropyl, morpholino-1-ethylpropyl, morpholinohexyl, morpholino-4-methylpentyl, and morpholino-2-ethylbutyl. Preferred examples thereof include morpholinomethyl.

In the present invention, "(morpholino)$C_{1-4}$ alkyl" means a $C_{1-4}$ alkyl group substituted with morpholino. "$C_{1-4}$ alkyl"

is as defined above. Specific examples thereof include morpholinomethyl, morpholinoethyl, morpholino-n-propyl, morpholinoisopropyl, morpholino-n-butyl, morpholinoisobutyl, morpholino-sec-butyl, morpholino-t-butyl, and morpholino-1-methylpropyl. Preferred examples thereof include morpholinomethyl.

In the present invention, "(oxetanyl)$C_{1-4}$ alkyl" means a $C_{1-4}$ alkyl group substituted with oxetanyl. "$C_{1-4}$ alkyl" is as defined above. Specific examples thereof include oxetanylmethyl, oxetanylethyl, oxetanyl-n-propyl, oxetanylisopropyl, oxetanyl-n-butyl, oxetanylisobutyl, oxetanyl-sec-butyl, oxetanyl-t-butyl, and oxetanyl-1-methylpropyl. Preferred examples thereof include oxetanylmethyl.

In the present invention, "(4- to 6-membered heterocycloalkyl)$C_{1-4}$ alkyl" means $C_{1-4}$ alkyl substituted with 4- to 6-membered heterocycloalkyl. "$C_{1-4}$ alkyl" is as defined above. "4- to 6-membered heterocycloalkyl" means a saturated heterocyclic group composed of 4 to 6 ring-constituting atoms containing one to three heteroatoms selected from O, S, and N. "(4- to 6-membered heterocycloalkyl)$C_{1-4}$ alkyl" includes "(morpholino)$C_{1-4}$ alkyl" and "(oxetanyl)$C_{1-4}$ alkyl".

In the present invention, "(carboxy)$C_{1-8}$ alkyl" means $C_{1-8}$ alkyl substituted with carboxy. "$C_{1-8}$ alkyl" is as defined above. Specific examples thereof include carboxy-n-hexyl, carboxy-n-heptyl, carboxy-5-methylhexyl, carboxy-1-propylbutyl, carboxy-2-ethyl-2-methylbutyl, carboxy-n-octyl, carboxy-5-methylheptyl, carboxy-2,3-dimethylhexyl, carboxy-1-methyl-1-propylbutyl, and carboxy-2,2-diethylbutyl. Preferred examples thereof include carboxy-n-hexyl, carboxy-n-heptyl, and carboxy-n-octyl.

In the present invention, "($C_{1-6}$ alkoxy)$C_{1-8}$ alkyl" means $C_{1-8}$ alkyl substituted with $C_{1-6}$ alkoxy. "$C_{1-6}$ alkoxy" and "$C_{1-8}$ alkyl" are as defined above and below. Specific examples thereof include ethoxy-n-propyl, n-propoxy-n-propyl, n-butoxy-n-propyl, n-heptoxypropyl, n-propoxy-n-hexyl, n-butoxy-n-hexyl, n-propoxy-n-heptyl, and n-butoxy-n-heptyl. Preferred examples thereof include n-propoxy-n-propyl and n-butoxy-n-heptyl.

In the present invention, "($C_{1-3}$ alkoxy)$C_{1-4}$ alkyl" means $C_{1-4}$ alkyl substituted with $C_{1-3}$ alkoxy. "$C_{1-3}$ alkoxy" and "$C_{1-4}$ alkyl" are as defined above and below. Specific examples thereof include methoxymethyl, methoxyethyl, ethoxymethyl, methoxy-n-propyl, ethoxy-n-propyl, methoxy-n-butyl, and ethoxy-n-butyl.

In the present invention, "($C_{1-4}$ alkoxy)$C_{1-4}$ alkyl" means $C_{1-4}$ alkyl substituted with $C_{1-4}$ alkoxy. "$C_{1-4}$ alkoxy" and "$C_{1-4}$ alkyl" are as defined above and below. Specific examples thereof include the groups listed above in the definition of "($C_{1-3}$ alkoxy)$C_{1-4}$ alkyl" as well as n-butoxymethyl, n-butoxyethyl, n-butoxy-n-propyl, and n-butoxy-n-butyl.

In the present invention, "($C_{1-3}$ alkoxy)$C_{1-6}$ alkyl" means $C_{1-6}$ alkyl substituted with $C_{1-3}$ alkoxy. "$C_{1-3}$ alkoxy" and "$C_{1-6}$ alkyl" are as defined above and below. Specific examples thereof include the groups listed above in the definitions of "($C_{1-3}$ alkoxy)$C_{1-4}$ alkyl" and "($C_{1-4}$ alkoxy)$C_{1-4}$ alkyl". Preferred examples thereof include methoxy-n-propyl.

In the present invention, "[HO—((CH$_2$)$_o$O)$_p$]$C_{1-6}$ alkyl" refers to $C_{1-6}$ alkyl substituted with a group —(O(CH$_2$)$_o$)$_p$—OH. $C_{1-6}$ alkyl is as defined above. Specific examples thereof include [HO—((CH$_2$)$_2$O)$_3$]propyl.

In the present invention, "$C_{1-5}$ alkylene" refers to a divalent group derived from a linear or branched saturated aliphatic hydrocarbon having 1 to 5 carbon atoms by the loss of two arbitrary hydrogen atoms. "$C_{1-5}$ alkylene" includes "$C_{1-3}$ alkylene". Specific examples thereof include —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH(CH$_2$CH$_3$)—, —C(CH$_2$CH$_3$)$_2$—, and —CH(CH$_2$CH$_2$CH$_3$)—. —CH$_2$— is preferred.

In the present invention, two or more substituents $R^2$ on a 5- to 8-membered saturated heterocyclic ring may together form $C_{1-5}$ alkylene that links the ring atoms to which they are attached. In this case, the saturated heterocyclic ring forms a bicyclo ring or tricycle ring and so on.

In the present invention, "$C_{2-10}$ alkynyl" refers to a monovalent group derived from a linear or branched aliphatic hydrocarbon having 2 to 10 carbon atoms and having at least one triple bond (two adjacent SP carbon atoms) by the loss of one arbitrary hydrogen atom. Specific examples thereof include ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-hexynyl, heptynyl, heptadiynyl, octynyl, and octadiynyl.

In the present invention, "optionally substituted $C_{2-10}$ alkynyl" means unsubstituted $C_{2-10}$ alkynyl described above or $C_{2-10}$ alkynyl on which one or more hydrogen atoms are replaced with predetermined substituent(s). Two or more substituents on this group may be the same as or different from each other. One carbon atom may be substituted with a plurality of substituents.

In the present invention, "$C_{2-6}$ alkynyl" refers to a monovalent group derived from a linear or branched aliphatic hydrocarbon having 2 to 6 carbon atoms and having at least one triple bond (two adjacent SP carbon atoms) by the loss of one arbitrary hydrogen atom. Specific examples thereof include ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, and 1-hexynyl.

In the present invention, "optionally substituted $C_{2-6}$ alkynyl" means unsubstituted $C_{2-6}$ alkynyl described above or $C_{2-6}$ alkynyl on which one or more hydrogen atoms are replaced with predetermined substituent(s). Two or more substituents on this group may be the same as or different from each other. One carbon atom may be substituted with a plurality of substituents.

In the present invention, "(carboxy)$C_{2-6}$ alkynyl" means $C_{2-6}$ alkynyl substituted with carboxy. $C_{2-6}$ alkynyl is as defined above. Specific examples thereof include carboxyethynyl, carboxy-1-propynyl, carboxy-2-propynyl, carboxy-1-butynyl, carboxy-2-butynyl, carboxy-3-butynyl, carboxy-1-methyl-2-propynyl, carboxy-1-pentynyl, carboxy-2-pentynyl, carboxy-3-pentynyl, carboxy-4-pentynyl, carboxy-1-methyl-2-butynyl, carboxy-1-methyl-3-butynyl, carboxy-2-methyl-3-butynyl, carboxy-3-methyl-1-butynyl, carboxy-1,1-dimethyl-2-propynyl, and carboxy-1-hexynyl. Preferred examples thereof include carboxy-1-pentynyl and carboxy-1-hexynyl.

In the present invention, "($C_{1-6}$ alkoxy)$C_{2-8}$ alkynyl" means $C_{2-8}$ alkynyl substituted with $C_{1-6}$ alkoxy. $C_{1-6}$ alkoxy and $C_{2-8}$ alkynyl are as defined above. Specific examples thereof include ethoxy-1-propynyl, propoxy-1-propynyl, butoxy-1-propynyl, propoxy-1-butynyl, propoxy-1-hexynyl, butoxy-1-hexynyl, propoxy-1-heptynyl, and butoxy-1-heptynyl. Preferred examples thereof include ethoxy-1-propynyl, propoxy-1-propynyl, butoxy-1-propynyl, propoxy-1-butynyl, propoxy-1-hexynyl, and butoxy-1-heptynyl.

In the present invention, "(morpholino)$C_{2-6}$ alkynyl" means $C_{2-6}$ alkynyl substituted with morpholino. $C_{2-6}$ alkynyl is as defined above. Specific examples thereof include morpholinoethynyl, morpholino-1-propynyl, morpholino-2-propynyl, morpholino-1-butynyl, morpholino-2-butynyl, morpholino-3-butynyl, morpholino-1-pentynyl, morpholino-2-pentynyl, morpholino-3-pentynyl, morpholino-4-pentynyl, and morpholino-1-hexynyl. Preferred examples thereof include morpholino-1-propynyl, morpholino-1-butynyl, and morpholino-1-heptynyl.

In the present invention, examples of "(morpholino)$C_{2-6}$ alkynyl substituted with oxo group(s)" include (morpholino)$C_{2-6}$ alkynyl substituted with one or two oxo groups. Preferred examples thereof include 3-(3-oxomorpholin-4-yl)-1-propynyl and (1,1-dioxothiomorpholin-4-yl)-1-propynyl.

In the present invention, "(3- to 6-membered oxacycloalkyl)$C_{2-6}$ alkynyl" means $C_{2-6}$ alkynyl substituted with 3- to 6-membered oxacycloalkyl. 3- to 6-Membered oxacycloalkyl and $C_{2-6}$ alkynyl are as defined in the specification.

In the present invention, "(oxetanyl)$C_{2-6}$ alkynyl" means $C_{2-6}$ alkynyl substituted with oxetanyl. $C_{2-6}$ alkynyl is as defined above. Specific examples thereof include oxetanylethynyl, oxetanyl-1-propynyl, oxetanyl-2-propynyl, oxetanyl-1-butynyl, oxetanyl-2-butynyl, oxetanyl-3-butynyl, oxetanyl-1-pentynyl, oxetanyl-2-pentynyl, oxetanyl-3-pentynyl, oxetanyl-4-pentynyl, and oxetanyl-1-hexynyl. Preferred examples thereof include oxetanyl-1-propynyl, oxetanyl-1-butynyl, and oxetanyl-1-pentynyl.

In the present invention, "(pyrrolidino)$C_{2-6}$ alkynyl" means $C_{2-6}$ alkynyl substituted with pyrrolidino. $C_{2-6}$ alkynyl is as defined above. Specific examples thereof include pyrrolidinoethynyl, pyrrolidino-1-propynyl, pyrrolidino-2-propynyl, pyrrolidino-1-butynyl, pyrrolidino-2-butynyl, pyrrolidino-3-butynyl, pyrrolidino-1-pentynyl, pyrrolidino-2-pentynyl, pyrrolidino-3-pentynyl, pyrrolidino-4-pentynyl, and pyrrolidino-1-hexynyl. Preferred examples thereof include pyrrolidino-1-propynyl.

In the present invention, "($C_{3-6}$ cycloalkyl)$C_{2-6}$ alkynyl" means $C_{2-6}$ alkynyl substituted with $C_{3-6}$ cycloalkyl. $C_{3-6}$ cycloalkyl and $C_{2-6}$ alkynyl are as defined above. Specific examples thereof include cyclopropylethynyl, cyclobutylethynyl, cyclopentylethynyl, cyclohexylethynyl, cyclopropyl-1-propynyl, cyclobutyl-1-propynyl, cyclopentyl-1-propynyl, cyclohexyl-1-propynyl, cyclopropyl-1-butynyl, cyclobutyl-1-butynyl, cyclopentyl-1-butynyl, and cyclohexyl-1-butynyl. Preferred examples thereof include cyclopropylethynyl, cyclobutylethynyl, cyclopentylethynyl, cyclopropyl-1-propynyl, cyclobutyl-1-propynyl, and cyclopentyl-1-propynyl.

In the present invention, "[HO—((CH$_2$)$_o$O)$_p$]$C_{2-8}$ alkynyl" means $C_{2-8}$ alkynyl substituted with a group —O(CH$_2$)$_o$)$_p$—OH. $C_{2-8}$ alkynyl is as defined above. Specific examples thereof include [HO—((CH$_2$)$_2$O)$_3$]propynyl and [HO—((CH$_2$)$_2$O)$_2$]propynyl.

In the present invention, "[N—(($C_{1-3}$ alkoxy)$C_{1-4}$ alkyl)-N—($C_{1-3}$ alkyl)amino]$C_{2-6}$ alkynyl" means $C_{2-6}$ alkynyl substituted with N—(($C_{1-3}$ alkoxy)$C_{1-4}$ alkyl)-N—($C_{1-3}$ alkyl)amino. In this context, "[N—(($C_{1-3}$ alkoxy)$C_{1-4}$ alkyl)-N—($C_{1-3}$ alkyl)amino]" and "$C_{2-6}$ alkynyl" are as defined in this specification. Specific examples include [N-(2-methoxyethyl)-N-(methyl)amino]ethynyl, [N-(2-methoxy-1,1-dimethylethyl)-N-(methyl)amino]ethynyl, and [N-(2-methoxy-2-methyl-1-propyl)-N-(methyl)amino]ethynyl.

In the present invention, "$C_{1-3}$ alkoxy" means a $C_{1-3}$ alkyl-O— group. In this context, $C_{1-3}$ alkyl is as defined above. Specific examples thereof include methoxy, ethoxy, 1-propoxy, and 2-propoxy.

In the present invention, "$C_{1-4}$ alkoxy" means a $C_{1-4}$ alkyl-O— group. In this context, $C_{1-4}$ alkyl is as defined above. Specific examples thereof include methoxy, ethoxy, 1-propoxy, 2-propoxy, n-butoxy, i-butoxy, sec-butoxy, and t-butoxy.

In the present invention, "$C_{1-5}$ alkoxy" means a $C_{1-5}$ alkyl-O— group. In this context, $C_{1-5}$ alkyl is as defined above. Specific examples thereof include methoxy, ethoxy, 1-propoxy, 2-propoxy, n-butoxy, i-butoxy, sec-butoxy, t-butoxy, and 1-pentyloxy.

In the present invention, "$C_{1-6}$ alkoxy" means a $C_{1-6}$ alkyl-O— group. In this context, $C_{1-6}$ alkyl is as defined above. Specific examples thereof include methoxy, ethoxy, 1-propoxy, 2-propoxy, n-butoxy, i-butoxy, sec-butoxy, t-butoxy, 1-pentyloxy, and 1-hexyloxy.

In the present invention, "$C_{1-8}$ alkoxy" means a $C_{1-8}$ alkyl-O— group. Specific examples thereof include the groups listed above in the definition of "$C_{1-6}$ alkoxy" as well as 1-heptyloxy and 1-octyloxy.

In the present invention, "(carboxy)$C_{1-8}$ alkoxy" means $C_{1-6}$ alkoxy substituted with one carboxy group. "$C_{1-8}$ alkoxy" is as defined above. Specific examples thereof include carboxy-n-propoxy, carboxy-n-butoxy, carboxy-n-pentoxy, and carboxy-n-hexoxy.

In the present invention, "(morpholino)$C_{1-6}$ alkoxy" means $C_{1-6}$ alkoxy substituted with morpholino. "$C_{1-6}$ alkoxy" is as defined above. Specific examples thereof include morpholinomethoxy, morpholinoethoxy, morpholino-1-propoxy, morpholino-2-propoxy, morpholino-n-butoxy, morpholino-1-butoxy, morpholino-sec-butoxy, morpholino-t-butoxy, morpholino-1-pentyloxy, and morpholino-1-hexyloxy. Preferred examples thereof include morpholinoethoxy.

In the present invention, "(3- to 6-membered oxacycloalkyl)$C_{1-4}$ alkoxy" means $C_{1-4}$ alkoxy substituted with 3- to 6-membered oxacycloalkyl. "$C_{1-4}$ alkoxy" is as defined above. 3- to 6-membered oxacycloalkyl means a saturated heterocyclic group composed of 3 to 6 ring-constituting atoms containing one or two, (preferably one) oxygen atom. "(3- to 6-membered oxacycloalkyl)$C_{1-4}$ alkoxy" includes (oxiranyl)$C_{1-4}$ alkoxy, (oxetanyl)$C_{1-4}$ alkoxy, and (oxolanyl)$C_{1-4}$ alkoxy. Specific examples thereof include oxiranylmethoxy, oxiranylethoxy, oxiranyl-1-propoxy, oxiranyl-n-butoxy, oxetanylmethoxy, oxetanylethoxy, oxetanyl-1-propoxy, oxetanyl-n-butoxy, oxolanylmethoxy, oxolanylethoxy, oxolanyl-1-propoxy, and oxolanyl-n-butoxy. Preferred examples thereof include oxolanylmethoxy, oxiranylmethoxy, and oxetanylmethoxy.

In the present invention, "3- to 6-membered oxacycloalkyloxy" means 3- to 6-membered oxacycloalkyl-O—. "3- to 6-membered oxacycloalkyl" is as defined above. Specific examples thereof include oxiranyloxy, oxetanyloxy, oxolanyloxy, and oxanyloxy. Oxetanyloxy, oxolanyloxy, or oxanyloxy is preferred.

In the present invention, "4- to 6-membered nitrogen containing heterocycloalkyloxy" means 4- to 6-membered nitrogen containing heterocycloalkyl-O—. "4- to 6-membered nitrogen containing heterocycloalkyl" means a saturated heterocyclic group composed of 4 to 6 ring-constituting atoms containing one or two nitrogen atoms. Specific examples thereof include pyrrolidinyloxy and azetidinyloxy.

In the present invention, "(pyridinyl)$C_{1-4}$ alkoxy" means $C_{1-4}$ alkoxy substituted with pyridinyl. "$C_{1-4}$ alkoxy" is as defined above. Specific examples thereof include pyridinylmethoxy, pyridinylethoxy, pyridinyl-1-propoxy, and pyridinyl-n-butoxy. Preferred examples thereof include pyridinylmethoxy.

In the present invention, "(pyrimidinyl)$C_{1-4}$ alkoxy" means $C_{1-4}$ alkoxy substituted with pyrimidinyl. "$C_{1-4}$ alkoxy" is as defined above. Specific examples thereof include pyrimidinylmethoxy, pyrimidinylethoxy, pyrimidinyl-1-propoxy, and pyrimidinyl-n-butoxy. Preferred examples thereof include pyrimidinylmethoxy.

In the present invention, "(1,2,4-triazolyl)$C_{1-4}$ alkoxy" means $C_{1-4}$ alkoxy substituted with 1,2,4-triazolyl. "$C_{1-4}$ alkoxy" is as defined above. Specific examples thereof include 1,2,4-triazolylmethoxy, 1,2,4-triazolylethoxy, 1,2,4-triazolyl-1-propoxy, and 1,2,4-triazolyl-n-butoxy. Preferred examples thereof include 1,2,4-triazolylethoxy.

In the present invention, "(3- to 6-membered heterocycloalkyl)$C_{1-6}$ alkoxy" means $C_{1-6}$ alkoxy substituted with 3- to 6-membered heterocycloalkyl. 3- to 6-membered heterocycloalkyl means a saturated heterocyclic group composed of 3 to 6 ring-constituting atoms containing one to three heteroatoms selected from O, S, and N. $C_{1-6}$ alkoxy is as defined above. "(3- to 6-membered heterocycloalkyl)$C_{1-6}$ alkoxy" includes (morpholino)$C_{1-6}$alkoxy, (3- to 6-membered oxacycloalkyl)$C_{1-4}$ alkoxy, (pyrrolidinyl)$C_{1-4}$ alkoxy, (azetidinyl)$C_{1-4}$ alkoxy, and (piperidinyl)$C_{1-4}$ alkoxy. Specific examples thereof include morpholinomethoxy, morpholinoethoxy, morpholino-1,1-dimethyl-ethoxy(morpholino-t-butoxy), morpholino-1-methyl-ethoxy (morpholino-2-propoxy), tetrahydrofuranylmethoxy, pyrrolidinylmethoxy, pyrrolidinylethoxy, azetidinylmethoxy, azetidinylethoxy, piperidinylmethoxy, piperidinylethoxy, piperazinylmethoxy, piperazinylethoxy.

In the present invention, "(5- or 6-membered heteroaryl) $C_{1-4}$ alkoxy" means $C_{1-4}$ alkoxy substituted with 5- or 6-membered heteroaryl. 5- or 6-membered heteroaryl and $C_{1-4}$ alkoxy are as defined herein. Specific examples thereof include 1,2,4-triazolylethoxy.

In the present invention, "($C_{1-6}$ alkoxy)$C_{1-6}$ alkoxy" means $C_{1-6}$ alkoxy substituted with $C_{1-6}$ alkoxy. "$C_{1-6}$ alkoxy" is as defined above. "($C_{1-6}$ alkoxy)$C_{1-6}$ alkoxy" includes "($C_{1-4}$ alkoxy)$C_{1-6}$ alkoxy", "$C_{1-3}$ alkoxy($C_{1-4}$ alkoxy)", and the like. Specific examples thereof include methoxymethoxy, methoxyethoxy, ethoxymethoxy, ethoxyethoxy, methoxypropoxy, ethoxypropoxy, propoxymethoxy, propoxyethoxy, propoxypropoxy, methoxybutoxy, ethoxybutoxy, propoxybutoxy, butoxymethoxy, butoxyethoxy, butoxypropoxy, butoxybutoxy, methoxypentoxy, ethoxypentoxy, propoxypentoxy, butoxypentoxy, pentoxymethoxy, pentoxyethoxy, pentoxypropoxy, pentoxybutoxy, pentoxypentoxy, methoxyhexoxy, ethoxyhexoxy, propoxyhexoxy, butoxyhexoxy, pentoxyhexoxy, hexoxymethoxy, hexoxyethoxy, hexoxypropoxy, hexoxybutoxy, hexoxypentoxy, and hexoxyhexoxy. Preferred examples thereof include propoxybutoxy, propoxypentoxy, and propoxyhexoxy.

In the present invention, "($C_{1-6}$ alkoxy)$C_{1-8}$ alkoxy" means $C_{1-8}$ alkoxy substituted with $C_{1-6}$ alkoxy. "$C_{1-6}$ alkoxy" and "$C_{1-8}$ alkoxy" are as defined above. Specific examples thereof include the groups listed above in the definition of "($C_{1-6}$ alkoxy)$C_{1-6}$ alkoxy" as well as hexoxyheptyloxy and hexoxyoctyloxy.

In the present invention, "($C_{1-3}$ alkoxy($C_{1-4}$ alkoxy))$C_{1-4}$ alkoxy" means $C_{1-4}$ alkoxy substituted with $C_{1-3}$ alkoxy ($C_{1-4}$ alkoxy). "$C_{1-3}$ alkoxy($C_{1-4}$ alkoxy)" means $C_{1-4}$ alkoxy substituted with $C_{1-3}$ alkoxy. "$C_{1-4}$ alkoxy" and "$C_{1-3}$ alkoxy" are as defined above. Specific examples thereof include methoxyethoxyethoxy, ethoxyethoxyethoxy, and methoxyethoxymethoxy.

In the present invention, "[N—(($C_{1-3}$ alkoxy)$C_{1-4}$ alkyl)-N—($C_{1-3}$ alkyl)amino]$C_{1-4}$ alkoxy" means $C_{1-4}$ alkoxy substituted with N—(($C_{1-3}$ alkoxy)$C_{1-4}$ alkyl)-N—($C_{1-3}$ alkyl) amino. In this context, "[N—(($C_{1-3}$ alkoxy)$C_{1-4}$ alkyl)-N—($C_{1-3}$ alkyl)amino]" means amino substituted with ($C_{1-3}$ alkoxy)$C_{1-4}$ alkyl and $C_{1-3}$ alkyl. ($C_{1-3}$ alkoxy)$C_{1-4}$ alkyl and $C_{1-3}$ alkyl are as defined above. Specific examples of "[N—(($C_{1-3}$ alkoxy)$C_{1-4}$ alkyl)-N—($C_{1-3}$ alkyl)amino]$C_{1-4}$ alkoxy" include [Nmethoxyethyl)-N-(methyl)amino]ethoxy, [N-(methoxy-1,1-dimethylethyl)-N-(methyl)amino]ethoxy, and [N-(-methoxy-2-methyl-1-propyl)-N-(methyl)amino] ethoxy.

In the present invention, "[N-(3- to 6-membered heterocycloalkyl)-N—($C_{1-3}$ alkyl)amino]$C_{1-4}$ alkoxy" means $C_{1-4}$ alkoxy substituted with N-(3- to 6-membered heterocycloalkyl)-N—($C_{1-3}$ alkyl)amino. In this context, "[N-(3- to 6-membered heterocycloalkyl)-N—($C_{1-3}$ alkyl)amino]" means amino substituted with 3- to 6-membered heterocycloalkyl and $C_{1-3}$ alkyl. 3- to 6-membered heterocycloalkyl is as defined herein. Specific examples thereof include [N-tetrahydrofuranyl-N-(methyl)amino]ethoxy, [N-tetrahydropyranyl-N-(methyl)amino]ethoxy, and [N-oxetanyl-N-(methyl)amino]ethoxy.

In the present invention, [N,N-di((hydroxy)$C_{1-4}$ alkyl)-amino]$C_{1-4}$ alkoxy means $C_{1-4}$ alkoxy substituted with N,N-di((hydroxy)$C_{1-4}$ alkyl)-amino. "[N,N-di((hydroxy)$C_{1-4}$ alkyl)-amino]" means amino substituted with two (hydroxy) $C_{1-4}$ alkyl groups. (Hydroxy)$C_{1-4}$ alkyl means $C_{1-4}$ alkyl substituted with one hydroxy group. Specific examples thereof include [N,N-di(2-hydroxyethyl)amino]ethoxy.

In the present invention, "[N—(($C_{1-3}$ alkoxy)carbonyl) $C_{1-3}$ alkyl-N—($C_{1-3}$ alkyl)amino]$C_{1-4}$ alkoxy" means $C_{1-4}$ alkoxy substituted with N—(($C_{1-3}$ alkoxy)carbonyl)$C_{1-3}$ alkyl-N—($C_{1-3}$ alkyl)amino. [N—(($C_{1-3}$ alkoxy)carbonyl) $C_{1-3}$ alkyl-N—($C_{1-3}$ alkyl)amino] means amino substituted with (($C_{1-3}$ alkoxy)carbonyl)$C_{1-3}$ alkyl and $C_{1-3}$ alkyl. "(($C_{1-3}$ alkoxy)carbonyl)$C_{1-3}$ alkyl" means $C_{1-3}$ alkyl substituted with ($C_{1-3}$ alkoxy)carbonyl. Specific examples thereof include [N-((methoxy)carbonyl)methyl-N-methylamino]ethoxy.

In the present invention, "[N-(hydroxy)$C_{1-4}$ alkyl-N—($C_{1-3}$ alkyl)amino]$C_{1-4}$ alkoxy" means $C_{1-4}$ alkoxy substituted with N-(hydroxy)$C_{1-4}$ alkyl-N—($C_{1-3}$ alkyl)amino. "N-(hydroxy)$C_{1-4}$ alkyl-N—($C_{1-3}$ alkyl)amino" means amino substituted with (hydroxy)$C_{1-4}$ alkyl and $C_{1-3}$ alkyl. "(Hydroxy)$C_{1-4}$ alkyl" means $C_{1-4}$ alkyl substituted with one hydroxy group. Specific examples thereof include [N-(2-hydroxyethyl)-N-methylamino]ethoxy.

In the present invention, "[N,N-di(($C_{1-3}$ alkoxy)$C_{1-4}$ alkyl)amino]$C_{1-6}$ alkoxy" means $C_{1-6}$ alkoxy substituted with N,N-di(($C_{1-3}$ alkoxy)$C_{1-4}$ alkyl)amino. "N,N-di(($C_{1-3}$ alkoxy)$C_{1-4}$ alkyl)amino" means amino substituted with two ($C_{1-3}$ alkoxy)$C_{1-4}$ alkyl groups. "($C_{1-3}$ alkoxy)$C_{1-4}$ alkyl" is as defined above. Specific examples thereof include [N,N-di((methoxy)ethoxy)amino]ethoxy.

In the present invention, "[N,N-di($C_{1-3}$ alkyl)amino]$C_{1-6}$ alkoxy" means $C_{1-6}$ alkoxy substituted with N,N-di($C_{1-3}$ alkyl)amino. "N,N-di($C_{1-3}$ alkyl)amino" means amino substituted with two $C_{1-3}$ alkyl groups. "$C_{1-6}$ alkoxy" and "$C_{1-3}$ alkyl" are as defined above. Specific examples thereof include 3-[N,N-di(methyl)amino]-2,2-dimethyl-propoxy.

In the present invention, "[N—[N—($C_{1-4}$ alkyl) carbonyl-N—($C_{1-3}$ alkyl)amino]$C_{1-4}$ alkyl-N—($C_{1-3}$ alkyl)amino] $C_{1-4}$ alkoxy" means $C_{1-4}$ alkoxy substituted with N—[N—($C_{1-4}$ alkyl) carbonyl-N—($C_{1-3}$ alkyl)amino]$C_{1-4}$ alkyl-N—($C_{1-3}$ alkyl)amino. $C_{1-4}$ alkoxy is as defined before. "N—[N—($C_{1-4}$ alkyl) carbonyl-N—($C_{1-3}$ alkyl)amino]$C_{1-4}$ alkyl-N—($C_{1-3}$ alkyl) amino" means amino substituted with [N—($C_{1-4}$ alkyl) carbonyl-N—($C_{1-3}$ alkyl) amino]$C_{1-4}$ alkyl and $C_{1-3}$ alkyl. $C_{1-3}$ alkyl is as defined before. "[N—($C_{1-4}$ alkyl)

carbonyl-N—($C_{1-3}$ alkyl) amino]$C_{1-4}$ alkyl" means $C_{1-4}$ alkyl substituted with N—($C_{1-4}$ alkyl) carbonyl-N—($C_{1-3}$ alkyl) amino. "N—($C_{1-4}$ alkyl) carbonyl-N—($C_{1-3}$ alkyl) amino" means amino substituted with ($C_{1-4}$ alkyl) carbonyl and $C_{1-3}$ alkyl. Specific examples thereof include 2-[N-[2-(N-acetyl-N-(methyl) amino)ethyl]-N-(methyl) amino]ethoxy.

In the present invention, "[N—[N—($C_{1-4}$ alkyl) carbonyl-amino]$C_{1-4}$ alkyl-N—($C_{1-3}$ alkyl) amino]$C_{1-4}$ alkoxy" means $C_{1-4}$ alkoxy substituted with N—[N—($C_{1-4}$ alkyl) carbonyl-amino]$C_{1-4}$ alkyl-N—($C_{1-3}$ alkyl) amino. $C_{1-4}$ alkoxy is as defined before. "N—[N—($C_{1-4}$ alkyl) carbonyl-amino]$C_{1-4}$ alkyl-N—($C_{1-3}$ alkyl) amino" means amino substituted with [N—($C_{1-4}$ alkyl) carbonyl-amino]$C_{1-4}$ alkyl and $C_{1-3}$ alkyl. $C_{1-3}$ alkyl is as defined before. "[N—($C_{1-4}$ alkyl) carbonyl-amino]$C_{1-4}$ alkyl" means $C_{1-4}$ alkyl substituted with a N—($C_{1-4}$ alkyl) carbonyl-amino. "N—($C_{1-4}$ alkyl) carbonyl-amino" means amino substituted with a ($C_{1-4}$ alkyl) carbonyl. Specific examples thereof include 2-[N-[2-(acetylamino)ethyl]-N-(methyl) amino]ethoxy.

In the present invention, "$C_{1-3}$ alkylthio" means a $C_{1-3}$ alkyl-S— group. In this context, $C_{1-3}$ alkyl is as defined above. Specific examples thereof include methylthio, ethylthio, n-propylthio, and i-propylthio.

In the present invention, "$C_{1-4}$ alkylthio" means a $C_{1-4}$ alkyl-S— group. In this context, $C_{1-4}$ alkyl is as defined above. Specific examples thereof include methylthio, ethylthio, n-propylthio, i-propylthio, n-butylthio, i-butylthio, and t-butylthio.

In the present invention, "(morpholino)$C_{1-4}$ alkylthio" means $C_{1-4}$ alkylthio substituted with morpholino. $C_{1-4}$ alkylthio is as defined above. Specific examples thereof include morpholinomethylthio, morpholinoethylthio, morpholino-n-propylthio, morpholino-1-propylthio, morpholino-n-butylthio, morpholino-1-butylthio, and morpholino-t-butylthio. Preferred examples thereof include morpholinoethylthio.

In the present invention, "(5- or 6-membered heterocycloalkyl)$C_{1-4}$ alkylthio" means $C_{1-4}$ alkylthio substituted with 5- or 6-membered heterocycloalkyl. 5- or 6-membered heterocycloalkyl and $C_{1-4}$ alkylthio are as defined herein. "(5- or 6-membered heterocycloalkyl)$C_{1-4}$ alkylthio" includes "(morpholino)$C_{1-4}$ alkylthio". Preferred examples thereof include 2-morpholinoethylthio.

In the present invention, "($C_{1-6}$ alkyl)carbonyl" means a $C_{1-6}$ alkyl-C(O)— group. In this context, $C_{1-6}$ alkyl is as defined above. "($C_{1-6}$ alkyl)carbonyl" includes "($C_{1-4}$ alkyl) carbonyl". Specific examples thereof include methylcarbonyl, ethylcarbonyl, n-propylcarbonyl, i-propylcarbonyl, n-butylcarbonyl, i-butylcarbonyl, sec-butylcarbonyl, t-butylcarbonyl, 1-methylpropylcarbonyl, n-pentylcarbonyl, isopentylcarbonyl, 2-methylbutylcarbonyl, 1,1-dimethylpropylcarbonyl, 1-ethylpropylcarbonyl, hexylcarbonyl, 4-methylpentylcarbonyl, and 2-ethylbutylcarbonyl.

In the present invention, "di($C_{1-3}$ alkyl)amino)carbonyl" means carbonyl substituted with di($C_{1-3}$ alkyl)amino. "Di ($C_{1-3}$ alkyl)amino" means amino substituted with two $C_{1-3}$ alkyl groups. Specific examples thereof include dimethylaminocarbonyl and diethylaminocarbonyl.

In the present invention, "($C_{1-3}$ alkyl)sulfonyl" means a $C_{1-3}$ alkyl-SO$_2$— group. In this context, $C_{1-3}$ alkyl is as defined above. Specific examples thereof include methylsulfonyl, ethylsulfonyl, and n-propylsulfonyl. Preferred examples thereof include methylsulfonyl.

In the present invention, "($C_{1-6}$ alkoxy)carbonyl" means a $C_{1-6}$ alkyl-O—C(O)— group. In this context, $C_{1-6}$ alkyl is as defined above. Specific examples thereof include groups listed later in the definition of "($C_{1-4}$ alkoxy)carbonyl" as well as n-pentyloxycarbonyl, isopentyloxycarbonyl, 2-methylbutoxycarbonyl, 1,1-dimethylpropoxycarbonyl, 1-ethylpropoxycarbonyl, hexyloxycarbonyl, 4-methylpentyloxycarbonyl, and 2-ethylbutoxycarbonyl.

In the present invention, "($C_{1-4}$ alkoxy)carbonyl" means a $C_{1-4}$ alkyl-O—C(O)— group. In this context, $C_{1-4}$ alkyl is as defined above. Specific examples thereof include methoxycarbonyl, ethoxycarbonyl, n-propoxycarbonyl, i-propoxycarbonyl, n-butoxycarbonyl, i-butoxycarbonyl, sec-butoxycarbonyl, t-butoxycarbonyl, and 1-methylpropoxycarbonyl.

In the present invention, "($C_{1-3}$ alkoxy)carbonyl" means a $C_{1-3}$ alkyl-O—C(O)— group. In this context, $C_{1-3}$ alkyl is as defined above. Specific examples thereof include methoxycarbonyl, ethoxycarbonyl, n-propoxycarbonyl, and i-propoxycarbonyl.

In the present invention, "(($C_{1-4}$ alkoxy)carbonyl)$C_{1-6}$ alkyl" means $C_{1-6}$ alkyl substituted with ($C_{1-4}$ alkoxy)carbonyl. In this context, ($C_{1-4}$ alkoxy)carbonyl and $C_{1-6}$ alkyl are as defined above. Specific examples thereof include methoxycarbonylmethyl, methoxycarbonylethyl, ethoxycarbonylmethyl, ethoxycarbonylethyl, n-propoxycarbonylmethyl, and i-propoxycarbonylmethyl. Preferred examples thereof include methoxycarbonylmethyl and methoxycarbonylethyl.

In the present invention, "(($C_{1-3}$ alkoxy)carbonyl)$C_{1-3}$ alkoxy" means $C_{1-3}$ alkoxy substituted with a ($C_{1-3}$ alkoxy) carbonyl group. In this context, ($C_{1-3}$ alkoxy)carbonyl and $C_{1-3}$ alkyl are as defined above. Specific examples thereof include methoxycarbonylmethoxy, methoxycarbonylethoxy, ethoxycarbonylmethoxy, ethoxycarbonylethoxy, n-propoxycarbonylmethoxy, and i-propoxycarbonylmethoxy. Preferred examples thereof include methoxycarbonylmethoxy and methoxycarbonylethoxy.

In the present invention, "$C_{6-10}$ aryl" means a monovalent aromatic hydrocarbon ring group. Examples of $C_{6-10}$ aryl include phenyl, 1-naphthyl, and 2-naphthyl.

In the present invention, "($C_{6-10}$ aryl)carbonyl" means a $C_{6-10}$ aryl-C(O)— group. In this context, $C_{6-10}$ aryl is as defined above. Specific examples thereof include phenylcarbonyl, 1-naphthylcarbonyl, and 2-naphthylcarbonyl.

In the present invention, "5- to 10-membered heteroaryl" means an aromatic ring group composed of 5 to 10 ring-constituting atoms containing one or several (e.g., 1 to 5, preferably 1 to 3) heteroatoms. The ring may be a monocyclic or bicyclic ring. Examples of "5- to 10-membered heteroaryl" include "5- or 6-membered heteroaryl". Specific examples of "5- to 10-membered heteroaryl" include thienyl, pyridazinyl, pyrazinyl, thiazolyl, oxazolyl, isothiazolyl, thiadiazolyl, oxadiazolyl, isoxazolyl, pyrazolyl, quinolinyl, isoquinolyl, benzothiazolyl, benzoxazolyl, benzimidazolyl, pyridinyl, pyrimidinyl, indolyl, imidazolyl, furyl, thioxazolyl, pyrrolyl, tetrazolyl, oxopyrimidinyl, naphthyl, benzodioxinyl, benzisoxazolyl, benzisothiazolyl, indazolyl, benzothienyl, benzofuranyl, benzopyranyl, and triazolyl.

In the present invention, "5- or 6-membered heteroaryl" means an aromatic ring group composed of 5 or 6 ring-constituting atoms containing one or several (e.g., 1 to 4, preferably 1 to 3, more preferably 1 or 2) heteroatoms. Specific examples thereof include thienyl, pyridazinyl, pyrazinyl, thiazolyl, oxazolyl, isothiazolyl, thiadiazolyl, oxadiazolyl, isoxazolyl, pyrazolyl, pyridinyl, pyrimidinyl, furyl, thioxazolyl, and triazolyl.

In the present invention, a "$C_{3-6}$ saturated carbocyclic ring" refers to a cycloalkane ring having 3 to 6 ring-constituting carbon atoms and includes, for example, cyclopropane, cyclobutane, cyclopentane, and cyclohexane. In the formula (I), $R^1$ and $R^5$ together with the carbon atom to which they are attached may form a $C_{3-6}$ saturated carbocyclic ring. In this case, the $C_{3-6}$ saturated carbocyclic ring forms a spiro ring. In the formula (I), the $C_{3-6}$ saturated carbocyclic ring formed by $R^1$ and $R^5$ together with the carbon atom to which they are attached is preferably cyclobutane, cyclopentane, or cyclohexane, particularly preferably cyclobutane or cyclopentane.

In the present invention, a "5- to 8-membered saturated heterocyclic ring" means a saturated heterocyclic group composed of 5 to 8 ring-constituting atoms containing one N as a heteroatom. Specific examples thereof include pyrrolidine, piperidine, azepane, and azocane and particularly include pyrrolidine and piperidine.

In the present invention, n is preferably an integer selected from 1 to 3, particularly preferably 1 or 2.

When Re (or Rx) is $C_{6-10}$ aryl optionally substituted with one or more substituents Ra (or Ry) or 5- to 10-membered heteroaryl optionally substituted with one or more substituents Ra (or Ry), the $C_{6-10}$ aryl is preferably phenyl, and the 5- to 10-membered heteroaryl is preferably indolyl. Particularly, when $R^4$ and $R^5$ together with the carbon atom and nitrogen atom to which they are attached do not form a 5- to 8-membered saturated heterocyclic ring, Re is preferably phenyl.

In the present invention, $Ar^1$ (or $Ar^{101}$) is preferably phenyl, naphthyl, furyl, thienyl, pyridazinyl, pyrazinyl, thiazolyl, oxazolyl, isothiazolyl, thiadiazolyl, oxadiazolyl, isoxazolyl, pyrazolyl, quinolinyl, isoquinolyl, benzothiazolyl, benzoxazolyl, benzimidazolyl, pyridinyl, pyrimidinyl, or indolyl. These groups are each optionally substituted with one to three substituents selected from Rb (or $Rz^1$), Rc (or $Rz^2$), and Rd (or $Rz^3$). When $R^4$ and $R^5$ together with the carbon atom to which they are attached form a 5- to 8-membered saturated heterocyclic ring or in the case of the compound represented by the formula (II), $Ar^1$ (or $Ar^{101}$) is more preferably phenyl, furyl, pyridinyl, or pyrimidinyl.

When $R^4$ and $R^5$ together with the carbon atom and nitrogen atom to which they are attached do not form a 5- to 8-membered saturated heterocyclic ring, $Ar^1$ is preferably phenyl, pyridinyl, or pyrimidinyl.

In the present invention, Rd (or $Rz^3$) is preferably phenyl, thienyl, pyridinyl, pyrimidinyl, quinolinyl, pyrazolyl, imidazolyl, isoxazolyl, oxazolyl, thiazolyl, isothiazolyl, pyridazinyl, pyrazinyl, furyl, thiadiazolyl, thioxazolyl, oxadiazolyl, pyrrolyl, tetrazolyl, oxopyrimidinyl, naphthyl, benzodioxinyl, isoquinolinyl, benzoxazolyl, benzothiazolyl, benzisoxazolyl, benzisothiazolyl, indolyl, indazolyl, benzothienyl, benzofuranyl, benzopyranyl, piperazinyl, piperidyl, morpholinyl, thiomorpholinyl, pyrrolidinyl, dioxopyrrolidinyl, dioxopiperidinyl, dioxotetrahydropyrimidinyl, oxoimidazolidinyl, or dioxoimidazolidinyl. These groups are each optionally substituted with one or more substituents $R^{14}$. When $R^4$ and $R^5$ together with the carbon atom and the nitrogen atom to which they are attached form a 5- to 8-membered saturated heterocyclic ring or in the case of the compound represented by the formula (II), Rd (or $Rz^3$) is preferably phenyl, thienyl, pyridinyl, pyrimidinyl, quinolinyl, piperidinyl, morpholinyl, thiomorpholinyl, or piperazinyl, more preferably phenyl, thienyl, pyridinyl, pyrimidinyl, quinolinyl, or piperidinyl. When $R^4$ and $R^5$ together with the carbon atom and the nitrogen atom to which they are attached do not form a 5- to 8-membered saturated heterocyclic ring, Rd (or $Rz^3$) is preferably phenyl, pyridinyl, pyrimidinyl, morpholinyl, thiomorpholinyl, piperidinyl, or piperazinyl, more preferably phenyl, pyridinyl, or pyrimidinyl.

In the present invention, "$C_{3-6}$ cycloalkyl" means a cyclic saturated aliphatic hydrocarbon group having 3 to 6 carbon atoms. Specific examples thereof include cyclopropyl, cyclobutyl, cyclopentyl, and cyclohexyl.

In the present invention, "$C_{3-7}$ cycloalkyl" means a cyclic saturated aliphatic hydrocarbon group having 3 to 7 carbon atoms. Specific examples thereof include cyclopropyl, cyclobutyl, cyclopentyl, cyclohexyl, and cycloheptyl.

In the present invention, "3- to 10-membered heterocycloalkyl" means a saturated heterocyclic group composed of 3 to 10 ring-constituting atoms containing one to three heteroatoms selected from O, S, and N. The heterocycloalkyl may be monocyclic, bicyclic, or spiro-cyclic heterocycloalkyl. Specific examples of "3- to 10-membered heterocycloalkyl" include groups listed later in the definition of "4- to 10-membered heterocycloalkyl" as well as oxiranyl.

In the present invention, "4- to 10-membered heterocycloalkyl" means a saturated heterocyclic group composed of 4 to 10 ring-constituting atoms containing one to three heteroatoms selected from O, S, and N. The heterocycloalkyl may be monocyclic, bicyclic, or spiro-cyclic heterocycloalkyl. Examples of "4- to 10-membered heterocycloalkyl" include "5- to 10-membered heterocycloalkyl", "5- to 8-membered heterocycloalkyl", "6- to 8-membered heterocycloalkyl", and "5- or 6-membered heterocycloalkyl". Specific examples of "4- to 10-membered heterocycloalkyl" include groups listed later in the definition of "5- to 10-membered heterocycloalkyl" as well as oxetanyl, azetidinyl, and 3,7-dioxa-9-azabicyclo[3.3.1]nonanyl.

In the present invention, "5- to 10-membered heterocycloalkyl" means a saturated heterocyclic group composed of 5 to 10 ring-constituting atoms containing one to three heteroatoms selected from O, S, and N. The heterocycloalkyl may be monocyclic, bicyclic, or spiro-cyclic heterocycloalkyl. Examples of "5- to 10-membered heterocycloalkyl" include "6- to 8-membered heterocycloalkyl" and "5- or 6-membered heterocycloalkyl". Specific examples of "5- to 10-membered heterocycloalkyl" include piperazinyl, piperidinyl, morpholinyl, thiomorpholinyl, pyrrolidinyl, tetrahydropyranyl, tetrahydrofuranyl, 2-oxa-6-azaspiro[3.3]heptyl, 2-azaspiro[3.3]heptyl, 2,6-diazaspiro[3.3]heptyl, and 2-thia-6-azaspiro[3.3]heptyl.

In the present invention, "4- to 8-membered heterocycloalkyl" means a saturated heterocyclic group composed of 4 to 8 ring-constituting atoms containing one to three heteroatoms selected from O, S, and N. The heterocycloalkyl may be monocyclic, bicyclic, or spiro-cyclic heterocycloalkyl. Specific examples of "4- to 8-membered heterocycloalkyl" include those described as specific examples of "5- to 8-membered heterocycloalkyl".

In the present invention, "5- to 8-membered heterocycloalkyl" means a saturated heterocyclic group composed of 5 to 8 ring-constituting atoms containing one to three heteroatoms selected from O, S, and N. The heterocycloalkyl may be monocyclic, bicyclic, or spiro-cyclic heterocycloalkyl. Examples of "5- to 8-membered heterocycloalkyl" include "6- to 8-membered heterocycloalkyl" and "5- or 6-membered heterocycloalkyl". Specific examples of "5- to 8-membered heterocycloalkyl" include those described as specific examples of "6- to 8-membered heterocycloalkyl".

In the present invention, "6- to 8-membered heterocycloalkyl" means a saturated heterocyclic group composed of 6 to 8 ring-constituting atoms containing one to three heteroatoms selected from O, S, and N. The heterocycloalkyl may be monocyclic, bicyclic, or spiro-cyclic heterocycloalkyl. Specific examples thereof include piperazinyl, piperidinyl, morpholinyl, thiomorpholinyl, tetrahydrofuranyl, 2-oxa-6-azaspiro[3.3]heptyl, 2-azaspiro[3.3]heptyl, 2,6-diazaspiro[3.3]heptyl, and 2-thia-6-azaspiro[3.3]heptyl, and particularly include 2-oxo-6-azaspiro[3.3]heptyl, 2-azaspiro[3.3]heptyl, 2,6-diazaspiro[3.3]heptyl, and 2-thia-6-azaspiro[3.3]heptyl.

In the present invention, "3- to 6-membered heterocycloalkyl" means a saturated heterocyclic group composed of 3 to 6 ring-constituting atoms containing one to three heteroatoms selected from O, S, and N. Specific examples thereof include the groups listed later in the definition of "5- or 6-membered heterocycloalkyl" as well as oxetanyl.

In the present invention, "4- to 6-membered heterocycloalkyl" means a saturated heterocyclic group composed of 4 to 6 ring-constituting atoms containing one to three heteroatoms selected from O, S, and N. Specific examples thereof include the groups listed later in the definition of "5- or 6-membered heterocycloalkyl".

In the present invention, "5- or 6-membered heterocycloalkyl" means a saturated heterocyclic group composed of 5 or 6 ring-constituting atoms containing one to three heteroatoms selected from O, S, and N. Specific examples of the heterocycloalkyl include piperazinyl, piperidinyl, morpholinyl, thiomorpholinyl, pyrrolidinyl, tetrahydropyranyl, and tetrahydrofuranyl.

In the present invention, "3- to 6-membered oxacycloalkyl" means a saturated heterocyclic group composed of 3 to 6 ring-constituting atoms containing one or two oxygen atoms. Specific examples thereof include oxetanyl, tetrahydrofuranyl and tetrahydropyranyl.

In the present invention, "3- to 10-membered heterocycloalkyloxy" means a 3- to 10-membered heterocycloalkyl-O— group. In this context, 3- to 10-membered heterocycloalkyl is as defined above. Specific examples thereof include oxiranyloxy, oxetanyloxy, tetrahydrofuranyloxy, and tetrahydropyranyloxy. Tetrahydropyranyloxy is preferred.

In the present invention, "5- to 10-membered heterocycloalkyloxy" means a 5- to 10-membered heterocycloalkyl-O— group. In this context, 5- to 10-membered heterocycloalkyl is as defined above. "5- to 10-membered heterocycloalkyloxy" is preferably tetrahydropyranyloxy or tetrahydrofuranyloxy, particularly preferably tetrahydropyranyloxy.

In the present invention, "4- to 6-membered heterocycloalkyloxy" means a 4- to 6-membered heterocycloalkyl-O— group. In this context, 4- to 6-membered heterocycloalkyl is as defined above.

In the present invention, "5- or 6-membered heterocycloalkyloxy" means a 5- or 6-membered heterocycloalkyl-O— group. In this context, 5- or 6-membered heterocycloalkyl is as defined above.

In the present invention, "3- to 6-membered heterocycloalkyloxy" means a 3- to 6-membered heterocycloalkyl-O— group. In this context, 3- to 6-membered heterocycloalkyl is as defined above.

In the present invention, "3- to 10-membered heterocycloalkyl", "4- to 10-membered heterocycloalkyl", "5- to 10-membered heterocycloalkyl", "5- to 8-membered heterocycloalkyl", "6- to 8-membered heterocycloalkyl", "4- to 8-membered heterocycloalkyl", "3- to 6-membered heterocycloalkyl", "5- or 6-membered heterocycloalkyl", "5- to 10-membered heterocycloalkyloxy", "3- to 6-membered heterocycloalkyloxy", "5- or 6-membered heterocycloalkyloxy", or "4- to 6-nitrogen containing heterocycloalkyloxy" may be substituted with predetermined substituent(s). In this case, the substituent(s) are added to each of these groups via a carbon atom or a heteroatom constituting the ring of the heterocycloalkyl or the heterocycloalkyloxy.

When Re (or Rx) is 5- to 10-membered heteroaryl optionally substituted with one or more substituents Ra (or Ry), this group contains, for example, one to three nitrogen atoms as ring-constituting groups.

When Ra (or Ry) is 5- to 10-membered heterocycloalkyloxy, 3- to 6-membered heterocycloalkyloxy, or 4- to 6-membered heterocycloalkyloxy, this group contains, for example, one to three oxygen atoms or one nitrogen atom as ring-constituting groups. Examples of the heterocycloalkyloxy group include tetrahydropyranyloxy, oxetanyloxy, pyrrolidinyloxy, azetidinyloxy, and piperidinyloxy.

When $R^{10}$ (or $R^{110}$) is 3- to 10-membered heterocycloalkyl, 4- to 10-membered heterocycloalkyl, 5- to 10-membered heterocycloalkyl, 3- to 6-membered heterocycloalkyl, or 5- or 6-membered heterocycloalkyl, this group contains, for example, one to three heteroatoms selected from a nitrogen atom, an oxygen atom, and a sulfur atom, preferably a nitrogen atom and an oxygen atom, as ring-constituting groups. When $R^{10}$ (or $R^{110}$) is 3- to 10-membered heterocycloalkyl, 4- to 10-membered heterocycloalkyl, 5- to 10-membered heterocycloalkyl, 3- to 6-membered heterocycloalkyl, or 5- or 6-membered heterocycloalkyl, this group is preferably morpholinyl, homomorpholinyl, thiomorpholinyl, piperidinyl, piperazinyl, homopiperazinyl, pyrrolidinyl, azetidinyl, tetrahydropyranyl, or tetrahydrofuranyl, more preferably morpholinyl. These groups are each optionally substituted with the substituent(s) described as substituents for the corresponding heterocycloalkyl group.

When $R^{11}$ (or $R^{111}$) is 3- to 10-membered heterocycloalkyl, 4- to 10-membered heterocycloalkyl, 5- to 10-membered heterocycloalkyl, or 5- or 6-membered heterocycloalkyl, this group contains, for example, one to three heteroatoms selected from a nitrogen atom and an oxygen atom as ring-constituting groups.

When $R^{11}$ (or $R^{111}$) is $C_{3-6}$ cycloalkyl, 3- to 10-membered heterocycloalkyl, 4- to 10-membered heterocycloalkyl, 5- to 10-membered heterocycloalkyl, or 5- or 6-membered heterocycloalkyl, this group is preferably cyclopentyl, morpholinyl, pyrrolidinyl, homomorpholinyl, thiomorpholinyl, piperidinyl, piperazinyl, homopiperazinyl, tetrahydropyranyl, or tetrahydrofuranyl, more preferably cyclopentyl, morpholinyl, or pyrrolidinyl. These groups are each optionally substituted with the substituent(s) described as substituents for the corresponding cycloalkyl or heterocycloalkyl group.

When $R^{12}$ (or $R^{112}$) is 3- to 10-membered heterocycloalkyl, 4- to 10-membered heterocycloalkyl, 5- to 10-membered heterocycloalkyl, 3- to 6-membered heterocycloalkyl, or 5- or 6-membered heterocycloalkyl, this group contains, for example, one to three heteroatoms selected from a nitrogen atom, an oxygen atom, and a sulfur atom, preferably a nitrogen atom and an oxygen atom as ring-constituting groups.

When $R^{12}$ (or $R^{112}$) is 5- to 10-membered heteroaryl or 5- or 6-membered heteroaryl, this group contains, for example, one to three heteroatoms selected from a nitrogen atom, an oxygen atom, and a sulfur atom, preferably a nitrogen atom and an oxygen atom as ring-constituting groups. Further preferably, this group contains one nitrogen atom as a hetero atom.

When $R^{12}$ (or $R^{112}$) is 3- to 10-membered heterocycloalkyl, 4- to 10-membered heterocycloalkyl, 5- to 10-membered heterocycloalkyl, 3- to 6-heterocycloalkyl, 5- or 6-membered heterocycloalkyl, 5- to 10-membered heteroaryl, or 5- or 6-membered heteroaryl, this group is preferably morpholinyl, tetrahydrofuranyl, tetrahydropyranyl, pyrrolidinyl, piperidinyl, piperazinyl, azetidinyl, thiomorpholinyl, oxetanyl, pyridinyl or 1,2,4-triazolyl, more preferably morpholinyl, tetrahydrofuranyl, pyridinyl, or 1,2, 4-triazolyl. These groups are each optionally substituted with the substituent(s) described as substituents for the corresponding heterocycloalkyl or heteroaryl group.

When $R^{13}$ (or $R^{113}$) is 3- to 10-membered heterocycloalkyl, 4- to 10-membered heterocycloalkyl, 5- to 10-membered heterocycloalkyl, or 5- or 6-membered heterocycloalkyl, this group contains, for example, one to three heteroatoms selected from a nitrogen atom, an oxygen atom, and a sulfur atom, preferably a nitrogen atom and an oxygen atom as ring-constituting groups.

When $R^{13}$ (or $R^{113}$) is 4- to 10-membered heterocycloalkyl, 5- to 10-membered heterocycloalkyl, or 5- or 6-membered heterocycloalkyl, this group is preferably morpholinyl, homomorpholinyl, thiomorpholinyl, piperidinyl, piperazinyl, homopiperazinyl, pyrrolidinyl, azetidinyl, or tetrahydropyranyl, more preferably morpholinyl. These groups are each optionally substituted with the substituent(s) described as substituents for the corresponding heterocycloalkyl group.

When $R^{10}$ (or $R^{110}$), $R^{11}$ (or $R^{111}$), $R^{12}$ (or $R^{112}$), $R^{13}$ (or $R^{113}$), or $R^{15}$ (or $R^{115}$) is $C_{3-6}$ cycloalkyl optionally substituted with one or more hydroxy groups, 3- to 10-membered heterocycloalkyl, 3- to 8-membered heterocycloalkyl, 5- or 6-membered heterocycloalkyl (these heterocycloalkyl groups are each optionally substituted with one or more substituents selected from substituents described as substitutents for the corresponding heterocycloalkyl group, such as oxo, a halogen atom, $C_{1-4}$ alkyl (wherein the $C_{1-4}$ alkyl group is optionally substituted with one or more hydroxy groups)), or 5- to 10-membered heteroaryl, this cycloalkyl group is preferably cyclopentyl, cyclohexyl, or cyclobutyl (these groups are each optionally substituted with one or more hydroxy groups); this heterocycloalkyl group is preferably tetrahydrofuranyl, pyrrolidinyl, morpholinyl, homomorpholinyl, thiomorpholinyl, piperidinyl, piperazinyl, homopiperazinyl, azetidinyl, or tetrahydropyranyl (these groups are each optionally substituted with one or more of the substituents described above); and this heteroaryl group is preferably pyridinyl, pyrimidinyl, pyridazinyl, pyrazinyl, 1,2,4-triazolyl. The cycloalkyl group is more preferably cyclopentyl (this group is optionally substituted with one or more hydroxy groups); the heterocycloalkyl group is more preferably tetrahydrofuranyl, pyrrolidinyl, or morpholinyl (these groups are each optionally substituted with one or more of the substituents described above); and the heteroaryl group is more preferably pyridinyl.

When $Ar^1$ (or $Ar^{101}$) is 5- to 10-membered heteroaryl or 5- to 6-membered heteroaryl, this group contains, for example, one to three heteroatoms selected from a nitrogen atom, an oxygen atom, and a sulfur atom as ring-constituting groups. $Ar^1$ (or $Ar^{101}$) is optionally substituted with one to three substituents selected from Rb (or $Rz^1$; the same holds true for the description below), Rc (or $Rz^2$; the same holds true for the description below), and Rd (or $Rz^3$; the same holds true for the description below), i.e., optionally substituted with Rb, Rc, or Rd, by Rb and Rc, Rc and Rd, or Rb and Rd, or by Rb, Rc, and Rd.

When Rd (or $Rz^3$) is 5- to 10-membered heterocycloalkyl optionally substituted with one or more substituents $R^{14}$ (or $R^{114}$), this group contains, for example, one to three heteroatoms selected from a nitrogen atom, an oxygen atom and a sulfur atom, as ring-constituting groups.

When Rd (or $Rz^3$) is 5- to 10-membered heteroaryl or 5- to 6-membered heteroaryl optionally substituted with one or more substituents $R^{14}$ (or $R^{114}$), this group contains, for example, one to three heteroatoms selected from a nitrogen atom and a sulfur atom as ring-constituting groups.

When $R^{14}$ (or $R^{114}$; the same holds true for the description below) is 5- to 10-membered heterocycloalkyl, this group contains, for example, one to three heteroatoms selected from a nitrogen atom and an oxygen atom as ring-constituting groups. When $R^{14}$ is 5- to 10-membered heterocycloalkyl, this group is preferably 2-oxa-6-azaspiro[3.3]heptyl, 2-azaspiro[3.3]heptyl, 2,6-diazaspiro[3.3]heptyl, or 2-thia-6-azaspiro[3.3]heptyl, particularly preferably 2-oxa-6-azaspiro[3.3]heptyl.

When Re (or Rx) is $C_{6-10}$ aryl (for example phenyl) optionally substituted with one or more substituents Ra (or Ry) or 5- to 10-membered heteroaryl optionally substituted with one or more substituents Ra (or Ry), this group is substituted with, for example, 1 to 4 substituents Ra (or Ry), preferably 1 to 3 substituents Ra (or Ry).

When $R^{10}$ (or $R^{110}$; the same holds true for the description below), $R^{11}$ (or $R^{111}$; the same holds true for the description below), $R^{12}$ (or $R^{112}$; the same holds true for the description below), $R^{13}$ (or $R^{113}$; the same holds true for the description below), or $R^{15}$ (or $R^{115}$; the same holds true for the description below) is $C_{1-6}$ alkoxy optionally substituted with one or more hydroxy groups, this group is substituted with, for example, 1 to 5 hydroxy groups, preferably 1 to 4 hydroxy groups.

When $R^{10}$, R, $R^{12}$, $R^{13}$, or $R^{15}$ is 5- to 10-membered heterocycloalkyl optionally substituted with one or more oxo groups, this group is substituted with, for example, 1 to 3 oxo groups, preferably 1 or 2 oxo groups.

When $R^{10}$, $R^{11}$, $R^{12}$, $R^{13}$, or $R^{15}$ is $C_{3-6}$ cycloalkyl optionally substituted with one or more hydroxy groups, this group is substituted with, for example, 1 to 3 hydroxy groups, preferably 1 or 2 hydroxy groups.

When Rb, Rc, or Rd is 5- to 10-membered heterocycloalkyl optionally substituted with one or more substituents $R^{14}$, $C_{6-10}$ aryl optionally substituted with one or more substituents $R^{14}$, or 5- to 10-membered heteroaryl optionally substituted with one or more substituents $R^{14}$, this group is substituted with, for example, 1 to 4 substituents $R^{14}$, preferably 1 to 3 substituents $R^{14}$.

When $R^4$ is $C_{6-10}$ aryl optionally substituted with one or more substituents Rg, this $C_{6-10}$ aryl group is preferably phenyl.

In the group $—NR^{39}R^{40}$, $R^{39}$ is preferably a hydrogen atom or $C_{1-3}$ alkyl, more preferably methyl. $R^{40}$ is preferably $C_{1-3}$ alkyl, $C_{1-3}$ alkoxy-substituted $C_{1-4}$ alkyl, a group —CH(($CH_2$)$_{v1}$COOR$^{57}$)—($CH_2$)$_{v2}$—COOR$^{57}$, 4- to 6-membered heterocycloalkyl, a group —($CH_2$)$_w$—$SO_3H$, or a group —($CH_2$)$_{x1}$—CH(COOH)—($CH_2$)$_{x2}$—$SO_3H$, more preferably methoxyethyl, 2-methoxy-1,1-dimethylethyl, 2-methoxy-2-methyl-1-propyl, a group —$C_2H_3$-(COOH)$_2$, a group —$C_3H_5$-(COOH)$_2$, oxetanyl, methyl, a group —$C_2H_4$—$SO_3H$, or a group —CH(COOH)—$CH_2$—$SO_3H$. Examples of the group —$NR^{39}R^{40}$ include N—(($C_{1-3}$ alkoxy)$C_{1-4}$ alkyl)-N—($C_{1-3}$ alkyl)amino. In this context, "[N—(($C_{1-3}$ alkoxy)$C_{1-4}$ alkyl)-N—($C_{1-3}$ alkyl)amino]" is as defined above. The group —$NR^{39}R^{40}$ is preferably N-(2-methoxyethyl)-N-(methyl)amino, [N-(2-methoxy-1,1-dimethylethyl)-N-(methyl)amino]ethoxy, [N-(2-methoxy-2,2-dimethylethyl)-N-(methyl)amino]ethoxy, a group —NH—CH(COOH)—$CH_2$(COOH), a group —NH—CH($CH_2$COOH)—$CH_2$COOH, N-oxetanyl-N-methylamino, dimethylamino, a group —NH—C$_2$H$_4$—SO$_3$H, or a group —NH—CH(COOH)—CH$_2$—SO$_3$H.

In the group —(O(CH$_2$)$_{q1}$)$_{q2}$—NR$^{41}$R$^{42}$, q1 is preferably 2, and q2 is preferably an integer selected from 2 to 5. R$^{41}$ is preferably a hydrogen atom or methyl, and R$^{42}$ is preferably C$_{1-6}$ alkyl (preferably n-hexyl) substituted with 1 to 5 hydroxy groups (preferably 5 hydroxy groups) or methoxyethyl.

In the group —(O(CH$_2$)$_{r1}$)$_{r2}$—C(O)NR$^{43}$R$^{44}$, r1 is preferably 2 or 3, and r2 is preferably 1. R$^{43}$ is preferably methyl. R$^{44}$ is preferably C$_{1-6}$ alkyl (preferably n-hexyl) substituted with 1 to 5 hydroxy groups (preferably 5 hydroxy groups).

The compound of the formula (I) wherein R$^1$ and R$^5$ together with the carbon atom to which they are attached form a C$_{3-6}$ saturated carbocyclic ring can be represented by the following formula (I-a) or (I-b):

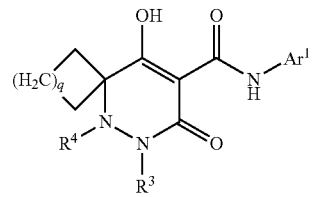

(I-a)

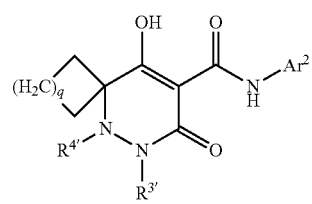

(I-b)

The group —(CH$_2$)$_q$— wherein q is 0 means a single bond.

In the present invention, the compound of the formula (I) wherein R$^3$ is C$_{1-4}$ alkyl substituted with Re, which can be represented by the formula (I-c) shown below. In the present invention, the compound of the formula (I) wherein R$^3$ is C$_{1-4}$ alkyl substituted with Re, Re is substituted with one to three substituents Ra, and the one to three substituents Ra are one substituent selected from Ri, Rj, and Rk, two substituents selected from combinations of Ri and Rj, Ri and Rk, and Rj and Rk, or three substituents Ri, Rj, and Rk can be represented by the formula (I-d) shown below.

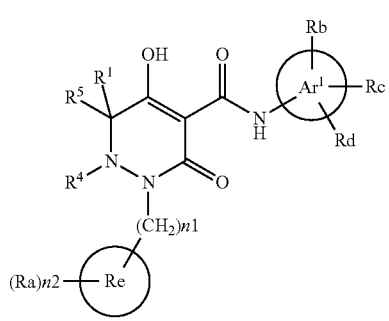

(I-c)

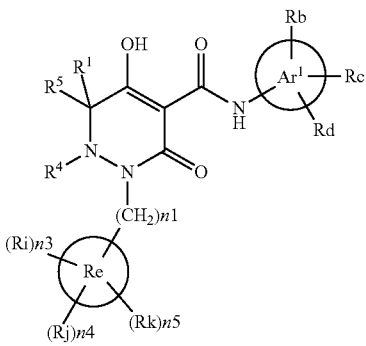

(I-d)

In the formula (I-c), n1 is an integer selected from 1 to 4; n2 is an integer selected from 0 or more; and R$^1$, R$^4$, R$^5$, Ar$^1$, Ra, Rb, Rc, Rd, and Re are as defined in any of (1-1) to (1-48), (2-1) to (2-25), (3-1) to (3-12), (4-1) to (4-12), (5-1) to (5-12), and (6-1) to (6-10). In the formula (I-d), n3, n4, and n5 are each independently an integer selected from 0 and 1, provided that at least one of n3, n4, and n5 is 1; n1 is as defined above; R$^1$, R$^4$, R$^5$, Ar1, Rb, Rc, Rd, and Re are as defined in any of (1-1) to (1-48), (2-1) to (2-25), (3-1) to (3-12), (4-1) to (4-12), (5-1) to (5-12), and (6-1) to (6-10).

In the present invention, n2 is preferably an integer selected from 1 to 4, more preferably an integer selected from 1 to 3.

In the present invention, the phrase "optionally substituted with" or "substituted with" means "optionally substituted with one substituent" or "substituted with one substituent" respectively unless a number of substituents (for example, "one or more", "one to three", "one or two", "two" or "one") is specified. For example, "B optionally substituted with A" and "B substituted with A" mean "B optionally substituted with one A" and "B substituted with one A" respectively.

In the present invention, examples of the salt of the compound represented by the formula (I), (II), (III), (I-a), (I-b), (I-c), or (I-d) include acid-addition salts and base-addition salts. Examples of the acid-addition salts include: hydrochloride, hydrobromide, hydroiodide, phosphate, phosphonate, and sulfate; sulfonates such as methanesulfonate, ethanesulfonate, benzenesulfonate, and p-toluenesulfonate; and carboxylates such as acetate, citrate, malate, tartrate, succinate, salicylate, maleate, fumarate, benzoate, malonate, glycolate, oxalate, glucuronate adipate, glutarate, ketoglutarate, and hippurate. Examples of the base-addition salts include: alkali metal salts such as sodium salt and potassium salt; alkaline earth metal salts such as magnesium salt and calcium salt; ammonium salts such as ammonium salt, alkylammonium salt, dialkylammonium salt, trialkylammonium salt, and tetraalkylammonium salt; and amino acid salts such as lysine salt, arginine salt, glycine salt, valine salt, threonine, salt, serine salt, proline salt, and alanine salt. These salts are each produced by the contact of the compound with an acid or a base available in pharmaceutical production.

In the present invention, the compound represented by the formula (I), (II), (III), (I-a), (I-b), (I-c), or (I-d) or the salt thereof may be an anhydrate or may form a solvate such as a hydrate. In this context, the "solvate" refers to a solid formed by a complex of the compound molecule and a solvent molecule and refers to, for example, a hydrate formed from water as a solvent. The solvate other than the hydrate includes a solid containing an alcohol (e.g., methanol, ethanol, and n-propanol), dimethylformamide, or the like.

The compound represented by the formula (I), (II), (III), (I-a), (I-b), (I-c), or (I-d) and the salt thereof may be found as some tautomers, for example, keto and enol forms, imine and enamine forms, and mixtures thereof. Such tautomers are present as a tautomeric mixture in a solution. In a solid form, one of the tautomers is usually predominant. Although one of the tautomers may be described herein, all tautomers of the compound of the present invention are included in the present invention.

The present invention further includes all stereoisomers (e.g., enantiomers and diastereomers (including cis and trans geometric isomers)) of the compound represented by the formula (I), (II), (III), (I-a), (I-b), (I-c), or (I-d), racemates of the isomers, and other mixtures. The compound of the present invention may have, for example, one or more asymmetric atoms. The compound of the present invention includes racemic mixtures, diastereomeric mixtures, and enantiomers of such a compound.

The compound represented by the formula (I), (II), (III), (I-a), (I-b), (I-c), or (I-d) may be obtained in a free form. In this case, the free compound can be converted by a routine method to the salt that may be formed by the compound or to the hydrate or the solvate of the compound or the salt.

Alternatively, the compound represented by the formula (I), (II), (III), (I-a), (I-b), (I-c), or (I-d) may be obtained as the salt, hydrate, or solvate of the compound. In this case, this form can be converted to the free form of the compound according to a routine method.

Each element constituting the compound represented by the formula (I), (II), (III), (I-a), (I-b), (I-c), or (I-d) may be any isotope. The present invention encompasses a compound of the formula (I), (II), (III), (I-a), (I-b), (I-c), or (I-d) containing such an isotope. The isotope in the compound refers to a variant of the element in which at least one atom is replaced with an atom with the same atomic number (the same number of protons) and a different mass number (total number of protons and neutrons). Examples of the isotope contained in the pharmaceutical drug of the present invention include a hydrogen atom, a carbon atom, a nitrogen atom, an oxygen atom, a phosphorus atom, a sulfur atom, a fluorine atom, and a chlorine atom including $^{2}H$, $^{3}H$, $^{13}C$, $^{14}C$, $^{15}N$, $^{17}O$, $^{18}O$, $^{32}P$, $^{35}S$, $^{18}F$, and $^{36}Cl$. Particularly, a radioisotope, such as $^{3}H$ or $^{14}C$, which undergoes radioactive decay are useful in, for example, the in vivo histological distribution tests of the pharmaceutical drug or the compound. Stable isotopes rarely vary in abundance without decay and are also free from radioactivity. These stable isotopes can therefore be used with safety. The isotope in the compound serving as an active ingredient in the pharmaceutical drug of the present invention can be converted according to a routine method by the replacement of a reagent used in synthesis with a reagent containing the corresponding isotope.

The compound represented by the formula (I), (II), (III), (I-a), (I-b), (I-c), or (I-d) may be administered in the form of a prodrug. The present invention also includes such a prodrug of the compound represented by the formula (I), (II), (III), (I-a), (I-b), (I-c), or (I-d). In this context, the "prodrug" of the present invention means a derivative of the compound of the formula (I), (II), (III), (I-a), (I-b), (I-c), or (I-d) that is converted after administration to the compound of the formula (I), (II), (III), (I-a), (I-b), (I-c), or (I-d) or the pharmaceutically acceptable salt thereof through enzymatic or nonenzymatic degradation under physiological conditions. The prodrug may be inactive when administered to a patient. The prodrug is converted in vivo to the active compound of the formula (I), (II), (III), (I-a), (I-b), (I-c), or (I-d).

The prodrug is converted to, for example, a desired pharmaceutical formulation at a particular pH or by the action of an enzyme. The prodrug is typically a compound that forms a free acid in vivo and a compound having a hydrolyzable ester group. Such a hydrolyzable ester group is, for example, but not limited to, a group represented by the formula —COORx, wherein Rx is selected from $C_{1-4}$ alkyl, $C_2$-7 alkanoyloxymethyl, 1-($C_{4-9}$ alkanoyloxy)ethyl, 1-methyl-1-($C_{5-10}$ alkanoyloxy)-ethyl, ($C_{3-6}$ alkoxy)carbonyloxymethyl, 1-[($C_{4-7}$ alkoxy)carbonyloxy]ethyl, 1-methyl-1-[($C_{5-8}$ alkoxy)carbonyloxy]ethyl, N—[($C_{3-9}$ alkoxy)carbonyl]aminomethyl, 1-(N—[($C_{4-10}$ alkoxy)carbonyl]amino)ethyl, 3-phthalidyl, 4-crotonolactonyl, γ-butyrolacton-4-yl, [N,N-di($C_{1-2}$ alkyl)amino]$C_{2-3}$ alkyl (e.g., N,N-dimethylaminoethyl), (carbamoyl)$C_{1-2}$ alkyl, [N,N-di($C_{1-2}$ alkyl)carbamoyl]$C_{1-2}$ alkyl, (piperidino)$C_2$-3 alkyl, (pyrrolidino)$C_2$-3 alkyl, and (morpholino)$C_2$-3 alkyl.

Pharmaceutical Drug of the Present Invention

One aspect of the present invention provides a pharmaceutical drug and a pharmaceutical composition containing the compound represented by the formula (I), (II), (III), (I-a), (I-b), (I-c), or (I-d) or the salt thereof, or the solvate of the compound or the salt. In this invention, "pharmaceutical composition" refers to a mixture containing certain amounts or proportions of specific ingredients.

The pharmaceutical drug of the present invention contains the compound represented by the formula (I), (II), (III), (I-a), (I-b), (I-c), or (I-d) as an active ingredient and further contains a pharmaceutically acceptable carrier. The term "pharmaceutically acceptable carrier" used herein means one or more compatible solid or liquid excipients or encapsulating materials that are suitable for administration to mammals. The term "pharmaceutically acceptable" used herein means pharmaceutically available from the viewpoint of efficacy, safety, etc. The pharmaceutically acceptable carrier used is suitable for administration to an animal, preferably a mammal, to be treated, from the viewpoint of safety and has sufficiently high purity.

Examples of a material that may be used as the pharmaceutically acceptable carrier include: sugars such as lactose, glucose, and sucrose; starches such as corn starch and potato starch; cellulose and its derivatives such as carboxymethylcellulose sodium, ethylcellulose, and methylcellulose; tragacanth gum powder; malt; gelatin; talc; solid lubricants such as stearic acid and magnesium stearate; calcium sulfate; plant oils such as peanut oil, cottonseed oil, sesame oil, olive oil, corn oil, and cacao oil; polyhydric alcohols such as propylene glycol, glycerin, sorbitol, mannitol, and polyethylene glycol; alginic acid; emulsifiers such as TWEEN; wetting agents such as lecithin; colorants; flavors; tableting agents; stabilizers; antioxidants; antiseptics; pyrogen-free water; isotonic saline; and phosphate buffer solutions.

The compound of the present invention may be used as a NaPi-IIb inhibitor or a preventive and/or therapeutic agent for hyperphosphatemia, secondary hyperparathyroidism, or chronic renal failure. In this case, or in a case where the pharmaceutical composition of the present invention may be used, examples of an administration method thereof include oral, rectal, parenteral (intravenous, intramuscular, or subcutaneous), intracisternal, intravaginal, intraperitoneal, intravesical and local (drip, powder, ointment, gel, or cream) routes, and inhalation (into the oral cavity or using nasal sprays). Examples of the dosage form thereof include tablets, capsules, granules, powders, pills, aqueous and non-aqueous oral solutions and suspensions, and parenteral solutions charged in containers adapted to division into individual doses. Alternatively, the dosage form may be adapted to various administration methods encompassing controlled-release formulations as in subcutaneous implantation.

These preparations are produced by a well known method using additives such as excipients, lubricants (coating agents), binders, disintegrants, stabilizers, corrigents, and diluents.

Examples of the excipients can include starches such as starch, potato starch, and corn starch, lactose, crystalline cellulose, and calcium hydrogen phosphate.

Examples of the coating agents can include ethylcellulose, hydroxypropylcellulose, hydroxypropylmethylcellulose, shellac, talc, carnauba wax, and paraffin.

Examples of the binders can include polyvinylpyrrolidone, Macrogol, and the same compounds as those listed as the excipients.

Examples of the disintegrants can include the same compounds as those listed as the excipients and chemically modified starches and celluloses such as croscarmellose sodium, carboxymethyl starch sodium, and cross-linked polyvinylpyrrolidone.

Examples of the stabilizers can include: p-hydroxybenzoate esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid.

Examples of the corrigents can include sweeteners, acidulants, and flavors usually used.

The liquid preparations can be produced using a solvent such as ethanol, phenol, chlorocresol, purified water, or distilled water.

Examples of the surfactants or emulsifiers can include polyoxyl 40 stearate and Lauromacrogol.

When the compound of the present invention is used as a NaPi-IIb inhibitor, PiT-1 inhibitor, PiT-2 inhibitor or a preventive and/or therapeutic agent for hyperphosphatemia, secondary hyperparathyroidism, or chronic renal failure, the amount of the pharmaceutical drug of the present invention used differs depending on symptoms, age, body weight, relative health conditions, the presence of other medications, administration methods, etc. In the case of oral agents, a general effective amount, for example, for a patient (warm-blooded animal, particularly a human) is preferably 1 to 20 mg/kg body weight, more preferably 1 to 10 mg/kg body weight, per day in terms of the amount of the active ingredient (the compound of the present invention represented by the formula (I)). The daily dose in an adult patient having a normal body weight is in the range of preferably 60 to 1200 mg.

The pharmaceutical composition of the present invention may contain a pharmaceutically acceptable carrier, in addition to an active ingredient (for example, the compound represented by the formula (I), (II), (III), (I-a), (I-b), (I-c), or (I-d)).

The pharmaceutical composition of the present invention may be used in the prevention or treatment of a disease selected from hyperphosphatemia, secondary hyperparathyroidism, chronic kidney disease, and arteriosclerosis associated with vascular calcification, or in the prevention or suppression of ectopic calcification.

Chronic kidney disease is basically classified into stages 1 to 5 according to GFR (glomerular filtration rate): GFR of 90 or more is classified as stage 1, GFR of 60 or more to less than 90 as stage 2; GFR of 30 or more to less than 60 as stage 3; GFR of 15 or more to less than 30 as stage 4; and GFR of less than 15 as stage 5 ("Clinical Practice Guidelines for CKD 2012" Japanese Journal of Nephrology, 2012; 54 (8); 1031-1189).

As one embodiment of the present invention, the pharmaceutical composition of the present invention is used for the prevention or treatment of chronic kidney disease of stages 2 to 4 classified by GFR.

The present inventors have found that, in animal models of hyperphosphatemia and chronic kidney disease, the expression level of NaPi-IIb in the gastrointestinal tract was lowered while the expression levels of PiT-1 and PiT-2 did not change, and as a result, the proportion of phosphate absorption by PiT-1 and PiT-2 with respect to the total phosphate absorption in the gastrointestinal tract became relatively high. From the findings, the present inventors have found that inhibition of PiT-1 or PiT-2 provides an excellent effect in the prevention or treatment of a disease selected from hyperphosphatemia, secondary hyperparathyroidism, chronic kidney disease, and arteriosclerosis associated with vascular calcification, or in the prevention or suppression of ectopic calcification. Further, the inventors have found that, in the prevention or treatment of a disease selected from hyperphosphatemia, secondary hyperparathyroidism, chronic kidney disease, and arteriosclerosis associated with vascular calcification, or in the prevention or suppression of ectopic calcification, a better effect was obtained when all of the transporters, NaPi-IIb, PiT-1, and PiT-2 were inhibited, compared to when only NaPi-IIb was inhibited.

In the pharmaceutical composition of the present invention, in the case of administering a substance that inhibits one or more transporters selected from NaPi-IIb, PiT-1, and PiT-2 and a phosphorus adsorbent to prevent or treat hyperphosphatemia, secondary hyperparathyroidism, chronic kidney disease, and vascular calcification or to prevent or suppress ectopic calcification, the substance that inhibits one or more transporters selected from NaPi-IIb, PiT-1, and PiT-2 (hereinafter referred to as "transporter inhibitory substance") and the phosphorus adsorbent may be administered simultaneously or separately. The pharmaceutical composition of the present invention may be provided in the form of a combined drug containing both a transporter inhibitory substance and a phosphorus adsorbent. Further, a medicament containing a transporter inhibitory substance and a medicament containing a phosphorus adsorbent may be provided separately and be used simultaneously or sequentially. Furthermore, the pharmaceutical composition may be provided as a kit comprising a medicament containing a transporter inhibitory substance and that containing a phosphorus adsorbent.

In the pharmaceutical composition above, in the case of providing a transporter inhibitory substance and a phosphorous adsorbent that are incorporated in different medicaments, the dosage forms of the medicaments may be the same as, or different from, each other. For example, the medicaments may be both one of parenteral preparations, injections, drops, and intravenous drips but may differ from each other in dosage form, or the medicaments may be both one of parenteral preparations, injections, drops, and intravenous drips and may be the same as each other in dosage form. In addition, one or more further preparations may be combined with the pharmaceutical composition.

In another aspect, the present invention provides a pharmaceutical composition containing a substance that inhibits one or more transporters selected from NaPi-IIb, PiT-1, and PiT-2 (hereinafter referred to as "transporter inhibitory substance") as an active ingredient, and this composition is used in combination with a phosphorus adsorbent to prevent or treat hyperphosphatemia, secondary hyperparathyroidism, chronic kidney disease, and vascular calcification or to prevent or suppress ectopic calcification. When the pharmaceutical composition of the present invention containing a transporter inhibitory substance as an active ingredient is used in combination with a phosphorus adsorbent, the composition may be administered simultaneously with the phosphorus adsorbent. Also the composition may be administered before or after administration of the phosphorus adsorbent. In a case where a transporter inhibitory substance is administered after administration of a phosphorus adsorbent, timing of administration of the transporter inhibitory substance may be optimized by measuring the residual concentration of phosphorus adsorbent in a subject. This concentration may be determined based on the results of analysis of samples collected from the subject, through an analysis method known to those skilled in the art using a variety of separators such as chromatography.

In another aspect, the present invention provides a pharmaceutical composition that contains a phosphorus adsorbent as an active ingredient, and this composition is used in combination with a substance that inhibits one or more transporters selected from NaPi-IIb, PiT-1, and PiT-2 (hereinafter referred to as "transporter inhibitory substance") to prevent or treat hyperphosphatemia, secondary hyperparathyroidism, chronic kidney disease, and vascular calcification or to prevent or suppress ectopic calcification. When the pharmaceutical composition containing a phosphorus adsorbent as an active ingredient is used in combination with a transporter inhibitory substance, the composition may be administered simultaneously with the transporter inhibitory substance or also may be administered before or after administration of the transporter inhibitory substance.

In a case where a phosphorus adsorbent is administered before administration of a transporter inhibitory substance, timing of administration of the phosphorus adsorbent may be optimized by measuring the residual concentration of the phosphorus adsorbent in a subject. This concentration may be determined based on the results of analysis of samples collected from the subject, through an analysis method known to those skilled in the art using a variety of separators such as chromatography.

Substances that Inhibit One or More Transporters Selected from NaPi-IIb, PiT-1, and PiT-2

In the present invention, a "substance that inhibits one or more transporters selected from NaPi-IIb, PiT-1, and PiT-2" includes any substances (compounds, antibodies, antibody fragments, and the like) that inhibit phosphorus absorption in the gastrointestinal tract performed by one or more sodium-dependent phosphate transporters selected from NaPi-IIb, PiT-1, and PiT-2. The term "substance that inhibits one or more transporters selected from NaPi-IIb, PiT-1, and PiT-2" includes a "substance that inhibits one or more transporters selected from PiT-1 and PiT-2." Examples of the "substance that inhibits one or more transporters selected from NaPi-IIb, PiT-1, and PiT-2" may include a substance that inhibits NaPi-IIb, a substance that inhibits PiT-1, a substance that inhibits PiT-2, a substance that inhibits NaPi-IIb and PiT-1, a substance that inhibits NaPi-IIb and PiT-2, a substance that inhibits PiT-1 and PiT-2, and a substance that inhibits NaPi-IIb, PiT-1, and PiT-2.

Specific examples of a "low-molecular compound that inhibits one or more transporters selected from NaPi-IIb, PiT-1, and PiT-2" may include the compounds according to (1-1) to (1-49) or salts thereof, or solvates of the compounds or the salts, which are described as components of pharmaceutical compositions. Other specific examples may include the compounds disclosed in WO2012/006475, WO2011/136269, WO2013/062065, WO2013/082756, WO2013/082751, and WO2013/129435, or salts thereof, or solvates of the compounds or the salts.

Further specific examples may include a compound represented by the formula selected from the following formulae (1)-(5), or a salt thereof, or a solvate of the compound or the salt.

(1)

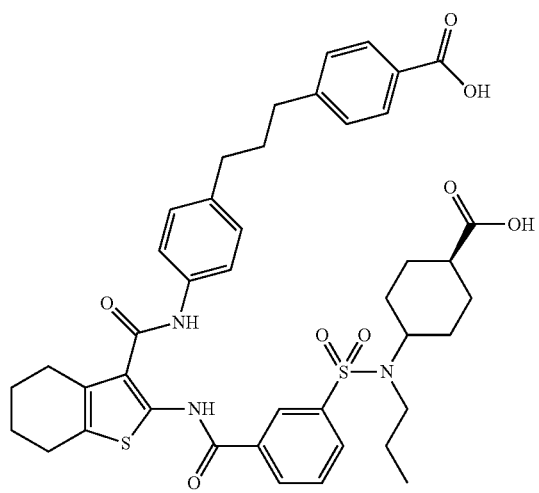

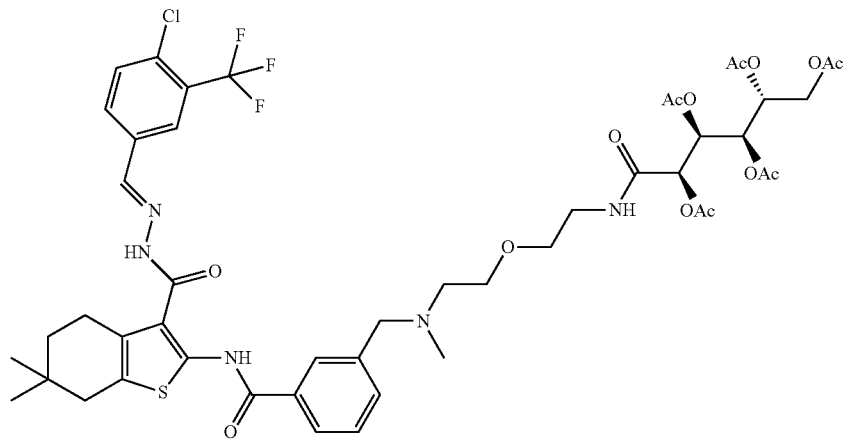

(2)

(wherein Ac means an acetyl group)

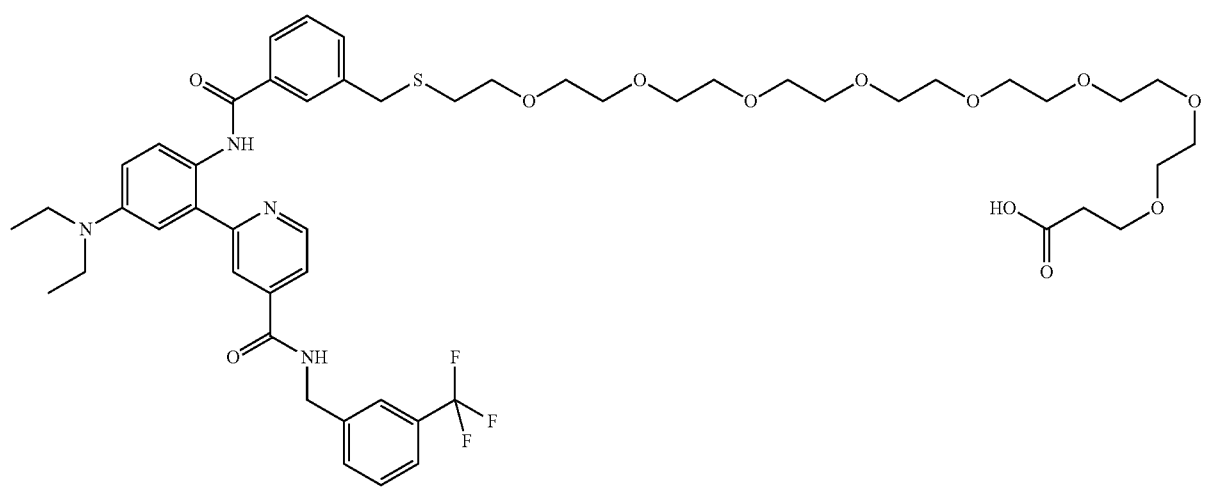

(3)

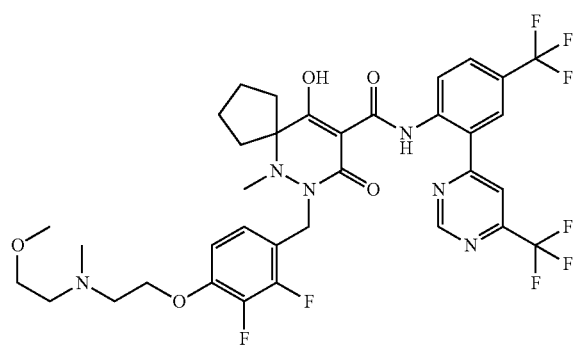

(4)

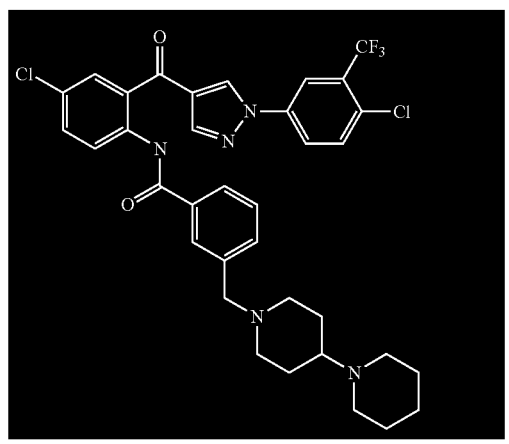

(5)

With regard to the route of administration of a substance that inhibits one or more transporters selected from NaPi-IIb, PiT-1, and PiT-2, either of an oral or parenteral route can be preferably used, but an oral route is more preferable. The dosage form used for oral administration may be selected as appropriate from any forms, such as liquid, powder, granular, tablet, enteric coated, and capsule dosage forms, for example. Such a dosage form is prepared as a drug product by a method known to those skilled in the art. For example, an active ingredient is first combined as appropriate with a pharmacologically acceptable carrier or medium, specifically including but not limited to sterile water or normal saline, plant oil, emulsifier, suspension, surfactant, stabilizer, flavoring agent, excipient, vehicle, antiseptic, or binder, and then the combined components are blended into a unit dosage form required in generally acceptable pharmaceutical practice, and formulated into a drug product by a formulation process, such as freeze-drying or tableting.

Phosphorus Adsorbent

In the present invention, a "phosphorus adsorbent" includes any phosphorus adsorbents that are known, or suggested, as suppressing phosphorus absorption in the gastrointestinal tract by adsorbing phosphorus. The "phosphorus adsorbent" includes, but not limited to: nonmetallic polymer adsorbents typified by bixalomer, sevelamer carbonate, and sevelamer hydrochloride; calcium salt preparations typified by precipitated calcium carbonate, calcium acetate, calcium citrate, calcium alginate, and calcium salt of keto-acid; and metallic adsorbents typified by lanthanum carbonate, aluminum hydroxide, iron preparations (sucroferric oxyhydroxide (polynuclear iron(III) oxide hydroxides), polynuclear iron(III)-oxyhydroxide), Fermagate (magnesium iron hydroxycarbonate), and ferric citrate hydrate).

With regard to the route of administration of a phosphorus adsorbent used in the present invention, either of an oral or parenteral route can be preferably used, but an oral route is more preferable. The dosage form used for oral administration may be selected as appropriate from any forms, such as liquid, powder, granular, tablet, enteric coated, and capsule dosage forms, for example. A phosphorus adsorbent having such a dosage form is prepared as a drug product by a method known to those skilled in the art. For example, a phosphorus adsorbent is first combined as appropriate with a pharmacologically acceptable carrier or medium, specifically including but not limited to sterile water or normal saline, plant oil, emulsifier, suspension, surfactant, stabilizer, flavoring agent, excipient, vehicle, antiseptic, or binder, and then the combined components are blended into a unit dosage form required in generally acceptable pharmaceutical practice, and formulated into a drug product by a formulation process, such as freeze-drying or tableting.

In the present invention, the combined use of a substance that inhibits one or more transporters selected from NaPi-IIb, PiT-1, and PiT-2 (hereinafter referred to as "transporter inhibitory substance") and a phosphorus adsorbent means that the transporter inhibitory substance and the phosphorus adsorbent are administered or used (hereinafter simply referred to as "administered") in combination, and thus the order of administration, interval of administration, or the like should not be construed in a limited manner. Further, a transporter inhibitory substance and a phosphorus adsorbent may be combined and used as a kit. Furthermore, in a case where a transporter inhibitory substance and a phosphorus adsorbent are used in combination according to the present invention, the dose of each of the two drugs can be reduced, if desired, compared to that required in a case where one of them is administered alone.

In a case where a transporter inhibitory substance and a phosphorus adsorbent are separately administered, the interval of administration of the transporter inhibitory substance and the phosphorus adsorbent is not specifically limited and may be determined taking into consideration factors such as the administration route or dosage form. For example, the interval may be 0 hour to 168 hours, preferably, 0 hour to 72 hours, more preferably, 0 hour to 24 hours, and yet more preferably, 0 hour to 12 hours. Also, not only the factors such as the administration route or dosage form, but also the residual concentration of each of the transporter inhibitory substance and the phosphorus adsorbent in a subject may be considered. More specifically, in a case where a phosphorus adsorbent is administered before administration of a transporter inhibitory substance, the transporter inhibitory substance may be administered at a point when the detected residual concentration of phosphorus adsorbent in the subject reaches a level at which the desired effect by the phosphorus adsorbent may be achieved. This concentration may be determined based on the results of analysis of samples collected from the subject, through an analysis method known to those skilled in the art using a variety of separators such as chromatography.

Conversely, in a case where a transporter inhibitory substance is administered before administration of a phosphorus adsorbent, the phosphorus adsorbent may be administered at a point when the detected residual concentration of transporter inhibitory substance in a subject reaches a level at which the desired effect by the phosphorus adsorbent may be achieved. This concentration may be determined based on the results of analysis of samples collected from the subject, through an analysis method known to those skilled in the art using a variety of separators such as chromatography.

In a case where the pharmaceutical composition of the present invention is provided in the form of a combined drug containing both a transporter inhibitory substance and a phosphorus adsorbent, the content of each of the transporter inhibitory substance and the phosphorus adsorbent is not specifically limited. With regard to the route of administration of the combined drug, either of an oral or parenteral route can be preferably used, but an oral route is more preferable. The dosage form for oral administration may be selected as appropriate from any forms, such as liquid, powder, granular, tablet, enteric coated, and capsule dosage forms, for example. A phosphorus adsorbent having such a dosage form is prepared as a drug product by a method known to those skilled in the art.

Hereinafter, general methods for producing the compound of the present invention and Examples will be shown.

General Synthesis Method

The compound of the present invention can be synthesized by various methods.

Some of the methods will be described with reference to schemes shown below. These schemes are provided for illustrative purposes, and the present invention is not limited by chemical reactions and conditions described herein. Although some substituents are excluded from the schemes shown below for easy understanding, such exclusion is not intended to limit the disclosure of the schemes. Typical compounds of the present invention can be synthesized using appropriate intermediates, compounds known in the art, and reagents. In the formulas of the general synthesis methods described below, variable groups represented by $R^1$, $R^2$, etc. and variables represented by n, etc. have the same meanings as those of the variable groups represented by $R^1$, $R^2$, etc. and the variables represented by n, etc. in the compounds represented by general formulas defined herein.

The compound of the present invention can be synthesized by production methods shown below.

Scheme 1 (Method A)

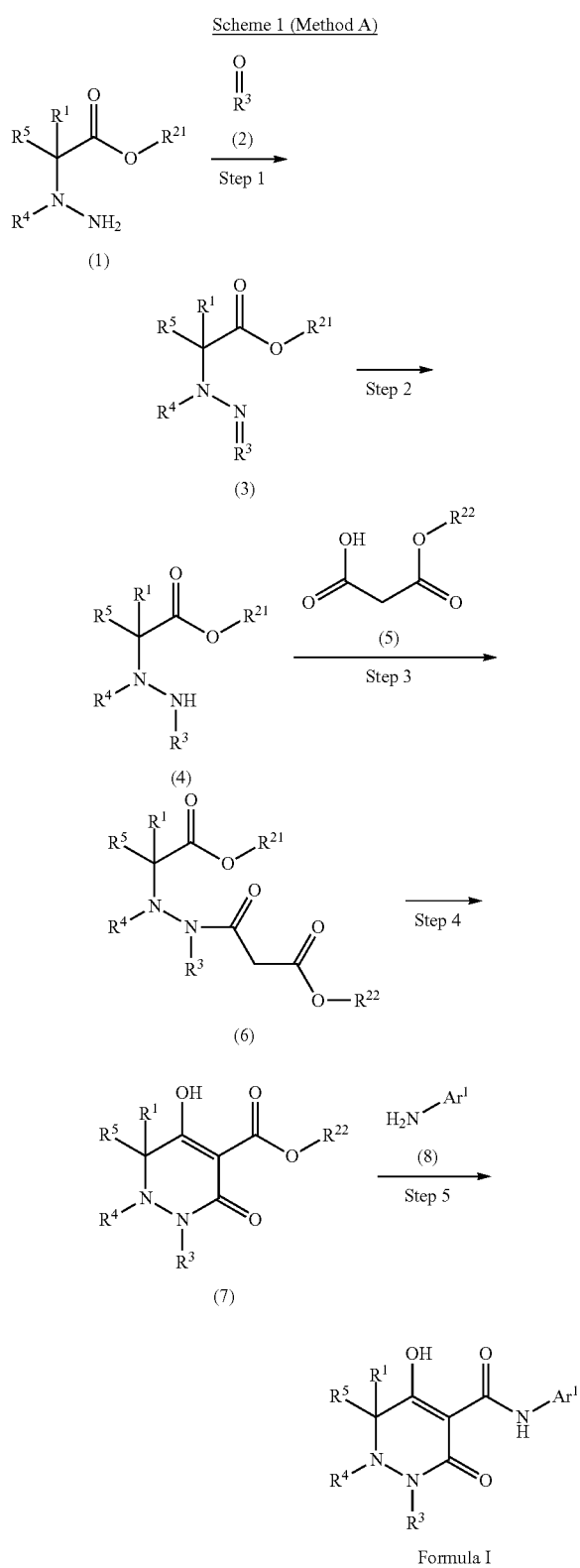

Formula I wherein $R^{21}$ represents $C_{1-3}$ alkyl; $R^{22}$ represents $C_{1-5}$ alkyl; and $R^3$=O (2) represents aldehyde or ketone formed by the conversion of a carbon atom at the linkage position of alkyl represented by $R^3$ to carbonyl.

Step 1 involves reacting a compound of the formula (1) with aldehyde or ketone (2) in an appropriate solvent such as methanol or dichloromethane to synthesize a compound (3). The reaction is performed at a temperature of, for example, 0° C. to room temperature for a time of, for example, 0.5 hours to 24 hours. The obtained hydrazone derivative (3) is isolated by a general technique and may be purified, if necessary, by crystallization or chromatography.

A large number of applicable methods have been reported as to the synthesis method for the hydrazine (1) shown in Scheme 1 (this reaction can be performed with reference to, for example, Synthetic communications, 40, 654-660; 2010, Journal of Heterocyclic Chemistry, 24 (3), 725-731; 1987, and Synthesis, (6), 423-424; 1979).

Step 2 involves reducing the hydrazone (3) in the presence of a reducing agent such as sodium cyanoborohydride or borane pyridine in an appropriate solvent such as methanol or acetic acid to obtain hydrazine (4). The reaction is performed at a temperature of, for example, 0° C. to 50° C. for a time of, for example, 0.5 hours to 60 hours. The obtained hydrazine (4) is isolated by a general technique and may be purified, if necessary, by crystallization or chromatography.

Step 3 involves reacting the hydrazine (4) with half ester (5) using a condensing agent such as N,N'-dicyclohexylcarbodiimide (DCC), 4-(4,6-dimethoxy-1,3,5-triazin-2-yl)-4-methyl morpholinium chloride n-hydrate (DMT-MM), O-(7-azabenzotriazol-1-yl)-N,N,N',N'-tetramethyl uronium hexafluorophosphate (HATU), bromo-tris-pyrrolidino-phosphonium hexafluorophosphate (PyBrop), or 1-propanephosphonic acid cyclic anhydride (T3P) in an appropriate solvent such as dichloromethane, N,N-dimethylformamide, N,N-dimethylacetamide, acetonitrile, tetrahydrofuran, or ethyl acetate. The reaction is performed at a temperature of, for example, 0° C. to 50° C. for a time of, for example, 0.5 hours to 24 hours. The obtained ester form (6) is isolated by a general technique and may be purified, if necessary, by crystallization or chromatography.

The half ester (5) shown in Scheme 1 can be synthesized from Meldrum's acid and an alcohol (this reaction can be performed with reference to, for example, Organic Letters, 7 (3), 463-465; 2005).

Step 4 involves cyclizing the ester form (6) using a base such as potassium carbonate, cesium carbonate, sodium methoxide, or sodium hydride in an appropriate solvent such as methanol, N,N-dimethylformamide, N,N-dimethylacetamide, dimethyl sulfoxide, diethyl ether, or tetrahydrofuran. The reaction is performed at a temperature of, for example, 0° C. to 110° C. for a time of, for example, 0.5 hours to 24 hours. The obtained cyclized form (7) is isolated by a general technique and may be purified, if necessary, by crystallization or chromatography.

Step 5 involves reacting the cyclized form (7) with various amines (8) in an appropriate solvent such as benzene, toluene, xylene, ethyl acetate, tetrahydrofuran, N,N-dimethylformamide, N,N-dimethylacetamide, or dimethyl sulfoxide. The reaction is performed at a temperature of, for example, 50° C. to 120° C. for a time of, for example, 0.5 hours to 5 hours. The obtained amide form (formula I) is isolated by a general technique and may be purified, if necessary, by crystallization or chromatography.

$R^{21}$ is preferably methyl, and $R^{22}$ is preferably methyl or i-butyl.

The compound of the formula I can also be synthesized through the reaction between a keto form (9) and isocyanate as shown in Scheme 2 (Method B).

Scheme 2 (Method B)

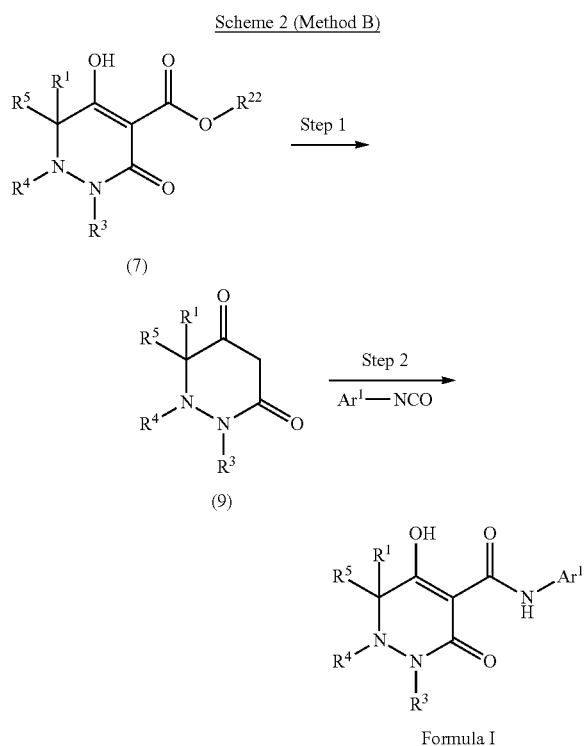

Formula I wherein $R^{22}$ is as defined in Scheme 1.

The keto form (9) as a product in Step 1 can be synthesized by the decarboxylation of an ester form (7) (this reaction can be performed with reference to, for example, Synthesis, (15), 2487-2491; 2009).

Step 2 involves reacting the keto form (9) with isocyanate in the presence of a base such as sodium hydride, potassium carbonate, or cesium carbonate in an appropriate solvent such as N,N-dimethylformamide, N,N-dimethylacetamide, or tetrahydrofuran. The reaction is performed at a temperature of, for example, 0° C. to 50° C. for a time of, for example, 0.5 hours to 5 hours. The obtained amide form (formula I) is isolated by a general technique and may be purified, if necessary, by crystallization or chromatography.

The compound of the formula I can also be synthesized by the cyclization of an amide form as shown in Scheme 3 (Method C).

Scheme 3 (Method C)

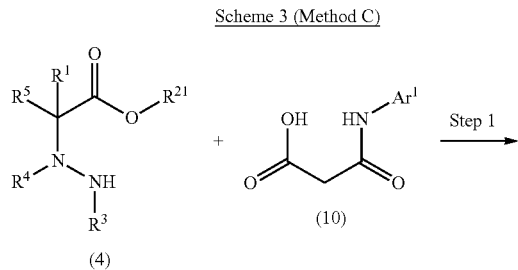

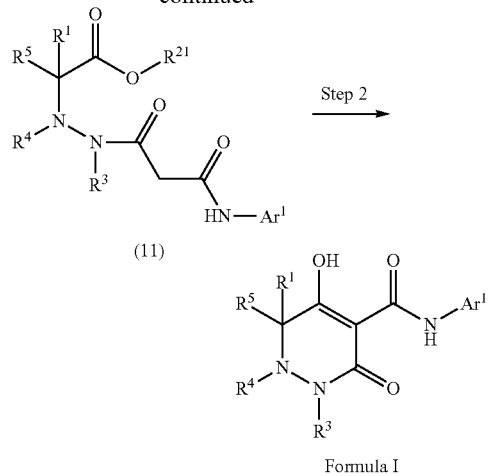

Formula I wherein $R^{21}$ is as defined in Scheme 1.

Step 1 involves reacting the hydrazine (4) with half amide (10) in the presence of a condensing agent such as N,N'-dicyclohexylcarbodiimide (DCC), 4-(4,6-dimethoxy-1,3,5-triazin-2-yl)-4-methyl morpholinium chloride n-hydrate (DMT-MM), O-(7-azabenzotriazol-1-yl)-N,N,N',N'-tetramethyl uronium hexafluorophosphate (HATU), bromo-tris-pyrrolidino-phosphonium hexafluorophosphate (PyBrop), or 1-propanephosphonic acid cyclic anhydride (T3P) in an appropriate solvent such as dichloromethane, N,N-dimethylformamide, N,N-dimethylacetamide, acetonitrile, tetrahydrofuran, or ethyl acetate. The reaction is performed at a temperature of, for example, 0° C. to 50° C. for a time of, for example, 0.5 hours to 24 hours. The obtained amide form (11) is isolated by a general technique and may be purified, if necessary, by crystallization or chromatography.

The half amide (10) shown in Scheme 3 can be synthesized from Meldrum's acid and amine (this reaction can be performed with reference to, for example, Bioorganic & Medicinal Chemistry Letters, 19 (13), 3632-3636; 2009).

Step 2 involves cyclizing the amide form (11) using a base such as sodium methoxide, potassium carbonate, cesium carbonate, or sodium hydride in an appropriate solvent such as methanol, N,N-dimethylformamide, N,N-dimethylacetamide, or tetrahydrofuran. The reaction is performed at a temperature of, for example, 0° C. to 110° C. for a time of, for example, 0.5 hours to 24 hours. The obtained compound of the formula I is isolated by a general technique and may be purified, if necessary, by crystallization or chromatography.

The compound of the formula I can also be synthesized by alkylation as shown in Scheme 4 (Method D).

Scheme 4 (Method D)

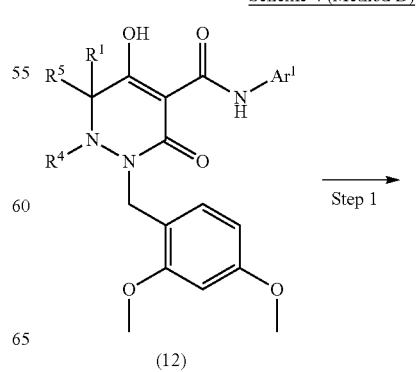

-continued

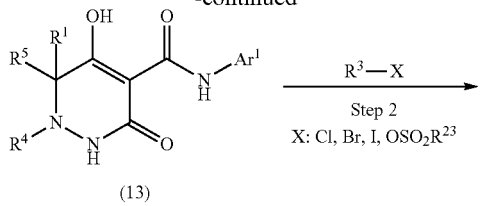

(13)

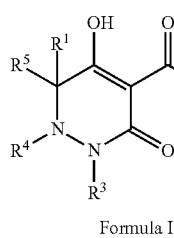

Formula I

Three exemplary methods of Step 1 will be shown below.

Method 1 involves debenzylating a compound (12) using a palladium catalyst such as palladium(0)-carbon or palladium(II) hydroxide-carbon or a platinum catalyst such as platinum oxide ($PtO_2$) in an appropriate solvent such as methanol, ethyl acetate, N,N-dimethylformamide, or N,N-dimethylacetamide in a hydrogen atmosphere. The reaction is performed at a temperature of, for example, room temperature to the boiling point of the solvent for a time of, for example, 1 hour to 24 hours. Method 2 involves reacting the compound (12) in the presence of an oxidizing agent such as 2,3-dichloro-5,6-dicyano-p-benzoquinone or ammonium hexanitratocerate(IV) in an appropriate solvent such as dichloromethane or acetonitrile. The reaction is performed at a temperature of, for example, room temperature to the boiling point of the solvent for a time of, for example, 1 hour to 60 hours. Method 3 involves reacting the compound (12) in the presence of an organic acid such as trifluoroacetic acid or trifluoromethanesulfonic acid in an appropriate solvent such as dichloromethane or methanol. The reaction is performed at a temperature of, for example, 0° C. to the boiling point of the solvent for a time of, for example, 0.5 hours to 5 hours. The obtained NH form (13) is isolated by a general technique and may be purified, if necessary, by crystallization or chromatography.

Step 2 involves reacting the NH form (13) with an alkylating agent such as alkyl halide or alkyl sulfonate in the presence of an appropriate base such as sodium hydride, potassium t-butoxide, or potassium pentoxide in an appropriate solvent such as N,N-dimethylformamide, N,N-dimethylacetamide, tetrahydrofuran, or dimethyl sulfoxide. The reaction is performed at a temperature of, for example, 0° C. to the boiling point of the solvent for a time of, for example, 0.5 hours to 24 hours. The obtained compound of the formula I is isolated by a general technique and may be purified, if necessary, by crystallization or chromatography.

In $-OSO_2R^{23}$ shown in this scheme, $R^{23}$ is $C_{1-5}$ alkyl optionally substituted with one or more halogen atoms or aryl, wherein the aryl group is optionally substituted with one or more halogen atoms or alkyl groups. Specific examples of $R^{23}$ include methyl, trifluoromethyl, phenyl, and 4-methylphenyl.

The compound of the formula I can also be synthesized by alkylation as shown in Scheme 5 (Method E).

Scheme 5 (Method E)

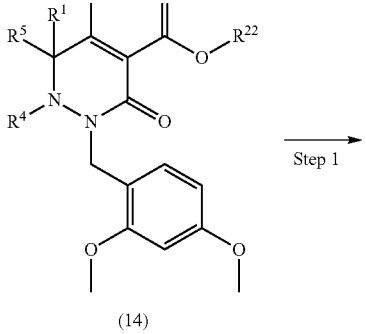

(14)

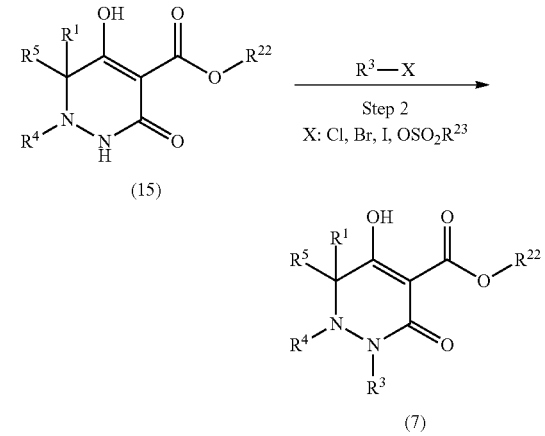

(15)

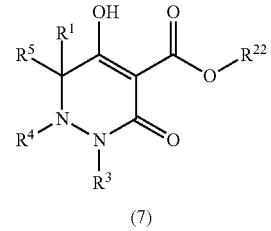

(7)

wherein $R^{22}$ is as defined in Scheme 1.

The reaction of Step 1 of Scheme 5 (Method E) can be pursued in the same way as in Step 1 of Scheme 4 (Method D).

The reaction of Step 2 of Scheme 5 (Method E) can be pursued in the same way as in Step 2 of Scheme 4 (Method D). The compound of the formula I can be obtained in the same way as in Step 5 of Scheme 1 from the obtained ester form (7).

Side chain introduction method

Scheme 6 (Method F)

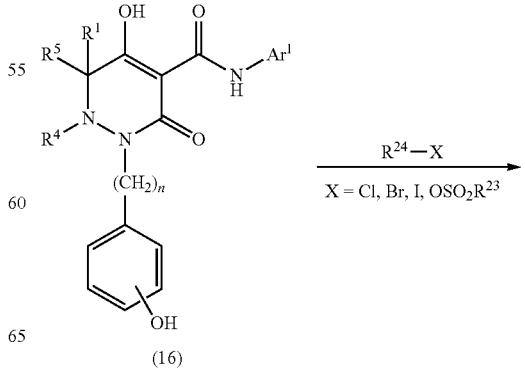

(16)

-continued

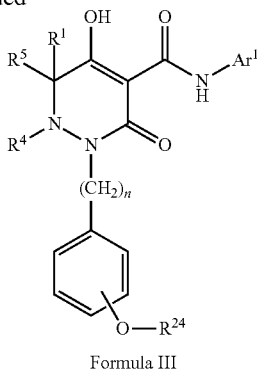

Formula III wherein n is an integer selected from 1 to 10, and $R^{24}$ is $C_{1-8}$ alkoxy optionally substituted with one or more substituents $R^{12}$.

The method of Scheme 6 (Method F) involves reacting a phenol derivative (16) with an alkylating agent such as alkyl halide or alkyl sulfonate in the presence of an appropriate base such as sodium hydride, potassium carbonate, cesium carbonate, potassium t-butoxide, or potassium pentoxide in an appropriate solvent such as tetrahydrofuran, acetonitrile, N,N-dimethylformamide, N,N-acetamide, dimethyl sulfoxide, or acetone. The reaction is performed at a temperature of, for example, 0° C. to the boiling point of the solvent for a time of, for example, 0.5 hours to 12 hours. The obtained compound represented by the formula III is isolated by a general technique and may be purified, if necessary, by crystallization or chromatography. The compound obtained in Scheme 6 can be subjected, if necessary, to the deprotection reaction of various protective groups and other procedures to synthesize a derivative.

Scheme 7 (Method G)

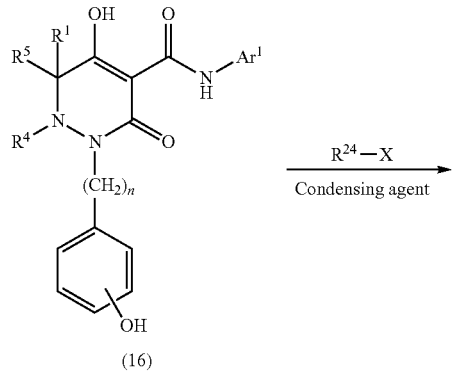

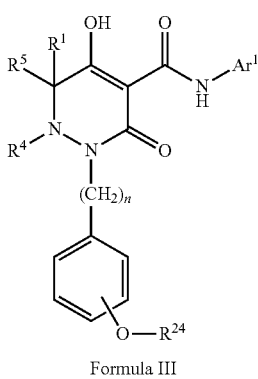

Formula III wherein n and $R^{24}$ are as defined in Scheme 6.

The method of Scheme 7 (Method G) involves reacting a phenol derivative (16) with various alcohols using an appropriate Mitsunobu reagent such as diethyl azodicarboxylate (DEAD), diisopropyl azodicarboxylate (DIAD), N,N,N',N'-tetraisopropylazodicarboxamide (TIPA), 1,1'-(azodicarbonyl)dipiperidine (ADDP), or N,N,N',N'-tetramethylazodicarboxamide (TMAD) in the presence of an appropriate trivalent organic phosphorus reagent such as triphenylphosphine or tributylphosphine in an appropriate solvent such as dichloromethane, tetrahydrofuran, acetonitrile, toluene, or benzene. The reaction is performed at a temperature of, for example, 0° C. to the boiling point of the solvent for a time of, for example, 0.5 hours to 24 hours. The obtained compound represented by the formula III is isolated by a general technique and may be purified, if necessary, by crystallization or chromatography. The compound obtained in Scheme 7 can be subjected, if necessary, to the deprotection reaction of various protective groups and other procedures to synthesize a derivative.

Scheme 8 (Method H)

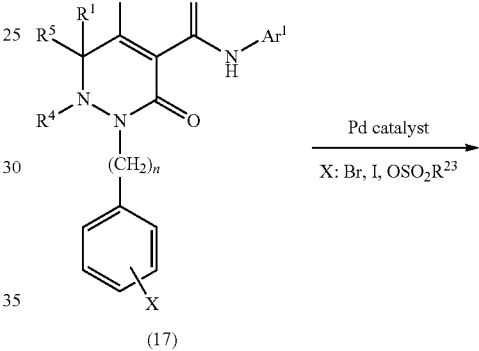

Formula IV wherein n is an integer selected from 1 to 10, and $R^{25}$ is ($C_{1-4}$ alkoxy)carbonyl, $C_{1-10}$ alkyl optionally substituted with one or more substituents $R^{10}$, $C_{2-10}$ alkynyl optionally substituted with one or more substituents $R^{11}$, or $C_{1-4}$ alkylthio optionally substituted with one or more substituents $R^{13}$.

The method of Scheme 8 (Method H) involves reacting a bromobenzene or iodobenzene derivative (17) using a palladium catalyst such as tetrakis(triphenylphosphine)palladium(0) (Pd(Ph$_3$P)$_4$), tris(dibenzylideneacetone)dipalladium(0) (Pd$_2$(dba)$_3$), 1,1'-bis(diphenylphosphino)ferrocene-palladium(II) dichloride-dichloromethane complex (PdCl$_2$(dppf).CH$_2$Cl$_2$), palladium(II) acetate (Pd(OAc)$_2$), or dichlorobis(triphenylphosphine)palladium(II) (PdCl$_2$(Ph$_3$P)$_2$) supplemented, if necessary, with a phosphine ligand such as triphenylphosphine (Ph₃P), tri-t-butylphosphine (tBu₃P), or tri-o-tolylphosphine ((o-tol)₃P), a copper catalyst such as copper(I) iodide, and an appropriate base such as sodium carbonate, triethylamine, or potassium carbonate in an appropriate solvent such as dichloromethane, tetrahydrofuran, N,N-dimethylformamide, N,N-dimethylacetamide, toluene, benzene, 1,2-dimethoxyethane, 1,4-dioxane, ethanol, or acetonitrile to introduce thereinto, for example, sulfur, alkane, alkyne, or alkoxycarbonyl. When $R^{25}$ is $(C_{1-4}$ alkoxy)carbonyl, for example, carbon monooxide and $C_{1-4}$ alcohol can be used as a reagent in the reaction. When $R^{25}$ is $C_{1-10}$ alkyl optionally substituted with one or more substituents $R^{10}$ or $C_{2-10}$ alkynyl, for example, acetylene or $(C_{1-8}$ alkyl)-C≡CH can be used as a reagent in the reaction. When $R^{25}$ is $C_{1-4}$ alkylthio optionally substituted with one or more substituents $R^{13}$, for example, $C_{1-4}$ alkylmercaptan can be used as a reagent in the reaction. The reaction is performed at a temperature of, for example, 0° C. to the boiling point of the solvent for a time of, for example, 0.5 hours to 60 hours. The obtained compound represented by the formula IV is isolated by a general technique and may be purified, if necessary, by crystallization or chromatography. The compound obtained in Scheme 8 can be subjected, if necessary, to the hydrogenation reaction of a double bond and a triple bond, the oxidation reaction or alkylation of a sulfur atom, the deprotection reaction of various protective groups, and other procedures to synthesize a derivative.

wherein $R^{22}$, $R^{23}$, and $R^{25}$ are as defined in Schemes 1 and 8.

The reaction of Scheme 9 (Method I) can be pursued in the same way as in Scheme 8 with a compound (18) as a starting material. The compound of the formula IV can be obtained in the same way as in Step 5 of Scheme 1 from the obtained ester form (19).

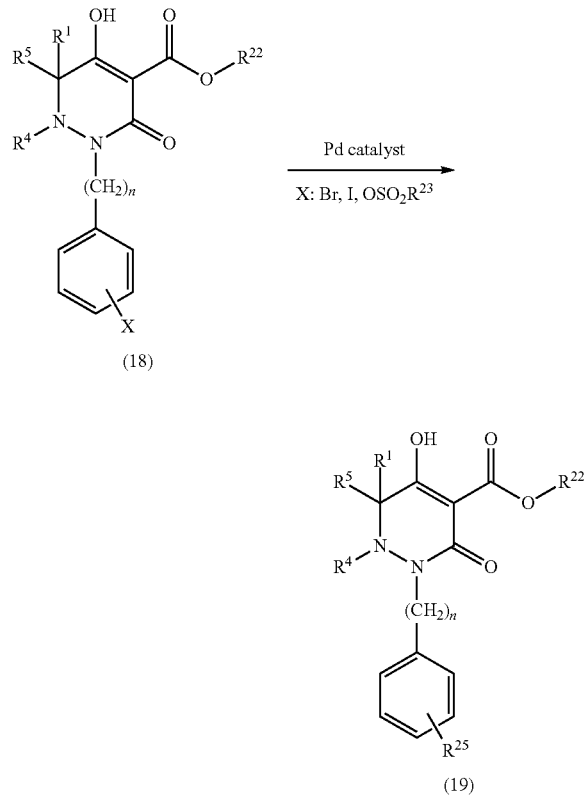

wherein
Ar¹ is $C_{6-10}$ aryl or 5- to 10-membered heteroaryl, wherein this group is optionally substituted with Rb and/or Rc; and
Rd is selected from 5- to 10-membered heterocycloalkyl optionally substituted with one or more substituents $R^{14}$, $C_{6-10}$ aryl optionally substituted with one or more substituents $R^{14}$, and 5- to 10-membered heteroaryl optionally substituted with one or more substituents $R^{14}$.

Examples of —B(pin) in the above formula include the following structure:

The method of Scheme 10 (Method J) involves reacting an aryl halide derivative (20) with aryl boronic acid, heteroaryl boronic acid, heterocycloalkyl boronic acid, aryl boronic acid ester, heteroaryl boronic acid ester, heterocycloalkyl boronic acid ester, aryltrialkyltin, heteroaryltrialkyltin, heterocycloalkyltrialkyltin, or the like using a palladium catalyst such as tetrakis(triphenylphosphine)palladium(0) (Pd(Ph₃P)₄), tris(dibenzylideneacetone)dipalladium(0) (Pd₂(dba)₃), 1,1'-bis(diphenylphosphino)ferrocene-palladium(II) dichloride-dichloromethane complex (PdCl₂(dppf).CH₂Cl₂), or palladium(II) acetate (Pd(OAc)₂) supplemented, if necessary, with a phosphine ligand such as triphenylphosphine (Ph₃P), tri-t-butylphosphine (tBu₃P), or tri-o-tolylphosphine ((o-tol)₃P) and an appropriate base such as sodium carbonate, triethylamine, or potassium carbonate in an appropriate solvent such as tetrahydrofuran, acetonitrile, toluene, N,N-dimethylformamide, N,N-dimethylacetamide, 1,2-dimethoxyethane (DME), or 1,4-dioxane in a nitrogen atmosphere to introduce an aryl group thereinto. The reaction is performed at a temperature of, for example, room temperature to the boiling point of the solvent for a time of, for example, 0.5 hours to 12 hours. The obtained bisaryl form (formula V) is isolated by a general technique and may be purified, if necessary, by crystallization or chromatography.

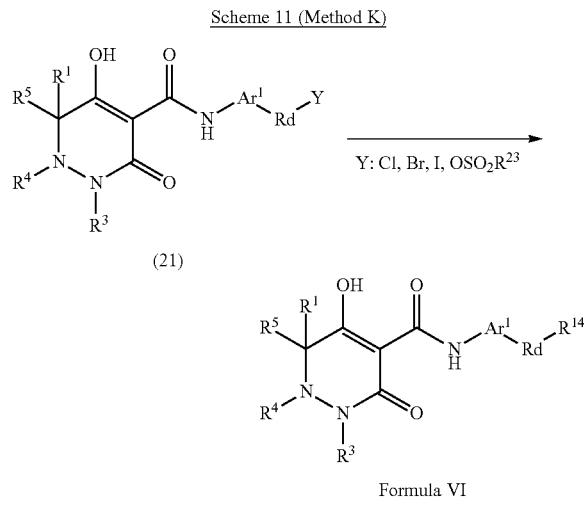

Scheme 11 (Method K)

wherein
$R^{23}$ is as defined above;
$Ar^1$ and Rd are as defined in Scheme 10; and
$R^{14}$ is selected from cyano, $C_{1-4}$ alkoxy optionally substituted with one or more halogen atoms, and —$NR^{27}R^{28}$ ($R^{27}$ and $R^{28}$ are each independently selected from optionally ($C_{1-3}$ alkoxy)carbonyl-substituted $C_{1-4}$ alkyl).

The method of Scheme 11 (Method K) involves reacting heteroaryl halide or sulfonic acid heteroaryl ester (21) with a nucleophile such as amine, nitrile, or alcohol, if necessary in the presence of a base such as sodium hydride, sodium alkoxide, potassium carbonate, sodium carbonate, triethylamine, diisopropylethylamine, or diazabicycloundecene (DBU) in an appropriate solvent such as N,N-dimethylformamide, N,N-dimethylacetamide, tetrahydrofuran, or dimethyl sulfoxide. The reaction is performed at a temperature of, for example, room temperature to the boiling point of the solvent for a time of, for example, 0.5 hours to 24 hours. The obtained bisaryl form (formula VI) is isolated by a general technique and may be purified, if necessary, by crystallization or chromatography.

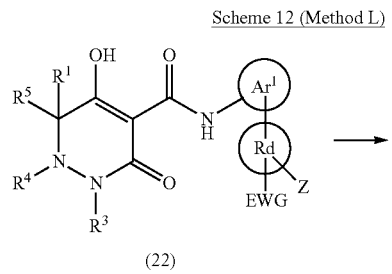

Scheme 12 (Method L)

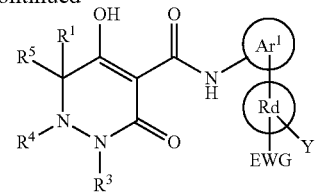

Formula VII

Z: F, Cl, Br, I, $OSO_2R^{23}$, $NO_2$ EWG: Electron-withdrawing substituent (CN, $COOCH_3$, $SO_2CH_3$, etc.)

wherein
$R^{23}$ is as defined in Scheme 11;
Rd is 5- to 10-membered heterocycloalkyl, $C_{6-10}$ aryl, or 5- to 10-membered heteroaryl; and
Y is selected from cyano, $C_{1-4}$ alkoxy optionally substituted with one or more halogen atoms, and —$NR^{27}R^{28}$ ($R^{27}$ and $R^{28}$ are each independently selected from optionally ($C_{1-4}$ alkoxy)carbonyl-substituted $C_{1-4}$ alkyl).

The method of Scheme 12 (Method L) involves reacting heteroaryl halide, sulfonic acid heteroaryl ester, or nitroheteroaryl (22) having an electron-withdrawing substituent (EWG) with a nucleophile such as amine, nitrile, or alcohol, if necessary in the presence of a base such as sodium hydride, sodium alkoxide, potassium carbonate, sodium carbonate, triethylamine, diisopropylethylamine, or diazabicycloundecene (DBU) in an appropriate solvent such as N,N-dimethylformamide, N,N-dimethylacetamide, tetrahydrofuran, dimethyl sulfoxide, or an alcoholic solvent. The reaction is performed at a temperature of, for example, room temperature to the boiling point of the solvent for a time of, for example, 0.5 hours to 24 hours. The obtained bisaryl form (the formula VII) is isolated by a general technique and may be purified, if necessary, by crystallization or chromatography.

Starting material synthesis

Scheme 13 (Method M)

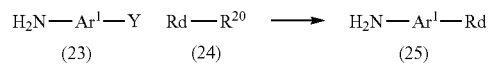
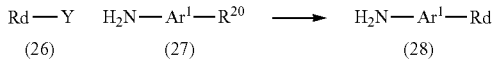

$R^{20}$: $B(OH)_2$, B(pin), $SnBu_3$
Y: Cl, Br, I, $OSO_2R^7$ wherein $Ar^1$ and Rd are as defined in Scheme 10.

According to Scheme 13 (Method M), the arylamine (8) (wherein Rd is 5- to 10-membered heterocycloalkyl optionally substituted with one or more substituents $R^{14}$, $C_{6-10}$ aryl optionally substituted with one or more substituents $R^{14}$, or 5- to 10-membered heteroaryl optionally substituted with one or more substituents $R^{14}$) for use in the reaction of Step 5 of Scheme 1 is synthesized. This method involves reacting aryl halide (23) or (26) with aryl boronic acid, aryl boronic acid ester, aryltrialkyltin, or the like in the presence of a palladium catalyst such as tetrakis(triphenylphosphine)palladium(0) supplemented, if necessary, with a base such as triethylamine, sodium carbonate, potassium carbonate, cesium carbonate, or sodium hydroxide in an appropriate solvent such as water, toluene, ethanol, N,N-dimethylformamide, N,N-dimethylacetamide, 1,4-dioxane, 1,2-dimethoxyethane, or tetrahydrofuran. The reaction is performed at a temperature of, for example, room temperature to the boiling point of the solvent for a time of, for example, 0.5 hours to 24 hours. The obtained bisaryl form (25) or (28) is isolated by a general technique and may be purified, if necessary, by crystallization or chromatography.

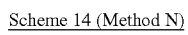

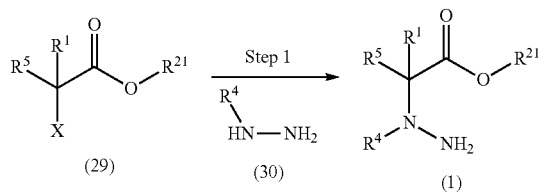

X: Cl, Br, I wherein $R^1$, $R^4$, $R^5$, and $R^{21}$ are as defined above.

According to Scheme 14 (Method N), the hydrazine for use in the reaction of Step 1 of Scheme 1 is synthesized. The compound (1) can be synthesized with reference to, for example, Bioorganic & Medicinal Chemistry Letters 13 (2003) 2413-2418.

hydride, potassium carbonate, or cesium carbonate or a silver salt such as silver(I) oxide in the presence of alkyl halide in an appropriate solvent such as N,N-dimethylformamide, N,N-dimethylacetamide, tetrahydrofuran, or dimethyl sulfoxide. The reaction is performed at a temperature of, for example, 0° C. to 80° C. for a time of, for example, 0.5 hours to 5 hours. The obtained N-alkyl form (33) is isolated by a general technique and may be purified, if necessary, by crystallization or chromatography.

Step 2 involves deprotecting the carbamate (33), for example, in the presence of an acid such as hydrochloric acid or trifluoroacetic acid or by catalytic hydrogen reduction in the presence of a catalyst such as palladium. The reaction is performed at a temperature of, for example, 0° C. to 50° C. for a time of, for example, 0.5 hours to 24 hours. The reaction solvent used is, for example, an appropriate solvent such as dichloromethane or acetonitrile for the acidic conditions or, for example, a solvent such as ethyl acetate, N,N-dimethylformamide, N,N-dimethylacetamide, dimethyl sulfoxide, or methanol for the catalytic hydrogen reduction. The obtained N-alkyl form (34) is isolated by a general technique and may be purified, if necessary, by crystallization or chromatography. The hydrazine (1) shown in Scheme 1 can be synthesized from the amine (34) with reference to, for example, Synthetic communications, 40, 654-660; 2010, Journal of Heterocyclic Chemistry, 24 (3), 725-731; 1987, and Synthesis, (6), 423-424; 1979.

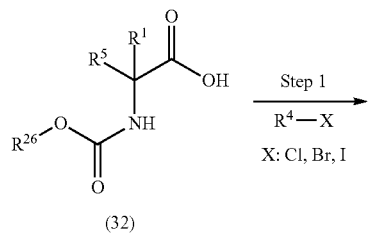

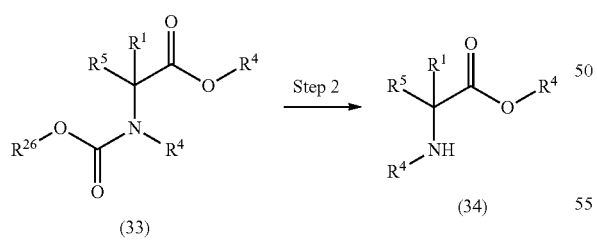

wherein $R^{26}$ is benzyl, methyl, or t-butyl, and $R^1$, $R^4$, and $R^5$ are as defined above.

According to Scheme 15 (Method O), the amine (34) for synthesis of the hydrazine (1) for use in the reaction of Step 1 of Scheme 1 is synthesized.

Step 1 involves N-alkylating a carbamate-protected amino acid using an appropriate base reagent such as sodium

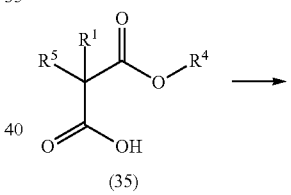

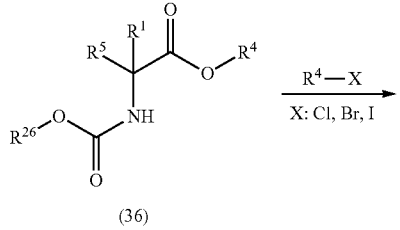

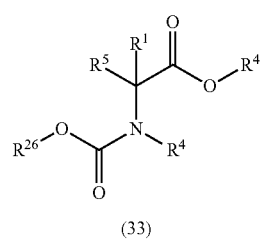

wherein $R^1$, $R^4$, $R^5$, and $R^{26}$ are as defined above.

According to Scheme 16 (Method P), the carbamate-protected amino acid (36) for synthesis of the compound (33) for use in the reaction of Step 1 of Scheme 15 is synthesized. The compound (36) can be synthesized using Curtius rearrangement for carboxylic acid (35) (this reaction can be performed with reference to, for example, J. Org. Chem., 1994, 59 (26), 8215-8219). The compound (33) can be synthesized in the same way as in Step 1 of Scheme 15.

Hereinafter, the present invention will be described in more detail with reference to Reference Examples and Examples. However, the present invention is not limited by these examples.

by Agilent Technologies, Inc.) or AVANCE3 Cryo-TCI (Bruker Corp.) (s=singlet, brs=broad singlet, d=doublet, t=triplet, q=quartet, dd=double doublet, ddd=double double doublet, dt=double triplet, td=triple doublet, and m=multiplet). Mass spectrometry was performed using a mass spectrometer SQD (manufactured by Waters Corp.), 2020 (manufactured by Shimadzu Corp.), or 2010EV (manufactured by Shimadzu Corp.). Retention time measurement and mass spectrometry in LCMS were performed using the following apparatuses and analysis conditions:

TABLE 1

| LCMS analysis condition No. | Apparatus | Column | Mobile phase and gradient |
|---|---|---|---|
| SMD-TFA05 | nexera/2020 | Kinetex 2.1 mmI.D. × 50 mm | 0.05% TFA/0.05% TFA MeCN = 95/5 → 0/100(1.5 min) → 0/100(0.5 min), 1 mL/min |
| SMD-TFA50 | nexera/2020 | Kinetex 2.1 mmI.D. × 50 mm | 0.05% TFA/0.05% TFA MeCN = 50/50 → 0/100(1 min) → 0/100(1 min), 1 ml/min |
| SMD-FA05 | nexera/2020 | Ascentis Express C18 2.1 mmI.D. × 50 mm | $H_2O$(0.1% FA)/MeCN(0.1% FA) 95/5 → 0/100(1.5 min) → 100(0.6 min), 1 mL/min |
| SQD-AA05 | UPLC/SQD | Ascentis Express C18 2.1 mmI.D. × 50 mm | 10 mMAcONH$_4$/MeOH = 95/5 → 0/100(1 min) → 100(0.4 min), 1 mL/min |
| SQD-AA50 | UPLC/SQD | Ascentis Express C18 2.1 mmI.D. × 50 mm | 10 mMAcONH$_4$/MeOH = 50/50 → 0/100(0.7 min) → 100(0.7 min), 1 mL/min |
| SQD-FA05 | UPLC/SQD | Ascentis Express C18 2.1 mmI.D. × 50 mm | $H_2O$(0.1% FA)/MeCN(0.1% FA) = 95/5 → 0/100(1 min) → 100(0.4 min), 1 mL/min |
| SQD-FA50 | UPLC/SQD | Ascentis Express C18 2.1 mmI.D. × 50 mm | $H_2O$(0.1% FA)/MeCN(0.1% FA) = 50/50 → 0/100(0.7min) → 100(0.7 min), 1 mL/min |
| SMD-AA05 | nexera/2020 | Ascentis Express C18 2.1 mmI.D. × 50 mm | 10 mM AcONH4/MeOH = 95/5 → 0/100(1.5 min) → 100(0.7 min), 1 mL/min |
| QC-SMD-TFA05 | nexera/2020 | Acquity 2.1 mmI.D. × 50 mm | 0.05% TFA/0.05% TFA MeCN = 95/5 → 0/100(1.5 min) → 0/100(0.5 min), 1 ml/min |
| Ph-SMD-TFA05 | UFLC-MS 2010EV | shim-pack XR-ODS 3.0 mmI.D. × 50 mm | 0.05% TFA/0.05% TFA MeCN = 95/5 → 0/100(2 min) → 0/100(1.1 min), 1 mL/min |
| ZQ-01 | 2525BGM/ 2996PDA/ ZQ2000 | Chromolith Flash RP-18e 4.6 mmI.D. × 25 mm | 10 mM AcONH4/MeOH = 95/5 → 0/100(3 min) → 100(2 min), 2 mL/min |
| SQD-TFA05 | UPLC/SQD | Ascentis Express C18 2.1 mmI.D. × 50 mm | $H_2O$0.1% TFA)/ MeCN(0.1% TFA) = 95/5 → 0/100(1 min) → 100(0.4 min), 1 mL/min |

EXAMPLES

The contents of the present invention will be further described with reference to Examples and Reference Examples below. However, the present invention is not limited by the contents of these examples. All starting materials and reagents were obtained from commercial suppliers or synthesized using methods known in the art. Each compound is purified by HPLC using AutoPurification HPLC/MS System (manufactured by Waters Corp.). $^1$H-NMR or $^{13}$C-NMR spectra were measured using Me$_4$Si as an internal standard and Agilent 400-MR (manufactured A compound having a C=N bond in a hydrazone structural formula represented by the following formula

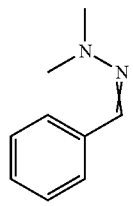

was used in next reaction without particular confirmation of whether the compound was in a cis form or a trans form or a mixture thereof.

Example 1

(4aS)-1-[(3-Fluorophenyl)methyl]-4-hydroxy-N-[5-methyl-2-(trifluoromethyl)furan-3-yl]-2-oxo-4a,5,6,7-tetrahydropyrrolo[1,2-b]pyridazine-3-carboxamide First Step (S)-1-[(3-Fluoro-benzylidene)-amino]-pyrrolidine-2-carboxylic acid methyl ester

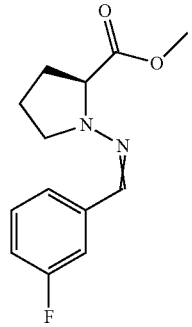 [SMILES: COC(=O)[C@@H]1CCCN1N=Cc1cccc(F)c1]

L-proline methyl ester hydrochloride (5.00 g, 30.2 mmol) was suspended in dichloromethane (60.4 mL), p-toluenesulfonic acid monohydrate (6.03 g, 31.7 mmol) was added, and the mixture was stirred under nitrogen atmosphere at room temperature for 10 minutes. After the reaction mixture was concentrated at reduced pressure and toluene was added, for azeotropic removal of water suspended in dichloromethane (60.4 mL), sodium nitrite (2.19 g, 31.7 mmol) was added, and the mixture was stirred under nitrogen atmosphere at room temperature for 2 hours. After the reaction mixture was filtered, the resultant was concentrated at reduced pressure to obtain (S)-1-nitroso-pyrrolidine-2-carboxylic acid methyl ester as a crude product. The obtained crude product was dissolved in acetic acid (30.2 mL) and water (30.2 mL), then zinc (19.7 g, 302 mmol) was added at 0° C., and the mixture was stirred under nitrogen atmosphere at room temperature for 1 hour. After sodium bicarbonate was added to the reaction mixture at 0° C., methanol (60.4 mL) and 3-fluoro-benzaldehyde (3.20 mL, 30.2 mmol) were added, and the mixture was stirred under nitrogen atmosphere at room temperature for 2 hours. After the reaction mixture was filtered, the resultant was concentrated at reduced pressure and then extracted with ethyl acetate. The organic layer was washed with water and a brine, dried over sodium sulfate, filtered, and concentrated at reduced pressure, and the resultant residue was purified by column chromatography on silica gel (hexane/ethyl acetate) to obtain the title compound (5.68 g, 75%).

LCMS: m/z 251[M+H]$^+$

HPLC retention time: 0.97 minutes (analysis condition SQD-AA05)

Second Step (4aS)-1-[(3-Fluorophenyl)methyl]-4a,5,6,7-tetrahydropyrrolo[1,2-b]pyridazine-2,4-dione

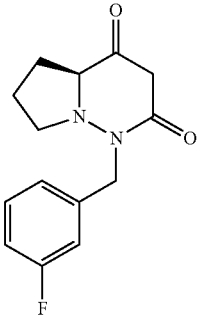 [SMILES: O=C1CC(=O)N(Cc2cccc(F)c2)N2CCC[C@@H]12]

(S)-1-[(3-Fluoro-benzylidene)-amino]-pyrrolidine-2-carboxylic acid methyl ester (5.68 g, 22.7 mmol) was dissolved in acetic acid (22.7 mL) and methanol (22.7 mL), sodium cyanoborohydride (5.70 g, 90.8 mmol) was added, and the mixture was stirred under nitrogen atmosphere at room temperature for 14 hours. A saturated aqueous sodium bicarbonate solution was added to the reaction mixture, then the mixture was concentrated at reduced pressure and extracted with ethyl acetate. The organic layer was washed with a brine, dried over sodium sulfate, filtered, and concentrated at reduced pressure to obtain (S)-1-(3-fluoro-benzylamino)-pyrrolidine-2-carboxylic acid methyl ester as a crude product. The obtained crude product was dissolved in tetrahydrofuran (22.7 mL), tripotassium phosphate (9.64 g, 45.4 mmol) and chlorocarbonyl-acetic acid methyl ester (2.67 mL, 45.4 mmol) were added at 0° C., and the mixture was stirred under nitrogen atmosphere at room temperature for 3 hours. 1 N hydrochloric acid was added to the reaction mixture, and the mixture was extracted with ethyl acetate. The organic layer was washed with a saturated aqueous sodium bicarbonate solution and a brine, dried over sodium sulfate, filtered, and concentrated at reduced pressure to obtain (S)-1-[(3-fluoro-benzyl)-(2-methoxycarbonyl-acetyl)-amino]-pyrrolidine-2-carboxylic acid methyl ester as a crude product. The obtained crude product was dissolved in N,N-dimethylformamide (22.7 mL), cesium carbonate (22.2 g, 68.1 mmol) was added, and the mixture was stirred under nitrogen atmosphere at 80° C. for 9 hours. 1 N hydrochloric acid was added to the reaction mixture, and the mixture was extracted with ethyl acetate. The organic layer was washed with water and a brine, dried over sodium sulfate, filtered, and concentrated at reduced pressure to obtain (S)-1-(3-fluoro-benzyl)-4-hydroxy-2-oxo-1,2,4a,5,6,7-hexahydro-pyrrolo[1,2-b]pyridazine-3-carboxylic acid methyl ester as a crude product. The obtained crude product was dissolved in acetonitrile (227 mL), water (0.41 mL, 22.7 mmol) was added, and the mixture was heated under reflux for 2 hours under nitrogen atmosphere. The reaction mixture was concentrated at reduced pressure and the resultant residue was purified by column chromatography on silica gel (hexane/ethyl acetate) to obtain the title compound (4.01 g, 67%).

LCMS: m/z 263[M+H]$^+$

HPLC retention time: 0.81 minutes (analysis condition SQD-AA05)

Third Step (4aS)-1-[(3-Fluorophenyl)methyl]-4-hydroxy-N-[5-methyl-2-(trifluoromethyl)furan-3-yl]-2-oxo-4a,5,6,7-tetrahydropyrrolo[1,2-b]pyridazine-3-carboxamide

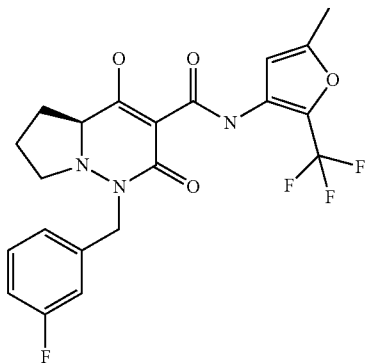 [SMILES: Cc1cc(NC(=O)C2=C(O)[C@@H]3CCCN3N(Cc3cccc(F)c3)C2=O)c(C(F)(F)F)o1]

(4aS)-1-[(3-Fluorophenyl)methyl]-4a,5,6,7-tetrahydropyrrolo[1,2-b]pyridazine-2,4-dione (1.50 g, 5.72 mmol) was dissolved in N,N-dimethylformamide (4.00 mL), and then 3-isocyanato-5-methyl-2-trifluoromethyl-furan (1.20 g, 6.29 mmol) and sodium hydride (50% by weight dispersion in mineral oil, 0.33 g, 6.86 mmol) were added, and the mixture was stirred under nitrogen atmosphere at room temperature for 90 minutes. 1 N hydrochloric acid was added to the reaction mixture, and the mixture was extracted with ethyl acetate. The organic layer was washed with water and a brine, dried over sodium sulfate, filtered, and concentrated at reduced pressure, and the resultant residue was purified by column chromatography on silica gel (hexane/ethyl acetate) to obtain the title compound (1.62 g, 63%).

LCMS: m/z 454[M+H]$^+$

HPLC retention time: 1.10 minutes (analysis condition SQD-AA05)

Example 2

(4aR)-1-[(3-Fluorophenyl)methyl]-4-hydroxy-N-[5-methyl-2-(trifluoromethyl)furan-3-yl]-2-oxo-4a,5,6,7-tetrahydropyrrolo[1,2-b]pyridazine-3-carboxamide In a similar manner to First to Third Steps of Example 1, the compounds described in the following Table were synthesized from D-proline methyl ester hydrochloride and 3-fluoro-benzaldehyde.

TABLE 2

| Structure | Compound name | Analysis condition | HPLC Retention time (min) | m/z |
|---|---|---|---|---|
| 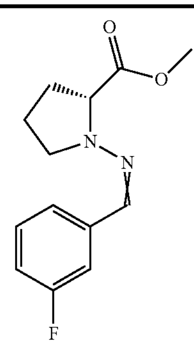 | (R)-1-[(3-Fluoro-benzylidene)-amino]-pyrrolidine-2-carboxylic acid methyl ester | SQD-AA05 | 0.97 | 251 |
| 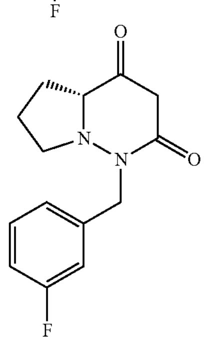 | (4aR)-1-[(3-Fluorophenyl)methyl]-4a,5,6,7-tetrahydropyrrolo[1,2-b]pyridazine-2,4-dione | SQD-AA05 | 0.81 | 263 |
| 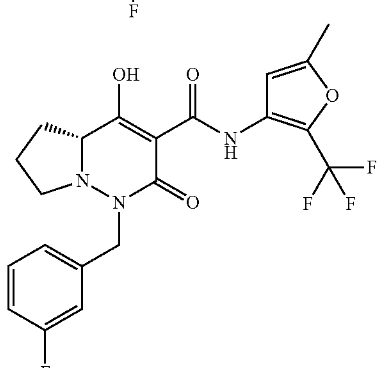 | (4aR)-1-[(3-Fluorophenyl)methyl]-4-hydroxy-N-[5-methyl-2-(trifluoromethyl)furan-3-yl]-2-oxo-4a,5,6,7-tetrahydropyrrolo[1,2-b]pyridazine-3-carboxamide | SQD-AA05 | 1.10 | 454 |

Example 3

(4aS)-1-[(3-Fluorophenyl)methyl]-4-hydroxy-6,6-dimethyl-N-[5-methyl-2-(trifluoromethyl)furan-3-yl]-2-oxo-5,7-dihydro-4aH-pyrrolo[1,2-b]pyridazine-3-carboxamide First Step (S)-4,4-Dimethyl-pyrrolidine-2-carboxylic acid ethyl ester hydrochloride

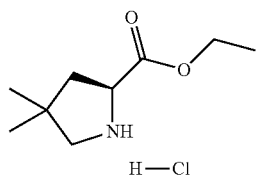

A 1,4-dioxane solution (4 M, 5.00 mL) of hydrogen chloride was added to (S)-4,4-dimethyl-pyrrolidine-1,2-dicarboxylic acid 1-tert-butyl ester 2-ethyl ester (500 mg, 1.84 mmol), and the mixture was stirred under nitrogen atmosphere at room temperature for 1 hour. The reaction mixture was concentrated at reduced pressure, and toluene was added for azeotropic removal to obtain the title compound as a crude product.

Second Step

In a similar manner to First to Third Steps of Example 1, the compounds described in the following Table were synthesized from the obtained (S)-4,4-dimethyl-pyrrolidine-2-carboxylic acid ethyl ester hydrochloride and 3-fluorobenzaldehyde.

TABLE 3

| Structure | Compound name | Analysis condition | HPLC Retention time (min) | m/z |
|---|---|---|---|---|
| 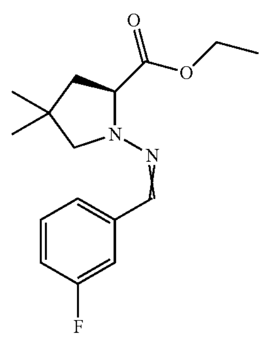 [SMILES: CCOC(=O)[C@@H]1CC(C)(C)CN1N=Cc1cccc(F)c1] | (S)-1-[(3-Fluoro-benzylidene)-amino]-4,4-dimethyl-pyrrolidine-2-carboxylic acid ethyl ester | SQD-AA05 | 1.09 | 293 |
| 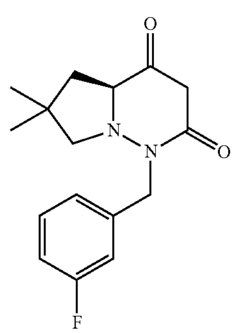 [SMILES: CC1(C)C[C@H]2C(=O)CC(=O)N(Cc3cccc(F)c3)N2C1] | (4aS)-1-[(3-Fluorophenyl)methyl-6,6-dimethyl-5,7-dihydro-4aH-pyrrolo[1,2-b]pyridazine-2,4-dione | SQD-AA05 | 0.94 | 291 |
| 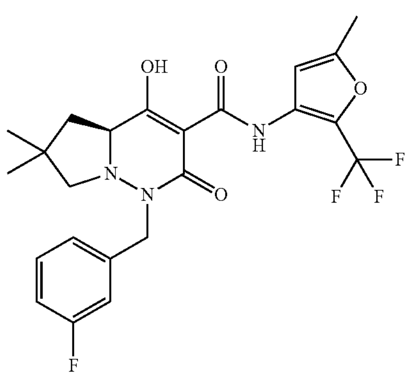 [SMILES: Cc1cc(NC(=O)C2=C(O)[C@@H]3CC(C)(C)CN3N(Cc3cccc(F)c3)C2=O)c(C(F)(F)F)o1] | (4aS)-1-[(3-Fluorophenyl)methyl]-4-hydroxy-6,6-dimethyl-N-[5-methyl-2-(trifluoromethyl)furan-3-yl]-2-oxo-5,7-dihydro-4aH-pyrrolo[1,2-b]pyridazine-3-carboxamide | SQD-AA05 | 1.15 | 482 |

Example 4

(4aS)-1-[(3-Fluorophenyl)methyl]-4-hydroxy-7,7-dimethyl-N-[5-methyl-2-(trifluoromethyl)furan-3-yl]-2-oxo-5,6-dihydro-4aH-pyrrolo[1,2-b]pyridazine-3-carboxamide First Step (S)-5,5-Dimethyl-pyrrolidine-2-carboxylic acid methyl ester hydrochloride

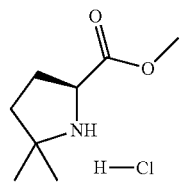

(S)-5,5-Dimethyl-pyrrolidine-1,2-dicarboxylic acid 1-tert-butyl ester (500 mg, 2.06 mmol) was dissolved in N,N-dimethylformamide (2.06 mL), and then cesium carbonate (1.00 g, 3.08 mmol) and iodomethane (0.154 mL, 2.47 mmol) were added, and the mixture was stirred under nitrogen atmosphere at room temperature for 2 hours. 1 N hydrochloric acid was added to the reaction mixture, and the mixture was extracted with ethyl acetate. The organic layer was washed with water, a saturated sodium bicarbonate solution, and a brine, dried over sodium sulfate, filtered, and concentrated at reduced pressure to obtain (S)-5,5-dimethyl-pyrrolidine-1,2-dicarboxylic acid 1-tert-butyl ester 2-methyl ester as a crude product. A 1,4-Dioxane solution (4 M, 5.00 mL) of hydrogen chloride was added to the obtained crude product, and the mixture was stirred under nitrogen atmosphere at room temperature for 1 hour. The reaction mixture was concentrated at reduced pressure, and toluene was added for azeotropic removal to obtain the title compound as a crude product.

Second Step

In a similar manner to First to Third Steps of Example 1, the compounds described in the following Table were synthesized from the obtained (S)-5,5-dimethyl-pyrrolidine-2-carboxylic acid methyl ester hydrochloride and 3-fluorobenzaldehyde.

TABLE 4

| Structure | Compound name | Analysis condition | HPLC Retention time (min) | m/z |
|---|---|---|---|---|
| 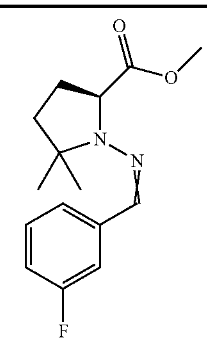 | (S)-1-[(3-Fluoro-benzylidene)-amino]-5,5-dimethyl-pyrrolidine-2-carboxylic acid methyl ester | SQD-AA05 | 1.10 | 279 |
| 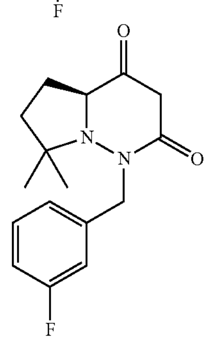 | (4aS)-1-[(3-Fluorophenyl)methyl]-7,7-dimethyl-5,6-dihydro-4aH-pyrrolo[1,2-b]pyridazine-2,4-dione | SQD-AA05 | 0.93 | 291 |
| 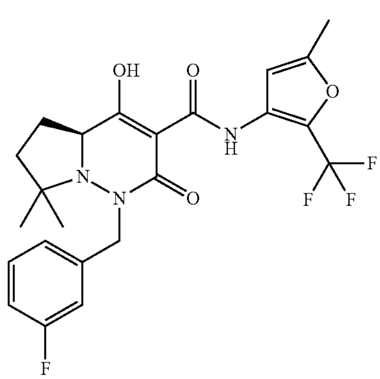 [SMILES: Cc1cc(NC(=O)C2=C(O)[C@@H]3CCC(C)(C)N3N(Cc3cccc(F)c3)C2=O)c(C(F)(F)F)o1] | (4aS)-1-[(3-Fluorophenyl)methyl]-4-hydroxy-7,7-dimethyl-N-[5-methyl-2-(trifluoromethyl)furan-3-yl]-2-oxo-5,6-dihydro-4aH-pyrrolo[1,2-b]pyridazine-3-carboxamide | SQD-AA05 | 1.13 | 482 |

Example 5

(4aS)-1-[(2,3-Difluorophenyl)methyl]-6,6-difluoro-4-hydroxy-N-[5-methyl-2-(trifluoromethyl)furan-3-yl]-2-oxo-5,7-dihydro-4aH-pyrrolo[1,2-b]pyridazine-3-carboxamide (S)-4,4-Difluoropyrrolidine-1,2-dicarboxylic acid 2-methyl 1-tert-butyl diester was used as a starting material, 2,3-difluorobenzaldehyde was used as a reagent, and operations similar to those of Example 3 were carried out to synthesize the compounds described in the following Table.

TABLE 5

| Structure | Compound name | Analysis condition | HPLC Retention time (min) | m/z |
|---|---|---|---|---|
| 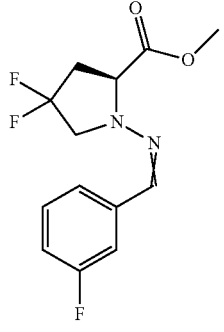 [SMILES: COC(=O)[C@@H]1CC(F)(F)CN1N=Cc1cccc(F)c1] | (S)-1-((2,3-Difluorobenzylidene)amino)-4,4-difluoropyrrolidine-2-carboxylic acid methyl ester | SMD-TFA05 | 1.24 | 305 |
| 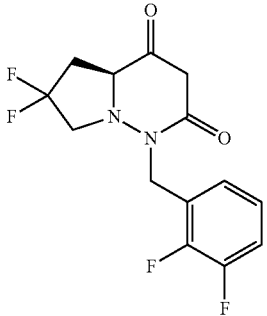 [SMILES: O=C1CC(=O)N(Cc2cccc(F)c2F)N2CC(F)(F)C[C@@H]12] | (4aS)-1-[(2,3-Difluorophenyl)methyl]-6,6-difluoro-5,7-dihydro-4aH-pyrrolo[1,2-b]pyridazine-2,4-dione | SMD-TFA05 | 1.04 | 317 |
| 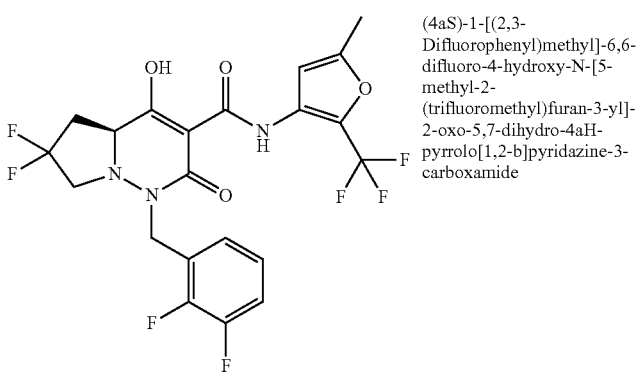 | (4aS)-1-[(2,3-Difluorophenyl)methyl]-6,6-difluoro-4-hydroxy-N-[5-methyl-2-(trifluoromethyl)furan-3-yl]-2-oxo-5,7-dihydro-4aH-pyrrolo[1,2-b]pyridazine-3-carboxamide | SMD-TFA05 | 1.55 | 508 |

Example 6

(4aR)-1-[(3-Fluorophenyl)methyl]-4-hydroxy-4a-methyl-N-[5-methyl-2-(trifluoromethyl)furan-3-yl]-2-oxo-6,7-dihydro-5H-pyrrolo[1,2-b]pyridazine-3-carboxamide First Step (R)-2-Methyl-pyrrolidine-2-carboxylic acid methyl ester hydrochloride

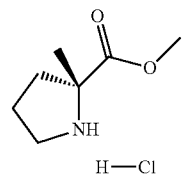

(R)-2-Methyl-pyrrolidine-2-carboxylic acid (300 mg, 2.32 mmol) was dissolved in dioxane (1.20 mL) and water (0.60 mL), and then sodium hydroxide (139 mg, 3.48 mmol) and di-tert-butyl dicarbonate (608 mg, 2.79 mmol) were added at 0° C., and the mixture was stirred at room temperature for 2 hours. 1 N hydrochloric acid was added to the reaction mixture, and the mixture was extracted with ethyl acetate. The organic layer was washed with a brine, dried over sodium sulfate, filtered, and concentrated at reduced pressure to obtain (R)-2-methyl-pyrrolidine-1,2-dicarboxylic acid 1-tert-butyl ester as a crude product. In a similar manner to First Step of Example 4, the title compound was obtained from the obtained (R)-2-methyl-pyrrolidine-1,2-dicarboxylic acid 1-tert-butyl ester as a crude product.

Second Step

In a similar manner to First to Third Steps of Example 1, the compounds described in the following Table were synthesized from the obtained (R)-2-methyl-pyrrolidine-2-carboxylic acid methyl ester hydrochloride and 3-fluoro-benzaldehyde.

TABLE 6

| Structure | Compound name | Analysis condition | HPLC Retention time (min) | m/z |
|---|---|---|---|---|
| 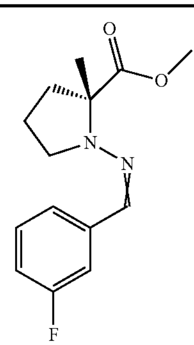 | (R)-1-[(3-Fluoro-benzylidene)-amino]-2-methyl-pyrrolidine-2-carboxylic acid methyl ester | SQD-AA05 | 1.04 | 265 |
| 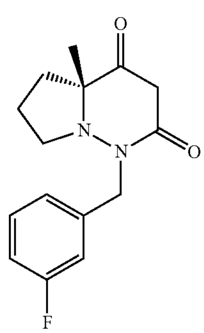 [SMILES: C[C@]12CCCN1N(Cc1cccc(F)c1)C(=O)CC2=O] | (4aR)-1-[(3-Fluorophenyl)methyl]-4a-methyl-6,7-dihydro-5H-pyrrolo[1,2-b]pyridazine-2,4-dione | SQD-AA05 | 0.89 | 277 |
| 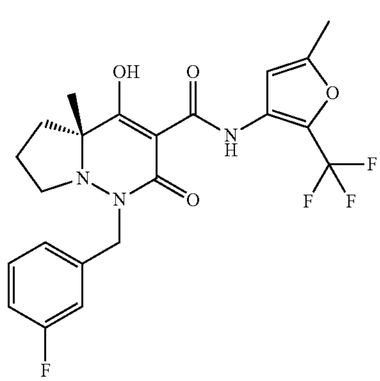 [SMILES: Cc1cc(NC(=O)C2=C(O)[C@@]3(C)CCCN3N(Cc3cccc(F)c3)C2=O)c(C(F)(F)F)o1] | (4aR)-1-[(3-Fluorophenyl)methyl]-4-hydroxy-4a-methyl-N-[5-methyl-2-(trifluoromethyl)furan-3-yl]-2-oxo-6,7-dihydro-5H-pyrrolo[1,2-b]pyridazine-3-carboxamide | SQD-AA05 | 1.15 | 468 |

Example 7

(4aR)-1-[(2,3-Difluorophenyl)methyl]-4-hydroxy-4a-methyl-N-[5-methyl-2-(trifluoromethyl)furan-3-yl]-2-oxo-6,7-dihydro-5H-pyrrolo[1,2-b]pyridazine-3-carboxamide First Step In a similar manner to First to Third Steps of Example 1, the compounds described in the following Table were synthesized from (R)-2-methyl-pyrrolidine-2-carboxylic acid methyl ester hydrochloride obtained in First Step of Example 6 and 2,3-difluoro-benzaldehyde.

TABLE 7

| Structure | Compound name | Analysis condition | HPLC Retention time (min) | m/z |
|---|---|---|---|---|
| 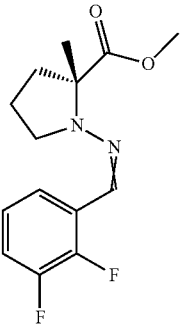 [SMILES: COC(=O)[C@@]1(C)CCCN1N=Cc1cccc(F)c1F] | (R)-1-[(2,3-Difluoro-benzylidene)-amino]-2-methyl-pyrrolidine-2-carboxylic acid methyl ester | SQD-AA05 | 1.08 | 283 |
| 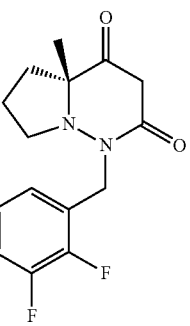 | (4aR)-1-[(2,3-Difluorophenyl)methyl]-4a-methyl-6,7-dihydro-5H-pyrrolo[1,2-b]pyridazine-2,4-dione | SQD-AA05 | 0.89 | 295 |
| 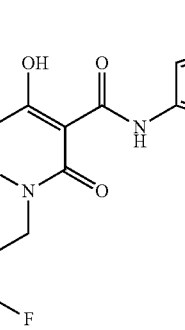 | (4aR)-1-[(2,3-Difluorophenyl)methyl]-4-hydroxy-4a-methyl-N-[5-methyl-2-(trifluoromethyl)furan-3-yl]-2-oxo-6,7-dihydro-5H-pyrrolo[1,2-b]pyridazine-3-carboxamide | SQD-AA05 | 1.16 | 486 |

Example 8

(4aS)-1-[(3-Fluorophenyl)methyl]-4-hydroxy-4a-methyl-N-[5-methyl-2-(trifluoromethyl)furan-3-yl]-2-oxo-6,7-dihydro-5H-pyrrolo[12-b]pyridazine-3-carboxamide

First Step (S)-2-Methyl-pyrrolidine-2-carboxylic acid methyl ester hydrochloride

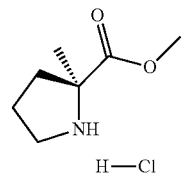

In a similar manner to First Step of Example 6, the title compound was obtained from (S)-2-methyl-pyrrolidine-2-carboxylic acid as a crude product.

Second Step

In a similar manner to First to Third Steps of Example 1, the compounds described in the following Table were synthesized from (S)-2-methyl-pyrrolidine-2-carboxylic acid methyl ester hydrochloride obtained in First Step and 3-fluorobenzaldehyde.

TABLE 8

| Structure | Compound name | Analysis condition | HPLC Retention time (min) | m/z |
|---|---|---|---|---|
| | (S)-1-[(3-Fluorobenzylidene)-amino]-2-methyl-pyrrolidine-2-carboxylic acid methyl ester | SQD-AA05 | 1.04 | 265 |
| 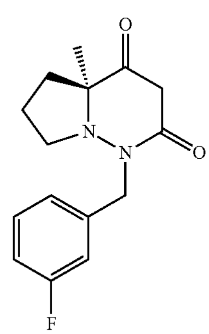 [SMILES: C[C@@]12CCCN1N(Cc1cccc(F)c1)C(=O)CC2=O] | (4aS)-1-[(3-Fluorophenyl)methyl]-4a-methyl-6,7-dihydro-5H-pyrrolo[1,2-b]pyridazine-2,4-dione | SQD-AA05 | 0.92 | 277 |
| 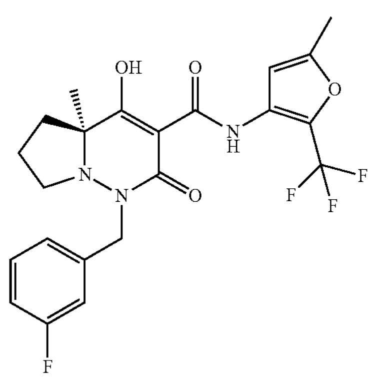 [SMILES: Cc1cc(NC(=O)C2=C(O)[C@]3(C)CCCN3N(Cc3cccc(F)c3)C2=O)c(C(F)(F)F)o1] | (4aS)-1-[(3-Fluorophenyl)methyl]-4-hydroxy-4a-methyl-N-[5-methyl-2-(trifluoromethyl)furan-3-yl]-2-oxo-6,7-dihydro-5H-pyrrolo[1,2-b]pyridazine-3-carboxamide | SQD-AA05 | 1.15 | 468 |

Example 9

(4aR)-4a-Ethyl-1-[(3-fluorophenyl)methyl]-4-hydroxy-N-[5-methyl-2-(trifluoromethyl)furan-3-yl]-2-oxo-6,7-dihydro-5H-pyrrolo[1,2-b]pyridazine-3-carboxamide By carrying out operations similar to those of First to Third Steps of Example 1, the compounds described in the following Table were synthesized from (S)-2-ethyl-pyrrolidine-2-carboxylic acid ethyl ester hydrochloride and 3-fluorobenzaldehyde.

TABLE 9

| Structure | Compound name | Analysis condition | HPLC Retention time (min) | m/z |
|---|---|---|---|---|
| 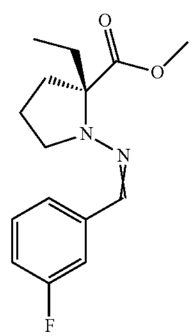 [SMILES: CC[C@]1(C(=O)OC)CCCN1N=Cc1cccc(F)c1] | (R)-2-Ethyl-1-[(3-fluoro-benzylidene)-amino]-pyrrolidine-2-carboxylic acid ethyl ester | SQD-AA05 | 1.14 | 293 |
| 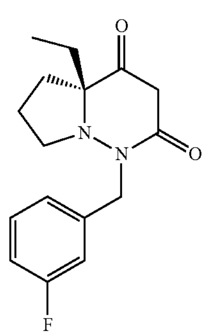 [SMILES: CC[C@]12CCCN1N(Cc1cccc(F)c1)C(=O)CC2=O] | (4aR)-4a-Ethyl-1-[(3-(-fluorophenyl)methyl]-6,7-dihydro-5H-pyrrolo[1,2-b]pyridazine-2,4-dione | SQD-AA05 | 0.96 | 291 |
| 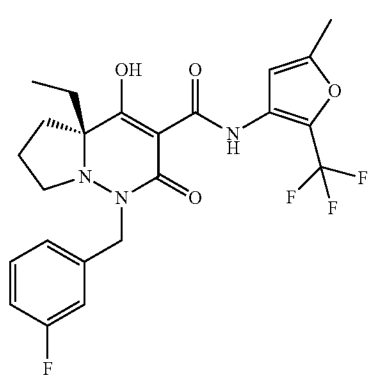 [SMILES: CC[C@]12CCCN1N(Cc1cccc(F)c1)C(=O)C(C(=O)Nc1cc(C)oc1C(F)(F)F)=C2O] | (4aR)-4a-Ethyl-1-[(3-fluorophenyl)methyl]-4-hydroxy-N-[5-methyl-2-(trifluoromethyl)furan-3-yl]-2-oxo-6,7-dihydro-5H-pyrrolo[1,2-b]pyridazine-3-carboxamide | SQD-AA05 | 1.22 | 482 |

Example 10

(4aR)-1-[(2,3-Difluorophenyl)methyl]-4a-ethyl-4-hydroxy-N-[5-methyl-2-(trifluoromethyl)furan-3-yl]-2-oxo-6,7-dihydro-5H-pyrrolo[1,2-b]pyridazine-3-carboxamide By carrying out operations similar to those of First to Third Steps of Example 1, the compounds described in the following Table were synthesized from (R)-2-ethyl-pyrrolidine-2-carboxylic acid ethyl ester hydrochloride and 2,3-difluorobenzaldehyde.

TABLE 10

| Structure | Compound name | Analysis condition | HPLC Retention time (min) | m/z |
|---|---|---|---|---|
| 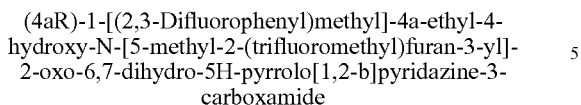 | (R)-1-[(2,3-Difluoro-benzylidene)-amino]-2-ethyl-pyrrolidine-2-carboxylic acid ethyl ester | SQD-AA05 | 1.08 | 283 |
| 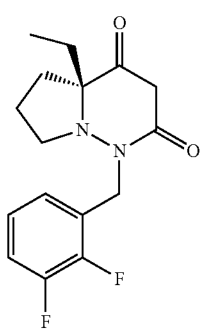 [SMILES: CC[C@]12CCCN1N(Cc1cccc(F)c1F)C(=O)CC2=O] | (4aR)-1-[(2,3-Difluorophenyl)methyl]-4a-ethyl-6,7-dihydro-5H-pyrrolo[1,2-b]pyridazine-2,4-dione | SQD-AA05 | 0.89 | 295 |
| 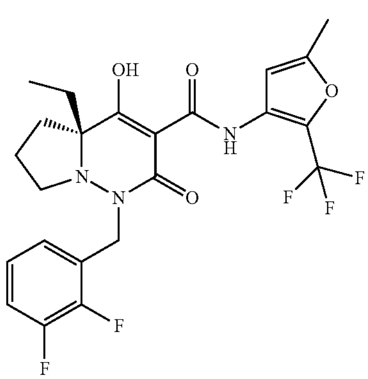 [SMILES: CC[C@]12CCCN1N(Cc1cccc(F)c1F)C(=O)C(C(=O)Nc1cc(C)oc1C(F)(F)F)=C2O] | (4aR)-1-[(2,3-Difluorophenyl)methyl]-4a-ethyl-4-hydroxy-N-[5-methyl-2-(trifluoromethyl)furan-3-yl]-2-oxo-6,7-dihydro-5H-pyrrolo[1,2-b]pyridazine-3-carboxamide | SQD-AA05 | 1.20 | 500 |

Example 11

(4aR)-1-[(3-Fluorophenyl)methyl]-4-hydroxy-N-[5-methyl-2-(trifluoromethyl)furan-3-yl]-2-oxo-4a-propyl-6,7-dihydro-5H-pyrrolo[1,2-b]pyridazine-3-carboxamide By carrying out operations similar to those of First to Third Steps of Example 1, the compounds described in the following Table were synthesized from (R)-2-methyl-pyrrolidine-2-carboxylic acid ethyl ester hydrochloride and 3-fluorobenzaldehyde.

Example 12

(4aR)-1-[(2,3-Difluorophenyl)methyl]-4-hydroxy-N-[5-methyl-2-(trifluoromethyl)furan-3-yl]-2-oxo-4a-propyl-6,7-dihydro-5H-pyrrolo[1,2-b]pyridazine-3-carboxamide By carrying out operations similar to those of First to Third Steps of Example 1, the compounds described in the following Table were synthesized from (R)-2-propyl-pyrrolidine-2-carboxylic acid ethyl ester hydrochloride and 2,3-difluorobenzaldehyde.

TABLE 11

| Structure | Compound name | Analysis condition | HPLC Retention time (min) | m/z |
|---|---|---|---|---|
| 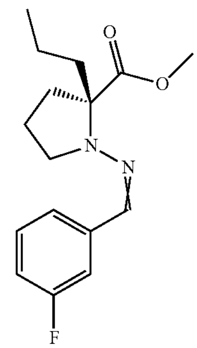 [SMILES: CCC[C@]1(C(=O)OC)CCCN1N=Cc1cccc(F)c1] | (R)-1-[(3-Fluoro-benzylidene)-amino]-2-propyl-pyrrolidine-2-carboxylic acid ethyl ester | SQD-AA05 | 1.16 | 307 |
| 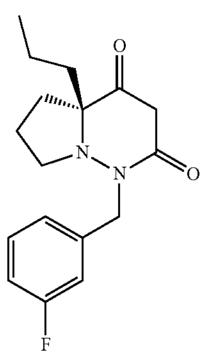 [SMILES: CCC[C@]12CCCN1N(Cc1cccc(F)c1)C(=O)CC2=O] | (4aR)-1-[(3-Fluorophenyl)methyl]-4a-propyl-6,7-dihydro-5H-pyrrolo[1,2-b]pyridazine-2,4-dione | SQD-AA05 | 0.99 | 305 |
| 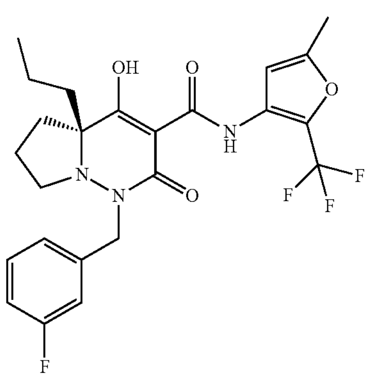 [SMILES: CCC[C@]12CCCN1N(Cc1cccc(F)c1)C(=O)C(C(=O)Nc1cc(C)oc1C(F)(F)F)=C2O] | (4aR)-1-[(3-Fluorophenyl)methyl]-4-hydroxy-N-[5-methyl-2-(trifluoromethyl)furan-3-yl]-2-oxo-4a-propyl-6,7-dihydro-5H-pyrrolo[1,2-b]pyridazine-3-carboxamide | SQD-AA05 | 1.22 | 496 |

TABLE 12

| Structure | Compound name | Analysis condition | HPLC Retention time (min) | m/z |
|---|---|---|---|---|
| 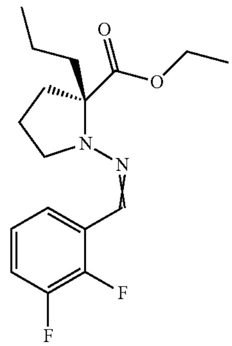 [SMILES: CCC[C@]1(C(=O)OCC)CCCN1N=Cc1cccc(F)c1F] | (R)-1-[(2,3-Difluoro-benzylidene)-amino]-2-propyl-pyrrolidine-2-carboxylic acid ethyl ester | SQD-AA05 | 1.25 | 325 |
| 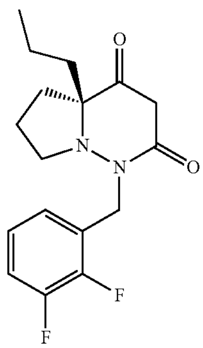 [SMILES: CCC[C@]12CCCN1N(Cc1cccc(F)c1F)C(=O)CC2=O] | (4aR)-1-[(2,3-Difluorophenyl)methyl]-4a-propyl-6,7-dihydro-5H-pyrrolo[1,2-b]pyridazine-2,4-dione | SQD-AA05 | 1.03 | 323 |
| 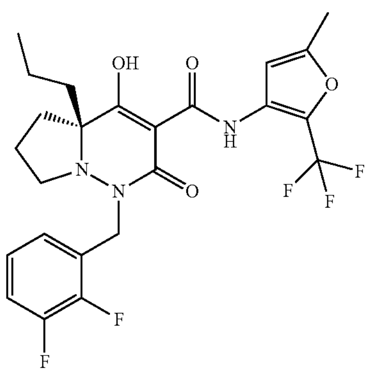 [SMILES: CCC[C@]12CCCN1N(Cc1cccc(F)c1F)C(=O)C(C(=O)Nc1cc(C)oc1C(F)(F)F)=C2O] | (4aR)-1-[(2,3-Difluorophenyl)methyl-]-4-hydroxy-N-[5-methyl-2-(trifluoromethyl)furan-3-yl]-2-oxo-4a-propyl-6,7-dihydro-5H-pyrrolo[1,2-b]pyridazine-3-carboxamide | SQD-AA05 | 1.23 | 514 |

Example 13

6-[[2,3-Difluoro-4-[2-[2-methoxyethyl(methyl)amino]ethoxy]phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide First Step 2,3-Difluoro-1-[2-[2-methoxyethyl(methyl)amino]ethoxy]benzene

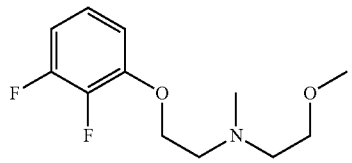 [SMILES: COCCN(C)CCOc1cccc(F)c1F]

2,3-Difluoro-1-[2-chloroethoxy]benzene (4.20 g, 22.0 mmol) was dissolved in N,N-dimethylformamide (32.9 mL), N-(2-methoxyethyl)-N-methylamine (4.35 g, 48.8 mmol), potassium iodide (6.08 g, 36.6 mmol), and tripotassium phosphate (7.77 g, 36.6 mmol) were added at 25° C., and the mixture was stirred under nitrogen atmosphere at 100° C. for 2 hours. After the reaction mixture was cooled to 25° C., water (47.0 mL) was added, and the resultant was extracted with isopropyl acetate (47.0 mL). 1 N hydrochloric acid (47.0 mL) was added to the organic layer for extraction, a 5 N aqueous sodium hydroxide solution (14.1 mL) was added to the obtained aqueous solution for basification, and the mixture was extracted with isopropyl acetate (47.0 mL). The organic layer was concentrated at reduced pressure to obtain the title compound (5.15 g, 95%).

$^1$H-NMR (DMSO-$D_6$) δ: 7.16-7.10 (1H, m), 7.06-7.03 (1H, m), 6.99-6.96 (1H, m), 4.15 (2H, t, J=5.7 Hz), 3.41 (2H, t, J=6.0 Hz), 3.22 (3H, s), 2.78 (2H, t, J=6.0 Hz), 2.59 (2H, t, J=6.0 Hz), 2.28 (3H, s).

Second Step 2,3-Difluoro-4-[2-[2-methoxyethyl(methyl)amino]ethoxy]benzaldehyde

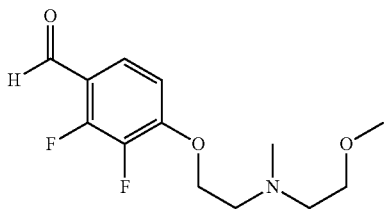 [SMILES: COCCN(C)CCOc1ccc(C=O)c(F)c1F]

N,N-Diisopropylamine (5.92 mL) was dissolved in tetrahydrofuran (62.6 mL), and a solution of n-butyllithium in hexane (1.6 M, 26.2 mL, 41.9 mmol) was added dropwise at −20° C. After the mixture was stirred at −20° C. for 30 minutes, it was cooled to −50° C., and a solution of 2,3-difluoro-1-[2-[2-methoxyethyl(methyl)amino]ethoxy]benzene (5.15 g, 21.0 mmol) in tetrahydrofuran (21.0 mL) was added dropwise. After the mixture was stirred at −40° C. for 2 hours, N,N-dimethylformamide (4.94 mL) was added, and the mixture was stirred for 30 minutes. After the reaction mixture was heated to −15° C., a solution of acetic acid (7.31 mL) in water (26.1 mL) and toluene (15.7 mL) were added for liquid-liquid extraction. The organic layer was concentrated at reduced pressure, and the resultant residue was purified by column chromatography on silica gel (ethyl acetate/hexane/triethylamine) to obtain the title compound (2.90 g, 50%).

$^1$H-NMR (DMSO-D$_6$) δ: 10.04 (1H, s), 7.69-7.64 (1H, m), 7.27-7.24 (1H, m), 4.28 (2H, t, J=5.7 Hz), 3.41 (2H, t, J=6.0 Hz), 3.22 (3H, s), 2.81 (2H, t, J=5.7 Hz), 2.60 (2H, t, J=6.0 Hz), 2.28 (3H, s).

Third Step

Methyl 1-[[(E)-2,3-difluoro-4-[2-[2-[methoxyethyl(methyl)amino]ethoxy]phenyl methylideneamino]-methylamino]cyclobutane-1-carboxylate

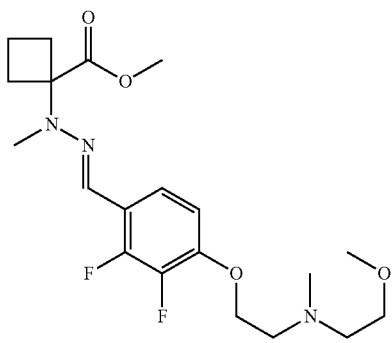 [SMILES: COCCN(C)CCOc1ccc(/C=N/N(C)C2(C(=O)OC)CCC2)c(F)c1F]

Methyl 1-(methylamino)cyclobutanecarboxylate para-toluenesulfonate (1.75 g, 5.54 mmol) (see Reference Example 86) was dissolved in acetic acid (1.60 mL, 27.7 mmol) and water (9.0 mL), a solution of sodium nitrite (0.45 g, 6.59 mmol) dissolved in water (1.00 mL) was added at 25° C., and the mixture was stirred under nitrogen atmosphere for 30 minutes. Ethyl acetate (3.50 mL) and sodium chloride (1.00 g) were added to the reaction mixture, and the organic layer after liquid-liquid extraction was washed with a 15% aqueous dipotassium hydrogenphosphate solution. Methanol (10.0 mL) was added to the organic layer after the washing, and 12 N hydrochloric acid (3.60 mL) was added at −10° C. Zinc dust (0.73 g, 11.1 mmol) was added to the reaction mixture at −30° C., and the mixture was stirred for 1 hour. A 28% aqueous ammonia (3.66 mL) was added to the reaction mixture, a solution of 2,3-difluoro-4-[2-[2-methoxyethyl(methyl)amino]ethoxy]benzaldehyde (1.00 g, 3.66 mmol) in ethyl acetate (2.75 mL) was added at 0° C., and the mixture was stirred for 30 minutes. After the reaction mixture was concentrated, ethyl acetate and a 15% aqueous potassium dihydrogenphosphate solution were added for liquid-liquid extraction, and subsequently, the organic layer was washed with a 15% aqueous sodium hydrogen sulfite solution and a 15% aqueous dipotassium hydrogenphosphate solution. The organic layer was concentrated at reduced pressure, and the resultant residue was purified by column chromatography on silica gel (ethyl acetate/methanol) to obtain the title compound (1.07 g, 70%).

LCMS: m/z 414[M+H]$^+$

HPLC retention time: 0.65 minutes (SQD-TFA05)

Fourth Step

Methyl 1-[[[2,3-difluoro-4-[2-[2-methoxyethyl(methyl)amino]ethoxy]phenyl]methyl-[3-oxo-3-r[4-(trifluoromethyl)-2-[6-(trifluoromethyl)pyrimidin-4-yl]anilino]propanoyl]amino]-methylamino]cyclobutane-1-carboxylate

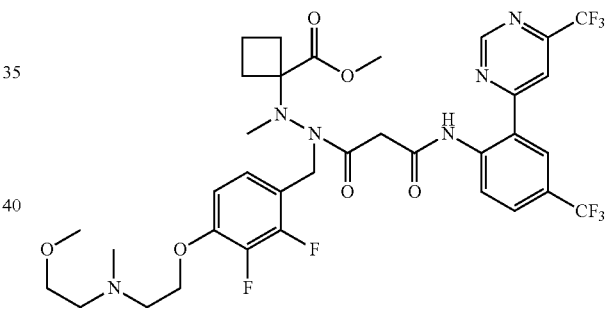

Methyl 1-[[(E)-[2,3-difluoro-4-[2-[2-methoxyethyl(methyl)amino]ethoxy]phenyl]methylideneamino]-methylamino]cyclobutane-1-carboxylate (1.00 g, 2.42 mmol) was dissolved in ethyl acetate (8.1 mL), methanesulfonic acid (1.18 mL, 18.1 mmol) was added at 0° C., and the mixture was stirred under nitrogen atmosphere for 10 minutes. 5-Ethyl-2-methylpyridine borane (0.72 mL, 4.84 mmol) was added to the reaction mixture at 0° C., and the mixture was stirred under nitrogen atmosphere for 30 minutes. After methanol (0.81 mL) was added to the reaction mixture at 0° C., a 5 M aqueous sodium hydroxide solution (2.44 mL) was added, and the mixture was stirred at 0° C. for 1 hour. A 25% aqueous tripotassium phosphate solution was added to the reaction mixture for liquid-liquid extraction. The organic layer was washed with a 15% aqueous sodium chloride solution, and the resultant was concentrated at reduced pressure to obtain methyl 1-[[[2,3-difluoro-4-[2-[2-methoxyethyl(methyl)amino]ethoxy]phenyl]methylamino]-methylamino]cyclobutane-1-carboxylate as a crude product.

The obtained crude product and 3-oxo-3-[4-(trifluoromethyl)-2-[6-(trifluoromethyl)pyrimidin-4-yl]anilino]propanoate (Reference Example 82) (1.05 g, 2.66 mmol) were dissolved in ethyl acetate (8.00 mL) and N,N-dimethylformamide (4.00 mL), pyridine (1.00 mL) and 2,4,6-tripropyl-1,3,5,2,4,6-trioxatriphosphinane 2,4,6-trioxide (a 1.7 M ethyl acetate solution, 2.85 mL, 4.84 mmol) were added at −10° C., and the mixture was stirred under nitrogen atmosphere for 30 minutes. A 10% aqueous sodium chloride solution was added to the reaction mixture for liquid-liquid extraction. The organic layer was washed with a 15% aqueous dipotassium hydrogenphosphate solution, and the resultant was concentrated at reduced pressure. The resultant residue was purified by column chromatography on silica gel (ethyl acetate/methanol) to obtain the title compound (1.90 g, 97%).

LCMS: m/z 791[M+H]$^+$

HPLC retention time: 0.81 minutes (SQD-TFA05)

Fifth Step

6-[[2,3-Difluoro-4-[2-[2-methoxyethyl(methyl)amino]ethoxy]benzyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide

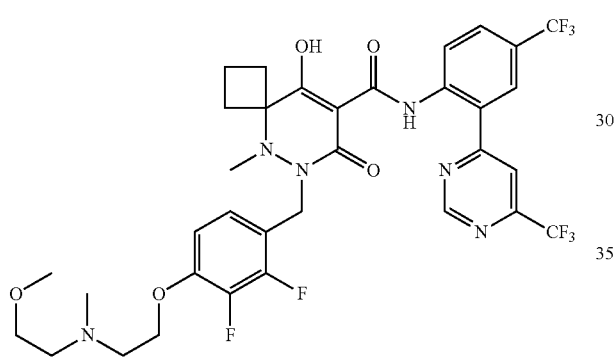

Methyl 1-[[[2,3-Difluoro-4-[2-[2-methoxyethyl(methyl)amino]ethoxy]phenyl]methyl-[3-oxo-3 [4-(trifluoromethyl)-2-[6-(trifluoromethyl)pyrimidin-4-yl]anilino]propanoyl]amino]-methylamino]cyclobutane-1-carboxylate (2.06 g, 2.60 mmol) was suspended in isopropanol (28.8 mL), potassium carbonate (718 mg, 5.20 mmol) was added, and the mixture was stirred under nitrogen atmosphere at 50° C. for 8 hours. After the reaction mixture was concentrated, 1 M hydrochloric acid (2.60 mL, 2.60 mmol) was added, and the resultant was extracted with ethyl acetate. After the organic layer was washed with a 10% aqueous potassium dihydrogenphosphate solution and a 10% aqueous sodium chloride solution, the organic layer was concentrated. The resultant residue was purified by column chromatography on silica gel (ethyl acetate/methanol) to obtain the title compound (1.72 g, 87%).

Although tautomers of the title compound exist, isomers may be observed in some cases and not in other cases according to the type of the solvent for measurement. For example, $^1$H-NMR and $^{13}$C-NMR of major tautomers (chloroform-D) are as follows.

LCMS: m/z 759[M+H]$^+$

HPLC retention time: 0.91 minutes (SQD-TFA05)

$^1$H-NMR (CDCl$_3$) δ: 16.57 (1H, s), 12.81 (1H, s), 9.61 (1H, s), 8.50 (1H, d, J=8.7 Hz), 7.95 (1H, s), 7.90 (1H, d, J=1.6 Hz), 7.80 (1H, dd, J=8.7, 1.6 Hz), 7.01 (1H, ddd, J=9.1, 7.2, 1.8 Hz), 6.72 (1H, ddd, J=8.7, 7.2, 1.3 Hz), 5.08-5.03 (1H, m), 4.19-4.16 (1H, m), 4.19-4.16 (1H, m), 3.54-3.51 (2H, m), 3.37 (3H, s), 2.93 (2H, brs), 2.73 (2H, brs), 2.56 (1H, m), 2.43 (3H, brs), 2.41 (3H, s), 1.86 (1H, m), 1.84 (1H, m), 1.82 (1H, m), 1.71 (1H, m), 1.58 (1H, m).

$^{13}$C-NMR (CDCl$_3$) δ: 186.1 (qC), 169.8 (qC), 165.7 (qC), 162.8 (qC), 159.3 (CH), 156.6 (qC, q, J$_{CF}$=36.3 Hz), 150.4 (qC, dd, J$_{CF}$=248.4, 10.5 Hz), 147.9 (qC), 141.1 (qC, dd, J$_{CF}$=248.0, 15.0 Hz), 138.8 (qC), 128.3 (CH, q, J$_{CF}$=3.3 Hz), 127.8 (qC), 127.1 (CH), 126.9 (qC, q, J$_{CF}$=33.6 Hz), 125.1 (CH), 124.7 (CH), 123.6 (qC, q, J$_{CF}$=271.8 Hz), 120.5 (qC, q, J$_{CF}$=275.4 Hz), 117.9 (qC, d, J$_{CF}$=11.8 Hz), 115.9 (CH), 109.2 (CH, s), 92.3 (qC), 70.5 (CH$_2$), 68.1 (CH$_2$), 64.1 (qC), 58.9 (CH$_3$), 57.4 (CH$_2$), 56.3 (CH$_2$), 43.4 (CH$_3$), 41.5 (CH$_2$), 35.0 (CH$_3$), 32.4 (CH$_2$), 24.4 (CH$_2$), 13.4 (CH$_2$).

Example 14

7-[[2,3-Difluoro-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide First Step Methyl 1-[[(E)-2,3-[difluoro-4-[2-[2-methoxyethyl(methyl)amino]ethoxy]phenyl]methylideneamino]-methylamino]cyclopentane-1-carboxylate

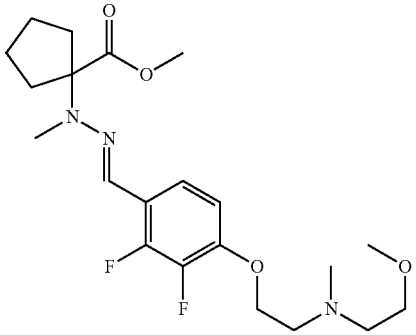 [SMILES: COCCN(C)CCOc1ccc(/C=N/N(C)C2(C(=O)OC)CCCC2)c(F)c1F]

Methyl 1-(methylamino)cyclopentanecarboxylate para-toluenesulfonate (3.60 g, 10.9 mmol) (see Reference Example 88) was dissolved in acetic acid (3.10 mL, 54.2 mmol) and water (18.0 mL), a solution of sodium nitrite (0.91 g, 13.2 mmol) dissolved in water (2.00 mL) was added at 25° C., and the mixture was stirred under nitrogen atmosphere for 30 minutes. Ethyl acetate (7.00 mL) and sodium chloride (2.00 g) were added to the reaction mixture, and the organic layer after liquid-liquid extraction was washed with a 15% aqueous dipotassium hydrogenphosphate solution. Methanol (20.0 mL) was added to the organic layer after the washing, and 12 N hydrochloric acid (7.30 mL) was added at −10° C. Zinc dust (1.44 g, 22.0 mmol) was added to the reaction mixture at −30° C., and the mixture was stirred for 1 hour. 28% aqueous ammonia (7.30 mL) was added to the reaction mixture, a solution of 2,3-difluoro-4-[2-[2-methoxyethyl(methyl)amino]ethoxy]benzaldehyde (2.00 g, 7.30 mmol) (Second Step of Example 13) in ethyl acetate (5.40 mL) was added at 0° C., and the mixture was stirred for 30 minutes. After the reaction mixture was concentrated, ethyl acetate and a 15% aqueous potassium dihydrogenphosphate solution were added for liquid-liquid extraction, and subsequently, the organic layer was washed with a 15% aqueous sodium hydrogen sulfite solution and a 15% aqueous dipotassium hydrogenphosphate solution. The organic layer was concentrated at reduced pressure, and the resultant residue was purified by column chromatography on silica gel (ethyl acetate/methanol) to obtain the title compound (2.82 g, 90%).

LCMS: m/z 428[M+H]$^+$
HPLC retention time: 0.61 minutes (SQD-FA05)
Second Step

Methyl 1-[[r[2,3-difluoro-4-[2-[2-methoxyethyl(methyl)amino]ethoxy]phenyl]methyl-[3-oxo-3-[4-(trifluoromethyl)-2-[6-(trifluoromethyl)pyrimidin-4-yl]anilino]propanoyl]amino]-methylamino]cyclopentane-1-carboxylate

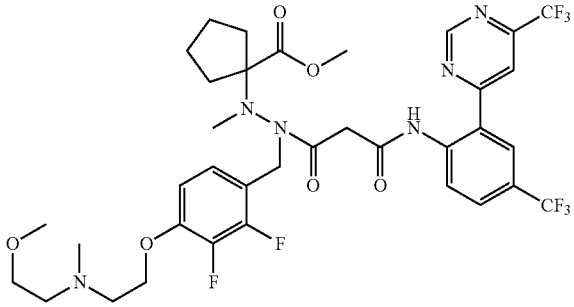 [SMILES: COCCN(C)CCOc1ccc(CN(C(=O)CC(=O)Nc2ccc(C(F)(F)F)cc2-c2cc(C(F)(F)F)ncn2)N(C)C2(C(=O)OC)CCCC2)c(F)c1F]

Methyl 1-[[(E)-[2,3-difluoro-4-[2-[2-methoxyethyl(methyl)amino]ethoxy]phenyl]methylideneamino]-methylamino]cyclopentane-1-carboxylate (1.00 g, 2.34 mmol) was dissolved in ethyl acetate (10.0 mL), methanesulfonic acid (1.14 mL, 17.6 mmol) was added at 0° C., and the mixture was stirred under nitrogen atmosphere for 10 minutes. 5-Ethyl-2-methylpyridine borane (0.70 mL, 4.70 mmol) was added to the reaction mixture at 0° C., and the mixture was stirred under nitrogen atmosphere for 30 minutes. After methanol (1.00 mL) was added to the reaction mixture at 0° C., a 5 M aqueous sodium hydroxide solution (3.00 mL) was added, and the mixture was stirred at 0° C. for 1 hour. A 25% aqueous tripotassium phosphate solution was added to the reaction mixture for liquid-liquid extraction. The organic layer was washed with a 15% aqueous sodium chloride solution, and the resultant was concentrated at reduced pressure to obtain methyl 1-[[[2,3-difluoro-4-[2-[2-methoxyethyl(methyl)amino]ethoxy]phenyl]methylamino]-methylamino]cyclopentane-1-carboxylate as a crude product.

The obtained crude product and 3-oxo-3-[4-(trifluoromethyl)-2-[6-(trifluoromethyl)pyrimidin-4-yl]anilino]propanoate (1.00 g, 2.54 mmol) were dissolved in ethyl acetate (8.00 mL) and N,N-dimethylformamide (4.00 mL), and then pyridine (1.00 mL) and 2,4,6-tripropyl-1,3,5,2,4,6-trioxatriphosphinane 2,4,6-trioxide (a 1.7 M ethyl acetate solution, 2.75 mL, 4.68 mmol) were added at −10° C., and the mixture was stirred under nitrogen atmosphere for 30 minutes. A 10% aqueous sodium chloride solution was added to the reaction mixture for liquid-liquid extraction. The organic layer was washed with a 15% aqueous dipotassium hydrogenphosphate solution, and the resultant was concentrated at reduced pressure. The resultant residue was purified by column chromatography on silica gel (ethyl acetate/methanol) to obtain the title compound (1.82 g, 97%).

LCMS: m/z 805[M+H]$^+$
HPLC retention time: 0.74 minutes (SQD-FA05)
Third Step

7-[[2,3-Difluoro-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

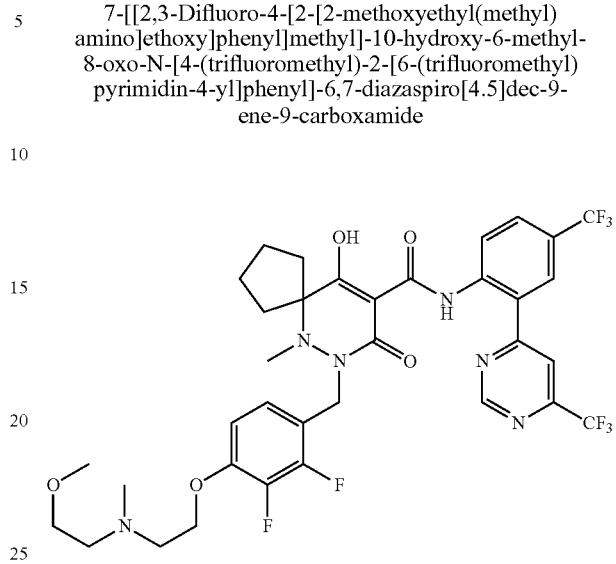

Methyl 1-[[[2,3-difluoro-4-[2-[2-methoxyethyl(methyl)amino]ethoxy]phenyl]methyl-[3-oxo-3-[4-(trifluoromethyl)-2-[6-(trifluoromethyl)pyrimidin-4-yl]anilino]propanoyl]amino]-methylamino]cyclopentane-1-carboxylate (500 mg, 0.62 mmol) was suspended in isopropanol (7.00 mL), potassium carbonate (175 mg, 1.27 mmol) was added, and the mixture was stirred under nitrogen atmosphere at 60° C. for 8 hours. After the reaction mixture was concentrated, 1 M hydrochloric acid (1.24 mL, 1.24 mmol) was added, and the mixture was extracted with ethyl acetate. After the organic layer was washed with a 10% aqueous potassium dihydrogenphosphate solution and a 10% aqueous sodium chloride solution, the organic layer was concentrated. The resultant residue was purified by column chromatography on silica gel (ethyl acetate/methanol) to obtain the title compound (432 mg, 90%).

Although tautomers of the title compound exist, isomers may be observed in some cases and not in other cases according to the type of the solvent for measurement. For example, $^1$H-NMR and $^{13}$C-NMR of major tautomers (chloroform-D) are as follows.

LCMS: m/z 773[M+H]$^+$
HPLC retention time: 0.95 minutes (SQD-FA05)
$^1$H-NMR (CDCl$_3$) δ: 16.55 (1H, s), 12.83 (1H, s), 9.62 (1H, s), 8.49 (1H, d, J=8.7 Hz), 7.96 (1H, d, J=1.2 Hz), 7.90 (1H, d, J=1.6 Hz), 7.79 (1H, dd, J=8.7, 2.0 Hz), 7.04 (1H, dd, J=7.4, 7.4 Hz), 6.73 (1H, dd, J=7.4, 7.4 Hz), 5.05 (1H, d, J=14.2 Hz), 4.19-4.18 (1H, m), 4.19 (2H, brs), 3.55 (2H, brs), 3.37 (3H, s), 2.96 (2H, s), 2.76 (2H, s), 2.48 (3H, s), 2.45 (3H, s), 2.15 (1H, m), 1.74 (2H, m), 1.57 (1H, m), 1.50 (1H, m), 1.45 (2H, m), 1.30 (1H, m).
$^{13}$C-NMR (CDCl$_3$) δ: 187.8 (qC), 169.9 (qC), 165.7 (qC), 163.1 (qC), 159.3 (CH), 156.6 (qC, q, J=36.3 Hz), 150.4 (qC, dd, J$_{CF}$=248.6, 10.6 Hz), 147.9 (qC), 141.1 (qC, dd, J$_{CF}$=248.3, 14.7 Hz), 138.8 (qC), 128.3 (CH), 127.8 (qC), 127.1 (CH), 126.9 (qC, q, J$_{CF}$=33.4 Hz), 125.5 (CH), 124.7 (CH), 123.6 (qC, q, J$_{CF}$=272.1 Hz), 120.5 (qC, q, J$_{CF}$=275.4 Hz), 117.6 (qC, q, J$_{CF}$=12.7 Hz), 116.0 (CH), 109.3 (CH), 93.1 (qC), 71.4 (qC), 70.4 (CH$_2$), 68.0 (CH$_2$), 58.9 (CH$_3$), 57.3 (CH$_2$), 56.3 (CH$_2$), 43.3 (CH$_3$), 41.6 (CH$_2$), 37.6 (CH$_2$), 36.8 (CH$_3$), 31.4 (CH$_2$), 24.8 (CH$_2$), 23.3 (CH$_2$).

Example 15

(4aR)-1-[(3-Fluorophenyl)methyl]-4-hydroxy-N-[5-methyl-2-(trifluoromethyl)furan-3-yl]-2-oxo-5,6,7,8-tetrahydro-4aH-pyrido[1,2-b]pyridazine-3-carboxamide First Step (R)-Piperidine-2-carboxylic acid methyl ester hydrochloride

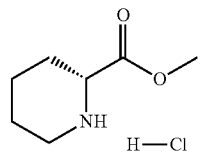

(R)-Piperidine-2-carboxylic acid (300 mg, 2.32 mmol) was dissolved in methanol (4.64 mL), thionyl chloride (0.508 mL, 6.97 mmol) was added dropwise at 0° C., and the mixture was stirred at 50° C. for 18 hours. The reaction mixture was concentrated at reduced pressure, and toluene was added for azeotropic removal to obtain the title compound as a crude product.

Second Step

In a similar manner to First to Third Steps of Example 1, the compounds described in the following Table were synthesized from the obtained (R)-piperidine-2-carboxylic acid methyl ester hydrochloride and 3-fluoro-benzaldehyde.

TABLE 13

| Structure | Compound name | Analysis condition | HPLC Retention time (min) | m/z |
|---|---|---|---|---|
| 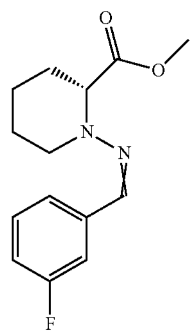 [SMILES: COC(=O)[C@H]1CCCCN1N=Cc1cccc(F)c1] | (R)-1-[(3-Fluoro-benzylidene)-amino]-piperidine-2-carboxylic acid methyl ester | SQD-AA05 | 1.02 | 265 |
| 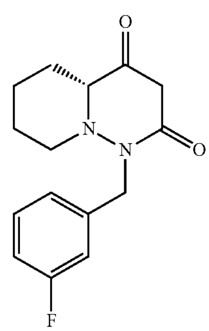 [SMILES: O=C1CC(=O)N(Cc2cccc(F)c2)N2CCCC[C@H]12] | (4aR)-1-[(3-Fluorophenyl)methyl]-5,6,7,8-tetrahydro-4aH-pyrido[1,2-b]pyridazine-2,4-dione | SQD-AA05 | 0.90 | 277 |
| 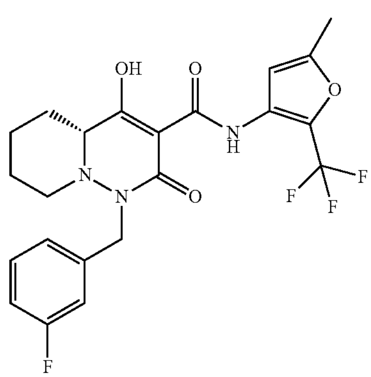 [SMILES: Cc1cc(NC(=O)C2=C(O)[C@H]3CCCCN3N(Cc3cccc(F)c3)C2=O)c(C(F)(F)F)o1] | (4aR)-1-[(3-Fluorophenyl)methyl]-4-hydroxy-N-[5-methyl-2-(trifluoromethyl)furan-3-yl]-2-oxo-5,6,7,8-tetrahydro-4aH-pyrido[1,2-b]pyridazine-3-carboxamide | SQD-AA05 | 1.17 | 468 |

Example 16

(4aS)-1-[(3-Fluorophenyl)methyl]-4-hydroxy-N-[5-methyl-2-(trifluoromethyl)furan-3-yl]-2-oxo-5,6,7,8-tetrahydro-4aH-pyrido[1,2-b]pyridazine-3-carboxamide In a similar manner to First to Third Steps of Example 1, the compounds described in the following Table were synthesized from (S)-piperidine-2-carboxylic acid methyl ester hydrochloride and 3-fluoro-benzaldehyde.

TABLE 14

| Structure | Compound name | Analysis condition | HPLC Retention time (min) | m/z |
|---|---|---|---|---|
| 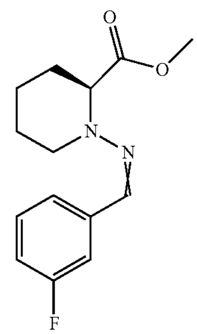 [SMILES: COC(=O)[C@@H]1CCCCN1N=Cc1cccc(F)c1] | (S)-1-[(3-Fluoro-benzylidene)-amino]-piperidine-2-carboxylic acid methyl ester | SQD-AA05 | 1.03 | 265 |
| 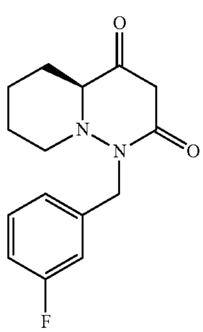 [SMILES: O=C1CC(=O)N(Cc2cccc(F)c2)N2CCCC[C@@H]12] | (4aS)-1-[(3-Fluorophenyl)methyl]-5,6,7,8-tetrahydro-4aH-pyrido[1,2-b]pyridazine]-2,4-dione | SQD-AA05 | 0.91 | 277 |
| 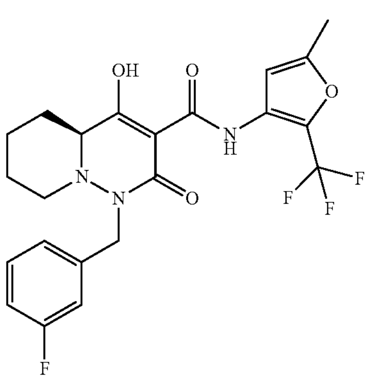 [SMILES: Cc1cc(NC(=O)C2=C(O)[C@@H]3CCCCN3N(Cc3cccc(F)c3)C2=O)c(C(F)(F)F)o1] | (4aS)-1-[(3-Fluorophenyl)methyl]-4-hydroxy-N-[5-methyl-2-(trifluoromethyl)furan-3-yl]-2-oxo-5,6,7,8-tetrahydro-4aH-pyrido[1,2-b]pyridazine-3-carboxamide | SQD-AA05 | 1.16 | 468 |

Example 17

(4aS)-1-[(5,6-Difluoro-1H-indol-7-yl)methyl]-4-hydroxy-N-[5-methyl-2-(trifluoromethyl)furan-3-yl]-2-oxo-5,6,7,8-tetrahydro-4aH-pyrido[1,2-b]pyridazine-3-carboxamide

In a similar manner to First to Third Steps of Example 1, the compounds described in the following Table were synthesized from (S)-piperidine-2-carboxylic acid methyl ester hydrochloride and 5,6-difluoro-1H-indole-7-carbaldehyde.

TABLE 15

| Structure | Compound name | Analysis condition | HPLC Retention time (min) | m/z |
|---|---|---|---|---|
| 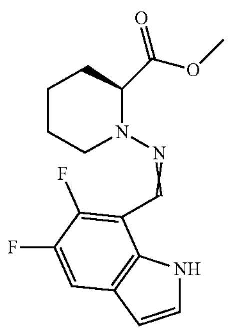 [SMILES: COC(=O)[C@@H]1CCCCN1N=Cc1c(F)c(F)cc2cc[nH]c12] | (S)-1-[(5,6-Difluoro-1H-indol-7-ylmethylene)-amino]-piperidine-2-carboxylic acid methyl ester | SQD-AA05 | 1.03 | 323 |
| 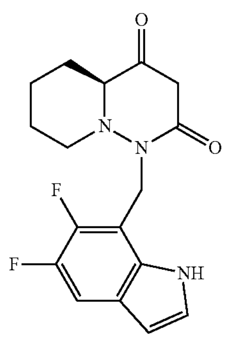 [SMILES: O=C1CC(=O)N(Cc2c(F)c(F)cc3cc[nH]c23)N2CCCC[C@@H]12] | (4aS)-1-[(5,6-Difluoro-1H-indol-7-yl)methyl]-5,6,7,8-tetrahydro-4aH-pyrido[1,2-b]pyridazine-2,4-dione | SQD-AA05 | 1.00 | 334 |
| 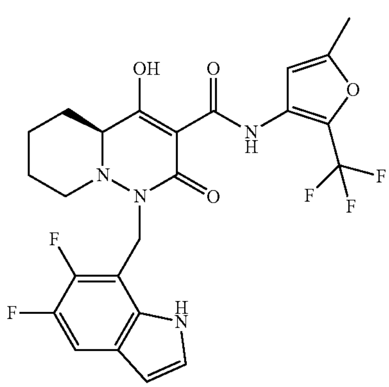 [SMILES: Cc1cc(NC(=O)C2=C(O)[C@@H]3CCCCN3N(Cc3c(F)c(F)cc4cc[nH]c34)C2=O)c(C(F)(F)F)o1] | (4aS)-1-[(5,6-Difluoro-1H-indol-7-yl)methyl]-4-hydroxy-N-[5-methyl-2-(trifluoromethyl)furan-3-yl]-2-oxo-5,6,7,8-tetrahydro-4aH-pyrido[1,2-b]pyridazine-3-carboxamide | SQD-AA05 | 1.16 | 525 |

Example 18

1-[(3-Fluorophenyl)methyl]-4-hydroxy-4a-methyl-N-[5-methyl-2-(trifluoromethyl)furan-3-yl]-2-oxo-5,6,7,8-tetrahydropyrido[1,2-b]pyridazine-3-carboxamide First Step 2-Methyl-piperidine-2-carboxylic acid methyl ester hydrochloride

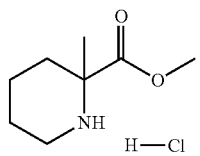

In a similar manner to First Step of Example 4, the title compound was obtained from 2-methyl-piperidine-1,2-dicarboxylic acid 1-tert-butyl ester as a crude product.

Second Step

In a similar manner to First to Third Steps of Example 1, the compounds described in the following Table were synthesized from the obtained 2-methyl-piperidine-2-carboxylic acid methyl ester hydrochloride and 3-fluoro-benzaldehyde.

TABLE 16

| Structure | Compound name | Analysis condition | HPLC Retention time (min) | m/z |
|---|---|---|---|---|
| 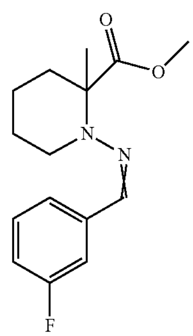 [SMILES: COC(=O)C1(C)CCCCN1N=Cc1cccc(F)c1] | 1-[(3-Fluoro-benzylidene)-amino]-2-methyl-piperidine-2-carboxylic acid methyl ester | SQD-AA05 | 1.07 | 279 |
| 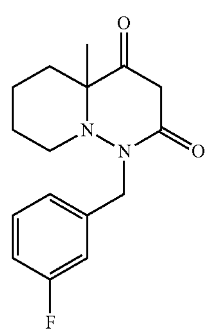 [SMILES: CC12CCCCN1N(Cc1cccc(F)c1)C(=O)CC2=O] | 1-[(3-Fluorophenyl)methyl]-4a-methyl-5,6,7,8-tetrahydropyrido[1,2-b]pyridazine-2,4-dione | ZQ-01 | 2.53 | 291 |
| 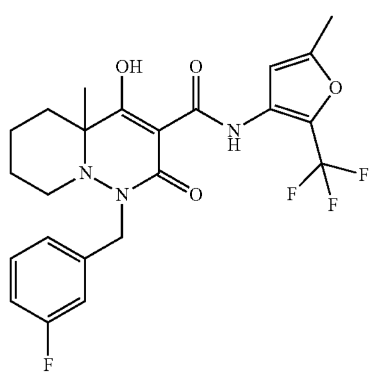 [SMILES: Cc1cc(NC(=O)C2=C(O)C3(C)CCCCN3N(Cc3cccc(F)c3)C2=O)c(C(F)(F)F)o1] | 1-[(3-Fluorophenyl)methyl]-4-hydroxy-4a-methyl-N-[5-methyl-2-(trifluoromethyl)furan-3-yl]-2-oxo-5,6,7,8-tetrahydropyrido[1,2-b]pyridazine-3-carboxamide | SQD-AA05 | 1.18 | 482 |

Example 19

1-[2,3-(Difluorophenyl)methyl]-4a-ethyl-4-hydroxy-N-[5-methyl-2-(trifluoromethyl)furan-3-yl]-2-oxo-5,6,7,8-tetrahydropyrido[12-b]pyridazine-3-carboxamide

First Step

2-Ethyl-piperidine-2-carboxylic acid methyl ester hydrochloride

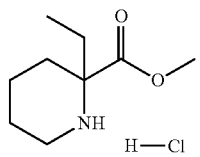

In a similar manner to First Step of Example 6, the title compound was obtained from 2-ethyl-piperidine-2-carboxylic acid hydrochloride as a crude product.

Second Step

In a similar manner to First to Third Steps of Example 1, the compounds described in the following Table were synthesized from the obtained 2-ethyl-piperidine-2-carboxylic acid methyl ester hydrochloride and 2,3-difluoro-benzaldehyde.

TABLE 17

| Structure | Compound name | Analysis condition | HPLC Retention time (min) | m/z |
|---|---|---|---|---|
| | 1-{[1-(2,3-Difluorophenyl)-met-(Z)-ylidene]-amino}-2-ethyl-piperidine-2-carboxylic acid methyl ester | SQD-AA05 | 1.16 | 311 |
| 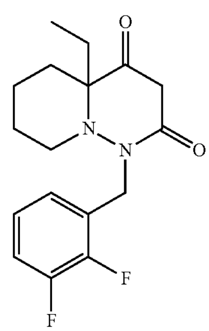 [SMILES: CCC12CCCCN1N(Cc1cccc(F)c1F)C(=O)CC2=O] | 1-[(2,3-Difluorophenyl)methyl]-4a-ethyl-5,6,7,8-tetrahydropyrido[1,2-b]pyridazine-2,4-dione | SQD-AA05 | 1.00 | 323 |
| 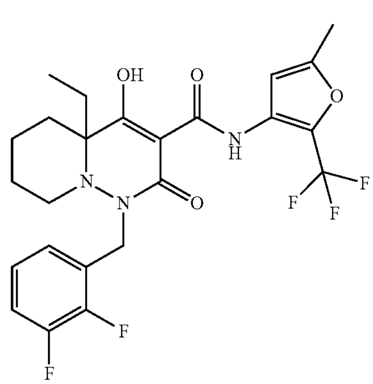 [SMILES: CCC12CCCCN1N(Cc1cccc(F)c1F)C(=O)C(C(=O)Nc1cc(C)oc1C(F)(F)F)=C2O] | 1-[(2,3-Difluorophenyl)methyl]-4a-ethyl-4-hydroxy-N-[5-methyl-2-(trifluoromethyl)furan-3-yl]-2-oxo-5,6,7,8-tetrahydropyrido[1,2-b]pyridazine-3-carboxamide | SQD-AA05 | 1.23 | 514 |

Example 20

(4aS,5S,8R)-1-(3-Fluorobenzyl)-4-hydroxy-N-(5-methyl-2-(trifluoromethyl)furan-3-yl)-2-oxo-2,4a,5,6,7,8-hexahydro-1H-5,8-methanopyrido[1,2-b]pyridazine-3-carboxamide First Step (1 S,3 S,6R)-2-Aza-bicyclo[2.2.1]heptane-3-carboxylic acid methyl ester hydrochloride

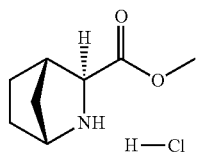

(1R,3 S,4S)-2-Aza-bicyclo[2.2.1]heptane-2,3-dicarboxylic acid 2-tert-butyl ester (500 mg, 2.07 mmol) was dissolved in N,N-dimethylformamide (2.07 mL), cesium carbonate (1.01 g, 3.11 mmol) and iodomethane (0.155 mL, 2.49 mmol) were added, and the mixture was stirred under nitrogen atmosphere at room temperature for 1 hour. 1 N hydrochloric acid was added to the reaction mixture, and the mixture was extracted with ethyl acetate.

The organic layer was washed with water, a saturated sodium bicarbonate solution, a 10% aqueous sodium thiosulfate solution, and a brine, dried over sodium sulfate, filtered, and concentrated at reduced pressure to obtain (1R,3S,4S)-2-aza-bicyclo[2.2.1]heptane-2,3-dicarboxylic acid 2-tert-butyl ester 3-methyl ester as a crude product. A solution of hydrogen chloride in 1,4-dioxane (4 M, 5.00 mL) was added to the obtained crude product, and the mixture was stirred under nitrogen atmosphere at room temperature for 1 hour. The reaction mixture was concentrated at reduced pressure, and toluene was added for azeotropic removal to obtain the title compound as a crude product.

Second Step

In a similar manner to First to Third Steps of Example 1, the compounds described in the following Table were synthesized from the obtained (1 S,3 S,6R)-2-aza-bicyclo[2.2.1]heptane-3-carboxylic acid methyl ester hydrochloride and 3-fluoro-benzaldehyde.

TABLE 18

| Structure | Compound name | Analysis condition | HPLC Retention time (min) | m/z |
|---|---|---|---|---|
| 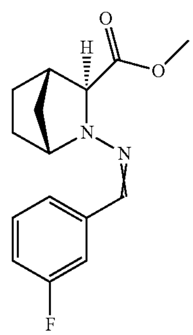 [SMILES: COC(=O)[C@@H]1[C@H]2CC[C@H](C2)N1N=Cc1cccc(F)c1] | (1R,3S,4S)-2-[(3-Fluoro-benzylidene)-amino]-2-aza-bicyclo[2.2.1]heptane-3-carboxylic acid methyl ester | SQD-AA05 | 1.02 | 277 |
| 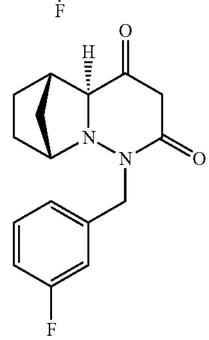 | (4aS,5S,8R)-1-(3-Fluorobenzyl)tetrahydro-1H-5,8-methanopyrido[1,2-b]pyridazine-2,4(3H,4aH)-dione | SQD-AA05 | 0.90 | 289 |
| 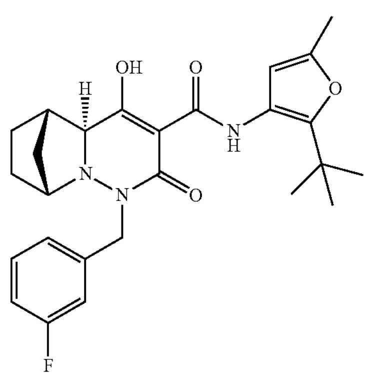 [SMILES: Cc1cc(NC(=O)C2=C(O)[C@@H]3[C@H]4CC[C@H](C4)N3N(Cc3cccc(F)c3)C2=O)c(C(C)(C)C)o1] | (4aS,5S,8R)-1-(3-Fluorobenzyl)-4-hydroxy-N-(5-methyl-2-(trifluoromethyl)furan-3-yl)-2-oxo-2,4a,5,6,7,8-hexahydro-1H-5,8-methanopyrido[1,2-b]pyridazine-3-carboxamide | SQD-AA05 | 1.17 | 480 |

Reference Example 1-1

(4aR)-1-[(2,3-Difluorophenyl)methyl]-4-hydroxy-4a-methyl-2-oxo-6,7-dihydro-5H-pyrrolo[1,2-b]pyridazine-3-carboxylic acid 2-methylpropyl ester

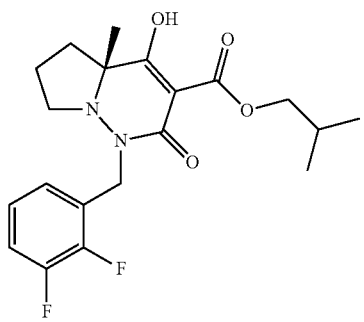 [SMILES: CC(C)COC(=O)C1=C(O)[C@@]2(C)CCCN2N(Cc2cccc(F)c2F)C1=O]

First Step

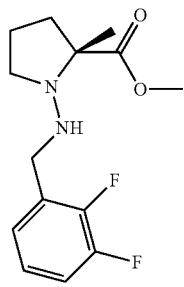 [SMILES: COC(=O)[C@@]1(C)CCCN1NCc1cccc(F)c1F]

(R)-1-((2,3-(Difluorobenzylidene)amino)-2-methylpyrrolidine-2-carboxylic acid methyl ester (1.31 g, 4.63 mmol) was dissolved in methanol (4.6 mL) and acetic acid (4.6 mL), cyano sodium borohydride (1.19 g, 18.98 mmol) was added, and the mixture was stirred at room temperature for 3 hours. A saturated aqueous sodium bicarbonate solution was added, and the mixture was extracted with ethyl acetate. The organic layer was washed with a brine, dried over anhydrous sodium sulfate, and filtered, and the solvent was distilled away at reduced pressure to obtain a crude product (1.34 g, 102%) of (R)-1-((2,3-(difluorobenzyl)amino)-2-methylpyrrolidine-2-carboxylic acid methyl ester.

Second Step

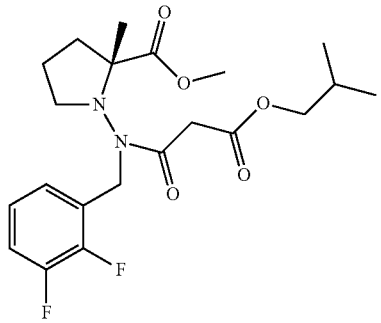 [SMILES: COC(=O)[C@@]1(C)CCCN1N(Cc1cccc(F)c1F)C(=O)CC(=O)OCC(C)C]

(R)-1-((2,3-(Difluorobenzyl)amino)-2-methylpyrrolidine-2-carboxylic acid methyl ester (3.24 g, 11.39 mmol) and 3-butyloxy-3-propionic acid (2.19 g, 13.67 mmol) were dissolved in dichloromethane (17.7 mL), and then bromotri(pyrrolidin-1-yl)phosphonium hexafluorophosphate (6.9 g, 14.81 mmol) and triethylamine (6.37 mL, 45.6 mmol) were added, and the mixture was stirred at room temperature for 30 minutes. Dichloromethane and 1 N hydrochloric acid were added to the reaction mixture, and the mixture was stirred at room temperature for 10 minutes. The organic layer was separated and concentrated at reduced pressure. The resultant residue was purified by column chromatography on silica gel (hexane/ethyl acetate) to obtain (R)-1-(N-(2,3-difluorobenzyl)-3-isobutoxy-3-oxopropanamide)-2-methylpyrrolidine-2-carboxylic acid methyl ester (4.58 g, 94%).

LCMS: m/z 427[M+H]$^+$

HPLC retention time: 1.33 minutes (analysis condition SMD-TFA05)

Third Step (R)-1-(N-(2,3-Difluorobenzyl)-3-isobutoxy-3-oxopropanamide)-2-methylpyrrolidine-2-carboxylic acid methyl ester (30.4 g, 71.2 mmol) was dissolved in N,N-dimethylformamide (142 mL), cesium carbonate (69.6 g, 214 mmol) was added, and the mixture was stirred at 80° C. for 1 hour. After the mixture was left to cool, it was concentrated at reduced pressure, 2 N hydrochloric acid was added, and the mixture was extracted with ethyl acetate. The organic layer was washed with water, dried over anhydrous magnesium sulfate, filtered, and concentrated at reduced pressure. The resultant residue was purified by column chromatography on silica gel (0-80% ethyl acetate/hexane) to obtain the title compound (25.33 g, 90%).

LCMS: m/z 395[M+H]$^+$

HPLC retention time: 1.05 minutes (analysis condition SQD-FA05)

Reference Example 1-2

Methyl (4aR)-4-hydroxy-4a-methyl-2-oxo-1-pentyl-6,7-dihydro-5H-pyrrolo[1,2-b]pyridazine-3-carboxylate

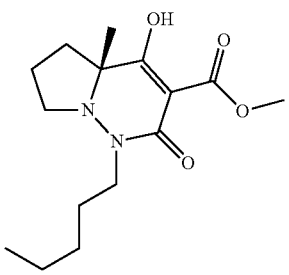 [SMILES: CCCCCN1C(=O)C(C(=O)OC)=C(O)[C@@]2(C)CCCN12]

Normal-pentyl aldehyde (0.959 g, 11.1 mmol) was used as a reagent, and operations similar to those of First Step of Reference Example 1-1 were carried out to obtain (R)-1-(pentylamino)-2-methylpyrrolidine-2-carboxylic acid methyl ester (1.73 g) as a crude product. The obtained hydrazine derivative was dissolved in tetrahydrofuran (14 mL), tripotassium phosphate (6.41 g, 30.2 mmol) and methyl 3-chloro-3-oxopropanoate (1.62 mL, 15.1 mmol) were added, and the mixture was stirred at room temperature overnight. Ethyl acetate (100 mL) was added to the reaction mixture, and after the organic layer was washed with 1 N hydrochloric acid, water, and a brine, it was dried over magnesium sulfate. After the resultant was filtered, the filtrate was concentrated at reduced pressure, and the residue was purified by column chromatography on silica gel (hexane/ethyl acetate) to obtain (R)-1-(3-methoxy-3-oxo-N-pentylpropanamide)-2-methylpyrrolidine-2-carboxylic acid methyl ester (1.84 g, 84%) as yellow oil. The obtained amide body (1.84 g, 5.59 mmol) was dissolved in N,N-dimethylformamide (25 mL), cesium carbonate (5.47 g, 16.8 mmol) was added, and the mixture was stirred at 80° C. for 2 hours. After the reaction mixture was cooled to room temperature, ethyl acetate (50 mL) was added, and after the organic layer was washed with 1 N hydrochloric acid, water, and a brine, it was dried over magnesium sulfate. After the resultant was filtered, the filtrate was concentrated at reduced pressure to obtain the title compound (1.84 g).

LCMS: m/z 297[M+H]$^+$

HPLC retention time: 1.22 minutes (analysis condition SMD-TFA05)

Reference Example 2

(R)-2,5,5-Trimethylpyrrolidine-2-carboxylic methyl ester

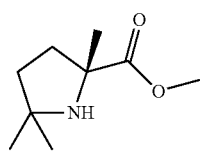

First Step

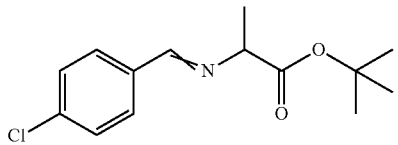 [SMILES: CC(N=Cc1ccc(Cl)cc1)C(=O)OC(C)(C)C]

4-Chlorobenzaldehyde (0.736 g, 5.23 mmol) was added to a suspension of 2-amino propanoate tert-butyl ester (0.80 g, 5.51 mmol) and magnesium sulfate (0.66 g, 5.51 mmol) in dichloromethane (7.3 mL), and the mixture was stirred at room temperature for 2 days. The reaction mixture was filtered, and the obtained filtrate was concentrated at reduced pressure. The residue was dissolved in diethyl ether, washed with water and a brine, and the organic layer was dried over magnesium sulfate and filtered. The filtrate was concentrated at reduced pressure to obtain 2-((4-chlorobenzylidene)amino)propanoate tert-butyl ester (1.29 g) as a crude product.

Second Step

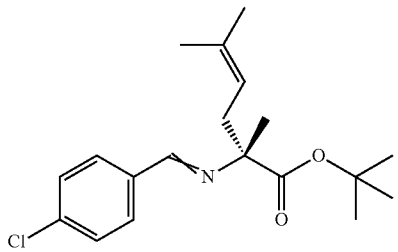 [SMILES: CC(C)=CC[C@@](C)(N=Cc1ccc(Cl)cc1)C(=O)OC(C)(C)C]

2-((4-Chlorobenzylidene)amino)propanoate tert-butyl ester (2.18 g, 12.2 mmol) obtained in First Step and (S)-4,4-dibutyl-2,6-bis(3,4,5-trifluorophenyl)-4,5-dihydro-3H-dinaphtho[7,6,1,2-cde]azepinium bromide (91 mg, 0.122 mmol) were dissolved in toluene (85 mL), and 1-bromo-3-methyl-2-butene (1.71 mL, 14.61 mmol) and cesium hydroxide (9.13 g, 60.9 mmol) were added at 0° C. After the reaction mixture was stirred at 0° C. for 4 hours, water was added, and the mixture was extracted with dichloromethane. The organic layer was washed with a brine, dried over sodium sulfate, and filtered. The obtained filtrate was concentrated at reduced pressure to obtain (R)-2-((4-chlorobenzylidene)amino)-2,5-dimethylhex-4-enoic acid tert-butyl ester as a crude product.

Third Step

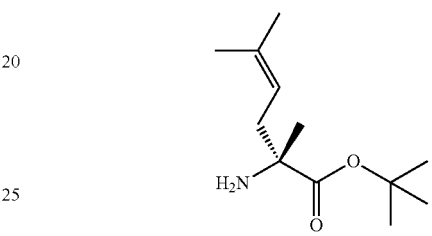

1 N hydrochloric acid (97 mL, 97 mmol) was slowly added to a solution of (R)-2-((4-chlorobenzylidene)amino)-2,5-dimethylhex-4-enoic acid tert-butyl ester (4.09 g, 12.2 mmol) obtained in Second Step in diethyl ether (97 mL). The reaction mixture was intensely stirred at room temperature for 4 hours. The organic layer was separated, and the aqueous layer was washed with diethyl ether. After the aqueous layer was adjusted to pH 9, it was extracted with dichloromethane. The extracts were combined, dried, and filtered, and the filtrate was concentrated at reduced pressure to obtain (R)-2-amino-2,5-dimethylhex-4-enoic acid tert-butyl ester as a crude product.

Fourth Step

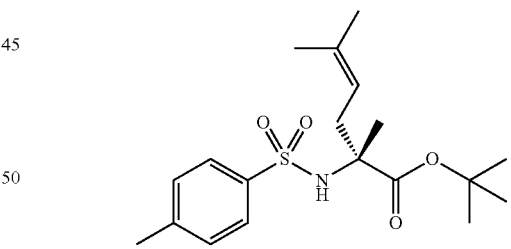

(R)-2-Amino-2,5-dimethylhex-4-enoic acid tert-butyl ester (1.03 g, 4.83 mmol) obtained in Third Step was dissolved in dichloromethane (9.7 mL), p-toluenesulfonyl chloride (1.11 g, 5.79 mmol), triethylamine (0.81 mL, 5.79 mmol), and 4-dimethylaminopyridine (5.90 mg, 0.048 mmol) were added, and the mixture was stirred at room temperature overnight. 1 N hydrochloric acid was added to the reaction mixture, and the mixture was extracted with dichloromethane. The extracts were combined, washed with a brine, dried over sodium sulfate, and filtered, and subsequently, the filtrate was concentrated at reduced pressure. The residue was purified by column chromatography on silica gel (hexane/ethyl acetate) to obtain (R)-2,5-dimethyl- 2-(4-methylphenylsulfonamide)hex-4-enoic acid tert-butyl ester (1.47 g, 83%) as yellow oil.
LCMS: m/z 368[M+H]+
HPLC retention time: 1.40 minutes (analysis condition SMD-TFA05)

Fifth Step

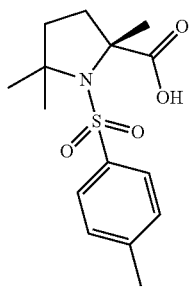 [SMILES: Cc1ccc(S(=O)(=O)N2C(C)(C)CC[C@]2(C)C(=O)O)cc1]

(R)-2,5-Dimethyl-2-(4-methylphenylsulfonamide)hex-4-enoic acid tert-butyl ester (1.47 g, 4.00 mmol) obtained in Fourth Step was dissolved in chloroform (16.0 mL), and the solution was cooled to 0° C. Trifluoromethanesulfonic acid (0.14 mL, 1.60 mmol) was added at 0° C., and the reaction mixture was stirred at 0° C. for 1 hour and at room temperature for 2 hours. A saturated sodium bicarbonate solution was added to the reaction mixture, and the mixture was extracted with dichloromethane. The extracts were combined, washed with a brine, and dried over sodium sulfate. After the resultant was filtered, the filtrate was concentrated at reduced pressure to obtain (R)-2,5,5-trimethyl-1-tosylpyrrolidine-2-carboxylic acid as a crude product.

Sixth Step

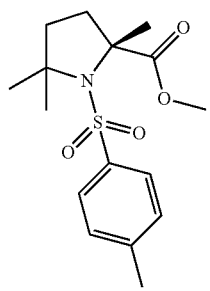

Iodomethane (2.99 mL, 4.80 mmol) was added to a suspension of (R)-2,5,5-trimethyl-1-tosylpyrrolidine-2-carboxylic acid (1.25 g, 4.00 mmol) obtained in Fifth Step and potassium carbonate (829 mg, 6.00 mmol) in N,N-dimethylformamide (16.0 mL). The reaction mixture was stirred at room temperature for 1 hour. 1 N hydrochloric acid was added, and the mixture was extracted with ethyl acetate. The extracts were combined, washed with a brine, and dried over sodium sulfate. After the resultant was filtered, the filtrate was concentrated at reduced pressure, and the residue was purified by column chromatography on silica gel (hexane/ethyl acetate) to obtain (R)-2,5,5-trimethyl-1-tosylpyrrolidine-2-carboxylic acid methyl ester (1.24 g, 3.81 mmol) as a pale yellow solid.
LCMS: m/z 326[M+H]+
HPLC retention time: 1.20 minutes (analysis condition SMD-TFA05)

Seventh Step
(R)-2,5,5-Trimethyl-1-tosylpyrrolidine-2-carboxylic acid methyl ester (1.24 g, 3.81 mmol) obtained in Sixth Step was dissolved in methanol (38.1 mL), and magnesium (1.85 g, 76 mmol) was added. The reaction mixture was stirred at room temperature for 28 hours. 1 N hydrochloric acid was added, and the aqueous layer was washed with dichloromethane. The water layer was adjusted to pH 9 and extracted with dichloromethane. The extracts were combined, dried over sodium sulfate, and filtered. The filtrate was concentrated at reduced pressure to obtain the title compound (611 mg, 3.57 mmol) as colorless oil.
1H-NMR (CDCl3) δ: 3.73 (3H, s), 2.36-2.30 (1H, m), 1.88-1.80 (1H, m), 1.69-1.53 (2H, m), 1.39 (3H, s), 1.18 (3H, s), 1.17 (3H, s).

Reference Example 3

2,3-Difluoro-4-(2-morpholinoethoxy)benzaldehyde

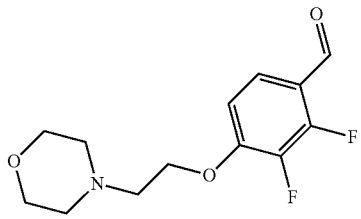 [SMILES: O=Cc1ccc(OCCN2CCOCC2)c(F)c1F]

First Step

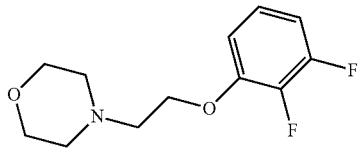 [SMILES: Fc1cccc(OCCN2CCOCC2)c1F]

4-(2-Chloroethyl)morpholine hydrochloride (4.72 g, 25.4 mmol), cesium carbonate (18.8 g, 57.7 mmol), and tetrabutylammonium iodide (0.511 g, 1.38 mmol) were added to a solution of 2,3-difluorophenol (3.00 g, 23.1 mmol) in acetonitrile (46.1 mL), and the mixture was stirred at 65° C. for 4 hours. After cooling to room temperature, the reaction mixture was filtered through a celite pad, and the filtrate was concentrated at reduced pressure. The residue was dissolved in ethyl acetate, washed with water, a 2 N aqueous sodium hydroxide solution, water, and a brine, and the organic layer was dried over sodium sulfate. After the resultant was filtered, the filtrate was concentrated at reduced pressure, and the residue was purified by column chromatography on silica gel (hexane/ethyl acetate) to obtain 4-(2-(2,3-difluorophenoxy)ethyl)morpholine (5.60 g, 99%) as colorless oil.
LCMS: m/z 244[M+H]+
HPLC retention time: 0.68 minutes (analysis condition SMD-TFA05)

Second Step
A solution of 4-(2-(2,3-difluorophenoxy)ethyl)morpholine (1.00 g, 4.11 mmol) and N,N,N',N'-tetramethylethylenediamine (0.62 mL, 4.11 mmol) in tetrahydrofuran (13.7 mL) was cooled to −78° C., and n-butyllithium (2.14 mL, 5.34 mmol) was added. After the mixture was stirred at −78° C. for 1 hour, N,N-dimethylformamide (0.35 mL, 4.52 mmol) was added at −78° C. The reaction mixture was slowly heated to −10° C., and the reaction was stopped with a saturated aqueous ammonium chloride solution. The aqueous layer was extracted with ethyl acetate, and the extracts were combined and washed with a brine, dried over sodium sulfate, and filtered. The filtrate was concentrated at reduced pressure, and the residue was purified by C18 reverse-phase column chromatography (acetonitrile/water) to obtain the title compound (758 mg, 68%) as yellow oil.

LCMS: m/z 272[M+H]$^+$

HPLC retention time: 0.62 minutes (analysis condition SMD-TFA05)

Reference Example 4

(4aR)-1-[[2,3-Difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxylic acid 2-methylpropyl ester

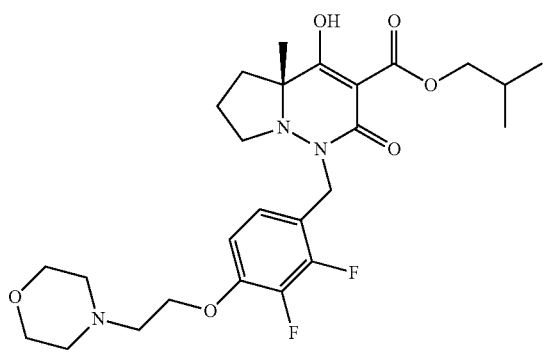 [SMILES: CC(C)COC(=O)C1=C(O)[C@@]2(C)CCCN2N(Cc2ccc(OCCN3CCOCC3)c(F)c2F)C1=O]

First Step

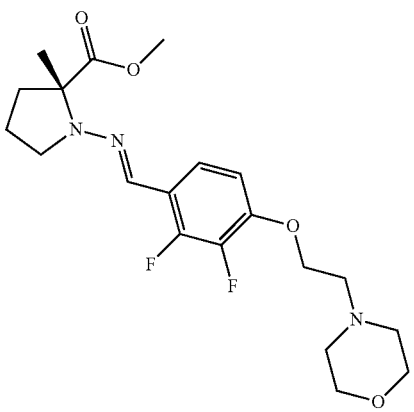 [SMILES: COC(=O)[C@@]1(C)CCCN1/N=C/c1ccc(OCCN2CCOCC2)c(F)c1F]

2,3-Difluoro-4-(2-morpholinoethoxy)benzaldehyde and methyl (R)-2-methyl-pyrrolidine-2-carboxylic acid hydrochloride were used, and operations similar to those of First to Third Steps of Example 1 were carried out to synthesize methyl (2R)-1-[(E)-[2,3-difluoro-4-(2-morpholin-4-ylethoxy)phenyl]methylideneamino]-2-methylpyrrolidine-2-carboxylate.

LCMS: m/z 412[M+H]$^+$

HPLC retention time: 0.95 minutes (analysis condition SMD-TFA05)

Second Step

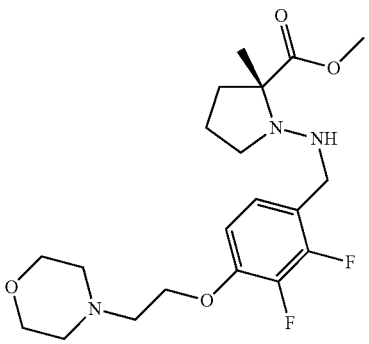 [SMILES: COC(=O)[C@@]1(C)CCCN1NCc1ccc(OCCN2CCOCC2)c(F)c1F]

(R)-1-((2,3-Difluoro-4-(2-morpholinoethoxy)benzylidene)amino)-2-methylpyrrolidine-2-carboxylic acid methyl ester was used, and operations similar to those of First Step of Reference Example 1-1 were carried out to obtain (R)-1-((2,3-difluoro-4-(2-morpholinoethoxy)benzyl)amino)-2-methylpyrrolidine-2-carboxylic acid methyl ester as a crude product.

LCMS: m/z 414[M+H]$^+$

HPLC retention time: 0.63 minutes (analysis condition SMD-TFA05)

Third Step (R)-1-((2,3-Difluoro-4-(2-morpholinoethoxy)benzyl)amino)-2-methylpyrrolidine-2-carboxylic acid methyl ester and 3-butyloxy-3-propionic acid were used, and operations similar to those of Reference Example 1-2 were carried out to synthesize (R)-1-(N-(2,3-difluoro-4-(2-morpholinoethoxy)benzyl)-3-isobutoxy-3-oxopropanamide)-2-methylpyrrolidine-2-carboxylic acid methyl ester.

LCMS: m/z 556[M+H]$^+$

HPLC retention time: 1.03 minutes (analysis condition SMD-TFA05)

Fourth Step (R)-1-(N-(2,3-Difluoro-4-(2-morpholinoethoxy)benzyl)-3-isobutoxy-3-oxopropanamide)-2-methylpyrrolidine-2-carboxylic acid methyl ester was used, and operations similar to those of Reference Example 1-2 were carried out to synthesize the title compound.

LCMS: m/z 524[M+H]$^+$

HPLC retention time: 1.04 minutes (analysis condition SMD-TFA05)

The ester intermediates described in the following Table were synthesized using the corresponding aldehyde reagents and proline derivatives to carry out operations similar to those of Reference Example 1-1 or Reference Example 1-2.

TABLE 19
| Reference Example No. | Ester | LCMS analysis condition No. | Retention time (min) | Ester intermediate m/z |
|---|---|---|---|---|
| 5 | 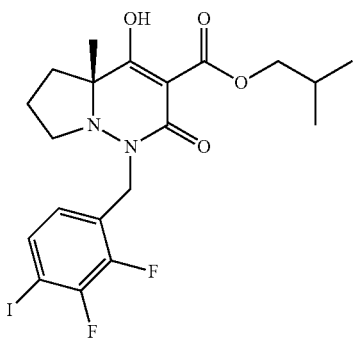 [SMILES: CC(C)COC(=O)C1=C(O)[C@@]2(C)CCCN2N(Cc2ccc(I)c(F)c2F)C1=O] | SQD-FA05 | 1.12 | 521 [M + H]+ |
| 6 | 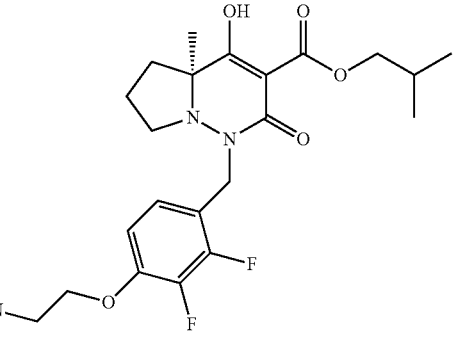 | SQD-FA05 | 0.62 | 524 [M + H]+ |
| 7 | 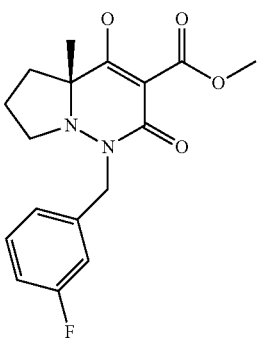 [SMILES: COC(=O)C1=C(O)[C@@]2(C)CCCN2N(Cc2cccc(F)c2)C1=O] | SMD-TFA50 | 0.47 | 335 [M + H]+ |
| 8 | 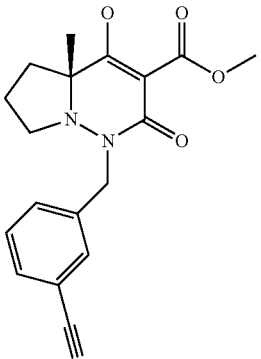 | SMD-TFA05 | 1.08 | 342 [M + H]+ |

TABLE 19-continued

| Reference Example No. | Ester | LCMS analysis condition No. | Retention time (min) | Ester intermediate m/z |
|---|---|---|---|---|
| 9 | (structure) | SMD-TFA50 | 0.88 | 413 [M + H]+ |
| 10 | (structure) | SQD-FA05 | 0.82 | 362 [M + H]+ |
| 11 | (structure) | SQD-FA05 | 1.12 | 423 [M + H]+ |
| 12 | (structure) | SMD-TFA05 | 1.14 | 377 [M + H]+ |

Reference Example 13

4-(Trifluoromethyl)-2-[6-(trifluoromethyl)pyridin-3-yl]aniline

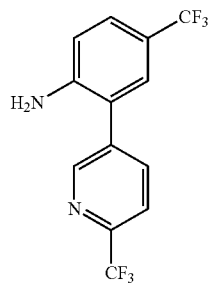

Toluene (900 mL), ethanol (226 mL), and water (450 mL) were added to 2-(tetramethyl-1,3,2-dioxaborolan-2-yl)-4-(trifluoromethyl)aniline (60.00 g, 209 mmol), 5-bromo-2-(trifluoromethyl)pyridine (50.80 g, 225 mmol), tetrakis(triphenylphosphine)palladium (9.000 g, 7.79 mmol), and potassium carbonate (129.0 g, 930 mmol) under nitrogen atmosphere, and the mixture was stirred at 110° C. for 3 hours. The reaction mixture was concentrated at reduced pressure, water (1,000 mL) was added, and the mixture was extracted with ethyl acetate. The organic layer was washed with water, dried over sodium sulfate, filtered, and concentrated at reduced pressure. The resultant residue was purified by column chromatography on silica gel (ethyl acetate/petroleum ether) to obtain the title compound (63 g, 98%).

LCMS: m/z 307[M+H]$^+$

HPLC retention time: 0.99 minutes (analysis condition SQD-AA05)

Reference Example 14

2-Iodo-5-(2-methoxyethoxy)-4-(trifluoromethyl)aniline

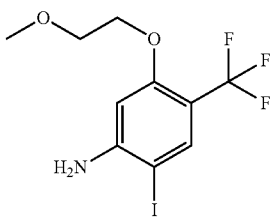 [SMILES: COCCOc1cc(N)c(I)cc1C(F)(F)F]

First Step

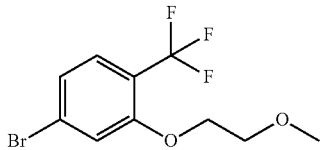 [SMILES: COCCOc1cc(Br)ccc1C(F)(F)F]

2-Methoxyethanol (0.097 mL, 1.24 mmol) was dissolved in N-methylpyrrolidone (2 mL) under nitrogen atmosphere, sodium hydride (60 wt. %, a mineral oil dispersion, 30 mg, 1.24 mmol) was added, and after the mixture was stirred at room temperature for 30 minutes, 4-bromo-2-fluoro-1-(trifluoromethyl)benzene (0.118 mL, 0.823 mmol) was added, and the mixture was stirred at room temperature for 7 days. A 0.37 M aqueous potassium dihydrogenphosphate solution was added to the reaction mixture, and the mixture was extracted with ethyl acetate. The organic layer was washed with a brine, dried over anhydrous magnesium sulfate, filtered, and concentrated at reduced pressure. The resultant residue was purified by column chromatography on silica gel (0-10% ethyl acetate/hexane) to obtain 4-bromo-2-(2-methoxyethoxy)-1-(trifluoromethyl)benzene (231.2 mg, 94%).

HPLC retention time: 0.63 minutes (analysis condition SQD-AA50)

TLC (silica gel plate) Rf value: 0.37 (10% ethyl acetate/hexane)

Second Step

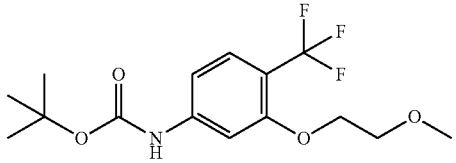 [SMILES: COCCOc1cc(NC(=O)OC(C)(C)C)ccc1C(F)(F)F]

4-Bromo-2-(2-methoxyethoxy)-1-(trifluoromethyl)benzene (231.2 mg, 0.773 mmol), carbamic acid t-butyl (109 mg, 0.928 mmol), palladium acetate (II) (5.21 mg, 0.023 mmol), 2-dicyclohexylphosphino-2',4',6'-triisopropyl-1,1'-biphenyl (33.2 mg, 0.07 mmol), and cesium carbonate (353 mg, 1.08 mmol) were dissolved in 1,4-dioxane (5.2 mL), and the mixture was stirred under nitrogen atmosphere at 100° C. overnight. A 0.37 M aqueous potassium dihydrogenphosphate solution was added to the reaction mixture, and the mixture was extracted with ethyl acetate. The organic layer was washed with a brine, dried over anhydrous magnesium sulfate, filtered, and concentrated at reduced pressure. The resultant residue was purified by column chromatography on silica gel (0-20% ethyl acetate/hexane) to obtain (3-(2-methoxyethoxy)-4-(trifluoromethyl)phenyl)carbamic acid tert-butyl (192.5 mg, 74%).

LCMS: m/z 334[M−H]$^-$

HPLC retention time: 1.02 minutes (analysis condition SQD-AA05)

Third Step

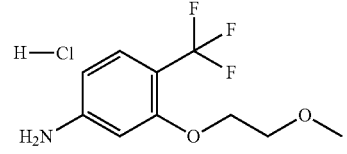

A solution of 4 N hydrogen chloride/1,4-dioxane (3.9 mL) was added to (3-(2-methoxyethoxy)-4-(trifluoromethyl)phenyl)carbamic acid tert-butyl ester (192.5 mg, 0.574 mmol), and the mixture was stirred at room temperature overnight. The reaction mixture was concentrated at reduced pressure, ether/hexane (1/3) was added to the resultant residue, the deposited solid was collected by filtration, and the resultant was dried under vacuum to obtain 3-(2-methoxyethoxy)-4-(trifluoromethyl)aniline hydrochloride (128.1 mg, 82%).

LCMS: m/z 236[M+H]$^+$

HPLC retention time: 0.83 minutes (analysis condition SQD-AA05)

Fourth Step 3-(2-Methoxyethoxy)-4-(trifluoromethyl)aniline hydrochloride (55.9 mg, 0.206 mmol) was dissolved in acetic acid (1.03 mL), N-iodosuccinimide (50.9 mg, 0.226 mmol) was added, and the mixture was stirred at room temperature for 2 hours and 20 minutes. The reaction mixture was concentrated at reduced pressure, ethyl acetate was added, washed with 0.5 N sodium hydroxide and a brine, dried over anhydrous magnesium sulfate, filtered, and concentrated at reduced pressure. The resultant residue was purified by column chromatography on silica gel (0-40% ethyl acetate/hexane) to obtain the title compound (69.2 mg, 93%).

LCMS: m/z 362[M+H]$^+$

HPLC retention time: 1.19 minutes (analysis condition SMD-TFA05)

Reference Example 15

2',3'-Dimethoxy-4-(2-methoxyethoxy)-5-(trifluoromethyl)-[1,1'-biphenyl]-2-amine

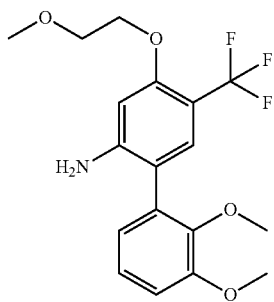 [SMILES: COCCOc1cc(N)c(-c2cccc(OC)c2OC)cc1C(F)(F)F]

Toluene (2.7 mL) and ethanol (1.1 mL) were added to 2-iodo-5-(2-methoxyethoxy)-4-(trifluoromethyl)aniline (69.2 mg, 0.192 mmol), (2,3-dimethoxyphenyl)boronic acid (34.9 mg, 0.192 mmol), and 1,1'-bis(diphenylphosphino)ferrocene dichloropalladium (II) (7.9 mg, 0.0096 mmol), then a 2M aqueous potassium carbonate solution (0.38 mL) was added, and the mixture was stirred under nitrogen atmosphere at 100° C. for 1 hour. A 0.37 M aqueous potassium dihydrogenphosphate solution was added to the reaction mixture, and the mixture was extracted with ethyl acetate. The organic layer was washed with a brine, dried over anhydrous magnesium sulfate, filtered, and concentrated at reduced pressure. The resultant residue was purified by column chromatography on silica gel (0-40% ethyl acetate/hexane), to obtain the title compound (41.1 mg, 58%).

LCMS: m/z 372[M+H]$^+$

HPLC retention time: 1.21 minutes (analysis condition SMD-TFA05)

The boronic acid derivatives and halides described in the following Table were used, and operations similar to those of Reference Example 13 or Reference Example 15 were carried out to synthesize aniline intermediates described in the following Table.

TABLE 20

| Reference Example No. | Aniline | Boronic acid derivative | Halide | Aniline intermediate m/z |
|---|---|---|---|---|
| 16 | | | | 298 [M + H]$^+$ |
| 17 | | | | 281 [M + H]$^+$ |

TABLE 20-continued

| Reference Example No. | Aniline | Boronic acid derivative | Halide | Aniline intermediate m/z |
|---|---|---|---|---|
| 18 | | | | 359 [M + H]+ |
| 19 | | | | 281 [M + H]+ |
| 20 | | | | 326 [M + H]+ |
| 21 | | | | 312 [M + H]+ |

TABLE 20-continued

| Reference Example No. | Aniline | Boronic acid derivative | Halide | Aniline intermediate m/z |
|---|---|---|---|---|
| 22 | | | | 372 [M + H]+ |
| 23 | | | | 351 [M + H]+ |
| 24 | | | | 323 [M + H]+ |
| 25 | | | | 323 [M + H]+ |

TABLE 20-continued

| Reference Example No. | Aniline | Boronic acid derivative | Halide | Aniline intermediate m/z |
|---|---|---|---|---|
| 26 | | | | 346 [M + H]+ |
| 27 | | | | 264 [M + H]+ |
| 28 | | | | 267 [M − H]− |
| 29 | | | | 285 [M + H]+ |

TABLE 20-continued

| Reference Example No. | Aniline | Boronic acid derivative | Halide | Aniline intermediate m/z |
|---|---|---|---|---|
| 30 | | | | 273 [M + H]+ |
| 31 | | | | 274 [M + H]+ |
| 32 | | | | 264 [M + H]+ |
| 33 | | | | 298 [M + H]+ |

TABLE 20-continued

| Reference Example No. | Aniline | Boronic acid derivative | Halide | Aniline intermediate m/z |
|---|---|---|---|---|
| 34 | | | | 283 [M + H]+ |
| 35 | | | | 307 [M + H]+ |
| 36 | | | | 269 [M + H]+ |
| 37 | | | | 385 [M + H]+ |

TABLE 20-continued

| Reference Example No. | Aniline | Boronic acid derivative | Halide | Aniline intermediate m/z |
|---|---|---|---|---|
| 38 | | | | 307 [M − H]− |
| 39 | | | | 264 [M + H]+ |
| 40 | | | | 294 [M + H]+ |
| 41 | | | | 307 [M + H]+ |

TABLE 20-continued

| Reference Example No. | Aniline | Boronic acid derivative | Halide | Aniline intermediate m/z |
|---|---|---|---|---|
| 42 | | | | 307 [M + H]+ |
| 43 | | | | 278 [M + H]+ |
| 44 | | | | 308 [M + H]+ |
| 45 | | | | 286 [M + H]+ |

TABLE 20-continued

| Reference Example No. | Aniline | Boronic acid derivative | Halide | Aniline intermediate m/z |
|---|---|---|---|---|
| 46 | | | | 308 [M + H]+ |
| 47 | | | | 289 [M + H]+ |
| 48 | | | | 287 [M + H]+ |
| 49 | | | | 264 [M + H]+ |

TABLE 20-continued
| Reference Example No. | Aniline | Boronic acid derivative | Halide | Aniline intermediate m/z |
|---|---|---|---|---|
| 50 | 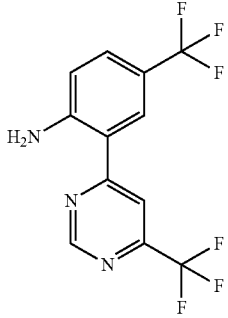 [SMILES: Nc1ccc(C(F)(F)F)cc1-c1cc(C(F)(F)F)ncn1] | 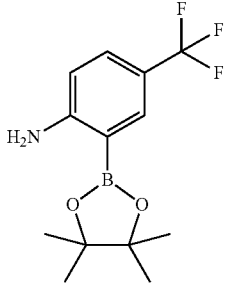 | 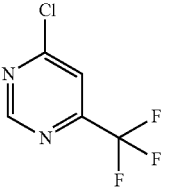 [SMILES: FC(F)(F)c1cc(Cl)ncn1] | 308 [M + H]⁺ |
| 51 | 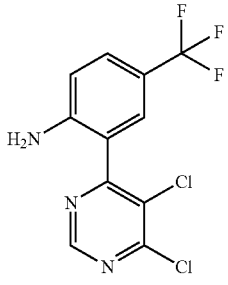 [SMILES: Nc1ccc(C(F)(F)F)cc1-c1ncnc(Cl)c1Cl] | 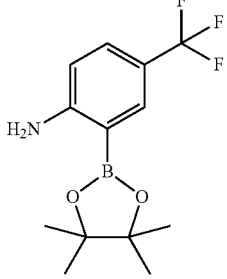 | 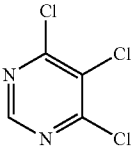 | 308 [M + H]⁺ |
| 52 | 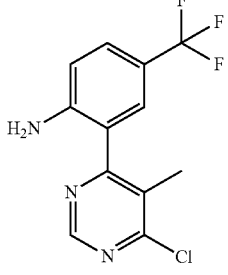 | 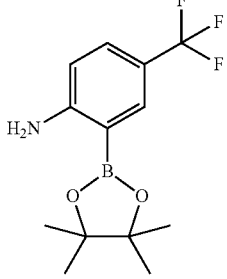 | 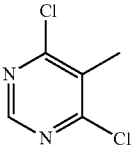 | 288 [M + H]⁺ |
| 53 | 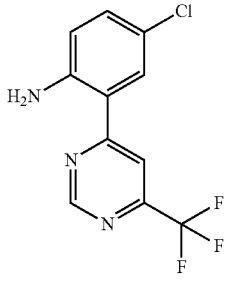 [SMILES: Nc1ccc(Cl)cc1-c1cc(C(F)(F)F)ncn1] | 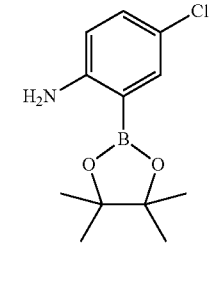 | 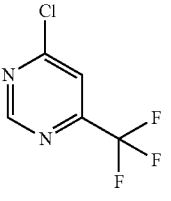 [SMILES: FC(F)(F)c1cc(Cl)ncn1] | 274 [M + H]⁺ |
| 54 | 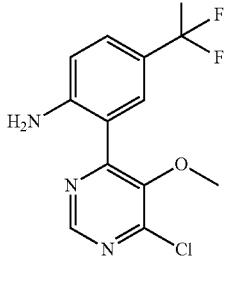 | 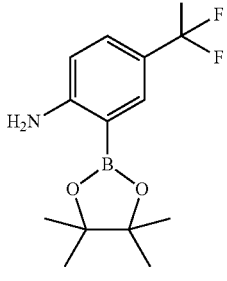 | 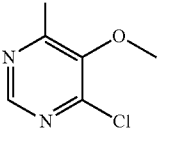 | 304 [M + H]⁺ |

TABLE 20-continued

| Reference Example No. | Aniline | Boronic acid derivative | Halide | Aniline intermediate m/z |
|---|---|---|---|---|
| 55 | | | | 332 [M + H]+ |
| 56 | | | | 286 [M + H]+ |
| 57 | | | | 300 [M + H]+ |
| 58 | | | | 274 [M + H]+ |

TABLE 20-continued

| Reference Example No. | Aniline | Boronic acid derivative | Halide | Aniline intermediate m/z |
|---|---|---|---|---|
| 59 | 2-amino-5-(trifluoromethyl)phenyl-pyrimidine-2-carbonitrile | 2-amino-5-(trifluoromethyl)phenylboronic acid pinacol ester | 5-bromopyrimidine-2-carbonitrile | 263 [M − H]⁻ |
| 60 | 3-amino-6-(trifluoromethyl)-2-(2-(methylthio)pyrimidin-5-yl)pyridine | 2-(methylthio)pyrimidin-5-ylboronic acid | 3-amino-2-bromo-6-(trifluoromethyl)pyridine | 287 [M + H]⁺ |
| 61 | 2-(5-chloropyrazin-2-yl)-4-(trifluoromethyl)aniline | 2-amino-5-(trifluoromethyl)phenylboronic acid pinacol ester | 2,5-dichloropyrazine | 274 [M + H]⁺ |
| 62 | 2-(5-bromopyrazin-2-yl)-4-(trifluoromethyl)aniline | 2-amino-5-(trifluoromethyl)phenylboronic acid pinacol ester | 2,5-dibromopyrazine | 319 [M + H]⁺ |

Reference Example 63

6-(2-Amino-5-(trifluoromethyl)phenyl)pyrimidine-4-carbonitrile

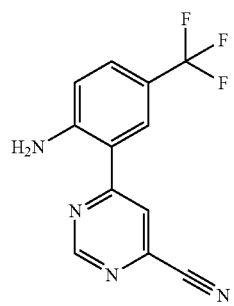 [SMILES: N#Cc1cc(-c2cc(C(F)(F)F)ccc2N)ncn1]

2-(6-Chloropyrimidin-4-yl)-4-(trifluoromethyl)aniline (1.0 g, 3.65 mmol) and 1,4-diazabicyclo[2.2.2]octane (0.246 g, 2.19 mmol) were dissolved in dimethylsulfoxide (3 mL), an aqueous solution (3 mL) of potassium cyanide (0.95 g, 14.6 mmol) was added at 0° C., and the mixture was stirred at room temperature overnight. A 0.37 M aqueous potassium dihydrogenphosphate solution was added to the reaction mixture, and the mixture was extracted with ethyl acetate. The organic layer was washed with a brine, dried over anhydrous magnesium sulfate, filtered, and concentrated at reduced pressure. The resultant residue was purified by C18 reverse-phase column chromatography (40-100% acetonitrile/water) to obtain the title compound (365.6 mg, 38%).

LCMS: m/z 265[M+H]$^+$

HPLC retention time: 1.16 minutes (analysis condition SMD-TFA05)

Reference Example 64

5-(2-Amino-5-(trifluoromethyl)phenyl)-4-methoxypyrimidine-2-carbonitrile

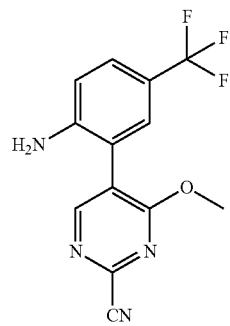 [SMILES: COc1nc(C#N)ncc1-c1cc(C(F)(F)F)ccc1N]

A mixture of 2-(2-chloro-4-methoxypyrimidin-5-yl)-4-(trifluoromethyl)aniline (89 mg, 0.293 mmol), zinc dicyanide (20.65 mg, 0.176 mmol), 1,1'-bis(diphenylphosphino)ferrocene (18.07 mg, 0.032 mmol), and tris(dibenzylideneacetone)dipalladium(0).chloroform adduct (30.3 mg, 0.029 mmol) in N,N-dimethylformamide (1.5 mL) was heated and stirred under nitrogen atmosphere at 80° C. for 1 hour. Further, the reaction mixture was heated and stirred at 110° C. for 9 hours. The reaction mixture was purified by C18 reverse-phase column chromatography (acetonitrile-water, 0.03% formic acid) to obtain 5-(2-amino-5-(trifluoromethyl)phenyl)-4-methoxypyrimidine-2-carbonitrile (57 mg, 66%).

LCMS: m/z 295[M+H]$^+$

HPLC retention time: 0.82 minutes (analysis condition SQD-FA05)

Reference Example 65

6-(2-Amino-5-(trifluoromethyl)phenyl)-5-chloropyrimidine-4-carbonitrile

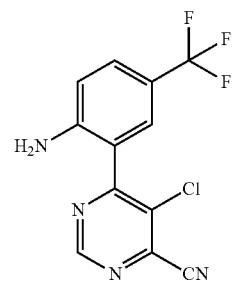 [SMILES: N#Cc1ncnc(-c2cc(C(F)(F)F)ccc2N)c1Cl]

2-(5,6-Dichloropyrimidin-4-yl)-4-(trifluoromethyl)aniline was used, and operations similar to those of Reference Example 63 were carried out to synthesize the title compound.

LCMS: m/z 299[M+H]$^+$

HPLC retention time: 0.82 minutes (analysis condition SQD-FA05)

Reference Example 66

6-(2-Amino-5-(trifluoromethyl)phenyl)-5-methoxypyrimidine-4-carbonitrile

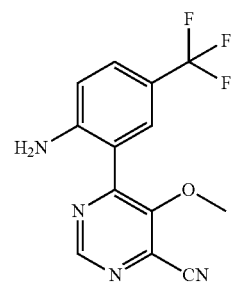 [SMILES: COc1c(C#N)ncnc1-c1cc(C(F)(F)F)ccc1N]

2-(6-Chloro-5-methoxypyrimidin-4-yl)-4-(trifluoromethyl)aniline was used, and operations similar to those of Reference Example 63 were carried out to synthesize the title compound.

LCMS: m/z 295[M+H]$^+$

HPLC retention time: 0.81 minutes (analysis condition SQD-FA05)

Reference Example 67

6-(2-Amino-5-(trifluoromethyl)phenyl)-5-methylpyrimidine-4-carbonitrile

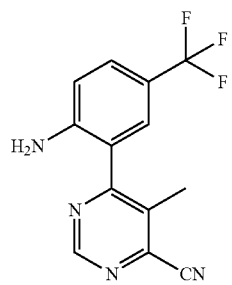 [SMILES: Cc1c(C#N)ncnc1-c1cc(C(F)(F)F)ccc1N]

2-(6-Chloro-5-methylpyrimidin-4-yl)-4-(trifluoromethyl)aniline was used, and operations similar to those of Reference Example 63 were carried out to synthesize the title compound.

LCMS: m/z 279[M+H]$^+$

HPLC retention time: 0.78 minutes (analysis condition SQD-FA05)

Reference Example 68

5-(2-Amino-5-(trifluoromethyl)phenyl)pyrazine-2-carbonitrile

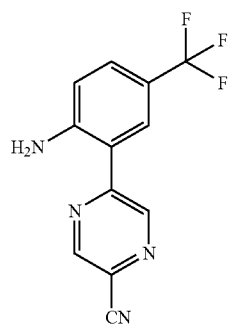 [SMILES: N#Cc1cnc(-c2cc(C(F)(F)F)ccc2N)cn1]

A mixture of 2-(5-bromopyrazin-2-yl)-4-(trifluoromethyl)aniline (27.6 mg, 0.087 mmol), zinc dicyanide (6.1 mg, 0.052 mmol), and tetrakis(triphenylphosphine)palladium(0) (5 mg, 0.0043 mmol) in N,N-dimethylformamide (0.4 mL) was heated and stirred under nitrogen atmosphere at 80° C. for 18 hours. The reaction mixture was purified by C18 reverse-phase column chromatography (acetonitrile-water, 0.03% formic acid) to obtain 5-(2-amino-5-(trifluoromethyl)phenyl)pyrazine-2-carbonitrile.

LCMS: m/z 265[M+H]$^+$

HPLC retention time: 0.81 minutes (analysis condition SQD-FA05)

Reference Example 69

2-(6-Methylpyrimidin-4-yl)-4-(trifluoromethyl)aniline

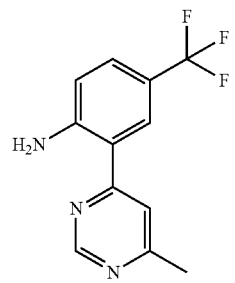 [SMILES: Cc1cc(-c2cc(C(F)(F)F)ccc2N)ncn1]

2-(6-Chloropyrimidin-4-yl)-4-(trifluoromethyl)aniline (51.9 mg, 0.19 mmol), trimethyl boroxine (0.053 mL, 0.379 mmol), bis(triphenylphosphine)palladium (II) chloride (13.3 mg, 0.019 mmol), and tripotassium phosphate (161 mg, 0.759 mmol) were dissolved in 1,4-dioxane (0.95 mL), and the mixture was stirred at 90° C. for 1 hour. A 0.37 M aqueous potassium dihydrogenphosphate solution was added to the reaction mixture, and the mixture was extracted with ethyl acetate. The organic layer was washed with a brine, dried over anhydrous magnesium sulfate, filtered, and concentrated at reduced pressure. The resultant residue was purified by column chromatography on silica gel (0-30% ethyl acetate/hexane) to obtain the title compound (27.4 mg, 57%).

LCMS: m/z 254[M+H]$^+$

HPLC retention time: 0.93 minutes (analysis condition SQD-AA05)

Reference Example 70

2-(Trifluoromethyl)-4-(6-(trifluoromethyl)pyridin-3-yl)pyrimidin-5-amine

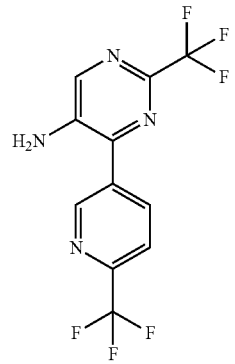 [SMILES: Nc1cnc(C(F)(F)F)nc1-c1ccc(C(F)(F)F)nc1]

First Step

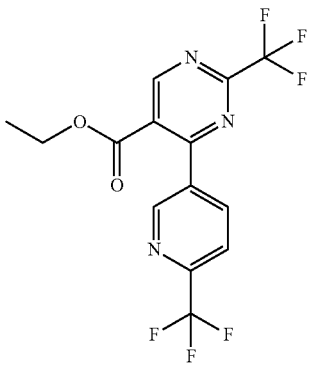 [SMILES: CCOC(=O)c1cnc(C(F)(F)F)nc1-c1ccc(C(F)(F)F)nc1]

4-Iodo-2-(trifluoromethyl)pyrimidine-5-carboxylic acid ethyl ester and (6-(trifluoromethyl)pyridin-3-yl)boronic acid were used, and operations similar to those of Reference Example 13 were carried out to synthesize 2-(trifluoromethyl)-4-(6-(trifluoromethyl)pyridin-3-yl)pyrimidine-5-carboxylic acid ethyl ester.

LCMS: m/z 366[M+H]$^+$

HPLC retention time: 1.26 minutes (analysis condition SMD-TFA05)

Second Step

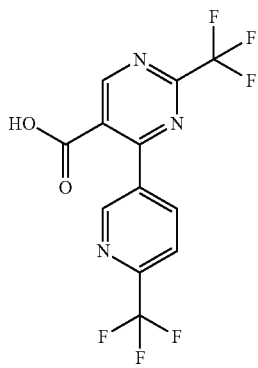 [SMILES: O=C(O)c1cnc(C(F)(F)F)nc1-c1ccc(C(F)(F)F)nc1]

2-(Trifluoromethyl)-4-(6-(trifluoromethyl)pyridin-3-yl) pyrimidine-5-carboxylic acid ethyl ester obtained in First Step (36 mg, 0.10 mmol) was dissolved in a mixture solution of ethanol (1 mL) and water (1 mL), and sodium hydroxide (7.9 mg, 0.20 mmol) was added at room temperature. After the mixture was stirred at room temperature for 1 hour, the solvent was concentrated at reduced pressure, and 1 N hydrochloric acid (5 mL) was added to the residue. After the resultant was extracted with ethyl acetate, the organic layer was dried over magnesium sulfate and filtered. The filtrate was concentrated at reduced pressure to obtain 2-(trifluoromethyl)-4-(6-(trifluoromethyl)pyridin-3-yl)pyrimidine-5-carboxylic acid as a crude product (30 mg).

LCMS: m/z 338[M+H]$^+$

HPLC retention time: 1.05 minutes (analysis condition SMD-TFA05)

Third Step

N,N-dimethylformamide (1.5 mL) was added to 2-(trifluoromethyl)-4-(6-(trifluoromethyl)pyridin-3-yl)pyrimidine-5-carboxylic acid obtained in Second Step (30 mg, 0.09 mmol), triethylamine (8.9 mg, 0.09 mmol), and diphenylphosphoryl azide (DPPA, 24.3 mg, 0.09 mmol), and the mixture was stirred at 60° C. for 3 hours. Water (1.5 mL) was added to the reaction mixture, and the resultant was stirred at 80° C. for 3 hours. The reaction mixture was cooled to room temperature, a 1 N aqueous sodium hydroxide solution was added, and after the resultant was extracted with ethyl acetate, it was dried over magnesium sulfate and filtered. The filtrate was concentrated at reduced pressure to obtain the title compound (26 mg) as a crude product.

LCMS: m/z 309[M+H]$^+$

HPLC retention time: 1.08 minutes (analysis condition SMD-TFA05)

Reference Example 71

4-Bromo-2-(6-(trifluoromethyl)pyrimidin-4-yl)aniline

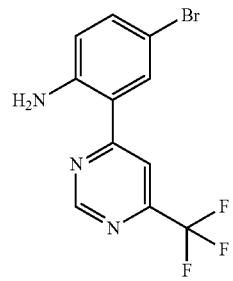 [SMILES: Nc1ccc(Br)cc1-c1cc(C(F)(F)F)ncn1]

2-(4,4,5,5-Tetramethyl-1,3,2-dioxaborolan-2-yl)aniline and 4-chloro-6-(trifluoromethyl)pyrimidine were used as a reagent and a starting material, respectively, and operations similar to those of Reference Example 13 were carried out to obtain 2-(6-(trifluoromethyl)pyrimidin-4-yl)aniline. 1-Bromopyrrolidine-2,5-dione (66.2 mg, 0.372 mmol) was added to a solution of 2-(6-(trifluoromethyl)pyrimidin-4-yl) aniline (89 mg, 0.372 mmol) in acetic acid (0.94 mL)/water (0.0067 mL) at room temperature. The reaction mixture was heated to 55° C. and stirred for 3.5 hours. The reaction mixture was cooled to room temperature, and azeotropic removal with toluene was carried out three times. The residue was purified by C18 reverse-phase column chromatography (acetonitrile/water) to obtain the title compound (60 mg, 50%) as a yellow solid.

LCMS: m/z 318[M+H]$^+$

HPLC retention time: 1.24 minutes (analysis condition SMD-TFA05)

Example 21

(4aR)-1-[(2,3-Difluorophenyl)methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide

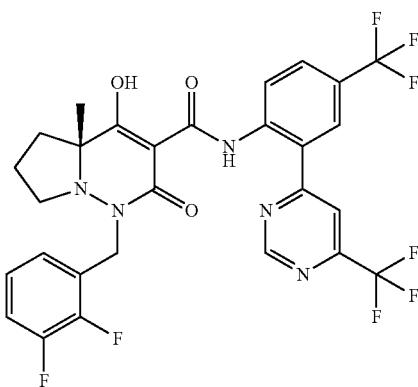 [SMILES: C[C@]12CCCN1N(Cc1cccc(F)c1F)C(=O)C(C(=O)Nc1ccc(C(F)(F)F)cc1-c1cc(C(F)(F)F)ncn1)=C2O]

(4aR)-1-[(2,3-Difluorophenyl)methyl]-4-hydroxy-4a-methyl-2-oxo-6,7-dihydro-5H-pyrrolo[1,2-b]pyridazine-3-carboxylic acid 2-methylpropyl ester (20 mg, 0.0567 mmol) and 4-(trifluoromethyl)-2-(6-(trifluoromethyl)pyrimidin-4-yl)aniline (Reference Example 50, 18 mg, 0.0596 mmol) were dissolved in toluene (0.2 mL), and the mixture was stirred at 90° C. for 3.5 hours. After the mixture was left to cool, the resultant was concentrated at reduced pressure, and the resultant residue was purified by C18 reverse-phase column chromatography (acetonitrile/water) to obtain the title compound (36 mg, 99%).

LCMS: m/z 628[M+H]$^+$

HPLC retention time: 1.17 minutes (analysis condition SQD-AA05)

Major Tautomer $^1$H-NMR (CDCl$_3$) δ: 16.47 (1H, s), 12.91 (1H, s), 9.60 (1H, s), 8.47 (1H, d, J=8.7 Hz), 7.95 (1H, s), 7.90 (1H, s), 7.79 (1H, d, J=8.7 Hz), 7.13-7.10 (2H, m), 7.05-7.03 (1H, m), 5.08 (1H, d, J=14.3 Hz), 4.47 (1H, d, J=14.3 Hz), 3.33 (1H, ddd, J=9.0, 9.0, 3.2 Hz), 2.76 (1H, ddd, J=9.0, 8.7, 8.7 Hz), 2.56-2.54 (1H, m), 1.76-1.73 (1H, m), 1.69-1.64 (2H, m), 1.00 (3H, s).

Minor Tautomer $^1$H-NMR (CDCl$_3$) δ: 18.22 (1H, s), 12.98 (1H, s), 9.59 (1H, s), 8.33 (1H, d, J=8.7 Hz), 7.92 (2H, d, J=9.6 Hz), 7.79 (1H, d, J=8.7 Hz), 7.14-7.06 (3H, m), 5.10 (1H, d, J=14.0 Hz), 4.52 (1H, d, J=14.6 Hz), 3.29-3.25 (1H, m), 2.78-2.75 (1H, m), 2.64-2.59 (1H, m), 1.73-1.66 (2H, m), 1.49-1.46 (1H, m), 0.84 (3H, s).

The appropriate aniline reagents of Reference Example 13 and 15 to 71 and the appropriate ester intermediates of Reference Examples 1-1 and 1-2 and Reference Examples 4 to 12 were used, and operations similar to those of Example 21 were carried out to synthesize the compounds described in the following Table. Note that in Examples 59 and 60, N,N-dimethylformamide was used as a solvent instead of toluene.

TABLE 21

| Example No. | Structural formula | LCMS analysis condition No. | Retention time (min) | m/z [M + H]$^+$ |
| --- | --- | --- | --- | --- |
| 22 | | QC-SMD-TFA05 | 1.26 | 728 |
| 23 | | QC-SMD-TFA05 | 1.65 | 619 |

TABLE 21-continued

| Example No. | Structural formula | LCMS analysis condition No. | Retention time (min) | m/z [M + H]⁺ |
|---|---|---|---|---|
| 24 | | QC-SMD-TFA05 | 1.63 | 599 |
| 25 | | QC-SMD-TFA05 | 1.61 | 615 |
| 26 | | QC-SMD-TFA05 | 1.75 | 571 |
| 27 | | QC-SMD-TFA05 | 1.63 | 519 |

TABLE 21-continued

| Example No. | Structural formula | LCMS analysis condition No. | Retention time (min) | m/z [M + H]+ |
|---|---|---|---|---|
| 28 | | SQD-AA05 | 1.18 | 510 |
| 29 | | SQD-AA05 | 1.16 | 528 |
| 30 | | SQD-AA05 | 1.17 | 560 |
| 31 | | SQD-AA05 | 1.22 | 526 |

TABLE 21-continued

| Example No. | Structural formula | LCMS analysis condition No. | Retention time (min) | m/z [M + H]+ |
|---|---|---|---|---|
| 32 | | QC-SMD-TFA05 | 1.64 | 528 |
| 33 | | SQD-AA05 | 1.17 | 588 |
| 34 | | SQD-AA05 | 1.17 | 610 |
| 35 | | SQD-AA05 | 1.19 | 492 |

TABLE 21-continued

| Example No. | Structural formula | LCMS analysis condition No. | Retention time (min) | m/z [M + H]+ |
|---|---|---|---|---|
| 36 | | SQD-AA05 | 1.16 | 510 |
| 37 | | QC-SMD-TFA05 | 1.74 | 570 |
| 38 | | QC-SMD-TFA05 | 1.72 | 526 |
| 39 | | QC-SMD-TFA05 | 1.76 | 567 |

TABLE 21-continued

| Example No. | Structural formula | LCMS analysis condition No. | Retention time (min) | m/z [M + H]+ |
|---|---|---|---|---|
| 40 | | SQD-AA05 | 1.11 | 577 |
| 41 | | QC-SMD-TFA05 | 1.8 | 586 |
| 42 | | QC-SMD-TFA05 | 1.77 | 620 |
| 43 | | QC-SMD-TFA05 | 1.71 | 526 |

TABLE 21-continued
| Example No. | Structural formula | LCMS analysis condition No. | Retention time (min) | m/z [M + H]+ |
|---|---|---|---|---|
| 44 | 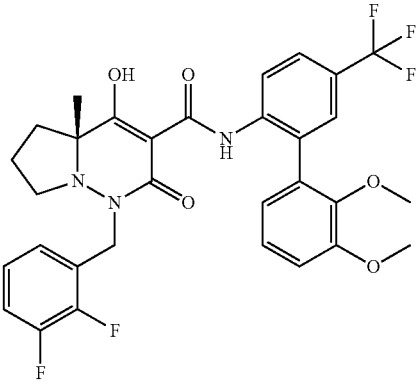 [SMILES: COc1cccc(-c2cc(C(F)(F)F)ccc2NC(=O)C2=C(O)[C@@]3(C)CCCN3N(Cc3cccc(F)c3F)C2=O)c1OC] | SQD-AA05 | 1.22 | 618 |
| 45 | 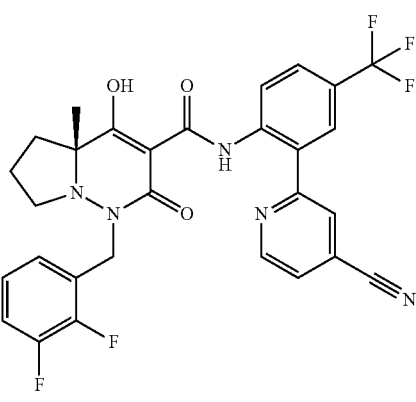 [SMILES: C[C@]12CCCN1N(Cc1cccc(F)c1F)C(=O)C(C(=O)Nc1ccc(C(F)(F)F)cc1-c1cc(C#N)ccn1)=C2O] | SQD-AA05 | 1.16 | 584 |
| 46 | 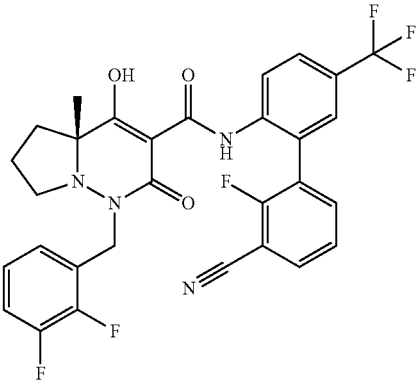 [SMILES: C[C@]12CCCN1N(Cc1cccc(F)c1F)C(=O)C(C(=O)Nc1ccc(C(F)(F)F)cc1-c1cccc(C#N)c1F)=C2O] | SQD-AA05 | 1.17 | 601 |
| 47 | 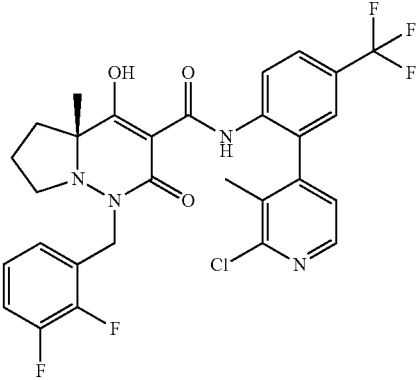 [SMILES: Cc1c(-c2cc(C(F)(F)F)ccc2NC(=O)C2=C(O)[C@@]3(C)CCCN3N(Cc3cccc(F)c3F)C2=O)ccnc1Cl] | QC-SMD-TFA05 | 1.71 | 607 |

TABLE 21-continued

| Example No. | Structural formula | LCMS analysis condition No. | Retention time (min) | m/z [M + H]+ |
|---|---|---|---|---|
| 48 | | QC-SMD-TFA05 | 1.61 | 601 |
| 49 | | QC-SMD-TFA05 | 1.64 | 624 |
| 50 | | QC-SMD-TFA05 | 1.68 | 679 |
| 51 | | QC-SMD-TFA05 | 1.59 | 607 |

TABLE 21-continued

| Example No. | Structural formula | LCMS analysis condition No. | Retention time (min) | m/z [M + H]+ |
|---|---|---|---|---|
| 52 | | QC-SMD-TFA05 | 1.25 | 713 |
| 53 | | QC-SMD-TFA05 | 1.29 | 748 |
| 54 | | QC-SMD-TFA05 | 1.62 | 607 |

TABLE 21-continued

| Example No. | Structural formula | LCMS analysis condition No. | Retention time (min) | m/z [M + H]+ |
|---|---|---|---|---|
| 55 | | QC-SMD-TFA05 | 1.29 | 744 |
| 56 | | QC-SMD-TFA05 | 1.64 | 615 |
| 57 | | QC-SMD-TFA05 | 1.62 | 585 |

TABLE 21-continued

| Example No. | Structural formula | LCMS analysis condition No. | Retention time (min) | m/z [M + H]+ |
|---|---|---|---|---|
| 58 | | QC-SMD-TFA05 | 1.65 | 552 |
| 59 | | QC-SMD-TFA05 | 1.3 | 772 |
| 60 | | QC-SMD-TFA05 | 1.35 | 772 |
| 61 | | QC-SMD-TFA05 | 1.73 | 655 |

TABLE 21-continued
| Example No. | Structural formula | LCMS analysis condition No. | Retention time (min) | m/z [M + H]+ |
|---|---|---|---|---|
| 62 | 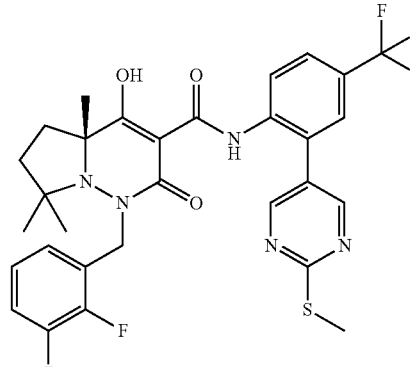 | QC-SMD-TFA05 | 1.72 | 634 |
| 63 | 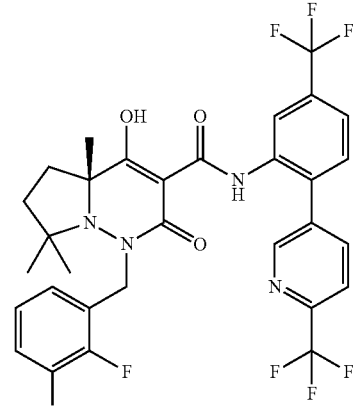 | QC-SMD-TFA05 | 1.73 | 655 |
| 64 | 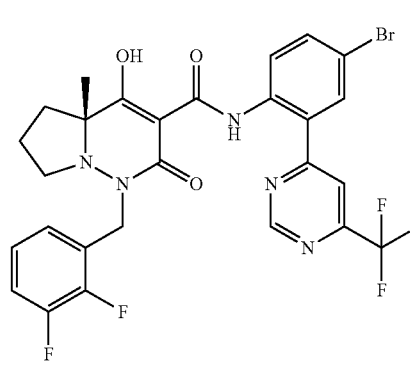 | QC-SMD-TFA05 | 1.65 | 638 |
| 65 | 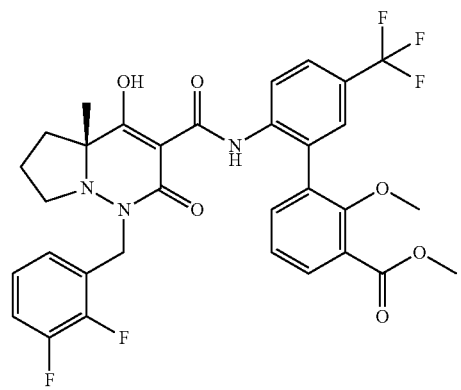 [SMILES: COC(=O)c1cccc(-c2cc(C(F)(F)F)ccc2NC(=O)C2=C(O)[C@@]3(C)CCCN3N(Cc3cccc(F)c3F)C2=O)c1OC] | QC-SMD-TFA05 | 1.67 | 646 |

TABLE 21-continued

| Example No. | Structural formula | LCMS analysis condition No. | Retention time (min) | m/z [M + H]+ |
|---|---|---|---|---|
| 66 | | QC-SMD-TFA05 | 1.73 | 632 |
| 67 | | QC-SMD-TFA05 | 1.61 | 594 |
| 68 | | SQD-AA05 | 1.14 | 618 |
| 69 | | QC-SMD-TFA05 | 1.68 | 608 |

TABLE 21-continued

| Example No. | Structural formula | LCMS analysis condition No. | Retention time (min) | m/z [M + H]+ |
|---|---|---|---|---|
| 70 | | QC-SMD-TFA05 | 1.70 | 628 |
| 71 | | QC-SMD-TFA05 | 1.69 | 671 |
| 72 | | QC-SMD-TFA05 | 1.65 | 620 |
| 73 | | QC-SMD-TFA05 | 1.72 | 638 |

TABLE 21-continued

| Example No. | Structural formula | LCMS analysis condition No. | Retention time (min) | m/z [M + H]+ |
|---|---|---|---|---|
| 74 | | QC-SMD-TFA05 | 1.71 | 594 |
| 75 | | SQD-AA05 | 1.20 | 510 |
| 76 | | SQD-AA05 | 1.19 | 466 |
| 77 | | SQD-AA05 | 1.24 | 492 |

TABLE 21-continued

| Example No. | Structural formula | LCMS analysis condition No. | Retention time (min) | m/z [M + H]+ |
|---|---|---|---|---|
| 78 | | SQD-AA05 | 1.11 | 493 |
| 79 | | SQD-AA05 | 1.10 | 449 |
| 80 | | QC-SMD-TFA05 | 1.67 | 603 |
| 81 | | QC-SMD-TFA05 | 1.40 | 589 |

TABLE 21-continued

| Example No. | Structural formula | LCMS analysis condition No. | Retention time (min) | m/z [M + H]+ |
|---|---|---|---|---|
| 82 | | QC-SMD-TFA05 | 1.58 | 584 |
| 83 | | SQD-AA05 | 1.19 | 609 |
| 84 | | SQD-AA05 | 1.19 | 627 |
| 85 | | QC-SMD-TFA05 | 1.70 | 705 |

TABLE 21-continued

| Example No. | Structural formula | LCMS analysis condition No. | Retention time (min) | m/z [M + H]+ |
|---|---|---|---|---|
| 86 | | QC-SMD-TFA05 | 1.66 | 593 |
| 87 | | QC-SMD-TFA05 | 1.60 | 666 |
| 88 | | SQD-AA05 | 1.16 | 540 |
| 89 | | SQD-AA05 | 1.19 | 482 |

TABLE 21-continued

| Example No. | Structural formula | LCMS analysis condition No. | Retention time (min) | m/z [M + H]+ |
|---|---|---|---|---|
| 90 | | SQD-AA05 | 1.17 | 627 |
| 91 | | SMD-AA05 | 1.71 | 627 |
| 92 | | QC-SMD-TFA05 | 1.66 | 692 |

TABLE 21-continued

| Example No. | Structural formula | LCMS analysis condition No. | Retention time (min) | m/z [M + H]+ |
|---|---|---|---|---|
| 93 | | QC-SMD-TFA05 | 1.72 | 589 |
| 94 | | QC-SMD-TFA05 | 1.59 | 584 |
| 95 | | QC-SMD-TFA05 | 1.60 | 585 |
| 96 | | QC-SMD-TFA05 | 1.68 | 606 |

TABLE 21-continued

| Example No. | Structural formula | LCMS analysis condition No. | Retention time (min) | m/z [M + H]+ |
|---|---|---|---|---|
| 97 | | QC-SMD-TFA05 | 1.71 | 605 |
| 98 | | QC-SMD-TFA05 | 1.65 | 652 |
| 99 | | QC-SMD-TFA05 | 1.60 | 629 |
| 100 | | QC-SMD-TFA05 | 1.64 | 585 |

TABLE 21-continued

| Example No. | Structural formula | LCMS analysis condition No. | Retention time (min) | m/z [M + H]+ |
|---|---|---|---|---|
| 101 | | QC-SMD-TFA05 | 1.65 | 598 |
| 102 | | QC-SMD-TFA05 | 1.29 | 722 |
| 103 | | QC-SMD-TFA05 | 1.30 | 734 |
| 104 | | QC-SMD-TFA05 | 1.28 | 735 |

TABLE 21-continued

| Example No. | Structural formula | LCMS analysis condition No. | Retention time (min) | m/z [M + H]+ |
|---|---|---|---|---|
| 105 | | QC-SMD-TFA05 | 1.64 | 606 |
| 106 | | QC-SMD-TFA05 | 1.25 | 757 |
| 107 | | SMD-TFA05 | 1.27 | 723 |
| 108 | | QC-SMD-TFA05 | 1.30 | 757 |

Although tautomers of for the compounds described in this table exist, for example, ¹H-NMR of Examples 22 and 52 is as follows.

Example 22

Major Tautomer

¹H-NMR (CDCl₃) δ: 16.12 (1H, s), 11.93 (1H, s), 9.35 (1H, s), 8.54 (1H, d, J=8.8 Hz), 7.77 (1H, d, J=8.9 Hz), 7.59 (1H, s), 6.97 (1H, dd, J=7.8, 7.8 Hz), 6.76 (1H, dd, J=7.8, 7.8 Hz), 4.81 (1H, d, J=14.2 Hz), 4.32 (1H, d, J=14.3 Hz), 4.20 (2H, t, J=5.7 Hz), 3.74 (4H, t, J=4.5 Hz), 3.29 (1H, ddd, J=8.8, 8.7, 3.0 Hz), 2.84 (2H, t, J=5.6 Hz), 2.67 (1H, ddd, J=8.8, 8.8, 8.8 Hz), 2.61-2.59 (4H, m), 2.55-2.53 (1H, m), 2.45 (3H, s), 1.74-1.71 (1H, m), 1.67-1.62 (2H, m), 0.99 (3H, s).

Minor Tautomer

¹H-NMR (CDCl₃) δ: 17.93 (1H, s), 12.03 (1H, s), 9.32 (1H, s), 8.36 (1H, d, J=8.9 Hz), 7.77 (1H, d, J=8.9 Hz), 7.61 (1H, s), 7.06 (1H, dd, J=18.5, 10.0 Hz), 6.73 (1H, t, J=10.0 Hz), 5.00 (1H, d, J=14.4 Hz), 4.42 (1H, d, J=14.6 Hz), 4.19 (2H, q, J=6.7 Hz), 3.74 (4H, t, J=4.5 Hz), 3.24-3.22 (1H, m), 2.84 (2H, t, J=5.6 Hz), 2.70-2.66 (1H, m), 2.60 (4H, s), 2.55-2.49 (1H, m), 2.40 (3H, s), 1.67-1.62 (2H, m), 1.44-1.41 (1H, m), 0.79 (3H, s).

Example 52

Major Tautomer

¹H-NMR (CDCl₃) δ: 16.13 (1H, s), 11.97 (1H, s), 8.87 (1H, d, J=5.0 Hz), 8.46 (1H, d, J=8.6 Hz), 7.81 (1H, s), 7.74 (1H, d, J=8.6 Hz), 7.60 (1H, d, J=4.9 Hz), 7.53 (1H, s), 6.99 (1H, dd, J=7.8, 7.8 Hz), 6.78 (1H, dd, J=7.8, 7.8 Hz), 4.83 (1H, d, J=14.3 Hz), 4.31 (1H, d, J=14.3 Hz), 4.20 (2H, t, J=5.7 Hz), 3.74 (4H, t, J=4.2 Hz), 3.31 (1H, ddd, J=8.8, 8.8, 3.0 Hz), 2.85-2.83 (2H, m), 2.69 (1H, ddd, J=8.8, 8.8, 8.8 Hz), 2.61 (4H, brs), 2.56-2.51 (1H, m), 1.75-1.72 (1H, m), 1.67-1.65 (2H, m), 0.99 (3H, s).

Minor Tautomer

¹H-NMR (CDCl₃) δ: 17.91 (1H, s), 12.05 (1H, s), 8.82 (1H, d, J=4.9 Hz), 8.24 (1H, d, J=8.5 Hz), 7.77 (1H, s), 7.74 (1H, d, J=8.6 Hz), 7.58 (1H, d, J=5.0 Hz), 7.54 (1H, brs), 7.06 (1H, t, J=7.8 Hz), 6.73 (1H, t, J=7.7 Hz), 5.01 (1H, d, J=14.4 Hz), 4.43 (1H, d, J=14.5 Hz), 4.19 (2H, dd, J=12.1, 6.2 Hz), 3.74 (4H, t, J=4.2 Hz), 3.27-3.24 (1H, m), 2.84 (2H, s), 2.74-2.72 (1H, m), 2.61 (3H, brs), 2.50-2.46 (1H, m), 1.78-1.63 (3H, m), 1.45-1.42 (1H, m), 0.81 (3H, s).

Example 109

(4aR)—N-[2-(5-Cyano-6-methylpyridin-3-yl)-4-(trifluoromethyl)phenyl]-1-[(2,3-difluorophenyl)methyl]-4-hydroxy-4a-methyl-2-oxo-6,7-dihydro-5H-pyrrolo[1,2-b]pyridazine-3-carboxamide

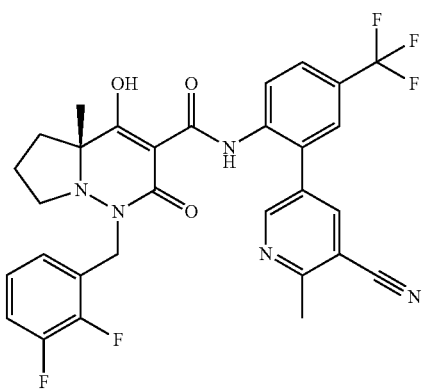 [SMILES: Cc1ncc(-c2cc(C(F)(F)F)ccc2NC(=O)C2=C(O)[C@@]3(C)CCCN3N(Cc3cccc(F)c3F)C2=O)cc1C#N]

(4aR)—N-[2-(6-Chloro-5-cyanopyridin-3-yl)-4-(trifluoromethyl)phenyl]-1-[(2,3-difluorophenyl)methyl]-4-hydroxy-4a-methyl-2-oxo-6,7-dihydro-5H-pyrrolo[1,2-b]pyridazine-3-carboxamide (Example 68) was used as a starting material, and operations similar to those of Reference Example 69 were carried out to obtain the title compound.

LCMS: m/z 598[M+H]⁺

HPLC retention time: 1.63 minutes (analysis condition QC-SMD-TFA05)

Example 110

(4aR)-1-[(2,3-(Difluorophenyl)methyl]-N-[2-[1-(dimethylsulfamoyl)piperidin-4-yl]-4-(trifluoromethyl)phenyl]-4-hydroxy-4a-methyl-2-oxo-6,7-dihydro-5H-pyrrolo[1,2-b]pyridazine-3-carboxamide

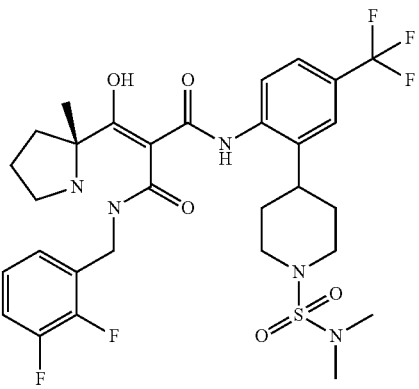 [SMILES: CN(C)S(=O)(=O)N1CCC(c2cc(C(F)(F)F)ccc2NC(=O)/C(C(=O)NCc2cccc(F)c2F)=C(\O)[C@@]2(C)CCCN2)CC1]

First Step

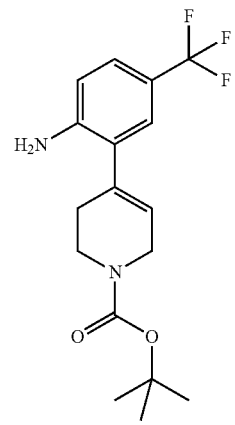 [SMILES: CC(C)(C)OC(=O)N1CC=C(c2cc(C(F)(F)F)ccc2N)CC1]

2-Bromo-4-(trifluoromethyl)aniline and (1-(tert-butoxycarbonyl)-1,2,3,6-tetrahydropyridin-4-yl)boronic acid were used as a reagent and a starting material, respectively, and operations similar to those of Reference Example 13 were carried out to obtain 4-(2-amino-5-(trifluoromethyl)phenyl)-5,6-dihydropyridine-1(2H)-carboxylic acid tert-butyl.

LCMS: m/z 243[M+H—C₄H₉OCO]⁺

HPLC retention time: 1.31 minutes (analysis condition SMD-TFA05)

Second Step

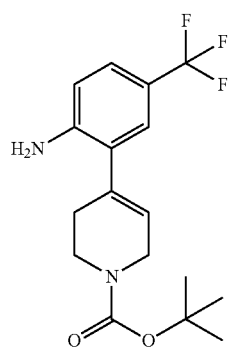 [SMILES: CC(C)(C)OC(=O)N1CC=C(c2cc(C(F)(F)F)ccc2N)CC1]

The aniline derivative obtained in First Step (0.73 g, 2.13 mmol) was dissolved in methanol (21.2 mL), palladium hydroxide-carbon (20 wt. %, 0.15 g, 0.21 mmol) was added, and the mixture was stirred under hydrogen atmosphere at room temperature overnight. After the reaction mixture was filtered through a celite, pad the filtrate was concentrated at reduced pressure to obtain 4-(2-amino-5-(trifluoromethyl)phenyl)piperidine-1-carboxylic acid tert-butyl ester (0.70 g, 91%) as a crude product.

Third Step

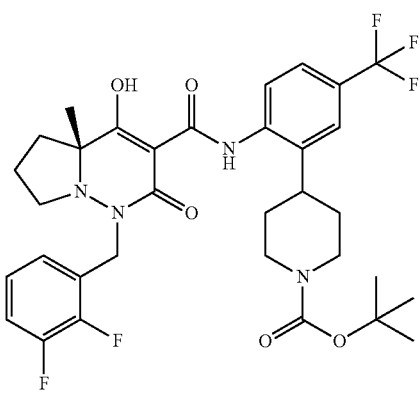 [SMILES: CC(C)(C)OC(=O)N1CCC(c2cc(C(F)(F)F)ccc2NC(=O)C2=C(O)[C@@]3(C)CCCN3N(Cc3cccc(F)c3F)C2=O)CC1]

The aniline derivative obtained in Second Step and the compound described in Reference Example 1-1 were used as a reagent and a starting material, respectively, and operations similar to those of Example 21 were carried out to obtain 4-[2-[[(4aR)-1-[(2,3-difluorophenyl)methyl]-4-hydroxy-4a-methyl-2-oxo-6,7-dihydro-5H-pyrrolo[1,2-b]pyridazine-3-carbonyl]amino]-5-(trifluoromethyl)phenyl]piperidine-1-carboxylic acid tert-butyl.

LCMS: m/z 565[M+H—C₄H₉OCO]⁺

HPLC retention time: 1.78 minutes (analysis condition SMD-TFA05)

Fourth Step

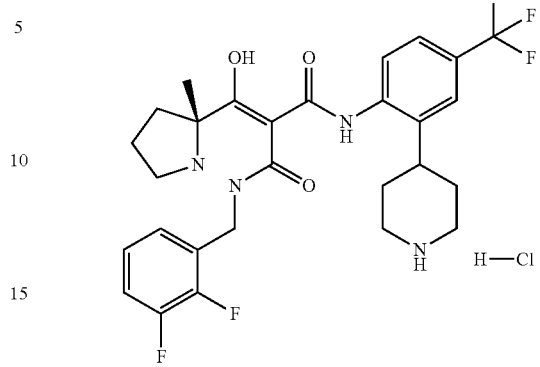

A 4 N hydrogen chloride/dioxane solution (5 mL) was added to the amide derivative obtained in Third Step (0.81 g, 1.23 mmol) at 0° C., and the mixture was stirred at room temperature for 1 hour. The reaction mixture was concentrated at reduced pressure to obtain (4aR)-1-[(2,3-difluorophenyl)methyl]-4-hydroxy-4a-methyl-2-oxo-N-[2-piperidin-4-yl-4-(trifluoromethyl)phenyl]-6,7-dihydro-5H-pyrrolo[1,2-b]pyridazine-3-carboxamide hydrochloride (776 mg) as a yellow amorphous solid.

LCMS: m/z 565[M+H]⁺

HPLC retention time: 1.24 minutes (analysis condition SMD-TFA05)

Fifth Step

The hydrochloride obtained in Fourth Step (0.030 g, 0.050 mmol) was dissolved in N,N-dimethylformamide (0.25 mL), and then triethylamine (0.021 mL, 0.15 mmol) and dimethylsulfamoyl chloride (0.0054 mL, 0.050 mmol) were added at room temperature, and the mixture was stirred for 2 hours. The reaction mixture was purified directly by C18 reverse-phase column chromatography (acetonitrile/water) to obtain the title compound (24 mg, 71%) as a white amorphous solid.

LCMS: m/z 672[M+H]⁺

HPLC retention time: 1.66 minutes (analysis condition QC-SMD-TFA05)

Example 111

(4aR)—N-[2-[5-Cyano-6-(2-oxa-6-azaspiro[3.3]heptan-6-yl)pyridin-3-yl]-4-(trifluoromethyl)phenyl]-1-[(2,3-difluorophenyl)methyl]-4-hydroxy-4a-methyl-2-oxo-6,7-dihydro-5H-pyrrolo[1,2-b]pyridazine-3-carboxamide

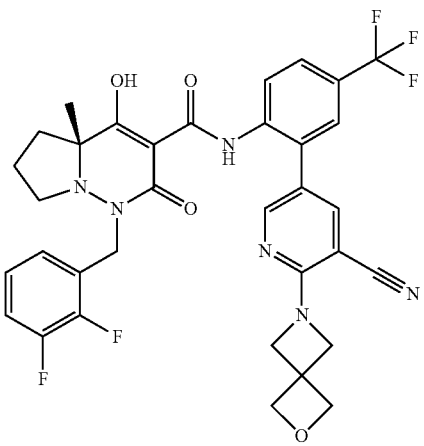 [SMILES: C[C@]12CCCN1N(Cc1cccc(F)c1F)C(=O)C(C(=O)Nc1ccc(C(F)(F)F)cc1-c1cnc(N3CC4(COC4)C3)c(C#N)c1)=C2O]

(4aR)—N-[2-(6-Chloro-5-cyanopyridin-3-yl)-4-(trifluoromethyl)phenyl]-1-[(2,3-difluorophenyl)methyl]-4-hydroxy-4a-methyl-2-oxo-6,7-dihydro-5H-pyrrolo[1,2-b]pyridazine-3-carboxamide (Example 68) (20 mg, 0.032 mmol) was dissolved in 1,2-dichloroethane (0.32 mL) under nitrogen atmosphere, 2-oxa-6-azaspiro[3.3]heptane oxalate (24.5 mg, 0.129 mmol) and N,N-diisopropylethylamine (0.068 mL, 0.388 mmol) were added, and the mixture was stirred at room temperature overnight and at 60° C. for 2 days. A 0.37 M aqueous potassium dihydrogenphosphate solution and dichloromethane were added to the reaction mixture, the mixture was intensely stirred, and subsequently, the water layer was separated by a phase separator, and the organic layer was concentrated at reduced pressure. The resultant residue was purified by C18 reverse-phase column chromatography (30-95% acetonitrile/water) to obtain the title compound (19.7 mg, 89%).

LCMS: m/z 681[M+H]$^+$

HPLC retention time: 0.99 minutes (analysis condition SMD-TFA50)

Example 112

Methyl 2-[[5-[2-[[(4aR)-1-[(2,3-difluorophenyl)methyl]-4-hydroxy-4a-methyl-2-oxo-6,7-dihydro-5H-pyrrolo[1,2-b]pyridazine-3-carbonyl]amino]-5-(trifluoromethyl)phenyl]-3-cyanopyridin-2-yl]-methylamino]acetate

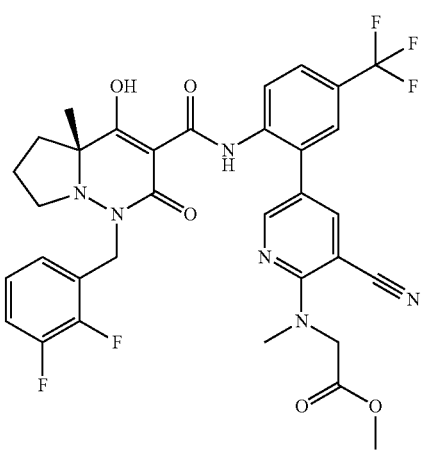 [SMILES: COC(=O)CN(C)c1ncc(-c2cc(C(F)(F)F)ccc2NC(=O)C2=C(O)[C@@]3(C)CCCN3N(Cc3cccc(F)c3F)C2=O)cc1C#N]

N-Methylglycine methyl ester was used as a reagent, and operations similar to those of Example 111 were carried out to synthesize the title compound.

LCMS: m/z 685[M+H]$^+$

HPLC retention time: 1.65 minutes (analysis condition QC-SMD-TFA05)

Example 113

(4aR)—N-[2-(6-Cyano-5-methylsulfanylpyridin-3-yl)-4-(trifluoromethyl)phenyl]-1-[(2,3-difluorophenyl)methyl]-4-hydroxy-4a-methyl-2-oxo-6,7-dihydro-5H-pyrrolo[1,2-b]pyridazine-3-carboxamide

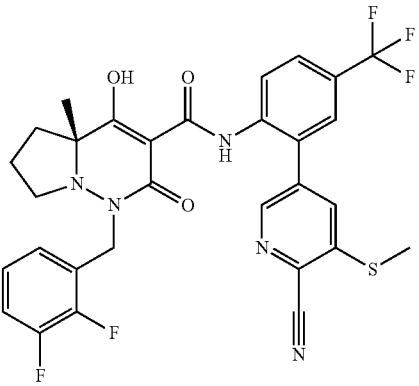 [SMILES: CSc1cc(-c2cc(C(F)(F)F)ccc2NC(=O)C2=C(O)[C@@]3(C)CCCN3N(Cc3cccc(F)c3F)C2=O)cnc1C#N]

(4aR)—N-[2-(6-Cyano-5-nitropyridin-3-yl)-4-(trifluoromethyl)phenyl]-1-[(2,3-difluorophenyl)methyl]-4-hydroxy-4a-methyl-2-oxo-6,7-dihydro-5H-pyrrolo[1,2-b]pyridazine-3-carboxamide (Example 99) (26.1 mg, 0.042 mmol) was dissolved in N,N-dimethylformamide (0.3 mL), sodium thiomethoxide (2.91 mg, 0.042 mmol) was added, and the mixture was stirred at room temperature for 3 days. A 0.37 M aqueous potassium dihydrogenphosphate solution was added to the reaction mixture, and the mixture was extracted with ethyl acetate. The organic layer was washed with a brine, dried over anhydrous magnesium sulfate, filtered, and concentrated at reduced pressure. The resultant residue was purified by C18 reverse-phase column chromatography (30-90% acetonitrile (0.1% formic acid)/water (0.1% formic acid) to obtain the title compound (17.7 mg, 49%).

LCMS: m/z 630[M+H]$^+$

HPLC retention time: 1.04 minutes (analysis condition SMD-TFA50)

Example 114

(4aR)—N-[2-(6-Cyano-5-methoxypyridin-3-yl)-4-(trifluoromethyl)phenyl]-1-[(2,3-difluorophenyl)methyl]-4-hydroxy-4a-methyl-2-oxo-6,7-dihydro-5H-pyrrolo[1,2-b]pyridazine-3-carboxamide

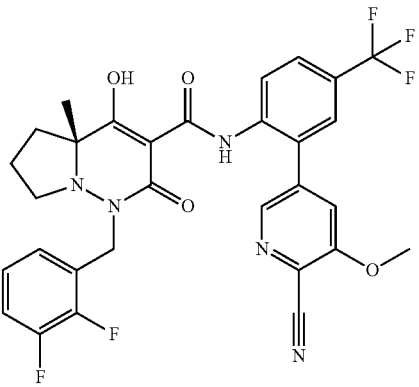

Sodium methoxide was used as a reagent, and operations similar to those of Example 113 were carried out to synthesize the title compound.

LCMS: m/z 614[M+H]$^+$

HPLC retention time: 1.62 minutes (analysis condition QC-SMD-TFA05)

Reference Example 72

7-[4-[[(4aR)-4-Hydroxy-4a-methyl-3-(2-methyl-propoxycarbonyl)-2-oxo-6,7-dihydro-5H-pyrrolo[1,2-b]pyridazin-1-yl]methyl]-2,3-difluorophenyl]hept-6-ynoate

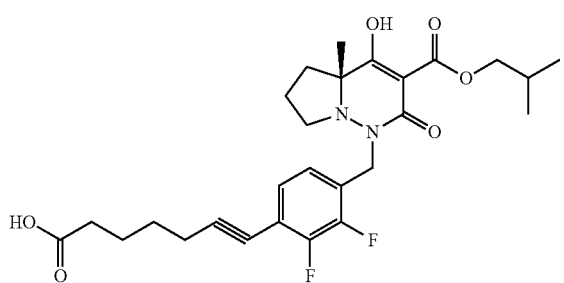 [SMILES: CC(C)COC(=O)C1=C(O)[C@@]2(C)CCCN2N(Cc2ccc(C#CCCCCC(=O)O)c(F)c2F)C1=O]

A suspension of (4aR)-1-[(2,3-difluoro-4-iodophenyl)methyl]-4-hydroxy-4a-methyl-2-oxo-6,7-dihydro-5H-pyrrolo[1,2-b]pyridazine-3-carboxylic acid 2-methylpropyl ester (Reference Example 5) (250 mg, 0.480 mmol), hept-6-ynoic acid (0.182 mL, 1.44 mmol), copper (I) iodide (18.3 mg, 0.0960 mmol), triethylamine (0.335 mL, 2.40 mmol), and bis(triphenylphosphine)palladium (II) chloride (33.7 mg, 0.0480 mmol) in tetrahydrofuran (0.961 mL) was stirred under nitrogen atmosphere at room temperature for 2.5 hours. At the same time, the completely same reaction was run in another vessel on the same scale, and both resultants were combined and purified by C18 reverse-phase column chromatography to obtain the title compound (328 mg, 66%) as yellow oil.

LCMS: m/z 519[M+H]$^+$

HPLC retention time: 1.00 minute (analysis condition SQD-FA05)

Reference Example 73

7-[4-[[(4aR)-4-Hydroxy-4a-methyl-3-(2-methyl-propoxycarbonyl)-2-oxo-6,7-dihydro-5H-pyrrolo[1,2-b]pyridazin-1-yl]methyl]-2,3-difluorophenyl]heptanoate

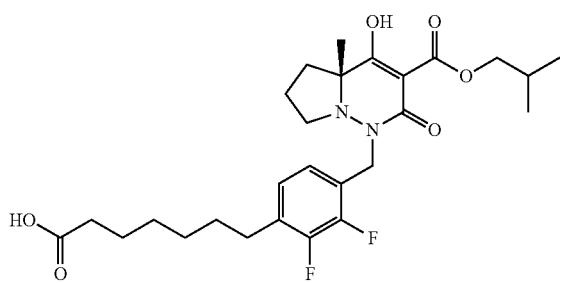 [SMILES: CC(C)COC(=O)C1=C(O)[C@@]2(C)CCCN2N(Cc2ccc(CCCCCCC(=O)O)c(F)c2F)C1=O]

A solution of 7-[4-[[(4aR)-4-hydroxy-4a-methyl-3-(2-methylpropoxycarbonyl)-2-oxo-6,7-dihydro-5H-pyrrolo[1,2-b]pyridazin-1-yl]methyl]-2,3-difluorophenyl]hept-6-ynoic acid (Reference Example 72) (358 mg, 0.69 mmol) and palladium hydroxide-carbon (20 wt. %, about 50% wet with water, 145 mg) in 2,2,2-trifluoroethanol (7 mL) was stirred under hydrogen atmosphere at room temperature for 2 hours. Further, palladium hydroxide-carbon (20 wt. %, about 50% wet with water, 145 mg) was added, and the reaction mixture was stirred at room temperature for 1 hour. After the reaction mixture was filtered through a celite pad, the filtrate was concentrated to obtain the title compound (361 mg, 100%) as light brown oil.

LCMS: m/z 523[M+H]$^+$

HPLC retention time: 1.05 minutes (analysis condition SQD-AA05)

Example 115

7-[4-[[(4aR)-4-Hydroxy-4a-methyl-3-[[2-(6-methyl-sulfanylpyridin-3-v1)-4-(trifluoromethyl)phenyl]carbamoyl]-2-oxo-6,7-dihydro-5H-pyrrolo[1,2-b]pyridazin-1-yl]methyl]-2,3-difluorophenyl]heptanoate

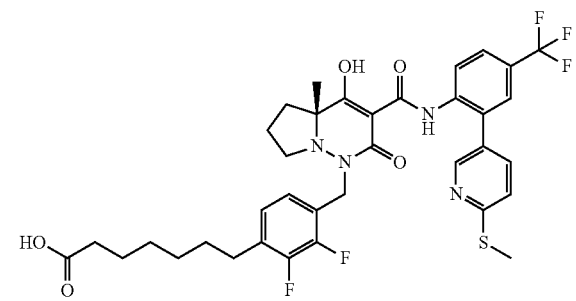 [SMILES: CSc1ccc(-c2cc(C(F)(F)F)ccc2NC(=O)C2=C(O)[C@@]3(C)CCCN3N(Cc3ccc(CCCCCCC(=O)O)c(F)c3F)C2=O)cn1]

7-[4-[[(4aR)-4-Hydroxy-4a-methyl-3-(2-methylpropoxy-carbonyl)-2-oxo-6,7-dihydro-5H-pyrrolo[1,2-b]pyridazin-1-yl]methyl]-2,3-difluorophenyl]heptanoate (Reference Example 73) and 2-(6-(methylthio)pyridin-3-yl)-4-(trifluoromethyl)aniline were used, and operations similar to those of Example 21 were carried out to synthesize the title compound.

LCMS: m/z 733[M+H]$^+$

HPLC retention time: 1.25 minutes (analysis condition SQD-FA05)

Example 116

7-[4-[[(4aR)-3-[[4-Chloro-2-[6-(trifluoromethyl)pyridin-3-yl]phenyl]carbamoyl]-4-hydroxy-4a-methyl-2-oxo-6,7-dihydro-5H-pyrrolo[1,2-b]pyridazin-1-yl]methyl]-2,3-difluorophenyl]heptanoate

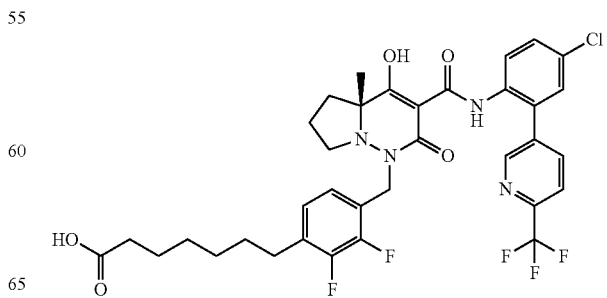

7-[4-[[(4aR)-4-Hydroxy-4a-methyl-3-(2-methylpropoxy-carbonyl)-2-oxo-6,7-dihydro-5H-pyrrolo[1,2-b]pyridazin-1-yl]methyl]-2,3-difluorophenyl]heptanoate (Reference Example 73) and 4-chloro-2-(6-(trifluoromethyl)pyridin-3-yl)aniline were used, and operations similar to those of Example 21 were carried out to synthesize the title compound.

LCMS: m/z 721[M+H]$^+$

HPLC retention time: 1.22 minutes (analysis condition SQD-FA05)

Example 117

7-[4-[[(4aR)-4-Hydroxy-4a-methyl-3-[[2-(6-methyl-sulfanylpyridin-3-yl)-4-(trifluoromethyl)phenyl]carbamoyl]-2-oxo-6,7-dihydro-5H-pyrrolo[1,2-b]pyridazin-1-yl]methyl]-2,3-difluorophenyl]hept-6-ynoate

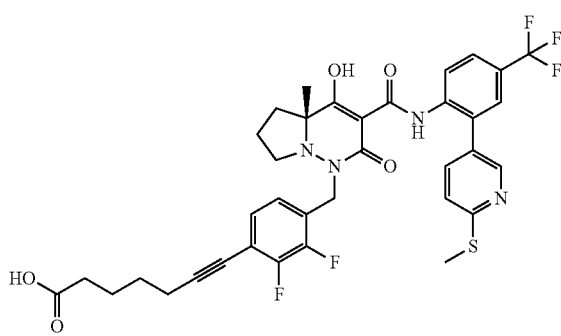 [SMILES: CSc1ccc(-c2cc(C(F)(F)F)ccc2NC(=O)C2=C(O)[C@@]3(C)CCCN3N(Cc3ccc(C#CCCCCC(=O)O)c(F)c3F)C2=O)cn1]

7-[4-[[(4aR)-4-Hydroxy-4a-methyl-3-(2-methylpropoxy-carbonyl)-2-oxo-6,7-dihydro-5H-pyrrolo[1,2-b]pyridazin-1-yl]methyl]-2,3-difluorophenyl]hept-6-ynoic acid (Reference Example 72) was used as a starting material, 2-(6-(methylthio)pyridin-3-yl)-4-(trifluoromethyl)aniline was used as a reagent, and operations similar to those of Example 21 were carried out to synthesize the title compound.

LCMS: m/z 729[M+H]$^+$

HPLC retention time: 1.61 minutes (analysis condition SMD-TFA05)

Example 118

7-[4-[[(4aR)-4-Hydroxy-4a-methyl-3-[[2-(2-methyl-sulfanylpyrimidin-5-yl)-4-(trifluoromethyl)phenyl]carbamoyl]-2-oxo-6,7-dihydro-5H-pyrrolo[1,2-b]pyridazin-1-yl]methyl]-2,3-difluorophenyl]hept-6-ynoate

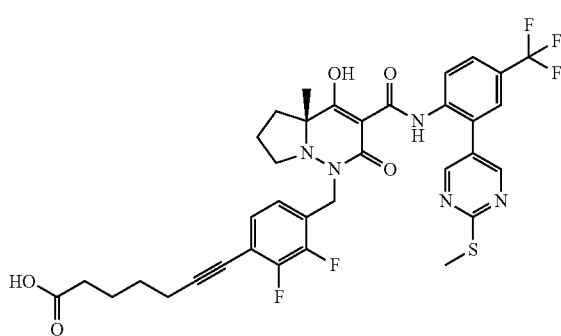 [SMILES: CSc1ncc(-c2cc(C(F)(F)F)ccc2NC(=O)C2=C(O)[C@@]3(C)CCCN3N(Cc3ccc(C#CCCCCC(=O)O)c(F)c3F)C2=O)cn1]

7-[4-[[(4aR)-4-Hydroxy-4a-methyl-3-(2-methylpropoxy-carbonyl)-2-oxo-6,7-dihydro-5H-pyrrolo[1,2-b]pyridazin-1-yl]methyl]-2,3-difluorophenyl]hept-6-ynoic acid (Reference Example 72) and 2-(2-(methylthio)pyrimidin-5-yl)-4-(trifluoromethyl)aniline were used, and operations similar to those of Example 21 were carried out to synthesize the title compound.

LCMS: m/z 730[M+H]$^+$

HPLC retention time: 1.58 minutes (analysis condition SMD-TFA05)

Example 119

7-[4-[[(4aR)-4-Hydroxy-4a-methyl-2-oxo-3-[[4-(trifluoromethyl)-2-[5-(trifluoromethyl)pyridin-3-yl]phenyl]carbamoyl]-6,7-dihydro-5H-pyrrolo[1,2-b]pyridazin-1-yl]methyl]-2,3-difluorophenyl]hept-6-ynoate

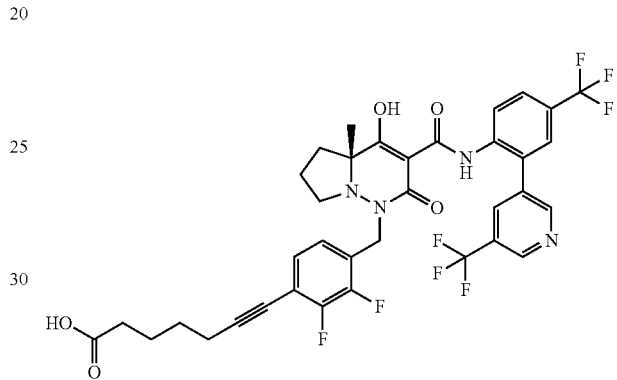

7-[4-[[(4aR)-4-Hydroxy-4a-methyl-3-(2-methylpropoxy-carbonyl)-2-oxo-6,7-dihydro-5H-pyrrolo[1,2-b]pyridazin-1-yl]methyl]-2,3-difluorophenyl]hept-6-ynoic acid (Reference Example 72) and 4-(trifluoromethyl)-2-(5-(trifluoromethyl)pyridin-3-yl)aniline were used, and operations similar to those of Example 21 were carried out to synthesize the title compound.

LCMS: m/z 751[M+H]$^+$

HPLC retention time: 1.60 minutes (analysis condition SMD-TFA05)

Reference Example 74

(4aR)-1-[[4-[4-[[(4S)-2,2-Dimethyl-1,3-dioxolan-4-yl]methoxy]butoxy]-2,3-difluorophenyl]methyl]-4-hydroxy-4a-methyl-2-oxo-6,7-dihydro-5H-pyrrolo[1,2-b]pyridazine-3-carboxylic acid 2-methylpropyl ester

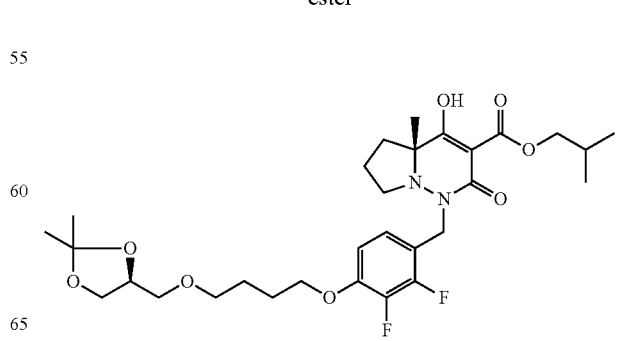

First Step

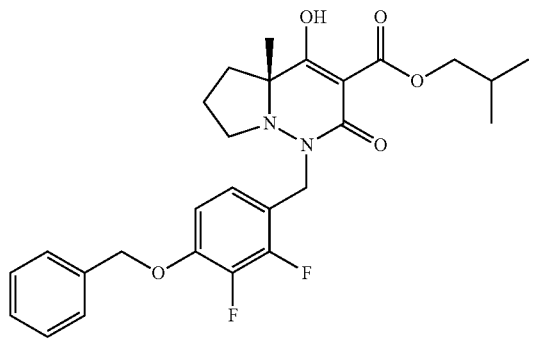 [SMILES: CC(C)COC(=O)C1=C(O)[C@@]2(C)CCCN2N(Cc2ccc(OCc3ccccc3)c(F)c2F)C1=O]

4-(Benzyloxy)-2,3-difluorobenzaldehyde and (R)-2-methyl-pyrrolidine-2-carboxylic acid methyl ester hydrochloride were used as a reagent and a starting material, respectively, and operations similar to those of First Step of Example 1 and Reference Example 1-1 were carried out to synthesize (4aR)-1-[(2,3-difluoro-4-phenylmethoxyphenyl)methyl]-4-hydroxy-4a-methyl-2-oxo-6,7-dihydro-5H-pyrrolo[1,2-b]pyridazine-3-carboxylic acid 2-methylpropyl ester.

Second Step

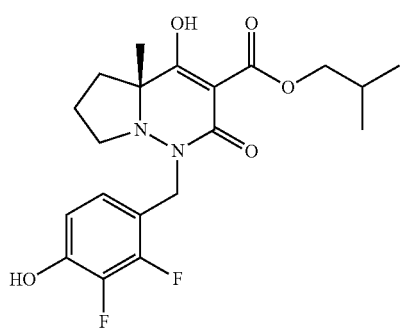 [SMILES: CC(C)COC(=O)C1=C(O)[C@@]2(C)CCCN2N(Cc2ccc(O)c(F)c2F)C1=O]

Palladium-carbon (10 wt. %, 120 mg) was added to a solution of (4aR)-1-[(2,3-difluoro-4-phenylmethoxyphenyl)methyl]-4-hydroxy-4a-methyl-2-oxo-6,7-dihydro-5H-pyrrolo[1,2-b]pyridazine-3-carboxylic acid 2-methylpropyl ester (1.56 g, 3.12 mmol) in ethyl acetate (100 mL), and the mixture was stirred under hydrogen atmosphere at room temperature for 30 minutes. The reaction mixture was filtered through celite, the filtrate was concentrated at reduced pressure, and the residue was purified by column chromatography on silica gel (dichloromethane/methanol) to obtain (4aR)-1-[(2,3-difluoro-4-hydroxyphenyl)methyl]-4-hydroxy-4a-methyl-2-oxo-6,7-dihydro-5H-pyrrolo[1,2-b]pyridazine-3-carboxylic acid 2-methylpropyl ester (1.02 g, 80%).

LCMS: m/z 411 [M+H]$^+$
HPLC retention time: 1.24 minutes (analysis condition SMD-TFA05)

Third Step

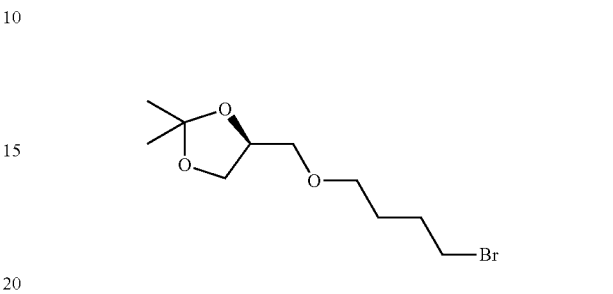

A 60% sodium hydroxide solution (2 mL, 30.3 mmol) was added to a mixture of (S)-(2,2-dimethyl-1,3-dioxolan-4-yl)methanol (2.00 g, 15.1 mmol) and 1,4-dibromobutane (5.42 mL, 45.4 mmol). Tetrabutylammonium hydrogensulfate (257 mg, 0.757 mmol) was added to this mixture, and the resultant was intensely stirred at room temperature overnight. After water was added, the layer was extracted with hexane/diethyl ether (1:4) four times, and the organic layers were combined and dried over magnesium sulfate. After the resultant was filtered, the filtrate was concentrated at reduced pressure, and the residue was purified by column chromatography on silica gel (hexane/ethyl acetate) to obtain (S)-4-((4-bromobutoxy)methyl)-2,2-dimethyl-1,3-dioxolane (2.54 g, 63%) as colorless oil.

Fourth Step

Cesium carbonate (1.20 mg, 3.65 mmol) was added to a solution of (4aR)-1-[(2,3-difluoro-4-hydroxyphenyl)methyl]-4-hydroxy-4a-methyl-2-oxo-6,7-dihydro-5H-pyrrolo[1,2-b]pyridazine-3-carboxylic acid 2-methylpropyl ester (500 mg, 1.22 mmol) and (S)-4-((4-bromobutoxy)methyl)-2,2-dimethyl-1,3-dioxolane (374 mg, 1.40 mmol) in acetonitrile (15.2 mL), and the mixture was stirred at 70° C. for 1 hour. After the mixture was cooled to room temperature, a 0.37 M aqueous potassium dihydrogenphosphate solution was added, and the aqueous layer was extracted with ethyl acetate. The organic layers were combined, washed with a brine, and dried over magnesium sulfate. After the resultant was filtered, the filtrate was concentrated at reduced pressure, and the residue was purified by column chromatography on silica gel (dichloromethane/methanol) to obtain the title compound (414 mg, 57%).

LCMS: m/z 597[M+H]$^+$
HPLC retention time: 1.52 minutes (analysis condition SMD-TFA05)

Example 120

(4aR)-1-[[4-[4-[(2R)-2,3-Dihydroxypropoxy]butoxy]-2,3-difluorophenyl]methyl]-4-hydroxy-4a-methyl-N-[2-(6-methylsulfanylpyridin-3-yl)-4-(trifluoromethyl)phenyl]-2-oxo-6,7-dihydro-5H-pyrrolo[1,2-b]pyridazine-3-carboxamide

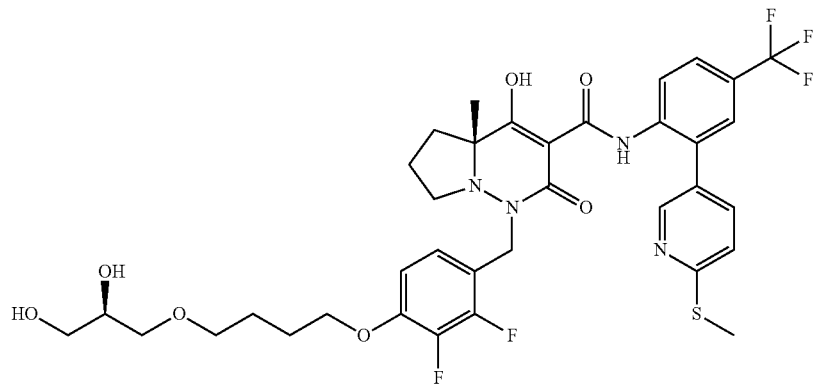 [SMILES: CSc1ccc(-c2cc(C(F)(F)F)ccc2NC(=O)C2=C(O)[C@@]3(C)CCCN3N(Cc3ccc(OCCCCOC[C@H](O)CO)c(F)c3F)C2=O)cn1]

(4aR)-1-[[4-[4-[[(4S)-2,2-Dimethyl-1,3-dioxolan-4-yl]methoxy]butoxy]-2,3-difluorophenyl]methyl]-4-hydroxy-4a-methyl-2-oxo-6,7-dihydro-5H-pyrrolo[1,2-b]pyridazine-3-carboxylic acid 2-methylpropyl ester (Reference Example 74) (10.6 mg, 0.018 mmol) and 2-(6-(methylthio)pyridin-3-yl)-4-(trifluoromethyl)aniline (5.1 mg, 0.018 mmol) were dissolved in toluene (0.5 mL), and the mixture was stirred at 100° C. for 1 hour. The reaction mixture was concentrated at reduced pressure, the resultant residue was dissolved in methanol (0.5 mL), p-toluenesulfonic acid.monohydrate (3.4 mg, 0.018 mmol) was added, and the mixture was stirred at room temperature for 1 hour and a half. Water was added to the reaction mixture, and the resultant white turbid solution was purified by C18 reverse-phase column chromatography (30-90% acetonitrile (0.1% trifluoroacetic acid)/water (0.1% trifluoroacetic acid)) to obtain the title compound (6.3 mg, 46%) as a light brown amorphous solid.

LCMS: m/z 767[M+H]$^+$

HPLC retention time: 1.51 minutes (analysis condition QC-SMD-TFA05)

Example 121

(4aR)—N-[4-Chloro-2-[6-(trifluoromethyl)pyridin-3-yl]phenyl]-1-[[4-[4-[(2R)-2,3-dihydroxypropoxy]butoxy]-2,3-difluorophenyl]methyl]-4-hydroxy-4a-methyl-2-oxo-6,7-dihydro-5H-pyrrolo[1,2-b]pyridazine-3-carboxamide

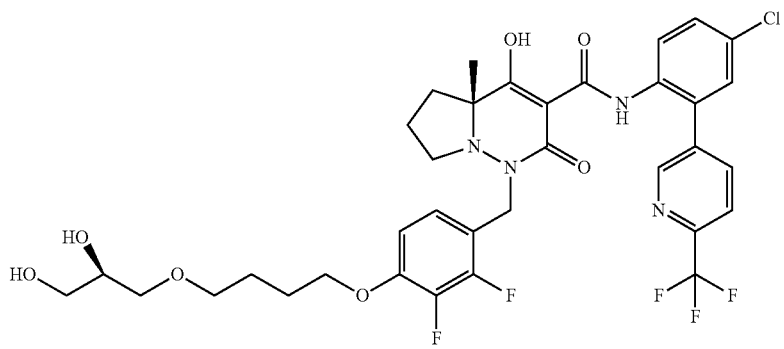 [SMILES: C[C@]12CCCN1N(Cc1ccc(OCCCCOC[C@H](O)CO)c(F)c1F)C(=O)C(C(=O)Nc1ccc(Cl)cc1-c1ccc(C(F)(F)F)nc1)=C2O]

(4aR)-1-[[4-[4-[[(4S)-2,2-Dimethyl-1,3-dioxolan-4-yl]methoxy]butoxy]-2,3-difluorophenyl]methyl]-4-hydroxy-4a-methyl-2-oxo-6,7-dihydro-5H-pyrrolo[1,2-b]pyridazine-3-carboxylic acid 2-methylpropyl ester (Reference Example 74) and 4-chloro-2-(6-(trifluoromethyl)pyridin-3-yl)aniline were used, and operations similar to those of Example 120 were carried out to synthesize the title compound.

LCMS: m/z 755[M+H]+

HPLC retention time: 1.50 minutes (analysis condition QC-SMD-TFA05)

Example 122

(4aR)—N-[4-Bromo-2-(6-chloropyridin-3-yl)phenyl]-1-[(2,3-difluorophenyl)methyl]-4-hydroxy-4a-methyl-2-oxo-6,7-dihydro-5H-pyrrolo[1,2-b]pyridazine-3-carboxamide

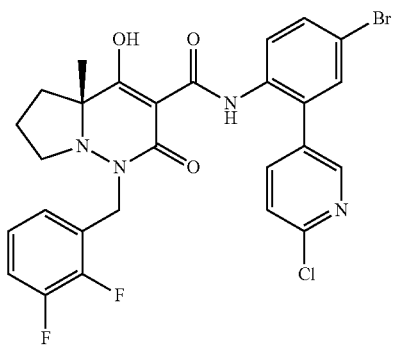 [SMILES: C[C@]12CCCN1N(Cc1cccc(F)c1F)C(=O)C(C(=O)Nc1ccc(Br)cc1-c1ccc(Cl)nc1)=C2O]

Dimethoxyethane (0.2 mL), ethylene glycol (0.2 mL), and water (0.1 mL) were added to (4aR)—N-(4-bromo-2-iodophenyl)-1-[(2,3-difluorophenyl)methyl]-4-hydroxy-4a-methyl-2-oxo-6,7-dihydro-5H-pyrrolo[1,2-b]pyridazine-3-carboxamide (Example 331) (14.8 mg, 0.02 mmol), potassium carbonate (9.7 mg, 0.07 mmol), tetrakis(triphenylphosphine)palladium (2.3 mg, 0.002 mmol), and (6-chloropyridin-3-yl)boronic acid (3.1 mg, 0.02 mmol), and the mixture was stirred at 100° C. for 2 hours. The insolubles were filtered, and the filtrate was purified directly by HPLC (YMC-Actus ODS-A 20×100 mm 0.005 mm, 0.1% formic acid acetonitrile/0.1% formic acid water) to obtain the title compound (4.8 mg, 40%) as a white amorphous solid.

LCMS: m/z 604[M+H]+

HPLC retention time: 0.89 minutes (analysis condition SQD-FA05)

Reference Example 75

((4S,5S)-5-((Hept-6-yn-1-yloxy)methyl)-2,2-dimethyl-1,3-dioxolan-4-yl)methanol

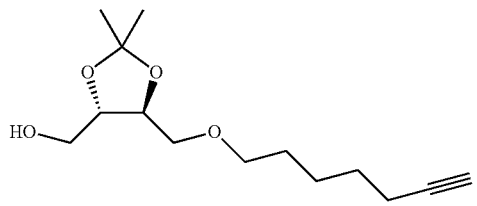 [SMILES: C#CCCCCCOC[C@@H]1OC(C)(C)O[C@H]1CO]

Sodium hydride (60 wt. %, a mineral oil dispersion, 36 mg, 0.824 mmol) was added to a solution of ((4S,5S)-2,2-dimethyl-1,3-dioxolane-4,5-diyl)dimethanol (133 mg, 0.824 mmol) in N,N-dimethylformamide (1.1 mL) at room temperature. After the reaction mixture was stirred at room temperature for 30 minutes, hept-6-yn-1-yl methanesulfonate (105 mg, 0.550 mmol) was added, and the mixture was stirred at room temperature overnight. Water was slowly added to the reaction mixture, and the resultant was extracted with ethyl acetate. The organic layers were combined and concentrated at reduced pressure, and the residue was purified by column chromatography on silica gel to obtain ((4S,5S)-5-((hept-6-yn-1-yloxy)methyl)-2,2-dimethyl-1,3-dioxolan-4-yl)methanol (99.6 mg, 71%).

Reference Example 76

(R)-4-((3-Bromopropoxy)methyl)-2,2-dimethyl-1,3-dioxolane

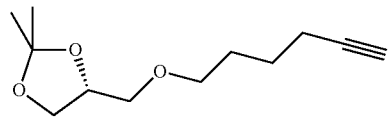

(R)-(−)-2,2-Dimethyl-1,3-dioxolane-4-methanol (615 mg, 4.66 mmol) 6-bromo-1-hexyne (500 mg, 3.1 mmol) was dissolved in N,N-dimethylformamide (10 mL), sodium hydride (60 wt. %, a mineral oil dispersion, 186 mg, 4.66 mmol) was added, and the mixture was stirred at room temperature for 12 hours. The reaction mixture was added to water and extracted with diethyl ether. After the organic layer was washed with a brine and dried over sodium sulfate, the resultant was concentrated at reduced pressure. The resultant residue was purified by column chromatography on silica gel to obtain (R)-4-((hex-5-yn-1-yloxy)methyl)-2,2-dimethyl-1,3-dioxolane (390 mg, 59%) as clear liquid.

$^1$H-NMR (CDCl$_3$) δ: 4.24 (1H, dt, J=12.0, 6.4 Hz), 4.04 (1H, dd, J=8.0, 6.4 Hz), 3.71 (1H, dd, J=8.3, 6.4 Hz), 3.54-3.44 (3H, m), 3.41 (1H, dd, J=11.0, 5.0 Hz), 2.20 (4H, td, J=7.0, 3.0 Hz), 1.92 (4H, t, J=3.0 Hz), 1.72-1.64 (2H, m), 1.62-1.53 (2H, m), 1.40 (3H, s), 1.34 (3H, s).

Reference Example 77

4-(Prop-2-yn-1-yl)morpholin-3-one

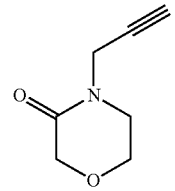

Sodium hydride (60 wt. %, a mineral oil dispersion, 187 mg, 4.68 mmol) was added to a solution of morpholin-3-one (430 mg, 4.25 mmol) in tetrahydrofuran (5 mL) at 0° C., and the mixture was stirred at room temperature for 10 minutes, and 3-bromoprop-1-yne (607 mg, 5.1 mmol) was added to the reaction mixture, and the mixture was stirred at room temperature for 2 hours. The reaction mixture was diluted with ethyl acetate (50 mL), and after the reaction mixture was washed serially with a saturated aqueous ammonium chloride solution, water, and a brine and dried over magnesium sulfate, the resultant was concentrated at reduced pressure. The resultant residue was purified by column chromatography on silica gel to obtain the title compound (312 mg, 53%) as clear oil.

¹H-NMR (CDCl₃) δ: 4.29 (2H, d, J=2.4 Hz), 4.19 (2H, s), 3.93 (2H, t, J=5.2 Hz), 3.51 (2H, t, J=5.2 Hz), 2.25 (1H, m).

Example 123

(4aR)-1-[[2,3-Difluoro-4-[3-(4-hydroxybutoxy)prop-1-ynil]phenyl]methyl]-N-[2-(2,3-dimethoxyphenyl)-4-(trifluoromethyl)phenyl]-4-hydroxy-4a-methyl-2-oxo-6,7-dihydro-5H-pyrrolo[1,2-b]pyridazine-3-carboxamide

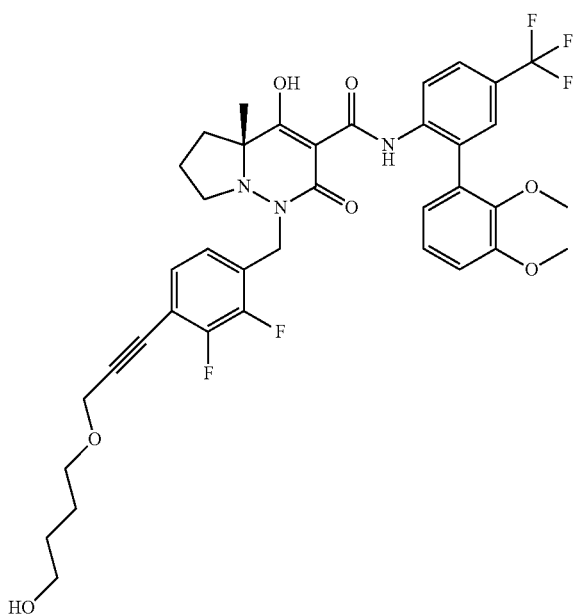 [SMILES: COc1cccc(-c2cc(C(F)(F)F)ccc2NC(=O)C2=C(O)[C@@]3(C)CCCN3N(Cc3ccc(C#CCOCCCCO)c(F)c3F)C2=O)c1OC]

4-(Prop-2-yn-1-yloxy)butan-1-ol (15.5 mg, 0.121 mmol) and triethylamine (0.020 mL, 0.141 mmol) were added to a solution of (4aR)-1-[2,3-(difluoro-4-iodophenyl)methyl]-N-[2-(2,3-dimethoxyphenyl)-4-(trifluoromethyl)phenyl]-4-hydroxy-4a-methyl-2-oxo-6,7-dihydro-5H-pyrrolo[1,2-b]pyridazine-3-carboxamide (Example 321) (30 mg, 0.040 mmol), bis(triphenylphosphine)palladium (II) chloride (2.83 mg, 0.0404 mmol), and copper (I) iodide (1.54 mg, 0.0081 mmol) in N,N-dimethylformamide (0.40 mL) under nitrogen atmosphere at 0° C. The reaction mixture was stirred at room temperature for 14 hours. Formic acid was added to the reaction mixture, and the mixture was purified directly by C18 reverse-phase column chromatography to obtain the title compound (15 mg, 50%) as a white amorphous solid.

LCMS: m/z 744[M+H]⁺

HPLC retention time: 1.63 minutes (analysis condition QC-SMD-TFA05)

Example 124

(4aR)-1-[[2,6-Difluoro-4-[7-[(2S,3S)-2,3,4-trihydroxybutoxy]hept-1-ynil]phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide

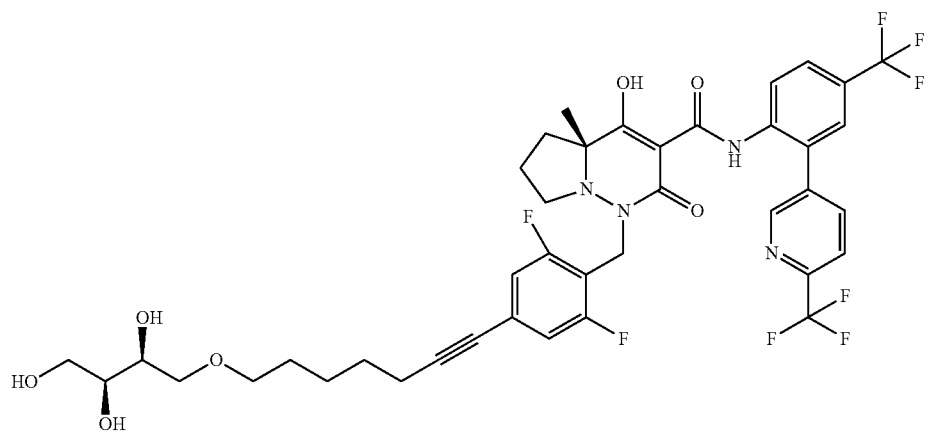 [SMILES: C[C@]12CCCN1N(Cc1c(F)cc(C#CCCCCCOC[C@H](O)[C@@H](O)CO)cc1F)C(=O)C(C(=O)Nc1ccc(C(F)(F)F)cc1-c1ccc(C(F)(F)F)nc1)=C2O]

((4S,5S)-2,2-Dimethyl-1,3-dioxolane-4,5-diyl)dimethanol (23.9 mg, 0.093 mmol) and triethylamine (0.019 mL, 0.140 mmol) were added to a solution of (4aR)-1-[(2,6-difluoro-4-iodophenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide (Example 322) (35 mg, 0.047 mmol), bis(triphenylphosphine)palladium (II) chloride (3.27 mg, 0.0465 mmol), and copper (I) iodide (1.77 mg, 0.0093 mmol), in N,N-dimethylformamide (0.47 mL) under nitrogen atmosphere at 0° C. The reaction mixture was stirred at room temperature overnight. Trifluoroacetic acid/water (1:1, 1.4 mL) and dimethyl sulfoxide (0.7 mL) were added to the reaction mixture, and the mixture was stirred at room temperature for 1 hour. The reaction mixture was purified directly by C18 reverse-phase column chromatography to obtain the title compound (32 mg, 82%) as an orange amorphous solid.

LCMS: m/z 841[M+H]$^+$

HPLC retention time: 0.90 minutes (analysis condition SMD-TFA50)

Example 125

(4aR)-1-[[2,6-Difluoro-4-[7-[(2S,3S)-2,3,4-trihydroxybutoxy]heptyl]phenyl]methyl-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide

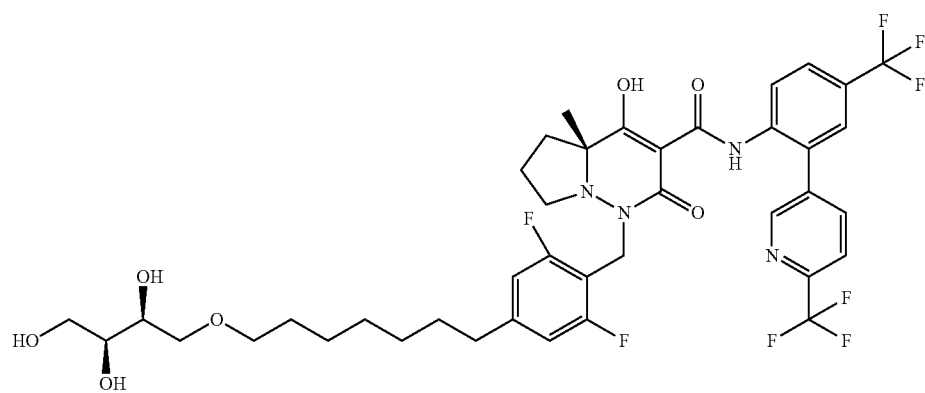 [SMILES: C[C@]12CCCN1N(Cc1c(F)cc(CCCCCCCOC[C@H](O)[C@@H](O)CO)cc1F)C(=O)C(C(=O)Nc1ccc(C(F)(F)F)cc1-c1ccc(C(F)(F)F)nc1)=C2O]

A suspension of (4aR)-1-[[2,6-difluoro-4-[7-[(2S,3S)-2,3,4-trihydroxybutoxy]hept-1-ynil]phenyl]methyl]-4-hydroxy-4a-methyl-2-oxo-N-[4-(trifluoromethyl)-2-[6-(trifluoromethyl)-pyridin-3-yl]phenyl]-6,7-dihydro-5H-pyrrolo[1,2-b]pyridazine-3-carboxamide (Example 124) (20 mg, 0.024 mmol) and palladium hydroxide-carbon (20 wt. %, 3.34 mg, 0.00476 mmol) in ethyl acetate was stirred under hydrogen atmosphere at room temperature for 10 hours. The reaction mixture was filtered through a celite pad, and the filtrate was concentrated at reduced pressure. The residue was purified by C18 reverse-phase column chromatography to obtain the title compound (11.5 mg, 57%) as a colorless amorphous solid.

LCMS: m/z 845[M+H]$^+$

HPLC retention time: 1.60 minutes (analysis condition QC-SMD-TFA05)

Example 126

(4aR)-1-[(4-Ethynyl-2,3-difluorophenyl)methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide

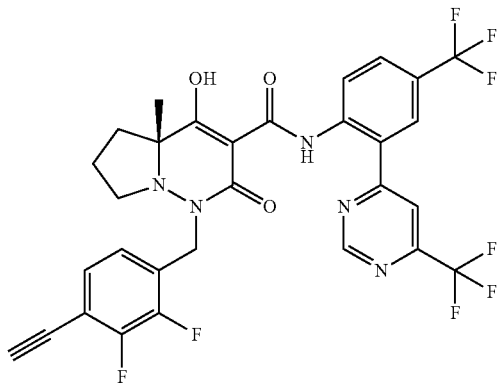 [SMILES: C#Cc1ccc(CN2C(=O)C(C(=O)Nc3ccc(C(F)(F)F)cc3-c3cc(C(F)(F)F)ncn3)=C(O)[C@@]3(C)CCCN23)c(F)c1F]

Triisopropylsilyl acetylene was used as a reagent, and operations similar to those of First Step of Example 123 were carried out to obtain (4aR)-1-[[2,3-difluoro-4-[2-tri(propan-2-yl)silylethynyl]phenyl]methyl]-4-hydroxy-4a-methyl-2-oxo-N-[4-(trifluoromethyl)-2-[6-(trifluoromethyl) pyrimidin-4-yl]phenyl]-6,7-dihydro-5H-pyrrolo[1,2-b] pyridazine-3-carboxamide as a crude product. The obtained crude product was dissolved in tetrahydrofuran (0.15 mL), a 1 M tetrahydrofuran solution (0.12 mL) of tetrabutylammonium fluoride was added, and the mixture was stirred at room temperature for 1 hour. Trifluoroacetic acid (0.5 mL), water (0.5 mL), and dimethylsulfoxide (1 mL) were added to the reaction mixture, and the mixture was purified by C18 reverse-phase column chromatography to obtain the title compound (22 mg, 84%) as a white amorphous solid.

LCMS: m/z 652[M+H]$^+$

HPLC retention time: 0.87 minutes (analysis condition SQD-FA50).

The appropriate iodide derivatives of Examples 319-323 and appropriate terminal alkyne reagents were used, and operations similar to those of Example 123 were carried out to synthesize the compounds described in the following Table.

TABLE 22
| Example No. | Structural formula | LCMS analysis condition No. | Retention time (min) | m/z [M + H]+ |
|---|---|---|---|---|
| 127 | 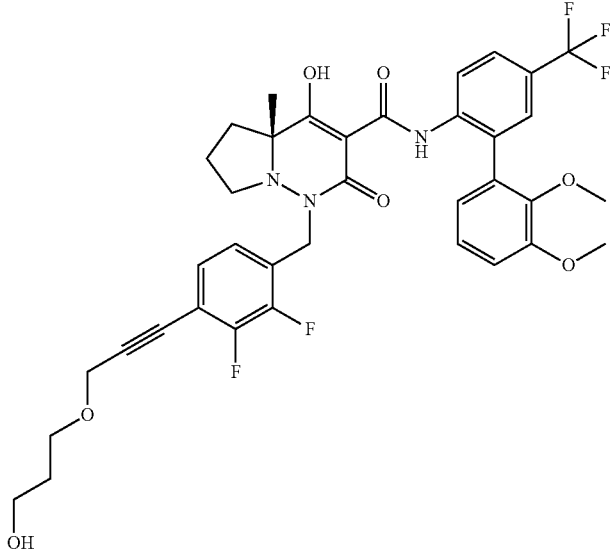 [SMILES: COc1cccc(-c2cc(C(F)(F)F)ccc2NC(=O)C2=C(O)[C@@]3(C)CCCN3N(Cc3ccc(C#CCOCCCO)c(F)c3F)C2=O)c1OC] | SQD-AA05 | 1.18 | 730 |
| 128 | 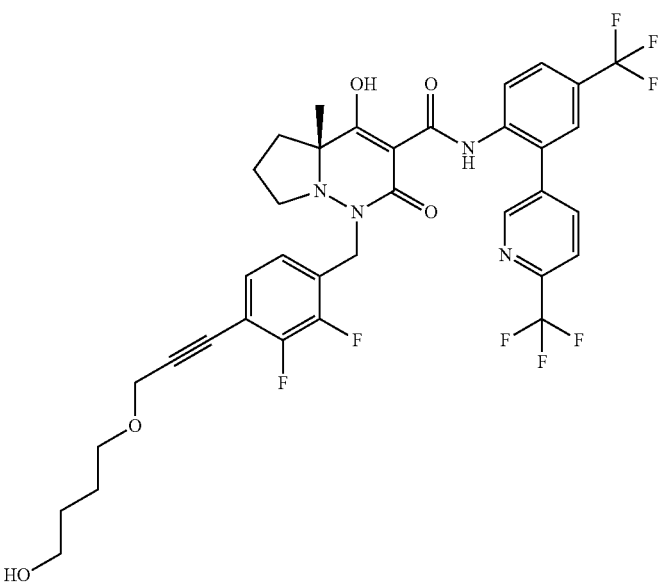 [SMILES: C[C@]12CCCN1N(Cc1ccc(C#CCOCCCCO)c(F)c1F)C(=O)C(C(=O)Nc1ccc(C(F)(F)F)cc1-c1ccc(C(F)(F)F)nc1)=C2O] | QC-SMD-TFA05 | 1.60 | 753 |
| 129 | 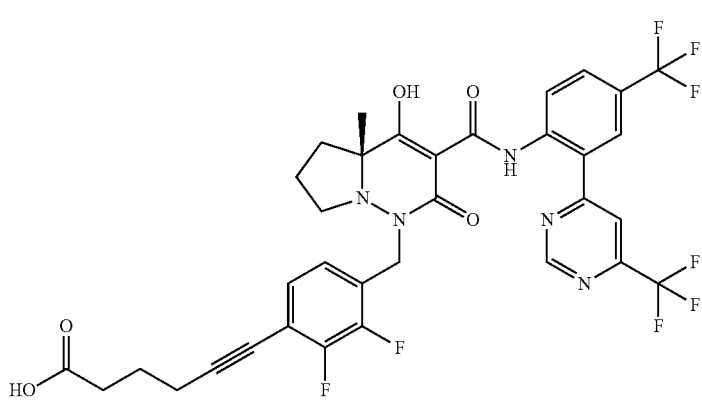 [SMILES: C[C@]12CCCN1N(Cc1ccc(C#CCCCC(=O)O)c(F)c1F)C(=O)C(C(=O)Nc1ccc(C(F)(F)F)cc1-c1cc(C(F)(F)F)ncn1)=C2O] | QC-SMD-TFA05 | 1.62 | 738 |

TABLE 22-continued

| Example No. | Structural formula | LCMS analysis condition No. | Retention time (min) | m/z [M + H]+ |
|---|---|---|---|---|
| 130 | | QC-SMD-TFA05 | 1.69 | 735 |
| 131 | | SQD-AA05 | 1.14 | 631 |
| 132 | | QC-SMD-TFA05 | 1.33 | 750 |

TABLE 22-continued
| Example No. | Structural formula | LCMS analysis condition No. | Retention time (min) | m/z [M + H]+ |
|---|---|---|---|---|
| 133 | 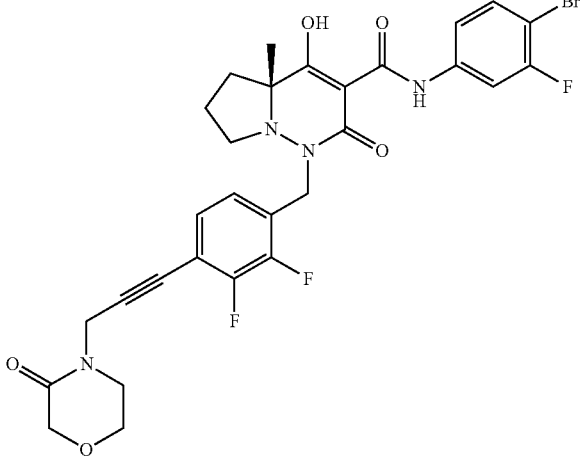 | QC-SMD-TFA05 | 1.56 | 648 |
| 134 | 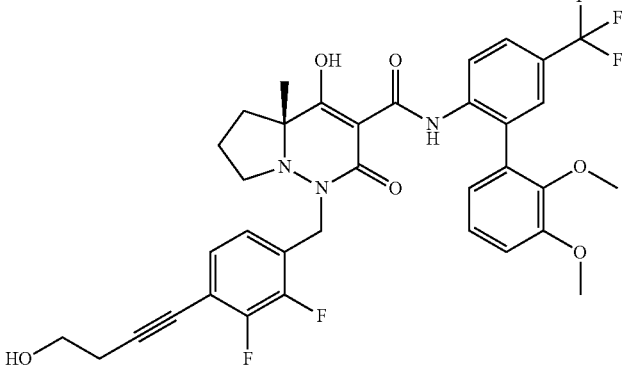 | QC-SMD-TFA05 | 1.60 | 686 |
| 135 | 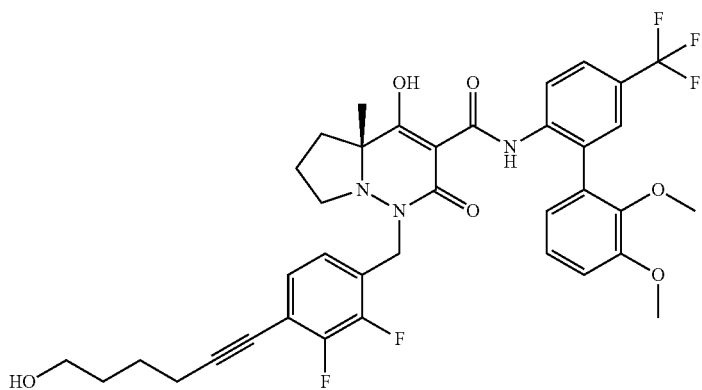 [SMILES: COc1cccc(-c2cc(C(F)(F)F)ccc2NC(=O)C2=C(O)[C@@]3(C)CCCN3N(Cc3ccc(C#CCCCCO)c(F)c3F)C2=O)c1OC] | QC-SMD-TFA05 | 1.65 | 714 |

TABLE 22-continued

| Example No. | Structural formula | LCMS analysis condition No. | Retention time (min) | m/z [M + H]+ |
|---|---|---|---|---|
| 136 | | QC-SMD-TFA05 | 1.57 | 804 |
| 137 | | QC-SMD-TFA05 | 1.58 | 716 |
| 138 | | QC-SMD-TFA05 | 1.62 | 700 |

TABLE 22-continued

| Example No. | Structural formula | LCMS analysis condition No. | Retention time (min) | m/z [M + H]⁺ |
|---|---|---|---|---|
| 139 | 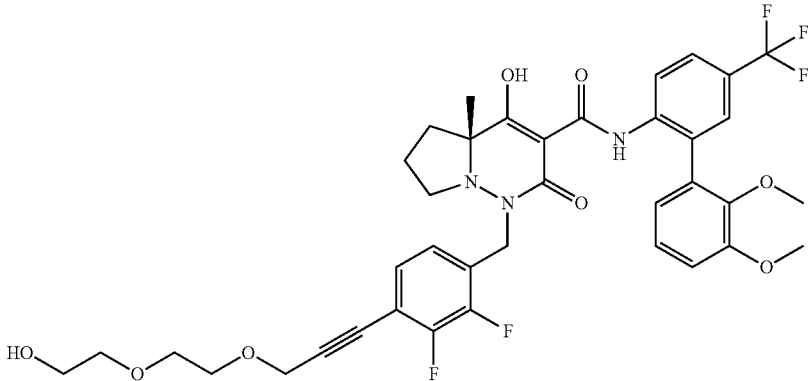 [SMILES: COc1cccc(-c2cc(C(F)(F)F)ccc2NC(=O)C2=C(O)[C@@]3(C)CCCN3N(Cc3ccc(C#CCOCCOCCO)c(F)c3F)C2=O)c1OC] | QC-SMD-TFA05 | 1.57 | 760 |
| 140 | 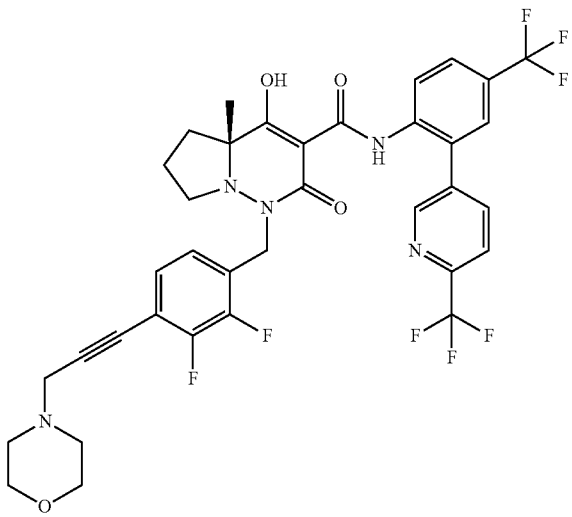 [SMILES: C[C@]12CCCN1N(Cc1ccc(C#CCN3CCOCC3)c(F)c1F)C(=O)C(C(=O)Nc1ccc(C(F)(F)F)cc1-c1ccc(C(F)(F)F)nc1)=C2O] | QC-SMD-TFA05 | 1.34 | 750 |

Although tautomers of some of the compounds described in this table exist, isomers may be observed in some cases and not in other cases according to the type of the solvent for measurement. For example, ¹H-NMR of Example 129 (dimethylsulfoxide-D6) and Example 140 (chloroform-D) is as follows.

Example 129

¹H-NMR (DMSO-D₆) δ: 16.58 (1H, brs), 12.80 (1H, brs), 12.15 (1H, brs), 9.59 (1H, s), 8.59-8.56 (1H, brm), 8.48-8.38 (1H, m), 8.27 (1H, brs), 7.99 (1H, d, J=9.8 Hz), 7.28 (1H, q, J=6.8 Hz), 7.24 (1H, q, J=7.3 Hz), 5.11 (1H, d, J=14.7 Hz), 4.47-4.38 (1H, m), 3.41-3.30 (2H, m), 2.73 (1H, q, J=8.6 Hz), 2.54 (2H, t, J=6.4 Hz), 2.49-2.36 (1H, m), 2.40 (2H, t, J=7.8 Hz), 1.84-1.75 (2H, m), 1.63 (2H, brs), 0.92 (3H, brs).

Example 140

Major Tautomer

¹H-NMR (CDCl₃) δ: 11.82 (1H, s), 8.78 (1H, d, J=2.0 Hz), 8.44 (1H, d, J=8.6 Hz), 7.97 (1H, dd, J=8.1, 1.9 Hz), 7.86 (1H, d, J=8.2 Hz), 7.73 (1H, dd, J=8.7, 1.9 Hz), 7.56 (1H, d, J=1.8 Hz), 7.15-7.11 (1H, m), 6.98-6.94 (1H, m), 4.84 (1H, d, J=14.3 Hz), 4.32 (1H, d, J=13.9 Hz), 3.85-3.79 (4H, m), 3.68 (2H, s), 3.27 (1H, td, J=8.7, 3.2 Hz), 2.83-2.77 (4H, m), 2.73-2.64 (1H, m), 2.58-2.48 (1H, m), 1.80-1.58 (3H, m), 0.99 (3H, s).

Minor Tautomer

¹H-NMR (CDCl₃) δ: 11.91 (1H, s), 8.72 (1H, d, J=2.2 Hz), 8.19 (1H, d, J=8.2 Hz), 7.96-7.92 (1H, m), 7.80 (1H, d, J=8.2 Hz), 7.75-7.71 (1H, m), 7.58-7.55 (1H, m), 7.17-7.07 (1H, m), 6.99-6.93 (1H, m), 5.07 (1H, d, J=14.7 Hz), 4.47 (1H, d, J=14.9 Hz), 3.79-3.85 (4H, m), 3.67 (2H, s), 3.30-3.20 (1H, m), 2.83-2.77 (4H, m), 2.73-2.64 (1H, m), 2.58-2.48 (1H, m), 1.81-1.58 (3H, m), 0.79 (3H, s).

The appropriate iodide derivatives of Examples 319 to 323 and appropriate terminal alkyne reagents were used, and operations similar to those of Example 123 and Example 125 were carried out to synthesize the compounds described in the following Table.

TABLE 23

| Example No. | Structural formula | LCMS analysis condition No. | Retention time (min) | m/z [M + H]+ |
|---|---|---|---|---|
| 141 | | QC-SMD-TFA05 | 1.61 | 743 |
| 142 | | QC-SMD-TFA05 | 1.59 | 808 |

The appropriate iodide derivatives of Examples 319 to 323 and appropriate terminal alkyne reagents including that in Reference Example 76 were used, and operations similar to those of Example 124 were carried out to synthesize the compounds described in the following Table.

TABLE 24

| Example No. | Structural formula | LCMS analysis condition No. | Retention time (min) | m/z [M + H]+ |
|---|---|---|---|---|
| 143 | | QC-SMD-TFA05 | 1.56 | 797 |

TABLE 24-continued

| Example No. | Structural formula | LCMS analysis condition No. | Retention time (min) | m/z [M + H]+ |
|---|---|---|---|---|
| 144 | | QC-SMD-TFA05 | 1.58 | 797 |
| 145 | | QC-SMD-TFA05 | 1.51 | 769 |

Example 146

(4aR)-1-[[2,6-Dichloro-4-(2-morpholin-4-ylethoxy) phenyl]methyl]-4-hydroxy-4a-methyl-2-oxo-N-[2-(trifluoromethyl)-4-[6-(trifluoromethyl)pyridin-3-yl] pyrimidin-5-yl]-6,7-dihydro-5H-pyrrolo[1,2-b] pyridazine-3-carboxamide hydrochloride

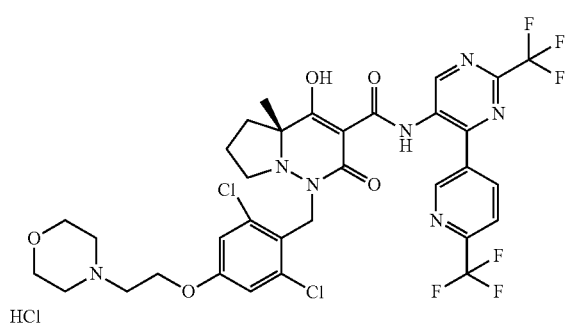 [SMILES: C[C@]12CCCN1N(Cc1c(Cl)cc(OCCN3CCOCC3)cc1Cl)C(=O)C(C(=O)Nc1cnc(C(F)(F)F)nc1-c1ccc(C(F)(F)F)nc1)=C2O ; Cl]

(4aR)-1-[(2,6-Dichloro-4-hydroxyphenyl)methyl]-4-hydroxy-4a-methyl-2-oxo-N-[2-(trifluoromethyl)-4-[6-(trifluoromethyl)pyridin-3-yl]pyrimidin-5-yl]-6,7-dihydro-5H-pyrrolo[1,2-b]pyridazine-3-carboxamide (Example 328) (22 mg, 0.032 mmol), 4-(2-chloroethyl)morpholine hydrochloride (12.1 mg, 0.065 mmol), and tetra n-butylammonium iodide (1.2 mg, 0.0033 mmol) were dissolved in N,N-dimethylformamide (0.2 mL), cesium carbonate (64 mg, 0.20 mmol) was added, and the mixture was stirred under nitrogen atmosphere at 60° C. for 3 hours. Dimethylsulfoxide (0.4 mL) and concentrated hydrochloric acid (0.1 mL) were added to the reaction mixture at 0° C., and after the mixture was stirred for 5 minutes, the resultant was purified directly by C-18 reverse-phase column chromatography on silica gel (water/acetonitrile) to obtain the title compound (23 mg, 88%) as a white amorphous solid.

LCMS: m/z 790[M+H]+

HPLC retention time: 1.26 minutes (analysis condition SMD-TFA05)

Example 147

(4aR)-1-[[4-[3-[(2R)-2,3-Dihydroxypropoxy]propoxy]-2,3-difluorophenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide

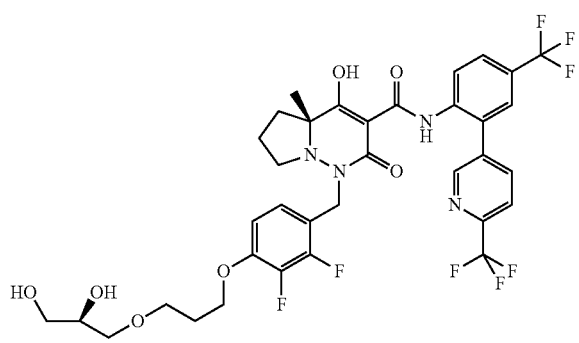 [SMILES: C[C@]12CCCN1N(Cc1ccc(OCCCOC[C@H](O)CO)c(F)c1F)C(=O)C(C(=O)Nc1ccc(C(F)(F)F)cc1-c1ccc(C(F)(F)F)nc1)=C2O]

First Step

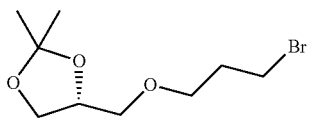

Water (10 mL) and sodium hydroxide (1.75 g, 43.8 mmol) were added to 1,3-dibromopropane (9.17 g, 45.4 mmol), (S)-(2,2-dimethyl-1,3-dioxolan-4-yl)methanol (1.5 g, 11.4 mmol), and hydrogensulfate tetra n-butylammonium (0.19 g, 0.57 mmol), and the mixture was stirred under nitrogen atmosphere at room temperature for 16 hours. Water (30 mL) was added to the reaction mixture, and after the resultant was extracted with diethyl ether, the organic layer was dried over magnesium sulfate and filtered. The filtrate was concentrated at reduced pressure, and the resultant residue was purified by column chromatography on silica gel (hexane/ethyl acetate) to obtain (S)-4-((3-bromopropoxy)methyl)-2,2-dimethyl-1,3-dioxolane (640 mg, 22%) as clear liquid.

Second Step (4aR)-1-[(2,3-Difluoro-4-hydroxyphenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide (Example 324) (1.0 g, 1.56 mmol) and (S)-4-((3-bromopropoxy)methyl)-2,2-dimethyl-1,3-dioxolane (0.47 g, 1.87 mmol) were dissolved in N,N-dimethylformamide (3 mL), cesium carbonate (0.86 g, 6.23 mmol) was added, and the mixture was stirred under nitrogen atmosphere at 80° C. for 2 hours. Diethyl ether (30 mL) was added to the reaction mixture, and the insolubles were filtered and concentrated at reduced pressure. After methanol (10 mL) was added to the resultant residue, concentrated hydrochloric acid (2 mL) was added dropwise at 0° C., and the mixture was stirred at room temperature for 2 hours. The reaction mixture was blown with nitrogen for 1 hour to remove an excessive amount of hydrogen chloride, and subsequently, dimethylsulfoxide (5 mL) was added, methanol was removed at reduced pressure, and the resultant residue was purified by C-18 reverse-phase column chromatography on silica gel (water/acetonitrile) to obtain the title compound (1.2 g, 95%) as a white amorphous solid.

LCMS: m/z 775[M+H]$^+$

HPLC retention time: 1.49 minutes (analysis condition SMD-TFA05)

Major Tautomer $^1$H-NMR (CDCl$_3$) δ: 16.21 (1H, s), 11.91 (1H, s), 8.78 (1H, s), 8.44 (1H, d, J=8.7 Hz), 7.98 (1H, d, J=8.0 Hz), 7.87 (1H, d, J=8.0 Hz), 7.73 (1H, d, J=8.7 Hz), 7.55 (1H, s), 6.92 (1H, dd, J=7.8, 7.5 Hz), 6.71 (1H, dd, J=7.8, 7.5 Hz), 4.73 (1H, d, J=14.2 Hz), 4.30 (1H, d, J=14.2 Hz), 4.14 (2H, t, J=6.2 Hz), 3.89-3.87 (1H, m), 3.72-3.69 (3H, m), 3.65-3.64 (1H, m), 3.57-3.54 (2H, m), 3.27-3.24 (1H, m), 2.70-2.62 (1H, m), 2.56-2.55 (1H, m), 2.53-2.50 (1H, m), 2.12-2.08 (3H, m), 1.73-1.70 (1H, m), 1.67-1.61 (2H, m), 1.00 (3H, s).

Minor Tautomer $^1$H-NMR (CDCl$_3$) δ: 17.97 (1H, s), 11.89 (1H, s), 8.71 (1H, s), 8.19 (1H, d, J=8.6 Hz), 7.94 (1H, d, J=7.9 Hz), 7.79 (1H, d, J=8.0 Hz), 7.73 (1H, d, J=8.6 Hz), 7.55 (1H, s), 7.06-7.04 (1H, m), 6.73-6.70 (1H, m), 4.99 (1H, d, J=14.4 Hz), 4.42 (1H, d, J=14.4 Hz), 4.14 (2H, t, J=6.2 Hz), 3.89-3.88 (1H, m), 3.72-3.69 (3H, m), 3.65-3.64 (1H, m), 3.57-3.54 (2H, m), 3.25-3.24 (1H, m), 2.70-2.62 (2H, m), 2.41-2.39 (1H, m), 2.12-2.08 (3H, m), 1.67-1.61 (2H, m), 1.43-1.37 (1H, m), 0.77 (3H, s).

Reference Example 78

(S)-4-(((5-Bromopentyl)oxy)methyl)-2,2-dimethyl-1,3-dioxolane

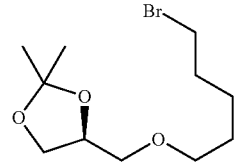

1,5-Dibromopentane and (S)-(2,2-dimethyl-1,3-dioxolan-4-yl)methanol were used, and operations similar to those of First Step of Example 147 were carried out to obtain (S)-4-((hex-5-yn-1-yloxy)methyl)-2,2-dimethyl-1,3-dioxolane as clear liquid.

$^1$H-NMR (CDCl$_3$) δ: 4.25 (1H, dt, J=12.0, 6.0 Hz), 4.05 (1H, dd, J=6.4, 8.0 Hz), 3.72 (1H, dd, J=6.4, 8.0 Hz), 3.53-3.37 (6H, m), 1.87 (2H, dt, J=14.2, 7.1 Hz), 1.64-1.54 (2H, m), 1.54-1.44 (2H, m), 1.41 (3H, s), 1.35 (3H, s).

Reference Example 79

(R)-4-(((5-Bromopentyl)oxy)methyl)-2,2-dimethyl-1,3-dioxolane

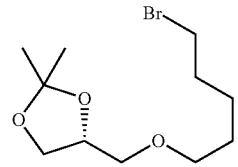

1,5-Dibromopentane and (R)-(2,2-dimethyl-1,3-dioxolan-4-yl)methanol were used, and operations similar to those of First Step of Example 147 were carried out to obtain (R)-4-(((5-Bromopentyl)oxy)methyl)-2,2-dimethyl-1,3-dioxolane.

Example 148

(4aR)-1-[[2,6-Dichloro-4-(2-morpholin-4-ylethoxy)phenyl]methyl]-4-hydroxy-4a-methyl-2-oxo-N-[6-(trifluoromethyl)-2-[6-(trifluoromethyl)pyridin-3-yl]pyridin-3-yl]-6,7-dihydro-5H-pyrrolo[1,2-b]pyridazine-3-carboxamide hydrochloride

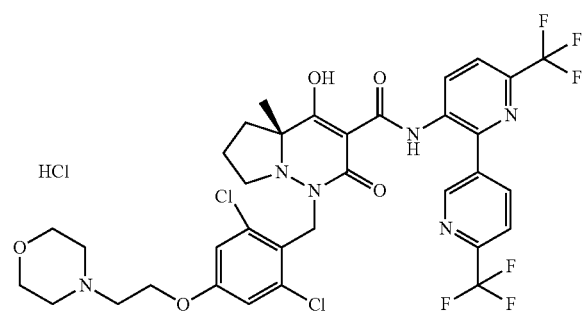 [SMILES: C[C@]12CCCN1N(Cc1c(Cl)cc(OCCN3CCOCC3)cc1Cl)C(=O)C(C(=O)Nc1ccc(C(F)(F)F)nc1-c1ccc(C(F)(F)F)nc1)=C2O ; Cl]

(4aR)-1-[(2,6-Dichloro-4-hydroxyphenyl)methyl]-4-hydroxy-4a-methyl-2-oxo-N-[6-(trifluoromethyl)-2-[6-(trifluoromethyl)pyridin-3-yl]pyridin-3-yl]-6,7-dihydro-5H-pyrrolo[1,2-b]pyridazine-3-carboxamide (Example 329) and 4-(2-chloroethyl)morpholine hydrochloride were used, and operations similar to those of Example 146 were carried out to synthesize the title compound.

LCMS: m/z 789[M+H]+

HPLC retention time: 1.29 minutes (analysis condition QC-SMD-TFA05)

Example 149

(4aR)-1-[[3-Chloro-4-(2-morpholin-4-ylethoxy)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide

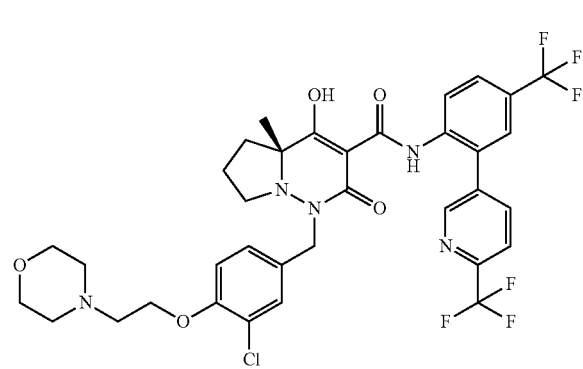 [SMILES: C[C@]12CCCN1N(Cc1ccc(OCCN3CCOCC3)c(Cl)c1)C(=O)C(C(=O)Nc1ccc(C(F)(F)F)cc1-c1ccc(C(F)(F)F)nc1)=C2O]

First Step

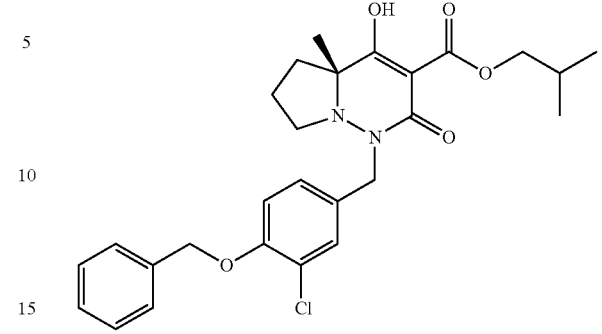

4-(Benzyloxy)-3-chlorobenzaldehyde and (R)-2-methylpyrrolidine-2-carboxylic acid methyl ester hydrochloride were used, and operations similar to those of Reference Example 4 were carried out to synthesize (4aR)-1-[(3-chloro-4-phenylmethoxyphenyl)methyl]-4-hydroxy-4a-methyl-2-oxo-6,7-dihydro-5H-pyrrolo[1,2-b]pyridazine-3-carboxylic acid 2-methylpropyl ester.

Second Step

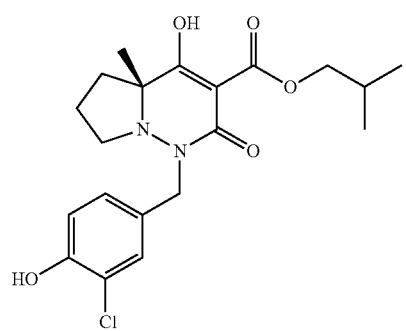 [SMILES: CC(C)COC(=O)C1=C(O)[C@@]2(C)CCCN2N(Cc2ccc(O)c(Cl)c2)C1=O]

(4aR)-1-[(3-Chloro-4-phenylmethoxyphenyl)methyl]-4-hydroxy-4a-methyl-2-oxo-6,7-dihydro-5H-pyrrolo[1,2-b]pyridazine-3-carboxylic acid 2-methylpropyl ester was used, and operations similar to those of Second Step of Reference Example 74 were carried out to synthesize (4aR)-1-[(3-chloro-4-hydroxyphenyl)methyl]-4-hydroxy-4a-methyl-2-oxo-6,7-dihydro-5H-pyrrolo[1,2-b]pyridazine-3-carboxylic acid 2-methylpropyl ester.

Third Step

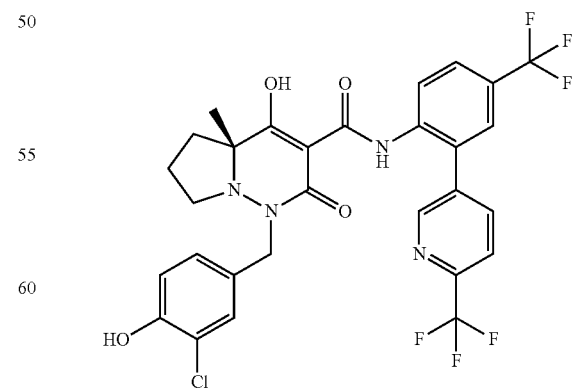

(4aR)-1-[(3-Chloro-4-hydroxyphenyl)methyl]-4-hydroxy-4a-methyl-2-oxo-6,7-dihydro-5H-pyrrolo[1,2-b]

pyridazine-3-carboxylic acid 2-methylpropyl ester and 4-(trifluoromethyl)-2-(6-(trifluoromethyl)pyridin-3-yl)aniline (Reference Example 13) were used, and operations similar to those of Example 21 were carried out to synthesize (4aR)-1-[(3-chloro-4-hydroxyphenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide.

Fourth Step (4aR)-1-[(3-Chloro-4-hydroxyphenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide and 4-(2-chloroethyl)morpholine hydrochloride were used, and operations similar to those of Example 146 were carried out to synthesize the title compound.

LCMS: m/z 754[M+H]+

HPLC retention time: 1.32 minutes (analysis condition QC-SMD-TFA05)

Example 150

Methyl 2-[4-[[(4aR)-4-Hydroxy-4a-methyl-2-oxo-3-[[4-(trifluoromethyl)-2-[6-(trifluoromethyl)pyridin-3-yl]phenyl]carbamoyl-6,7-dihydro-5H-pyrrolo[1,2-b]pyridazin-1-yl]methyl]-2,3-difluorophenoxy]acetate

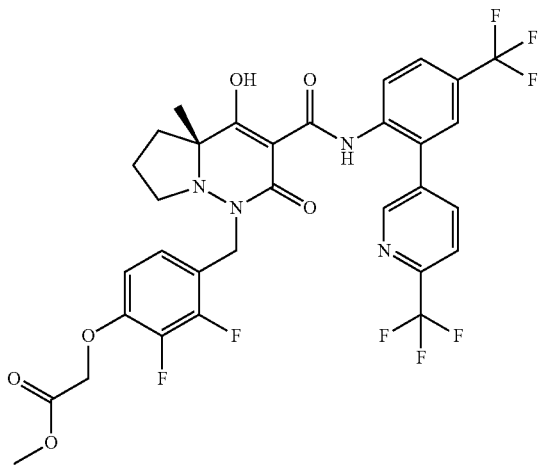 [SMILES: COC(=O)COc1ccc(CN2C(=O)C(C(=O)Nc3ccc(C(F)(F)F)cc3-c3ccc(C(F)(F)F)nc3)=C(O)[C@@]3(C)CCCN23)c(F)c1F]

First Step

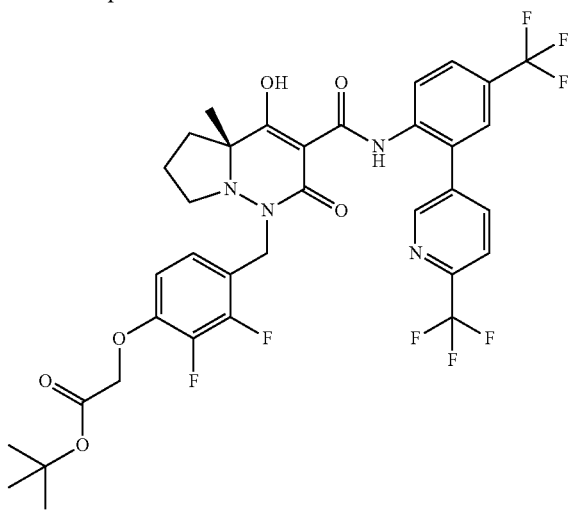

(4aR)-1-[(2,3-Difluoro-4-hydroxyphenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide (Example 324) and bromoacetic acid tert-butyl ester were used, and operations similar to those of Example 146 were carried out to synthesize 2-[4-[[(4aR)-4-hydroxy-4a-methyl-2-oxo-3-[[4-(trifluoromethyl)-2-[6-(trifluoromethyl)pyridin-3-yl]phenyl]carbamoyl]-6,7-dihydro-5H-pyrrolo[1,2-b]pyridazin-1-yl]methyl]-2,3-difluorophenoxy]acetic acid tert-butyl ester.

LCMS: m/z 757[M+H]+

HPLC retention time: 1.23 minutes (analysis condition SQD-FA05)

Second Step

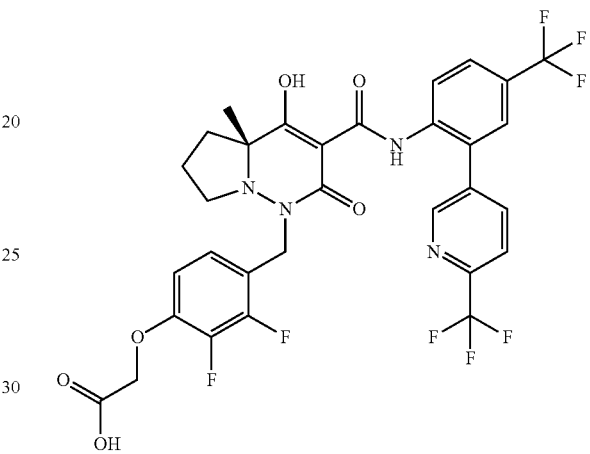

Trifluoroacetic acid (0.3 mL, 4 mmol) was added to a solution of 2-[4-[[(4aR)-4-hydroxy-4a-methyl-2-oxo-3-[[4-(trifluoromethyl)-2-[6-(trifluoromethyl)pyridin-3-yl]phenyl]carbamoyl]-6,7-dihydro-5H-pyrrolo[1,2-b]pyridazin-1-yl]methyl]-2,3-difluorophenoxy]acetic acid tert-butyl ester (14.7 mg, 0.019 mmol) in dichloromethane (0.075 mL) at room temperature, and the mixture was stirred at room temperature for 2 hours. The reaction mixture was concentrated at reduced pressure, and the resultant residue was purified by reverse-phase column chromatography (0.1% formic acid, acetonitrile/water) to obtain 2-[4-[[(4aR)-4-hydroxy-4a-methyl-2-oxo-3-[[4-(trifluoromethyl)-2-[6-(trifluoromethyl)pyridin-3-yl]phenyl]carbamoyl]-6,7-dihydro-5H-pyrrolo[1,2-b]pyridazin-1-yl]methyl]-2,3-difluorophenoxy]acetic acid (12.3 mg, 90%).

LCMS: m/z 701[M+H]+

HPLC retention time: 1.08 minutes (analysis condition SQD-FA05)

Third Step (Diazomethyl)trimethylsilane (0.0125 mL, 0.025 mmol) was added to a solution of 2-[4-[[(4aR)-4-hydroxy-4a-methyl-2-oxo-3-[[4-(trifluoromethyl)-2-[6-(trifluoromethyl)pyridin-3-yl]phenyl]carbamoyl]-6,7-dihydro-5H-pyrrolo[1,2-b]pyridazin-1-yl]methyl]-2,3-difluorophenoxy]acetic acid (9 mg, 0.013 mmol) in benzene (0.13 mL)-methanol (0.08 mL) at room temperature, and the mixture was stirred at room temperature for 1 hour. After formic acid (0.005 mL) was added to the reaction mixture, the resultant was concentrated at reduced pressure, and the resultant residue was purified by reverse-phase column chromatography (0.1% formic acid, acetonitrile/water) to obtain the title compound (8.3 mg, 90%) as a white amorphous solid.

LCMS: m/z 715[M+H]+

HPLC retention time: 1.60 minutes (analysis condition QC-SMD-TFA05)

Example 151

(4aR)-1-[[2,3-Difluoro-4-(pyridin-4-ylmethoxy)phenyl]methyl]-N-[2-(2,3-dimethoxyphenyl)-4-(trifluoromethyl)phenyl]-4-hydroxy-4a-methyl-2-oxo-6,7-dihydro-5H-pyrrolo[1,2-b]pyridazine-3-carboxamide

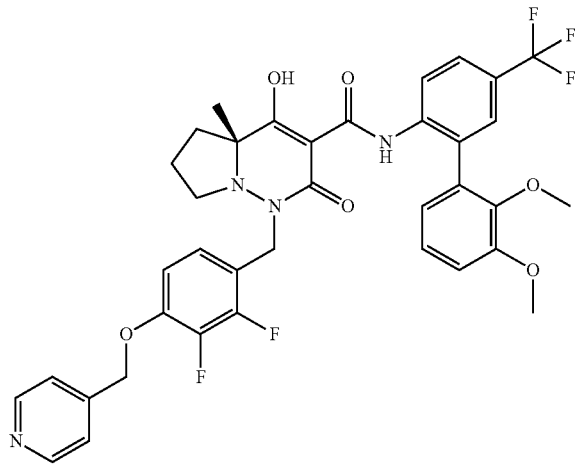 [SMILES: COc1cccc(-c2cc(C(F)(F)F)ccc2NC(=O)C2=C(O)[C@@]3(C)CCCN3N(Cc3ccc(OCc4ccncc4)c(F)c3F)C2=O)c1OC]

(4aR)-1-[(2,3-Difluoro-4-hydroxyphenyl)methyl]-N-[2-(2,3-dimethoxyphenyl)-4-(trifluoromethyl)phenyl]-4-hydroxy-4a-methyl-2-oxo-6,7-dihydro-5H-pyrrolo[1,2-b]pyridazine-3-carboxamide (Example 325) and 4-(bromomethyl)pyridine hydrobromate were used, and operations similar to those of Example 146 were carried out to synthesize the title compound.

LCMS: m/z 725[M+H]$^+$

HPLC retention time: 1.37 minutes (analysis condition QC-SMD-TFA05)

The phenolic derivatives of Examples 326, 327, and 330 and alkyl bromide reagents including those in Reference Examples 78 and 79 were used, and operations similar to those of Second Step of Example 147 were carried out to synthesize the compounds of the Examples described in the following Table.

TABLE 25

| Example No. | Structural formula | LCMS analysis condition No. | Retention time (min) | m/z [M + H]$^+$ |
|---|---|---|---|---|
| 152 | | QC-SMD-TFA05 | 1.53 | 790 |
| 153 | | QC-SMD-TFA05 | 1.56 | 803 |

TABLE 25-continued

| Example No. | Structural formula | LCMS analysis condition No. | Retention time (min) | m/z [M + H]+ |
|---|---|---|---|---|
| 154 | (structure) | QC-SMD-TFA05 | 1.60 | 817 |
| 155 | (structure) | QC-SMD-TFA05 | 1.60 | 817 |
| 156 | (structure) | QC-SMD-TFA05 | 1.49 | 819 |

Although tautomers of some of the compounds described in this table exist, isomers may be observed in some cases and not in other cases according to the type of the solvent for measurement. For example, ¹H-NMR of Example 152 (chloroform-D) and Example 156 (dimethylsulfoxide-D6) is as follows.

Example 152

Major Tautomer

¹H-NMR (CDCl₃) δ: 16.43 (1H, s), 12.92 (1H, s), 9.61 (1H, s), 8.47 (1H, d, J=8.7 Hz), 7.95 (1H, s), 7.90 (1H, s), 7.79 (1H, d, J=8.7 Hz), 7.04 (1H, dd, J=8.1, 8.1 Hz), 6.70 (1H, dd, J=8.1, 8.1 Hz), 4.98 (1H, d, J=14.3 Hz), 4.41 (1H, d, J=14.3 Hz), 4.07 (2H, t, J=6.2 Hz), 3.87 (1H, brs), 3.73-3.71 (1H, m), 3.66-3.64 (1H, m), 3.56 (2H, m), 3.53-3.52 (2H, m), 3.33-3.31 (1H, m), 2.74 (1H, ddd, J=8.5, 8.5, 8.5 Hz), 2.55-2.53 (2H, m), 2.11 (1H, brs), 1.92-1.88 (2H, m), 1.82-1.77 (2H, m), 1.74-1.73 (1H, m), 1.68-1.62 (2H, m), 1.01 (2H, s).

Minor Tautomer

¹H-NMR (CDCl₃) δ: 18.16 (1H, s), 12.97 (1H, s), 9.59 (1H, s), 8.33 (1H, d, J=8.7 Hz), 7.92 (2H, d, J=10.9 Hz), 7.79 (1H, d, J=8.4 Hz), 7.04 (1H, t, J=8.1 Hz), 6.70 (1H, t, J=7.5 Hz), 5.01 (1H, d, J=17.3 Hz), 4.45 (1H, d, J=14.6 Hz), 4.07 (2H, t, J=6.2 Hz), 3.87 (1H, s), 3.72 (1H, d, J=10.7 Hz), 3.65 (1H, d, J=11.9 Hz), 3.54 (4H, dt, J=19.0, 6.0 Hz), 3.26 (1H, s), 2.74 (1H, dd, J=16.6, 8.5 Hz), 2.63-2.61 (2H, m), 2.11 (1H, s), 1.92-1.88 (2H, m), 1.74-1.73 (2H, m), 1.67-1.65 (2H, m), 1.50-1.47 (1H, m), 0.85 (3H, s).

Example 156

¹H-NMR (DMSO-D₆) δ: 15.77 (1H, brs), 12.17 (1H, brs), 9.71 (1H, s), 9.14 (1H, s), 8.54 (1H, d, J=6.6 Hz), 8.16 (1H, d, J=8.1 Hz), 7.13 (1H, brs), 7.00 (1H, t, J=6.8 Hz), 4.99-4.17 (3H, m), 4.08 (2H, t, J=6.1 Hz), 3.59-3.54 (1H, m), 3.41-3.24 (6H, m), 2.70 (1H, q, J=8.1 Hz), 2.41 (1H, brs), 1.79-1.48 (8H, m), 1.47-1.31 (4H, m), 0.92 (3H, brs).

Example 157

(4aR)-1-[[2,3-Difluoro-4-(2-morpholin-4-ylethoxy)phenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide

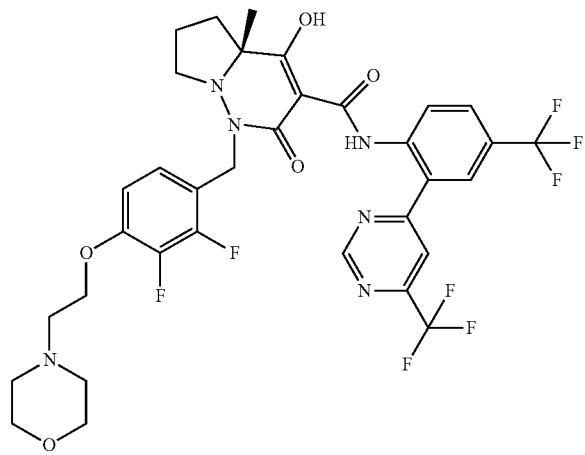 [SMILES: C[C@]12CCCN1N(Cc1ccc(OCCN3CCOCC3)c(F)c1F)C(=O)C(C(=O)Nc1ccc(C(F)(F)F)cc1-c1cc(C(F)(F)F)ncn1)=C2O]

Triphenylphosphine (17.2 mg, 0.066 mmol), N-(2-hydroxy ethyl)morpholine (7.5 mg, 0.057 mmol), and diethyl azodicarboxylate (0.03 mL, 0.065 mmol) were added to a solution of (4aR)-1-[(2,3-difluoro-4-hydroxyphenyl)methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide (Example 327) (10.6 mg, 0.016 mmol) in tetrahydrofuran (0.2 mL), and the mixture was stirred at room temperature for 1.5 hours. After the reaction mixture was concentrated, the residue was purified by reverse-phase column chromatography on silica gel to obtain the title compound (8.0 mg, 0.011 mmol) as a white solid. It was confirmed by measuring $^1$H-NMR and $^{13}$C-NMR that this solid included two tautomers.

LCMS: m/z 757[M+H]$^+$
HPLC retention time: 1.30 minutes (SMD-TFA05)

Major Tautomer
$^1$H-NMR (CDCl$_3$) δ: 16.44 (1H, s), 12.92 (1H, s), 9.61 (1H, d, J=1.0 Hz), 8.47 (1H, d, J=8.7 Hz), 7.95 (1H, d, J=1.0 Hz), 7.90 (1H, d, J=2.0 Hz), 7.79 (1H, dd, J=8.7, 2.0 Hz), 7.05 (1H, ddd, J=9.0, 6.8, 2.2 Hz), 6.71 (1H, ddd, J=9.0, 7.5, 1.2 Hz), 4.99 (1H, d, J=14.2 Hz), 4.40 (1H, d, J=14.2 Hz), 4.19 (2H, t, J=5.7 Hz), 3.74 (4H, t, J=4.6 Hz), 3.32 (1H, ddd, J=8.9, 8.9, 3.5 Hz), 2.84 (2H, t, J=5.7 Hz), 2.74 (1H, ddd, J=8.9, 8.9, 8.9 Hz), 2.61-2.59 (4H, m), 2.56-2.54 (1H, m), 1.76-1.73 (1H, m), 1.68-1.63 (2H, m), 1.00 (3H, s).
$^{13}$C-NMR (CDCl$_3$) δ: 187.4 (qC), 169.8 (qC), 165.7 (qC), 162.5 (qC), 159.3 (CH), 156.6 (qC, J$_{CF}$=36.3 Hz), 150.3 (qC, J$_{CF}$=248.7, 10.5 Hz), 147.8 (qC, J$_{CF}$=5.5 Hz), 141.3 (qC, J$_{CF}$=247.9, 14.6 Hz), 138.7 (qC), 128.3 (CH, J$_{CF}$=3.3 Hz), 128.0 (qC), 127.1 (CH, J$_{CF}$=3.8 Hz), 127.0 (qC, J$_{CF}$=33.5 Hz), 125.1 (CH), 124.8 (CH), 123.6 (qC, J$_{CF}$=272.0 Hz), 120.5 (qC, J$_{CF}$=275.4 Hz), 118.4 (qC, J$_{CF}$=12.7 Hz), 116.0 (CH, J$_{CF}$=2.5 Hz), 109.5 (CH, J$_{CF}$=2.5 Hz), 93.6 (qC), 68.0 (CH$_2$), 66.9 (CH$_2$×2), 64.2 (qC), 57.5 (CH$_2$), 54.1 (CH$_2$×2), 51.9 (CH$_2$), 43.2 (CH$_2$), 31.9 (CH$_2$), 22.4 (CH$_3$), 19.1 (CH$_2$).

Minor Tautomer
$^1$H-NMR (CDCl$_3$) δ: 18.17 (1H, s), 12.97 (1H, s), 9.59 (1H, s), 8.33 (1H, d, J=8.7 Hz), 7.93 (1H, s), 7.91 (1H, d, J=2.0 Hz), 7.79 (1H, dd, J=8.7, 2.0 Hz), 7.05 (1H, ddd, J=9.0, 6.8, 2.2 Hz), 6.71 (1H, ddd, J=9.0, 7.5, 1.2 Hz), 5.02 (1H, d, J=14.5 Hz), 4.45 (1H, d, J=14.5 Hz), 4.19 (2H, t, J=5.7 Hz), 3.74 (4H, t, J=4.6 Hz), 3.25 (1H, ddd, J=8.8, 8.8, 3.2 Hz), 2.84 (2H, t, J=5.7 Hz), 2.74 (1H, ddd, J=8.9, 8.9, 8.9 Hz), 2.61-2.59 (4H, m), 2.56-2.54 (1H, m), 1.76-1.73 (1H, m), 1.68-1.63 (1H, m), 1.49-1.47 (1H, m), 0.84 (3H, s).
$^{13}$C-NMR (CDCl$_3$) δ: 191.8 (qC), 170.2 (qC), 168.1 (qC), 165.5 (qC), 159.3 (CH), 156.6 (qC, J$_{CF}$=36.3 Hz), 150.3 (qC, J$_{CF}$=248.7, 10.5 Hz), 147.8 (qC, J$_{CF}$=5.5 Hz), 141.3 (qC, J$_{CF}$=247.9, 14.6 Hz), 138.7 (qC), 128.2 (CH, J$_{CF}$=3.3 Hz), 128.2 (qC), 127.1 (CH, J$_{CF}$=3.8 Hz), 127.0 (qC, J$_{CF}$=33.5 Hz), 125.1 (CH), 125.4 (CH), 123.6 (qC, J$_{CF}$=272.0 Hz), 120.5 (qC, J$_{CF}$=275.4 Hz), 118.4 (qC, J$_{CF}$=12.7 Hz), 116.0 (CH, J$_{CF}$=2.5 Hz), 109.5 (CH, J$_{CF}$=2.5 Hz), 84.3 (qC), 68.0 (CH$_2$), 66.9 (CH$_2$×2), 64.2 (qC), 57.5 (CH$_2$), 54.1 (CH$_2$×2), 50.7 (CH$_2$), 44.0 (CH$_2$), 31.1 (CH$_2$), 21.8 (CH$_3$), 18.6 (CH$_2$).

The appropriate phenol intermediates of Examples 324, 325, and 327 and appropriate alcohol reagents were used, and operations similar to those of Example 156 were carried out to synthesize the compounds of the Examples described in the following Table.

TABLE 26

| Example No. | Structural formula | LCMS analysis condition No. | Retention time (min) | m/z [M + H]$^+$ |
| --- | --- | --- | --- | --- |
| 158 | | QC-SMD-TFA05 | 1.68 | 718 |

TABLE 26-continued

| Example No. | Structural formula | LCMS analysis condition No. | Retention time (min) | m/z [M + H]+ |
|---|---|---|---|---|
| 159 | | QC-SMD-TFA05 | 1.69 | 718 |
| 160 | | SMD-TFA05 | 1.17 | 727 |
| 161 | | QC-SMD-TFA05 | 1.32 | 756 |

| Example No. | Structural formula | LCMS analysis condition No. | Retention time (min) | m/z [M + H]+ |
|---|---|---|---|---|
| 162 | | QC-SMD-TFA05 | 1.61 | 730 |

Example 163

(4aR)-1-[[2,3-Difluoro-4-(2-morpholin-4-ylethylsulfanyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide hydrochloride

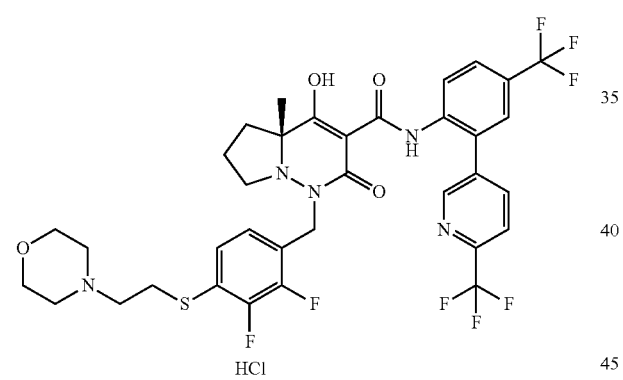

Cesium carbonate (67 mg, 0.206 mmol) was added to a solution of (4aR)-1-[(2,3-difluoro-4-iodophenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide (Example 320) (30 mg, 0.04 mmol), palladium acetate (1.79 mg, 0.0080 mmol), triphenylphosphine (8.37 mg, 0.032 mmol), and triisopropylsilanethiol (9.87 mg, 0.052 mmol) in toluene (0.399 mL), and the mixture was stirred at 100° C. for 2 hours and 45 minutes. Subsequently, palladium acetate (1.79 mg, 0.0080 mmol), triisopropylsilanethiol (9.87 mg, 0.052 mmol), and 1,4-dioxane (0.4 mL) were further added, and the mixture was stirred at 110° C. for 2 hours.

After the reaction mixture was cooled to room temperature, 4-(2-chloroethyl)morpholine hydrochloric acid (37.1 mg, 0.199 mmol) was added to this reaction mixture, and after the resultant was heated at 100° C. for several hours, it was cooled to room temperature. This reaction mixture was purified by C18 reverse-phase column chromatography. A 4 N hydrogen chloride/1,4-dioxane solution was added to the obtained compound, and the solution was concentrated and dried to obtain the title compound (17 mg, 53%) as a white solid.

LCMS: m/z 772[M+H]+

HPLC retention time: 1.35 minutes (analysis condition QC-SMD-TFA05)

Example 164

(4aR)-1-[[2,3-Difluoro-4-(morpholin-4-ylmethyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide hydrochloride

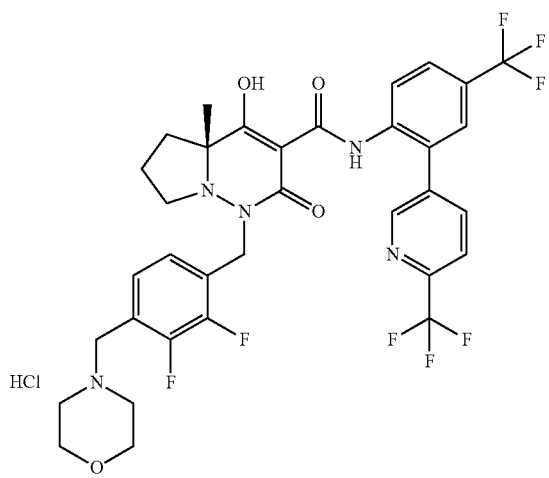 [SMILES: Cl ; C[C@]12CCCN1N(Cc1ccc(CN3CCOCC3)c(F)c1F)C(=O)C(C(=O)Nc1ccc(C(F)(F)F)cc1-c1ccc(C(F)(F)F)nc1)=C2O]

First Step

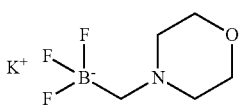

A solution of (bromomethyl)potassium trifluoroborate (100 mg, 0.50 mmol), morpholine (45.7 mg, 0.525 mmol), and potassium carbonate (69.1 mg, 0.50 mmol) in tetrahydrofuran (0.50 mL) was heated at 80° C. for 1 hour, and then the resultant was cooled to room temperature. After the reaction mixture was filtered and washed with acetone (15 mL), the solution was dried to obtain trifluoro(morpholinomethyl)potassium borate (68 mg, 66%) as a crude product.

Second Step

Palladium acetate (2.45 mg, 0.0109 mmol), dicyclohexyl(2',4',6'-triisopropyl-[1,1'-biphenyl]-2-yl)phosphine (10.39 mg, 0.022 mmol), and cesium carbonate (89 mg, 0.272 mmol) were added twice to a solution of trifluoro(morpholinomethyl)potassium borate (28.2 mg, 0.136 mmol) obtained in First Step and (4aR)-1-[(2,3-difluoro-4-iodophenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide (Example 320) (41 mg, 0.054 mmol) in a mixture of dioxane and water (0.495 mL and 0.0495 mL), and the mixture was heated and stirred at 80° C. overnight. After the reaction mixture was cooled to room temperature, this reaction mixture was purified by reverse-phase column chromatography. The obtained compound was dissolved in ethanol, then a 4 N hydrogen chloride/dioxane solution were added, and the resultant was dried to obtain the title compound (28 mg, 68%) as a white solid.

LCMS: m/z 726[M+H]$^+$

HPLC retention time: 1.28 minutes (analysis condition QC-SMD-TFA05)

Major Tautomer $^1$H-NMR (CDCl$_3$) δ: 13.60 (1H, s), 11.74 (1H, s), 8.74 (1H, d, J=2.0 Hz), 8.44 (1H, d, J=8.6 Hz), 7.95 (1H, dd, J=8.0, 1.8 Hz), 7.86 (1H, d, J=8.0 Hz), 7.75 (1H, m), 7.72 (1H, dd, J=8.6, 2.0 Hz), 7.54 (1H, d, J=1.8 Hz), 7.17 (1H, t, J=6.7 Hz), 4.86 (1H, d, J=14.9 Hz), 4.37-4.22 (4H, m), 3.97 (2H, dd, J=13.2, 2.6 Hz), 3.35 (2H, d, J=10.4 Hz), 3.27 (1H, dt, J=8.7, 3.2 Hz), 2.92 (2H, m), 2.71 (1H, dd, J=16.7, 8.7 Hz), 2.60-2.51 (1H, m), 1.87-1.58 (4H, m), 1.04 (3H, s).

Minor Tautomer $^1$H-NMR (CDCl$_3$) δ: 11.91 (1H, s), 8.70 (1H, d, J=2.0 Hz), 8.17 (1H, d, J=8.6 Hz), 7.80 (1H, d, J=8.0 Hz), 7.57 (1H, d, J=2.0 Hz), 7.32 (1H, t, J=6.9 Hz), 5.12 (1H, d, J=14.9 Hz), 4.48-4.38 (4H, m), 0.80 (3H, s).

Example 165

Methyl 4-[[(4aR)-4-Hydroxy-4a-methyl-2-oxo-3-[[4-(trifluoromethyl)-2-[6-(trifluoromethyl)pyridin-3-yl]phenyl]carbamoyl]-6,7-dihydro-5H-pyrrolo[1,2-b]pyridazin-1-yl]methyl]-3,5-difluorobenzoate

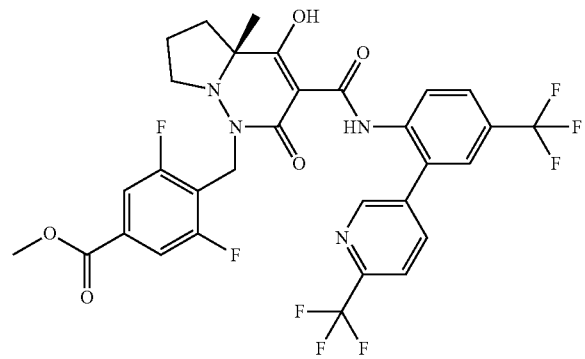 [SMILES: COC(=O)c1cc(F)c(CN2C(=O)C(C(=O)Nc3ccc(C(F)(F)F)cc3-c3ccc(C(F)(F)F)nc3)=C(O)[C@@]3(C)CCCN23)c(F)c1]

Molybdenum hexacarbonyl (70.2 mg, 0.266 mmol), 1,1'-bis(diphenylphosphino)ferrocene dichloropalladium (II) (a 1:1 dichloromethane complex) (4.4 mg, 0.0053 mmol), and 1,8-diazabicyclo[5.4.0]undec-7-ene (0.0024 mL, 0.159 mmol) were added to a solution of (4aR)-1-[(2,6-difluoro-4-iodophenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide (Example 322) (40 mg, 0.053 mmol) in methanol (2 mL), and the mixture was stirred under nitrogen atmosphere at 70° C. for 4 hours. The reaction mixture was added to 1 N hydrochloric acid, the resultant was extracted with dichloromethane, and after the organic layer was dried over anhydrous magnesium sulfate, the resultant was filtered and concentrated at reduced pressure. The resultant residue was purified by preparative TLC (hexane:ethyl acetate=2:1) to obtain the title compound (29.3 mg, 81%) as light brown oil.

LCMS: m/z 685[M+H]$^+$

HPLC retention time: 1.68 minutes (analysis condition QC-SMD-TFA05)

Reference Example 80

(4aR)—N-(4-Bromo-3,5-difluorophenyl)-4-hydroxy-4a-methyl-2-oxo-1,5,6,7-tetrahydropyrrolo[1,2-b]pyridazine-3-carboxamide

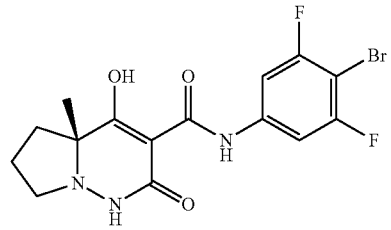 [SMILES: C[C@]12CCCN1NC(=O)C(C(=O)Nc1cc(F)c(Br)c(F)c1)=C2O]

First Step

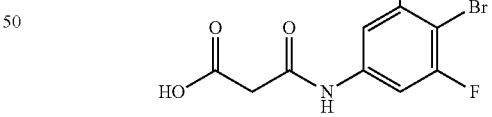

A solution of 4-bromo-3,5-difluoroaniline (2.00 g, 9.62 mmol) and Meldrum's acid (2.77 g, 19.2 mmol) in toluene (18 mL) was stirred at 90° C. for 3 hours. After the reaction mixture was cooled to 0° C., the deposit was collected by filtration. The obtained solid was purified by reverse-phase column chromatography (0.1% formic acid water/acetonitrile) to obtain 3-((4-bromo-3,5-difluorophenyl)amino)-3-oxopropanoate (2.00 g, 71%) as white powder.

LCMS: m/z 294[M+H]$^+$

HPLC retention time: 0.66 minutes (analysis condition SQD-FA05)

299

Second Step

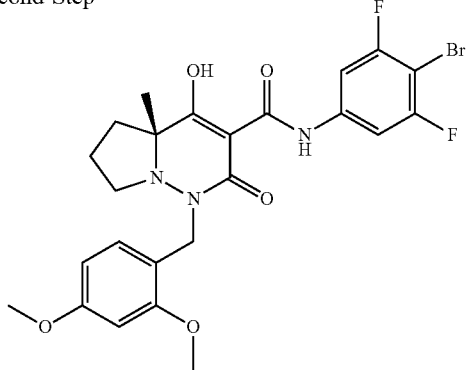

2,4-Dimethoxybenzaldehyde, (R)-2-methyl-pyrrolidine-2-carboxylic acid methyl ester hydrochloride, and 3-((4-bromo-3,5-difluorophenyl)amino)-3-oxopropanoate were used, and operations similar to those of Reference Example 1-1 were carried out to synthesize (4aR)—N-(4-bromo-3,5-difluorophenyl)-1-[(2,4-(dimethoxyphenyl)methyl]-4-hydroxy-4a-methyl-2-oxo-6,7-dihydro-5H-pyrrolo[1,2-b]pyridazine-3-carboxamide.

LCMS: m/z 554[M+H]+

HPLC retention time: 1.64 minutes (analysis condition SQD-FA05)

Third Step (4aR)—N-(4-Bromo-3,5-difluorophenyl)-1-[(2,4-(dimethoxyphenyl)methyl]-4-hydroxy-4a-methyl-2-oxo-6,7-dihydro-5H-pyrrolo[1,2-b]pyridazine-3-carboxamide (910 mg, 1.65 mmol) and triisopropylsilane (0.68 mL, 3.29 mmol) were dissolved in trifluoroacetic acid (6 mL), and after the mixture was cooled to 0° C., trifluoromethanesulfonic acid (0.15 mL, 1.65 mmol) was added dropwise. After the mixture was stirred at room temperature for 30 minutes, the reaction mixture was added to ice-cold water (50 mL), neutralized with potassium carbonate (5.5 g, 39.8 mmol), and extracted three times with ethyl acetate (100 mL). After the organic layer was washed with a brine, the resultant was dried over sodium sulfate. The resultant was filtered, the filtrate was concentrated at reduced pressure, and the resultant residue was purified by C-18 reverse-phase column chromatography (0.1% formic acid water/acetonitrile) to obtain the title compound (590 mg, 89%) as a white solid.

LCMS: m/z 402[M+H]+

HPLC retention time: 0.70 minutes (analysis condition SQD-FA05)

Reference Example 81

(4aR)-4-Hydroxy-4a-methyl-2-oxo-N-[4-(trifluoromethyl)-2-[6-(trifluoromethyl)pyridin-3-yl]phenyl]-1,5,6,7-tetrahydropyrrolo[1,2-b]pyridazine-3-carboxamide

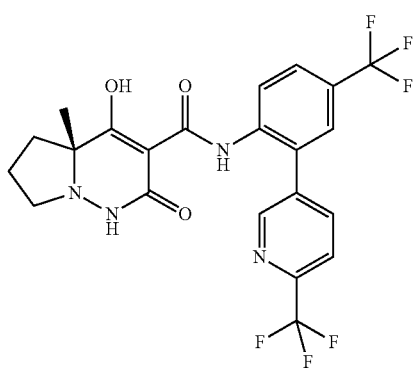 [SMILES: C[C@]12CCCN1NC(=O)C(C(=O)Nc1ccc(C(F)(F)F)cc1-c1ccc(C(F)(F)F)nc1)=C2O]

300

First Step

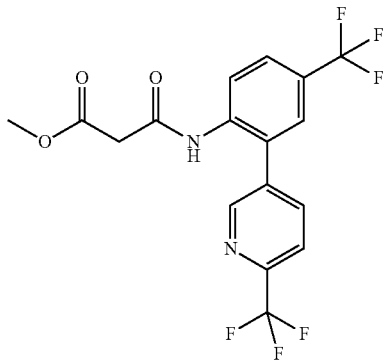 [SMILES: COC(=O)CC(=O)Nc1ccc(C(F)(F)F)cc1-c1ccc(C(F)(F)F)nc1]

4-(Trifluoromethyl)-2-(6-(trifluoromethyl)pyridin-3-yl)aniline (Reference Example 42) (2.0 g) was dissolved in tetrahydrofuran (30 mL), tripotassium phosphate (4.16 g) was added, and the mixture was stirred at room temperature for 3 minutes. Methyl 3-chloro-3-oxopropanoate (1.40 mL) was added, and the mixture was stirred at room temperature for 10 minutes. Ethyl acetate (100 mL) and water (100 mL) were added for separation, and the organic layer was washed with a 12% brine and concentrated at reduced pressure to obtain propanedioic acid 3-O— [4-(trifluoromethyl)-2-[6-(trifluoromethyl)pyridin-3-yl]phenyl]1-O-methyl as a crude product.

LCMS: m/z 407[M+H]+

HPLC retention time: 0.81 minutes (analysis condition SQD-FA05)

Second Step

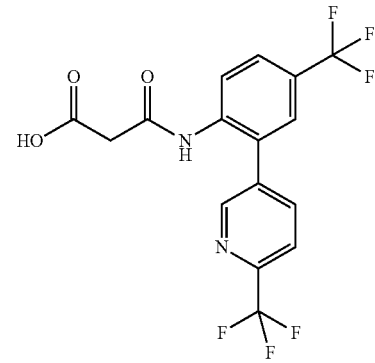 [SMILES: O=C(O)CC(=O)Nc1ccc(C(F)(F)F)cc1-c1ccc(C(F)(F)F)nc1]

Methanol (20 mL) and a 10 N aqueous sodium hydroxide solution (1.96 mL) were added to 3-O-[4-(trifluoromethyl)-2-[6-(trifluoromethyl)pyridin-3-yl]phenyl]1-O-methyl obtained in First Step, and the mixture was stirred at room temperature for 10 hours. 6 N hydrochloric acid was added to adjust the pH to 3, ethyl acetate and water were added for separation, and the organic layer was dried over anhydrous magnesium sulfate and the solvent was distilled away at reduced pressure. Hexane (90 mL) and ethyl acetate (10 mL) were added to the resultant residue, the mixture was stirred and then filtered, and the resultant solid was dried to obtain 3-oxo-3-((4-(trifluoromethyl)-2-(6-(trifluoromethyl)pyridin-3-yl)phenyl)amino)propanoate (2.34 g, two-step yield 91%).

LCMS: m/z 393[M+H]+

HPLC retention time: 0.29 minutes (analysis condition SQD-FA50)

Third Step

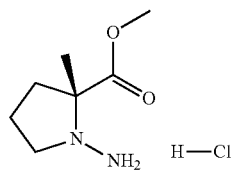

(R)-2-Methylpyrrolidine-2-carboxylic acid methyl ester hydrochloride (8.4 g, 46.8 mmol) was suspended in dichloromethane (50 mL), p-toluenesulfonic acid.monohydrate (9.34 g, 49.1 mmol) was added, and the mixture was stirred under nitrogen atmosphere at room temperature for 10 minutes. The reaction mixture was concentrated at reduced pressure, toluene was added for azeotropic removal, then the residue was suspended in dichloromethane (50 mL), sodium nitrite (3.55 g, 69.0 mmol) was added, and the mixture was stirred under nitrogen atmosphere at room temperature for 2 hours. After the reaction mixture was filtered, the resultant was concentrated at reduced pressure to obtain (S)-1-nitroso-pyrrolidine-2-carboxylic acid methyl ester as a crude product. The obtained crude product was dissolved in acetic acid (200 mL) and methanol (30 mL), zinc powder (29.4 g, 4501 mmol) was added in divided portions under nitrogen stream, at 0° C., and it was added, and the mixture was stirred for 1 hour. Methanol (100 mL) was added to the reaction mixture, the mixture was filtered through a celite pad, and then the filtrate was concentrated at reduced pressure. After a similar operation was repeated twice, the resultant residue was purified by column chromatography on silica gel (dichloromethane/methanol). After a 4 N hydrogen chloride/1,4-dioxane solution was added to the obtained fraction, the resultant was concentrated at reduced pressure to obtain (R)-1-amino-2-methylpyrrolidine-2-carboxylic acid methyl ester hydrochloride (6.4 g, 70%).

LCMS: m/z 158.9[M+H]+

HPLC retention time: 0.33 minutes mass chromatogram (analysis condition SMD-TFA05)

Fourth Step

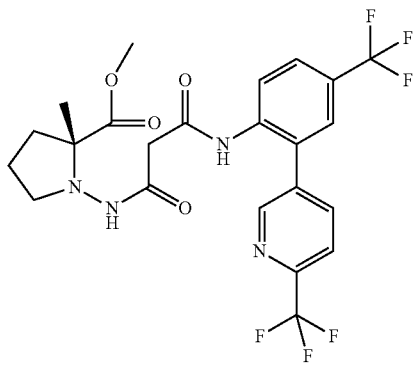 [SMILES: COC(=O)[C@@]1(C)CCCN1NC(=O)CC(=O)Nc1ccc(C(F)(F)F)cc1-c1ccc(C(F)(F)F)nc1]

(R)-2-Methyl-1-(3-oxo-3-((4-(trifluoromethyl)-2-(6-(trifluoromethyl)pyridin-3-yl)phenyl)amino)propanamide)pyrrolidine-2-carboxylic acid methyl ester and (R)-1-amino-2-methylpyrrolidine-2-carboxylic acid methyl ester hydrochloride were used as a reagent and a starting material, respectively, and operations similar to those of Second Step of Reference Example 1-1 were carried out to synthesize (R)-2-methyl-1-(3-oxo-3-((4-(trifluoromethyl)-2-(6-(trifluoromethyl)pyridin-3-yl)phenyl)amino)propanamide)pyrrolidine-2-carboxylic acid methyl ester.

LCMS: m/z 531[M−H]−

HPLC retention time: 0.88 minutes (SQD-FA05)

Fifth Step (R)-2-Methyl-1-(3-oxo-3-((4-(trifluoromethyl)-2-(6-(trifluoromethyl)pyridin-3-yl)phenyl)amino)propanamide)pyrrolidine-2-carboxylic acid methyl ester was used, and operations similar to those of Third Step of Reference Example 1-1 were carried out to synthesize the title compound.

LCMS: m/z 501[M+H]+

HPLC retention time: 1.03 minutes (SQD-FA05)

Reference Example 82

(4aR)-4-Hydroxy-4a-methyl-2-oxo-N-[4-(trifluoromethyl)-2-[6-(trifluoromethyl)pyrimidin-4-yl]phenyl]-1,5,6,7,-tetrahydropyrrolo[1,2-b]pyridazine-3-carboxamide

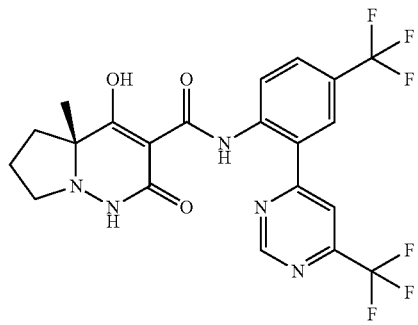 [SMILES: C[C@]12CCCN1NC(=O)C(C(=O)Nc1ccc(C(F)(F)F)cc1-c1cc(C(F)(F)F)ncn1)=C2O]

First Step

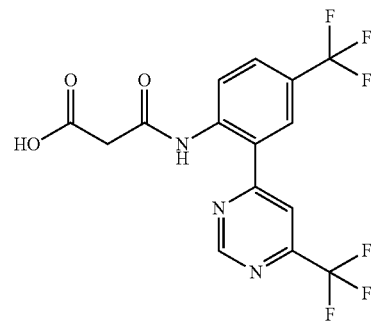 [SMILES: O=C(O)CC(=O)Nc1ccc(C(F)(F)F)cc1-c1cc(C(F)(F)F)ncn1]

4-(Trifluoromethyl)-2-(6-(trifluoromethyl)pyrimidin-4-yl)aniline (Reference Example 50) and Meldrum's acid were used, and operations similar to those of Second Step of Reference Example 80 were carried out to synthesize 3-oxo-3-((4-(trifluoromethyl)-2-(6-(trifluoromethyl)pyrimidin-4-yl)phenyl)amino)propanoate.

Second Step (R)-1-amino-2-methylpyrrolidine-2-carboxylic acid methyl ester hydrochloride and 3-oxo-3-((4-(trifluoromethyl)-2-(6-(trifluoromethyl)pyrimidin-4-yl)phenyl)amino)propanoate were used, and operations similar to those of Fourth and Fifth Steps of Reference Example 81 were carried out to synthesize the title compound.

LCMS: m/z 502[M+H]+

HPLC retention time: 1.02 minutes (SQD-FA05)

Example 166

(4aR)—N-(4-Bromo-3,5-difluorophenyl)-1-[(4-bromo-2-fluorophenyl)methyl]-4-hydroxy-4a-methyl-2-oxo-6,7-dihydro-5H-pyrrolo[1,2-b]pyridazine-3-carboxamide

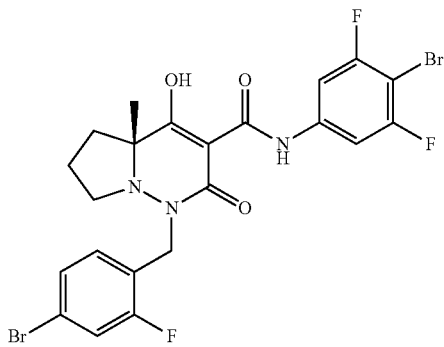 [SMILES: C[C@]12CCCN1N(Cc1ccc(Br)cc1F)C(=O)C(C(=O)Nc1cc(F)c(Br)c(F)c1)=C2O]

A 1.7 N toluene solution (0.0644 mL, 0.109 mmol) of 4-bromo-1-(bromomethyl)-2-fluorobenzene (14.7 mg, 0.055 mmol) and potassium 2,2-dimethylpropan-1-olate was added to a solution of (4aR)—N-(4-bromo-3,5-difluorophenyl)-4-hydroxy-4a-methyl-2-oxo-1,5,6,7-tetrahydropyrrolo[1,2-b]pyridazine-3-carboxamide (Reference Example 80) (20.0 mg, 0.050 mmol) in N,N-dimethylformamide (0.249 mL), and the mixture was stirred at room temperature for 15 minutes. The reaction mixture was purified directly by C18 reverse-phase column chromatography (0.1% formic acid acetonitrile/water) to obtain the title compound (6.0 mg, 20%) as a grayish white amorphous solid.

LCMS: m/z 588[M−H]⁻

HPLC retention time: 1.32 minutes (SQD-FA05)

The appropriate pyridazinone intermediates of Reference Examples 80 to 82 and appropriate benzylhalide reagents were used, and operations similar to those of Example 166 were carried out to synthesize the compounds of the Examples described in the following Table.

TABLE 27

| Example No. | Structural formula | LCMS analysis condition No. | Retention time (min) | m/z [M + H]⁺ |
|---|---|---|---|---|
| 167 | | QC-SMD-TFA05 | 1.65 | 657 |
| 168 | | SQD-AA05 | 1.20 | 625 |

TABLE 27-continued

| Example No. | Structural formula | LCMS analysis condition No. | Retention time (min) | m/z [M + H]+ |
|---|---|---|---|---|
| 169 | | SQD-AA05 | 1.19 | 625 |
| 170 | | QC-SMD-TFA05 | 1.67 | 627 |
| 171 | | QC-SMD-TFA05 | 1.68 | 627 |
| 172 | | SQD-AA05 | 1.16 | 627 |

TABLE 27-continued

| Example No. | Structural formula | LCMS analysis condition No. | Retention time (min) | m/z [M + H]+ |
|---|---|---|---|---|
| 173 | | QC-SMD-TFA05 | 1.67 | 627 |
| 174 | | QC-SMD-TFA05 | 1.74 | 544 |
| 175 | | QC-SMD-TFA05 | 1.66 | 651 |
| 176 | | SQD-AA05 | 1.18 | 651 |

TABLE 27-continued

| Example No. | Structural formula | LCMS analysis condition No. | Retention time (min) | m/z [M + H]+ |
|---|---|---|---|---|
| 177 | | QC-SMD-TFA05 | 1.68 | 658 |
| 178 | | QC-SMD-TFA05 | 1.65 | 617 |
| 179 | | QC-SMD-TFA05 | 1.64 | 617 |
| 180 | | QC-SMD-TFA05 | 1.76 | 626 |

TABLE 27-continued
| Example No. | Structural formula | LCMS analysis condition No. | Retention time (min) | m/z [M + H]+ |
|---|---|---|---|---|
| 181 | 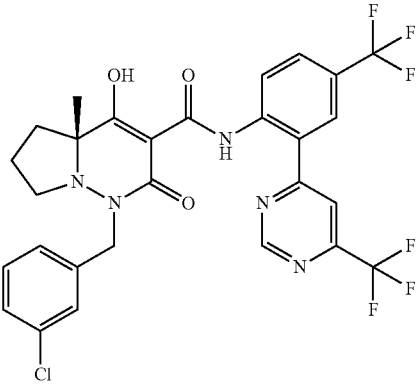 [SMILES: C[C@]12CCCN1N(Cc1cccc(Cl)c1)C(=O)C(C(=O)Nc1ccc(C(F)(F)F)cc1-c1cc(C(F)(F)F)ncn1)=C2O] | QC-SMD-TFA05 | 1.76 | 626 |
| 182 | 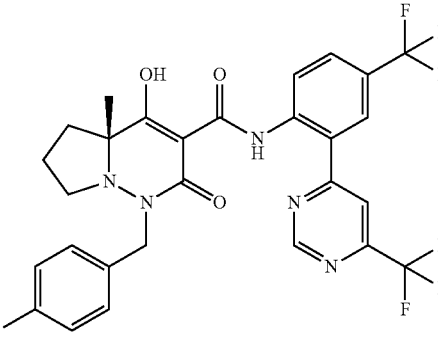 | QC-SMD-TFA05 | 1.76 | 626 |
| 183 | 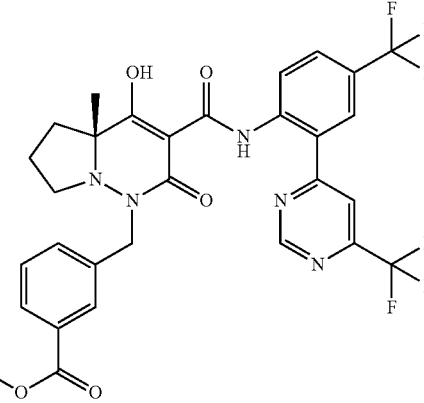 | QC-SMD-TFA05 | 1.68 | 650 |
| 184 | 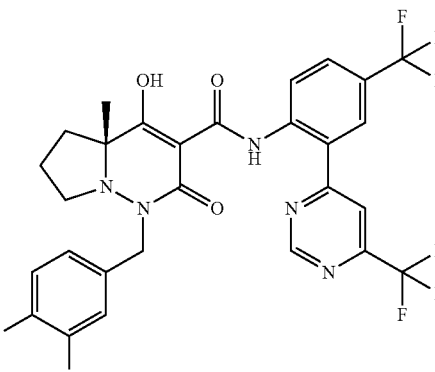 | QC-SMD-TFA05 | 1.76 | 688 |

TABLE 27-continued

| Example No. | Structural formula | LCMS analysis condition No. | Retention time (min) | m/z [M + H]+ |
|---|---|---|---|---|
| 185 | | QC-SMD-TFA05 | 1.76 | 606 |
| 186 | | QC-SMD-TFA05 | 1.76 | 606 |
| 187 | | QC-SMD-TFA05 | 1.77 | 606 |
| 188 | | QC-SMD-TFA05 | 1.72 | 592 |

TABLE 27-continued

| Example No. | Structural formula | LCMS analysis condition No. | Retention time (min) | m/z [M + H]+ |
|---|---|---|---|---|
| 189 | | QC-SMD-TFA05 | 1.76 | 676 |
| 190 | | SQD-AA05 | 1.15 | 528 |
| 191 | | SQD-AA05 | 1.16 | 528 |
| 192 | | QC-SMD-TFA05 | 1.70 | 528 |

TABLE 27-continued

| Example No. | Structural formula | LCMS analysis condition No. | Retention time (min) | m/z [M + H]+ |
| --- | --- | --- | --- | --- |
| 193 | | SQD-AA05 | 1.15 | 528 |
| 194 | | SQD-AA05 | 1.15 | 546 |
| 195 | | QC-SMD-TFA05 | 1.76 | 524 |
| 196 | | QC-SMD-TFA05 | 1.75 | 544 |

TABLE 27-continued

| Example No. | Structural formula | LCMS analysis condition No. | Retention time (min) | m/z [M + H]+ |
|---|---|---|---|---|
| 197 | | QC-SMD-TFA05 | 1.73 | 546 |
| 198 | | SQD-AA05 | 1.18 | 643 |
| 199 | | QC-SMD-TFA05 | 1.67 | 609 |
| 200 | | QC-SMD-TFA05 | 1.67 | 609 |

TABLE 27-continued

| Example No. | Structural formula | LCMS analysis condition No. | Retention time (min) | m/z [M + H]+ |
|---|---|---|---|---|
| 201 | | SQD-AA05 | 1.18 | 643 |
| 202 | | SQD-AA05 | 1.17 | 651 |
| 203 | | QC-SMD-TFA05 | 1.66 | 627 |
| 204 | | QC-SMD-TFA05 | 1.71 | 643 |

TABLE 27-continued
| Example No. | Structural formula | LCMS analysis condition No. | Retention time (min) | m/z [M + H]+ |
|---|---|---|---|---|
| 205 | 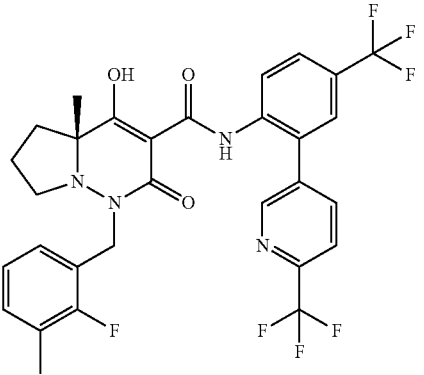 [SMILES: Cc1cccc(CN2C(=O)C(C(=O)Nc3ccc(C(F)(F)F)cc3-c3ccc(C(F)(F)F)nc3)=C(O)[C@@]3(C)CCCN23)c1F] | SQD-AA05 | 1.21 | 623 |
| 206 | 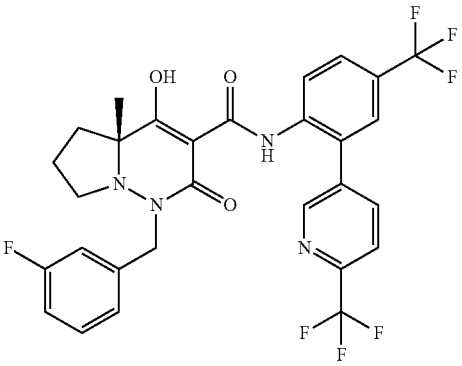 [SMILES: C[C@]12CCCN1N(Cc1cccc(F)c1)C(=O)C(C(=O)Nc1ccc(C(F)(F)F)cc1-c1ccc(C(F)(F)F)nc1)=C2O] | QC-SMD-TFA05 | 1.67 | 609 |
| 207 | 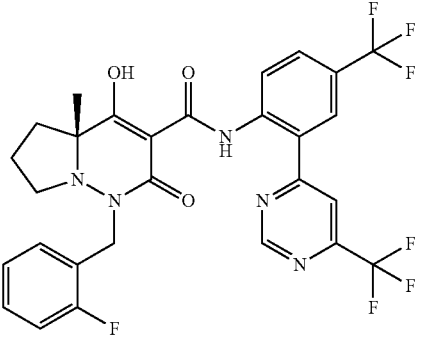 | QC-SMD-TFA05 | 1.68 | 610 |
| 208 | 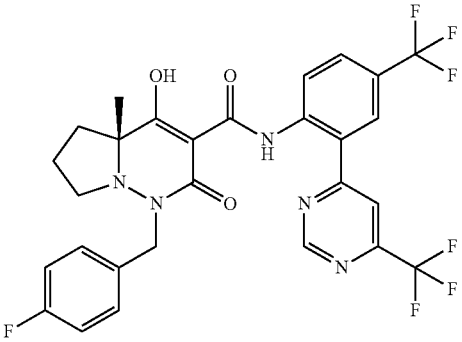 [SMILES: C[C@]12CCCN1N(Cc1ccc(F)cc1)C(=O)C(C(=O)Nc1ccc(C(F)(F)F)cc1-c1cc(C(F)(F)F)ncn1)=C2O] | QC-SMD-TFA05 | 1.68 | 610 |

TABLE 27-continued

| Example No. | Structural formula | LCMS analysis condition No. | Retention time (min) | m/z [M + H]+ |
|---|---|---|---|---|
| 209 | | QC-SMD-TFA05 | 1.72 | 644 |
| 210 | | QC-SMD-TFA05 | 1.72 | 644 |
| 211 | | QC-SMD-TFA05 | 1.71 | 644 |
| 212 | | QC-SMD-TFA05 | 1.70 | 628 |

TABLE 27-continued

| Example No. | Structural formula | LCMS analysis condition No. | Retention time (min) | m/z [M + H]+ |
|---|---|---|---|---|
| 213 | | QC-SMD-TFA05 | 1.71 | 628 |
| 214 | | QC-SMD-TFA05 | 1.71 | 628 |
| 215 | | QC-SMD-TFA05 | 1.76 | 624 |
| 216 | | QC-SMD-TFA05 | 1.78 | 571 |

TABLE 27-continued

| Example No. | Structural formula | LCMS analysis condition No. | Retention time (min) | m/z [M + H]+ |
|---|---|---|---|---|
| 217 | | QC-SMD-TFA05 | 1.77 | 589 |
| 218 | | QC-SMD-TFA05 | 1.62 | 517 |
| 219 | | QC-SMD-TFA05 | 1.76 | 526 |
| 220 | | QC-SMD-TFA05 | 1.62 | 517 |

TABLE 27-continued

| Example No. | Structural formula | LCMS analysis condition No. | Retention time (min) | m/z [M + H]+ |
|---|---|---|---|---|
| 221 | | QC-SMD-TFA05 | 1.76 | 526 |
| 222 | | QC-SMD-TFA05 | 1.62 | 517 |
| 223 | | QC-SMD-TFA05 | 1.76 | 526 |
| 224 | | SQD-AA05 | 1.18 | 589 |

TABLE 27-continued

| Example No. | Structural formula | LCMS analysis condition No. | Retention time (min) | m/z [M + H]+ |
|---|---|---|---|---|
| 225 | | QC-SMD-TFA05 | 1.68 | 590 |
| 226 | | QC-SMD-TFA05 | 1.61 | 615 |
| 227 | | SQD-AA05 | 1.11 | 615 |
| 228 | | SQD-AA05 | 1.11 | 615 |

TABLE 27-continued

| Example No. | Structural formula | LCMS analysis condition No. | Retention time (min) | m/z [M + H]+ |
|---|---|---|---|---|
| 229 | | QC-SMD-TFA05 | 1.67 | 644 |
| 230 | | QC-SMD-TFA05 | 1.66 | 644 |
| 231 | | QC-SMD-TFA05 | 1.71 | 627 |
| 232 | | QC-SMD-TFA05 | 1.70 | 627 |

| Example No. | Structural formula | LCMS analysis condition No. | Retention time (min) | m/z [M + H]+ |
|---|---|---|---|---|
| 233 | | QC-SMD-TFA05 | 1.70 | 645 |

Although the respective compounds described in this table include their tautomers, for example, ¹H-NMR of Example 196 is as follows.

Major Tautomer

¹H-NMR (400 MHz, CDCl₃) δ: 16.40 (1H, s), 12.00 (1H, s), 7.40-7.28 (4H, m), 7.11-7.04 (1H, m), 5.14 (1H, d, J=14.1 Hz), 4.47 (1H, d, J=14.1 Hz), 3.37-3.32 (1H, m), 2.82-2.76 (1H, m), 2.61-2.54 (1H, m), 1.76-1.61 (3H, m), 1.01 (3H, s).

Minor Tautomer

¹H-NMR (400 MHz, CDCl₃) δ: 16.40 (1H, s), 12.18 (1H, s), 7.40-7.28 (4H, m), 7.11-7.04 (1H, m), 5.11 (1H, d, J=14.4 Hz), 4.53 (1H, d, J=14.4 Hz), 3.32-3.26 (1H, m), 2.84-2.77 (1H, m), 2.65-2.61 (1H, m), 1.81-1.70 (3H, m), 0.88 (3H, s).

Example 234

(4aR)-4-Hydroxy-4a-methyl-2-oxo-1-(4,4,4-trifluorobutyl)-N-[4-(trifluoromethyl)-2-[6-(trifluoromethyl)pyrimidin-4-yl]phenyl-6,7-dihydro-5H-pyrrolo[1,2-b]pyridazine-3-carboxamide

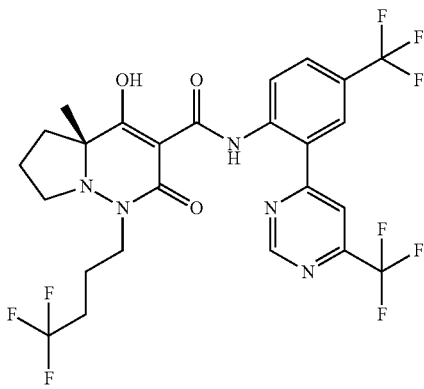 [SMILES: C[C@]12CCCN1N(CCCC(F)(F)F)C(=O)C(C(=O)Nc1ccc(C(F)(F)F)cc1-c1cc(C(F)(F)F)ncn1)=C2O]

Methyl (4aR)-1-[(2,4-dimethoxyphenyl)methyl]-4-hydroxy-4a-methyl-2-oxo-6,7-dihydro-5H-pyrrolo[1,2-b]pyridazine-3-carboxylate (Reference Example 12) and 1,1,1-trifluoro-4-iodobutane were used, and operations similar to those of Third Step of Reference Example 80, Example 166, and Example 21 were consecutively carried out to obtain the title compound.

LCMS: m/z 612[M+H]+

HPLC retention time: 1.63 minutes (analysis condition SMD-TFA05)

Example 235

Ethyl 7-[(4aR)-4-hydroxy-4a-methyl-2-oxo-3-[[4-(trifluoromethyl)-2-[6-(trifluoromethyl)pyridin-3-yl]phenyl]carbamoyl]-6,7-dihydro-5H-pyrrolo[1,2-b]pyridazin-1-yl]heptanoate

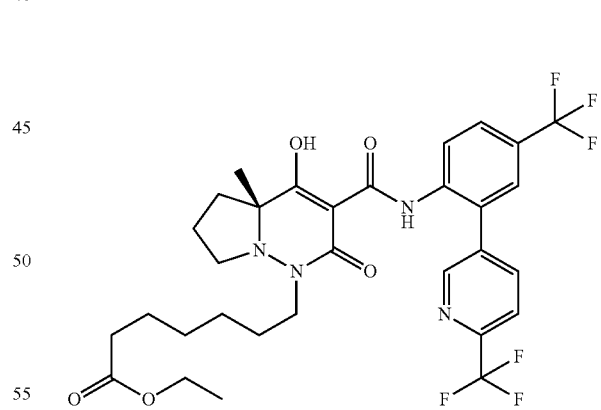

Methyl (4aR)-1-[(2,4-dimethoxyphenyl)methyl]-4-hydroxy-4a-methyl-2-oxo-6,7-dihydro-5H-pyrrolo[1,2-b]pyridazine-3-carboxylate (Reference Example 12) and ethyl 7-bromoheptanoate were used, and operations similar to those of Example 234 were carried out to obtain the title compound.

LCMS: m/z 657[M+H]+

HPLC retention time: 1.70 minutes (analysis condition QC-SMD-TFA05)

Example 236

(4aR)-4-Hydroxy-1-[8-[2-(2-methoxyethoxy)ethoxy]octyl]-4a-methyl-2-oxo-N-[4-(trifluoromethyl)-2-[6-(trifluoromethyl)pyrimidin-4-yl]phenyl-6,7-dihydro-5H-pyrrolo[1,2-b]pyridazine-3-carboxamide

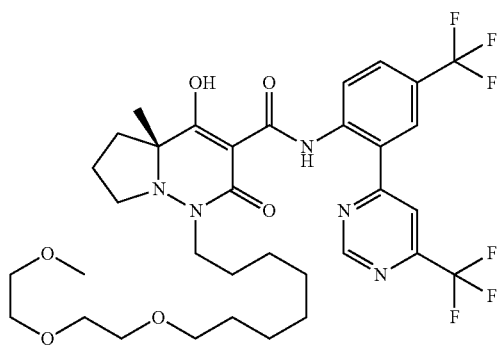 [SMILES: COCCOCCOCCCCCCCCN1C(=O)C(C(=O)Nc2ccc(C(F)(F)F)cc2-c2cc(C(F)(F)F)ncn2)=C(O)[C@@]2(C)CCCN12]

First Step

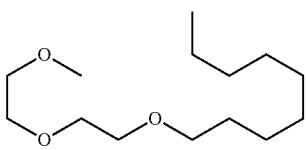 [SMILES: CCCCCCCCCOCCOCCOC]

Sodium iodide was added to a solution of 1-bromo-8-(2-(2-methoxyethoxy)ethoxy)octane (1.00 g, 3.21 mmol) in acetone, and the mixture was stirred at 60° C. for 2 hours. After the reaction mixture was cooled to room temperature, the precipitate was filtered for separation, and after the filtrate was washed with sodium thiosulfate and a brine, the resultant was dried over sodium sulfate. After the resultant was filtered, the filtrate was concentrated at reduced pressure to obtain 1-iodo-8-(2-(2-methoxyethoxy)ethoxy)octane (1.05 g, 91%) as yellow oil.

Second Step

Methyl (4aR)-1-[(2,4-(dimethoxyphenyl)methyl]-4-hydroxy-4a-methyl-2-oxo-6,7-dihydro-5H-pyrrolo[1,2-b]pyridazine-3-carboxylate (Reference Example 12) and the iodine body obtained in First Step was used, and operations similar to those of Example 234 were carried out to obtain the title compound.

LCMS: m/z 732[M+H]+

HPLC retention time: 1.76 minutes (analysis condition QC-SMD-TFA05)

Example 237

(3S)-3-Tert-butyl-N-[4-chloro-2-[6-(trifluoromethyl)pyrimidin-4-yl]phenyl]-1-[(2,3-difluorophenyl)methyl]-4-hydroxy-2-methyl-6-oxo-3H-pyrimidine-5-carboxamide First Step Methyl (2S)-3,3-Dimethyl-2-[methyl-[(2-methylpropan-2-yl)oxycarbonyl]amino]butanoate

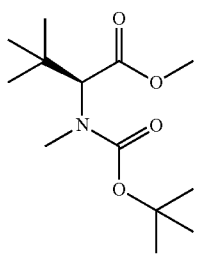 [SMILES: COC(=O)[C@@H](N(C)C(=O)OC(C)(C)C)C(C)(C)C]

(S)-2-((Tert-butoxycarbonyl)amino)-3,3-dimethyl butanoic acid (11.3 g, 48.9 mmol) was dissolved in N,N-dimethylformamide (114 mL), silver oxide (34.0 g, 147 mmol) and iodomethane (18.3 mL, 294 mmol) were added, and the mixture was stirred under nitrogen atmosphere at 45° C. overnight. The reaction mixture was diluted with ethyl acetate (200 mL) and filtered, water was added, and the resultant was extracted with ethyl acetate. The organic layer was washed with a brine, dried over sodium sulfate, filtered, and concentrated at reduced pressure, and the resultant residue was purified by column chromatography on silica gel (hexane/ethyl acetate) to obtain the title compound (12.7 g, 100%).

$^1$H-NMR (CDCl$_3$) δ: 4.75 (1H, s), 3.71 (3H, s), 2.94 (3H, s), 1.48 (9H, s), 1.08 (9H, s).

Second Step

Methyl (S)-3,3-Dimethyl-2-(methylamino)butanoate hydrochloride

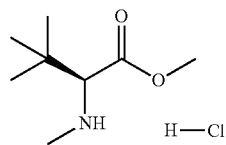

Hydrochloric acid (a dioxane solution, 122 mL, 489 mmol) was added to methyl ((2S)-3,3-dimethyl-2-[methyl-[(2-methylpropan-2-yl)oxycarbonyl]amino]butanoate (12.69 g), and the mixture was stirred at room temperature for 1 hour. The reaction mixture was concentrated at reduced pressure to obtain the title compound (9.58 g, 100%).

¹H-NMR (DMSO-D₆) δ: 9.00 (1H, brs), 3.89-3.86 (1H, m), 3.79 (3H, s), 2.54 (3H, s), 1.02 (9H, s).

Third Step

Methyl (2S)-2-[[(2,3-difluorophenyl)methylideneamino]-methylamino]-3,3-dimethylbutanoate

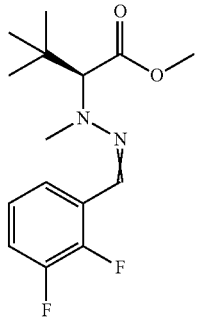 [SMILES: COC(=O)[C@@H](N(C)N=Cc1cccc(F)c1F)C(C)(C)C]

Methyl (S)-3,3-Dimethyl-2-(methylamino)butanoate hydrochloride (70.0 mg, 0.358 mmol) was dissolved in acetic acid (3.58 mmol, 205 μL) and water (716 μL), sodium nitrite (33.4 mg, 0.393 mmol) was added at 0° C., and the mixture was stirred under nitrogen atmosphere for 1 hour. Zinc (19.7 g, 302 mmol) was added to the reaction mixture at 0° C., and the mixture was stirred under nitrogen atmosphere for 4 hours. After the reaction mixture was filtered, methanol (3.58 mL) and 2,3-difluorobenzaldehyde (39.1 μL, 0.358 mmol) were added, and the mixture was stirred at room temperature for 30 minutes. The reaction mixture was concentrated at reduced pressure and diluted with ethyl acetate, and the organic layer was washed with a saturated sodium bicarbonate solution and a brine, and then the resultant was dried over sodium sulfate, filtered, and concentrated at reduced pressure, and the resultant residue was purified by column chromatography on silica gel (hexane/ethyl acetate) to obtain the title compound (44.2 mg, 41%).

LCMS: m/z 299[M+H]⁺

HPLC retention time: 1.13 minutes (analysis condition SQD-AA05)

Fourth Step (3S)-3-tert-Butyl-1-[(2,3-difluorophenyl)methyl]-4-hydroxy-2-methyl-6-oxo-3H-pyrimidine-5-carboxylic acid 2-methylpropyl ester

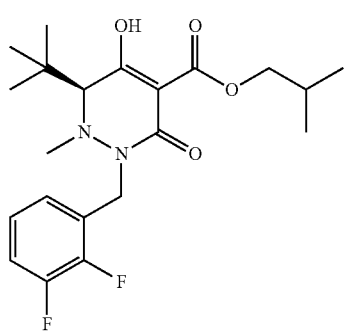 [SMILES: CC(C)COC(=O)C1=C(O)[C@H](C(C)(C)C)N(C)N(Cc2cccc(F)c2F)C1=O]

Methyl ((2S)-2-[[(2,3-difluorophenyl)methylideneamino]-methylamino]-3,3-dimethylbutanoate (44.2 mg, 0.148 mmol)) was dissolved in hydrochloric acid (a methanol solution, 442 μL), borane-pyridine (29.9 μL, 0.296 mmol) was added at 0° C., and the mixture was stirred under nitrogen atmosphere for 2 hours. The reaction mixture was concentrated at reduced pressure and diluted with ethyl acetate, the organic layer was washed with a 1 N aqueous dipotassium hydrogenphosphate solution and a brine, and the aqueous layer was separated by a phase separator and concentrated at reduced pressure to obtain methyl (2S)-2-[[(2,3-difluorophenyl)methylamino]-methylamino]-3,3-dimethylbutanoate as a crude product. The obtained crude product was dissolved in ethyl acetate (750 μL), and then 3-isobutoxy-3-oxopropanoate (0.026 g, 0.163 mmol), pyridine (35.8 μL, 0.444 mmol) and 2,4,6-tripropyl-1,3,5,2,4,6-trioxatriphosphinane 2,4,6-trioxide (an ethyl acetate solution, 174 μL, 0.296 mmol) were added at 0° C., and the mixture was stirred under nitrogen atmosphere for 1 hour. Water was added to the reaction mixture, and the resultant was extracted with ethyl acetate. The organic layer was washed with a 1 N aqueous dipotassium hydrogenphosphate solution and a brine, dried over sodium sulfate, filtered, and concentrated at reduced pressure to obtain methyl (2S)-2-[[(2,3-difluorophenyl)methyl-[3-(2-methylpropoxy)-3-oxopropanoyl]amino]-methylamino]-3,3-dimethylbutanoate as a crude product. The obtained crude product was dissolved in N,N-dimethylformamide (750 μL), cesium carbonate (121 mg, 0.370 mmol) was added, and the mixture was stirred under nitrogen atmosphere at 80° C. for 2 hours. 1 N Hydrochloric acid was added to the reaction mixture at 0° C., and the resultant was extracted with ethyl acetate. The organic layer was washed with a brine, dried over sodium sulfate, filtered, and concentrated at reduced pressure, and the resultant residue was purified by C18 reverse-phase column chromatography (acetonitrile/water) to obtain the title compound (48.1 mg, 79%).

LCMS: m/z 411.5[M+H]⁺

HPLC retention time: 1.03 minutes (analysis condition SQD-AA05)

Fifth Step (3S)-3-Tert-butyl-N-[4-chloro-2-[6-(trifluoromethyl)pyrimidin-4-yl]phenyl]-1-[(2,3-difluorophenyl)methyl]-4-hydroxy-2-methyl-6-oxo-3H-pyrimidine-5-carboxamide

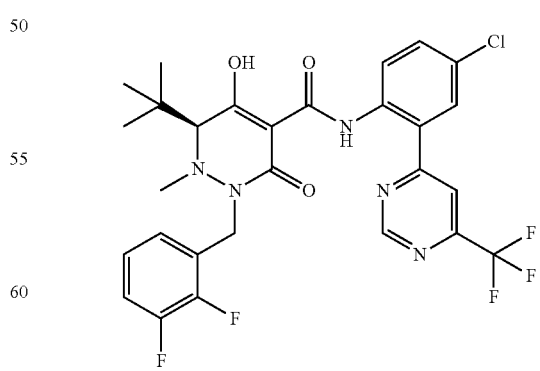

(3S)-3-tert-Butyl-1-[(2,3-difluorophenyl)methyl]-4-hydroxy-2-methyl-6-oxo-3H-pyridazine-5-carboxylic acid 2-methylpropyl ester (6.3 mg, 0.015 mmol) was dissolved in toluene (200 μL), 4-chloro-2-(6-(trifluoromethyl)pyrimidin-4-yl)aniline (Reference Example 53) (4.2 mg, 0.015 mmol) was added, and the mixture was heated for 1 hour. The reaction mixture was concentrated and the resultant residue was purified by C18 reverse-phase column chromatography (acetonitrile/water) to obtain the title compound (8.0 mg, 85%).

LCMS: m/z 610.3[M+H]$^+$

HPLC retention time: 1.72 minutes (analysis condition QC-SMD-TFA05)

Reference Example 83

Methyl (S)-2-(ethylamino)-3,3-dimethylbutanoate hydrochloride

First Step

Methyl (2S)-2-[benzyl(ethyl)amino]-3,3-dimethylbutanoate

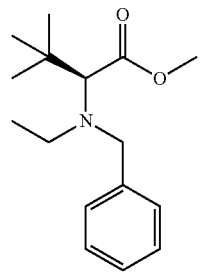 [SMILES: CCN(Cc1ccccc1)[C@H](C(=O)OC)C(C)(C)C]

Methyl (2S)-2-amino-3,3-dimethylbutanoate hydrochloride (5.27 g, 29.0 mmol) was suspended in dichloroethane (250 mL), and then benzaldehyde (2.93 mL, 29.0 mmol) and sodium triacetoxyhydroborate (12.3 g, 58.0 mmol) were added, and the mixture was stirred under nitrogen atmosphere at room temperature for 10 hours. The reaction mixture was diluted with ethyl acetate (200 mL) and filtered, water was added, and the resultant was extracted with ethyl acetate. A saturated sodium bicarbonate solution was added to the reaction mixture at 0° C., and the mixture was extracted with dichloromethane. The organic layer was washed with a brine, dried over sodium sulfate, filtered, and concentrated at reduced pressure to obtain (2S)-2-(benzylamino)-3,3-dimethylbutanoate methyl ester (6.82 g) as a crude product. A part of the obtained crude product (2.00 g, 8.50 mmol) was dissolved in dichloromethane (42.5 mL), acetaldehyde (2.39 mL, 42.5 mmol) and sodium triacetoxyhydroborate (3.60 g, 17.0 mmol) were added, and the mixture was stirred under nitrogen atmosphere at room temperature for 24 hours. A saturated sodium bicarbonate solution was added to the reaction mixture at 0° C., and the mixture was extracted with dichloromethane. The organic layer was washed with a brine, dried over sodium sulfate, filtered, and concentrated at reduced pressure, and the resultant residue was purified by column chromatography on silica gel (hexane/ethyl acetate) to obtain the title compound (1.65 g, 88%).

LCMS: m/z 264.3[M+H]$^+$

HPLC retention time: 1.14 minutes (analysis condition SMD-TFA05)

Second Step

Methyl (S)-3,3-dimethyl-2-(methylamino)butanoate hydrochloride

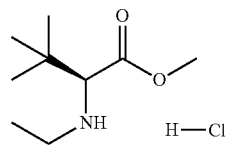

Methyl (2S)-2-[benzyl(ethyl)amino]-3,3-dimethylbutanoate (1.64 g, 6.23 mmol) was dissolved in ethyl acetate (6.23 mL), palladium hydroxide-carbon (20 wt. %, 328 mg) was added, and the mixture was stirred under hydrogen atmosphere at room temperature for 6 hours. The reaction mixture was filtered, hydrochloric acid (a dioxane solution, 4.67 mL, 18.7 mmol) was added, and then the resultant was concentrated at reduced pressure to obtain the title compound (922 mg, 71%).

$^1$H-NMR (DMSO-D$_6$) δ: 8.98 (1H, brs), 8.76 (1H, brs), 3.88 (1H, d, J=10.0 Hz), 3.78 (3H, s), 2.94 (2H, q, J=6.0 Hz), 1.22 (3H, t, J=7.3 Hz), 1.04 (9H, s).

Reference Example 84

Methyl (2S)-3,3-dimethyl-2-(2,2,2-trifluoroethylamino)butanoate

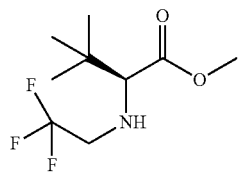

Methyl (2S)-2-amino-3,3-dimethylbutanoate hydrochloride (1.00 g, 5.50 mmol) was suspended in tetrahydrofuran (250 mL), and then trifluoromethanesulfonic acid 2,2,2-trifluoroethyl (1.59 mL, 11.0 mmol) and diisopropylethylamine (4.79 mL, 27.5 mmol) were added, and the mixture was stirred under nitrogen atmosphere at 60° C. for 27 hours. After the mixture was cooled to room temperature, the reaction mixture was filtered, concentrated hydrochloric acid was added, the resultant was concentrated at reduced pressure, and the resultant residue was purified by C18 reverse-phase column chromatography (acetonitrile/water) to obtain the title compound as a solution of acetonitrile/water.

LCMS: m/z 228.3[M+H]$^+$

HPLC retention time: 1.19 minutes (analysis condition SMD-TFA05)

Reference Example 85

Methyl 1-(methylamino)cyclobutanecarboxylate hydrochloride

First Step

Methyl 1-((tert-butoxycarbonyl)(methyl)amino)cyclobutanecarboxylate

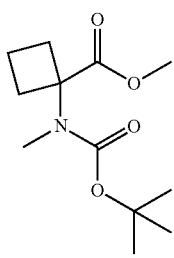 [SMILES: COC(=O)C1(N(C)C(=O)OC(C)(C)C)CCC1]

1-((tert-Butoxycarbonyl)amino)cyclobutanecarboxylic acid (1.00 g, 4.65 mmol) was dissolved in N,N-dimethylformamide (9.29 mL), and then sodium hydride (55%, 0.61 g, 13.9 mmol) and methyl iodide (1.45 mL, 23.3 mmol) were added at 0° C., and the mixture was stirred under nitrogen atmosphere at room temperature for 3 hours. A 1 N aqueous hydrochloric acid solution was added to the reaction mixture at 0° C., and the mixture was extracted with diethyl ether. The organic layer was washed with water, a saturated sodium bicarbonate solution, a 10 wt. % aqueous sodium thiosulfate solution, and a brine, the aqueous layer was separated by a phase separator, the resultant was concentrated at reduced pressure, and the resultant residue was purified by column chromatography on silica gel (hexane/ethyl acetate) to obtain the title compound (1.13 g, 100%).

LCMS: m/z 266.3[M+Na]$^+$

HPLC retention time: 0.92 minutes (analysis condition SQD-AA05)

Second Step

Methyl 1-(methylamino)cyclobutanecarboxylate hydrochloride

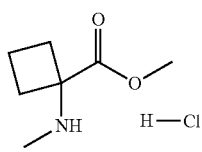

In a similar manner to Second Step of Example 237, the title compound was synthesized from methyl 1-((tert-butoxycarbonyl)(methyl)amino)cyclobutanecarboxylate.

$^1$H-NMR (DMSO-D$_6$) δ: 9.97 (2H, brs), 3.86 (3H, s), 2.60-2.57 (2H, m), 2.50-2.46 (5H, m), 2.06-2.03 (2H, m).

Reference Example 86

Methyl 1-(methylamino)cyclobutanecarboxylate 4-toluenesulfonate

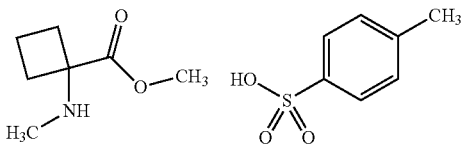

Methyl 1-(methylamino)cyclobutanecarboxylate hydrochloride (1.39 g, 7.75 mmol) was dissolved in ethyl acetate (15 mL), and then 4-toluenesulfonate monohydrate (1.47 g, 7.75 mmol) was added, the mixture was concentrated at reduced pressure, ethyl acetate (15 mL) was added, and the resultant was filtered to obtain the title compound (1.96 g, 80%).

$^1$H-NMR (DMSO-D$_6$) δ: 9.10 (2H, brs), 7.48 (2H, d, J=7.9 Hz), 7.12 (2H, d, J=7.9 Hz), 3.82 (3H, s), 2.56-2.31 (7H, m), 2.29 (3H, s), 2.05-1.99 (2H, m).

Reference Example 87

Methyl 1-(methylamino)cyclopentanecarboxylate hydrochloride

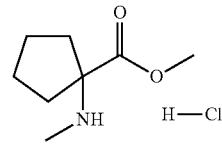

In a similar manner to First and Second Steps of Reference Example 85, the title compound was synthesized from 1-((tert-butoxycarbonyl)amino)cyclopentanecarboxylic acid.

$^1$H-NMR (DMSO-D$_6$) δ: 9.71 (2H, brs), 3.79 (3H, s), 3.34 (3H, s), 2.20-2.13 (2H, m), 2.05-1.98 (2H, m), 1.89-1.86 (2H, m), 1.74-1.71 (2H, m).

Reference Example 88

Methyl 1-(methylamino)cyclopentanecarboxylate 4-toluenesulfonate

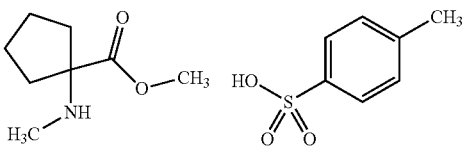

Methyl 1-(methylamino)cyclopentanecarboxylate hydrochloride (1.50 g, 7.75 mmol) was dissolved in ethyl acetate (15 mL), and then 4-toluenesulfonate monohydrate (1.47 g, 7.75 mmol) was added, the mixture was concentrated at reduced pressure, ethyl acetate (15 mL) was added, and the resultant was filtered to obtain the title compound (2.00 g, 78%).

¹H-NMR (DMSO-D₆) δ: 9.18 (2H, brs), 7.48 (2H, d, J=7.9 Hz), 7.11 (2H, d, J=7.9 Hz), 3.79 (3H, s), 2.57 (3H, brs), 2.29 (3H, s), 2.24-2.10 (2H, m), 1.99-1.86 (2H, m), 1.86-1.65 (2H, m).

Reference Example 89

Methyl 1-(methylamino)cyclohexanecarboxylate hydrochloride

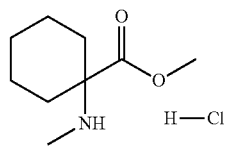

In a similar manner to First and Second Steps of Reference Example 85, the title compound was synthesized from 1-((tert-butoxycarbonyl)amino)cyclohexanecarboxylic acid.

¹H-NMR (DMSO-D₆) δ: 9.43 (2H, brs), 3.84 (3H, s), 2.51 (3H, s), 2.15-2.12 (2H, m), 1.77-1.73 (4H, m), 1.58-1.55 (1H, m), 1.47-1.44 (2H, m), 1.35-1.29 (1H, m).

LCMS: m/z 172.5 [M+H]⁺
LCMS: m/z 172.5[M+H]⁺
HPLC retention time: 0.52 minutes (analysis condition SMD-TFA05)

Reference Example 90

Methyl 2-ethyl-2-(methylamino)butanoate hydrochloride

First Step 2-(((Benzyloxy)carbonyl)amino)-2-ethylbutanoate methyl ester

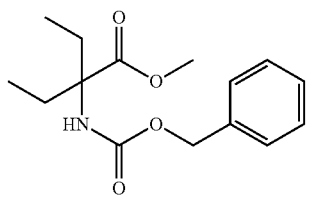 [SMILES: CCC(CC)(NC(=O)OCc1ccccc1)C(=O)OC]

2-Ethyl-2-(methoxycarbonyl)butanoate (307.0 mg, 1.76 mmol) was dissolved in toluene (11.7 mL), and then triethylamine (295 μL, 2.12 mmol) and diphenylphosphoryl azide (458 μL, 2.12 mmol) were added, and the mixture was stirred at room temperature for 1.5 hours and at 95° C. for 0.5 hours. Benzyl alcohol (1.1 mL, 10.6 mmol) was added, and the mixture was stirred at 95° C. overnight. The reaction mixture was concentrated at reduced pressure, diluted with diethyl ether, and the resultant was washed with 1 N hydrochloric acid, a saturated sodium bicarbonate solution, and a brine. The organic layer was dried over anhydrous sodium sulfate, filtered, and concentrated at reduced pressure. The resultant residue was purified by column chromatography on silica gel (ethyl acetate/hexane) to obtain the title compound (488.1 mg, 99%).

LCMS: m/z 280[M+H]⁺
HPLC retention time: 1.11 minutes (analysis condition SMD-TFA05)

Second Step

Methyl 2-(((benzyloxy)carbonyl)(methyl)amino)-2-ethylbutanoate

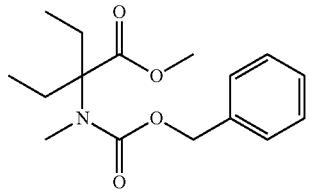 [SMILES: CCC(CC)(C(=O)OC)N(C)C(=O)OCc1ccccc1]

After a solution of methyl 2-(((benzyloxy)carbonyl)amino)-2-ethylbutanoate (481.3 mg, 1.72 mmol) in N,N-dimethylformamide (3.4 mL) was added to sodium hydride (83 mg, 3.45 mmol) at 0° C., methyl iodide (269 μL, 4.31 mmol) was added, and the mixture was stirred at room temperature for 2 hours. The reaction mixture was diluted with diethyl ether and washed with 1 N hydrochloric acid, water, a saturated sodium bicarbonate solution, an aqueous sodium thiosulfate solution, and a brine. The organic layer was dried over anhydrous sodium sulfate, filtered, and concentrated at reduced pressure. The resultant residue was purified by column chromatography on silica gel (ethyl acetate/hexane) to obtain the title compound (438.5 mg, 87%).

LCMS: m/z 294[M+H]⁺
HPLC retention time: 1.14 minutes (analysis condition SMD-TFA05)

Third Step

Methyl 2-ethyl-2-(methylamino)butanoate hydrochloride

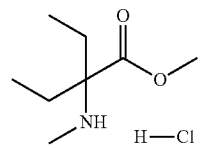

Palladium-carbon (10 wt. %, 15.8 mg) was added to a solution of methyl 2-(((benzyloxy)carbonyl)(methyl)amino)-2-ethylbutanoate (434.5 mg, 1.48 mmol) in methanol (7.4 mL), and the mixture was stirred under hydrogen atmosphere at room temperature for 1 hour. A hydrochloric acid-methanol solution (0.5 M, 14.8 mL) was added to the reaction mixture, and the resultant was filtered and concentrated at reduced pressure to obtain the title compound (281.9 mg, 97%).

¹H-NMR (CD₃OD) δ: 3.92 (3H, s), 3.34 (1H, m), 2.69 (3H, s), 2.04 (4H, m), 0.99 (6H, t).
LCMS: m/z 160[M+H]⁺
HPLC retention time: 0.49 minutes (analysis condition SMD-TFA05)

Reference Example 91

4-Chloro-5-methyl-6-(trifluoromethyl)pyrimidine

First Step

5-Methyl-6-(trifluoromethyl)pyrimidin-4(3H)-one

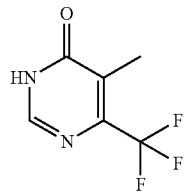

Ethyl 4,4,4-trifluoro-2-methyl-3-oxobutanoate (200 mg, 1.01 mmol) and formamidine hydrochloride (122 mg, 1.51 mmol) were dissolved in ethanol (2.0 mL), and the mixture was stirred at room temperature for 2 hours. Sodium ethoxide (172 mg, 2.52 mmol) was added, and the mixture was stirred at 80° C. for 4 hours. 1 N hydrochloric acid and water were added to the reaction mixture, and the resultant was extracted with ethyl acetate. The organic layer was washed with a brine, dried over anhydrous sodium sulfate, filtered, and concentrated at reduced pressure. The resultant residue was washed with diethyl ether to obtain the title compound (158 mg, 88%).

LCMS: m/z 179[M+H]$^+$

HPLC retention time: 0.46 minutes (analysis condition SQD-FA05)

Second Step

4-Chloro-5-methyl-6-(trifluoromethyl)pyrimidine

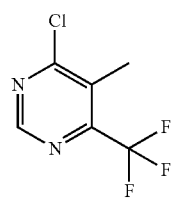

Phosphoryl chloride (1.06 mL, 11.4 mmol) was added to 5-methyl-6-(trifluoromethyl)pyrimidin-4(3H)-one (135 mg, 0.758 mmol), and the mixture was stirred at 100° C. for 1 hour. A saturated sodium bicarbonate solution was added to the reaction mixture, and the resultant was extracted with dichloromethane. The organic layer was washed with a brine, dried over anhydrous sodium sulfate, filtered, and concentrated at reduced pressure to obtain the title compound as a crude product.

LCMS: m/z 197[M+H]$^+$

HPLC retention time: 0.95 minutes (analysis condition SMD-TFA05)

Reference Example 92

4,5-Dichloro-6-(trifluoromethyl)pyrimidine

First Step

5-Chloro-6-(trifluoromethyl)pyrimidin-4(3H)-one

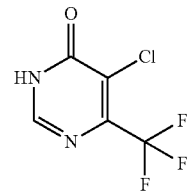 [SMILES: O=c1[nH]cnc(C(F)(F)F)c1Cl]

6-(Trifluoromethyl)pyrimidin-4(3H)-one (1.0 g, 6.1 mmol) and N-chlorosuccinimide (1.1 g, 7.9 mmol) were dissolved in N,N-dimethylformamide (5.0 mL), and the mixture was stirred at 50° C. for 9 hours. The reaction mixture was diluted with ethyl acetate and washed with water and a brine. The organic layer was dried over anhydrous sodium sulfate, filtered, and concentrated at reduced pressure. The resultant residue was purified by C18 reverse-phase column chromatography (water/acetonitrile, 0.1% formic acid) to obtain the title compound (368.5 mg, 31%).

LCMS: m/z 199[M+H]$^+$

HPLC retention time: 0.68 minutes (analysis condition SMD-TFA05)

Second Step 4,5-Dichloro-6-(trifluoromethyl)pyrimidine

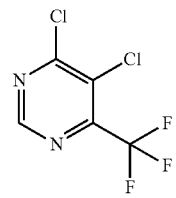

Phosphoryl chloride (1.4 mL, 15.1 mmol) was added to 5-chloro-6-(trifluoromethyl)pyrimidin-4(3H)-one (150.0 mg, 0.756 mmol), and the mixture was stirred at 100° C. for 1.5 hours. Ice-water was added to the reaction mixture and extracted with dichloromethane, the organic layer was dried over anhydrous sodium sulfate, filtered, and concentrated at reduced pressure to obtain the title compound (121.5 mg) as a crude product.

LCMS: m/z 217[M+H]$^+$

HPLC retention time: 1.03 minutes (analysis condition SMD-TFA05)

Reference Example 93

4-Chloro-2-(6-chloropyrimidin-4-yl)aniline

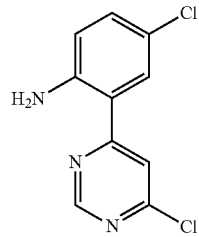

Dioxane (9.6 mL) was added to 2-amino-4-chloro-phenylboronic acid pinacol ester (608 mg, 2.4 mmol), 4,6-dichloropyridine (892 mg, 6.0 mmol), tetrakis(triphenylphosphine)palladium (138 mg, 0.12 mmol), and potassium phosphate (2.03 g, 9.6 mmol), and the mixture was stirred at 90° C. for 3 hours. The reaction mixture was diluted with water and extracted with ethyl acetate. The organic layer was concentrated at reduced pressure, and the resultant residue was purified by column chromatography on silica gel (ethyl acetate/hexane) to obtain the title compound (349.6 mg, 59%).

LCMS: m/z 240[M+H]$^+$

HPLC retention time: 1.14 minutes (analysis condition SMD-TFA05)

The boronic acid derivatives and halides described in the following Table were used to synthesize the aniline intermediates described in the following Table by carrying out operations similar to those of Reference Example 93.

TABLE 28

| Reference Example No. | Aniline | Boronic acid derivative | Halide | Aniline intermediate m/z |
|---|---|---|---|---|
| 94 | | | | 251 [M + H]$^+$ |
| 95 | | | | 255 [M + H]$^+$ |
| 96 | | | | 322 [M + H]$^+$ |

TABLE 28-continued

| Reference Example No. | Aniline | Boronic acid derivative | Halide | Aniline intermediate m/z |
|---|---|---|---|---|
| 97 | | | | 342 [M + H]+ |
| 98 | | | | 345 [M + H]+ |

Reference Example 99

6-(2-Amino-5-chlorophenyl)pyrimidine-4-carbonitrile

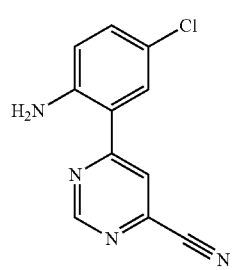 [SMILES: N#Cc1cc(-c2cc(Cl)ccc2N)ncn1]

4-Chloro-2-(6-chloropyrimidin-4-yl)aniline was used, and operations similar to those of Reference Example 63 were carried out to synthesize the title compound.

LCMS: m/z 265[M+H]+

HPLC retention time: 1.16 minutes (analysis condition SMD-TFA05)

Reference Example 100

6-(2-Amino-5-chlorophenyl)-5-methylpyrimidine-4-carbonitrile

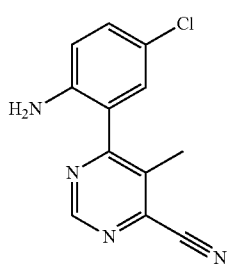 [SMILES: Cc1c(C#N)ncnc1-c1cc(Cl)ccc1N]

4-Chloro-2-(6-chloropyrimidin-4-yl)aniline was used, and operations similar to those of Reference Example 63 were carried out to synthesize the title compound.

LCMS: m/z 245[M+H]+

HPLC retention time: 0.75 minutes (analysis condition SQD-FA05)

Examples 238 to 300

The appropriate aniline reagents of Reference Examples 94 to 100 described in Table 30, the appropriate benzaldehyde derivatives of Reference Example 3 and those known from literature or commercialized, and the appropriate amines of Reference Examples 85 to 90 and those known from literature or commercialized were used to synthesize the compounds described in the following Table by carrying out operations similar to those of Third to Fifth Steps of Example 237.

Purification condition: HPLC

Mobile phase: MeCN/water (no additive), MeCN/water (0.1% formic acid), MeCN/water (0.1% NEt$_3$), or CHCl$_3$ Column:

YMC-Actus ODS-A (100×20 mml.D., S-5 μm, 12 nm)

YMC-Actus Triart C18 (100×30 mml.D., S-5 μm, 12 nm)

YMC-Actus Triart C18 (50×30 mml.D., S-5 μm, 12 nm)

JAI JAIGEL-H (600×20 mml.D., GPC)

TABLE 29

| Example No. | Structural formula | LCMS analysis condition No. | Retention time (min) | m/z [M + H]$^+$ |
|---|---|---|---|---|
| 238 | | QC-SMD-TFA05 | 1.71 | 643 |
| 239 | | QC-SMD-TFA05 | 1.71 | 609 |
| 240 | | SQD-AA05 | 1.72 | 544 |

TABLE 29-continued

| Example No. | Structural formula | LCMS analysis condition No. | Retention time (min) | m/z [M + H]+ |
|---|---|---|---|---|
| 241 | | QC-SMD-TFA05 | 1.74 | 523 |
| 242 | | QC-SMD-TFA05 | 1.72 | 577 |
| 243 | | QC-SMD-TFA05 | 1.75 | 576 |
| 244 | | QC-SMD-TFA05 | 1.65 | 499 |

TABLE 29-continued

| Example No. | Structural formula | LCMS analysis condition No. | Retention time (min) | m/z [M + H]+ |
|---|---|---|---|---|
| 245 | | QC-SMD-TFA05 | 1.75 | 623 |
| 246 | | QC-SMD-TFA05 | 1.78 | 558 |
| 247 | | QC-SMD-TFA05 | 1.71 | 677 |
| 248 | | SQD-AA05 | 1.59 | 612 |

TABLE 29-continued

| Example No. | Structural formula | LCMS analysis condition No. | Retention time (min) | m/z [M + H]+ |
|---|---|---|---|---|
| 249 | | QC-SMD-TFA05 | 1.69 | 630 |
| 250 | | QC-SMD-TFA05 | 1.69 | 596 |
| 251 | | QC-SMD-TFA05 | 1.67 | 595 |
| 252 | | QC-SMD-TFA05 | 1.69 | 630 |

TABLE 29-continued

| Example No. | Structural formula | LCMS analysis condition No. | Retention time (min) | m/z [M + H]+ |
|---|---|---|---|---|
| 253 | | QC-SMD-TFA05 | 1.68 | 629 |
| 254 | | QC-SMD-TFA05 | 1.70 | 530 |
| 255 | | QC-SMD-TFA05 | 1.69 | 594 |
| 256 | | QC-SMD-TFA05 | 1.68 | 593 |

TABLE 29-continued
| Example No. | Structural formula | LCMS analysis condition No. | Retention time (min) | m/z [M + H]⁺ |
|---|---|---|---|---|
| 257 | 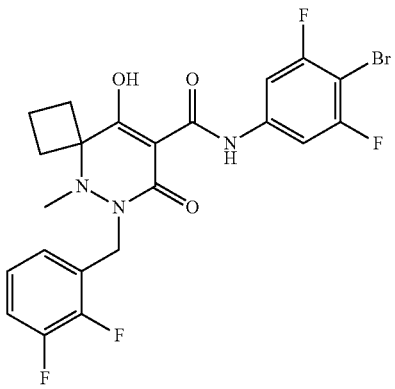 [SMILES: CN1N(Cc2cccc(F)c2F)C(=O)C(C(=O)Nc2cc(F)c(Br)c(F)c2)=C(O)C12CCC2] | QC-SMD-TFA05 | 1.71 | 528 |
| 258 | 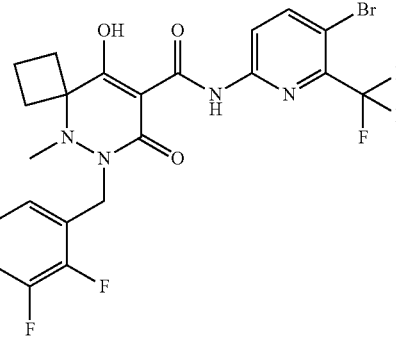 | QC-SMD-TFA05 | 1.69 | 561 |
| 259 | 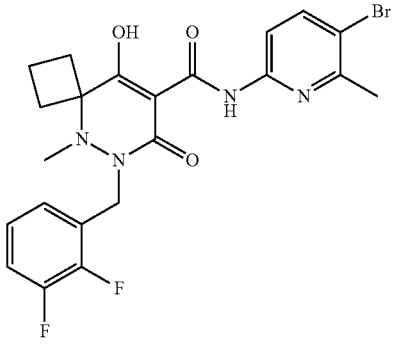 [SMILES: Cc1nc(NC(=O)C2=C(O)C3(CCC3)N(C)N(Cc3cccc(F)c3F)C2=O)ccc1Br] | QC-SMD-TFA05 | 1.70 | 507 |
| 260 | 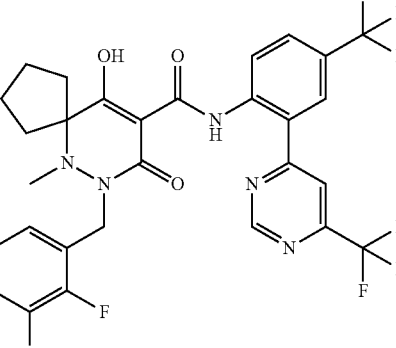 | SQD-AA05 | 1.20 | 642 |

TABLE 29-continued

| Example No. | Structural formula | LCMS analysis condition No. | Retention time (min) | m/z [M + H]+ |
|---|---|---|---|---|
| 261 | | SQD-AA05 | 1.23 | 608 |
| 262 | | QC-SMD-TFA05 | 1.74 | 521 |
| 263 | | QC-SMD-TFA05 | 1.72 | 575 |
| 264 | | QC-SMD-TFA05 | 1.36 | 773 |

TABLE 29-continued

| Example No. | Structural formula | LCMS analysis condition No. | Retention time (min) | m/z [M + H]+ |
|---|---|---|---|---|
| 265 | | QC-SMD-TFA05 | 1.35 | 739 |
| 266 | | QC-SMD-TFA05 | 1.36 | 772 |
| 267 | | QC-SMD-TFA05 | 1.34 | 738 |
| 268 | | QC-SMD-TFA05 | 1.36 | 750 |

TABLE 29-continued

| Example No. | Structural formula | LCMS analysis condition No. | Retention time (min) | m/z [M + H]+ |
|---|---|---|---|---|
| 269 | | QC-SMD-TFA05 | 1.33 | 716 |
| 270 | | QC-SMD-TFA05 | 1.31 | 744 |
| 271 | | QC-SMD-TFA05 | 1.30 | 729 |
| 272 | | QC-SMD-TFA05 | 1.28 | 696 |

TABLE 29-continued

| Example No. | Structural formula | LCMS analysis condition No. | Retention time (min) | m/z [M + H]+ |
|---|---|---|---|---|
| 273 | | QC-SMD-TFA05 | 1.26 | 774 |
| 274 | | QC-SMD-TFA05 | 1.30 | 710 |
| 275 | | QC-SMD-TFA05 | 1.33 | 719 |
| 276 | | QC-SMD-TFA05 | 1.36 | 753 |

TABLE 29-continued

| Example No. | Structural formula | LCMS analysis condition No. | Retention time (min) | m/z [M + H]+ |
|---|---|---|---|---|
| 277 | | QC-SMD-TFA05 | 1.34 | 695 |
| 278 | | QC-SMD-TFA05 | 1.38 | 787 |
| 279 | | QC-SMD-TFA05 | 1.33 | 759 |
| 280 | | QC-SMD-TFA05 | 1.32 | 758 |

TABLE 29-continued

| Example No. | Structural formula | LCMS analysis condition No. | Retention time (min) | m/z [M + H]+ |
|---|---|---|---|---|
| 281 | | QC-SMD-TFA05 | 1.30 | 724 |
| 282 | | QC-SMD-TFA05 | 1.31 | 756 |
| 283 | | QC-SMD-TFA05 | 1.27 | 728 |
| 284 | | QC-SMD-TFA05 | 1.35 | 791 |

TABLE 29-continued

| Example No. | Structural formula | LCMS analysis condition No. | Retention time (min) | m/z [M + H]+ |
|---|---|---|---|---|
| 285 | | QC-SMD-TFA05 | 1.33 | 771 |
| 286 | | QC-SMD-TFA05 | 1.33 | 737 |
| 287 | | QC-SMD-TFA05 | 1.34 | 770 |
| 288 | | QC-SMD-TFA05 | 1.32 | 736 |

TABLE 29-continued
| Example No. | Structural formula | LCMS analysis condition No. | Retention time (min) | m/z [M + H]⁺ |
|---|---|---|---|---|
| 289 | 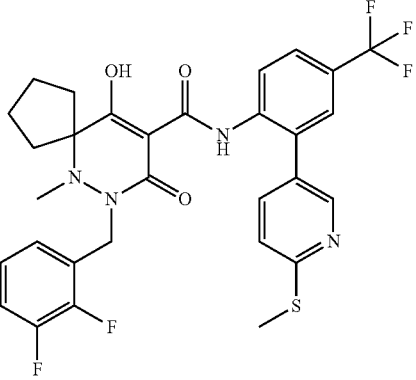 | QC-SMD-TFA05 | 1.34 | 748 |
| 290 | 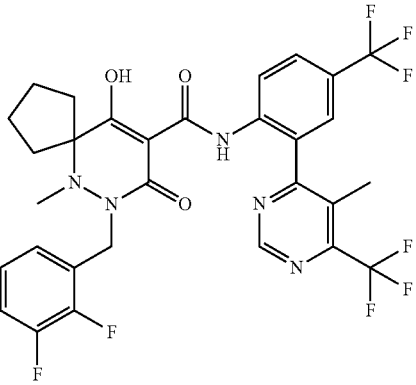 [SMILES: CN1N(Cc2cccc(F)c2F)C(=O)C(C(=O)Nc2ccc(C(F)(F)F)cc2-c2cc(C(F)(F)F)ncn2)=C(O)C12CCCC2] | QC-SMD-TFA05 | 1.35 | 785 |
| 291 | 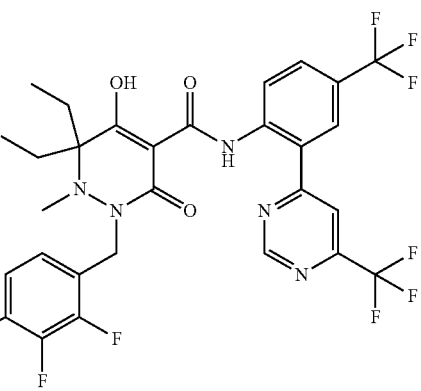 | QC-SMD-TFA05 | 1.36 | 773 |
| 292 | 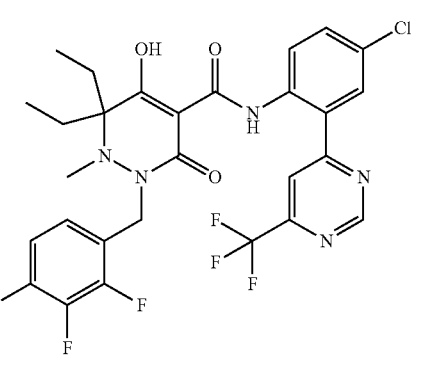 | QC-SMD-TFA05 | 1.34 | 739 |

TABLE 29-continued

| Example No. | Structural formula | LCMS analysis condition No. | Retention time (min) | m/z [M + H]+ |
|---|---|---|---|---|
| 293 | | QC-SMD-TFA05 | 1.35 | 772 |
| 294 | | QC-SMD-TFA05 | 1.33 | 738 |
| 295 | | SMD-TFA05 | 1.35 | 785 |
| 296 | | SMD-TFA05 | 1.35 | 799 |

TABLE 29-continued

| Example No. | Structural formula | LCMS analysis condition No. | Retention time (min) | m/z [M + H]+ |
|---|---|---|---|---|
| 297 | | SMD-TFA05 | 1.33 | 751 |
| 298 | | SMD-TFA05 | 1.33 | 718 |

Reference Example 101

Methyl 2-(2,3-difluorobenzyl)-5-hydroxy-6,6-dimethyl-3-oxo-1-phenyl-1,2,3,6-tetrahydropyridazine-4-carboxylate First Step

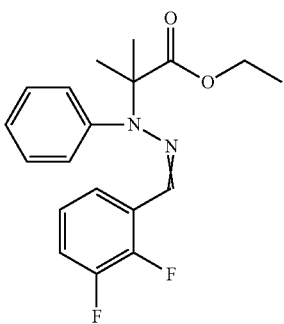 [SMILES: CCOC(=O)C(C)(C)N(N=Cc1cccc(F)c1F)c1ccccc1]

Phenylhydrazine (0.76 g, 7.1 mmol) and ethyl 2-bromo-2-methylpropionate (1.93 g, 9.9 mmol) were dissolved in N,N-diisopropylethylamine (1.00 g, 7.8 mmol), and the mixture was stirred and heated under nitrogen atmosphere at 110° C. for 4 hours. The reaction mixture was cooled to room temperature, concentrated at reduced pressure, and extracted with ethyl acetate. The organic layer was washed with water and a brine, dried over sodium sulfate, filtered, and concentrated at reduced pressure to obtain a crude product. Methanol (6 mL) and 2,3-difluoro-benzaldehyde (0.77 mL, 7.1 mmol) were added to the obtained crude product, and the mixture was stirred under nitrogen atmosphere at room temperature for 1 hour. The reaction mixture was concentrated at reduced pressure, and the resultant residue was purified by C-18 reverse-phase column chromatography on silica gel (0.1% formic acid water/0.1% formic acid acetonitrile) to obtain ethyl 2-(2-(2,3-difluorobenzylidene)-1-phenylhydrazinyl)-2-methylpropanoate (0.51 g, 21%) as yellow oil.

LCMS: m/z 347[M+H]+

HPLC retention time: 1.12 minutes (analysis condition SQD-FA05)

Second Step

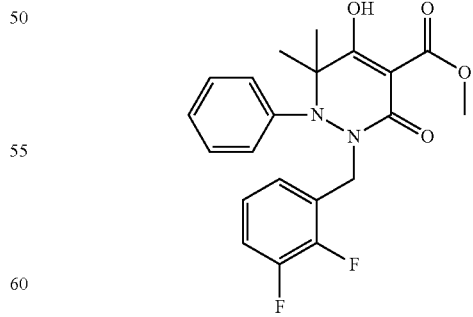

Ethyl 2-(2-(2,3-difluorobenzylidene)-1-phenylhydrazinyl)-2-methylpropanoate obtained in First Step was used, and operations similar to those of Reference Example 1-2 were carried out to obtain the title compound (0.38 g, 65%) as yellow oil.

LCMS: m/z 403[M+H]+
HPLC retention time: 0.97 minutes (analysis condition SQD-FA05)

Reference Example 102

Methyl 6-(2,3-difluorobenzyl)-9-hydroxy-5-methyl-7-oxo-5,6-diazaspiro[3.5]non-8-ene-8-carboxylate First Step

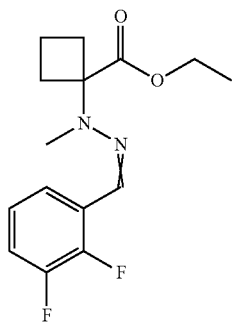 [SMILES: CCOC(=O)C1(N(C)N=Cc2cccc(F)c2F)CCC1]

Methylhydrazine (0.10 g, 2.17 mmol) and ethyl 1-bromocyclobutanecarboxylate (0.23 g, 1.1 mmol) were dissolved in N,N-diisopropylethylamine (0.30 g, 2.3 mmol), and the mixture was stirred and heated under nitrogen atmosphere at 110° C. for 15 hours. The reaction mixture was cooled to room temperature, filtered, concentrated at reduced pressure, and extracted with ethyl acetate. The organic layer was washed with water and a brine, dried over sodium sulfate, filtered, and concentrated at reduced pressure to obtain a crude product. The obtained crude product was added to the reaction mixture, and then methanol (2 mL) and 2,3-difluoro-benzaldehyde (0.12 mL, 1.1 mmol) were added, and the mixture was stirred under nitrogen atmosphere at room temperature for 1 hour. The reaction mixture was concentrated at reduced pressure, and the resultant residue was purified by C-18 reverse-phase column chromatography on silica gel (0.1% formic acid water/0.1% formic acid acetonitrile) to obtain ethyl 1-(2-(2,3-difluorobenzylidene)-1-methylhydrazinyl)cyclobutanecarboxylate (36 mg, 11%) as colorless oil.

LCMS: m/z 297[M+H]+
HPLC retention time: 1.15 minutes (analysis condition SQD-FA05)

Second Step

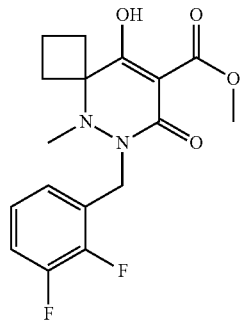 [SMILES: COC(=O)C1=C(O)C2(CCC2)N(C)N(Cc2cccc(F)c2F)C1=O]

Ethyl 1-(2-(2,3-difluorobenzylidene)-1-methylhydrazinyl)cyclobutanecarboxylate obtained in First Step was used, and operations similar to those of Second Step of Reference Example 101 were carried out to obtain the title compound (50 mg, 78%) as red oil.

LCMS: m/z 353[M+H]+
HPLC retention time: 0.93 minutes (analysis condition SQD-FA05)

Reference Example 103

Methyl 2-(2,3-difluorobenzyl)-5-hydroxy-1,6,6-trimethyl-3-oxo-1,2,3,6-tetrahydropyridazine-4-carboxylate First Step

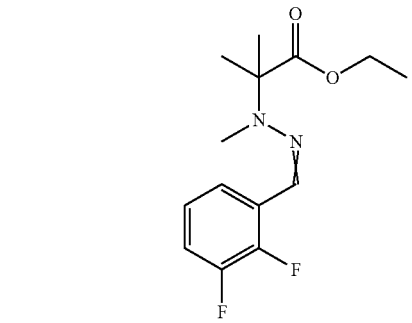 [SMILES: CCOC(=O)C(C)(C)N(C)N=Cc1cccc(F)c1F]

Methylhydrazine (0.46 g, 10.0 mmol) and ethyl 2-bromo-2-methylpropionate (1.07 g, 5.5 mmol) were dissolved in tetrahydrofuran (5.0 mL), and then N,N-diisopropylethylamine (0.84 g, 6.5 mmol) was added, and the mixture was stirred and heated under nitrogen atmosphere at 60° C. for 66 hours. After the reaction mixture was cooled to room temperature, methanol (60 mL) and 2,3-difluoro-benzaldehyde (0.55 mL, 5.0 mmol) were added to the reaction mixture, and the mixture was stirred under nitrogen atmosphere at room temperature for 1 hour. The reaction mixture was concentrated at reduced pressure, and the resultant residue was purified by C-18 reverse-phase column chromatography on silica gel (0.1% formic acid water/0.1% formic acid acetonitrile) to obtain ethyl 2-[2-(2,3-difluorobenzylidene)-1-methylhydrazinyl]-2-methylpropionate (0.8 g, 56%) as colorless oil.

LCMS: m/z 285[M+H]+
HPLC retention time: 1.00 minute (analysis condition SQD-FA05)

Second Step

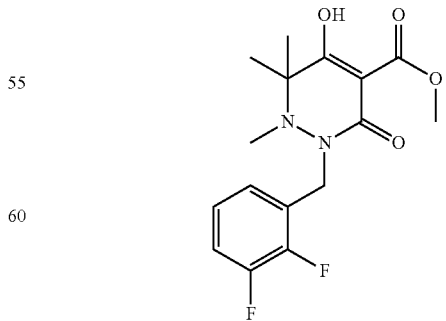

Ethyl 2-[2-(2,3-difluorobenzylidene)-1-methylhydrazinyl]-2-methylpropionate obtained in First Step was used, and operations similar to those of Second Step of Reference Example 101 were carried out to obtain the title compound (650 mg, 68%) as yellow oil.

LCMS: m/z 341[M+H]$^+$

HPLC retention time: 0.81 minutes (analysis condition SQD-FA05)

The appropriate aniline reagents and appropriate ester intermediates of Reference Examples 101 to 103 were used to synthesize the compounds described in the following Table by carrying out operations similar to those of Fifth Step of Example 237.

TABLE 30

| Example No. | Structural formula | LCMS analysis condition No. | Retention time (min) | m/z [M + H]$^+$ |
|---|---|---|---|---|
| 299 | | QC-SMD-TFA05 | 1.73 | 678 |
| 300 | | QC-SMD-TFA05 | 1.68 | 628 |
| 301 | | QC-SMD-TFA05 | 1.67 | 627 |

TABLE 30-continued

| Example No. | Structural formula | LCMS analysis condition No. | Retention time (min) | m/z [M + H]+ |
|---|---|---|---|---|
| 302 | | QC-SMD-TFA05 | 1.56 | 602 |
| 303 | | QC-SMD-TFA05 | 1.58 | 573 |
| 304 | | QC-SMD-TFA05 | 1.59 | 616 |
| 305 | | QC-SMD-TFA05 | 1.63 | 615 |

TABLE 30-continued
| Example No. | Structural formula | LCMS analysis condition No. | Retention time (min) | m/z [M + H]+ |
|---|---|---|---|---|
| 306 | 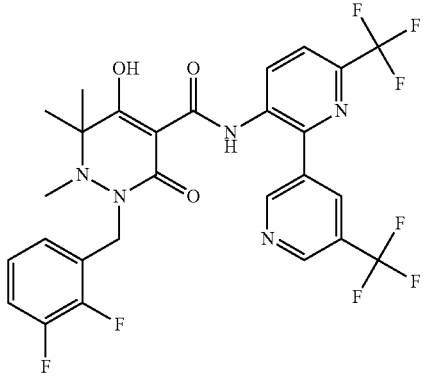 [SMILES: CN1N(Cc2cccc(F)c2F)C(=O)C(C(=O)Nc2ccc(C(F)(F)F)nc2-c2cncc(C(F)(F)F)c2)=C(O)C1(C)C] | QC-SMD-TFA05 | 1.58 | 616 |
| 307 | 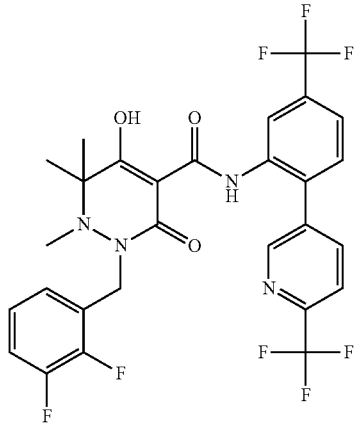 [SMILES: CN1N(Cc2cccc(F)c2F)C(=O)C(C(=O)Nc2cc(C(F)(F)F)ccc2-c2ccc(C(F)(F)F)nc2)=C(O)C1(C)C] | QC-SMD-TFA05 | 1.63 | 615 |
| 308 | 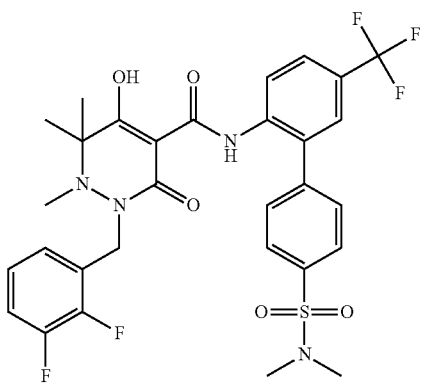 [SMILES: CN1N(Cc2cccc(F)c2F)C(=O)C(C(=O)Nc2ccc(C(F)(F)F)cc2-c2ccc(S(=O)(=O)N(C)C)cc2)=C(O)C1(C)C] | QC-SMD-TFA05 | 1.62 | 653 |

TABLE 30-continued

| Example No. | Structural formula | LCMS analysis condition No. | Retention time (min) | m/z [M + H]+ |
|---|---|---|---|---|
| 309 | | QC-SMD-TFA05 | 1.63 | 581 |
| 310 | | QC-SMD-TFA05 | 1.65 | 593 |
| 311 | | QC-SMD-TFA05 | 1.59 | 587 |
| 312 | | QC-SMD-TFA05 | 1.62 | 607 |

Example 313

2-[[2,3-Difluoro-4-(2-morpholin-4-ylethoxy)phenyl]methyl]-5-hydroxy-1,6,6-trimethyl-3-oxo-N-[4-(trifluoromethyl)-2-[6-(trifluoromethyl)pyrimidin-4-yl]phenyl]pyridazine-4-carboxamide First Step

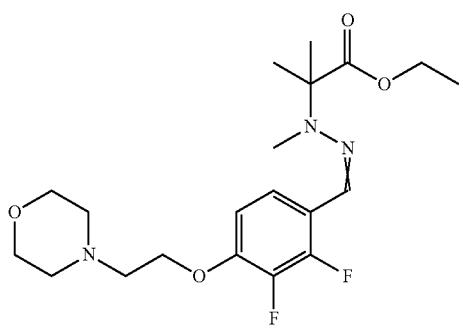 [SMILES: CCOC(=O)C(C)(C)N(C)N=Cc1ccc(OCCN2CCOCC2)c(F)c1F]

Methylhydrazine, ethyl 2-bromo-2-methylpropionate, and the aldehyde reagent synthesized in Reference Example 3 were used, and operations similar to those of First Step of Reference Example 103 were carried out to obtain ethyl 2-(2-(2,3-difluoro-4-(2-morpholinoethoxy)benzylidene)-1-methylhydrazinyl)-2-methylpropanoate.

LCMS: m/z 414[M+H]$^+$

HPLC retention time: 0.96 minutes (analysis condition SMD-TFA05)

Second Step

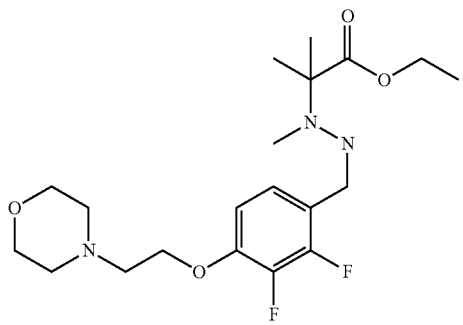 [SMILES: CCOC(=O)C(C)(C)N(C)NCc1ccc(OCCN2CCOCC2)c(F)c1F]

Ethyl 2-(2-(2,3-difluoro-4-(2-morpholinoethoxy)benzylidene)-1-methylhydrazinyl)-2-methylpropanoate (50 mg, 0.12 mmol) obtained in First Step was dissolved in a 10% hydrochloric acid-methanol solution (1.8 mL), borane-pyridine (28 mg, 0.30 mmol) was added at 0° C., and the mixture was stirred for 1.5 hours. The reaction mixture was concentrated at reduced pressure, a 1 N aqueous dipotassium hydrogenphosphate solution was added, and the mixture was extracted with ethyl acetate. The organic layer was washed with a brine, dried over anhydrous sodium sulfate and filtered, and the solvent was distilled away at reduced pressure to obtain ethyl 2-(2-(2,3-difluoro-4-(2-morpholinoethoxy)benzyl)-1-methylhydrazinyl)-2-methylpropanoate as a crude product.

LCMS: m/z 416[M+H]$^+$

HPLC retention time: 0.63 minutes (analysis condition SMD-TFA05)

Third Step

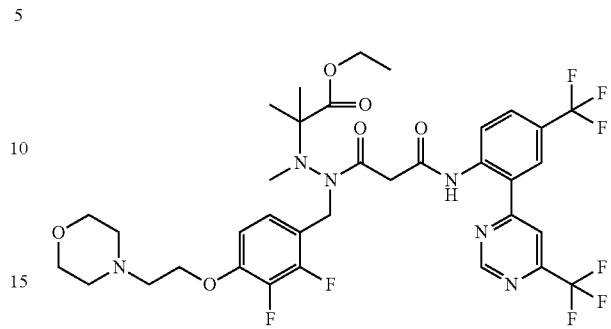

The crude product of ethyl 2-(2-(2,3-difluoro-4-(2-morpholinoethoxy)benzyl)-1-methylhydrazinyl)-2-methylpropanoate obtained in Second Step was dissolved in ethyl acetate (800 μL), and then the carboxylic acid reagent synthesized in First Step of Reference Example 82, pyridine (20 μL, 0.242 mmol), and 2,4,6-tripropyl-1,3,5,2,4,6-trioxatriphosphinane 2,4,6-trioxide (an ethyl acetate solution, 92 μL, 0.145 mmol) were added at 0° C., and the mixture was stirred under nitrogen atmosphere overnight. Water was added to the reaction mixture, and the resultant was extracted with ethyl acetate. The organic layer was washed with water and a brine, dried over sodium sulfate, filtered, and concentrated at reduced pressure to obtain ethyl 2-(2-(2,3-difluoro-4-(2-morpholinoethoxy)benzyl)-1-methyl-2-(3-oxo-3-((4-(trifluoromethyl)-2-(6-(trifluoromethyl)pyrimidin-4-yl)phenyl)amino)propanoyl)hydrazinyl)-2-methylpropanoate as a crude product.

LCMS: m/z 791[M+H]$^+$

HPLC retention time: 1.19 minutes (analysis condition SMD-TFA05)

Fourth Step

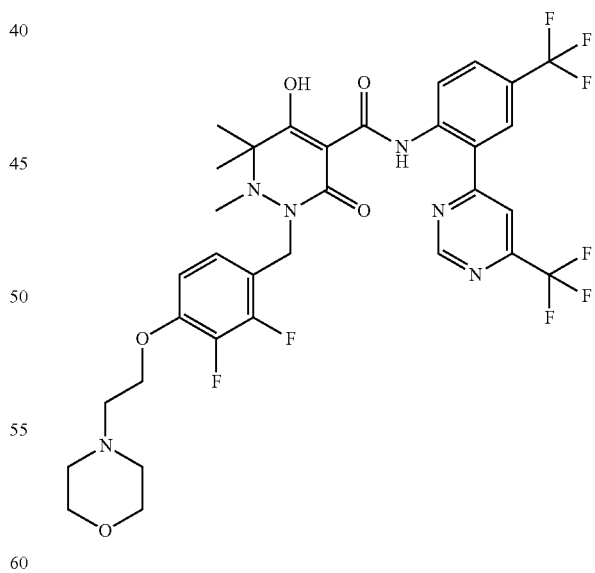

Ethyl 2-(2-(2,3-difluoro-4-(2-morpholinoethoxy)benzyl)-1-methyl-2-(3-oxo-3-((4-(trifluoromethyl)-2-(6-(trifluoromethyl)pyrimidin-4-yl)phenyl)amino)propanoyl)hydrazinyl)-2-methylpropanoate obtained in Third Step was used, and operations similar to those of Third Step of Reference Example 1-1 were carried out to synthesize the title compound (35.1 mg, 39% three-step yield).

LCMS: m/z 745[M+H]+
HPLC retention time: 1.27 minutes (analysis condition QC-SMD-TFA05)

Example 314

2-[[2,3-Difluoro-4-(2-morpholin-4-ylethoxy)phenyl]methyl]-5-hydroxy-1,6,6-trimethyl-3-oxo-N-[4-(trifluoromethyl)-2-[6-(trifluoromethyl)pyridin-3-yl]phenyl]pyridazine-4-carboxamide

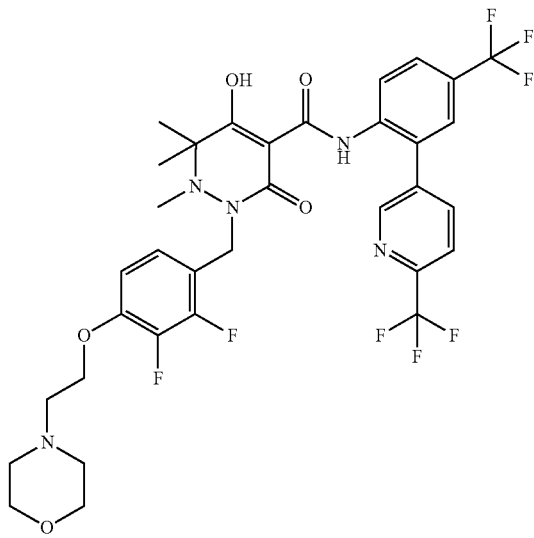 [SMILES: CN1N(Cc2ccc(OCCN3CCOCC3)c(F)c2F)C(=O)C(C(=O)Nc2ccc(C(F)(F)F)cc2-c2ccc(C(F)(F)F)nc2)=C(O)C1(C)C]

Ethyl 2-(2-(2,3-difluoro-4-(2-morpholinoethoxy)benzyl)-1-methylhydrazinyl)-2-methylpropanoate synthesized in Second Step of Example 313 and the carboxylic acid reagent synthesized in First Step of Reference Example 81 were used, and operations similar to those of Example 313 were carried out to synthesize the title compound (36.6 mg, 41% three-step yield).
LCMS: m/z 744[M+H]+
HPLC retention time: 1.28 minutes (analysis condition QC-SMD-TFA05)

Example 315

2-[[2,3-Difluoro-4-(3-morpholin-4-ylprop-1-ynil)phenyl]methyl]-5-hydroxy-1,6,6-trimethyl-3-oxo-N-[4-(trifluoromethyl)-2-(trifluoromethyl)pyrimidin-4-yl]phenyl]pyridazine-4-carboxamide First Step

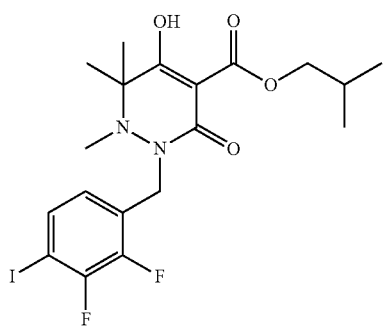 [SMILES: CC(C)COC(=O)C1=C(O)C(C)(C)N(C)N(Cc2ccc(I)c(F)c2F)C1=O]

2,3-Difluoro-4-iodobenzaldehyde and 3-isobutyloxy-3-oxopropionate were used, and operations similar to those of First and Second Steps of Reference Example 103 were carried out to synthesize isobutyl 2-(2,3-difluoro-4-iodobenzyl)-5-hydroxy-1,6,6-trimethyl-3-oxo-1,2,3,6-tetrahydropyridazine-4-carboxylate.
LCMS: m/z 509[M+H]+
HPLC retention time: 1.10 minutes (analysis condition SQD-FA05)

Second Step

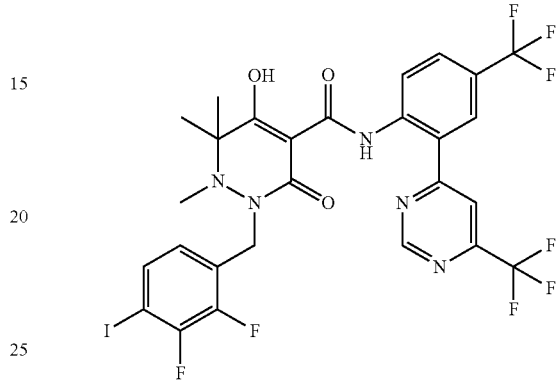

(2-(2,3-Difluoro-4-iodobenzyl)-5-hydroxy-1,6,6-trimethyl-3-oxo-1,2,3,6-tetrahydropyridazine-4-carboxylic acid isobutyl ester synthesized in First Step and 4-(trifluoromethyl)-2-(6-(trifluoromethyl)pyrimidin-4-yl)aniline (Reference Example 50) were used, and operations similar to those of Fifth Step of Example 237 were carried out to synthesize 2-(2,3-difluoro-4-iodobenzyl)-5-hydroxy-1,6,6-trimethyl-3-oxo-N-(4-(trifluoromethyl)-2-(6-(trifluoromethyl)pyrimidin-4-yl)phenyl)-1,2,3,6-tetrahydropyridazine-4-carboxamide.
LCMS: m/z 742[M+H]+
HPLC retention time: 1.25 minutes (analysis condition SQD-FA05)

Third Step

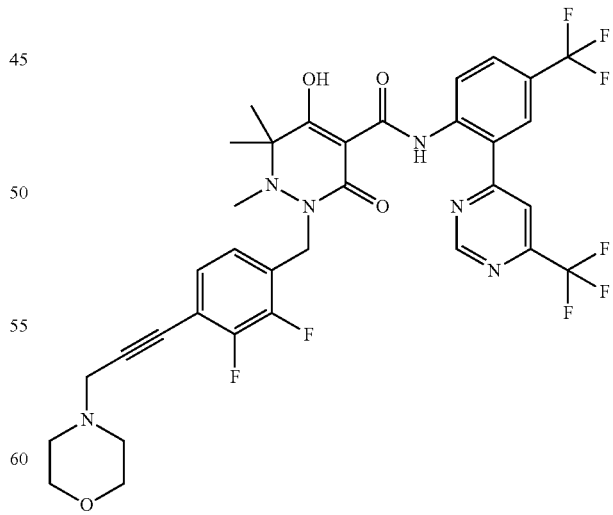

The iodine body synthesized in Second Step and 4-(prop-2-yn-1-yl)morpholine were used, and operations similar to those of Example 123 were carried out to synthesize the title compound.

LCMS: m/z 739[M+H]+
HPLC retention time: 1.31 minutes (analysis condition QC-SMD-TFA05)

Example 316

N-[4-Chloro-2-[6-(trifluoromethyl)pyrimidin-4-yl]phenyl]-2-[[2,3-difluoro-4-(3-morpholin-4-ylprop-1-ynil)phenyl]methyl-5-hydroxy-1,6,6-trimethyl-3-oxopyridazine-4-carboxamide

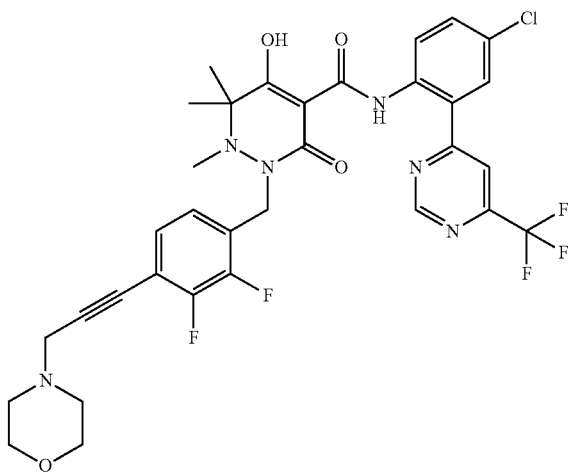 [SMILES: CN1N(Cc2ccc(C#CCN3CCOCC3)c(F)c2F)C(=O)C(C(=O)Nc2ccc(Cl)cc2-c2cc(C(F)(F)F)ncn2)=C(O)C1(C)C]

The aniline reagent synthesized in Reference Example 53 was used, and operations similar to those of Example 315 were carried out to synthesize the title compound.
LCMS: m/z 705[M+H]+
HPLC retention time: 1.29 minutes (analysis condition QC-SMD-TFA05)

Example 317

6-[[2,3-Difluoro-4-(2-morpholin-4-ylethoxy)phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide First Step Methyl 1-[[[2,3-difluoro-4-(2-morpholin-4-ylethoxy)phenyl]methylideneamino]-methylamino]cyclobutane-1-carboxylate

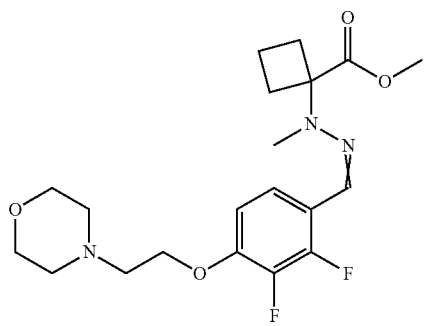 [SMILES: COC(=O)C1(N(C)N=Cc2ccc(OCCN3CCOCC3)c(F)c2F)CCC1]

Methyl 1-(methylamino)cyclobutanecarboxylate hydrochloride (Reference Example 85) (300 mg, 1.67 mmol) was dissolved in acetic acid (16.7 mmol, 956 μL) and water (956 μL), and then sodium nitrite (132 mg, 1.91 mmol) was added at 0° C., and the mixture was stirred under nitrogen atmosphere for 30 minutes. Zinc (1.09 g, 16.7 mmol) was added to the reaction mixture at 0° C., and the mixture was stirred under nitrogen atmosphere for 1.5 hours. After the reaction mixture was filtered, methanol (9.56 mL) and 2,3-difluoro-4-(2-morpholinoethoxy)benzaldehyde (324 mg, 1.19 mmol) were added, and the mixture was stirred at room temperature for 30 minutes. The reaction mixture was concentrated at reduced pressure and diluted with ethyl acetate, the organic layer was washed with a 1 M aqueous dipotassium hydrogenphosphate solution and a brine, dried over sodium sulfate, filtered, and concentrated at reduced pressure, and the resultant residue was purified by column chromatography on silica gel (aminosilica, hexane/ethyl acetate) to obtain the title compound (402 mg, 82%).
LCMS: m/z 412[M+H]+
HPLC retention time: 0.91 minutes (analysis condition SMD-TFA05)

Second Step

Methyl 1-[[[2,3-difluoro-4-(2-morpholin-4-ylethoxy)phenyl]methyl-[3-oxo-3-[4-(trifluoromethyl)-2-[6-(trifluoromethyl)pyrimidin-4-yl]anilino]propanoyl]amino]-methylamino]cyclobutane-1-carboxylate

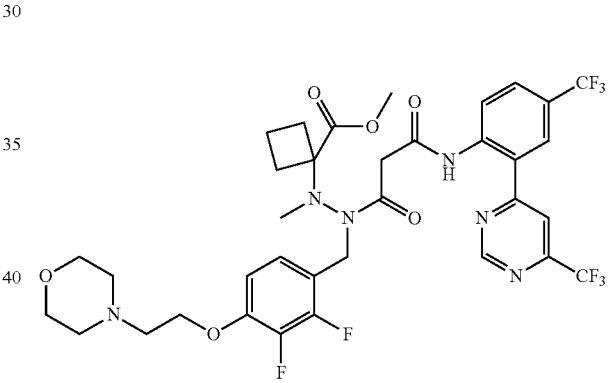

Methyl 1-[[[2,3-difluoro-4-(2-morpholin-4-ylethoxy)phenyl]methylideneamino]-methylamino]cyclobutane-1-carboxylate (27.5 g, 66.9 mmol) was dissolved in ethyl acetate (158 mL), and then hydrochloric acid (a 4 M ethyl acetate solution, 158 mL) was added at 0° C., and the mixture was stirred under nitrogen atmosphere for 10 minutes. 5-Ethyl-2-methylpyridine borane (19.9 mL, 134 mmol) was added to the reaction mixture at 0° C., and the mixture was stirred under nitrogen atmosphere for 30 minutes. After an aqueous sodium hydroxide solution (5 M, 115 mL) and an aqueous potassium phosphate solution (1 M, 50.0 mL) were added to the reaction mixture, the mixture was diluted with ethyl acetate, the organic layer was washed with a 1 M aqueous dipotassium hydrogenphosphate solution and a brine, dried over magnesium sulfate, filtered, and concentrated at reduced pressure to obtain methyl 1-[[[2,3-difluoro-4-(2-morpholin-4-ylethoxy)phenyl]methylamino]-methylamino]cyclobutane-1-carboxylate as a crude product. The obtained crude product and 3-oxo-3-[4-(trifluoromethyl)-2-[6-(trifluoromethyl)pyrimidin-4-yl]anilino]propanoate (First Step of Reference Example 82) (27.6 g, 70.2 mmol) were dissolved in ethyl acetate (279 mL) and N,N-dimethylformamide (139 mL), and then pyridine (5.40 mL, 66.9 mmol) and 2,4,6-tripropyl-1,3,5,2,4,6-trioxatriphosphinane 2,4,6-trioxide (a 1.7 M ethyl acetate solution, 79.0 mL, 134 mmol) were added at 0° C., and the mixture was stirred under nitrogen atmosphere for 30 minutes. A brine was added to the reaction mixture, and the mixture was extracted with ethyl acetate. The organic layer was washed with a 1 M aqueous dipotassium hydrogenphosphate solution and a brine, dried over magnesium sulfate, filtered, and concentrated at reduced pressure to obtain the title compound (1.15 g, 100%).

LCMS: m/z 789.1[M+H]$^+$

HPLC retention time: 1.01 minutes (analysis condition SMD-FA05)

Third Step

6-[[2,3-Difluoro-4-(2-morpholin-4-ylethoxy)phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide

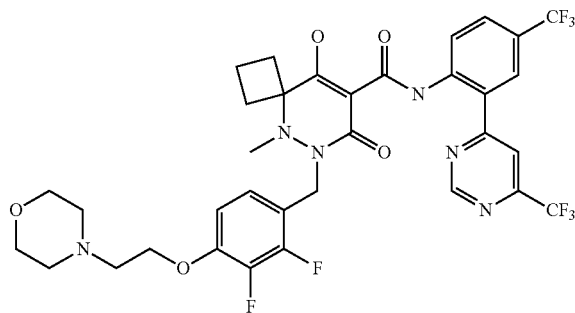 [SMILES: CN1N(Cc2ccc(OCCN3CCOCC3)c(F)c2F)C(=O)C(C(=O)Nc2ccc(C(F)(F)F)cc2-c2cc(C(F)(F)F)ncn2)=C(O)C12CCC2]

Methyl 1-[[[2,3-difluoro-4-(2-morpholin-4-ylethoxy)phenyl]methyl-[3-oxo-3-[4-(trifluoromethyl)-2-[6-(trifluoromethyl)pyrimidin-4-yl]anilino]propanoyl]amino]-methylamino]cyclobutane-1-carboxylate (1.14 g, 1.45 mmol) was dissolved in methanol (7.27 mL) and N,N-dimethylformamide (7.27 mL), and then potassium carbonate (602 mg, 4.36 mmol) was added, and the mixture was stirred under nitrogen atmosphere at room temperature for 1.5 hours. Formic acid and water were added to the reaction mixture, and the mixture was purified by C18 reverse-phase column chromatography (methanol/water) to obtain the title compound (840 mg, 76%).

LCMS: m/z 757.4[M+H]$^+$

HPLC retention time: 1.27 minutes (analysis condition SMD-TFA05)

Although tautomers of some of the title compounds exist, isomers may be observed in some cases and not in other cases according to the type of the solvent for measurement. For example, $^1$H-NMR and $^{13}$C-NMR of major tautomers in chloroform-D are as follows.

Example 317

Major Tautomer $^1$H-NMR (CDCl$_3$) δ: 16.58 (1H, s), 12.81 (1H, s), 9.60 (1H, s), 8.50 (1H, d, J=8.6 Hz), 7.95 (1H, s), 7.90 (1H, d, J=1.6 Hz), 7.80 (1H, dd, J=8.6, 1.6 Hz), 7.02 (1H, ddd, J=8.6, J$_{CF}$=7.2, 1.6 Hz), 6.72 (1H, ddd, J=8.6, J$_{CF}$=7.2, 1.6 Hz), 5.06 (1H, brs), 4.20 (1H, brs), 4.20 (2H, t, J=5.5 Hz), 3.74 (4H, t, J=4.1 Hz), 2.85 (2H, brs), 2.61 (4H, brs), 2.52 (1H, m), 2.41 (3H, s), 1.85-1.83 (3H, m), 1.73 (1H, m), 1.60 (1H, m).

$^{13}$C-NMR (CDCl$_3$) δ: 186.1 (qC), 169.8 (qC), 165.7 (qC), 162.8 (qC), 159.3 (qC), 156.6 (qC, q, J=36.4 Hz), 150.4 (qC, dd, J=248.7, 10.5 Hz), 147.8 (qC, d, J=5.5 Hz), 141.3 (qC, dd, J=248.1, 14.6 Hz), 138.8 (qC), 128.3 (CH, q, J=3.3 Hz), 127.7 (qC), 127.1 (CH), 127.0 (qC, q, J=33.4 Hz), 125.1 (CH), 124.7 (CH), 123.6 (qC, q, J=271.8 Hz), 120.5 (qC, q, J=275.4 Hz), 118.2 (qC, d, J=12.4 Hz), 115.9 (CH, q, J=2.5 Hz), 109.6 (CH, d, J=1.9 Hz), 92.3 (qC), 67.9 (CH$_2$), 66.9 (CH$_2$×2), 64.2 (qC), 57.5 (CH$_2$), 54.1 (CH$_2$×2), 41.6 (CH$_2$), 35.1 (CH$_3$), 32.4 (CH$_2$), 24.5 (CH$_2$), 13.4 (CH$_2$).

Example 318

7-[[2,3-Difluoro-4-(2-morpholin-4-ylethoxy)phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide First Step Methyl 1-[[[2,3-difluoro-4-(2-morpholin-4-ylethoxy)phenyl]methylideneamino]-methylamino]cyclopentane-1-carboxylate

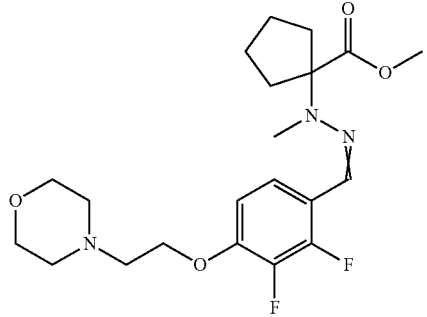 [SMILES: COC(=O)C1(N(C)N=Cc2ccc(OCCN3CCOCC3)c(F)c2F)CCCC1]

Methyl 1-(methylamino)cyclopentanecarboxylate hydrochloride (300 mg, 1.55 mmol) was dissolved in acetic acid (15.5 mmol, 887 μL) and water (887 μL), and then sodium nitrite (122 mg, 1.77 mmol) was added at 0° C., and the mixture was stirred under nitrogen atmosphere for 1 hour. Zinc (1.01 g, 15.5 mmol) was added to the reaction mixture at 0° C., and the mixture was stirred under nitrogen atmosphere for 1.5 hours. After the reaction mixture was filtered, methanol (8.87 mL) and 2,3-difluoro-4-(2-morpholinoethoxy)benzaldehyde (300 mg, 1.11 mmol) were added, and the mixture was stirred at room temperature for 30 minutes. The reaction mixture was concentrated at reduced pressure and diluted with ethyl acetate, the organic layer was washed with a 1 M aqueous dipotassium hydrogenphosphate solution and a brine, dried over sodium sulfate, filtered, and concentrated at reduced pressure, and the resultant residue was purified by column chromatography on silica gel (aminosilica, hexane/ethyl acetate) to obtain the title compound (375 mg, 80%).

LCMS: m/z 426.2[M+H]$^+$

HPLC retention time: 0.93 minutes (analysis condition SMD-TFA05)

Second Step

1-[[[2,3-Difluoro-4-(2-morpholin-4-ylethoxy)phenyl]methyl-[3-oxo-3-[4-(trifluoromethyl)-2-[6-(trifluoromethyl)pyrimidin-4-yl]anilino]propanoyl]amino]-methylamino]cyclopentane-1-carboxylic acid

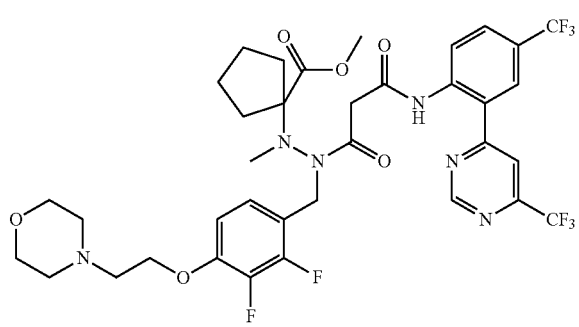 [SMILES: COC(=O)C1(N(C)N(Cc2ccc(OCCN3CCOCC3)c(F)c2F)C(=O)CC(=O)Nc2ccc(C(F)(F)F)cc2-c2cc(C(F)(F)F)ncn2)CCCC1]

Methyl 1-[[[2,3-difluoro-4-(2-morpholin-4-ylethoxy)phenyl]methylideneamino]-methylamino]cyclopentane-1-carboxylate (29.8 g, 70.3 mmol) was dissolved in ethyl acetate (172 mL), and then hydrochloric acid (a 4 M ethyl acetate solution, 172 mL) was added at 0° C., and the mixture was stirred under nitrogen atmosphere for 10 minutes. 5-Ethyl-2-methylpyridine borane (20.9 mL, 141 mmol) was added to the reaction mixture at 0° C., and the mixture was stirred under nitrogen atmosphere for 30 minutes. After an aqueous sodium hydroxide solution (5 M, 125 mL) and an aqueous potassium phosphate solution (1 M, 50.0 mL) were added to the reaction mixture, the mixture was diluted with ethyl acetate, the organic layer was washed with a 1 M aqueous potassium phosphate solution and a brine, dried over magnesium sulfate, filtered, and concentrated at reduced pressure to obtain methyl 1-[[[2,3-difluoro-4-(2-morpholin-4-ylethoxy)phenyl]methylamino]-methylamino]cyclopentane-1-carboxylate as a crude product.

The obtained crude product and 3-oxo-3-[4-(trifluoromethyl)-2-[6-(trifluoromethyl)pyrimidin-4-yl]anilino]propanoate (First Step of Reference Example 82) (29.0 g, 73.8 mmol) were dissolved in ethyl acetate (293 mL) and N,N-dimethylformamide (146 mL), and then pyridine (5.67 mL, 70.3 mmol) and 2,4,6-tripropyl-1,3,5,2,4,6-trioxatriphosphinane 2,4,6-trioxide (a 1.7 M ethyl acetate solution, 83.0 mL, 141 mmol) were added at 0° C., and the mixture was stirred under nitrogen atmosphere for 30 minutes. A brine was added to the reaction mixture, and the resultant was extracted with ethyl acetate. The organic layer was washed with a 1 M aqueous dipotassium hydrogenphosphate solution and a brine, dried over magnesium sulfate, filtered, and concentrated at reduced pressure, and the resultant residue was washed with methanol to obtain the title compound (39.4 g, 70%).

LCMS: m/z 803.1[M+H]$^+$

HPLC retention time: 1.03 minutes (analysis condition SMD-FA05)

Third Step

7-[[2,3-Difluoro-4-(2-morpholin-4-ylethoxy)phenyl]methyl]-10-hydroxy-6-methyl-8-oxo-N-[4-(trifluoromethyl)-2-[6-(trifluoromethylpyrimidin-4-yl]phenyl]-6,7-diazaspiro[4.5]dec-9-ene-9-carboxamide

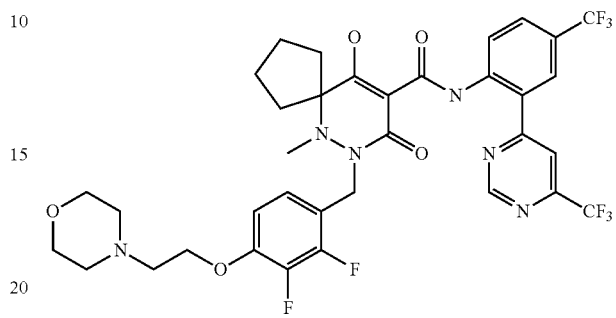

1-[[[2,3-Difluoro-4-(2-morpholin-4-ylethoxy)phenyl]methyl-[3-oxo-3-[4-(trifluoromethyl)-2-[6-(trifluoromethyl)pyrimidin-4-yl]anilino]propanoyl]amino]-methylamino]cyclopentane-1-carboxylic acid (15.0 g, 18.7 mmol) was dissolved in methanol (94.0 mL) and N,N-dimethylformamide (94.0 mL), and then potassium carbonate (7.76 g, 56.1 mmol) was added, and the mixture was stirred under nitrogen atmosphere at room temperature for 1.5 hours. Formic acid and water were added to the reaction mixture, and the mixture was purified by C18 reverse-phase column chromatography (methanol/water) to obtain the title compound (13.3 g, 92%).

LCMS: m/z 771.3[M+H]$^+$

HPLC retention time: 1.29 minutes (analysis condition SMD-TFA05)

Although tautomers of some of the title compounds exist, isomers may be observed in some cases and not in other cases according to the type of the solvent for measurement. For example, H-NMR and $^{13}$C-NMR of major tautomers in chloroform-D are as follows.

Example 318

Major Tautomer $^1$H-NMR (CDCl$_3$) δ: 16.55 (1H, s), 12.83 (1H, s), 9.62 (1H, s), 8.49 (1H, d, J=8.8 Hz), 7.96 (1H, s), 7.90 (1H, d, J=1.5 Hz), 7.79 (1H, dd, J=8.8, 1.5 Hz), 7.05 (1H, dd, J=8.1, 7.4 Hz), 6.73 (1H, dd, J=8.1, 7.4 Hz), 5.05 (1H, d, J=14.2 Hz), 4.21 (1H, d, J=14.2 Hz), 4.19 (2H, t, J=5.7 Hz), 3.74 (4H, t, J=4.6 Hz), 2.84 (2H, t, J=5.7 Hz), 2.60 (4H, m), 2.48 (3H, s), 2.16 (1H, m), 1.74 (2H, m), 1.59 (1H, m), 1.52 (1H, m), 1.47 (2H, m), 1.31 (2H, m).

$^{13}$C-NMR (CDCl$_3$) δ: 187.7 (qC), 169.9 (qC), 165.7 (qC), 163.2 (qC), 159.3 (CH), 156.6 (qC, q, J$_{CF}$=36.3 Hz), 150.4 (qC, dd, J$_{CF}$=248.7, 10.5 Hz), 147.9 (qC, d, J$_{CF}$=5.8 Hz), 141.3 (qC, dd, J$_{CF}$=248.3, 14.7 Hz), 138.8 (qC), 128.3 (CH, q, J$_{CF}$=3.3 Hz), 127.8 (qC), 127.1 (CH, q, J$_{CF}$=3.9 Hz), 126.9 (qC, q, J$_{CF}$=33.4 Hz), 125.5 (CH), 124.7 (CH), 123.6 (qC, q, J$_{CF}$=272.1 Hz), 120.5 (qC, q, J$_{CF}$=275.4 Hz), 117.8 (qC, d, J$_{CF}$=12.9 Hz), 116.0 (CH, q, J$_{CF}$=2.5 Hz), 109.7 (CH), 93.1 (qC), 71.4 (qC), 68.1 (CH$_2$), 66.9 (CH$_2$×2), 57.5 (CH$_2$), 54.2 (CH$_2$×2), 41.7 (CH$_2$), 37.6 (CH$_2$), 36.8 (CH$_2$), 31.4 (CH$_2$), 24.8 (CH$_2$), 23.3 (CH$_2$).

Example 319

(4aR)—N-(4-Bromo-3-fluorophenyl)-1-[(2,3-difluoro-4-iodophenyl)methyl]-4-hydroxy-4a-methyl-2-oxo-6,7-dihydro-5H-pyrrolo[1,2-b]pyridazine-3-carboxamide

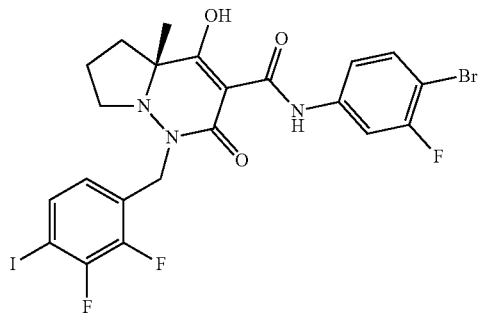 [SMILES: C[C@]12CCCN1N(Cc1ccc(I)c(F)c1F)C(=O)C(C(=O)Nc1ccc(Br)c(F)c1)=C2O]

First Step

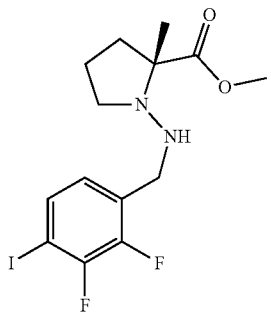 [SMILES: COC(=O)[C@@]1(C)CCCN1NCc1ccc(I)c(F)c1F]

(R)-2-Methyl-pyrrolidine-2-carboxylic acid methyl ester hydrochloride and 2,3-difluorobenzaldehyde were used, and then (R)-1-((2,3-difluoro-4-iodobenzylidene)amino)-2-methylpyrrolidine-2-carboxylic acid methyl ester (2.24 g, 5.49 mmol) obtained by carrying out operations similar to those of Example 1 was dissolved in acetic acid (5.0 mL) and methanol (5.5 mL), and then sodium cyanoborohydride (1.76 g, 28.0 mmol) was added, and the mixture was stirred under nitrogen atmosphere at room temperature for 14 hours. A saturated sodium bicarbonate solution was added to the reaction mixture, and the resultant was concentrated at reduced pressure and extracted with ethyl acetate. The organic layer was washed with a brine, dried over sodium sulfate, filtered, and concentrated at reduced pressure to obtain (R)-1-((2,3-difluoro-4-iodobenzyl)amino)-2-methyl-pyrrolidine-2-carboxylic acid methyl ester as a crude product.

Second Step

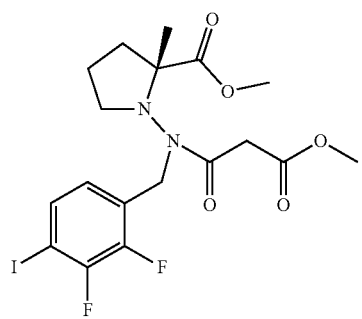 [SMILES: COC(=O)CC(=O)N(Cc1ccc(I)c(F)c1F)N1CCC[C@]1(C)C(=O)OC]

The crude product obtained in First Step was dissolved in tetrahydrofuran (5.5 mL), and then tripotassium phosphate (2.38 g, 11.2 mmol) and chlorocarbonyl-acetic acid methyl ester (1.00 mL, 9.06 mmol) were added at 0° C., and the mixture was stirred under nitrogen atmosphere at room temperature for 3 hours. 1 N hydrochloric acid was added to the reaction mixture, and the mixture was extracted with ethyl acetate. The organic layer was washed with a saturated sodium bicarbonate solution and a brine, dried over sodium sulfate, filtered, and concentrated at reduced pressure to obtain (S)-1-[(3-fluoro-benzyl)-(2-methoxycarbonyl-acetyl)-amino]-pyrrolidine-2-carboxylic acid methyl ester as a crude product.

Third Step

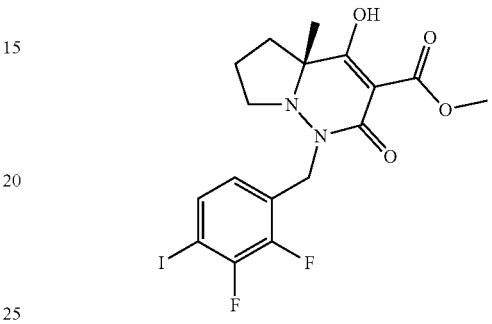

The obtained crude product was dissolved in N,N-dimethylformamide (1.5 mL), and then cesium carbonate (672 mg, 2.06 mmol) was added, and the mixture was stirred under nitrogen atmosphere at 80° C. for 5.5 hours. 1 N hydrochloric acid was added to the reaction mixture, and the mixture was extracted with ethyl acetate. The organic layer was washed with water and a brine, dried over sodium sulfate, filtered, and concentrated at reduced pressure to obtain methyl (4aR)-1-[(2,3-difluoro-4-iodophenyl)methyl]-4-hydroxy-4a-methyl-2-oxo-6,7-dihydro-5H-pyrrolo[1,2-b]pyridazine-3-carboxylate as a crude product.

Fourth Step

The crude product (328 mg, 0.686 mmol) obtained in Third Step and 4-bromo-3-fluoroaniline (145 mg, 0.763 mmol) were dissolved in toluene (3.4 mL), and the mixture was stirred at 110° C. for 1 hour. After the reaction mixture was left to cool, it was concentrated at reduced pressure, and the resultant residue was purified by column chromatography on silica gel (hexane/ethyl acetate) to obtain the title compound (402 mg, 92%) as a grayish white solid.

LCMS: m/z 479[M+H]$^+$

HPLC retention time: 0.97 minutes (analysis condition SQD-FA05)

Example 320

(4aR)-1-[(2,3-Difluoro-4-iodophenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide

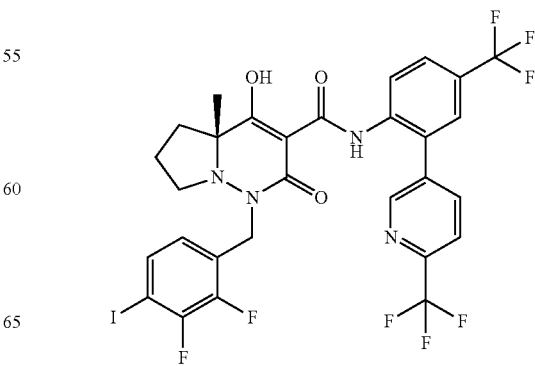

(4aR)-1-[(2,3-Difluoro-4-iodophenyl)methyl]-4-hydroxy-4a-methyl-2-oxo-6,7-dihydro-5H-pyrrolo[1,2-b]pyridazine-3-carboxylic acid 2-methylpropyl ester (Reference Example 5) (100 mg, 0.192 mmol) and 4-(trifluoromethyl)-2-(6-(trifluoromethyl)pyridin-3-yl)aniline (Reference Example 42) (73.6 mg, 0.240 mmol) were dissolved in toluene (0.96 mL), and the mixture was stirred at 100° C. for 40 minutes. After the reaction mixture was left to cool, it was concentrated at reduced pressure, and the resultant residue was purified by C18 reverse-phase column chromatography to obtain the title compound (120 mg, 83%) as a white amorphous solid.

LCMS: m/z 753[M+H]$^+$

HPLC retention time: 0.93 minutes (analysis condition SQD-FA50)

Example 321

(4aR)-1-[(2,3-Difluoro-4-iodophenyl)methyl]-N-[2-(2,3-dimethoxyphenyl)-4-(trifluoromethyl)phenyl]-4-hydroxy-4a-methyl-2-oxo-6,7-dihydro-5H-pyrrolo[1,2-b]pyridazine-3-carboxamide

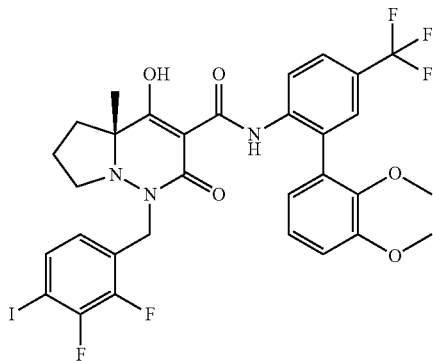 [SMILES: COc1cccc(-c2cc(C(F)(F)F)ccc2NC(=O)C2=C(O)[C@@]3(C)CCCN3N(Cc3ccc(I)c(F)c3F)C2=O)c1OC]

(4aR)-1-[(2,3-Difluoro-4-iodophenyl)methyl]-4-hydroxy-4a-methyl-2-oxo-6,7-dihydro-5H-pyrrolo[1,2-b]pyridazine-3-carboxylic acid 2-methylpropyl ester (Reference Example 5) and 2',3'-dimethoxy-5-(trifluoromethyl)-[1,1'-biphenyl]-2-amine (Reference Example 16) were used, and operations similar to those of Fourth Step of Example 319 were carried out to synthesize the title compound.

LCMS: m/z 744[M+H]$^+$

HPLC retention time: 1.19 minutes (SMD-TFA05)

Example 322

(4aR)-1-[(2,6-Difluoro-4-iodophenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide

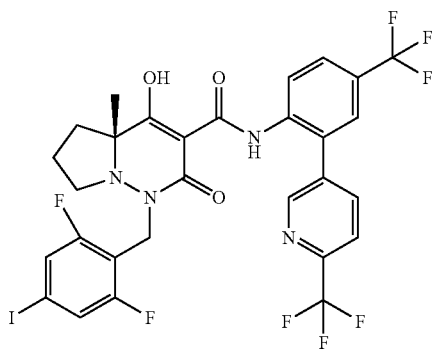 [SMILES: C[C@]12CCCN1N(Cc1c(F)cc(I)cc1F)C(=O)C(C(=O)Nc1ccc(C(F)(F)F)cc1-c1ccc(C(F)(F)F)nc1)=C2O]

First Step

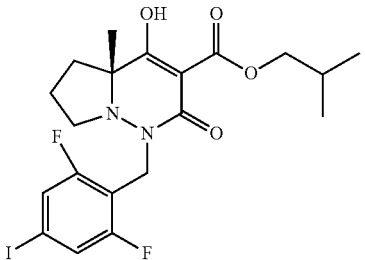 [SMILES: CC(C)COC(=O)C1=C(O)[C@@]2(C)CCCN2N(Cc2c(F)cc(I)cc2F)C1=O]

2,6-Difluoro-4-iodobenzaldehyde was used, and operations similar to those of First to Third Steps of Example 319 were carried out to synthesize (4aR)-1-[(2,6-difluoro-4-iodophenyl)methyl]-4-hydroxy-4a-methyl-2-oxo-6,7-dihydro-5H-pyrrolo[1,2-b]pyridazine-3-carboxylic acid 2-methylpropyl ester.

LCMS: m/z 521[M+H]$^+$

HPLC retention time: 1.51 minutes (analysis condition SMD-TFA05)

Second Step (4aR)-1-[(2,6-Difluoro-4-iodophenyl)methyl]-4-hydroxy-4a-methyl-2-oxo-6,7-dihydro-5H-pyrrolo[1,2-b]pyridazine-3-carboxylic acid 2-methylpropyl ester and 4-(trifluoromethyl)-2-(6-(trifluoromethyl)pyridin-3-yl)aniline (Reference Example 42) were used, and operations similar to those of Fourth Step of Example 319 were carried out to synthesize the title compound.

LCMS: m/z 753[M+H]$^+$

HPLC retention time: 1.76 minutes (analysis condition QC-SMD-TFA05)

Example 323

(4aR)-1-[(2,3-Difluoro-4-iodophenyl)methyl]-4-hydroxy-4a-methyl-2-oxo-N-[4-(trifluormethyl)-2-[6-(trifluormethyl)pyrimidin-4-yl]phenyl]-6,7-dihydro-5H-pyrrolo[1,2-b]pyridazine-3-carboxamide

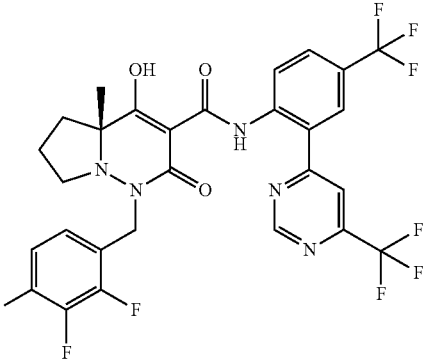

(4aR)-1-[(2,3-Difluoro-4-iodophenyl)methyl]-4-hydroxy-4a-methyl-2-oxo-6,7-dihydro-5H-pyrrolo[1,2-b]pyridazine-3-carboxylic acid 2-methylpropyl ester (Reference Example 5) and 4-(trifluoromethyl)-2-(6-(trifluoromethyl)pyrimidin-4-yl)aniline (Reference Example 50) were used, and operations similar to those of Fourth Step of Example 319 were carried out to synthesize the title compound.

LCMS: m/z 754[M+H]$^+$

HPLC retention time: 0.93 minutes (analysis condition SQD-FA50)

Example 324

(4aR)-1-[(2,3-Difluoro-4-hydroxyphenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide

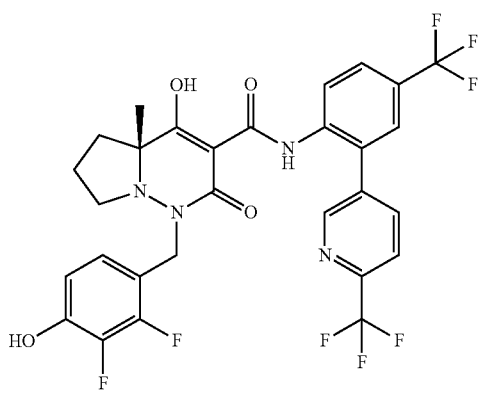 [SMILES: C[C@]12CCCN1N(Cc1ccc(O)c(F)c1F)C(=O)C(C(=O)Nc1ccc(C(F)(F)F)cc1-c1ccc(C(F)(F)F)nc1)=C2O]

(4aR)-1-[(2,3-Difluoro-4-iodophenyl)methyl]-4-hydroxy-4a-methyl-2-oxo-6,7-dihydro-5H-pyrrolo[1,2-b]pyridazine-3-carboxylic acid 2-methylpropyl ester (Reference Example 5) (1.086 g, 1.444 mmol), copper iodide (31.2 mg, 0.164 mmol), and 2-methyl-8-quinolinol (52.7 mg, 0.331 mmol) were dissolved in dimethylsulfoxide (4.1 mL) under nitrogen atmosphere, tetrabutylammonium hydroxide (4.24 g, 6.54 mmol) and water (1.56 mL) were added, and the mixture was stirred under nitrogen atmosphere at 100° C. for 5 hours. After the reaction mixture was left to cool, 1 N hydrochloric acid (5.1 mL), water (30 mL), and an appropriate amount of N-acetyl-L-cysteine were added to the reaction mixture, and the resultant was extracted with ethyl acetate. The organic layer was dried over magnesium sulfate, filtered, and concentrated at reduced pressure, and the resultant residue was purified by column chromatography on silica gel to obtain the title compound (834 mg, 90%) as a pale yellow amorphous solid.

LCMS: m/z 643[M+H]$^+$

HPLC retention time: 1.12 minutes (analysis condition SQD-FA05)

Example 325

(4aR)-1-[2,3-(Difluoro-4-hydroxyphenyl)methyl]-N-[2-(2,3-dimethoxyphenyl)-4-(trifluoromethyl)phenyl]-4-hydroxy-4a-methyl-2-oxo-6,7-dihydro-5H-pyrrolo[1,2-b]pyridazine-3-carboxamide

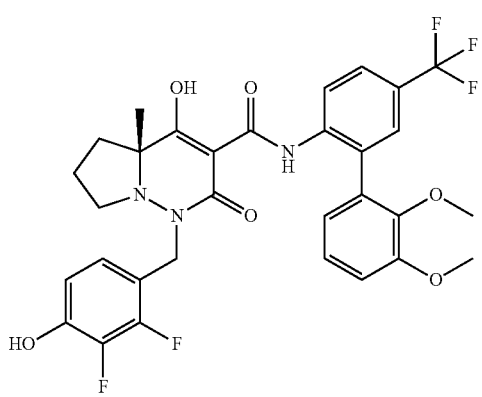 [SMILES: COc1cccc(-c2cc(C(F)(F)F)ccc2NC(=O)C2=C(O)[C@@]3(C)CCCN3N(Cc3ccc(O)c(F)c3F)C2=O)c1OC]

(4aR)-1-[2,3-(Difluoro-4-iodophenyl)methyl]-N-[2-(2,3-dimethoxyphenyl)-4-(trifluoromethyl)phenyl]-4-hydroxy-4a-methyl-2-oxo-6,7-dihydro-5H-pyrrolo[1,2-b]pyridazine-3-carboxamide (Example 321) was used, and operations similar to those of Example 324 were carried out to synthesize the title compound.

LCMS: m/z 634[M+H]$^+$

HPLC retention time: 1.14 minutes (analysis condition SQD-FA05)

Example 326

(4aR)-1-[(2,6-Difluoro-4-hydroxyphenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide

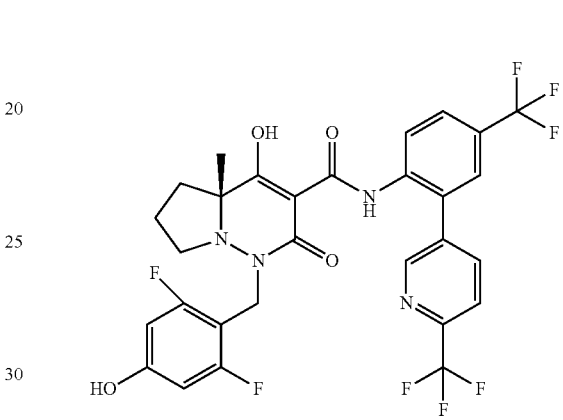

(4aR)-1-[(2,6-Difluoro-4-iodophenyl)methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide (Example 322) was used, and operations similar to those of Example 324 were carried out to synthesize the title compound.

LCMS: m/z 643[M+H]$^+$

HPLC retention time: 1.12 minutes (analysis condition SQD-FA05)

Example 327

(4aR)-1-[(2,3-Difluoro-4-hydroxyphenyl)methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide

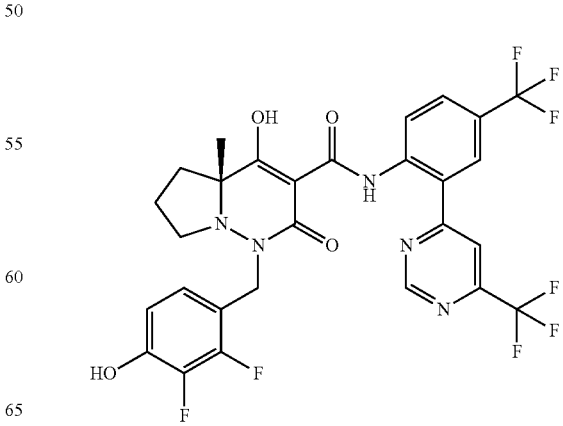

(4aR)-1-[(2,3-Difluoro-4-iodophenyl)methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide (Example 323) was used, and operations similar to those of Example 324 were carried out to synthesize the title compound.

LCMS: m/z 644[M+H]$^+$

HPLC retention time: 1.11 minutes (analysis condition SQD-FA05)

Example 328

(4aR)-1-[(2,6-Dichloro-4-hydroxyphenyl)methyl]-4-hydroxy-4a-methyl-2-oxo-N-[2-(trifluoromethyl)-4-[6-(trifluoromethyl)pyridin-3-yl]pyrimidin-5-yl]-6,7-dihydro-5H-pyrrolo[1,2-b]pyridazine-3-carboxamide

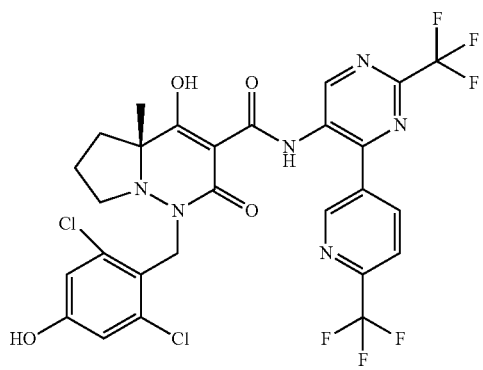 [SMILES: C[C@]12CCCN1N(Cc1c(Cl)cc(O)cc1Cl)C(=O)C(C(=O)Nc1cnc(C(F)(F)F)nc1-c1ccc(C(F)(F)F)nc1)=C2O]

First Step

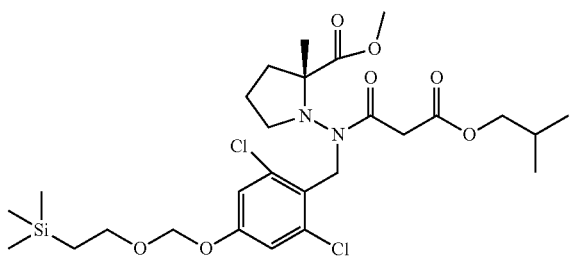 [SMILES: COC(=O)[C@@]1(C)CCCN1N(Cc1c(Cl)cc(OCOCC[Si](C)(C)C)cc1Cl)C(=O)CC(=O)OCC(C)C]

Methyl (R)-2-methylpyrrolidine-2-carboxylate hydrochloride (20 g, 111 mmol) was suspended in dichloromethane (100 mL), and then p-toluenesulfonic acid.monohydrate (25 g, 145 mmol) was added, and the mixture was stirred under nitrogen atmosphere at room temperature for 10 minutes. The reaction mixture was concentrated at reduced pressure, toluene was added for azeotropic removal, and then the residue was suspended in dichloromethane (250 mL), sodium nitrite (11.4 g, 165 mmol) was added, and the mixture was stirred under nitrogen atmosphere at room temperature for 2 hours. The reaction mixture was filtered and then concentrated at reduced pressure to obtain (S)-1-nitroso-pyrrolidine-2-carboxylic acid methyl ester as a crude product. The obtained crude product (362 mg, 2.10 mmol) was dissolved in acetic acid (10 mL) and methanol (1.0 mL), and then zinc (725 mg, 11.2 mmol) was added at 9° C., and the mixture was stirred under nitrogen atmosphere at 9° C. for 1 hour. After the reaction mixture was filtered through a celite pad, the filtrate was concentrated at reduced pressure. Methanol (1.0 mL) and 2,4-dichloro-4-hydroxybenzaldehyde (200 mg, 1.05 mmol) were added to the resultant residue, and the mixture was stirred under nitrogen atmosphere at room temperature for 2 hours. The reaction mixture was filtered and then concentrated at reduced pressure, and the resultant was extracted with ethyl acetate. The organic layer was washed with water and a brine, dried over sodium sulfate, filtered, and concentrated at reduced pressure, and the resultant residue was purified by column chromatography on silica gel (hexane/ethyl acetate) to obtain methyl (R)-1-((2,6-dichloro-4-hydroxybenzylidene)amino)-2-methylpyrrolidine-2-carboxylate. The obtained product (5.3 g, 16.0 mmol) was dissolved in acetonitrile (50 mL), and then 2-(chloromethoxy)ethyl trimethylsilane (3.2 g, 19.2 mmol) and cesium carbonate (6.3 g, 19.3 mmol) were added, and the mixture was stirred under nitrogen atmosphere at 25° C. for 24 hours. Water (100 mL) was added to the reaction mixture, and the resultant was extracted with ethyl acetate (100 mL) three times. The organic layer was washed with water and a brine, and then dried over sodium sulfate. The sodium sulfate was filtered off and the resultant was concentrated at reduced pressure to obtain a crude product of methyl (R)-1-((2,6-dichloro-4-((2-(trimethylsilyl)ethoxy)methoxy)benzylidene)amino)-2-methylpyrrolidine-2-carboxylate as a white solid. The obtained crude product was used to obtain methyl (R)-1-N-(2,6-dichloro-4-((2-(trimethylsilyl)ethoxy)methoxy)benzyl)-3-isobutoxy-3-oxopropanamide)-2-methylpyrrolidine-2-carboxylate by carrying out First and Second Steps of Reference Example 1-1.

LCMS: m/z 461[M+H]$^+$

HPLC retention time: 4.73 minutes (analysis condition Ph-SMD-TFA05)

Second Step

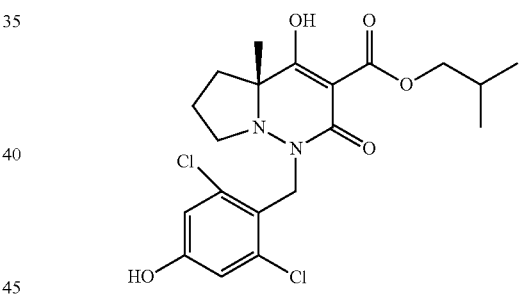

Methyl (R)-1-(N-(2,6-dichloro-4-((2-(trimethylsilyl)ethoxy)methoxy)benzyl)-3-isobutoxy-3-oxopropanamide)-2-methylpyrrolidine-2-carboxylate (7.02 g, 11.6 mmol) was dissolved in dichloromethane (85 mL), trifluoroacetic acid (35 mL) was added, and the mixture was stirred at room temperature for 30 minutes. The reaction mixture was concentrated at reduced pressure, and the resultant residue was purified by column chromatography on silica gel (hexane/ethyl acetate) to obtain methyl (R)-1-N-(2,6-dichloro-4-hydroxybenzyl)-3-isobutoxy-3-oxopropanamide)-2-methylpyrrolidine-2-carboxylate (5.0 g, 91%). The obtained methyl (R)-1-N-(2,6-dichloro-4-hydroxybenzyl)-3-isobutoxy-3-oxopropanamide)-2-methylpyrrolidine-2-carboxylate (5.0 g, 10.5 mmol) was used, and operations similar to those of Third Step of Reference Example 1-1 were carried out to obtain (4aR)-1-[(2,6-dichloro-4-hydroxyphenyl)methyl]-4-hydroxy-4a-methyl-2-oxo-6,7-dihydro-5H-pyrrolo[1,2-b]pyridazine-3-carboxylic acid 2-methylpropyl ester.

LCMS: m/z 443[M+H]$^+$

HPLC retention time: 1.32 minutes (analysis condition SMD-TFA05)

Third Step (4aR)-1-[(2,6-Dichloro-4-hydroxyphenyl)methyl]-4-hydroxy-4a-methyl-2-oxo-6,7-dihydro-5H-pyrrolo[1,2-b]pyridazine-3-carboxylic acid 2-methylpropyl ester and 2-(trifluoromethyl)-4-(6-(trifluoromethyl)pyridin-3-yl)pyrimidin-5-amine (Reference Example 70) were used, and operations similar to those of Example 21 were carried out to obtain the title compound.

LCMS: m/z 677[M+H]+

HPLC retention time: 1.51 minutes (analysis condition SMD-TFA05)

Example 329

(4aR)-1-[2,6-(-Dichloro-4-hydroxyphenyl)methyl]-4-hydroxy-4a-methyl-2-oxo-N-[6-(trifluoromethyl)-2-[6-(trifluoromethyl)pyridin-3-yl]pyridin-3-yl]-6,7-dihydro-5H-pyrrolo[1,2-b]pyridazine-3-carboxamide

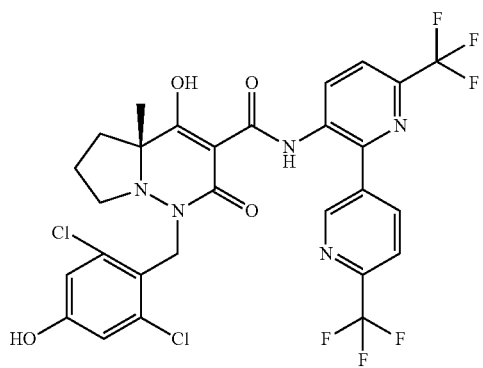 [SMILES: C[C@]12CCCN1N(Cc1c(Cl)cc(O)cc1Cl)C(=O)C(C(=O)Nc1ccc(C(F)(F)F)nc1-c1ccc(C(F)(F)F)nc1)=C2O]

(4aR)-1-[(2,6-Dichloro-4-hydroxyphenyl)methyl]-4-hydroxy-4a-methyl-2-oxo-6,7-dihydro-5H-pyrrolo[1,2-b]pyridazine-3-carboxylic acid 2-methylpropyl ester (Second Step of Example 328) and 6,6'-bis(trifluoromethyl)-[2,3'-bipyridine]-3-amine (Reference Example 44) were used, and operations similar to those of Third Step of Example 328 were carried out to obtain the title compound.

LCMS: m/z 676[M+H]+

HPLC retention time: 1.55 minutes (analysis condition SMD-TFA05)

Example 330

(4aR)-1-[2,3-(Difluoro-4-hydroxyphenyl)methyl]-4-hydroxy-4a-methyl-2-oxo-N-[2-(trifluoromethyl)-4-[6-(trifluoromethyl)pyridin-3-yl]pyrimidin-5-yl-6,7-dihydro-5H-pyrrolo[1,2-b]pyridazine-3-carboxamide

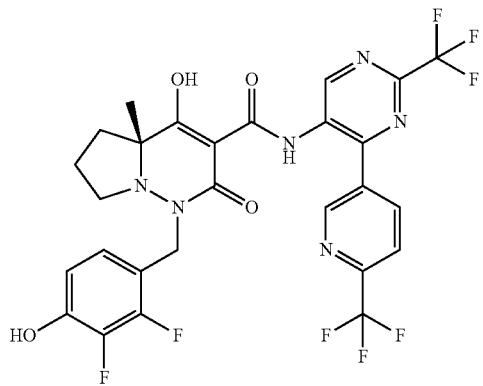 [SMILES: C[C@]12CCCN1N(Cc1ccc(O)c(F)c1F)C(=O)C(C(=O)Nc1cnc(C(F)(F)F)nc1-c1ccc(C(F)(F)F)nc1)=C2O]

First Step

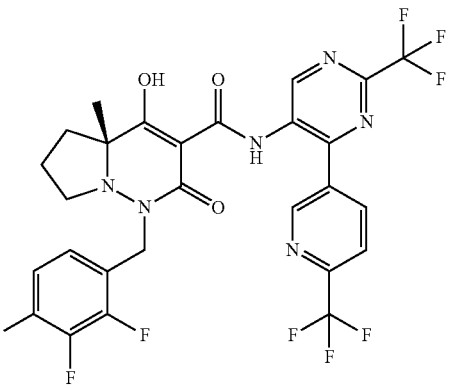

Methyl (4aR)-1-[(2,3-difluoro-4-iodophenyl)methyl]-4-hydroxy-4a-methyl-2-oxo-6,7-dihydro-5H-pyrrolo[1,2-b]pyridazine-3-carboxylate (Third Step of Example 319) and 2-(trifluoromethyl)-4-(6-(trifluoromethyl)pyridin-3-yl)pyrimidin-5-amine (Reference Example 70) were used, and operations similar to those of Fourth Step of Example 319 were carried out to synthesize ((4aR)-1-[(2,3-difluoro-4-iodophenyl)methyl]-4-hydroxy-4a-methyl-2-oxo-N-[2-(trifluoromethyl)-4-[6-(trifluoromethyl)pyridin-3-yl]pyrimidin-5-yl]-6,7-dihydro-5H-pyrrolo[1,2-b]pyridazine-3-carboxamide.

LCMS: m/z 755[M+H]+

HPLC retention time: 1.05 minutes (analysis condition SMD-TFA50)

Second Step

The iodide derivative obtained in First Step was used, and operations similar to those of Example 324 were carried out to synthesize the title compound.

LCMS: m/z 645[M+H]+

HPLC retention time: 1.43 minutes (analysis condition SMD-TFA05)

Example 331

(4aR)—N-(4-Bromo-2-iodophenyl)-1-[(2,3-difluorophenyl)methyl]-4-hydroxy-4a-methyl-2-oxo-6,7-dihydro-5H-pyrrolo[1,2-b]pyridazine-3-carboxamide

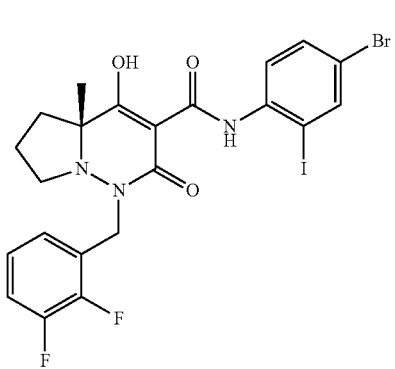 [SMILES: C[C@]12CCCN1N(Cc1cccc(F)c1F)C(=O)C(C(=O)Nc1ccc(Br)cc1I)=C2O]

First Step

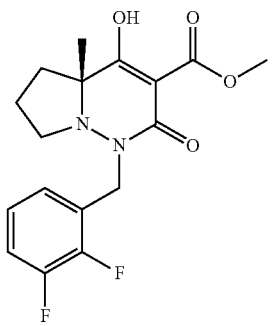 [SMILES: COC(=O)C1=C(O)[C@@]2(C)CCCN2N(Cc2cccc(F)c2F)C1=O]

(R)-2-Methyl-pyrrolidine-2-carboxylic acid methyl ester hydrochloride and 2,3-difluorobenzaldehyde were used, and operations similar to those of First to Third Steps of Example 319 were carried out to synthesize methyl (4aR)-1-[(2,3-difluorophenyl)methyl]-4-hydroxy-4a-methyl-2-oxo-6,7-dihydro-5H-pyrrolo[1,2-b]pyridazine-3-carboxylate.

Second Step

Methyl (4aR)-1-[(2,3-difluorophenyl)methyl]-4-hydroxy-4a-methyl-2-oxo-6,7-dihydro-5H-pyrrolo[1,2-b]pyridazine-3-carboxylate and 4-bromo-2-iodoaniline were used as reagents, and operations similar to those of Example 21 were carried out to synthesize the title compound.

LCMS: m/z 618[M+H]$^+$

HPLC retention time: 1.16 minutes (analysis condition SMD-TFA05)

Reference Example 104

Methyl 1-[[(E)-[2,3-difluoro-4-[2-[2-methoxyethyl (methyl)amino]ethoxy]phenyl]methylideneamino]-methylamino]cyclobutane-1-carboxylate hydrochloride

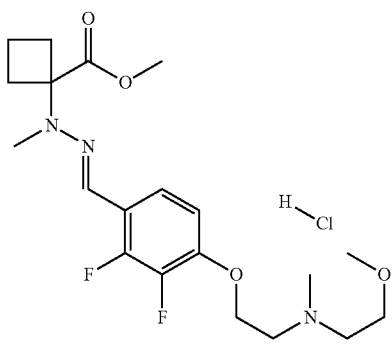

Methyl 1-[[(E)-[2,3-difluoro-4-[2-[2-methoxyethyl (methyl)amino]ethoxy]phenyl]methylideneamino]-methylamino]cyclobutane-1-carboxylate (Third Step of Example 13) (300 mg, 0.726 mmol) was dissolved in 2-butanone (1.50 mL), and pyridine hydrochloride (84.0 mg, 0.727 mmol) was added at 25° C., and the mixture was stirred under nitrogen atmosphere for 30 minutes. Heptane (1.50 mL) and a seed crystal (1.00 mg, 0.00222 mmol) were added to the reaction mixture, and then the mixture was stirred for 1 hour. Heptane (3.00 mL) was added to the reaction mixture, the mixture was stirred for 16 hours, and then the deposited crystal was collected by filtration to obtain the title compound (271 mg, 88%).

Melting point: 108° C.

$^1$H-NMR (DMSO-D$_6$) δ: 10.32 (1H, brs), 7.44 (1H, m), 7.29 (1H, s), 7.07 (1H, m), 4.49 (2H, t, J=4.4 Hz), 3.72 (2H, t, J=5.0 Hz), 3.63 (3H, s), 3.55-3.36 (4H, m), 3.44 (3H, s), 2.87 (3H, brs), 2.80 (3H, s), 2.48 (4H, m), 1.93 (2H, m).

The seed crystal used in Reference Example 104 was obtained by the following method.

Methyl 1-[[(E)-[2,3-difluoro-4-[2-[2-methoxyethyl (methyl)amino]ethoxy]phenyl]methylideneamino]-methylamino]cyclobutane-1-carboxylate (75.3 mg, 0.182 mmol) was dissolved in dimethylsulfoxide (0.317 mL), and 2 M hydrochloric acid (93.0 μL, 0.186 mmol) was added. The prepared solution (15.0 μL) was freeze-dried, 2-butanone (15.0 μL) and heptane (15.0 μL) were added to the obtained powder at 25° C., and the mixture was stirred for 4 days to obtain a deposit.

Reference Example 105

Methyl 1-[[(E)-[2,3-difluoro-4-[2-[2-methoxyethyl (methyl)amino]ethoxy]phenyl]methylideneamino]-methylamino]cyclopentane-1-carboxylate hydrochloride

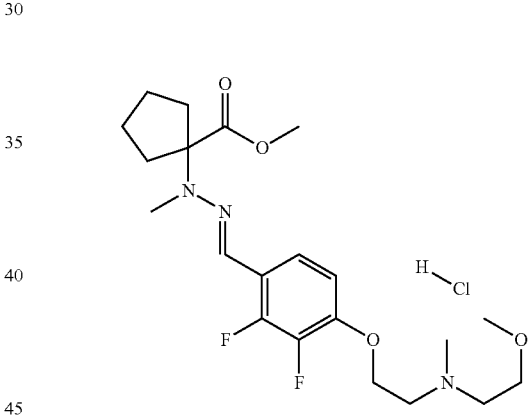

Methyl 1-[[(E)-[2,3-difluoro-4-[2-[2-methoxyethyl (methyl)amino]ethoxy]phenyl]methylideneamino]-methylamino]cyclopentane-1-carboxylate (First Step of Example 14) (300 mg, 0.702 mmol) was dissolved in 2-butanone (3.00 mL), pyridine hydrochloride (81.0 mg, 0.701 mmol) was added at 25° C., and the mixture was stirred under nitrogen atmosphere for 30 minutes. Heptane (1.00 mL) and a seed crystal (1.00 mg, 0.00215 mmol) were added to the reaction mixture, and then the mixture was stirred for 1 hour. Heptane (2.00 mL) was added to the reaction mixture, then the mixture was stirred for 2 hours, and the deposited crystal was collected by filtration to obtain the title compound (225 mg, 69%).

Melting point: 97° C.

$^1$H-NMR (DMSO-D$_6$) δ: 10.34 (1H, brs), 7.44 (1H, m), 7.26 (1H, s), 7.08 (1H, m), 4.50 (2H, t, J=4.4 Hz), 3.72 (2H, t, J=5.0 Hz), 3.60 (3H, s), 3.55-3.44 (4H, m), 3.35 (3H, s) 2.87 (3H, brs), 2.85 (3H, s), 2.25 (2H, m), 2.14 (2H, m), 1.70 (4H, m).

The seed crystal used in Reference Example 105 was obtained by the following method.

Methyl 1-[[(E)-[2,3-difluoro-4-[2-[2-methoxyethyl(methyl)amino]ethoxy]phenyl]methylideneamino]-methylamino]cyclopentane-1-carboxylate (50.0 mg, 0.117 mmol) was dissolved in 2-butanone (0.500 mL), pyridine hydrochloride (15.0 mg, 0.130 mmol) was added at 25° C., and the mixture was stirred under nitrogen atmosphere for 30 minutes. Heptane (0.500 mL) and methyl 1-[[(E)-[2,3-difluoro-4-[2-[2-methoxyethyl(methyl)amino]ethoxy]phenyl]methylideneamino]-methylamino]cyclobutane-1-carboxylate hydrochloride (1.00 mg, 0.00222 mmol) were added to the reaction mixture, and the mixture was stirred for 1 hour. The deposited crystal was collected by filtration to obtain a deposit (36.6 mg).

Example 332

4-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]butanoate

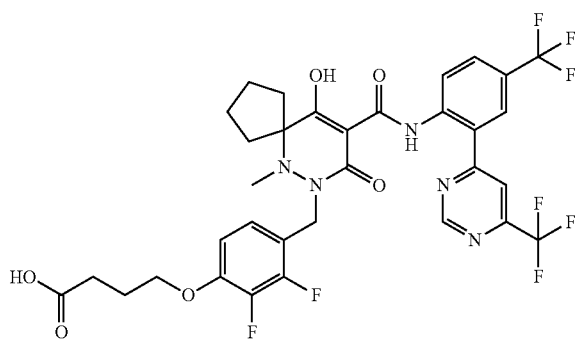 [SMILES: CN1N(Cc2ccc(OCCCC(=O)O)c(F)c2F)C(=O)C(C(=O)Nc2ccc(C(F)(F)F)cc2-c2cc(C(F)(F)F)ncn2)=C(O)C12CCCC2]

First Step

7-[(2,3-Difluoro-4-hydroxyphenyl)methyl]-10-hydroxy-6-methyl-8-oxo-6,7-diazaspiro[4.5]dec-9-ene-9-carboxylic acid 2-methylpropyl ester

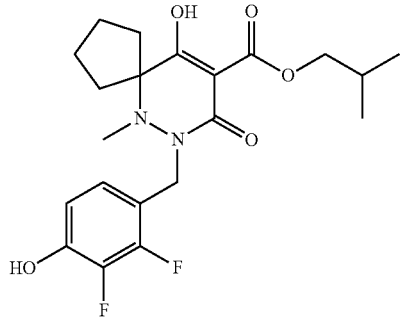 [SMILES: CC(C)COC(=O)C1=C(O)C2(CCCC2)N(C)N(Cc2ccc(O)c(F)c2F)C1=O]

2,3-Difluoro-4-hydroxybenzaldehyde and methyl 1-(methylamino)cyclopentanecarboxylate hydrochloride (Reference Example 87) were used to synthesize the title compound by a method similar to that of Reference Example 1-1.

LCMS: m/z 411 [M+H]$^+$

HPLC retention time: 1.18 minutes (SMD-TFA05)

Second Step

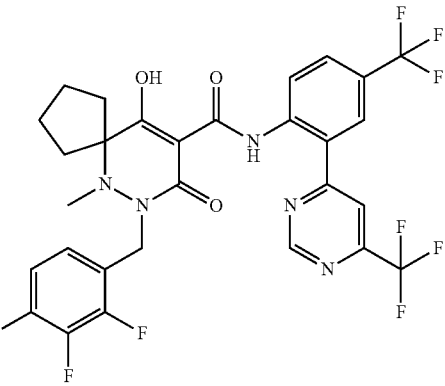

7-[(2,3-Difluoro-4-hydroxyphenyl)methyl]-10-hydroxy-6-methyl-8-oxo-6,7-diazaspiro[4.5]dec-9-ene-9-carboxylic acid 2-methylpropyl ester and 4-(trifluoromethyl)-2-[6-(trifluoromethyl)pyrimidin-4-yl]aniline (Reference Example 50) were used to synthesize 7-[(2,3-difluoro-4-hydroxyphenyl)methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide with reference to Example 21.

LCMS: m/z 658[M+H]$^+$

HPLC retention time: 1.57 minutes (SMD-TFA05)

Third Step

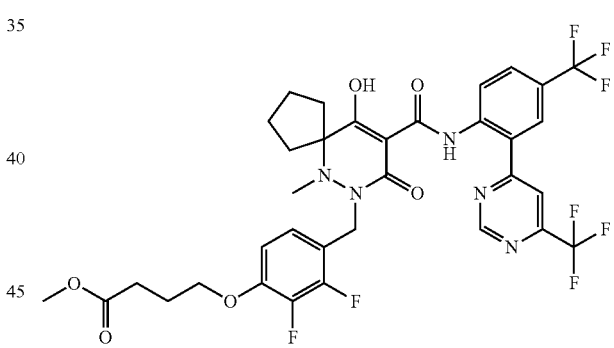

Cesium carbonate (20.4 mg, 0.113 mmol) was added to a solution of 7-[(2,3-difluoro-4-hydroxyphenyl)methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (24.7 mg, 0.038 mmol) and methyl 4-bromobutyrate (24.48 mg, 0.075 mmol) in acetonitrile (0.4 mL), and the mixture was stirred at 70° C. for 1 hour. The reaction mixture was cooled to 0° C., a 1 N-aqueous hydrochloric acid solution (0.063 mL, 0.375 mmol) was added, and the mixture was stirred for 10 minutes. The resultant was diluted with N,N-dimethyl formamide (0.6 mL) and purified by HPLC to obtain methyl 4-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]butyrate (10.6 mg, 37%).

Purification condition: HPLC

Mobile phase: MeCN/water (0.1% formic acid)

YMC-Actus Triart C18 (50×30 mml.D., S-5 μm, 12 nm)
LCMS: m/z 758[M+H]⁺
HPLC retention time: 1.72 minutes (SMD-FA05)

Fourth Step

Potassium trimethylsilanolate (5.38 mg, 0.042 mmol) was added to a solution of methyl 4-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]butyrate (10.6 mg, 0.014 mmol) in tetrahydrofuran (0.4 mL), and the mixture was stirred at room temperature for 2 hours. After the reaction mixture was concentrated, the resultant was diluted with N,N-dimethyl formamide (0.6 mL) and purified by HPLC to obtain the title compound (6.2 mg, 60%).

Purification condition: HPLC
Mobile phase: MeCN/water (0.1% formic acid)
YMC-Actus Triart C18 (50×30 mml.D., S-5 μm, 12 nm)
LCMS: m/z 744[M+H]⁺
HPLC retention time: 1.60 minutes (SMD-FA05)

In Examples 333 to 335, appropriate alkyl bromides were used, and operations similar to those of Example 332 were carried out to synthesize the compounds described in the following Table.

TABLE 31

| Example No. | Structural formula | LCMS Analysis condition | Retention time (min) | m/z [M + H]⁺ |
|---|---|---|---|---|
| 333 | | SMD-FA05 | 1.62 | 758 |
| 334 | | SMD-TFA05 | 1.64 | 772 |
| 335 | | SMD-TFA05 | 1.67 | 786 |

Reference Example 106

6-[(2,3-Difluoro-4-hydroxyphenyl)methyl]-9-hydroxy-5-methyl-7-oxo-5,6-diazaspiro[3.5]non-8-ene-8-carboxylic acid 2-methylpropyl ester

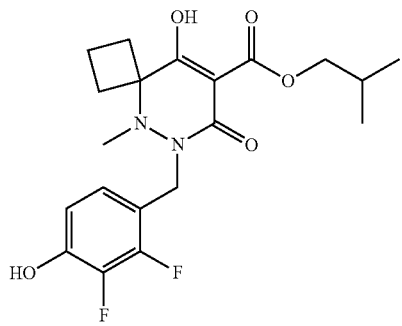 [SMILES: CC(C)COC(=O)C1=C(O)C2(CCC2)N(C)N(Cc2ccc(O)c(F)c2F)C1=O]

Methyl 1-(methylamino)cyclobutanecarboxylate hydrochloride was used as a starting material (Reference Example 85) to synthesize the title compound by a method similar to that of Example 332.

LCMS: m/z 411[M+H]+

HPLC retention time: 1.18 minutes (SMD-TFA05)

Reference Example 107

6-[(2,3-Difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide

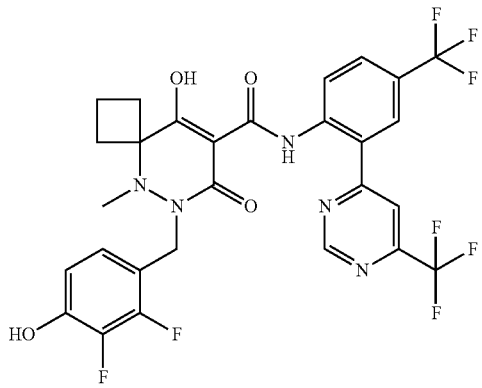 [SMILES: CN1N(Cc2ccc(O)c(F)c2F)C(=O)C(C(=O)Nc2ccc(C(F)(F)F)cc2-c2cc(C(F)(F)F)ncn2)=C(O)C12CCC2]

Methyl 1-(methylamino)cyclobutane-1-carboxylate hydrochloride was used as a starting material to synthesize the title compound by a method similar to that of Example 332.

LCMS: m/z 658[M+H]+

HPLC retention time: 1.48 minutes (SMD-TFA05)

Example 336

8-[[2,3-Difluoro-4-(2-morpholin-2-oxo-ethoxy)phenyl]methyl]-5-hydroxy-9-methyl-7-oxo-N-[4-(trifluoromethyl)-2-[6-(trifluoromethyl)pyrimidin-4-yl]phenyl]-8,9-diazaspiro[3.5]non-5-ene-6-carboxamide

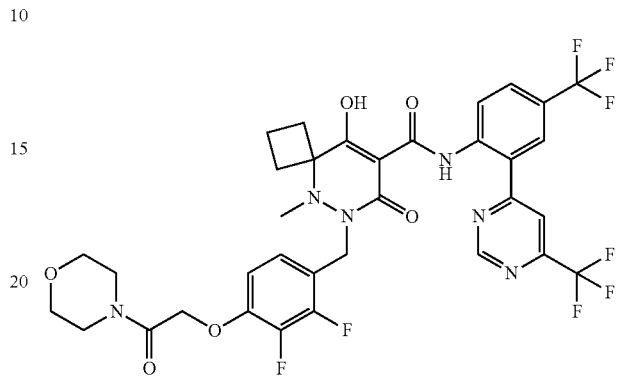

The title compound was synthesized from 6-[(2,3-difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide and 2-chloro-1-morpholin-4-yl-ethanone (Kapanda, Coco N. Journal of Medicinal Chemistry, 52 (22), 7310-7314; 2009) by a method similar to that of Third Step of Example 322.

LCMS: m/z 771[M+H]+

HPLC retention time: 1.43 minutes (analysis condition SMD-TFA05)

Example 337

8-[[2,3-Difluoro-4-[2-(2-oxomorpholin-4-yl)ethoxy]phenyl]methyl]-5-hydroxy-9-methyl-7-oxo-N-[4-(trifluoromethyl)-2-[6-(trifluoromethyl)pyrimidin-4-yl]phenyl]-8,9-diazaspiro[3.5]non-5-ene-6-carboxamide

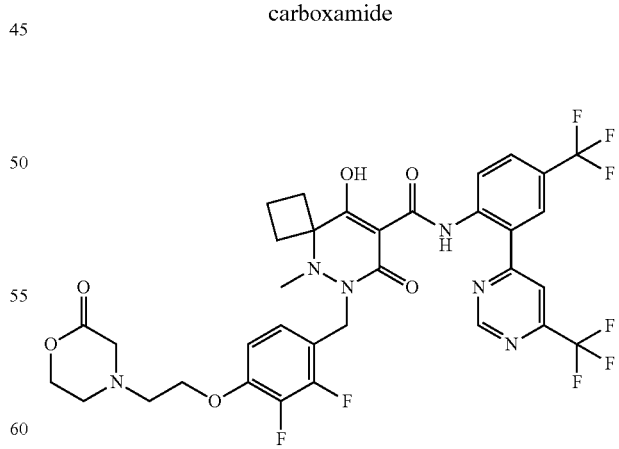

The title compound was obtained from 6-[(2,3-difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide and 4-(2-hydroxyethyl)morpholin-2-one (Khromov-Borisov, N. V.

and Remizov, A. L., Zhurnal Obshchei Khimii, 23, 598-605; 1953) by carrying out operations similar to those of Example 407.

LCMS: m/z 771[M+H]+

HPLC retention time: 1.38 minutes (analysis condition SMD-TFA05)

Reference Example 108

6-[[4-(2-Bromoethoxy)-2,3-difluorophenyl]methyl]-9-hydroxy-5-methyl-7-oxo-N-[4-(trifluoromethyl)-2-[6-(trifluoromethyl)pyrimidin-4-yl]phenyl-5,6-diazaspiro[3.5]non-8-ene-8-carboxamide

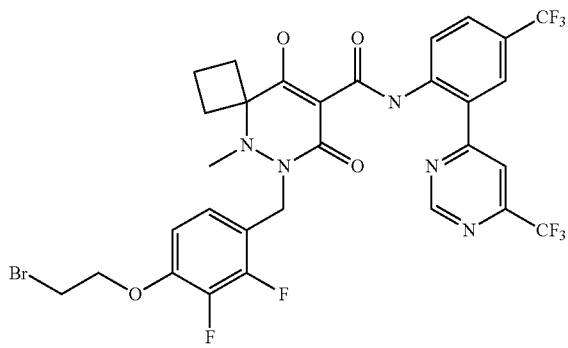 [SMILES: CN1N(Cc2ccc(OCCBr)c(F)c2F)C(=O)C(C(=O)Nc2ccc(C(F)(F)F)cc2-c2cc(C(F)(F)F)ncn2)=C(O)C12CCC2]

6-[(2,3-Difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (Reference Example 107) (3.00 g, 4.66 mmol) was dissolved in acetone (23.3 mL), then 1,2-dibromoethane (6.85 mL, 79.0 mmol) and potassium carbonate (1.29 g, 9.32 mmol) was added, and the mixture was stirred under nitrogen atmosphere at 60° C. for 15 hours. 1 N hydrochloric acid was added to the reaction mixture at 0° C., and the mixture was extracted with ethyl acetate. The organic layer was washed with a brine, the aqueous layer was separated by a phase separator, the resultant was concentrated at reduced pressure, and the resultant residue was purified by C18 reverse-phase column chromatography (acetonitrile/water) to obtain the title compound (3.19 g, 91%).

LCMS: m/z 749[M+H]+

HPLC retention time: 1.58 minutes (analysis condition SMD-TFA05)

Reference Example 109

7-[[4-(2-Bromoethoxy)-2,3-difluorophenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

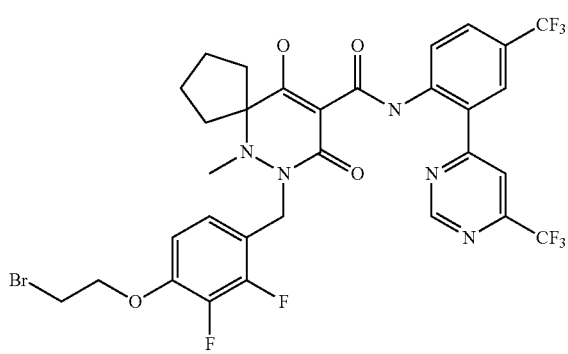 [SMILES: CN1N(Cc2ccc(OCCBr)c(F)c2F)C(=O)C(C(=O)Nc2ccc(C(F)(F)F)cc2-c2cc(C(F)(F)F)ncn2)=C(O)C12CCCC2]

The title compound was synthesized from 7-[(2,3-difluoro-4-hydroxybenzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide (Example 332) in a manner similar to that of Reference Example 106.

LCMS: m/z 764[M+H]+

HPLC retention time: 1.62 minutes (analysis condition SMD-TFA05)

Example 338

6-[[2,3-Difluoro-4-[2-[methyl(oxolan-3-yl)amino]ethoxy]phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide

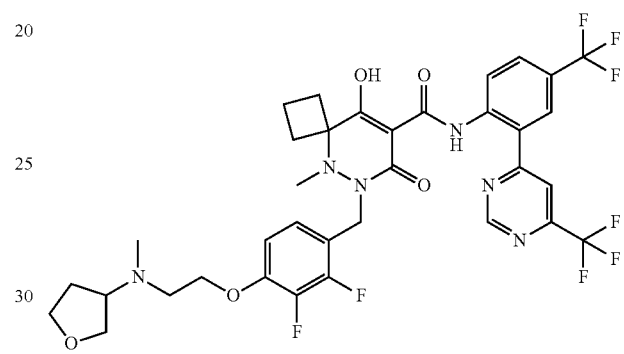

6-[[4-(2-Bromoethoxy)-2,3-difluorophenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (10.0 mg, 13.0 µmol) and N-methyltetrahydrofuran-3-amine (2.70 mg, 27.0 µmol) were dissolved in N,N-dimethyl formamide (100 µL), then N-ethyl-N-isopropylpropan-2-amine (4.6 µL, 27.0 µmol) and tetrabutylammonium iodide (0.5 mg, 1.33 µmol) were added, and the mixture was stirred at 80° C. for 1.5 hours. The reaction mixture was diluted with N,N-dimethyl formamide (0.5 mL) and purified by HPLC to obtain the title compound (8.0 mg, 78%).

Purification condition: HPLC
Mobile phase: MeCN/water (0.1% formic acid)
Column: YMC-Actus Triart C18 (50×30 mml.D., S-5 µm, 12 nm)
LCMS: m/z 771[M+H]+
HPLC retention time: 1.31 minutes (analysis condition SMD-TFA05)

Examples 339 to 380

Various amines which were known from literature or commercialized were used, and operations similar to those of Example 338 were carried out to synthesize the compounds described in the following Table. Note that if the amine was hydrochloride, the amine was not directly used for the reaction and used for the reaction after hydriodic acid (57 wt. %, 2 equivalent weight) was allowed to act and the corresponding hydroiodide was formed.

Purification condition: HPLC
Mobile phase: MeCN/water (0.1% formic acid)
Column: YMC-Actus Triart C18 (50×30 mml.D., S-5 µm, 12 nm, 100×30 mml.D., S-5 µm, 12 nm).

TABLE 32

| Example No. | Structural formula | LCMS analysis condition No. | Retention time (min) | m/z [M + H]+ |
|---|---|---|---|---|
| 339 | | SMD-TFA05 | 1.34 | 769 |
| 340 | | SMD-TFA05 | 1.34 | 783 |
| 341 | | SMD-TFA05 | 1.34 | 785 |
| 342 | | SMD-TFA05 | 1.35 | 785 |

TABLE 32-continued

| Example No. | Structural formula | LCMS analysis condition No. | Retention time (min) | m/z [M + H]+ |
|---|---|---|---|---|
| 343 | | SMD-TFA05 | 1.34 | 785 |
| 344 | | SMD-TFA05 | 1.35 | 785 |
| 345 | | SMD-TFA05 | 1.37 | 785 |

TABLE 32-continued

| Example No. | Structural formula | LCMS analysis condition No. | Retention time (min) | m/z [M + H]+ |
|---|---|---|---|---|
| 346 | | SMD-TFA05 | 1.33 | 773 |
| 347 | | SMD-TFA05 | 1.28 | 745 |
| 348 | | SMD-TFA05 | 1.37 | 803 |
| 349 | | SMD-TFA05 | 1.38 | 787 |

TABLE 32-continued

| Example No. | Structural formula | LCMS analysis condition No. | Retention time (min) | m/z [M + H]+ |
|---|---|---|---|---|
| 350 | | SMD-TFA05 | 1.38 | 787 |
| 351 | | SMD-TFA05 | 1.27 | 775 |
| 352 | | SMD-TFA05 | 1.51 | 739 |

TABLE 32-continued

| Example No. | Structural formula | LCMS analysis condition No. | Retention time (min) | m/z [M + H]+ |
|---|---|---|---|---|
| 353 | | SMD-TFA05 | 1.28 | 786 |
| 354 | | SMD-TFA05 | 1.31 | 800 |
| 355 | | SMD-TFA05 | 1.35 | 799 |

TABLE 32-continued

| Example No. | Structural formula | LCMS analysis condition No. | Retention time (min) | m/z [M + H]+ |
|---|---|---|---|---|
| 356 | | SMD-TFA05 | 1.35 | 771 |
| 357 | | SMD-TFA05 | 1.35 | 773 |
| 358 | | SMD-TFA05 | 1.16 | 840 |
| 359 | | SMD-TFA05 | 1.29 | 784 |

TABLE 32-continued
| Example No. | Structural formula | LCMS analysis condition No. | Retention time (min) | m/z [M + H]+ |
|---|---|---|---|---|
| 360 | 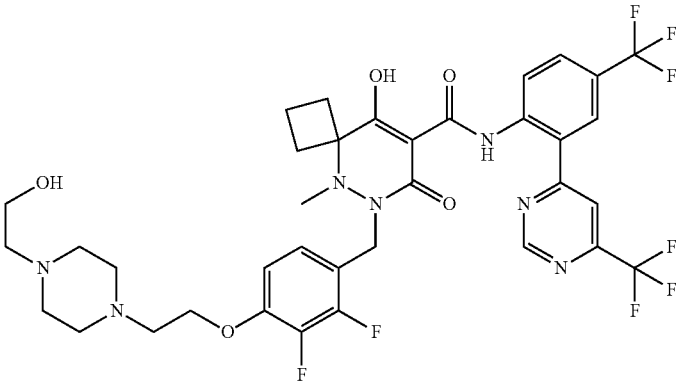 [SMILES: CN1N(Cc2ccc(OCCN3CCN(CCO)CC3)c(F)c2F)C(=O)C(C(=O)Nc2ccc(C(F)(F)F)cc2-c2cc(C(F)(F)F)ncn2)=C(O)C12CCC2] | SMD-TFA05 | 1.22 | 800 |
| 361 | 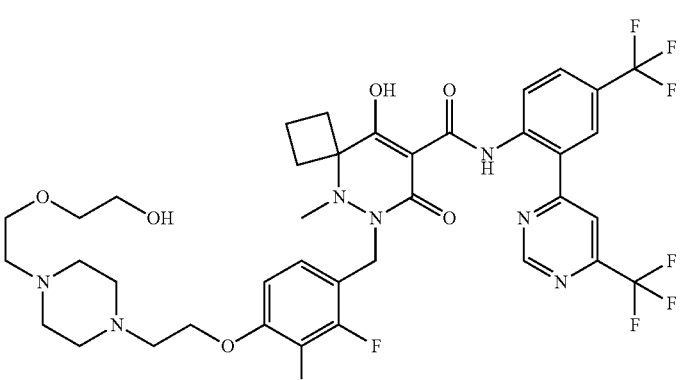 | SMD-TFA05 | 1.23 | 844 |
| 362 | 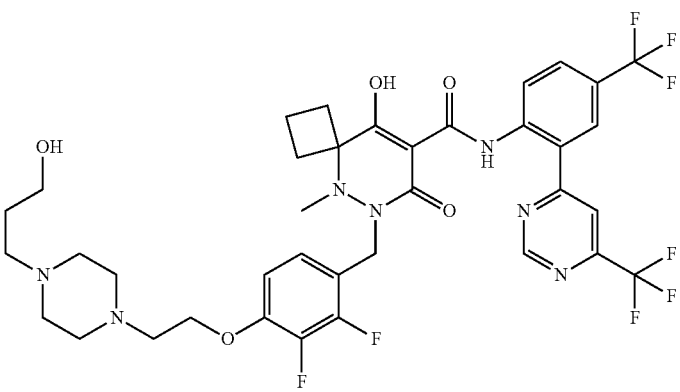 [SMILES: CN1N(Cc2ccc(OCCN3CCN(CCCO)CC3)c(F)c2F)C(=O)C(C(=O)Nc2ccc(C(F)(F)F)cc2-c2cc(C(F)(F)F)ncn2)=C(O)C12CCC2] | SMD-TFA05 | 1.23 | 814 |
| 363 | 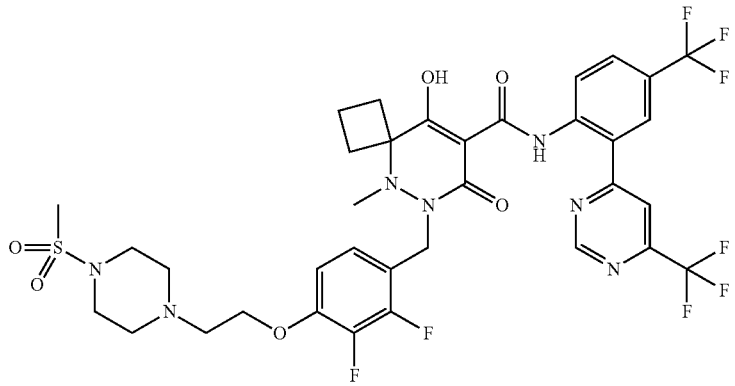 [SMILES: CN1N(Cc2ccc(OCCN3CCN(S(C)(=O)=O)CC3)c(F)c2F)C(=O)C(C(=O)Nc2ccc(C(F)(F)F)cc2-c2cc(C(F)(F)F)ncn2)=C(O)C12CCC2] | SMD-TFA05 | 1.31 | 834 |

TABLE 32-continued

| Example No. | Structural formula | LCMS analysis condition No. | Retention time (min) | m/z [M + H]+ |
|---|---|---|---|---|
| 364 | | SMD-TFA05 | 1.30 | 827 |
| 365 | | SMD-TFA05 | 1.35 | 799 |
| 366 | | SMD-TFA05 | 1.34 | 785 |
| 367 | | SMD-TFA05 | 1.36 | 797 |

TABLE 32-continued

| Example No. | Structural formula | LCMS analysis condition No. | Retention time (min) | m/z [M + H]+ |
|---|---|---|---|---|
| 368 | | SMD-TFA05 | 1.34 | 787 |
| 369 | | SMD-TFA05 | 1.39 | 777 |
| 370 | | SMD-TFA05 | 1.37 | 799 |
| 371 | | SMD-TFA05 | 1.36 | 799 |

TABLE 32-continued
| Example No. | Structural formula | LCMS analysis condition No. | Retention time (min) | m/z [M + H]+ |
|---|---|---|---|---|
| 372 | 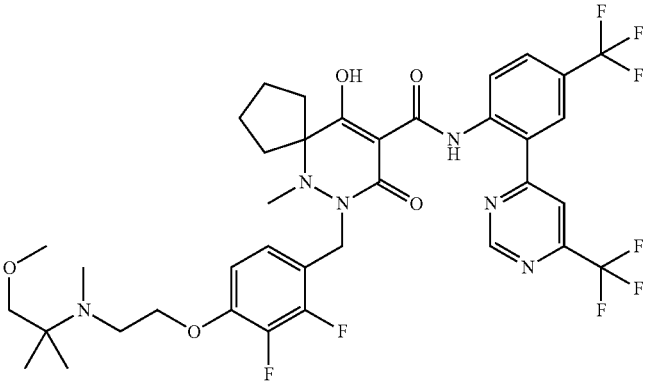 [SMILES: COCC(C)(C)N(C)CCOc1ccc(CN2C(=O)C(C(=O)Nc3ccc(C(F)(F)F)cc3-c3cc(C(F)(F)F)ncn3)=C(O)C3(CCCC3)N2C)c(F)c1F] | SMD-TFA05 | 1.40 | 801 |
| 373 | 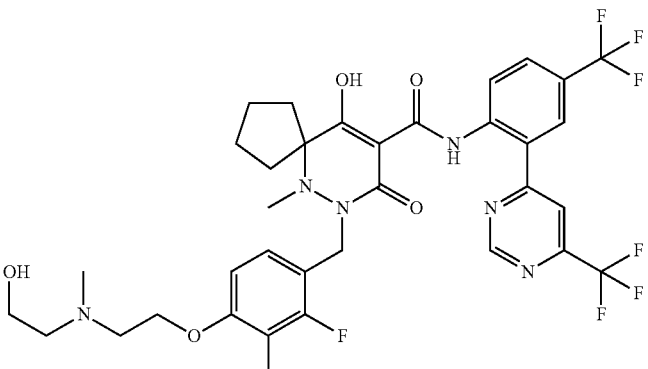 | SMD-TFA05 | 1.31 | 759 |
| 374 | 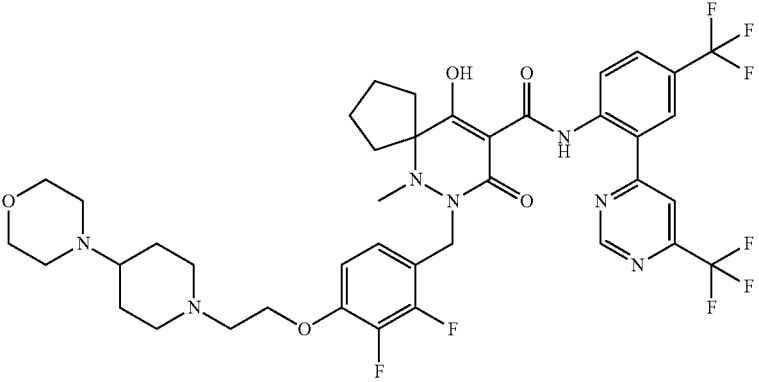 [SMILES: CN1N(Cc2ccc(OCCN3CCC(N4CCOCC4)CC3)c(F)c2F)C(=O)C(C(=O)Nc2ccc(C(F)(F)F)cc2-c2cc(C(F)(F)F)ncn2)=C(O)C12CCCC2] | SMD-TFA05 | 1.19 | 854 |
| 375 | 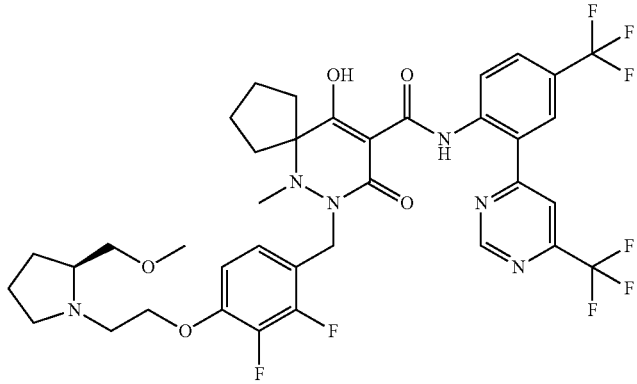 [SMILES: COC[C@@H]1CCCN1CCOc1ccc(CN2C(=O)C(C(=O)Nc3ccc(C(F)(F)F)cc3-c3cc(C(F)(F)F)ncn3)=C(O)C3(CCCC3)N2C)c(F)c1F] | SMD-TFA05 | 1.40 | 799 |

TABLE 32-continued

| Example No. | Structural formula | LCMS analysis condition No. | Retention time (min) | m/z [M + H]+ |
|---|---|---|---|---|
| 376 | | SMD-TFA05 | 1.25 | 814 |
| 377 | | SMD-TFA05 | 1.30 | 828 |
| 378 | | SMD-TFA05 | 1.26 | 858 |

TABLE 32-continued

| Example No. | Structural formula | LCMS analysis condition No. | Retention time (min) | m/z [M + H]+ |
|---|---|---|---|---|
| 379 | | SMD-TFA05 | 1.34 | 848 |
| 380 | | SMD-TFA05 | 1.37 | 783 |

Example 381

(2S)-2-[2-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]butanedioate

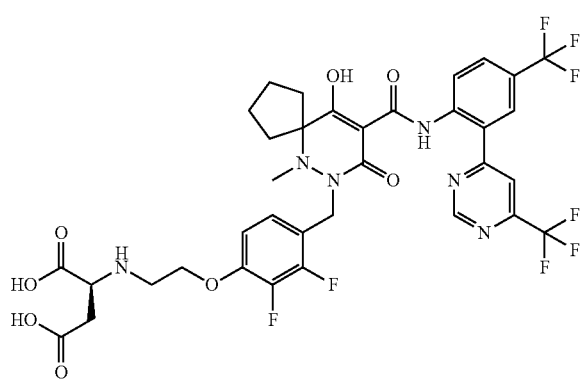 [SMILES: CN1N(Cc2ccc(OCCN[C@@H](CC(=O)O)C(=O)O)c(F)c2F)C(=O)C(C(=O)Nc2ccc(C(F)(F)F)cc2-c2cc(C(F)(F)F)ncn2)=C(O)C12CCCC2]

L-aspartate dimethyl ester hydrochloride (142 mg, 0.72 mmol) was dissolved in methanol (1.00 mL), hydroiodic acid (57 wt. %, 95.0 µL) was added, and the mixture was stirred for 1 minute. After the reaction mixture was concentrated at reduced pressure, methanol and toluene were added for azeotropic removal to obtain L-aspartate dimethyl ester hydroiodide as a crude product. The resultant hydroiodide of amine and 7-[[4-(2-bromoethoxy)-2,3-difluorophenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (110 mg, 0.14 mmol) (Reference Example 109) were dissolved in N,N-dimethyl formamide (480 µL), and then potassium phosphate (92.0 mg, 0.43 mmol) and tetrabutylammonium iodide (5.3 mg, 14.0 µmol) were added, and the mixture was stirred at 80° C. for 2 hours. After the reaction mixture was diluted with tetrahydrofuran (480 µL), potassium trimethylsilanolate (92.0 mg, 0.72 mmol) was added, and the mixture was stirred at 50° C. for 30 minutes and at 70° C. for 2 hours. The reaction mixture was diluted with formic acid and water, and the resultant was purified by HPLC to obtain the title compound (71.5 mg, 61%).

Purification condition: HPLC
Mobile phase: MeCN/water (0.1% formic acid)

Column: YMC-Actus Triart C18 (100×30 mm I.D., S-5 µm, 12 nm)

LCMS: m/z 817[M+H]⁺

HPLC retention time: 1.32 minutes (analysis condition SMD-TFA05)

Example 382

3-[2-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]pentanedioate

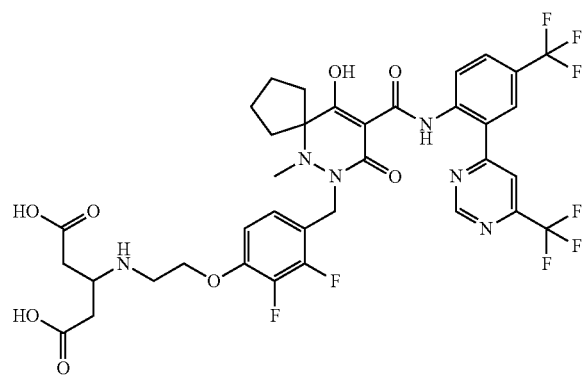 [SMILES: CN1N(Cc2ccc(OCCNC(CC(=O)O)CC(=O)O)c(F)c2F)C(=O)C(C(=O)Nc2ccc(C(F)(F)F)cc2-c2cc(C(F)(F)F)ncn2)=C(O)C12CCCC2]

First Step

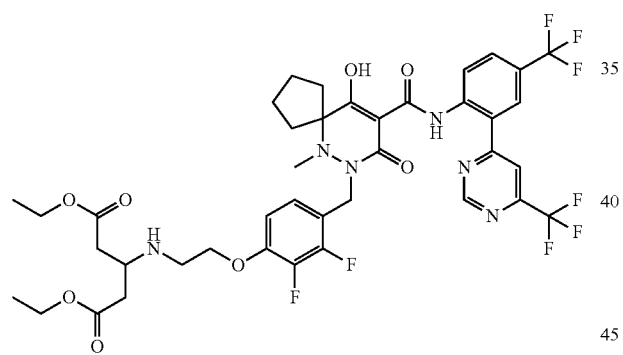

7-[[4-(2-Bromoethoxy)-2,3-difluorophenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (Reference Example 109) and diethyl 3-aminopentanedioate were used as reagents, and operations similar to those of Example 337 were carried out to synthesize diethyl 3-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]pentanedioate.

Second Step

Diethyl 3-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]pentanedioate (48.0 mg, 54.0 µmol) was dissolved in tetrahydrofuran (200 µL), potassium trimethylsilanolate (34.7 mg, 0.27 mmol) was added, and the mixture was stirred at 50° C. for 30 minutes. The reaction mixture was diluted with formic acid and water and purified by HPLC to obtain the title compound (32.4 mg, 72%).

Purification condition: HPLC

Mobile phase: MeCN/water (0.1% formic acid)

Column: YMC-Actus Triart C18 (50×30 mm I.D., S-5 µm, 12 nm)

LCMS: m/z 831[M+H]⁺

HPLC retention time: 1.32 minutes (analysis condition SMD-TFA05)

Example 383

6-[[4-[3-[(2R)-2,3-Dihydroxypropoxy]propoxy]-2,3-difluorophenyl]methyl]-9-hydroxy-5-methyl-7-oxo-N-[4-(trifluoromethyl)-2-[6-(trifluoromethyl)pyridin-3-yl]phenyl]5,6-diazaspiro[3.5]non-8-ene-8-carboxamide

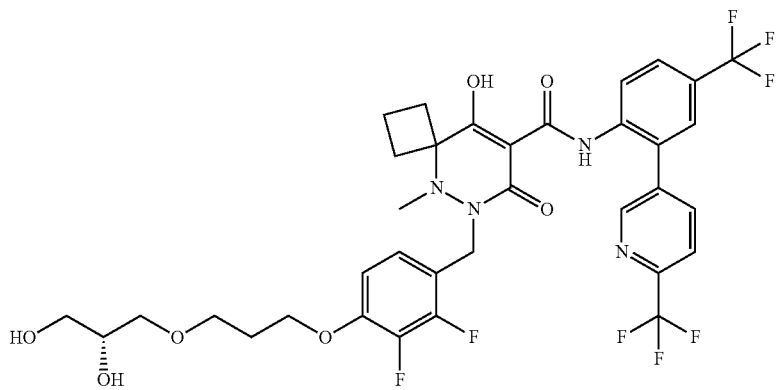 [SMILES: CN1N(Cc2ccc(OCCCOC[C@H](O)CO)c(F)c2F)C(=O)C(C(=O)Nc2ccc(C(F)(F)F)cc2-c2ccc(C(F)(F)F)nc2)=C(O)C12CCC2]

First Step

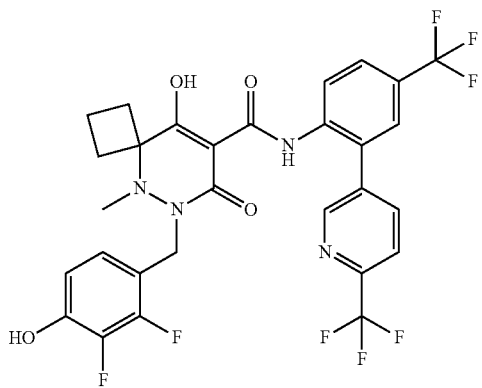 [SMILES: CN1N(Cc2ccc(O)c(F)c2F)C(=O)C(C(=O)Nc2ccc(C(F)(F)F)cc2-c2ccc(C(F)(F)F)nc2)=C(O)C12CCC2]

6-[(2,3-Difluoro-4-hydroxyphenyl)methyl]-9-hydroxy-5-methyl-7-oxo-5,6-diazaspiro[3.5]non-8-ene-8-carboxylic acid 2-methylpropyl ester (Reference Example 106) and 4-(trifluoromethyl)-2-[6-(trifluoromethyl)pyridin-3-yl]aniline (Reference Example 13) were used as reagents, and operations similar to those of Third Step of Example 149 were carried out to synthesize 6-[(2,3-difluoro-4-hydroxyphenyl)methyl]-9-hydroxy-5-methyl-7-oxo-N-[4-(trifluoromethyl)-2-[6-(trifluoromethyl)pyridin-3-yl]phenyl]-5,6-diazaspiro[3.5]non-8-ene-8-carboxamide.

Second Step

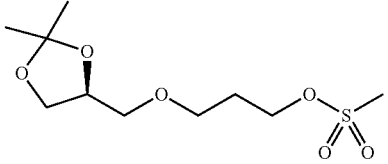

(S)-3-((2,2-Dimethyl-1,3-dioxolan-4-yl)methoxy)propan-1-ol (300 mg, 1.58 mmol) and triethylamine (0.33 mL, 2.37 mmol) were dissolved in tetrahydrofuran (7.88 mL), methanesulfonyl chloride (0.15 mL, 1.89 mmol) was added at 0° C., and the mixture was stirred at room temperature for 3 hours. After a 1 N aqueous dipotassium hydrogenphosphate solution was added to the reaction mixture and the mixture was extracted with ethyl acetate, the organic layer was washed with a saturated sodium bicarbonate solution and a brine. The organic layer was dried over anhydrous sodium sulfate, filtered, and concentrated at reduced pressure. The resultant residue was purified by column chromatography on silica gel (ethyl acetate/hexane) to obtain 3-[[(4S)-2,2-dimethyl-1,3-dioxolan-4-yl]methoxy]propyl methanesulfonate (316 mg, 75%).

LCMS: m/z 269[M+H]$^+$

HPLC retention time: 0.77 minutes (analysis condition SMD-TFA05)

Third Step

6-[(2,3-Difluoro-4-hydroxyphenyl)methyl]-9-hydroxy-5-methyl-7-oxo-N-[4-(trifluoromethyl)-2-[6-(trifluoromethyl)pyrydin-3-yl]phenyl]-5,6-diazaspiro[3.5]non-8-ene-8-carboxamide (15.0 mg, 23.0 μmol) and 3-[[(4S)-2,2-dimethyl-1,3-dioxolan-4-yl]methoxy]propyl methanesulfonate (8.77 mg, 33.0 μmol) were dissolved in acetonitrile (117 μL), cesium carbonate (22.8 mg, 233 μmol) was added, and the mixture was stirred at 75° C. for 1.5 hours. After the reaction mixture was cooled to room temperature, an aqueous hydrochloric acid solution (6N, 38.9 μL, 233 μmol) and methanol (38.9 μL) were added, and the mixture was stirred at room temperature for 1 hour. A 6 N aqueous sodium hydroxide solution was added to the reaction mixture, and after the mixture was filtered and concentrated, the resultant was diluted with N,N-dimethyl formamide (0.5 mL) and purified by HPLC to obtain the title compound (11.9 mg, 66%).

Purification condition: HPLC

Mobile phase: MeCN/water (0.1% formic acid)

Column: YMC-Actus Triart C18 (100×30 mmI.D., S-5 μm, 12 nm)

LCMS: m/z 775[M+H]$^+$

HPLC retention time: 1.40 minutes (analysis condition SMD-TFA05)

Examples 384 to 400

Bromide(2-[2-(3-bromopropoxy)ethoxy]oxane, 2-[2-(4-bromobutoxy)ethoxy]oxane, 2-[2-(5-bromopentoxy)ethoxy]oxane, 2-[3-(3-bromopropoxy)propoxy]oxane, 2-[3-(4-bromobutoxy)propoxy]oxane, 2-[3-(5-bromopentoxy)propoxy]oxane synthesized by a method similar to that of First Step of Example 147 by using alcohol(2-(oxan-2-yloxy)ethanol, 3-(oxan-2-yloxy)propan-1-ol), and dibromide (1,3-dibromopropane, 1,4-dibromobutane, 1,5-dibromopentane) which were known from literature or commercialized, and 3-[[(4S)-2,2-dimethyl-1,3-dioxolan-4-yl]methoxy]propyl methanesulfonate (Example 383), (S)-4-((4-bromobutoxy)methyl)-2,2-dimethyl-1,3-dioxolane (Reference Example 74), and (S)-4-(((5-bromopentyl)oxy)methyl)-2,2-dimethyl-1,3-dioxolane (Reference Example 78), 7-[(2,3-difluoro-4-hydroxyphenyl)methyl]-10-hydroxy-6-methyl-8-oxo-N-[4-(trifluoromethyl)-2-[6-(trifluoromethyl)pyrydin-3-yl]phenyl]-6,7-diazaspiro[4.5]dec-9-ene-9-carboxamide synthesized by a method similar to that of First Step of Example 383 by using 7-[(2,3-difluoro-4-hydroxyphenyl)methyl]-10-hydroxy-6-methyl-8-oxo-6,7-diazaspiro[4.5]dec-9-ene-9-carboxylic acid 2-methylpropyl ester (Example 332) and 4-(trifluoromethyl)-2-[6-(trifluoromethyl)pyridin-3-yl]aniline (Reference Example 13), 6-[(2,3-difluoro-4-hydroxyphenyl)methyl]-9-hydroxy-5-methyl-7-oxo-N-[4-(trifluoromethyl)-2-[6-(trifluoromethyl)pyrydin-3-yl]phenyl]-5,6-diazaspiro[3.5]non-8-ene-8-carboxamide (Example 383), 6-[(2,3-difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (Reference Example 107), or 7-(2,3-difluoro-4-hydroxybenzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide (Example 332) were used, and operations similar to those of Example 383 were carried out to synthesize the compounds described in the following Table.

Purification condition: HPLC

Mobile phase: MeCN/water (0.1% formic acid)

Column: YMC-Actus Triart C18 (50×30 mmI.D., S-5 μm, 12 nm, 100×30 mmI.D., S-5 μm, 12 nm)

TABLE 33

| Example No. | Structural formula | LCMS analysis condition No. | Retention time (min) | m/z [M + H]+ |
|---|---|---|---|---|
| 384 | | SMD-TFA05 | 1.51 | 789 |
| 385 | | SMD-TFA05 | 1.54 | 803 |
| 386 | | SMD-TFA05 | 1.43 | 789 |

TABLE 33-continued

| Example No. | Structural formula | LCMS analysis condition No. | Retention time (min) | m/z [M + H]+ |
|---|---|---|---|---|
| 387 | | SMD-TFA05 | 1.54 | 803 |
| 388 | | SMD-TFA05 | 1.57 | 817 |
| 389 | | SMD-TFA05 | 1.50 | 776 |

| Example No. | Structural formula | LCMS analysis condition No. | Retention time (min) | m/z [M+H]+ |
|---|---|---|---|---|
| 390 | | SMD-TFA05 | 1.52 | 790 |
| 391 | | SMD-TFA05 | 1.55 | 804 |
| 392 | | SMD-TFA05 | 1.52 | 790 |

TABLE 33-continued

| Example No. | Structural formula | LCMS analysis condition No. | Retention time (min) | m/z [M + H]+ |
|---|---|---|---|---|
| 393 | | SMD-TFA05 | 1.55 | 804 |
| 394 | | SMD-TFA05 | 1.58 | 818 |
| 395 | | SMD-TFA05 | 1.63 | 760 |

TABLE 33-continued

| Example No. | Structural formula | LCMS analysis condition No. | Retention time (min) | m/z [M + H]+ |
|---|---|---|---|---|
| 396 | | SMD-TFA05 | 1.65 | 774 |
| 397 | | SMD-TFA05 | 1.68 | 788 |
| 398 | | SMD-TFA05 | 1.66 | 774 |
| 399 | | SMD-TFA05 | 1.68 | 788 |

TABLE 33-continued

| Example No. | Structural formula | LCMS analysis condition No. | Retention time (min) | m/z [M + H]+ |
|---|---|---|---|---|
| 400 | | SMD-TFA05 | 1.57 | 802 |

Example 401

6-[[2,3-Difluoro-4-[2-(2-methoxyethoxy)ethoxy]phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide The title compound was synthesized from 6-[(2,3-difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (Reference Example 107) and 1-bromo-2-(2-methoxyethoxy)ethane in a manner similar to that of Third Step of Reference Example 383.

LCMS: m/z 746[M+H]+

HPLC retention time: 1.66 minutes (analysis condition SMD-TFA05)

Example 402

6-(2,3-Difluoro-4-(2-(methyl(oxetan-3-yl)amino)ethoxy)benzyl)-9-hydroxy-5-methyl-7-oxo-N-(4-(trifluoromethyl)-2-(6-(trifluoromethyl)pyrimidin-4-yl)phenyl)-5,6-diazaspiro[3.5]non-8-ene-8-carboxamide First Step

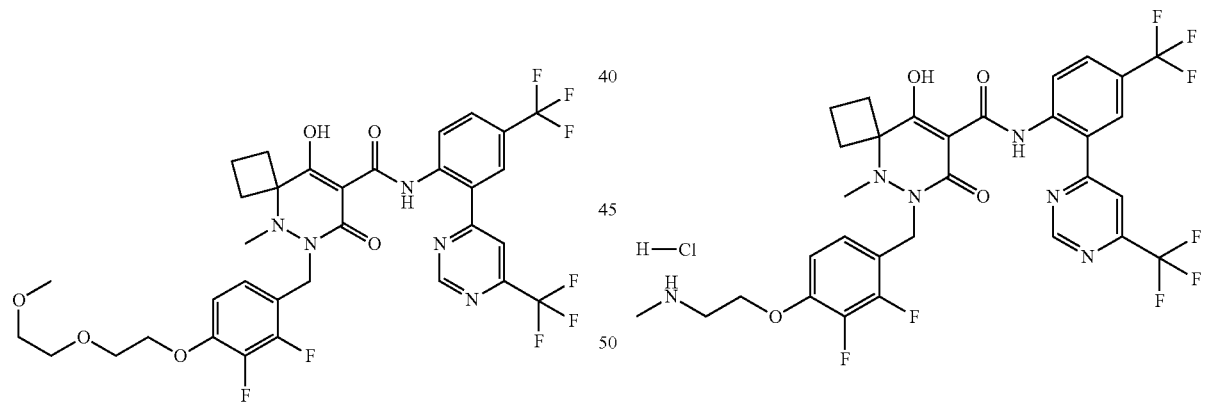

6-(4-(2-Bromoethoxy)-2,3-difluorobenzyl)-9-hydroxy-5-methyl-7-oxo-N-(4-(trifluoromethyl)-2-(6-(trifluoromethyl)pyrimidin-4-yl)phenyl)-5,6-diazaspiro[3.5]non-8-ene-8-carboxamide (10.0 mg, 0.013 mmol) (Reference Example 108) was dissolved in 1,3-dimethyl-2-imidazolidinone (100 μL), and then a 2.0 M methylamine-tetrahydrofuran solution (400 μL, 0.800 mmol), N,N-diisopropyl ethylamine (4.6 μL, 0.027 mmol), then tetrabutyl ammonium iodide (0.5 mg, 0.001 mmol) were added, and the mixture was stirred at 80° C. for 3 hours. The reaction mixture was concentrated at reduced pressure, a 0.5 M hydrochloric acid-methanol solution (80 μL, 0.040 mmol) was added, and normal butanol and toluene were added for azeotropic removal to obtain 6-(2,3-difluoro-4-(2-(methylamino)ethoxy)benzyl)-9-hydroxy-5-methyl-7-oxo-N-(4-(trifluoromethyl)-2-(6-(trifluoromethyl)pyrimidin-4-yl)phenyl)-5,6-diazaspiro[3.5]non-8-ene-8-carboxamide hydrochloride as a crude product.

LCMS: m/z 701[M+H]+

HPLC retention time: 1.27 minutes (analysis condition SMD-TFA05)

Second Step

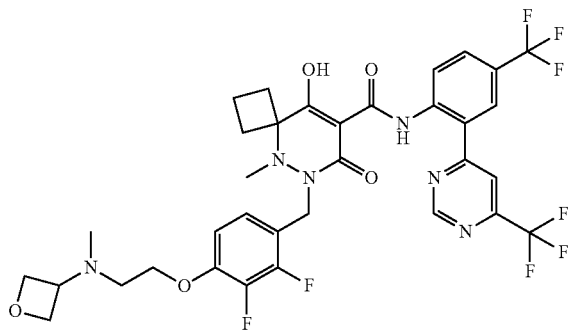 [SMILES: CN(CCOc1ccc(CN2C(=O)C(C(=O)Nc3ccc(C(F)(F)F)cc3-c3cc(C(F)(F)F)ncn3)=C(O)C3(CCC3)N2C)c(F)c1F)C1COC1]

The crude product of 6-(2,3-difluoro-4-(2-(methylamino)ethoxy)benzyl)-9-hydroxy-5-methyl-7-oxo-N-(4-(trifluoromethyl)-2-(6-(trifluoromethyl)pyrimidin-4-yl)phenyl)-5,6-diazaspiro[3.5]non-8-ene-8-carboxamide hydrochloride was dissolved in 1,2-dichloroethane (0.5 mL), then oxetan-3-one (6.25 µL, 0.104 mmol), triacetoxy sodium borohydride (16.5 mg, 0.078 mmol), and acetic acid (10 µL, 0.175 mmol) were added, and the mixture was stirred at room temperature for 1 hour. Oxetan-3-one (6.25 µL, 0.104 mmol) and triacetoxy sodium borohydride (16.5 mg, 0.078 mmol) were further added, and the mixture was stirred at room temperature for 1 hour. After the reaction mixture was concentrated and diluted with N,N-dimethyl formamide, the resultant was purified by HPLC to obtain the title compound (3.8 mg, two-step yield of 39%).

LCMS: m/z 757[M+H]+

HPLC retention time: 1.25 minutes (analysis condition SMD-TFA05)

Example 403

6-(2,3-Difluoro-4-(oxetan-3-yloxy)benzyl)-9-hydroxy-5-methyl-7-oxo-N-(4-(trifluoromethyl)-2-(6-(trifluoromethyl)pyrimidin-4-yl)phenyl)-5,6-diazaspiro[3.5]non-8-ene-8-carboxamide

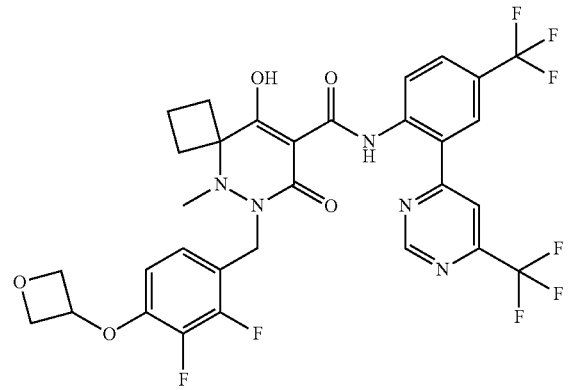 [SMILES: CN1N(Cc2ccc(OC3COC3)c(F)c2F)C(=O)C(C(=O)Nc2ccc(C(F)(F)F)cc2-c2cc(C(F)(F)F)ncn2)=C(O)C12CCC2]

6-[(2,3-Difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (Reference Example 107) was dissolved in acetonitrile (200 µL), then oxetan-3-yl 4-methylbenzenesulfonate (14.2 mg, 0.062 mmol) and cesium carbonate (30.4 mg, 0.093 mmol) were added, and the mixture was stirred at 80° C. overnight. After the reaction mixture was diluted with N,N-dimethyl formamide and water, the resultant was purified by HPLC to obtain the title compound (14.1 mg, 65%).

LCMS: m/z 700[M+H]+

HPLC retention time: 1.62 minutes (analysis condition SMD-TFA05)

Example 404

6-[[2,3-Difluoro-4-[[(2S)-1-(2-methoxyethyl)pyrrolidin-2-yl]methoxy]phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide

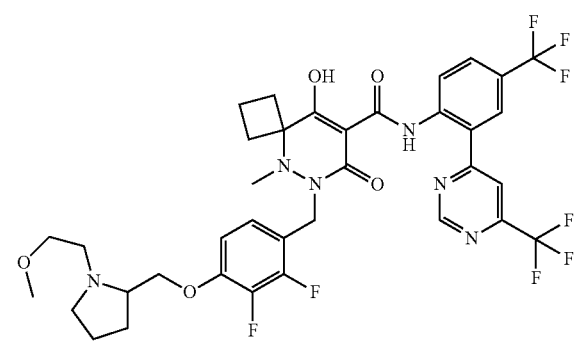 [SMILES: COCCN1CCCC1COc1ccc(CN2C(=O)C(C(=O)Nc3ccc(C(F)(F)F)cc3-c3cc(C(F)(F)F)ncn3)=C(O)C3(CCC3)N2C)c(F)c1F]

First Step

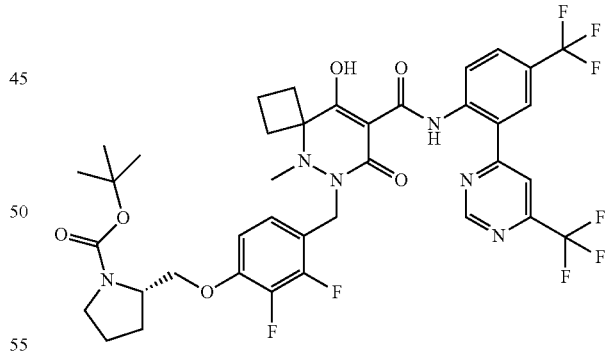

6-[(2,3-Difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (Reference Example 107) (100 mg, 0.16 mmol) and (S)-tert-butyl 2-(hydroxymethyl)pyrrolidine-1-carboxylate (62.6 mg, 0.31 mmol) were dissolved in tetrahydrofuran (311 µL), then N,N,N',N'-tetramethylazodicarboxamide (53.5 mg, 0.31 mmol) was added, and the mixture was stirred at 70° C. for 1 hour. The reaction mixture was concentrated at reduced pressure, and the resultant residue was purified by C18 reverse-phase column chromatography (acetonitrile/water) to obtain tert-butyl (2S)-2-[[2,3-difluoro-4-[[9-hydroxy-5-methyl-7-oxo-8-[[4-(trifluoromethyl)-2-[6-(trifluoromethyl)pyrimidin-4-yl]phenyl]carbamoyl]-5,6-diazaspiro[3.5]non-8-en-6-yl]methyl]phenoxy]methyl]pyrrolidine-1-carboxylate (115 mg, 90%).

LCMS: m/z 827[M+H]$^+$

HPLC retention time: 1.68 minutes (analysis condition SMD-TFA05)

Second Step

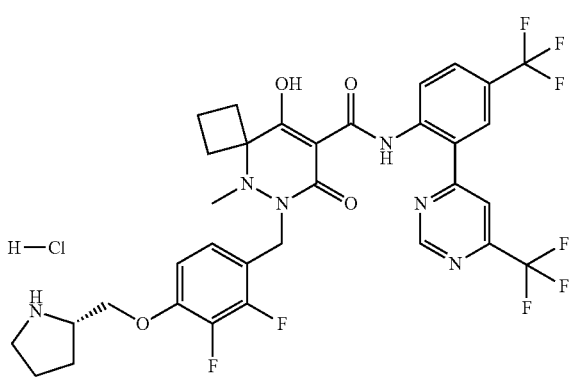 [SMILES: CN1N(Cc2ccc(OC[C@@H]3CCCN3)c(F)c2F)C(=O)C(C(=O)Nc2ccc(C(F)(F)F)cc2-c2cc(C(F)(F)F)ncn2)=C(O)C12CCC2 ; Cl]

Hydrochloric acid (a dioxane solution, 4 N, 1.00 mL, 4.00 mmol) was added to tert-butyl (2S)-2-[[2,3-difluoro-4-[[9-hydroxy-5-methyl-7-oxo-8-[[4-(trifluoromethyl)-2-[6-(trifluoromethyl)pyrimidin-4-yl]phenyl]carbamoyl]-5,6-diazaspiro[3.5]non-8-en-6-yl]methyl]phenoxy]methyl]pyrrolidine-1-carboxylate (104 mg, 0.13 mmol), and the mixture was stirred at room temperature for 1 hour. After the reaction mixture was concentrated at reduced pressure, toluene was added for azeotropic removal to obtain (S)-6-(2,3-difluoro-4-(pyrrolidin-2-ylmethoxy)benzyl)-9-hydroxy-5-methyl-7-oxo-N-(4-(trifluoromethyl)-2-(6-(trifluoromethyl)pyrimidin-4-yl)phenyl)-5,6-diazaspiro[3.5]non-8-ene-8-carboxamide hydrochloride (96 mg, 100%).

LCMS: m/z 727[M+H]$^+$

HPLC retention time: 1.27 minutes (analysis condition SMD-TFA05)

Third Step (S)-6-(2,3-Difluoro-4-(pyrrolidin-2-ylmethoxy)benzyl)-9-hydroxy-5-methyl-7-oxo-N-(4-(trifluoromethyl)-2-(6-(trifluoromethyl)pyrimidin-4-yl)phenyl)-5,6-diazaspiro[3.5]non-8-ene-8-carboxamide hydrochloride (10.0 mg, 13.0 μmol) and 1-bromo-2-methoxyethane (3.64 mg, 26.0 μmol) were dissolved in N,N-dimethyl formamide (100 μL), then N-ethyl-N-isopropylpropan-2-amine (6.9 μL, 39.0 μmol) and tetrabutylammonium iodide (0.5 mg, 1.31 μmol) were added, and the mixture was stirred at 80° C. for 1.5 hours. The reaction mixture was diluted with N,N-dimethyl formamide (0.5 mL) and purified by HPLC to obtain the title compound (3.2 mg, 31%).

Purification condition: HPLC

Mobile phase: MeCN/water (0.1% formic acid)

Column: YMC-Actus Triart C18 (50×30 mm I.D., S-5 μm, 12 nm)

LCMS: m/z 785[M+H]$^+$

HPLC retention time: 1.32 minutes (analysis condition SMD-TFA05)

Example 405

6-[[2,3-Difluoro-4-[(3R)-1-(2-methoxyethyl)pyrrolidin-3-yl]oxyphenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide

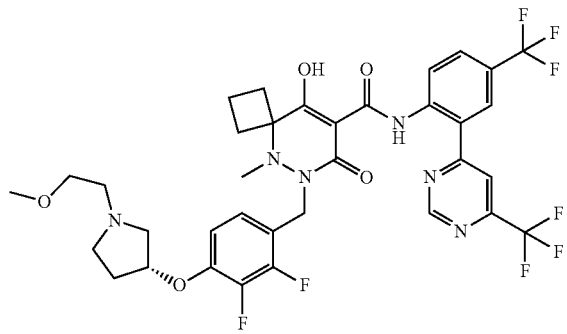 [SMILES: COCCN1CC[C@@H](Oc2ccc(CN3C(=O)C(C(=O)Nc4ccc(C(F)(F)F)cc4-c4cc(C(F)(F)F)ncn4)=C(O)C4(CCC4)N3C)c(F)c2F)C1]

The title compound was synthesized from 6-[(2,3-difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (Reference Example 107) and (S)-tert-butyl 3-hydroxy pyrrolidine-1-carboxylate in a manner similar to that of First to Third Steps of Example 404.

LCMS: m/z 771[M+H]$^+$

HPLC retention time: 1.30 minutes (analysis condition SMD-TFA05)

Example 406

6-[[2,3-Difluoro-4-[1-(2-methoxyethyl)azetidin-3-yl]oxyphenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide

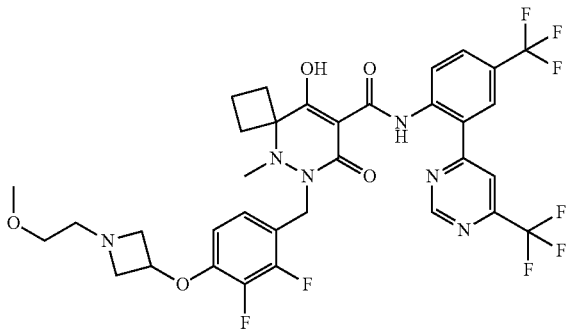 [SMILES: COCCN1CC(Oc2ccc(CN3C(=O)C(C(=O)Nc4ccc(C(F)(F)F)cc4-c4cc(C(F)(F)F)ncn4)=C(O)C4(CCC4)N3C)c(F)c2F)C1]

The title compound was synthesized from 6-[(2,3-difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (Reference Example 107) and tert-butyl 3-hydroxyazetidine-1-carboxylate in a manner similar to that of First to Third Steps of Example 404.

LCMS: m/z 756[M+H]+
HPLC retention time: 1.33 minutes (analysis condition SMD-TFA05)

Example 407

6-[[2,3-Difluoro-4-(2-methyl-1-morpholin-4-ylpropan-2-yl)oxyphenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide

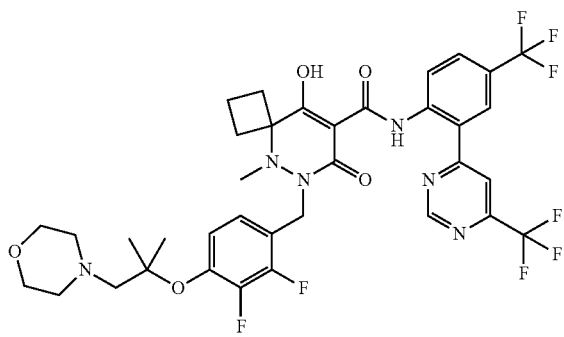 [SMILES: CN1N(Cc2ccc(OC(C)(C)CN3CCOCC3)c(F)c2F)C(=O)C(C(=O)Nc2ccc(C(F)(F)F)cc2-c2cc(C(F)(F)F)ncn2)=C(O)C12CCC2]

A tetrahydrofuran solution (1M) (0.109 mL, 0.109 mmol) of trimethylphosphine was added for as long as 30 seconds to a solution of 6-[(2,3-difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (10 mg, 0.016 mmol), 2-methyl-2-morpholinopropan-1-ol (17 mg, 0.106 mmol), and N,N,N',N'-tetramethylazodicarboxamide (18.7 mg, 0.106 mmol) in tetrahydrofuran (0.3 mL) in a state in which they were heated at 60° C. The reaction mixture was stirred at 60° C. for 16 hours. After the reaction mixture was cooled to room temperature, the resultant was blown with nitrogen to remove the solvent. The residue was dissolved in dimethylformamide and formic acid, and the resultant was purified by HPLC (0.1% formic acid water/0.1% formic acid acetonitrile) to obtain the title compound (4.3 mg, 34%).

LCMS: m/z 785[M+H]+
HPLC retention time: 1.30 minutes (SMD-TFA05)

Examples 408 to 411

Appropriate alkyl alcohols were used, and operations similar to those of Example 407 were carried out to synthesize the compounds described in the following Table.

TABLE 34

| Example No. | Structural formula | LCMS Analysis condition | Retention time (min) | m/z [M + H]+ |
|---|---|---|---|---|
| 408 | | SMD-TFA05 | 1.30 | 771 |
| 409 | | SMD-TFA05 | 1.31 | 742 |

TABLE 34-continued

| Example No. | Structural formula | LCMS Analysis condition | Retention time (min) | m/z [M + H]+ |
|---|---|---|---|---|
| 410 | | SMD-TFA05 | 1.33 | 756 |
| 411 | | SMD-TFA05 | 1.30 | 741 |

Example 412

7-(2,3-Difluoro-4-(2-(methyl(oxetan-3-yl)amino)ethoxy)benzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide First Step

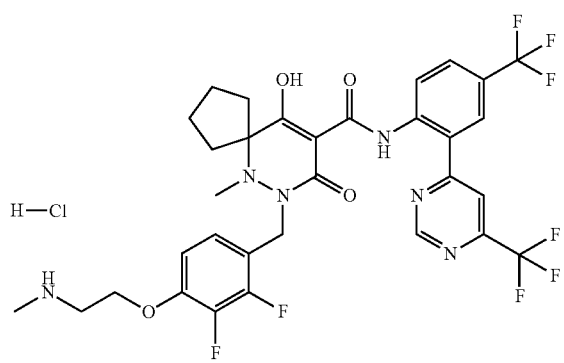 [SMILES: CNCCOc1ccc(CN2C(=O)C(C(=O)Nc3ccc(C(F)(F)F)cc3-c3cc(C(F)(F)F)ncn3)=C(O)C3(CCCC3)N2C)c(F)c1F ; Cl]

7-[[4-(2-Bromoethoxy)-2,3-difluorophenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (20.0 mg, 0.026 mmol) (Reference Example 109) was used, and operations similar to those of First Step of Example 402 were carried out to obtain a crude product of 7-(2,3-difluoro-4-(2-(methylamino)ethoxy)benzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide hydrochloride.

LCMS: m/z 715[M+H]+

HPLC retention time: 1.29 minutes (analysis condition SMD-TFA05)

Second Step

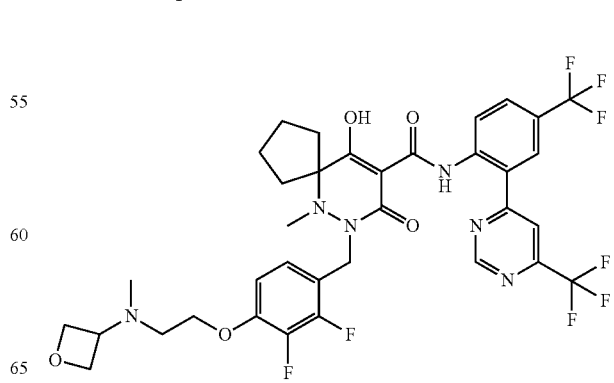

7-(2,3-Difluoro-4-(2-(methylamino)ethoxy)benzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide hydrochloride was used, and operations similar to those of Second Step of Example 402 were carried out to obtain the title compound (11.3 mg, two-step yield of 56%).

LCMS: m/z 771[M+H]⁺

HPLC retention time: 1.19 minutes (analysis condition SMD-TFA05)

$^1$H-NMR (DMSO-D$_6$) δ: 12.72 (1H, s), 9.59 (1H, s), 8.56 (1H, s), 8.42 (1H, d, J=8.8 Hz), 8.24 (1H, s), 7.97 (1H, d, J=7.3 Hz), 7.16 (1H, t, J=7.3 Hz), 7.04 (1H, t, J=7.6 Hz), 5.07 (1H, d, J=13.7 Hz), 4.52 (2H, t, J=6.6 Hz), 4.41 (2H, t, J=6.1 Hz), 4.16 (3H, t, J=5.4 Hz), 3.66 (1H, q, J=6.5 Hz), 2.67 (2H, t, J=5.4 Hz), 2.46 (3H, s), 2.18 (3H, s), 2.01 (1H, m), 1.59 (3H, m), 1.27 (3H, m), 1.07 (1H, m).

Example 413

6-[[2,3-Difluoro-4-[1-(2-methoxyethyl)azetidin-3-yl]oxyphenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide

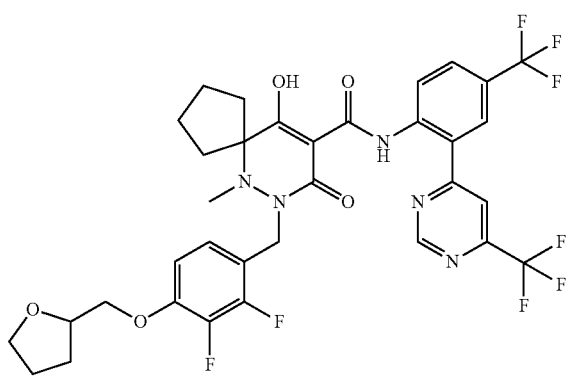 [SMILES: CN1N(Cc2ccc(OCC3CCCO3)c(F)c2F)C(=O)C(C(=O)Nc2ccc(C(F)(F)F)cc2-c2cc(C(F)(F)F)ncn2)=C(O)C12CCCC2]

The title compound was synthesized from 6-[(2,3-difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (Reference Example 107) and 2-(chloromethyl)tetrahydrofuran in a manner similar to that of Third Step of Example 383.

LCMS: m/z 742[M+H]⁺

HPLC retention time: 1.61 minutes (analysis condition SMD-TFA05)

Example 414

7-(4-(3-(Dimethylamino)-2,2-dimethylpropoxy)-2,3-difluorobenzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide

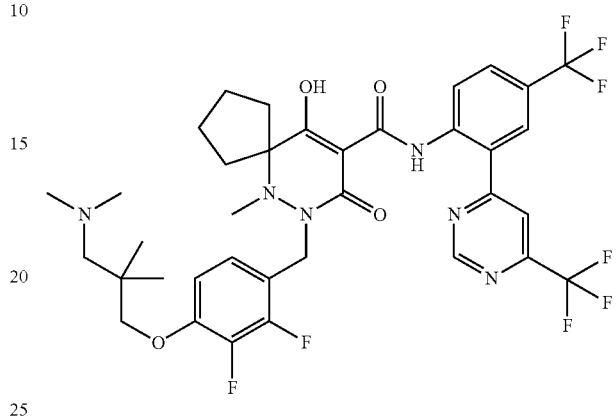

The title compound was synthesized from 7-[(2,3-difluoro-4-hydroxyphenyl)methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide and 3-(dimethylamino)-2,2-dimethylpropan-1-ol by a method similar to that of Example 407.

LCMS: m/z 771[M+H]⁺

HPLC retention time: 1.25 minutes (analysis condition SQD-FA05)

$^1$H-NMR (CDCl$_3$) δ: 16.47 (1H, s), 12.87 (1H, s), 9.60 (1H, s), 8.47 (1H, d, J=8.4 Hz), 7.95 (1H, s), 7.93 (1H, s), 7.79 (1H, d, J=8.4 Hz), 6.99 (1H, m), 6.72 (1H, m), 5.04 (1H, d, J=14.4 Hz), 4.4.19 (1H, d, J=14.4 Hz), 3.80 (2H, s), 2.48 (3H, s), 2.43-2.36 (8H, m), 1.85-1.32 (10H, m), 1.02 (6H, s).

Example 415

1-(2-(2,3-Difluoro-4-((10-hydroxy-6-methyl-8-oxo-9-((4-(trifluoromethyl)-2-(6-(trifluoromethyl)pyrimidin-4-yl)phenyl)carbamoyl)-6,7-diazaspiro[4.5]dec-9-en-7-yl)methyl)phenoxy)ethyl)-1,4-diazabicyclo[2.2.2]octan-1-ium formate

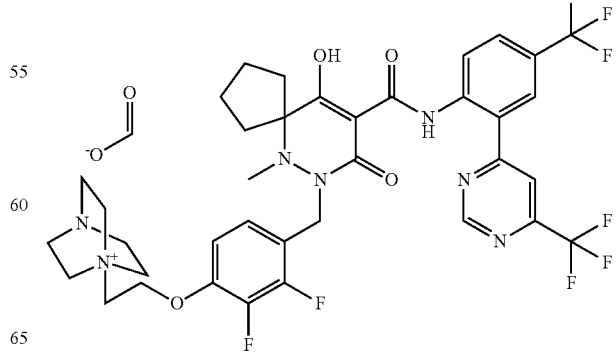

First Step

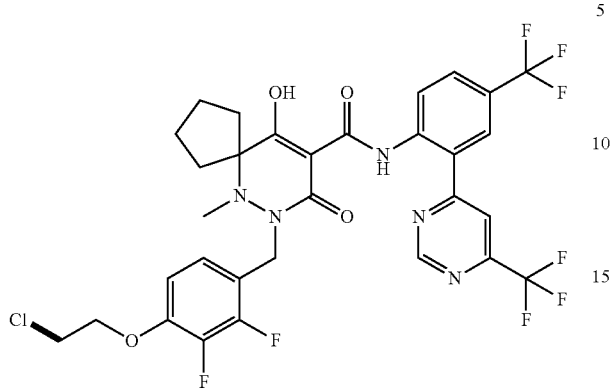

A solution of 7-[(2,3-difluoro-4-hydroxyphenyl)methyl]-10-hydroxy-6-methyl-8-oxo-6,7-diazaspiro[4.5]dec-9-ene-9-carboxylic acid 2-methylpropyl ester, 4-(trifluoromethyl)-2-[6-(trifluoromethyl)pyrimidin-4-yl]aniline (100 mg, 0.152 mmol), 1,2-dichloroethane (151 mg, 1.52 mmol), and potassium carbonate (42 mg, 0.304 mmol) in N,N-dimethyl formamide (1.01 mL) was heated at 60° C. for 18 hours. The residue was dissolved in N,N-dimethyl formamide and formic acid, and the reaction mixture was purified by C-18 reverse-phase column chromatography on silica gel (0.1% formic acid water/0.1% formic acid acetonitrile) to obtain 7-(4-(2-chloroethoxy)-2,3-difluorobenzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide (91 mg, 83%).

LCMS: m/z 720[M+H]$^+$

HPLC retention time: 1.697 minutes (SMD-TFA05)

Second Step

A solution of 7-(4-(2-chloroethoxy)-2,3-difluorobenzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide (93 mg, 0.126 mmol), 1,4-diazabicyclo[2.2.2]octane (142 mg, 1.26 mmol), and potassium carbonate (175 mg, 1.26 mmol) in acetone (3.16 mL) were stirred at 60° C. for 4 days. After the reaction mixture was cooled to room temperature, the resultant was blown with nitrogen gas to remove the solvent. The residue was dissolved in N,N-dimethyl formamide and formic acid, and the resultant was purified by HPLC (0.1% formic acid water/0.1% formic acid acetonitrile) to obtain the title compound (78 mg, 73%).

LCMS: m/z 796[M]$^+$

HPLC retention time: 1.05 minutes (analysis condition SQD-FA05)

Example 416

6-[[2,3-Difluoro-4-[1-(2-methoxyethyl)azetidin-3-yl]oxyphenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide

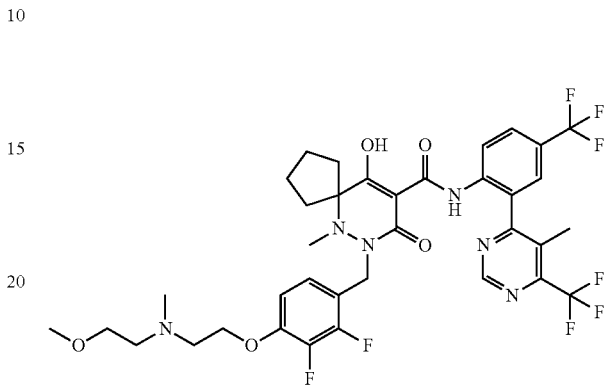

First Step

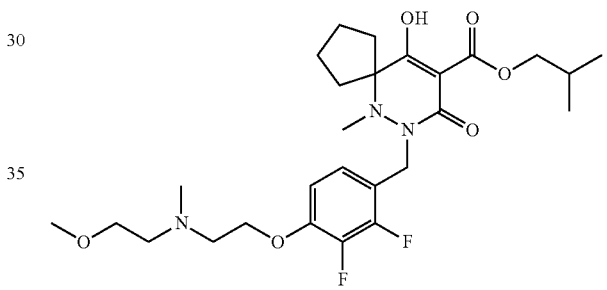

7-[[2,3-Difluoro-4-[2-[2-methoxyethyl(methyl)amino]ethoxy]phenyl]methyl]-10-hydroxy-6-methyl-8-oxo-6,7-diazaspiro[4.5]dec-9-ene-9-carboxylic acid 2-methylpropyl ester was synthesized from methyl 1-[[(E)-[2,3-difluoro-4-[2-[2-methoxyethyl(methyl)amino]ethoxy]phenyl]methylideneamino]-methylamino]cyclopentane-1-carboxylate hydrochloride (Reference Example 105) in a manner similar to that of Fourth Step of Example 237.

LCMS: m/z 540[M+H]$^+$

HPLC retention time: 1.11 minutes (analysis condition SMD-TFA05)

Second Step

The title compound was synthesized from 7-[[2,3-difluoro-4-[2-[2-methoxyethyl(methyl)amino]ethoxy]phenyl]methyl]-10-hydroxy-6-methyl-8-oxo-6,7-diazaspiro[4.5]dec-9-ene-9-carboxylic acid 2-methylpropyl ester and 2-(5-methyl-6-(trifluoromethyl)pyrimidin-4-yl)-4-(trifluoromethyl)aniline (Reference Example 96) in a manner similar to that of Fifth Step of Example 237.

LCMS: m/z 787[M+H]$^+$

HPLC retention time: 1.41 minutes (analysis condition SMD-TFA05)

Example 417

7-(2,3-Difluoro-4-((2-((2-methoxyethyl)(methyl)amino)ethyl)amino)benzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide

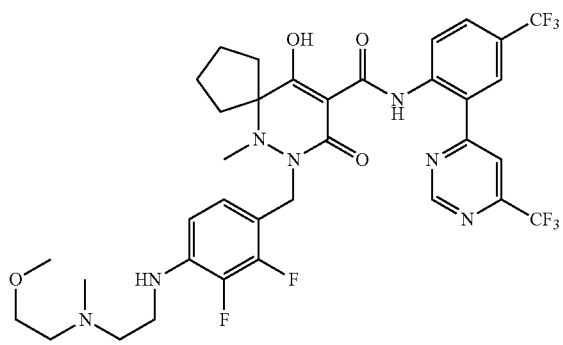 [SMILES: COCCN(C)CCNc1ccc(CN2C(=O)C(C(=O)Nc3ccc(C(F)(F)F)cc3-c3cc(C(F)(F)F)ncn3)=C(O)C3(CCCC3)N2C)c(F)c1F]

First Step

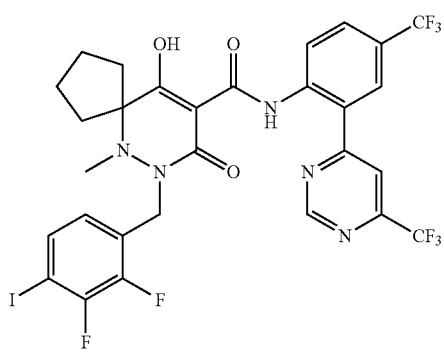 [SMILES: CN1N(Cc2ccc(I)c(F)c2F)C(=O)C(C(=O)Nc2ccc(C(F)(F)F)cc2-c2cc(C(F)(F)F)ncn2)=C(O)C12CCCC2]

2,3-Difluoro-4-iodobenzaldehyde and methyl 1-(methylamino)cyclopentane carboxylate hydrochloride were used, and operations similar to those of Third to Fifth Steps of Example 13 were carried out to synthesize the title compound (2.69 g, three-step yield of 69%).

LCMS: m/z 768[M+H]$^+$

HPLC retention time: 0.99 minutes (analysis condition SQD-FA50)

Second Step

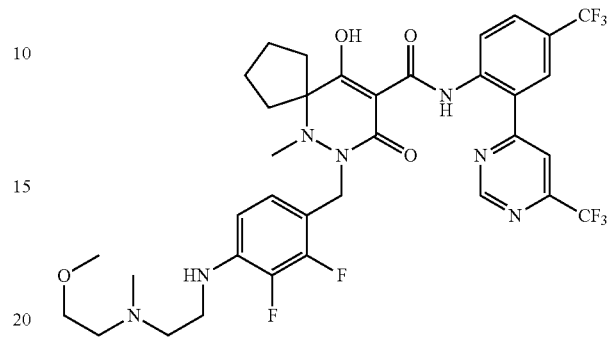

Dimethyl sulfoxide (1.07 mL) was added to a mixture of 7-(2,3-difluoro-4-iodobenzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide (205 mg, 0.267 mmol), copper (I) iodide (10.2 mg, 0.053 mmol), 2-((2,6-dimethylphenyl)amino)-2-oxoacetate (20.6 mg, 0.107 mmol), potassium phosphate (284 mg, 1.336 mmol), and N1-(2-methoxyethyl)-N1-methylethane-1,2-diamine (70.6 mg, 0.534 mmol), and the mixture was stirred under nitrogen atmosphere at 90° C. for 5 hours. Aqueous ammonia was added to the reaction mixture, and the mixture was extracted with ethyl acetate. The residue was purified by C18 reverse-phase column chromatography to obtain the title compound (210 mg, 95%).

LCMS: m/z 772[M+H]$^+$

HPLC retention time: 0.83 minutes (analysis condition SQD-FA05)

Example 418

7-[[2,3-Difluoro-4-[4-[methyl-[(2 S,3R,4R,5R)-2,3,4,5,6-pentahydroxyhexyl]amino]-4-oxobutoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

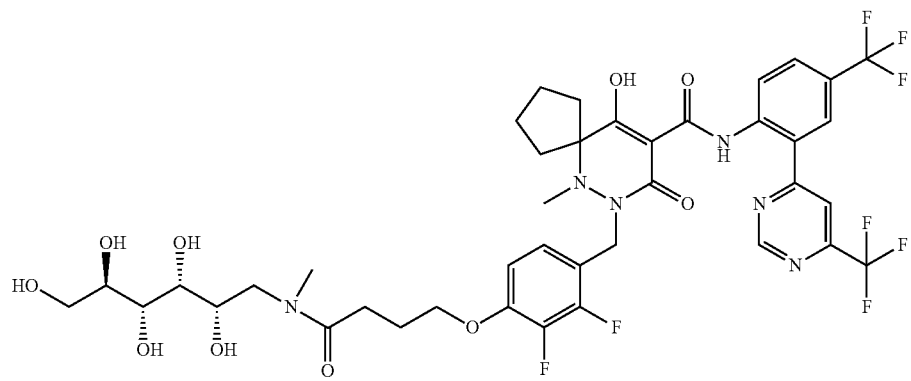 [SMILES: CN(C[C@H](O)[C@@H](O)[C@H](O)[C@H](O)CO)C(=O)CCCOc1ccc(CN2C(=O)C(C(=O)Nc3ccc(C(F)(F)F)cc3-c3cc(C(F)(F)F)ncn3)=C(O)C3(CCCC3)N2C)c(F)c1F]

4-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]butanoate (40 mg, 0.054 mmol) (Example 332) was dissolved in N,N-dimethyl formamide (1 mL), then (2R,3R,4R,5S)-6-(methylamino)hexane-1,2,3,4,5-pentol (31.5 mg, 0.161 mmol), HATU (40.9 mg, 0.108 mmol), and N-ethyl-N-isopropylpropan-2-amine (20.86 mg, 0.161 mmol) were added, and the mixture was stirred at room temperature for 15 hours. Water was added to the reaction mixture (0.2 mL), and the resultant was purified by C18 reverse-phase column chromatography to obtain the title compound (32 mg, 65%) as a white amorphous solid.

LCMS: m/z 921[M+H]$^+$

HPLC retention time: 1.01 minutes (analysis condition SQD-FA05)

Example 419

7-[[4-[2-[2-(2,3-Dihydroxypropylamino)ethoxy]ethoxy]-2,3-difluorophenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

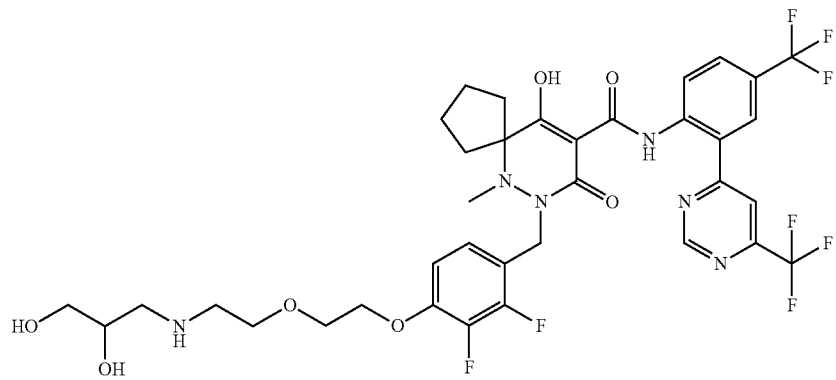 [SMILES: CN1N(Cc2ccc(OCCOCCNCC(O)CO)c(F)c2F)C(=O)C(C(=O)Nc2ccc(C(F)(F)F)cc2-c2cc(C(F)(F)F)ncn2)=C(O)C12CCCC2]

First Step

2-[2-(4-Methylphenyl)sulfonyloxyethoxy]ethyl 4-methylbenzenesulfonate

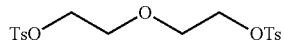 [SMILES: Cc1ccc(S(=O)(=O)OCCOCCOS(=O)(=O)c2ccc(C)cc2)cc1]

2,2'-Oxydiethanol (200 mg, 1.9 mmol) and triethylamine (572 mg, 5.65 mmol) were dissolved in dichloromethane (10 mL), then tosyl chloride (898 mg, 4.7 mol) was added, and the mixture was stirred at room temperature for 15 hours. The reaction mixture was purified by chromatography on silica gel (hexane:ethyl acetate=2:1) to obtain the title compound (620 mg, 79%) as a white plate-like crystal.

LCMS: m/z 415[M+H]$^+$

HPLC retention time: 0.88 minutes (analysis condition SQD-FA05)

Second Step

2-[2-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethoxy]ethyl 4-methylbenzenesulfonate

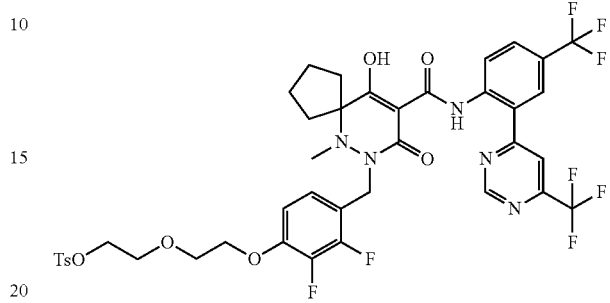

7-[(2,3-Difluoro-4-hydroxyphenyl)methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (100 mg, 0.152 mmol) was dissolved in acetonitrile (5 mL), then oxybis(ethane-2,1-diyl)bis(4-methylbenzenesulfonate) obtained in First Step (252 mg, 0.61 mmol) and cesium carbonate (49.6 mg, 0.152 mmol) were added, and the mixture was stirred at 50° C. for 4 hours. The reaction mixture was purified by C18 reverse-phase column chromatography to obtain the title compound (115 mg, 84%) as a white amorphous solid.

LCMS: m/z 900[M+H]$^+$

HPLC retention time: 1.25 minutes (analysis condition SQD-FA05)

Third Step

2-[2-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethoxy]ethyl 4-methylbenzenesulfonate obtained in Second Step (30 mg, 0.033 mmol) and 3-aminopropane-1,2-diol (9.11 mg, 0.1 mmol) were dissolved in acetonitrile (1 mL), and the mixture was stirred at 50° C. for 5 hours. The reaction mixture was purified by C18 reverse-phase column chromatography to obtain the title compound (18 mg, 66%) as a white amorphous solid.

LCMS: m/z 819[M+H]$^+$

HPLC retention time: 0.82 minutes (analysis condition SQD-FA05)

Example 420

7-[[2,3-Difluoro-4-[2-[2-[methyl-[(2S,3R,4R,5R)-2,3,4,5,6-pentahydroxyhexyl]amino]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

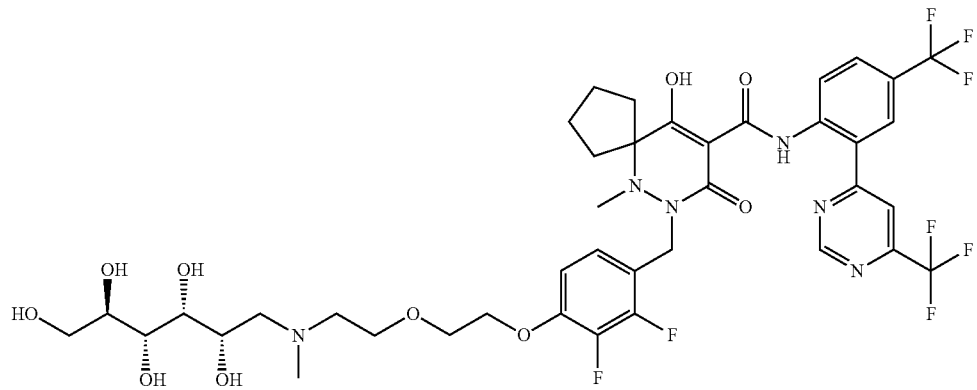 [SMILES: CN(CCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F)C[C@H](O)[C@@H](O)[C@H](O)[C@H](O)CO]

(2R,3R,4R,5S)-6-(Methylamino)hexane-1,2,3,4,5-pentol was used as a raw material, and operations similar to those of Example 419 were carried out to synthesize the title compound.

LCMS: m/z 923[M+H]$^+$

HPLC retention time: 0.79 minutes (analysis condition SQD-FA05)

Example 421

7-[[2,3-Difluoro-4-[2-[2-[2-[2-[2-[methyl-[(2R,3S,4S,5 S)-2,3,4,5,6-pentahydroxyhexyl]amino]ethoxy]ethoxy]ethoxy]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

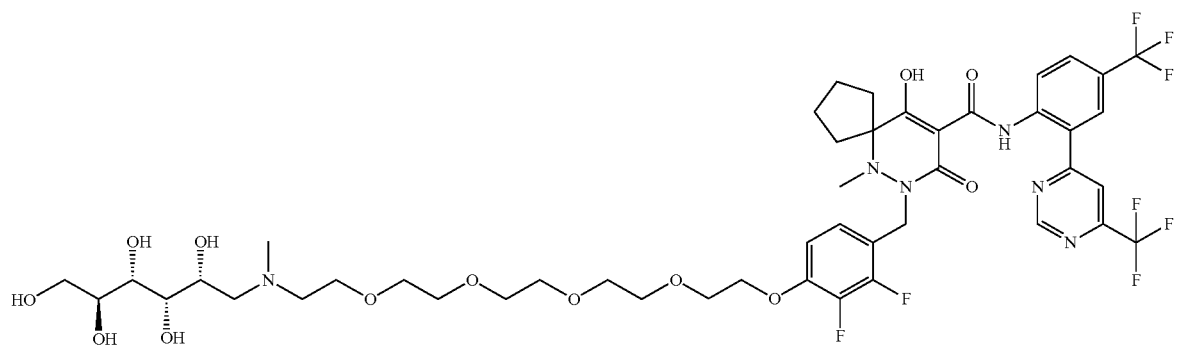 [SMILES: CN(CCOCCOCCOCCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F)C[C@@H](O)[C@H](O)[C@@H](O)[C@@H](O)CO]

2-[2-[2-[2-(2-Hydroxyethoxy)ethoxy]ethoxy]ethoxy]ethanol was used as a raw material, and operations similar to those of Example 419 were carried out to synthesize the title compound.

LCMS: m/z 1055[M+H]$^+$

HPLC retention time: 0.81 minutes (analysis condition SQD-FA05)

Example 422

7-[[2,3-Difluoro-4-[2-[2-[3-methyl-[(2S,3R,4R,5R)-2,3,4,5,6-pentahydroxyhexyl]amino]-3-oxopropoxy]ethoxy]ethoxy]phenyl methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

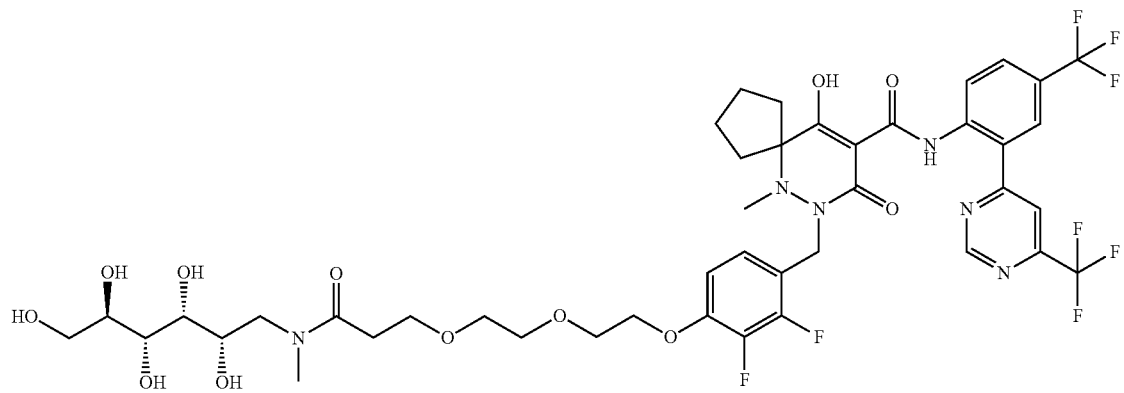 [SMILES: CN(C[C@H](O)[C@@H](O)[C@H](O)[C@H](O)CO)C(=O)CCOCCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F]

First Step tert-Butyl 3-[2-[2-(2-hydroxyethoxy)ethoxy]ethoxy]propanoate

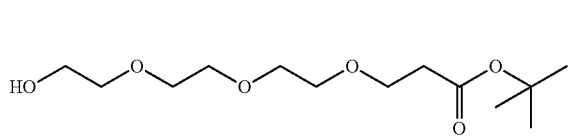 [SMILES: CC(C)(C)OC(=O)CCOCCOCCOCCO]

2-[2-(2-Hydroxyethoxy)ethoxy]ethanol (2 g, 13.3 mmol) was dissolved in THF (5 mL), and NaH (8 mg, 0.2 mol) was added. After the mixture was stirred at room temperature for 10 minutes, tert-butyl prop-2-enoate (0.5 g, 3.9 mmol) was slowly added, and the mixture was stirred at room temperature for 15 hours. The reaction mixture was concentrated, and the resultant residue was purified by column chromatography on silica gel (ethyl acetate) to obtain the target title compound (488 mg, 45%) as colorless clear oil.

$^1$H-NMR (CDCl$_3$) δ: 3.68-3.65 (4H, m), 3.62-3.55 (10H, m), 2.47 (2H, t, J=6.4 Hz), 1.44 (9H, s).

Second Step tert-Butyl 3-[2-[2-[2-(4-methylphenyl)sulfonyloxyethoxy]ethoxy]ethoxy]propanoate

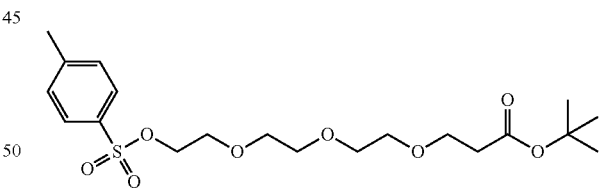

tert-Butyl 3-[2-[2-(2-hydroxyethoxy)ethoxy]ethoxy]propanoate (488 mg, 1.75 mmol) and triethylamine (532 mg, 5.26 mmol) were dissolved in dichloromethane (15 mL), and tosyl chloride (435 mg, 2.28 mmol) was added. After the mixture was stirred at room temperature for 17 hours, the reaction mixture was concentrated, and the resultant residue was purified by column chromatography on silica gel (hexane:ethyl acetate=1:2) to obtain the title compound (550 mg, 73%) as colorless clear oil.

LCMS: m/z 450[M+H$_2$O]$^+$

HPLC retention time: 0.90 minutes (analysis condition SQD-FA05)

Third Step tert-Butyl 3-[2-[2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethoxy]ethoxy]propanoate

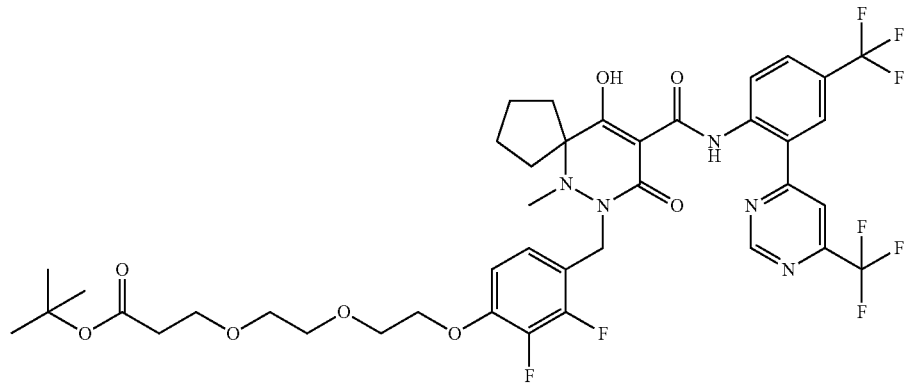 [SMILES: CN1N(Cc2ccc(OCCOCCOCCC(=O)OC(C)(C)C)c(F)c2F)C(=O)C(C(=O)Nc2ccc(C(F)(F)F)cc2-c2cc(C(F)(F)F)ncn2)=C(O)C12CCCC2]

After tert-butyl 3-[2-[2-[2-(4-methylphenyl)sulfonyloxyethoxy]ethoxy]ethoxy]propanoate (70 mg, 0.18 mmol) and 7-[(2,3-difluoro-4-hydroxyphenyl)methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (79 mg, 0.12 mmol) were dissolved in acetonitrile (2 mL), cesium carbonate (117 mg, 1.36 mol) was added, and the mixture was stirred at 70° C. for 2 hours. After water (0.1 mL) was added to the reaction mixture, the resultant was purified by C18 reverse-phase column chromatography to obtain the title compound (18 mg, 66%) as a white amorphous solid.

LCMS: m/z 874[M+H]$^+$

HPLC retention time: 1.29 minutes (analysis condition SQD-FA05)

Fourth Step

3-[2-[2-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethoxy]ethoxy]propanoate tert-Butyl 3-[2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethoxy]ethoxy]propanoate (100 mg, 0.114 mmol) was dissolved in dichloromethane (2 mL), and TFA (0.54 mL) was added at room temperature. After the reaction mixture was stirred at room temperature for 2 hours, the resultant was concentrated to distill TFA away. The resultant residue was directly used for the next reaction.

LCMS: m/z 818[M+H]$^+$

HPLC retention time: 1.15 minutes (analysis condition SQD-FA05)

Fifth Step

3-[2-[2-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethoxy]ethoxy]propanoate (40 mg, 0.05 mmol), 3-aminopropane-1,2-diol (9 mg, 0.1 mol), and HATU (37.2 mg, 0.1 mol) were dissolved in DMF (1 mL), then diisopropylethylamine (12.6 mg, 0.1 mmol) was added, and the mixture was stirred at room temperature for 15 hours. Water (0.1 mL) was added to the reaction mixture,

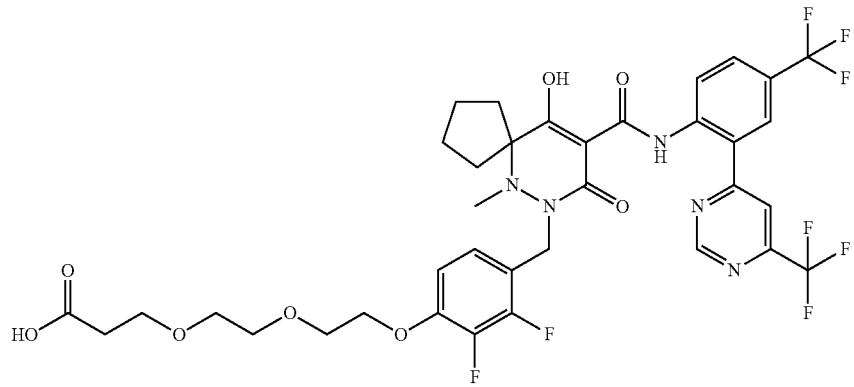 [SMILES: CN1N(Cc2ccc(OCCOCCOCCC(=O)O)c(F)c2F)C(=O)C(C(=O)Nc2ccc(C(F)(F)F)cc2-c2cc(C(F)(F)F)ncn2)=C(O)C12CCCC2]

and the resultant was purified by C18 reverse-phase column chromatography to obtain the title compound (18 mg, 41%) as a white amorphous solid.

LCMS: m/z 995[M+H]$^+$

HPLC retention time: 1.01 minutes (analysis condition SQD-FA05)

Examples 423 and 424

The compounds described in the following Table were synthesized by carrying out Steps similar to those of Example 422 by using 2-[2-(2-hydroxyethoxy)ethoxy]ethanol as a starting material.

TABLE 35

| Example No. | Structural formula |
|---|---|
| 423 | 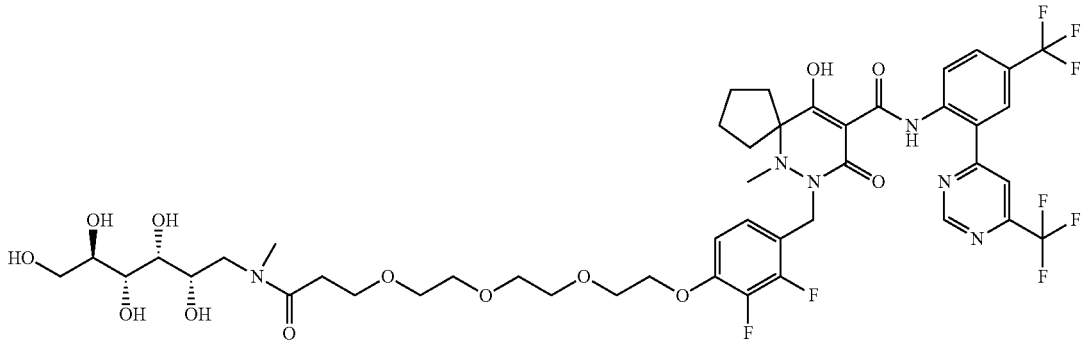 [SMILES: CN(C[C@H](O)[C@@H](O)[C@H](O)[C@H](O)CO)C(=O)CCOCCOCCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F] |
| 424 | 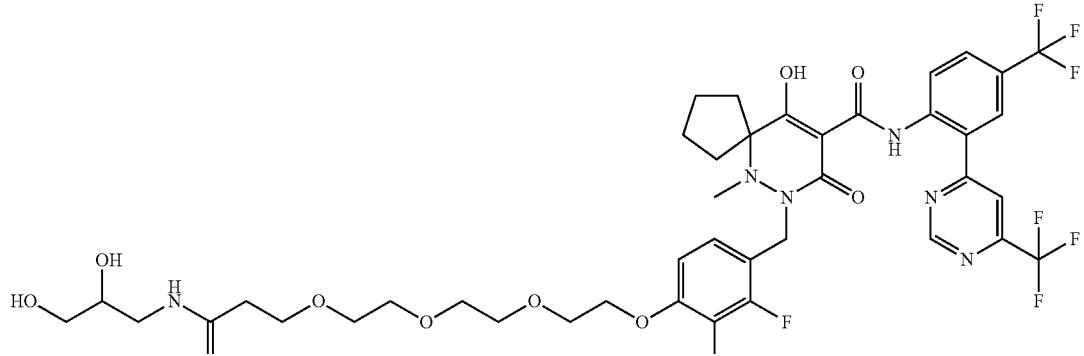 |

| Example No. | LCMS Analysis condition | Retention time (min) | m/z [M + H]$^+$ |
|---|---|---|---|
| 423 | SQD-FA05 | 1.02 | 1039 |
| 424 | SQD-FA05 | 1.06 | 935 |

Examples 425 and 426

The compounds described in the following Table were synthesized by carrying out Steps similar to those of Example 422 by using 2-[2-hydroxyethyl(methyl)amino]ethanol as a starting material.

TABLE 36
| Example No. | Structural formula |
|---|---|
| 425 | |
| 426 | |
| Example No. | LCMS Analysis condition | Retention time (min) | m/z [M + H]+ |
|---|---|---|---|
| 425 | SQD-FA05 | 0.77 | 1008 |
| 426 | SQD-FA05 | 0.78 | 904 |
Example 427
7-[[2,3-Difluoro-4-[2-[2-[[(2S,3R,4S,5S)-2,3,4,5,6-pentahydroxyhexanoyl]amino]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl-6,7-diazaspiro[4.5]dec-9-ene-9-carboxamide
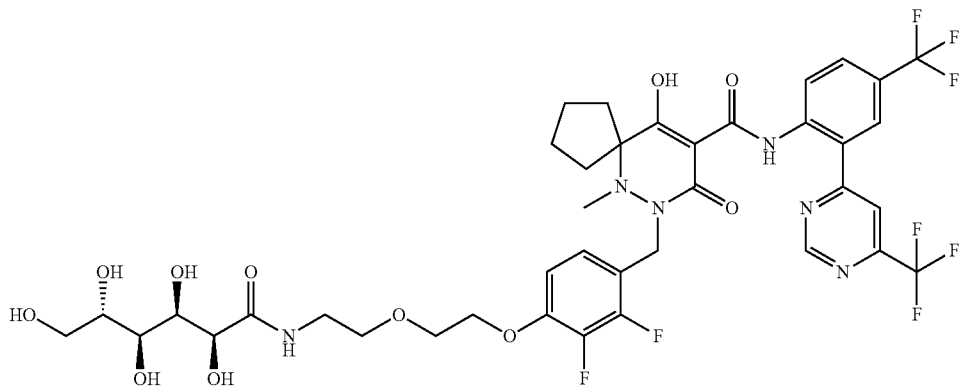 [SMILES: CN1N(Cc2ccc(OCCOCCNC(=O)[C@@H](O)[C@H](O)[C@@H](O)[C@@H](O)CO)c(F)c2F)C(=O)C(C(=O)Nc2ccc(C(F)(F)F)cc2-c2cc(C(F)(F)F)ncn2)=C(O)C12CCCC2]

First Step tert-Butyl N-[2-[2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethoxy]ethyl]carbamate

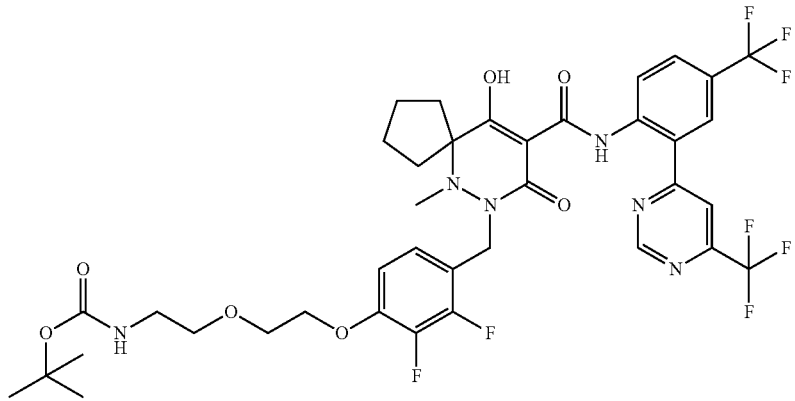 [SMILES: CN1N(Cc2ccc(OCCOCCNC(=O)OC(C)(C)C)c(F)c2F)C(=O)C(C(=O)Nc2ccc(C(F)(F)F)cc2-c2cc(C(F)(F)F)ncn2)=C(O)C12CCCC2]

After tert-butyl N-[2-(2-hydroxyethoxy)ethyl]carbamate (28 mg, 0.137 mmol), 7-[(2,3-difluoro-4-hydroxyphenyl)methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (30 mg, 0.046 mmol), and TMAD (15.7 mg, 0.091 mmol) were dissolved in THF (1 mL), tributylphosphine (18.5 mg, 0.091 mmol) was added. After the mixture was stirred at room temperature for 5 hours, the resultant was concentrated, and the residue was purified by C18 reverse-phase column chromatography to obtain the title compound (28 mg, 74%) as a white amorphous solid.

LCMS: m/z 845[M+H]$^+$

HPLC retention time: 1.25 minutes (analysis condition SQD-FA05)

Second Step

7-[[4-[2-(2-Aminoethoxy)ethoxy]-2,3-difluorophenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

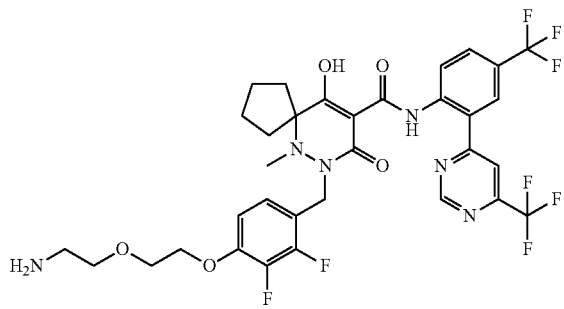 [SMILES: CN1N(Cc2ccc(OCCOCCN)c(F)c2F)C(=O)C(C(=O)Nc2ccc(C(F)(F)F)cc2-c2cc(C(F)(F)F)ncn2)=C(O)C12CCCC2]

tert-Butyl N-[2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethoxy]ethyl]carbamate (30 mg, 0.036 mmol) was dissolved in ethyl acetate (0.3 mL), then 4N—HCl ethyl acetate (1 mL) was added, and the mixture was stirred at room temperature for 15 hours. The reaction mixture was concentrated, and the resultant residue was used for the next reaction without purification.

LCMS: m/z 745[M+H]$^+$

HPLC retention time: 0.81 minutes (analysis condition SQD-FA05)

Third Step

7-[[4-[2-(2-Aminoethoxy)ethoxy]-2,3-difluorophenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (42 mg, 0.054 mmol) and (3R,4S,5S,6R)-3,4,5-trihydroxy-6-(hydroxymethyl)oxan-2-one (19.2 mg, 0.108 mmol) were dissolved in methanol (1 mL), and the resultant was stirred in a sealed tube at 70° C. for 20 hours. Water (0.1 mL) was added to the reaction mixture, and the resultant was purified by C18 reverse-phase column chromatography to obtain the title compound (30 mg, 61%) as a white amorphous solid.

LCMS: m/z 923[M+H]$^+$

HPLC retention time: 1.00 minute (analysis condition SQD-FA05)

Example 428

7-[[2,3-Difluoro-4-[2-[2-[2-[2-[[(2S,3R,4S,5S)-2,3,4,5,6-pentahydroxyhexanoyl]amino]ethoxy]ethoxy]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

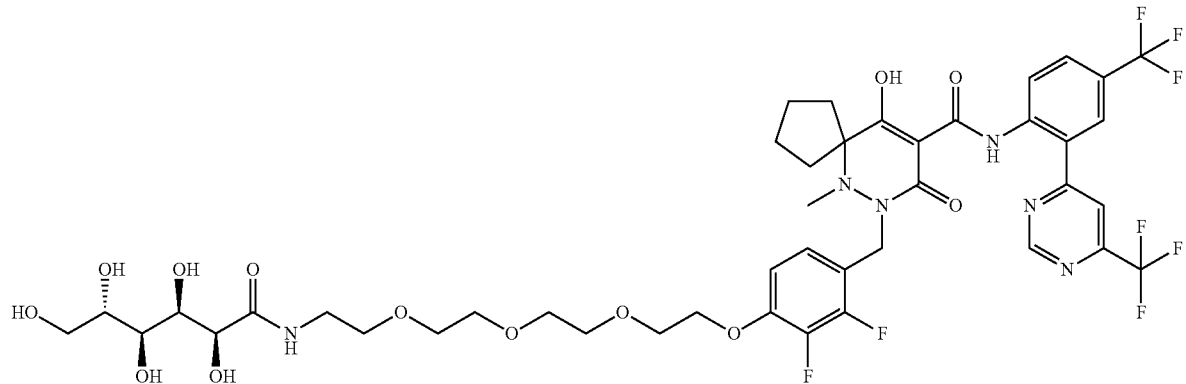 [SMILES: CN1N(Cc2ccc(OCCOCCOCCOCCNC(=O)[C@@H](O)[C@H](O)[C@@H](O)[C@@H](O)CO)c(F)c2F)C(=O)C(C(=O)Nc2ccc(C(F)(F)F)cc2-c2cc(C(F)(F)F)ncn2)=C(O)C12CCCC2]

The title compound was synthesized by carrying out Steps similar to those of Example 427 by using tert-butyl N-[2-[2-[2-(2-hydroxyethoxy)ethoxy]ethoxy]ethyl]carbamate as a starting material.

LCMS: m/z 1011[M+H]$^+$

HPLC retention time: 1.01 minutes (analysis condition SQD-FA05)

Example 429

7-[[2,3-Difluoro-4-[2-[2-[2-methoxyethyl(methyl)amino]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

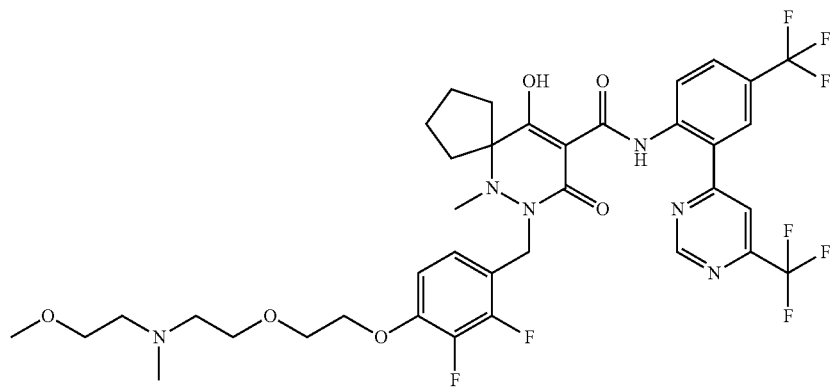 [SMILES: COCCN(C)CCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F]

First Step

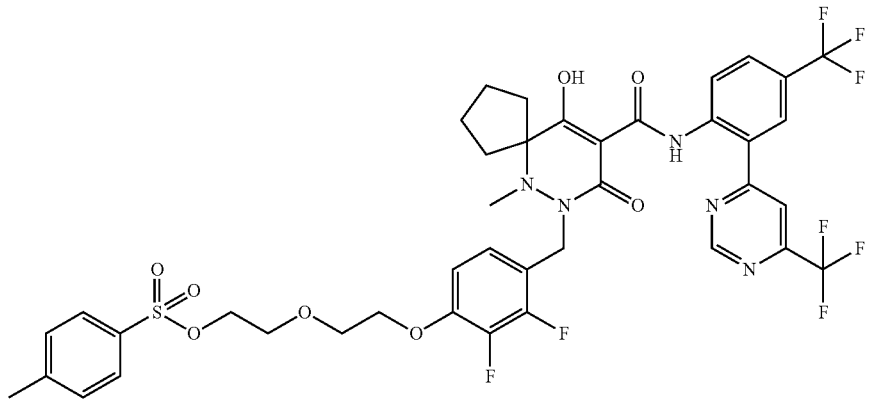 [SMILES: Cc1ccc(S(=O)(=O)OCCOCCOc2ccc(CN3C(=O)C(C(=O)Nc4ccc(C(F)(F)F)cc4-c4cc(C(F)(F)F)ncn4)=C(O)C4(CCCC4)N3C)c(F)c2F)cc1]

2-[2-(4-Methylphenyl)sulfonyloxyethoxy]ethyl 4-methylbenzenesulfonate (79 mg, 0.192 mmol) and cesium carbonate (15.6 mg, 0.048 mmol) were added to a solution of 7-[(2,3-difluoro-4-hydroxyphenyl)methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (Second Step of Example 332) (31.5 mg, 0.048 mmol) in acetonitrile (1 mL), and the mixture was stirred at 50° C. for 4 hours. After the reaction was completed, the reaction mixture was neutralized with formic acid, and the reaction mixture was purified by C18 reverse-phase column chromatography to obtain 2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethoxy]ethyl 4-methylbenzenesulfonate (35.9 mg, 83%).

LCMS: m/z 900[M+H]$^+$

HPLC retention time: 1.73 minutes (analysis condition SMD-TFA05)

Second Step

2-Methoxy-N-methyl ethanamine (0.043 mL, 0.399 mmol) was added to a solution of 2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethoxy]ethyl 4-methylbenzenesulfonate (35.9 mg, 0.04 mmol) in acetonitrile (0.6 mL), and the mixture was stirred at 50° C. for 6 hours. After the reaction was completed, the reaction mixture was purified by C18 reverse-phase column chromatography to obtain the title compound (22.3 mg, 68%).

LCMS: m/z 817[M+H]$^+$

HPLC retention time: 1.43 minutes (analysis condition SMD-TFA05)

Examples 430 to 434

Appropriate alkylating agents and commercial amines were used to synthesize the compounds described in the following Table by carrying out operations similar to those of Example 429.

TABLE 37

| Example No. | Structural formula |
|---|---|
| 430 | 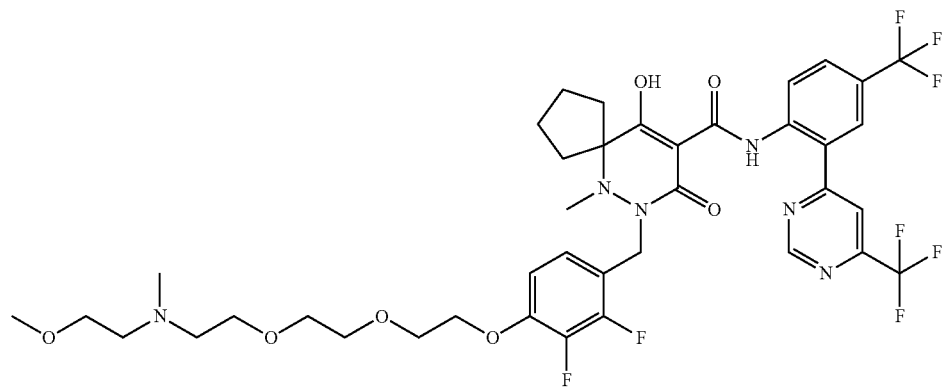 [SMILES: COCCN(C)CCOCCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F] |

TABLE 37-continued
431
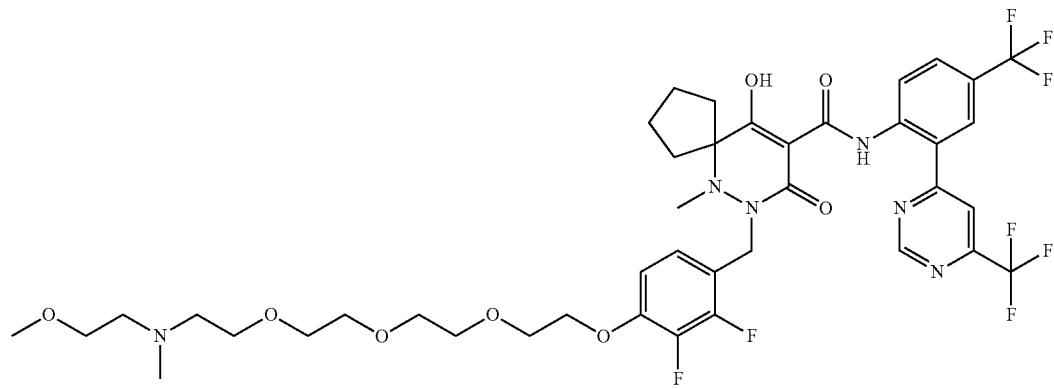 [SMILES: COCCN(C)CCOCCOCCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F]
432
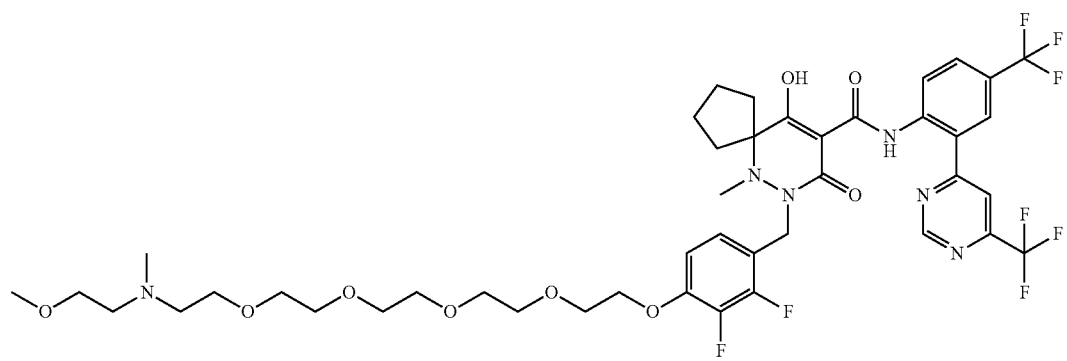 [SMILES: COCCN(C)CCOCCOCCOCCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F]
433
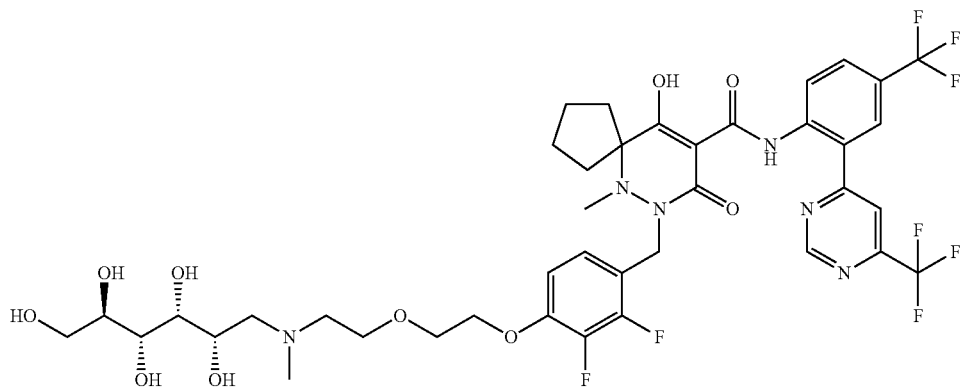 [SMILES: CN(CCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F)C[C@H](O)[C@@H](O)[C@H](O)[C@H](O)CO]
434
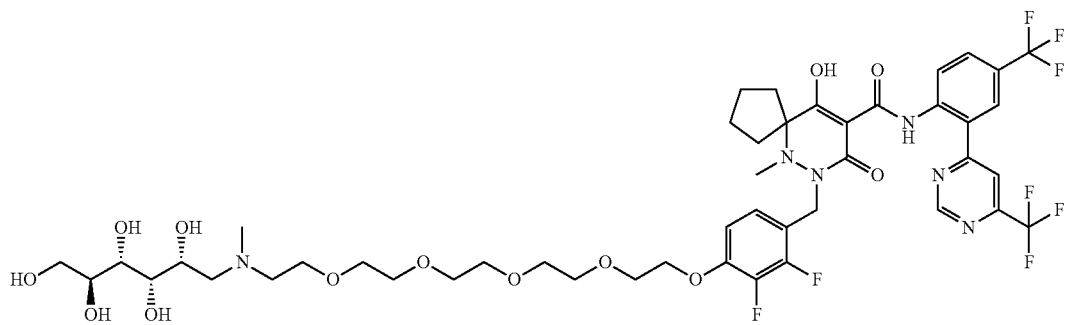 [SMILES: CN(CCOCCOCCOCCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F)C[C@@H](O)[C@H](O)[C@@H](O)[C@@H](O)CO]
| Example No. | LCMS Analysis condition | Retention time (min) | m/z [M + H]+ |
|---|---|---|---|
| 430 | SMD-TFA05 | 1.45 | 861 |
| 431 | SMD-TFA05 | 1.46 | 905 |

| | | | |
|---|---|---|---|
| 432 | SMD-TFA05 | 1.46 | 949 |
| 433 | SQD-FA05 | 0.79 | 923 |
| 434 | SQD-FA05 | 0.81 | 1055 |

Example 435

2-[2-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-methyl]phenoxy]ethylamino]ethanesulfonic acid

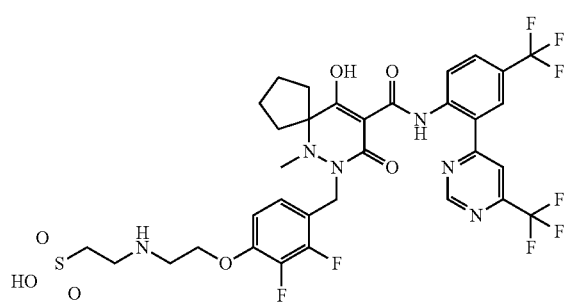

7-[[4-(2-Bromoethoxy)-2,3-difluorophenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (20 mg, 26.0 μmol) (Reference Example 109) was dissolved in N,N-dimethyl formamide (200 μL), then potassium phosphate (27.8 mg, 0.13 mmol) and tetrabutylammonium iodide (1.0 mg, 2.6 μmol) were added, and the mixture was stirred at 80° C. for 3 hours. After the reaction mixture was diluted with formic acid and water and filtered, the resultant was purified by HPLC to obtain the title compound (8.0 mg, 38%).

Purification condition: HPLC

Mobile phase: MeCN/water (0.1% formic acid)

Column: YMC-Actus Triart C18 (50×30 mm I.D., S-5 μm, 12 nm)

LCMS: m/z 809.1[M+H]⁺

HPLC retention time: 1.32 minutes (analysis condition SMD-TFA05)

Example 436

2-[2-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino ethanesulfonic acid

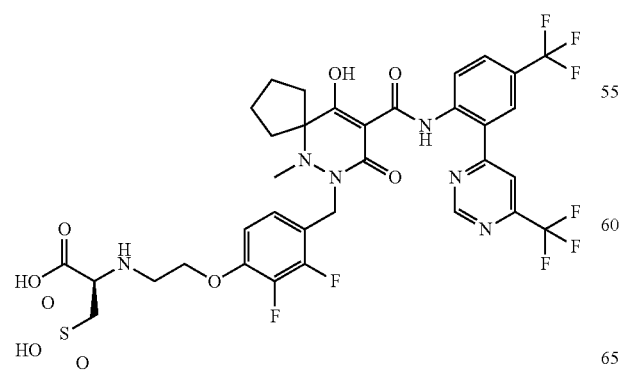

First Step (2R)-2-[2-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]-3-methoxy-3-oxopropane-1-sulfonic acid

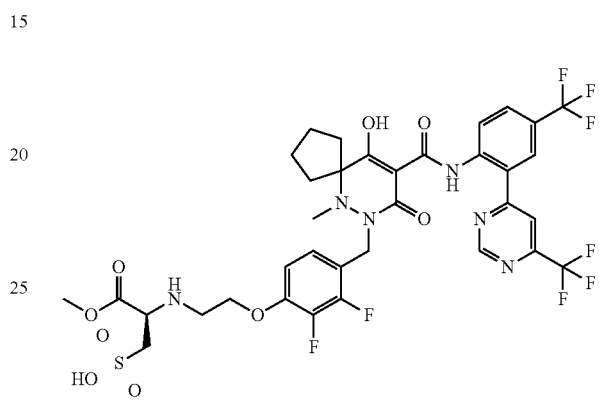

(2R)-2-[2-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]-3-methoxy-3-oxopropane-1-sulfonic acid was synthesized from 7-[[4-(2-bromoethoxy)-2,3-difluorophenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (Reference Example 109) and (R)-2-amino-3-methoxy-3-oxopropane-1-sulfonic acid hydrochloride in a manner similar to that of Example 381.

LCMS: m/z 867.0[M+H]⁺

HPLC retention time: 1.37 minutes (analysis condition SMD-TFA05)

Second Step

The title compound was synthesized from (2R)-2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]-3-methoxy-3-oxopropane-1-sulfonic acid in a manner similar to that of Reference Example 381.

LCMS: m/z 853.0[M+H]⁺

HPLC retention time: 1.31 minutes (analysis condition SMD-TFA05)

Reference Example 110

2-Chloro-N-(2-methoxyethyl)-N-methylethanamine hydrochloride

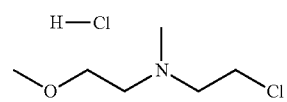

First Step

2-Methoxy-N-methylethanamine (17.0 g, 191 mmol) was dissolved in toluene (381 mL), then 2-bromoethanol (13.6 mL, 191 mmol) and triethylamine (26.6 mL, 191 mmol) were added, and the mixture was stirred at 100° C. for 2 hours. The reaction mixture was dried over magnesium sulfate, and the resultant was filtered and concentrated at reduced pressure to obtain 2-((2-methoxyethyl)(methyl)amino)ethanol (16.5 g) as a crude product.

Second Step 2-((2-Methoxyethyl)(methyl)amino)ethanol (16.4 g, 124 mmol) was dissolved in ethyl acetate (124 mL), then thionyl chloride (13.4 mL, 186 mmol) was added at 0° C., and the mixture was stirred at room temperature for 30 minutes. The reaction mixture was concentrated at reduced pressure to obtain the title compound (20.5 g, 88%).

$^1$H-NMR (DMSO-D$_6$) δ: 10.36 (1H, brs), 4.00 (2H, t, J=6.8 Hz), 3.70 (2H, t, J=4.9 Hz), 3.51-3.43 (4H, m), 3.30 (3H, s), 2.81 (3H, s).

Example 437

7-[[2,3-Difluoro-5-iodo-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

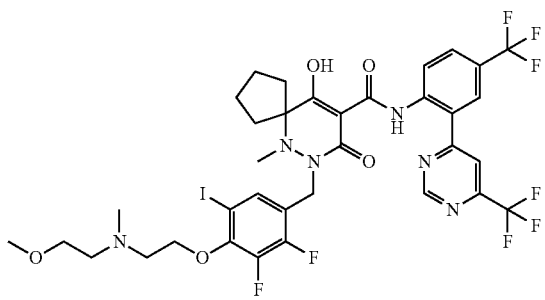 [SMILES: COCCN(C)CCOc1c(I)cc(CN2C(=O)C(C(=O)Nc3ccc(C(F)(F)F)cc3-c3cc(C(F)(F)F)ncn3)=C(O)C3(CCCC3)N2C)c(F)c1F]

First Step

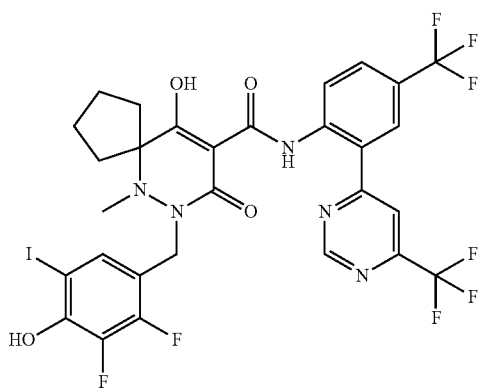 [SMILES: CN1N(Cc2cc(I)c(O)c(F)c2F)C(=O)C(C(=O)Nc2ccc(C(F)(F)F)cc2-c2cc(C(F)(F)F)ncn2)=C(O)C12CCCC2]

6-[(2,3-Difluoro-4-hydroxyphenyl)methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide (Reference Example 107) (500 mg, 0.76 mmol) was dissolved in N,N-dimethyl formamide (2.54 mL), then N-iodosuccinimide (222 mg, 0.99 mmol) was added, and the mixture was stirred under nitrogen atmosphere at room temperature for 2 hours. Methanol was added to the reaction mixture, and the mixture was purified by C18 reverse-phase column chromatography (acetonitrile/water) to obtain 7-[(2,3-difluoro-4-hydroxy-5-iodophenyl)methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (569 mg, 96%).

LCMS: m/z 784.1[M+H]$^+$

HPLC retention time: 1.67 minutes (analysis condition SMD-TFA05)

Second Step

7-[(2,3-Difluoro-4-hydroxy-5-iodophenyl)methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (341 mg, 0.43 mmol), 2-chloro-N-(2-methoxyethyl)-N-methylethanamine hydrochloride (82.0 mg, 0.43 mmol), cesium carbonate (425 mg, 1.31 mmol), tetrabutylammonium iodide (16.1 mg, 44.0 μmol), and methanol (17.7 μL) were dissolved in acetonitrile (4.35 mL), and the mixture was stirred under nitrogen atmosphere at 65° C. for 1.5 hours. An aqueous formic acid solution was added to the reaction mixture, and the resultant was purified by C18 reverse-phase column chromatography (acetonitrile/water) to obtain the title compound (341 mg, 87%).

LCMS: m/z 899.2[M+H]$^+$

HPLC retention time: 1.46 minutes (analysis condition SMD-TFA05)

Example 438

7-[[2,3-Difluoro-4-[2-[2-methoxyethyl(methyl)amino]ethoxy]-5-[3-methoxypropyl(methyl)carbamoyl]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

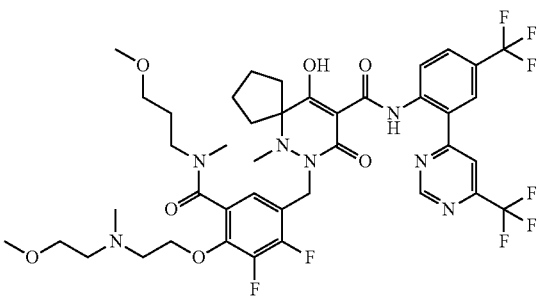 [SMILES: COCCCN(C)C(=O)c1cc(CN2C(=O)C(C(=O)Nc3ccc(C(F)(F)F)cc3-c3cc(C(F)(F)F)ncn3)=C(O)C3(CCCC3)N2C)c(F)c(F)c1OCCN(C)CCOC]

First Step

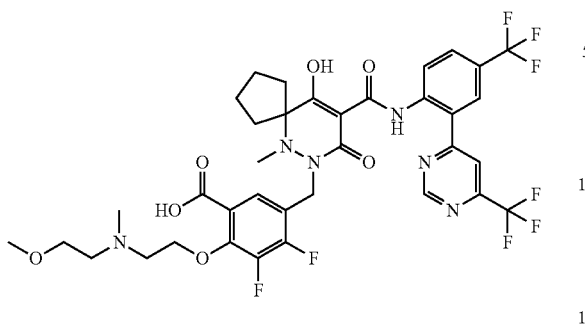

7-[[2,3-Difluoro-5-iodo-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (140 mg, 156 μmol), a tris(dibenzylideneacetone)dipalladium chloroform complex (16.1 mg, 16.0 μmol), xantphos (9.0 mg, 16.0 μmol), lithium chloride (39.6 mg, 0.94 mmol), lithium formate (40.5 mg, 0.78 mmol), and potassium trimethylsilanolate (60.0 mg, 0.47 mmol) were dissolved in N,N-dimethyl formamide (1.04 mL), then acetic anhydride (58.5 μL, 0.62 mmol) was added, and the mixture was stirred under nitrogen atmosphere at 85° C. for 30 minutes. N,N-dimethyl formamide and methanol were added to the reaction mixture, and the resultant was purified by C18 reverse-phase column chromatography (acetonitrile/water) to obtain 3,4-difluoro-5-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]-2-[2-[2-methoxyethyl(methyl)amino]ethoxy]benzoate (98.4 mg, 77%).

LCMS: m/z 817.3[M+H]$^+$

HPLC retention time: 1.41 minutes (analysis condition SMD-TFA05)

Second Step 3,4-Difluoro-5-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]-2-[2-[2-methoxyethyl(methyl)amino]ethoxy]benzoate (15.0 mg, 18.0 μmol), 3-methoxy-N-methylpropan-1-amine (3.79 mg, 37.0 μmol), 2-(3H-[1,2,3]triazolo[4,5-b]pyridin-3-yl)-1,1,3,3-tetramethylisouronium hexafluorophosphate (10.5 mg, 28.0 μmol), and N-ethyl-N-isopropylpropan-2-amine (9.6 μL, 55.0 μmol) were dissolved in N,N-dimethyl formamide (100 μL), and the mixture was stirred under nitrogen atmosphere at 40° C. for 2 hours. An aqueous formic acid solution was added to the reaction mixture, and the resultant was purified by HPLC to obtain the title compound (8.0 mg, 38%).

Purification condition: HPLC

Mobile phase: MeCN/water (0.1% formic acid)

Column: YMC-Actus Triart C18 (50×30 mm I.D., S-5 μm, 12 nm)

LCMS: m/z 902.1 [M+H]$^+$

HPLC retention time: 1.17 minutes (analysis condition SMD-FA05)

Reference Example 111

5-(2-Methoxyethoxy)-2-[5-methyl-6-(trifluoromethyl)pyrimidin-4-yl]-4-(trifluoromethyl)aniline

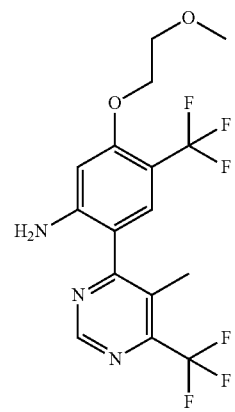 [SMILES: COCCOc1cc(N)c(-c2ncnc(C(F)(F)F)c2C)cc1C(F)(F)F]

First Step

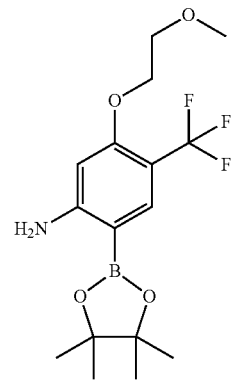 [SMILES: COCCOc1cc(N)c(B2OC(C)(C)C(C)(C)O2)cc1C(F)(F)F]

2-Iodo-5-(2-methoxyethoxy)-4-(trifluoromethyl)aniline (1.30 g, 3.60 mmol) (Reference Example 13), 4,4,4',4',5,5,5',5'-octamethyl-2,2'-bi(1,3,2-dioxaborolane) (2.74 g, 10.8 mmol), dicyclohexyl(2',4',6'-triisopropyl-[1,1'-biphenyl]-2-yl)phosphine (172 mg, 0.36 mmol), potassium acetate (1.06 g, 10.8 mmol), and palladium acetate (40.0 mg, 0.18 mmol) were dissolved in dioxane (12.0 mL), and the mixture was stirred under nitrogen atmosphere at 110° C. for 4 hours. Ethyl acetate was added to the reaction mixture, the mixture was filtered, the resultant was concentrated at reduced pressure, and the resultant residue was purified by C18 reverse-phase column chromatography (acetonitrile/water) to obtain 5-(2-methoxyethoxy)-2-(4,4,5,5-tetramethyl-1,3,2-dioxaborolan-2-yl)-4-(trifluoromethyl)aniline (183 mg, 14%).

LCMS: m/z 362.3[M+H]$^+$

HPLC retention time: 0.99 minutes (analysis condition SQD-FA05)

Second Step 5-(2-Methoxyethoxy)-2-(4,4,5,5-tetramethyl-1,3,2-dioxaborolan-2-yl)-4-(trifluoromethyl)aniline (183 mg, 0.51 mmol), 4-chloro-5-methyl-6-(trifluoromethyl)pyrimidine (Reference Example 91) (199 mg, 1.01 mmol), a 1,1'-bis(diphenylphosphino)ferrocene-palladium (II) dichloride-dichloromethane complex (41.7 mg, 51.0 µmol), and potassium carbonate (210 mg, 1.52 mol) were dissolved in dioxane (2.94 mL) and water (0.44 mL), and the mixture was stirred under nitrogen atmosphere at 90° C. for 1 hour. Water was added to the reaction mixture, and the resultant was extracted with ethyl acetate. The organic layer was washed with water and a brine, the aqueous layer was separated by a phase separator, the resultant was concentrated at reduced pressure, and the resultant residue was purified by column chromatography on silica gel (hexane/ethyl acetate) to obtain the title compound (180 mg, 90%).

LCMS: m/z 396.1[M+H]$^+$

HPLC retention time: 1.24 minutes (analysis condition SMD-TFA05)

Reference Example 112

7-[[2,3-Difluoro-4-[2-[2-methoxyethyl(methyl)amino]ethoxy]phenyl]methyl]-10-hydroxy-6-methyl-8-oxo-6,7-diazaspiro[4.5]dec-9-ene-9-carboxylic acid 2-methylpropyl ester

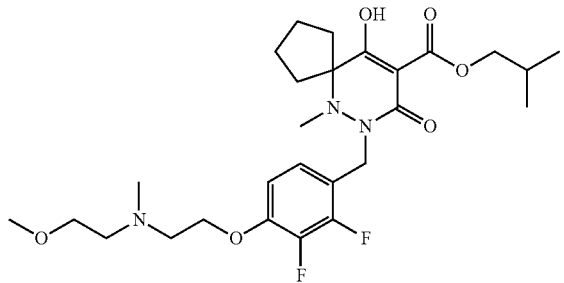 [SMILES: COCCN(C)CCOc1ccc(CN2C(=O)C(C(=O)OCC(C)C)=C(O)C3(CCCC3)N2C)c(F)c1F]

Methyl 1-[[[(E)-[2,3-difluoro-4-[2-[2-methoxyethyl(methyl)amino]ethoxy]phenyl]methylideneamino]-methylamino]cyclopentane-1-carboxylate hydrochloride (Reference Example 105) was used, and operations similar to those of Fourth Step of Example 237 were carried out to synthesize the title compound.

LCMS: m/z 540.2[M+H]$^+$

HPLC retention time: 1.11 minutes (analysis condition SMD-TFA05)

Example 439

7-[[2,3-Difluoro-4-[2-[2-methoxyethyl(methyl)amino]ethoxy]phenyl]methyl]-10-hydroxy-N-[5-(2-methoxyethoxy)-2-[5-methyl-6-(trifluoromethyl)pyrimidin-4-yl]-4-(trifluoromethyl)phenyl]-6-methyl-8-oxo-6,7-diazaspiro[4.5]dec-9-ene-9-carboxamide

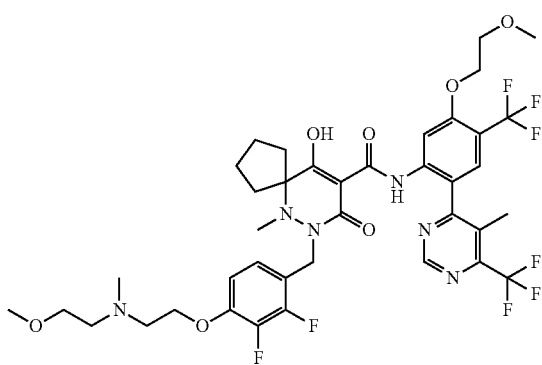

7-[[2,3-Difluoro-4-[2-[2-methoxyethyl(methyl)amino]ethoxy]phenyl]methyl]-10-hydroxy-6-methyl-8-oxo-6,7-diazaspiro[4.5]dec-9-ene-9-carboxylic acid 2-methylpropyl ester and 5-(2-methoxyethoxy)-2-[5-methyl-6-(trifluoromethyl)pyrimidin-4-yl]-4-(trifluoromethyl)aniline were used, and operations similar to those of Fifth Step of Example 237 were carried out to synthesize the title compound.

LCMS: m/z 861.4[M+H]$^+$

HPLC retention time: 1.40 minutes (analysis condition SMD-TFA05)

Example 440

9-[[2,3-Difluoro-4-[2-[2-methoxyethyl(methyl)amino]ethoxy]-5-(3-pyridinyl)phenyl]methyl]-6-hydroxy-10-methyl-8-oxo-N-[4-(trifluoromethyl)-2-[6-(trifluoromethyl)pyrimidin-4-yl]phenyl]-9,10-diazaspiro[4.5]dec-6-ene-7-carboxamide

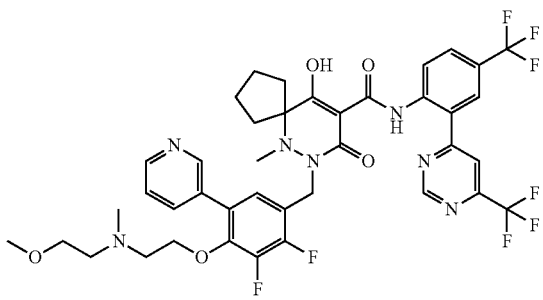 [SMILES: COCCN(C)CCOc1c(-c2cccnc2)cc(CN2C(=O)C(C(=O)Nc3ccc(C(F)(F)F)cc3-c3cc(C(F)(F)F)ncn3)=C(O)C3(CCCC3)N2C)c(F)c1F]

7-[[2,3-Difluoro-5-iodo-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide (10 mg, 11.0 µmol) (Example 437) was dissolved in 1,2-dimethoxyethane (80 µL), ethanol (80 µL), and water (80 µL), then 3-pyridinyl borate (2.1 mg, 17.0 µmol), tetrakis(triphenylphosphine)palladium (3.9 mg, 3.3 µmol), and sodium carbonate (3.9 mg, 33 µmol) were added, and the mixture was stirred at 80° C. for 16 hours. After the reaction mixture was diluted with formic acid and water and filtered, the resultant was purified by HPLC to obtain the title compound (2.3 mg, 24%).

Purification condition: HPLC

Mobile phase: MeCN/water (0.1% formic acid)

Column: YMC-Actus Triart C18 (50×30 mml.D., S-5 m, 12 nm)

LCMS: m/z 850[M+H]$^+$

HPLC retention time: 1.26 minutes (analysis condition SMD-TFA05)

Example 441

7-[[2,3-Difluoro-4-[2-[2-[2-[2-[2-[methyl-[(2S,3R,4R,5R)-2,3,4,5,6-pentahydroxyhexyl]amino]-2-oxoethoxy]ethoxy]ethoxy]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide

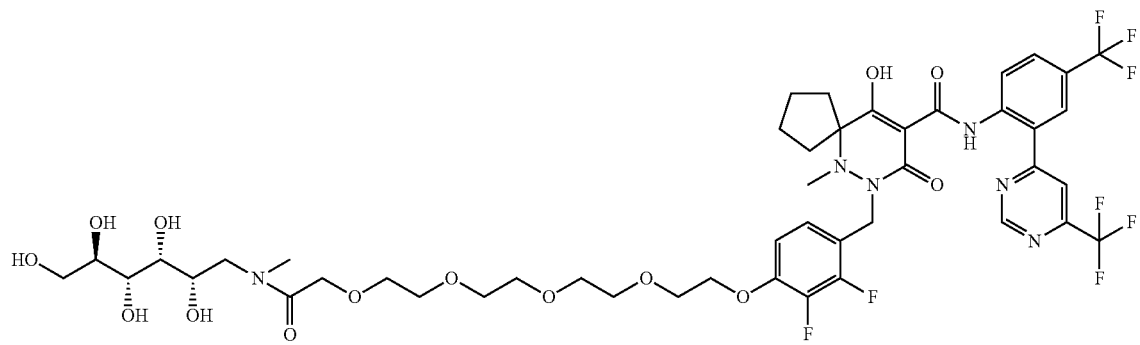 [SMILES: CN(C[C@H](O)[C@@H](O)[C@H](O)[C@H](O)CO)C(=O)COCCOCCOCCOCCOc1ccc(CN2C(=O)C(C(=O)Nc3ccc(C(F)(F)F)cc3-c3cc(C(F)(F)F)ncn3)=C(O)C3(CCCC3)N2C)c(F)c1F]

The title compound was synthesized by carrying out Steps and operations similar to those of Example 422 by using 2-[2-[2-[2-(2-hydroxyethoxy)ethoxy]ethoxy]ethoxy]ethanol and tert-butyl 2-bromoacetate as a starting material.

LCMS: m/z 1069[M+H]$^+$

HPLC retention time: 1.00 minute (analysis condition SQD-FA05)

Examples 442 to 445

The aniline compound of Example 417 and appropriate aldehydes or ketones were used, and the following operations were carried out to synthesize the compounds described in the following Table.

7-(2,3-Difluoro-4-((2-((2-methoxyethyl)(methyl)amino)ethyl)amino)benzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide and the corresponding aldehyde or ketone were dissolved in tetrahydrofuran, and 18 M sulfuric acid of an amount equivalent to one-fifth of the amount of tetrohydrofuran was added at 0° C. Subsequently, sodium tetrahydroborate was added in three batches, and the mixture was stirred at 0° C. or at room temperature for 3 hours and more. Triethylamine, water, and dimethylsulfoxide were added to the reaction mixture, and the resultant solution was purified by C18 reverse-phase column chromatography to synthesize the compounds of the Examples described in the following Table.

TABLE 38

| Example No. | Structural formula | LCMS analysis condition No. | Retention time (min) | m/z [M + H]$^+$ |
|---|---|---|---|---|
| 442 | | SQD-AA05 | 1.21 | 786 |

TABLE 38-continued

| Example No. | Structural formula | LCMS analysis condition No. | Retention time (min) | m/z [M + H]+ |
|---|---|---|---|---|
| 443 | 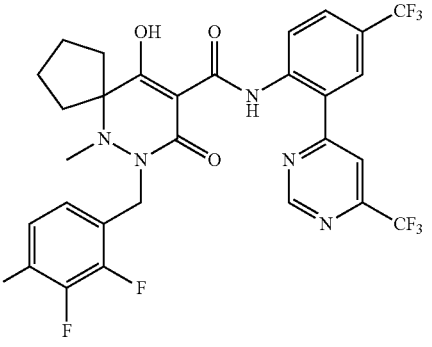 | SQD-AA05 | 1.22 | 800 |
| 444 | 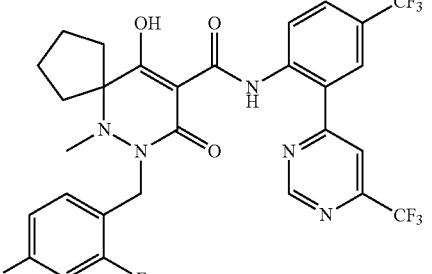 | SQD-AA05 | 1.24 | 814 |
| 445 | 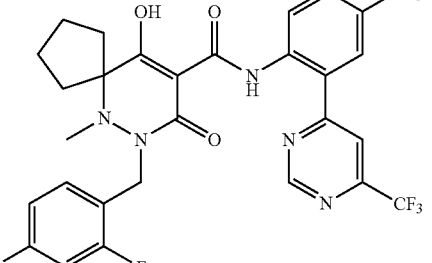 | SQD-AA05 | 1.23 | 814 |

Examples 446 and 447

The appropriate iodide derivative of Example 417, 3-morpholinopropan-1-amine, and 2-morpholinoethanamine were used, and operations similar to those of Example 417 were carried out to synthesize the compounds described in the following Table.

TABLE 39

| Example No. | Structural formula | LCMS analysis condition No. | Retention time (min) | m/z [M + H]+ |
|---|---|---|---|---|
| 446 | | SQD-AA50 | 0.88 | 784 |
| 447 | | SQD-AA50 | 0.87 | 770 |

Reference Example 113

Methyl 1-((methylamino)cyclopentanecarboxylate 4-toluenesulfonate

First Step

Methyl 1-((tert-butoxycarbonyl)amino)cyclopentane carboxylate

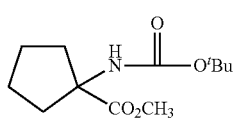

1-Aminocyclopentanecarboxylic acid hydrochloride (3.00 g, 18.1 mmol) was dissolved in methanol (18.0 mL), then thionyl chloride (1.32 mL, 18.1 mmol) was added at 0° C., and the mixture was stirred under nitrogen atmosphere at 50° C. for 3 hours. The reaction mixture was concentrated at reduced pressure, and water (6.00 mL) and triethylamine (7.55 mL, 54.3 mmol) were added to the resultant residue. Di-tert-butyl dicarbonate (3.95 g, 18.1 mmol) and tert-butyl methyl ester (24.0 mL) were added to this solution, and the mixture was stirred at 50° C. for 1 hour. The aqueous layer was separated, tetrahydrofuran (9.00 mL) was added to the organic layer, and the resultant was concentrated at reduced pressure. Tetrahydrofuran (15.0 mL) was added to the resultant residue, and the resultant was concentrated at reduced pressure to obtain the title compound as pale yellow oil.

$^1$H-NMR (DMSO-D6) δ: 7.28 (1H, brs), 3.58 (3H, s), 2.10-1.80 (4H, m), 1.67-1.55 (4H, m), 1.36 (9H, s).

Second Step

Methyl 1-((tert-butoxycarbonyl)methylamino)cyclopentanecarboxylate

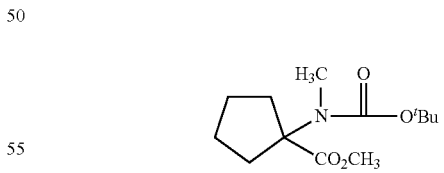

Methyl 1-((tert-butoxycarbonyl)amino)cyclopentanecarboxylate obtained in First Step was dissolved in 1-methyl 2-pyrrolidinone (24.0 mL), then sodium hydroxide (1.45 g, 36.2 mmol) and methyl iodide (3.38 mL, 54.3 mmol) were added, and the mixture was stirred at 50° C. for 7 hours. Water (30.0 mL) was added to this reaction mixture at room temperature, and the resultant was extracted with isopropyl acetate (15.0 mL) twice. The resultant organic layer was washed serially with a 10% aqueous sodium thiosulfate solution (15.0 mL) and a 10% aqueous sodium chloride solution (15.0 mL). The resultant organic layer was concentrated at reduced pressure to obtain the title compound (5.88 g, 83%).

$^1$H-NMR (DMSO-D$_6$) δ: 3.60 (3H, s), 2.87 (3H, s), 2.20-2.10 (2H, m), 1.96-1.87 (2H, m), 1.75-1.60 (4H, m), 1.34 (9H, s).

Third Step

Methyl 1-(methylamino)cyclopentanecarboxylate 4-toluenesulfonate

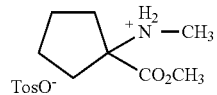

The title compound was synthesized from 1-((tert-butoxycarbonyl)amino)cyclopentanecarboxylic acid in a manner similar to that of Reference Examples 87 and 88.

Reference Example 114

2,3-Difluoro-4-[2-[2-methoxyethyl(methyl)amino]ethoxy]benzaldehyde hydrochloride

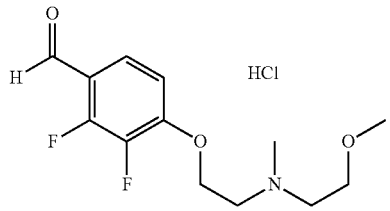 [SMILES: COCCN(C)CCOc1ccc(C=O)c(F)c1F ; Cl]

2,3-Difluoro-4-[2-[2-methoxyethyl(methyl)amino]ethoxy]benzaldehyde (200 mg, 0.73 mmol) was dissolved in 1 mL dimethoxyethane. Pyridine hydrochloride (85 mg, 0.73 mmol) was added, and the mixture was stirred. The generated crystal was filtered and dried at reduced pressure to obtain the title compound (68 mg, 30%).

$^1$H-NMR (DMSO-D$_6$) δ: 10.99 (1H, brs), 10.07 (1H, s), 7.73 (1H, m), 7.30 (1H, m), 4.67 (2H, t, J=4.9 Hz), 3.75 (2H, t, J=5.1 Hz), 3.30 (3H, s), 3.30-3.74 (4H, m), 2.87 (3H, brd, J=3.7 Hz).

Pharmacological Test

Test Example 1: Inhibitory Effect on $^{33}$PO$_4$ Uptake into Rat Small-Intestinal Brush Border Membrane Vesicles Brush border membrane vesicles (BBMVs) were prepared using the upper region of the small intestine of each Wistar female rat (4-5 weeks old). The preparation of BBMVs was performed according to the method of Murer et al. (Murer H, Hopfer U, Kinne R. Sodium/proton antiport in brush-border-membrane vesicles isolated from rat small intestine and kidney. 1976. J Am Soc Nephrol. 1998 January; 9 (1): 143-50). The $^{33}$PO$_4$ transport activity of the small-intestinal BBMVs was determined by the rapid filtration method. Each test compound was added at a final concentration of 1 µM to buffer A (110 mM NaCl, 60 mM mannitol, and 10 mM HEPES (pH 7.5)) containing 340 kBq/mL $^{33}$PO$_4$, or DMSO was added to buffer B (110 mM KCl, 60 mM mannitol, and 10 mM HEPES (pH 7.5)) containing 340 kBq/mL $^{33}$PO$_4$, and each resulting solution was added to the BBMVs sample and reacted for 60 seconds. Then, ice-cold buffer C (110 mM NaCl, 1 mM KH$_2$PO$_4$, and 10 mM HEPES (pH 7.5)) was added to each reaction mixture, which was immediately suction-filtered through a Millipore filter. The filter was washed with buffer C, and each sample was then dissolved in a liquid scintillator. The amount of $^{33}$PO$_4$ uptake into BBMVs was measured using a liquid scintillation counter. The rate of inhibition was determined according to the following expression:

Rate (%) of inhibition=(1−(Amount of $^{33}$PO$_4$ uptake into the test compound-supplemented and buffer A-treated BBMVs−Amount of $^{33}$PO$_4$ uptake into the DMSO-supplemented and buffer B-treated BBMVs)/(Amount of $^{33}$PO$_4$ uptake into the DMSO-supplemented and buffer A-treated BBMVs−Amount of $^{33}$PO$_4$ uptake into the DMSO-supplemented and buffer B-treated BBMVs))×100

The rate of inhibition of $^{33}$PO$_4$ uptake into the rat small-intestinal brush border membrane vesicles by 1 µM of the test compound (the rate of uptake inhibition) is shown in Tables 40-1 to 40-8.

TABLE 40-1

| Example No. | Rate of uptake inhibition (%) (1 µM) |
|---|---|
| 1 | 28 |
| 2 | 19 |
| 3 | 11 |
| 4 | 32 |
| 5 | 54 |
| 6 | 48 |
| 7 | 69 |
| 8 | 37 |
| 9 | 63 |
| 10 | 37 |
| 11 | 22 |
| 12 | 27 |
| 13 | 58 |
| 14 | 29 |
| 15 | 42 |
| 16 | 38 |
| 17 | 33 |
| 18 | 12 |
| 19 | 41 |
| 20 | 21 |
| 21 | 61 |
| 22 | 50 |
| 23 | 84 |
| 24 | 76 |
| 25 | 82 |
| 26 | 72 |
| 27 | 76 |
| 28 | 72 |
| 29 | 75 |
| 30 | 71 |
| 31 | 76 |
| 32 | 73 |
| 33 | 77 |
| 34 | 99 |
| 35 | 79 |
| 36 | 80 |
| 37 | 89 |
| 38 | 90 |
| 39 | 90 |
| 40 | 87 |
| 41 | 84 |
| 42 | 67 |
| 43 | 79 |
| 44 | 94 |
| 45 | 73 |
| 46 | 71 |
| 47 | 91 |
| 48 | 87 |
| 49 | 85 |

TABLE 40-1-continued

| Example No. | Rate of uptake inhibition (%) (1 μM) |
|---|---|
| 50 | 79 |
| 51 | 72 |
| 52 | 57 |
| 53 | 72 |
| 54 | 72 |
| 55 | 85 |
| 56 | 88 |
| 57 | 71 |
| 58 | 46 |
| 59 | 84 |
| 60 | 78 |
| 61 | 71 |
| 62 | 73 |

TABLE 40-2

| Example No. | Rate of uptake inhibition (%) (1 μM) |
|---|---|
| 63 | 72 |
| 64 | 77 |
| 65 | 98 |
| 66 | 96 |
| 67 | 91 |
| 68 | 84 |
| 69 | 74 |
| 70 | 79 |
| 71 | 97 |
| 72 | 92 |
| 73 | 74 |
| 74 | 82 |
| 75 | 74 |
| 76 | 77 |
| 77 | 80 |
| 78 | 71 |
| 79 | 71 |
| 80 | 75 |
| 81 | 74 |
| 82 | 100 |
| 83 | 90 |
| 84 | 91 |
| 85 | 71 |
| 86 | 83 |
| 87 | 84 |
| 88 | 39 |
| 89 | 67 |
| 90 | 91 |
| 91 | 87 |
| 92 | 81 |
| 93 | 56 |
| 94 | 73 |
| 95 | 80 |
| 96 | 83 |
| 97 | 89 |
| 98 | 53 |
| 99 | 82 |
| 100 | 69 |
| 101 | 57 |
| 102 | 65 |
| 103 | 78 |
| 104 | 73 |
| 105 | 72 |
| 106 | 79 |
| 107 | 54 |
| 108 | 54 |
| 109 | 52 |
| 110 | 57 |
| 111 | 56 |
| 112 | 43 |
| 113 | 84 |
| 114 | 86 |
| 115 | 85 |
| 116 | 72 |

TABLE 40-2-continued

| Example No. | Rate of uptake inhibition (%) (1 μM) |
|---|---|
| 117 | 78 |
| 118 | 81 |
| 119 | 71 |
| 120 | 66 |
| 121 | 72 |
| 122 | 82 |
| 123 | 87 |
| 124 | 81 |

TABLE 40-3

| Example No. | Rate of uptake inhibition (%) (1 μM) |
|---|---|
| 125 | 76 |
| 126 | 71 |
| 127 | 95 |
| 128 | 72 |
| 129 | 63 |
| 130 | 72 |
| 131 | 87 |
| 132 | 71 |
| 133 | 83 |
| 134 | 94 |
| 135 | 90 |
| 136 | 80 |
| 137 | 92 |
| 138 | 93 |
| 139 | 88 |
| 140 | 77 |
| 141 | 83 |
| 142 | 76 |
| 143 | 71 |
| 144 | 72 |
| 145 | 78 |
| 146 | 71 |
| 147 | 57 |
| 148 | 75 |
| 149 | 80 |
| 150 | 87 |
| 151 | 92 |
| 152 | 54 |
| 153 | 73 |
| 154 | 73 |
| 155 | 77 |
| 156 | 59 |
| 157 | 89 |
| 158 | 84 |
| 159 | 89 |
| 160 | 77 |
| 161 | 94 |
| 162 | 73 |
| 163 | 79 |
| 164 | 64 |
| 165 | 75 |
| 166 | 73 |
| 167 | 73 |
| 168 | 72 |
| 169 | 73 |
| 170 | 73 |
| 171 | 78 |
| 172 | 72 |
| 173 | 73 |
| 174 | 87 |
| 175 | 85 |
| 176 | 75 |
| 177 | 85 |
| 178 | 81 |
| 179 | 83 |
| 180 | 75 |
| 181 | 85 |
| 182 | 86 |

TABLE 40-3-continued

| Example No. | Rate of uptake inhibition (%) (1 μM) |
|---|---|
| 183 | 82 |
| 184 | 79 |
| 185 | 83 |
| 186 | 88 |

TABLE 40-4

| Example No. | Rate of uptake inhibition (%) (1 μM) |
|---|---|
| 187 | 80 |
| 188 | 93 |
| 189 | 73 |
| 190 | 84 |
| 191 | 87 |
| 192 | 88 |
| 193 | 82 |
| 194 | 80 |
| 195 | 76 |
| 196 | 90 |
| 197 | 82 |
| 198 | 75 |
| 199 | 79 |
| 200 | 80 |
| 201 | 77 |
| 202 | 75 |
| 203 | 91 |
| 204 | 87 |
| 205 | 86 |
| 206 | 76 |
| 207 | 73 |
| 208 | 90 |
| 209 | 76 |
| 210 | 71 |
| 211 | 72 |
| 212 | 98 |
| 213 | 79 |
| 214 | 91 |
| 215 | 86 |
| 216 | 76 |
| 217 | 83 |
| 218 | 82 |
| 219 | 95 |
| 220 | 96 |
| 221 | 82 |
| 222 | 97 |
| 223 | 77 |
| 224 | 74 |
| 225 | 76 |
| 226 | 71 |
| 227 | 82 |
| 228 | 77 |
| 229 | 73 |
| 230 | 75 |
| 231 | 80 |
| 232 | 79 |
| 233 | 75 |
| 234 | 73 |
| 235 | 65 |
| 236 | 60 |
| 237 | 51 |
| 238 | 47 |
| 239 | 48 |
| 240 | 72 |
| 241 | 86 |
| 242 | 69 |
| 243 | 63 |
| 244 | 71 |
| 245 | 40 |
| 246 | 52 |
| 247 | 51 |
| 248 | 45 |

TABLE 40-5

| Example No. | Rate of uptake inhibition (%) (1 μM) |
|---|---|
| 249 | 50 |
| 250 | 52 |
| 251 | 43 |
| 252 | 53 |
| 253 | 40 |
| 254 | 58 |
| 255 | 80 |
| 256 | 79 |
| 257 | 71 |
| 258 | 87 |
| 259 | 52 |
| 260 | 70 |
| 261 | 77 |
| 262 | 43 |
| 263 | 66 |
| 264 | 48 |
| 265 | 52 |
| 266 | 62 |
| 267 | 71 |
| 268 | 63 |
| 269 | 80 |
| 270 | 75 |
| 271 | 60 |
| 272 | 43 |
| 273 | 41 |
| 274 | 43 |
| 275 | 42 |
| 276 | 68 |
| 277 | 41 |
| 278 | 69 |
| 279 | 53 |
| 280 | 50 |
| 281 | 41 |
| 282 | 55 |
| 283 | 45 |
| 284 | 46 |
| 285 | 62 |
| 286 | 50 |
| 287 | 47 |
| 288 | 61 |
| 289 | 55 |
| 290 | 59 |
| 291 | 47 |
| 292 | 44 |
| 293 | 47 |
| 294 | 40 |
| 295 | 21 |
| 296 | 17 |
| 297 | 36 |
| 298 | 10 |
| 299 | 45 |
| 300 | 74 |
| 301 | 79 |
| 302 | 79 |
| 303 | 42 |
| 304 | 51 |
| 305 | 66 |
| 306 | 58 |
| 307 | 41 |
| 308 | 63 |
| 309 | 68 |
| 310 | 63 |

TABLE 40-6

| Example No. | Rate of uptake inhibition (%) (1 μM) |
|---|---|
| 311 | 65 |
| 312 | 74 |
| 313 | 65 |
| 314 | 72 |
| 315 | 63 |
| 316 | 64 |

TABLE 40-6-continued

| Example No. | Rate of uptake inhibition (%) (1 µM) |
|---|---|
| 317 | 57 |
| 318 | 43 |
| 332 | 3 |
| 333 | 29 |
| 334 | 22 |
| 335 | 30 |
| 336 | 44 |
| 337 | 47 |
| 338 | 66 |
| 339 | 66 |
| 340 | 63 |
| 341 | 64 |
| 342 | 43 |
| 343 | 68 |
| 344 | 58 |
| 345 | 73 |
| 346 | 42 |
| 347 | 28 |
| 348 | 31 |
| 349 | 55 |
| 350 | 45 |
| 351 | 22 |
| 352 | 27 |
| 353 | 26 |
| 354 | 31 |
| 355 | 36 |
| 356 | 58 |
| 357 | 45 |
| 358 | 34 |
| 359 | 37 |
| 360 | 21 |
| 361 | 20 |
| 362 | 17 |
| 363 | 11 |
| 364 | 36 |
| 365 | 34 |
| 366 | 38 |
| 367 | 43 |
| 368 | 26 |
| 369 | 43 |
| 370 | 41 |
| 371 | 38 |
| 372 | 38 |
| 373 | 27 |
| 374 | 42 |
| 375 | 31 |
| 376 | 33 |
| 377 | 29 |
| 378 | 35 |
| 379 | 37 |
| 380 | 43 |
| 381 | 28 |
| 382 | 21 |
| 383 | 26 |

TABLE 40-7

| Example No. | Rate of uptake inhibition (%) (1 µM) |
|---|---|
| 384 | 39 |
| 385 | 39 |
| 386 | 36 |
| 387 | 23 |
| 388 | 15 |
| 389 | 29 |
| 390 | 58 |
| 391 | 42 |
| 392 | 47 |
| 393 | 45 |
| 394 | 45 |
| 395 | 39 |
| 396 | 38 |
| 397 | 40 |

TABLE 40-7-continued

| Example No. | Rate of uptake inhibition (%) (1 µM) |
|---|---|
| 398 | 34 |
| 399 | 42 |
| 400 | 36 |
| 401 | 39 |
| 402 | 54 |
| 403 | 71 |
| 404 | 43 |
| 405 | 30 |
| 406 | 27 |
| 407 | 30 |
| 408 | 47 |
| 409 | 43 |
| 410 | 49 |
| 411 | 32 |
| 412 | 52 |
| 413 | 34 |
| 414 | 27 |
| 415 | 21 |
| 416 | 50 |
| 417 | 48 |
| 418 | 29 |
| 419 | 22 |
| 420 | 19 |
| 421 | 24 |
| 422 | 29 |
| 423 | 5 |
| 424 | 17 |
| 425 | 5 |
| 426 | 24 |
| 427 | 12 |
| 428 | 14 |
| 429 | 41 |
| 430 | 29 |
| 431 | 26 |
| 432 | 11 |
| 433 | 19 |
| 434 | 24 |
| 435 | 11 |
| 436 | 12 |
| 437 | 45 |
| 438 | 33 |
| 439 | 35 |
| 440 | 28 |
| 441 | 22 |
| 442 | 24 |
| 443 | 28 |

TABLE 40-8

| Example No. | Rate of uptake inhibition (%) (1 µM) |
|---|---|
| 444 | 24 |
| 445 | 29 |
| 446 | 31 |
| 447 | 50 |

Test Example 2: Inhibitory Effect on $PO_4$ Uptake into Human NaPi-IIb-Expressing Cell CHO cells were transfected with human NaPi-IIb expression plasmids, and a stably human NaPi-IIb-expressing cell line was obtained using G418. The human NaPi-IIb-expressing cells were inoculated to a 96-well plate and incubated overnight in a $CO_2$ incubator. The medium was replaced with buffer A (145 mM choline chloride, 3 mM KCl, 1 mM $CaCl_2$, 0.5 mM $MgCl_2$, 5 mM glucose, and 5 mM MES (pH 6.5)) and then replaced with buffer B (145 mM NaCl, 3 mM KCl, 1 mM $CaCl_2$, 0.5 mM $MgCl_2$, 5 mM glucose, and 5 mM MES (pH 6.5)) supplemented with each test compound at a final concentration of 1,3, 10, or 30 µM or buffer A supplemented with DMSO. After a given time, a 1/20 volume of buffer A containing $^{33}PO_4$ was added thereto and reacted at room temperature. After washing with ice-cold buffer A, a liquid scintillator was added to each reaction mixture, and the amount of $^{33}PO_4$ uptake was measured using TopCount. The rate of inhibition was determined according to the following expression:

Rate (%) of inhibition=(1−(Amount of $^{33}PO_4$ uptake in the test compound-supplemented and buffer $B$-treated well−Amount of $^{33}PO_4$ uptake in the DMSO-supplemented and buffer $A$-treated well)/(Amount of $^{33}PO_4$ uptake in the DMSO-supplemented and buffer $B$-treated well−Amount of $^{33}PO_4$ uptake in the DMSO-supplemented and buffer $A$-treated well))×100

$IC_{50}$ values (μM) were calculated from a straight line joining two points intersecting the 50% rate of inhibition. The $IC_{50}$ values of some compounds against $^{33}PO_4$ uptake into the human NaPi-IIb-expressing cells are shown in Tables 41-1 to 41-7.

TABLE 41-1

| Example No. | IC50 (μM) |
|---|---|
| 13 | 7.3 |
| 14 | 8.9 |
| 21 | 2.8 |
| 22 | 7.9 |
| 23 | 6.9 |
| 24 | 8.1 |
| 25 | 10.1 |
| 26 | 2.2 |
| 27 | 9.0 |
| 28 | 4.1 |
| 29 | 2.0 |
| 30 | 2.3 |
| 31 | 3.3 |
| 32 | 2.8 |
| 33 | 6.0 |
| 34 | 7.0 |
| 35 | 12.6 |
| 36 | 6.1 |
| 37 | 3.7 |
| 38 | 6.7 |
| 39 | 8.5 |
| 40 | 6.5 |
| 41 | 6.6 |
| 42 | 5.0 |
| 43 | 8.3 |
| 44 | 30.0 |
| 45 | 13.0 |
| 46 | 14.1 |
| 47 | 7.1 |
| 48 | 16.3 |
| 49 | 12.9 |
| 50 | 8.3 |
| 51 | 16.0 |
| 52 | 16.8 |
| 53 | 9.5 |
| 54 | 2.3 |
| 55 | 15.3 |
| 56 | 7.2 |
| 57 | 10.3 |
| 58 | 30.0 |
| 59 | 7.4 |
| 60 | 8.8 |
| 61 | 5.6 |
| 62 | 6.4 |
| 63 | 8.7 |
| 64 | 6.5 |
| 65 | 16.2 |
| 66 | 17.3 |
| 67 | 2.0 |
| 68 | 2.6 |
| 69 | 8.9 |
| 70 | 8.4 |
| 71 | 7.8 |
| 72 | 8.3 |

TABLE 41-1-continued

| Example No. | IC50 (μM) |
|---|---|
| 73 | 2.3 |
| 74 | 4.1 |
| 76 | 6.6 |
| 77 | 8.9 |
| 78 | 5.2 |
| 79 | 6.7 |
| 80 | 12.5 |
| 81 | 17.5 |
| 82 | 11.1 |
| 83 | 10.6 |

TABLE 41-2

| Example No. | IC50 (μM) |
|---|---|
| 84 | 7.9 |
| 85 | 6.2 |
| 86 | 5.3 |
| 87 | 8.3 |
| 89 | 4.8 |
| 90 | 2.4 |
| 91 | 15.7 |
| 92 | 20.2 |
| 93 | 17.4 |
| 94 | 8.8 |
| 95 | 5.4 |
| 96 | 2.8 |
| 97 | 2.7 |
| 98 | 10.6 |
| 99 | 4.3 |
| 100 | 6.7 |
| 101 | 9.4 |
| 102 | 10.9 |
| 103 | 11.0 |
| 104 | 10.8 |
| 105 | 6.3 |
| 106 | 12.0 |
| 107 | 25.9 |
| 108 | 26.1 |
| 109 | 9.4 |
| 110 | 19.8 |
| 111 | 20.0 |
| 112 | 30.0 |
| 113 | 15.5 |
| 114 | 7.9 |
| 115 | 6.9 |
| 116 | 8.1 |
| 117 | 9.5 |
| 118 | 9.1 |
| 119 | 9.2 |
| 120 | 20.5 |
| 121 | 16.0 |
| 122 | 8.6 |
| 123 | 14.8 |
| 124 | 2.5 |
| 125 | 1.3 |
| 126 | 5.5 |
| 127 | 17.6 |
| 128 | 12.0 |
| 129 | 13.7 |
| 130 | 8.9 |
| 131 | 15.3 |
| 132 | 5.0 |
| 133 | 13.1 |
| 134 | 19.7 |
| 135 | 12.3 |
| 136 | 17.6 |
| 137 | 19.7 |
| 138 | 11.9 |
| 139 | 17.0 |
| 140 | 16.2 |
| 141 | 7.8 |
| 142 | 17.6 |
| 143 | 6.7 |
| 144 | 2.1 |

TABLE 41-2-continued

| Example No. | IC50 (µM) |
|---|---|
| 145 | 7.1 |
| 146 | 10.2 |

TABLE 41-3

| Example No. | IC50 (µM) |
|---|---|
| 147 | 21.5 |
| 148 | 8.5 |
| 149 | 19.7 |
| 150 | 9.0 |
| 151 | 8.4 |
| 152 | 20.6 |
| 153 | 6.2 |
| 154 | 2.5 |
| 155 | 2.3 |
| 156 | 3.2 |
| 157 | 19.1 |
| 158 | 12.8 |
| 159 | 11.4 |
| 160 | 7.3 |
| 161 | 11.5 |
| 162 | 15.1 |
| 163 | 6.8 |
| 164 | 5.0 |
| 165 | 1.8 |
| 166 | 10.5 |
| 167 | 4.3 |
| 168 | 2.6 |
| 169 | 2.6 |
| 170 | 2.2 |
| 171 | 2.2 |
| 172 | 2.4 |
| 173 | 1.9 |
| 174 | 2.2 |
| 175 | 3.4 |
| 176 | 4.0 |
| 177 | 11.1 |
| 178 | 8.2 |
| 179 | 18.9 |
| 180 | 5.7 |
| 181 | 4.8 |
| 182 | 5.1 |
| 183 | 9.1 |
| 184 | 3.1 |
| 185 | 4.9 |
| 186 | 5.5 |
| 187 | 6.7 |
| 188 | 6.1 |
| 189 | 5.5 |
| 190 | 5.1 |
| 191 | 14.5 |
| 192 | 16.5 |
| 193 | 6.4 |
| 194 | 19.3 |
| 195 | 4.6 |
| 196 | 2.8 |
| 197 | 7.0 |
| 198 | 2.4 |
| 199 | 1.8 |
| 200 | 1.3 |
| 201 | 1.3 |
| 202 | 6.1 |
| 203 | 2.0 |
| 204 | 1.0 |
| 205 | 1.6 |
| 206 | 2.0 |
| 207 | 6.5 |
| 208 | 6.6 |

TABLE 41-4

| Example No. | IC50 (µM) |
|---|---|
| 209 | 4.8 |
| 210 | 1.7 |
| 211 | 5.7 |
| 212 | 2.9 |
| 213 | 6.4 |
| 214 | 7.0 |
| 215 | 6.2 |
| 216 | 8.0 |
| 217 | 4.7 |
| 218 | 7.2 |
| 219 | 4.2 |
| 220 | 12.2 |
| 221 | 6.6 |
| 222 | 17.6 |
| 223 | 17.9 |
| 224 | 7.2 |
| 225 | 5.1 |
| 226 | 3.1 |
| 227 | 3.7 |
| 228 | 5.7 |
| 229 | 1.5 |
| 230 | 2.1 |
| 231 | 5.6 |
| 232 | 4.2 |
| 233 | 2.3 |
| 234 | 9.4 |
| 235 | 4.8 |
| 236 | 24.7 |
| 237 | 12.8 |
| 238 | 8.5 |
| 239 | 8.5 |
| 240 | 9.1 |
| 241 | 16.5 |
| 242 | 7.8 |
| 243 | 7.4 |
| 244 | 7.3 |
| 245 | 7.7 |
| 246 | 8.6 |
| 247 | 8.2 |
| 248 | 17.6 |
| 249 | 9.8 |
| 250 | 17.9 |
| 251 | 7.6 |
| 252 | 9.5 |
| 253 | 4.4 |
| 254 | 9.7 |
| 255 | 9.8 |
| 256 | 4.4 |
| 257 | 6.0 |
| 258 | 2.7 |
| 259 | 10.0 |
| 260 | 6.4 |
| 261 | 7.7 |
| 262 | 9.9 |
| 263 | 3.0 |
| 264 | 19.4 |
| 265 | 13.3 |
| 266 | 11.6 |
| 267 | 7.5 |
| 268 | 7.4 |
| 269 | 4.5 |
| 270 | 14.6 |

TABLE 41-5

| Example No. | IC$_{50}$ (µM) |
|---|---|
| 271 | 17.3 |
| 272 | 19.5 |
| 273 | 13.2 |
| 274 | 17.0 |
| 275 | 16.8 |
| 276 | 15.8 |
| 277 | 17.8 |
| 278 | 6.6 |

TABLE 41-5-continued

| Example No. | IC$_{50}$ (µM) |
|---|---|
| 279 | 18.7 |
| 280 | 11.9 |
| 281 | 18.8 |
| 282 | 11.1 |
| 283 | 17.7 |
| 284 | 7.8 |
| 285 | 8.5 |
| 286 | 15.8 |
| 287 | 8.0 |
| 288 | 11.0 |
| 289 | 16.3 |
| 290 | 7.0 |
| 291 | 14.7 |
| 292 | 18.4 |
| 293 | 10.7 |
| 294 | 13.4 |
| 295 | 17.0 |
| 296 | 10.0 |
| 297 | 18.3 |
| 298 | >30 |
| 299 | 18.8 |
| 300 | 9.3 |
| 301 | 2.6 |
| 302 | 7.8 |
| 303 | 16.0 |
| 304 | 3.5 |
| 305 | 5.9 |
| 306 | 8.4 |
| 307 | 4.6 |
| 308 | 12.6 |
| 309 | 6.5 |
| 310 | 4.7 |
| 311 | 8.2 |
| 312 | 6.3 |
| 313 | 18.3 |
| 314 | 11.8 |
| 315 | 9.8 |
| 316 | 14.2 |
| 317 | 9.6 |
| 318 | 8.6 |
| 332 | 23.9 |
| 333 | 19.5 |
| 334 | 10.3 |
| 335 | 8.7 |
| 336 | 19.7 |
| 337 | 17.0 |
| 338 | 13.4 |
| 339 | 19.1 |
| 340 | 10.0 |
| 341 | 7.6 |
| 342 | 8.8 |
| 343 | 21.0 |
| 344 | 13.7 |
| 345 | 7.7 |
| 346 | 6.9 |
| 347 | 25.2 |

TABLE 41-6

| Example No. | IC$_{50}$ (µM) |
|---|---|
| 348 | 26.1 |
| 349 | 8.3 |
| 350 | 16.9 |
| 351 | 25.5 |
| 352 | 16.7 |
| 353 | 23.9 |
| 354 | 26.0 |
| 355 | 15.0 |
| 356 | 21.9 |
| 357 | 21.8 |
| 358 | 9.2 |
| 359 | 18.4 |
| 360 | 23.1 |
| 361 | 20.2 |

TABLE 41-6-continued

| Example No. | IC$_{50}$ (µM) |
|---|---|
| 362 | 18.8 |
| 363 | 28.0 |
| 364 | 20.9 |
| 365 | 12.2 |
| 366 | 16.3 |
| 367 | 14.0 |
| 368 | 14.7 |
| 369 | 21.8 |
| 370 | 18.2 |
| 371 | 8.5 |
| 372 | 16.3 |
| 373 | 23.5 |
| 374 | 16.4 |
| 375 | 17.8 |
| 376 | 21.4 |
| 377 | 8.7 |
| 378 | 18.0 |
| 379 | 27.3 |
| 380 | 20.2 |
| 381 | 22.0 |
| 382 | 21.0 |
| 383 | 20.9 |
| 384 | 11.0 |
| 385 | 6.2 |
| 386 | 18.9 |
| 387 | 10.7 |
| 388 | 6.9 |
| 389 | 24.6 |
| 390 | 7.8 |
| 391 | 7.0 |
| 392 | 15.8 |
| 393 | 8.1 |
| 394 | 6.7 |
| 395 | 15.2 |
| 396 | 9.5 |
| 397 | 8.6 |
| 398 | 9.9 |
| 399 | 7.8 |
| 400 | 9.2 |
| 401 | 14.5 |
| 402 | 12.8 |
| 403 | 6.3 |
| 404 | 10.1 |
| 405 | 27.7 |
| 406 | 23.1 |
| 407 | 6.9 |
| 408 | 14.6 |
| 409 | 10.5 |

TABLE 41-7

| Example No. | IC$_{50}$ (µM) |
|---|---|
| 410 | 8.4 |
| 411 | 12.8 |
| 412 | 19.0 |
| 413 | 11.3 |
| 414 | 4.6 |
| 415 | 18.5 |
| 416 | 5.8 |
| 417 | 2.2 |
| 418 | 10.9 |
| 419 | 24.8 |
| 420 | 18.6 |
| 421 | 19.5 |
| 423 | 20.0 |
| 424 | 29.0 |
| 425 | 28.1 |
| 426 | 26.1 |
| 427 | 17.4 |
| 428 | 23.0 |
| 429 | 7.7 |
| 430 | 4.6 |
| 431 | 6.2 |
| 432 | 6.3 |

TABLE 41-7-continued

| Example No. | IC$_{50}$ (μM) |
|---|---|
| 433 | 18.6 |
| 434 | 19.5 |
| 435 | 17.1 |
| 436 | 14.0 |
| 437 | 19.5 |
| 438 | 21.9 |
| 439 | 18.9 |
| 440 | 22.6 |
| 441 | 21.4 |
| 442 | 6.3 |
| 443 | 8.9 |
| 444 | 7.4 |
| 445 | 9.2 |
| 446 | 11.1 |
| 447 | 15.8 |

Test Example 3: Inhibitory Effect on $^{33}PO_4$ Uptake into Human PiT-1-Expressing Cell CHO cells were transfected with human PiT-1 expression plasmids or empty vectors to prepare human PiT-1-expressing cells and empty vector-expressing cells. The human PiT-1-expressing cells or the empty vector-expressing cells were inoculated to a 96-well plate and incubated overnight in a $CO_2$ incubator. The medium was replaced with buffer A (145 mM choline chloride, 3 mM KCl, 1 mM $CaCl_2$, 0.5 mM $MgCl_2$, 5 mM glucose, and 5 mM MES (pH 6.5)) and then replaced with buffer B (145 mM NaCl, 3 mM KCl, 1 mM $CaCl_2$, 0.5 mM $MgCl_2$, 5 mM glucose, and 5 mM MES (pH 6.5)) supplemented with each compound at a final concentration of 0.24, 1.2, 6, or 30 μM or buffer B supplemented with DMSO. After a given time, a 1/20 volume of buffer A containing $^{33}PO_4$ was added thereto and reacted at room temperature. After washing with ice-cold buffer A, a liquid scintillator was added to each reaction mixture, and the amount of $^{33}PO_4$ uptake was measured using TopCount. The rate of inhibition was determined according to the following expression:

Rate (%) of inhibition=(1−(Amount of $^{33}PO_4$ uptake in the compound-supplemented well containing the human PiT-1-expressing cells−Amount of $^{33}PO_4$ uptake in the compound-supplemented well containing the empty vector-expressing cells)/(Amount of $^{33}PO_4$ uptake in the DMSO-supplemented well containing the human PiT-1-expressing cells −Amount of $^{33}PO_4$ uptake in the DMSO-supplemented well containing the empty vector-expressing cells))×100

IC$_{50}$ values (μM) were calculated from a straight line joining two points intersecting the 50% rate of inhibition. The IC$_{50}$ values of some compounds against $^{33}PO_4$ uptake into the human PiT-1-expressing cells are shown in Table 42.

TABLE 42

| Example No. | IC$_{50}$ (μM) |
|---|---|
| 13 | 1.9 |
| 14 | 2.2 |
| 21 | 3.3 |
| 22 | 1.8 |
| 52 | 3.1 |
| 129 | 6.5 |
| 140 | 3.8 |
| 147 | 4.4 |
| 152 | 5.3 |
| 156 | 3.9 |
| 157 | 3.8 |
| 164 | 4.1 |
| 196 | 5.6 |

TABLE 42-continued

| Example No. | IC$_{50}$ (μM) |
|---|---|
| 264 | 4.6 |
| 265 | 4.6 |
| 267 | 4.1 |
| 269 | 7.9 |
| 270 | 3.4 |
| 317 | 3.3 |
| 318 | 3.3 |
| 333 | 3.6 |
| 345 | 1.2 |
| 410 | 2.9 |
| 414 | 1.9 |
| 416 | 0.9 |
| 418 | 4.1 |

Test Example 4: Inhibitory Effect on $^{33}PO_4$ Uptake into Human PiT-2-Expressing Cell CHO cells were transfected with human PiT-2 expression plasmids or empty vectors to prepare human PiT-2-expressing cells and empty vector-expressing cells. The human PiT-2-expressing cells or the empty vector-expressing cells were inoculated to a 96-well plate and incubated overnight in a $CO_2$ incubator. The medium was replaced with buffer A (145 mM choline chloride, 3 mM KCl, 1 mM $CaCl_2$, 0.5 mM $MgCl_2$, 5 mM glucose, and 5 mM MES (pH 6.5)) and then replaced with buffer B (145 mM NaCl, 3 mM KCl, 1 mM $CaCl_2$, 0.5 mM $MgCl_2$, 5 mM glucose, and 5 mM MES (pH 6.5)) supplemented with each compound at a final concentration of 0.24, 1.2, 6, or 30 M or buffer B supplemented with DMSO. After a given time, a 1/20 volume of buffer A containing $^{33}PO_4$ was added thereto and reacted at room temperature. After washing with ice-cold buffer A, a liquid scintillator was added to each reaction mixture, and the amount of $^{33}PO_4$ uptake was measured using TopCount. The rate of inhibition was determined according to the following expression:

Rate (%) of inhibition=(1−(Amount of $^{33}PO_4$ uptake in the compound-supplemented well containing the human PiT-2-expressing cells−Amount of $^{33}PO_4$ uptake in the compound-supplemented well containing the empty vector-expressing cells)/(Amount of $^{33}PO_4$ uptake in the DMSO-supplemented well containing the human PiT-2-expressing cells −Amount of $^{33}PO_4$ uptake in the DMSO-supplemented well containing the empty vector-expressing cells))×100

IC$_{50}$ values (μM) were calculated from a straight line joining two points intersecting the 50% rate of inhibition. The IC$_{50}$ values of some compounds against $^{33}PO_4$ uptake into the human PiT-2-expressing cells are shown in Table 43.

TABLE 43

| Example No. | IC$_{50}$ (μM) |
|---|---|
| 13 | 2.7 |
| 14 | 2.6 |
| 21 | 3.6 |
| 22 | 3.2 |
| 52 | 4.0 |
| 129 | 8.7 |
| 140 | 3.8 |
| 147 | 8.4 |
| 152 | 3.5 |
| 156 | 7.2 |
| 157 | 3.9 |
| 164 | 4.1 |
| 196 | 6.2 |
| 264 | 3.8 |
| 265 | 4.3 |

TABLE 43-continued

| Example No. | IC$_{50}$ (µM) |
|---|---|
| 267 | 4.7 |
| 269 | 10.6 |
| 270 | 3.6 |
| 317 | 2.9 |
| 318 | 3.7 |
| 333 | 10.4 |
| 345 | 1.4 |
| 410 | 3.3 |
| 414 | 1.2 |
| 416 | 1.4 |
| 418 | 4.6 |

Test Example 5: Suppressive Effect on Rise in Serum Phosphorus Concentration of Adenine-Induced Renal Failure Rat Adenine was forcedly administered orally to each Wistar male rat (7-8 weeks old) to impair renal functions and thereby prepare a hyperphosphatemia model (Katsumata K, Kusano K, Hirata M, Tsunemi K, Nagano N, Burke S K, Fukushima N. Sevelamer hydrochloride prevents ectopic calcification and renal osteodystrophy in chronic renal failure rats. Kidney Int. 2003 August; 64 (2): 441-50). Each test compound was mixed at a ratio of 0.1% of mass concentration with feed. The animal was fed with a given amount of the feed for 3 days. A group given feed non-supplemented with a test compound was used as a reference pathological group, and an adenine-unadministered group given feed non-supplemented with a test compound was used as a normal group. 3 days after the start of administration of the test compound, blood was collected from the jugular vein, and serum was collected. Serum phosphorus concentrations were measured by the Fiske-Subbarow method. The rate of suppression of a rise in serum phosphorus concentration was determined according to the following expression:

Rate (%) of suppression of a rise in serum phosphorus concentration=(1−[(Serum phosphorus concentration of the test compound-treated pathological group)−(Serum phosphorus concentration of the normal group)]/[(Serum phosphorus concentration of the reference pathological group)−(Serum phosphorus concentration of the normal group)])×100

As a result, each test compound was confirmed to have a suppressive effect on a rise in serum phosphorus concentration. Table 44 shows the rate (%) of suppression of a rise in serum phosphorus concentration by each test compound.

TABLE 44

| Example No. | Structural formula | Compound name | Rate of inhibition (%) |
|---|---|---|---|
| 13 | | 6-[[2,3-Difluoro-4-[2-[2-methoxyethyl(methyl)amino]ethoxy]phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide | 25% |
| 14 | | 7-[[2,3-Difluoro-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide | 39% |

TABLE 44-continued

| Example No. | Structural formula | Compound name | Rate of inhibition (%) |
|---|---|---|---|
| 21 | | (4aR)-1-[(2,3-Difluorophenyl)methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide | 24% |
| 22 | | (4aR)-N-[2-(6-Cyano-5-methylpyrimidin-4-yl)-4-(trifluoromethyl)phenyl]-1-[[2,3-difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxamide | 26% |
| 52 | | (4aR)-N-[2-(2-Cyanopyridin-4-yl)-4-(trifluoromethyl)phenyl]-1-[[2,3-difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxamide | 20% |

TABLE 44-continued

| Example No. | Structural formula | Compound name | Rate of inhibition (%) |
|---|---|---|---|
| 129 | | 6-[4-[[(4aR)-4-Hydroxy-4a-methyl-2-oxo-3-[[4-(trifluoromethyl)-2-[6-(trifluoromethyl)pyrimidin-4-yl]phenyl]carbamoyl]-6,7-dihydro-5H-pyrrolo[1,2-b]pyridazin-1-yl]methyl]-2,3-difluorophenyl]hex-5-ynoic acid | 17% |
| 140 | | (4aR)-1-[[2,3-Difluoro-4-(3-morpholin-4-ylprop-1-ynyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide | 39% |
| 147 | | (4aR)-1-[[4-[3-[(2R)-2,3-Dihydroxypropoxy]propoxy]-2,3-difluorophenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide | 35% |

TABLE 44-continued

| Example No. | Structural formula | Compound name | Rate of inhibition (%) |
|---|---|---|---|
| 152 | | (4aR)-1-[[4-[4-[(2R)-2,3-Dihydroxypropoxy]butoxy]-2,3-difluorophenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide | 26% |
| 156 | | (4aR)-1-[[4-[6-[(2R)-2,3-Dihydroxypropoxy]hexoxy]-2,3-difluorophenyl]methyl]-4-hydroxy-4a-methyl-2-oxo-N-[2-(trifluoromethyl)-4-[6-(trifluoromethyl)pyridin-3-yl]pyrimidin-5-yl]-6,7-dihydro-5H-pyrrolo[1,2-b]pyridazine-3-carboxamide | 21% |
| 157 | | (4aR)-1-[[2,3-Difluoro-4-(2-morpholin-4-ylethoxy)phenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide | 30% |

TABLE 44-continued

| Example No. | Structural formula | Compound name | Rate of inhibition (%) |
|---|---|---|---|
| 164 | | (4aR)-1-[[2,3-Difluoro-4-(morpholin-4-ylmethyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide; hydrochloride | 14% |
| 196 | | (4aR)-N-(4-Bromo-3,5-difluorophenyl)-1-[(3-chloro-2-fluorophenyl)methyl]-4-hydroxy-4a-methyl-2-oxo-6,7-dihydro-5H-pyrrolo[1,2-b]pyridazine-3-carboxamide | 35% |
| 264 | | (3S)-3-tert-Butyl-1-[[2,3-difluoro-4-(2-morpholin-4-ylethoxy)phenyl]methyl]-4-hydroxy-2-methyl-6-oxo-N-[4-(trifluoromethyl)-2-[6-(trifluoromethyl)pyrimidin-4-yl]phenyl]-3H-pyridazine-5-carboxamide | 15% |

TABLE 44-continued

| Example No. | Structural formula | Compound name | Rate of inhibition (%) |
|---|---|---|---|
| 265 | | (3S)-3-tert-Butyl-N-[4-chloro-2-[6-(trifluoromethyl)pyrimidin-4-yl]phenyl]-1-[[2,3-difluoro-4-(2-morpholin-4-ylethoxy)phenyl]methyl]-4-hydroxy-2-methyl-6-oxo-3H-pyridazine-5-carboxamide | 11% |
| 267 | | (3S)-3-tert-Butyl-N-[4-chloro-2-[6-(trifluoromethyl)pyridin-3-yl]phenyl]-1-[[2,3-difluoro-4-(2-morpholin-4-ylethoxy)phenyl]methyl]-4-hydroxy-2-methyl-6-oxo-3H-pyridazine-5-carboxamide | 18% |
| 269 | | (3S)-3-tert-Butyl-N-[4-chloro-2-(6-methylsulfanylpyridin-3-yl)phenyl]-1-[[2,3-difluoro-4-(2-morpholin-4-ylethoxy)phenyl]methyl]-4-hydroxy-2-methyl-6-oxo-3H-pyridazine-5-carboxamide | 15% |
| 270 | | (3S)-3-tert-Butyl-N-[2-(6-cyano-5-methylpyrimidin-4-yl)-4-(trifluoromethyl)phenyl]-1-[[2,3-difluoro-4-(2-morpholin-4-yl-ethoxy)phenyl]methyl]-4-hydroxy-2-methyl-6-oxo-3H-pyridazine-5-carboxamide | 20% |

TABLE 44-continued

| Example No. | Structural formula | Compound name | Rate of inhibition (%) |
|---|---|---|---|
| 317 | | 6-[[2,3-Difluoro-4-(2-morpholin-4-ylethoxy)phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide | 22% |
| 318 | | 7-[[2,3-Difluoro-4-(2-morpholin-4-ylethoxy)phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide | 32% |
| 333 | | 5-[2,3-Difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]pentanoic acid | 8% |
| 345 | | 6-[[2,3-Difluoro-4-[2-[(2S)-2-(methoxymethyl)pyrrolidin-1-yl]ethoxy]phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide | 19% |

TABLE 44-continued

| Example No. | Structural formula | Compound name | Rate of inhibition (%) |
|---|---|---|---|
| 410 | | 7-[[2,3-Difluoro-4-[2-[methyl(oxetan-3-yl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide | 25% |

Test Example 6: Suppressive Effect on Rise in Serum Phosphorus Concentration of Adenine-Induced Renal Failure Rat Each adenine-induced renal failure rat was prepared in the same way as in Test Example 5. Each test compound was mixed at a ratio of 0.05% of mass concentration with feed. The animal was fed with a given amount of the feed for 8 days. A group given feed non-supplemented with a test compound was used as a reference pathological group, and an adenine-unadministered group given feed non-supplemented with a test compound was used as a normal group. 8 days after the start of administration of the test compound, blood was collected from the jugular vein, and serum was collected. Serum phosphorus concentrations were measured by the Fiske-Subbarow method. The rate of suppression of a rise in serum phosphorus concentration was determined according to the following expression:

Rate (%) of suppression of a rise in serum phosphorus concentration=(1−[(Serum phosphorus concentration of the test compound-treated pathological group)−(Serum phosphorus concentration of the normal group)]/[(Serum phosphorus concentration of the reference pathological group)−(Serum phosphorus concentration of the normal group)])×100

As a result, each test compound was confirmed to have a suppressive effect on a rise in serum phosphorus concentration. Table 45 shows the rate (%) of suppression of a rise in serum phosphorus concentration by each test compound.

TABLE 45

| Example No. | Structural formula | Compound name | Rate of inhibition (%) |
|---|---|---|---|
| 414 | | 7-(4-(3-(Dimethylamino)-2,2-dimethylpropoxy)-2,3-difluorobenzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide | 37% |

TABLE 45-continued

| Example No. | Structural formula | Compound name | Rate of inhibition (%) |
|---|---|---|---|
| 416 | | 6-[[2,3-Difluoro-4-[1-(2-methoxyethyl)azetidin-3-yl]oxyphenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide | 38% |
| 418 | | 7-[[2,3-Difluoro-4-[4-[methyl-[(2S,3R,4R,5R)-2,3,4,5,6-pentahydroxyhexyl]amino]-4-oxobutoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide | 38% |

Test Example 7: Suppressive Effect on Rise in Serum Creatinine Concentration of Chronic Kidney Disease Model Rat After removing one kidney from each Fischer male rat (6-7 weeks old), an anti-Thy 1.1 antibody was intravenously administered to the rat to prepare a chronic kidney disease model having persistently impaired renal function (Kusano K, Saito H, Segawa H, Fukushima N, Miyamoto K. Mutant FGF23 prevents the progression of chronic kidney disease but aggravates renal osteodystrophy in uremic rats. J Nutr Sci Vitaminol (Tokyo). 2009 April; 55 (2): 99-105.) A test compound was mixed with feed at a ratio of 0.1% or 0.3% of mass concentration and the mixture was fed to the animal for 14 weeks. A group given feed non-supplemented with the test compound was used as a reference pathological group, and a group neither subjected to the kidney removal nor antibody administration and given feed non-supplemented with the test compound was used as a normal group. Fourteen weeks after the start of administration of the test compound, blood was collected from the abdominal aorta and serum was collected. As an indicator of renal damage, serum creatinine concentrations were measured by an enzyme assay (creatinase-sarcosine oxidase-POD method). The rate of suppression of a rise in serum creatinine concentration was determined according to the following expression:

Rate (%) of suppression of a rise in serum creatinine concentration=(1−[(Serum creatinine concentration of the test compound-treated pathological group)−(Serum creatinine concentration of the normal group)]/[(Serum creatinine concentration of the reference pathological group)−(Serum creatinine concentration of the normal group)])× 100

As a result, the test compound was confirmed to have a suppressive effect on a rise in serum creatinine concentration, namely, a suppressive effect on renal damage. Table 46 shows the rates (%) of suppression of a rise in serum creatinine concentration by the test compound.

TABLE 46

| Example No. | Structural formula | Compound name | dosage | Rate of inhibition (%) |
|---|---|---|---|---|
| 14 | | 7-[[2,3-difluoro-4-[2-[2-methoxyethyl(methyl)-amino]ethoxy]phenyl]-methyl]-10-hydroxy-6-methyl-8-oxo-N-[4-(trifluoromethyl)-2-[6-(trifluoromethyl)-pyrimidin-4-yl]phenyl]-6,7-diazaspiro[4.5]dec-9-ene-9-carboxamide | 0.1% 0.3% | 17% 24% |

Test Example 8: Suppressive Effect on Rise in Serum Parathyroid Hormone Concentration of Chronic Kidney Disease Model Rat Using serum collected from the same animal as that in test example 7 after 14 weeks from the start of administration of the test compound, concentrations of serum parathyroid hormone were measured by the ELISA method. The rate of suppression of a rise in concentration of serum parathyroid hormone was determined according to the following expression:

> Rate (%) of suppression of a rise in concentration of serum parathyroid hormone=(1−[(Serum parathyroid hormone concentration of the test compound-treated pathological group)−(Serum parathyroid hormone concentration of the normal group)]/[(Serum parathyroid hormone concentration of the reference pathological group)−(Serum parathyroid hormone concentration of the normal group)])×100

As a result, the test compound was confirmed to have a suppressive effect on a rise in serum parathyroid hormone concentration, namely, a suppressive effect on secondary hyperparathyroidism. Table 47 shows the rates (%) of suppression of a rise in serum parathyroid hormone concentration by the test compound.

TABLE 47

| Example No. | Structural formula | Compound name | dosage | Rate of inhibition (%) |
|---|---|---|---|---|
| 14 | | 7-[[2,3-difluoro-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide | 0.1% 0.3% | 13% 67% |

Test Example 9: Suppressive Effect on Calcium Deposition in Blood Vessel of Chronic Kidney Disease Model Rat From the same animal as that in Test Example 7, the thoracic aorta was collected 14 weeks after the start of administration of the test compound, and the dry weight was measured. The measured dry thoracic aorta was subjected to ashing and dissolved in a certain amount of hydrochloric acid, and then the calcium concentration in the solution was measured using OCPC method to determine the amount of calcium per gram of the thoracic aorta dry weight (Katsumata K, Kusano K, Hirata M, Tsunemi K, Nagano N, Burke S K, Fukushima N. Sevelamer hydrochloride prevents ectopic calcification and renal osteodystrophy in chronic renal failure rats. Kidney Int. 2003 August; 64(2): 441-450.) The rate of suppression of calcium deposition in blood vessel was determined according to the following expression:

Rate (%) of suppression of calcium deposition in blood vessel=(1−[(Amount of calcium per gram of dried blood vessel of the test compound-treated pathological group)−(Amount of calcium per gram of dried blood vessel of the normal group)]/[(Amount of calcium per gram of dried blood vessel of the reference pathological group)−(Amount of calcium per gram of dried blood vessel of the normal group)])×100

As a result, the test compound was confirmed to have a suppressive effect on calcium deposition in blood vessel, namely, a suppressive effect on vascular calcification. Table 48 shows the rates (%) of suppression of calcium deposition in blood vessel by the test compound.

TABLE 48

| Example No. | Structural formula | Compound name | dosage | Rate of inhibition (%) |
|---|---|---|---|---|
| 14 | | 7-[[2,3-difluoro-4-[2-[2-methoxyethyl(methyl)-amino]ethoxy]phenyl]-methyl]-10-hydroxy-6-methyl-8-oxo-N-[4-(trifluoromethyl)-2-[6-(trifluoromethyl)-pyrimidin-4-yl]phenyl]-6,7-diazaspiro[4.5]dec-9-ene-9-carboxamide | 0.1% 0.3% | 100% 100% |

Test Example 10: Suppressive Effect on Rise in Serum Phosphorus Concentration by Combined Use with Sevelamer Carbonate Adenine-induced renal failure rats were prepared in the same manner as in Test Example 5. Each of the animals was fed with a certain amount of one of the following feed for 14 days: feed containing a test compound at a concentration of 0.05% or 0.1% by mass; feed containing sevelamer carbonate at a concentration of 0.5% or 1.0% by mass; and feed containing the test compound at a concentration of 0.05% by mass in combination with sevelamer carbonate at a concentration of 0.5% by mass. A group given feed supplemented with neither the test compound nor sevelamer carbonate was used as a reference pathological group, and an adenine-unadministered group given feed supplemented with neither the test compound nor sevelamer carbonate was used as a normal group. Fourteen days after the start of administration of the test compound, blood was collected from the carotid artery and serum was collected. Serum phosphorus concentrations were measured by the Fiske-Subbarow method. The rate of suppression of a rise in serum phosphorus concentration was determined according to the following expression:

Rate (%) of suppression of a rise in serum phosphorus concentration=(1−[(Serum phosphorus concentration of the compound-treated pathological group)−(Serum phosphorus concentration of the normal group)]/[(Serum phosphorus concentration of the reference pathological group)−(Serum phosphorus concentration of the normal group)])×100

As a result, the combined use of the test compound and sevelamer carbonate was confirmed to have an additive suppressive effect on a rise in serum phosphorus concentration. Table 49 shows the rates (%) of suppression of a rise in serum phosphorus concentration by the test compound, sevelamer carbonate, and the combined use of the test compound and sevelamer carbonate.

TABLE 49

| Suppression rate of rise in serum phosphorus concentration (%) | test compound (compound of Example 14) | | |
|---|---|---|---|
| | 0% | 0.05% | 0.1% |
| Sevelamer carbonate 0% | 0% | 61% | 79% |
| 0.5% | 49% | 104% | — |
| 1.0% | 90% | — | — |

The invention claimed is:

1. A compound represented by the formula (I) or a salt thereof, or a solvate of the compound or the salt:

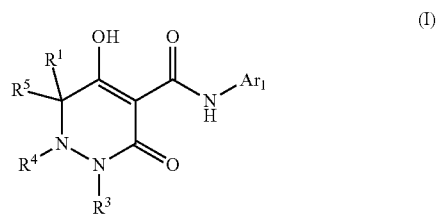

wherein $R^1$, $R^4$, and $R^5$ are as defined in any one of the following (1) to (3):

(1) $R^1$ is a hydrogen atom or $C_{1-10}$ alkyl;
$R^4$ is a hydrogen atom, $C_{1-4}$ alkyl optionally substituted with one or more substituents Rf, $C_{6-10}$ aryl optionally substituted with one or more substituents Rg, ($C_{1-6}$ alkyl)carbonyl, ($C_{6-10}$ aryl)carbonyl, a group —C(O)NR$^{37}$R$^{38}$, $C_{3-7}$ cycloalkyl, or 5- to 8-membered heterocycloalkyl; and
$R^5$ is a hydrogen atom or $C_{1-4}$ alkyl;
(2) $R^1$ and $R^5$ together with the carbon atom to which they are attached form a $C_{3-6}$ saturated carbocyclic ring; and $R^4$ is as defined above; and
(3) $R^1$ is a hydrogen atom or linear $C_{1-10}$ alkyl;
$R^4$ and $R^5$ together with the carbon atom and the nitrogen atom to which they are attached form a 5- to 8-membered saturated heterocyclic ring, wherein the saturated heterocyclic ring is optionally substituted with one or more substituents $R^2$;
$R^3$ is $C_{1-10}$ alkyl optionally substituted with one or more substituents Rh, or $R^3$ is $C_{1-4}$ alkyl substituted with Re;
$R^{37}$ and $R^{38}$ are each independently selected from a hydrogen atom and $C_{1-3}$ alkyl;
each $R^2$ is independently selected from $C_{1-5}$ alkyl and a halogen atom; and/or
two or more substituents $R^2$ on the 5- to 8-membered saturated heterocyclic ring may together form $C_{1-5}$ alkylene that links the ring atoms to which they are attached;
each Rh is independently selected from a halogen atom, ($C_{1-4}$ alkoxy)carbonyl, and a group —(O(CH$_2$)$_a$)$_b$—$C_{1-4}$ alkoxy, wherein a is an integer selected from 2 to 4, and b is an integer selected from 1 to 4;
Re is $C_{6-10}$ aryl optionally substituted with one or more substituents Ra, or 5- to 10-membered heteroaryl optionally substituted with one or more substituents Ra;
each Rf is independently selected from a halogen atom, hydroxy, cyano, carboxy, ($C_{1-6}$ alkoxy)carbonyl, $C_{1-6}$ alkoxy, and $C_{6-10}$ aryl optionally substituted with one or more substituents Rg;
each Rg is independently selected from a halogen atom, $C_{1-6}$ alkyl, $C_{2-6}$ alkynyl, and $C_{1-6}$ alkoxy, wherein the alkyl, alkynyl, and alkoxy groups are each optionally substituted with one or more substituents selected from hydroxy and cyano;
each Ra is independently selected from a halogen atom, hydroxy, nitro, cyano, ($C_{1-4}$ alkoxy)carbonyl, 3- to 10-membered heterocycloalkyloxy (the heterocycloalkyloxy group is optionally substituted with optionally $C_{1-4}$ alkoxy-substituted $C_{1-4}$ alkyl), $C_{1-10}$ alkyl optionally substituted with one or more substituents $R^{10}$, $C_{2-10}$ alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, $C_{1-4}$ alkylthio optionally substituted with one or more substituents $R^{13}$, a group —(O(CH$_2$)$_{q1}$)$_{q2}$—NR$^{41}$R$^{42}$ (wherein q1 is an integer selected from 1 to 4, and q2 is an integer selected from 2 to 6), a group —(O(CH$_2$)$_{r1}$)$_{r2}$—C(O)NR$^{43}$R$^{44}$ (wherein r1 is an integer selected from 1 to 4, and r2 is an integer selected from 1 to 4), a group —(O(CH$_2$)$_{s1}$)$_{s2}$—NR$^{45}$—C(O)R$^{46}$ (wherein s1 and s2 are each independently an integer selected from 2 to 4), a group —C(O)NR$^{47}$R$^{48}$, pyridinyl, pyrrolyl, a group —NR$^{49}$R$^{50}$, and a group —(O(CH$_2$)$_{y1}$)$_{y2}$—O—CH$_2$—C(O)NR$^{51}$R$^{52}$ (wherein y1 is an integer selected from 1 to 4, and y2 is an integer selected from 1 to 4);

$R^{10}$, $R^{11}$, $R^{12}$, $R^{13}$, and $R^{15}$ are each independently selected from a halogen atom, hydroxy, carboxy, $C_{1-6}$ alkoxy optionally substituted with one or more hydroxy groups, ($C_{1-4}$ alkoxy)$C_{1-6}$ alkoxy, ($C_{1-4}$ alkoxy)carbonyl, a group —(O(CH$_2$)$_o$)$_p$—OH (wherein o and p are each independently an integer selected from 2 to 4), $C_{3-6}$ cycloalkyl optionally substituted with one or more hydroxy groups, 3- to 10-membered heterocycloalkyl, 5- to 10-membered heteroaryl, and a group —NR$^{39}$R$^{40}$, wherein the 3- to 10-membered heterocycloalkyl group is optionally substituted with one or more substituents selected from oxo, a halogen atom, $C_{1-4}$ alkyl (wherein the alkyl group is optionally substituted with one or more hydroxy groups), $C_{1-4}$ alkoxy)$C_{1-4}$ alkyl (wherein the alkoxy moiety is optionally substituted with one or more hydroxy groups), $C_{1-4}$ alkoxy, ($C_{1-4}$ alkoxy)carbonyl, $C_{1-4}$ alkylthio, morpholino, ($C_{1-3}$ alkyl)sulfonyl, and —C(O)NR$^{53}$R$^{54}$;
Ar$^1$ is $C_{6-10}$ aryl or 5- to 10-membered heteroaryl, wherein the aryl and heteroaryl groups are each optionally substituted with one to three substituents selected from Rb, Rc, and Rd;
Rb, Rc, and Rd are each independently selected from optionally $C_{1-4}$ alkoxy-substituted $C_{1-5}$ alkoxy, a halogen atom, $C_{1-10}$ alkyl optionally substituted with one or more halogen atoms, a group —SF$_5$, cyano, hydroxy, 5- to 10-membered heterocycloalkyl optionally substituted with one or more substituents $R^{14}$, $C_{6-10}$ aryl optionally substituted with one or more substituents $R^{14}$, and 5- to 10-membered heteroaryl optionally substituted with one or more substituents $R^{14}$;
each $R^{14}$ is independently selected from a halogen atom, oxo, cyano, nitro, $C_{1-4}$ alkyl optionally substituted with one or more halogen atoms, $C_{1-4}$ alkoxy optionally substituted with one or more halogen atoms, ($C_{1-6}$ alkoxy)carbonyl, a group —NR$^{27}$R$^{28}$, a group —SO$_2$NR$^{35}$R$^{36}$, $C_{1-4}$ alkylthio, and 5- to 10-membered heterocycloalkyl;
$R^{27}$ and $R^{28}$ are each independently selected from a hydrogen atom and $C_{1-4}$ alkyl optionally substituted with ($C_{1-4}$ alkoxy)carbonyl;
$R^{35}$ and $R^{36}$ are each independently selected from a hydrogen atom and $C_{1-4}$ alkyl;
$R^{39}$ is a hydrogen atom, or optionally $C_{1-6}$ alkoxy-substituted $C_{1-6}$ alkyl;
$R^{40}$ is a hydrogen atom, optionally $C_{1-6}$ alkoxy-substituted $C_{1-6}$ alkyl, (($C_{1-4}$ alkoxy)carbonyl)$C_{1-6}$ alkyl, hydroxy-substituted $C_{1-6}$ alkyl, a group —(CH$_2$)$_u$—NR$^{55}$R$^{56}$ (wherein u is an integer selected from 1 to 4), a group —CH((CH$_2$)$_{v1}$COOR$^{57}$)—(CH$_2$)$_{v2}$—COOR$^{57}$ (wherein v1 is an integer selected from 0 to 2, and v2 is an integer selected from 1 to 3), a group —(CH$_2$)$_w$—SO$_3$H (wherein w is an integer selected from 1 to 4), a group —(CH$_2$)$_{x1}$—CH(COOH)—(CH$_2$)$_{x2}$—SO$_3$H (wherein x1 is an integer selected from 0 to 2, and x2 is an integer selected from 1 to 3), 3- to 6-membered oxacycloalkyl, or a group —(CH$_2$)$_{t1}$—O—(CH$_2$)$_{t2}$—C(O)NR$^{58}$R$^{59}$ (wherein t1 and t2 are each independently an integer selected from 1 to 3);
$R^{41}$ is a hydrogen atom or $C_{1-3}$ alkyl;
$R^{42}$ is $C_{1-8}$ alkyl substituted with one or more hydroxy groups, or ($C_{1-3}$ alkoxy)$C_{1-4}$ alkyl;
$R^{43}$ is a hydrogen atom or $C_{1-3}$ alkyl;
$R^{44}$ is $C_{1-8}$ alkyl substituted with one or more hydroxy groups, or
$R^{43}$ and $R^{44}$ together with the nitrogen atom to which they are attached may form morpholino;

$R^{45}$ is a hydrogen atom or $C_{1-3}$ alkyl;

$R^{46}$ is $C_{1-6}$ alkyl substituted with one or more hydroxy groups;

$R^{47}$ is $C_{1-3}$ alkyl;

$R^{48}$ is $(C_{1-3}$ alkoxy$)C_{1-4}$ alkyl;

$R^{49}$ is a hydrogen atom and $C_{1-4}$ alkyl;

$R^{50}$ is —$(CH_2)_z$—$NR^{60}R^{61}$ (z is an integer selected from 1 to 4, $R^{60}$ is a hydrogen atom or $C_{1-4}$ alkyl, and $R^{61}$ is $(C_{1-3}$ alkoxy$)C_{1-4}$ alkyl, or $R^{60}$ and $R^{61}$ together with the nitrogen atom to which they are attached may form morpholino);

$R^{51}$ is a hydrogen atom or $C_{1-4}$ alkyl;

$R^{52}$ is $C_{1-8}$ alkyl substituted with one or more hydroxy groups;

$R^{53}$ and $R^{54}$ are each independently selected from a hydrogen atom and $C_{1-4}$ alkyl;

$R^{55}$ is a hydrogen atom or $C_{1-4}$ alkyl;

$R^{56}$ is $(C_{1-4}$ alkyl)carbonyl;

$R^{57}$ is a hydrogen atom or $C_{1-4}$ alkyl;

$R^{58}$ is a hydrogen atom or $C_{1-3}$ alkyl; and $R^{59}$ is $C_{1-8}$ alkyl substituted with one or more hydroxy groups.

2. The compound according to claim 1 or a salt thereof, or a solvate of the compound or the salt, wherein each Ra is independently selected from a halogen atom, hydroxy, nitro, cyano, $(C_{1-4}$ alkoxy)carbonyl, 3- to 10-membered heterocycloalkyloxy, $C_{1-10}$ alkyl optionally substituted with one or more substituents $R^{10}$, $C_{2-10}$ alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, and $C_{1-4}$ alkylthio optionally substituted with one or more substituents $R^{13}$;

$R^{10}$, $R^{11}$, $R^{12}$, $R^{13}$, and $R^{15}$ are each independently selected from a halogen atom, hydroxy, carboxy, $C_{1-6}$ alkoxy optionally substituted with one or more hydroxy groups, $(C_{1-4}$ alkoxy)carbonyl, a group —$(O(CH_2)_o)_p$—OH (wherein o and p are each independently an integer selected from 2 to 4), $C_{3-6}$ cycloalkyl optionally substituted with one or more hydroxyl groups, 3- to 10-membered heterocycloalkyl, 5- to 10-membered heteroaryl, and a group —$NR^{39}R^{40}$, wherein the 3- to 10-membered heterocycloalkyl group is optionally substituted with one or more substituents selected from oxo, a halogen atom, and $C_{1-4}$ alkyl (wherein the alkyl group is optionally substituted with one or more hydroxy groups); and $R^{39}$ and $R^{40}$ are each independently selected from a hydrogen atom and optionally $C_{1-6}$ alkoxy-substituted $C_{1-6}$ alkyl.

3. The compound according to claim 1 or a salt thereof, or a solvate of the compound or the salt, wherein Rb is optionally $C_{1-4}$ alkoxy-substituted $C_{1-5}$ alkoxy or a halogen atom;

Rc is a halogen atom, $C_{1-10}$ alkyl optionally substituted with one or more halogen atoms, or a group —$SF_5$; and Rd is cyano, hydroxy, a halogen atom, $C_{1-4}$ alkyl optionally substituted with one or more halogen atoms, 5- to 10-membered heterocycloalkyl optionally substituted with one or more substituents $R^{14}$, $C_{6-10}$ aryl optionally substituted with one or more substituents $R^{14}$, or 5- to 10-membered heteroaryl optionally substituted with one or more substituents $R^{14}$.

4. The compound according to claim 1 or a salt thereof, or a solvate of the compound or the salt, wherein each Ra is independently selected from a halogen atom, nitro, cyano, $(C_{1-4}$ alkoxy)carbonyl, 3- to 6-membered heterocycloalkyloxy (the heterocycloalkyloxy group is optionally substituted with optionally $C_{1-4}$ alkoxy-substituted $C_{1-4}$ alkyl), $C_{1-10}$ alkyl optionally substituted with one or more substituents $R^{10}$, $C_{2-10}$ alkynyl optionally substituted with one or more substituents $R^{11}$, $C_{1-8}$ alkoxy optionally substituted with one or more substituents $R^{12}$, $C_{1-4}$ alkylthio optionally substituted with one or more substituents $R^{13}$, a group —$(O(CH_2)_{q1})_{q2}$—$NR^{41}R^{42}$, a group —$(O(CH_2)_{r1})_{r2}$—$C(O)NR^{43}R^{44}$, a group —$(O(CH_2)_{s1})_{s2}$—$NR^{45}$—$C(O)R^{46}$, a group —$C(O)NR^{47}R^{48}$, pyridinyl, pyrrolyl, a group —$NR^{49}R^{50}$, and a group —$(O(CH_2)_{y1})_{y2}$—O—$CH_2$—$NR^{51}R^{52}$;

$R^{10}$ is carboxy, 3- to 6-membered heterocycloalkyl, $C_{1-6}$ alkoxy optionally substituted with one or more hydroxy groups, or a group —$(O(CH_2)_o)_p$—OH;

$R^{11}$ is hydroxy, carboxy, 5- or 6-membered heterocycloalkyl optionally substituted with one or more oxo groups, $C_{1-6}$ alkoxy optionally substituted with one or more hydroxyl groups, a group —$(O(CH_2)_o)_p$—OH, $C_{3-6}$ cycloalkyl optionally substituted with one or more hydroxy groups, or a group —$NR^{39}R^{40}$;

$R^{12}$ is a halogen atom, hydroxy, carboxy, $C_{1-6}$ alkoxy optionally substituted with one or more hydroxy groups, $(C_{1-4}$ alkoxy$)C_{1-6}$ alkoxy, $(C_{1-3}$ alkoxy)carbonyl, 3- to 6-membered heterocycloalkyl, 5- or 6-membered heteroaryl, or a group —$NR^{39}R^{40}$, wherein the 3- to 6-membered heterocycloalkyl group is optionally substituted with one or more substituents selected from oxo, a halogen atom, $C_{1-4}$ alkyl (wherein the alkyl group is optionally substituted with one or more hydroxy groups), $(C_{1-4}$ alkoxy$)C_{1-4}$ alkyl (wherein the alkoxy moiety is optionally substituted with one or more hydroxy groups), $C_{1-4}$ alkoxy, $(C_{1-4}$ alkoxy)carbonyl, $C_{1-4}$ alkylthio, morpholino, $(C_{1-3}$ alkyl)sulfonyl, and —$C(O)NR^{53}R^{54}$;

$R^{13}$ is 5- or 6-membered heterocycloalkyl; and o and p are each independently an integer selected from 2 to 4.

5. The compound according to claim 1 or a salt thereof, or a solvate of the compound or the salt, wherein each Ra is independently selected from a halogen atom, nitro, cyano, $(C_{1-4}$ alkoxy)carbonyl, 3- to 6-membered heterocycloalkyloxy, $C_{1-10}$ alkyl optionally substituted with one or more substituents $R^{10}$, $C_{2-10}$ alkynyl optionally substituted with one or more substituents $R^{11}$, $C_{1-8}$ alkoxy optionally substituted with one or more substituents $R^{12}$, and $C_{1-4}$ alkylthio optionally substituted with one or more substituents $R^{13}$;

each $R^{10}$ is independently selected from carboxy, 3- to 6-membered heterocycloalkyl, $C_{1-6}$ alkoxy optionally substituted with one or more hydroxy groups, and a group —$(O(CH_2)_o)_p$—OH;

each $R^{11}$ is independently selected from hydroxy, carboxy, 5- or 6-membered heterocycloalkyl optionally substituted with one or more oxo groups, $C_{1-6}$ alkoxy optionally substituted with one or more hydroxy groups, a group —$(O(CH_2)_o)_p$—OH, and $C_{3-6}$ cycloalkyl optionally substituted with one or more hydroxy groups;

each $R^{12}$ is independently selected from a halogen atom, hydroxy, $C_{1-6}$ alkoxy optionally substituted with one or more hydroxy groups, $(C_{1-3}$ alkoxy)carbonyl, 3- to 6-membered heterocycloalkyl, 5- or 6-membered heteroaryl, and a group —$NR^{39}R^{40}$;

$R^{13}$ is 5- or 6-membered heterocycloalkyl; and
o and p are each independently an integer selected from 2 to 4.

6. The compound according to claim 1 or a salt thereof, or a solvate of the compound or the salt, wherein
each Ra is independently selected from a halogen atom, hydroxy, nitro, cyano, $C_{1-6}$ alkyl, (carboxy)$C_{1-8}$ alkyl, (morpholino)$C_{1-4}$ alkyl, [HO—$((CH_2)_oO)_p$]$C_{1-6}$ alkyl, ($C_{1-6}$ alkoxy)$C_{1-8}$ alkyl optionally substituted with one or more hydroxy groups, $C_{1-6}$ alkoxy optionally substituted with one or more halogen atoms, [N—(($C_{1-3}$ alkoxy)$C_{1-4}$ alkyl)-N—($C_{1-3}$ alkyl)amino]$C_{1-4}$ alkoxy, $C_{1-6}$ alkoxy substituted with one or more hydroxy groups, (($C_{1-3}$ alkoxy)carbonyl)$C_{1-3}$ alkoxy, ($C_{1-6}$ alkoxy)$C_{1-8}$ alkoxy optionally substituted with one or more hydroxy groups, ($C_{1-3}$ alkoxy($C_{1-4}$ alkoxy))$C_{1-4}$ alkoxy, (carboxy)$C_{1-8}$ alkoxy, (3- to 6-membered heterocycloalkyl)$C_{1-6}$ alkoxy (the heterocycloalkyl moiety is optionally substituted with one or more substituents selected from oxo, a halogen atom, $C_{1-4}$alkyl (the alkyl is optionally substituted with one or more hydroxy groups), $C_{1-4}$ alkoxy$C_{1-4}$ alkyl (the alkoxy moiety is optionally substituted with one or more hydroxyl groups), $C_{1-4}$ alkoxy, ($C_{1-4}$ alkoxy)carbonyl, $C_{1-4}$ alkylthio, morpholino, ($C_{1-3}$ alkyl)sulfonyl, and (di($C_{1-3}$ alkyl)amino)carbonyl), $C_{1-4}$ alkoxy substituted with a group —NH—CH(($CH_2)_{v1}$COOR$^{57}$)—($CH_2)_{v2}$—COOR$^{57}$, [N-(3- to 6-membered oxacycloalkyl)-N—($C_{1-3}$ alkyl)amino]$C_{1-4}$ alkoxy, [N,N-di((hydroxy)$C_{1-4}$ alkyl)-amino]$C_{1-4}$ alkoxy, [N—(($C_{1-3}$ alkoxy)carbonyl)$C_{1-3}$ alkyl-N—($C_{1-3}$ alkyl)amino]$C_{1-4}$ alkoxy, (pyridinyl)$C_{1-4}$ alkoxy, (pyrimidinyl)$C_{1-4}$ alkoxy, (1,2,4-triazolyl)$C_{1-4}$ alkoxy, [N-(hydroxy)$C_{1-4}$ alkyl-N—($C_{1-3}$ alkyl)amino]$C_{1-4}$ alkoxy, [N,N-di(($C_{1-3}$ alkoxy)$C_{1-4}$ alkyl)amino]$C_{1-6}$ alkoxy, [N,N-di($C_{1-3}$ alkyl)amino]$C_{1-6}$ alkoxy, [N—[N—($C_{1-4}$alkyl)carbonyl-N—($C_{1-3}$alkyl)amino]$C_{1-4}$ alkyl-N—($C_{1-3}$ alkyl) amino]$C_{1-4}$ alkoxy, [N—[N—($C_{1-4}$alkyl)carbonyl-amino]$C_{1-4}$ alkyl-N—($C_{1-3}$ alkyl) amino]$C_{1-4}$ alkoxy, a group —(O($CH_2)_{r1})_{r2}$—C(O)NR$^{43}$R$^{44}$, a group —(O($CH_2)_{q1})_{q2}$—NR$^{41}$R$^{42}$, $C_{1-4}$ alkoxy substituted with a group —NH—($CH_2)_w$—SO$_3$H, $C_{1-4}$ alkoxy substituted with a group —NH—($CH_2)_{x1}$—CH(COOH)—($CH_2)_{x2}$—SO$_3$H, a group —O($CH_2)_{s1})_{s2}$—NR$^{45}$—C(O)R$^{46}$, a group —C(O)NR$^{47}$R$^{48}$, pyridinyl, a group —NR$^{49}$R$^{50}$, a group —(O($CH_2)_{y1})_{y2}$—O—$CH_2$—C(O)NR$^{51}$R$^{52}$, (carboxy)$C_{2-6}$ alkynyl, (3- to 6-membered heterocycloalkyl)$C_{2-6}$ alkynyl optionally substituted with one or more oxo groups, $C_{2-8}$ alkynyl optionally substituted with one or more hydroxy groups, [HO—(($CH_2)_oO)_p$]$C_{2-8}$ alkynyl, ($C_{1-6}$ alkoxy)$C_{2-8}$ alkynyl optionally substituted with one or more hydroxy groups, ($C_{3-6}$ cycloalkyl)$C_{2-6}$ alkynyl optionally substituted with one or more hydroxy groups, [N—(($C_{1-3}$ alkoxy)$C_{1-4}$ alkyl)-N—($C_{1-3}$ alkyl)amino]$C_{2-6}$ alkynyl, ($C_{1-3}$ alkoxy)carbonyl, (morpholino)$C_{1-4}$ alkylthio optionally substituted with one or more oxo groups, 3- to 6-membered oxacycloalkyloxy, and 4- to 6-membered nitrogen containing heterocycloalkyloxy (the nitrogen containing heterocycloalkyl moiety is optionally substituted with one substituent selected from ($C_{1-3}$ alkoxy)$C_{1-4}$ alkyl and $C_{1-3}$ alkyl).

7. The compound according to claim 1 or a salt thereof, or a solvate of the compound or the salt, wherein
each Ra is independently selected from a halogen atom, hydroxy, cyano, $C_{1-6}$ alkyl, (carboxy)$C_{1-8}$ alkyl, (morpholino)$C_{1-4}$ alkyl, ($C_{1-6}$ alkoxy)$C_{1-8}$ alkyl substituted with one or more hydroxy groups, $C_{1-6}$ alkoxy optionally substituted with one or more halogen atoms, [N—(($C_{1-3}$ alkoxy)$C_{1-4}$ alkyl)-N—($C_{1-3}$ alkyl)amino]$C_{1-4}$ alkoxy, (morpholino)$C_{1-6}$ alkoxy (the morpholino moiety may be substituted with one or two substituents selected from oxo and $C_{1-3}$ alkyl), ($C_{1-6}$ alkoxy)$C_{1-8}$ alkoxy optionally substituted with one or more hydroxyl groups, ($C_{1-3}$ alkoxy($C_{1-4}$ alkoxy))$C_{1-4}$ alkoxy, (carboxy)$C_{1-8}$ alkoxy, (pyrrolidinyl)$C_{1-4}$ alkoxy (the pyrrolidinyl moiety is optionally substituted with ($C_{1-3}$ alkyl)$C_{1-4}$ alkoxy), $C_{1-4}$ alkoxy substituted with a group —NH—CH(($CH_2)_{v1}$COOR$^{57}$)—($CH_2)_{v2}$—COOR$^{57}$, [N-(oxetanyl)-N—($C_{1-3}$ alkyl)amino]$C_{1-4}$ alkoxy, [N,N-di($C_{1-3}$ alkyl)amino]$C_{1-6}$ alkoxy, a group —(O($CH_2)_{r1})_{r2}$—C(O)NR$^{43}$R$^{44}$, a group —(O($CH_2)_{q1})_{q2}$—NR$^{41}$R$^{42}$, $C_{1-4}$ alkoxy substituted with a group —NH—($CH_2)_w$—SO$_3$H, $C_{1-4}$ alkoxy substituted with a group —NH—($CH_2)_{x1}$—CH(COOH)—($CH_2)_{x2}$—SO$_3$H, (carboxy)$C_{2-6}$ alkynyl, (morpholino)$C_{2-6}$ alkynyl, $C_{2-8}$ alkynyl optionally substituted with one or more hydroxy groups, [HO—(($CH_2)_oO)_p$]$C_{2-8}$ alkynyl, ($C_{1-6}$ alkoxy)$C_{2-8}$ alkynyl substituted with one or more hydroxy groups, and ($C_{1-3}$ alkoxy)carbonyl.

8. The compound according to claim 1 or a salt thereof, or a solvate of the compound or the salt, wherein Ra is independently selected from a halogen atom, hydroxy, cyano, $C_{1-3}$ alkyl, (carboxy)$C_{1-8}$ alkyl, ($C_{1-6}$ alkoxy)$C_{1-8}$ alkyl substituted with one or more hydroxy groups, $C_{1-3}$ alkoxy optionally substituted with one or more halogen atoms, [N—(($C_{1-3}$ alkoxy)$C_{1-4}$ alkyl)-N—($C_{1-3}$ alkyl)amino]$C_{1-4}$ alkoxy, (morpholino)$C_{1-6}$ alkoxy, ($C_{1-6}$ alkoxy)$C_{1-8}$ alkoxy substituted with one or more hydroxy groups, (carboxy)$C_{2-6}$ alkynyl, (morpholino)$C_{2-6}$ alkynyl, $C_{2-8}$ alkynyl optionally substituted with one or more hydroxyl groups, [HO—(($CH_2)_oO)_p$]$C_{2-8}$ alkynyl, ($C_{1-6}$ alkoxy)$C_{2-8}$ alkynyl substituted with one or more hydroxyl groups, and ($C_{1-3}$ alkoxy)carbonyl.

9. The compound according to claim 1 or a salt thereof, or a solvate of the compound or the salt, wherein $R^3$ is methyl substituted with Re.

10. The compound according to claim 1 or a salt thereof, or a solvate of the compound or the salt, wherein $R^3$ is benzyl optionally substituted with one to three substituents Ra on the benzene ring.

11. The compound according to claim 1 or a salt thereof, or a solvate of the compound or the salt, wherein
Re is phenyl optionally substituted with one to three substituents Ra;
the one to three substituents Ra are one substituent selected from Ri, Rj, and Rk, two substituents selected from combinations of Ri and Rj, Ri and Rk, and Rj and Rk, or three substituents Ri, Rj, and Rk;
Ri is a halogen atom or $C_{1-3}$ alkoxy;
Rj is a halogen atom, nitro, or cyano; and
Rk is hydroxy, a halogen atom, ($C_{1-4}$ alkoxy)carbonyl, 5- to 10-membered heterocycloalkyloxy (the heterocycloalkyloxy group is optionally substituted with optionally $C_{1-4}$ alkoxy-substituted $C_{1-4}$ alkyl), $C_{1-10}$ alkyl optionally substituted with one or more substituents $R^{10}$, $C_{2-10}$ alkenyl optionally substituted with one or more substituents $R^{15}$, $C_{2-10}$ alkynyl optionally substituted with one or more substituents $R^{11}$, $C_{1-8}$ alkoxy optionally substituted with one or more substituents $R^{12}$, $C_{1-4}$ alkylthio optionally substituted with one or more substituents $R^{13}$, a group —(O($CH_2)_{q1})_{q2}$—NR$^{41}$R$^{42}$, a group —(O($CH_2)_{r1})_{r2}$—C(O)NR$^{43}$R$^{44}$, a group —(O($CH_2)_{s1})_{s2}$—NR$^{45}$—C(O)R$^{46}$, a group —C(O)NR$^{47}$R$^{48}$, pyridinyl, pyrrolyl, a group —NR$^{49}$R$^{50}$, or a group —(O(CH$_2$)$_{y1}$)$_{y2}$—O—CH$_2$—C(O)NR$^{51}$R$^{52}$.

12. The compound according to claim 1 or a salt thereof, or a solvate of the compound or the salt, wherein
Re is phenyl optionally substituted with one to three substituents Ra;
the one to three substituents Ra are one substituent selected from Ri, Rj, and Rk, two substituents selected from combinations of Ri and Rj, Ri and Rk, and Rj and Rk, or three substituents Ri, Rj, and Rk;
Ri is a halogen atom or C$_{1-3}$ alkoxy;
Rj is a halogen atom, nitro, or cyano; and
Rk is hydroxy, a halogen atom, (C$_{1-4}$ alkoxy)carbonyl, 5- to 10-membered heterocycloalkyloxy, C$_{1-10}$ alkyl optionally substituted with one or more substituents R$^{10}$, C$_{2-10}$ alkenyl optionally substituted with one or more substituents R$^{15}$, C$_{2-10}$ alkynyl optionally substituted with one or more substituents R$^{11}$, C$_{1-8}$ alkoxy optionally substituted with one or more substituents R$^{12}$, or C$_{1-4}$ alkylthio optionally substituted with one or more substituents R$^{13}$.

13. The compound according to claim 11 or a salt thereof, or a solvate of the compound or the salt, wherein
Rk is a halogen atom, hydroxy, C$_{1-6}$ alkyl, (carboxy)C$_{1-8}$ alkyl, (morpholino)C$_{1-4}$ alkyl, [HO—((CH$_2$)$_o$O)$_p$]C$_{1-6}$ alkyl, (C$_{1-6}$ alkoxy)C$_{1-8}$ alkyl optionally substituted with one or more hydroxy groups, C$_{1-6}$ alkoxy optionally substituted with one or more halogen atoms, [N—((C$_{1-3}$ alkoxy)C$_{1-4}$ alkyl)-N—(C$_{1-3}$ alkyl)amino]C$_{1-4}$ alkoxy, C$_{1-6}$ alkoxy substituted with one or more hydroxy groups, ((C$_{1-3}$ alkoxy)carbonyl)C$_{1-3}$ alkoxy, (C$_{1-6}$ alkoxy)C$_{1-8}$ alkoxy optionally substituted with one or more hydroxy groups, (C$_{1-3}$ alkoxy(C$_{1-4}$ alkoxy))C$_{1-4}$ alkoxy, (carboxy)C$_{1-8}$ alkoxy, (3- to 6-membered heterocycloalkyl)C$_{1-6}$ alkoxy (the heterocycloalkyl moiety contains one to three heteroatoms selected from O and N and is optionally substituted with one or more substituents selected from oxo, a halogen atom, C$_{1-4}$ alkyl (the alkyl is optionally substituted with one or more hydroxy groups), (C$_{1-4}$ alkoxy)C$_{1-4}$ alkyl (the alkoxy moiety is optionally substituted with one or more hydroxy groups), C$_{1-4}$ alkoxy, (C$_{1-4}$ alkoxy)carbonyl, C$_{1-4}$ alkylthio, morpholino, (C$_{1-3}$ alkyl)sulfonyl and (di(C$_{1-3}$ alkyl)amino)carbonyl), C$_{1-4}$ alkoxy substituted with a group —NH—CH((CH$_2$)$_{v1}$COOR$^{57}$)—(CH$_2$)$_{v2}$—COOR$^{57}$, [N-(3- to 6-membered oxacycloalkyl)-N—(C$_{1-3}$ alkyl)amino]C$_{1-4}$ alkoxy, [N,N-di((hydroxy)C$_{1-4}$ alkyl)-amino]C$_{1-4}$ alkoxy, [N—((C$_{1-3}$ alkoxy)carbonyl)C$_{1-3}$ alkyl-N—(C$_{1-3}$ alkyl)amino]C$_{1-4}$ alkoxy, (pyridinyl)C$_{1-4}$ alkoxy, (pyrimidinyl)C$_{1-4}$alkoxy, (1,2,4-triazolyl)C$_{1-4}$ alkoxy, [N-(hydroxy)C$_{1-4}$ alkyl-N—(C$_{1-3}$ alkyl)amino]C$_{1-4}$ alkoxy, [N,N-di(C$_{1-3}$ alkoxy(C$_{1-3}$ alkyl))amino]C$_{1-6}$ alkoxy, [N,N-di(C$_{1-3}$ alkyl)amino]C$_{1-6}$ alkoxy, [N—[N—(C$_{1-4}$ alkyl carbonyl-N—(C$_{1-3}$ alkyl)amino]C$_{1-4}$ alkyl-N—(C$_{1-3}$ alkyl)amino]C$_{1-4}$ alkoxy, [N—[N—(C$_{1-4}$ alkyl)carbonyl-amino]C$_{1-4}$ alkyl-N—(C$_{1-3}$ alkyl)amino]C$_{1-4}$ alkoxy, a group —(O(CH$_2$)$_{r1}$)$_{r2}$—C(O)NR$^{43}$R$^{44}$, a group —(O(CH$_2$)$_{q1}$)$_{q2}$—NR$^{41}$R$^{42}$, C$_{1-4}$ alkoxy substituted with a group —NH—(CH$_2$)$_w$—SO$_3$H, C$_{1-4}$ alkoxy substituted with a group —NH—(CH$_2$)$_{x1}$—CH(COOH)—(CH$_2$)$_{x2}$—SO$_3$H, a group —(O(CH$_2$)$_{s1}$)$_{s2}$—NR$^{45}$—C(O)R$^{46}$, a group —C(O)NR$^{47}$R$^{48}$, pyridinyl, a group —NR$^{49}$R$^{50}$, a group —(O(CH$_2$)$_{y1}$)$_{y2}$—O—CH$_2$—C(O)NR$^{51}$R$^{52}$, (carboxy)C$_{2-8}$ alkynyl, (3- to 6-membered heterocycloalkyl)C$_{2-6}$ alkynyl optionally substituted with one or more oxo groups, C$_{2-8}$ alkynyl optionally substituted with one or more hydroxy groups, [HO—((CH$_2$)$_o$O)$_p$]C$_{2-8}$ alkynyl, (C$_{1-6}$ alkoxy)C$_{2-8}$ alkynyl optionally substituted with one or more hydroxy groups, (C$_{3-6}$ cycloalkyl)C$_{2-6}$ alkynyl optionally substituted with one or more hydroxy groups, [N—((C$_{1-3}$ alkoxy)C$_{1-4}$ alkyl)-N—(C$_{1-3}$ alkyl)amino]C$_{2-6}$ alkynyl, (C$_{1-3}$ alkoxy)carbonyl, (morpholino)C$_{1-4}$ alkylthio, 3- to 6-membered oxacycloalkyloxy, or 3- to 6-membered nitrogen containing heterocycloalkyloxy (the heterocycloalkyl moiety is optionally substituted with one substituent selected from (C$_{1-3}$ alkoxy)C$_{1-4}$ alkyl and C$_{1-3}$ alkyl).

14. The compound according to claim 11 or a salt thereof, or a solvate of the compound or the salt, wherein
Rk is hydroxy, a halogen atom, C$_{1-6}$ alkyl, (carboxy)C$_{1-8}$ alkyl, (morpholino)C$_{1-4}$ alkyl, (C$_{1-6}$ alkoxy)C$_{1-8}$ alkyl substituted with one or more hydroxy groups, C$_{1-6}$ alkoxy optionally substituted with one or more halogen atoms, [N—((C$_{1-3}$ alkoxy)C$_{1-4}$ alkyl)-N—(C$_{1-3}$ alkyl)amino]C$_{1-4}$ alkoxy, (morpholino)C$_{1-6}$ alkoxy, (C$_{1-6}$ alkoxy)C$_{1-8}$ alkoxy optionally substituted with one or more hydroxy groups, (C$_{1-3}$ alkoxy(C$_{1-4}$ alkoxy))C$_{1-4}$ alkoxy, (carboxy)C$_{1-8}$ alkoxy, (pyrrolidinyl)C$_{1-4}$ alkoxy (the pyrrolidinyl moiety is substituted with (C$_{1-3}$ alkyl) C$_{1-4}$ alkoxy), C$_{1-4}$ alkoxy substituted with a group —NH—CH((CH$_2$)$_{v1}$COOR$^{57}$)—(CH$_2$)$_{v2}$—COOR$^{57}$, [N-(oxetanyl)-N—(C$_{1-3}$ alkyl)amino]C$_{1-4}$ alkoxy, [N,N-di(C$_{1-3}$ alkyl)amino]C$_{1-6}$ alkoxy, a group —(O(CH$_2$)$_{r1}$)$_{r2}$—C(O)NR$^{43}$R$^{44}$, a group —(O(CH$_2$)$_{q1}$)$_{q2}$—NR$^{41}$R$^{42}$, C$_{1-4}$ alkoxy substituted with a group —NH—(CH$_2$)$_w$—SO$_3$H, C$_{1-4}$ alkoxy substituted with a group —NH—(CH$_2$)$_{x1}$—CH(COOH)—(CH$_2$)$_{x2}$—SO$_3$H, (carboxy)C$_{2-8}$ alkynyl, (morpholino)C$_{2-6}$ alkynyl, C$_{2-8}$ alkynyl optionally substituted with one or more hydroxy groups, [HO—((CH$_2$)$_o$O)$_p$]C$_{2-8}$ alkynyl, (C$_{1-6}$ alkoxy)C$_{2-8}$ alkynyl substituted with one or more hydroxy groups, or (C$_{1-3}$ alkoxy)carbonyl.

15. The compound according to claim 11 or a salt thereof, or a solvate of the compound or the salt, wherein
Rk is hydroxy, a halogen atom, C$_{1-6}$ alkyl, (carboxy)C$_{1-8}$ alkyl, (C$_{1-6}$ alkoxy)C$_{1-8}$ alkyl substituted with one or more hydroxy groups, C$_{1-3}$ alkoxy optionally substituted with one or more halogen atoms, [N—((C$_{1-3}$ alkoxy)C$_{1-4}$ alkyl)-N—(C$_{1-3}$ alkyl)amino]C$_{1-4}$ alkoxy, (morpholino)C$_{1-6}$ alkoxy, (C$_{1-6}$ alkoxy)C$_{1-8}$ alkoxy substituted with one or more hydroxy groups, (carboxy)C$_{2-8}$ alkynyl, (morpholino)C$_{2-6}$ alkynyl, C$_{2-8}$ alkynyl optionally substituted with one or more hydroxyl groups, [HO—((CH$_2$)$_o$O)$_p$]C$_{2-8}$ alkynyl, (C$_{1-6}$ alkoxy)C$_{2-8}$ alkynyl substituted with one or more hydroxy groups, or (C$_{1-3}$ alkoxy)carbonyl.

16. The compound according to claim 1 or a salt thereof, or a solvate of the compound or the salt, wherein
R$^1$, R$^4$, and R$^5$ are as defined in any one of the following (1) to (3):
(1) R$^1$ is a hydrogen atom or C$_{1-6}$ alkyl;
R$^4$ is C$_{1-4}$ alkyl optionally substituted with one or more halogen atom(s), or phenyl; and
R$^5$ is a hydrogen atom or C$_{1-4}$ alkyl;
(2) R$^1$ and R$^5$ together with the carbon atom to which they are attached form a C$_{3-6}$ saturated carbocyclic ring; and
R$^4$ is as defined above; and
(3) R$^1$ is a hydrogen atom or linear C$_{1-6}$ alkyl; and
R$^4$ and R$^5$ together with the carbon atom and the nitrogen atom to which they are attached form a 5- to 8-membered saturated heterocyclic ring.

17. The compound according to claim 1 or a salt thereof, or a solvate of the compound or the salt, wherein
$R^1$, $R^4$, and $R^5$ are as defined in the following (1) or (2):
(1) $R^1$ is $C_{1-6}$ alkyl;
$R^4$ is optionally halogen atom-substituted $C_{1-4}$ alkyl or phenyl; and
$R^5$ is a hydrogen atom or $C_{1-4}$ alkyl; or
(2) $R^1$ and $R^5$ together with the carbon atom to which they are attached form a $C_{3-6}$ saturated carbocyclic ring; and
$R^4$ is as defined above;
$R^3$ is $C_{1-4}$ alkyl substituted with Re;
Re is phenyl optionally substituted with one or more substituents Ra;
each Ra is independently selected from a halogen atom, optionally $R^{11}$-substituted $C_{2-6}$ alkynyl, and optionally $R^{12}$-substituted $C_{1-6}$ alkoxy;
$R^{11}$ and $R^{12}$ are each independently selected from 5-or 6-membered heterocycloalkyl and —$NR^{39}R^{40}$;
$R^{39}$ and $R^{40}$ are each independently selected from hydrogen atom and optionally $C_{1-6}$ alkoxy-substituted $C_{1-6}$ alkyl;
$Ar^1$ is phenyl or 5-or 6-membered heteroaryl, wherein the phenyl and heteroaryl groups are each optionally substituted with one to three substituents selected from Rb, Rc, and Rd;
Rb, Rc, and Rd are each independently selected from a halogen atom, $C_{1-4}$ alkyl optionally substituted with one or more halogen atoms, phenyl optionally substituted with one or more substituents $R^{14}$, and 5-or 6-membered heteroaryl optionally substituted with one or more substituents $R^{14}$; and
each $R^{14}$ is independently selected from a halogen atom, cyano, $C_{1-4}$ alkyl optionally substituted with one or more halogen atoms, $C_{1-4}$ alkoxy, a group —$SO_2NR^{35}R^{36}$ (wherein $R^{35}$ and $R^{36}$ are each independently selected from $C_{1-4}$ alkyl), and $C_{1-4}$ alkylthio.

18. The compound according to claim 1 or a salt thereof, or a solvate of the compound or the salt, wherein
Rb is a halogen atom;
Rc is a halogen atom or $C_{1-4}$ alkyl optionally substituted with one or more halogen atoms; and
Rd is a halogen atom, $C_{1-4}$ alkyl optionally substituted with one or more halogen atoms, phenyl optionally substituted with one or more substituents $R^{14}$, or 5- or 6-membered heteroaryl optionally substituted with one or more substituents $R^{14}$.

19. The compound according to claim 1 or a salt thereof, or a solvate of the compound or the salt, wherein
Re is phenyl optionally substituted with one or more substituents Ra;
$R^{11}$ and $R^{12}$ are each independently selected from morpholinyl and a group —$NR^{39}R^{40}$;
$R^4$ is optionally halogen atom-substituted $C_{1-4}$ alkyl or phenyl;
$Ar^1$ is phenyl, pyridinyl, or pyrimidinyl, wherein the phenyl, pyridinyl, and pyrimidinyl groups are each optionally substituted with one to three substituents selected from Rb, Rc, and Rd;
Rb is a halogen atom;
Rc is a halogen atom or $C_{1-4}$ alkyl optionally substituted with one or more halogen atoms; and
Rd is a halogen atom, $C_{1-4}$ alkyl optionally substituted with one or more halogen atoms, phenyl, pyridinyl, or pyrimidinyl, wherein the phenyl, pyridinyl, and pyrimidinyl groups are each optionally substituted with one or more substituents $R^{14}$.

20. The compound according to claim 1 or a salt thereof, or a solvate of the compound or the salt, wherein
Re is phenyl optionally substituted with one to three substituents Ra;
the one to three substituents Ra are one substituent selected from Ri, Rj, and Rk, two substituents selected from combinations of Ri and Rj, Ri and Rk, and Rj and Rk, or three substituents Ri, Rj, and Rk;
Ri is a halogen atom;
Rj is a halogen atom; and
Rk is hydroxy, $C_{2-6}$ alkynyl optionally substituted with a substituent $R^{11}$, or $C_{1-6}$ alkoxy optionally substituted with a substituent $R^{12}$.

21. The compound according to claim 17, or a salt thereof, or a solvate of the compound or the salt, wherein $R^{11}$ and $R^{12}$ are each independently selected from morpholinyl, and [N-((methoxy)ethyl)-N-(methyl)amino].

22. The compound according to claim 1 or a salt thereof, or a solvate of the compound or the salt, wherein
$R^1$ and $R^5$ together with the carbon atom to which they are attached form a $C_{3-6}$ saturated carbocyclic ring;
$R^4$ is $C_{1-4}$ alkyl;
$R^3$ is $C_{1-4}$ alkyl substituted with Re;
Re is phenyl optionally substituted with one or more substituents Ra;
each Ra is independently selected from a halogen atom and $C_{1-4}$ alkoxy optionally substituted with one or more substituents $R^{12}$;
each $R^{12}$ is independently selected from 5-or 6-membered heterocycloalkyl and —$NR^{39}R^{40}$;
$R^{39}$ and $R^{40}$ are each independently selected from a hydrogen atom, and optionally $C_{1-4}$ alkoxy-substituted $C_{1-4}$ alkyl;
$Ar^1$ is phenyl or 5-or 6-membered heteroaryl, wherein the phenyl and heteroaryl groups are each optionally substituted with one to three substituents selected from Rb, Rc, and Rd;
Rb, Rc, and Rd are each independently selected from a halogen atom, $C_{1-4}$ alkyl optionally substituted with one or more halogen atoms, and 5-or 6-membered heteroaryl optionally substituted with one or more substituents $R^{14}$; and
each $R^{14}$ is independently selected from a halogen atom, cyano, $C_{1-4}$ alkyl optionally substituted with one or more halogen atoms, and $C_{1-4}$ alkylthio.

23. The compound according to claim 1 or a salt thereof, or a solvate of the compound or the salt, wherein
Rb is a halogen atom;
Rc is a halogen atom or $C_{1-4}$ alkyl optionally substituted with one or more halogen atoms; and
Rd is a halogen atom or 5-or 6-membered heteroaryl optionally substituted with one or more substituents $R^{14}$.

24. The compound according to claim 1 or a salt thereof, or a solvate of the compound or the salt, wherein
Re is phenyl optionally substituted with one to three substituents Ra;
the one to three substituents Ra are one substituent selected from Ri, Rj, and Rk, two substituents selected from combinations of Ri and Rj, Ri and Rk, and Rj and Rk, or three substituents Ri, Rj, and Rk;
Ri and Rj are each independently a halogen atom; and
Rk is $C_{1-4}$ alkoxy optionally substituted with one or more substituents $R^{12}$.

25. The compound according to claim 1 or a salt thereof, or a solvate of the compound or the salt, wherein
$Ar^1$ is phenyl or pyridinyl;
Rd is pyridinyl or pyrimidinyl;
$R^{12}$ is selected from morpholinyl, [N-((methoxy)ethyl)-N-(methyl)amiono], and [N,N-dimethylamino].

26. The compound according to claim 1 or a salt thereof, or a solvate of the compound or the salt, wherein
$Ar^1$ is 4-(trifluoromethyl)-2-(6-methylthiopyridin-3-yl)phenyl, 4-(trifluoromethyl)-2-(6-trifluoromethylpyridin-3-yl)phenyl, 4-(trifluoromethyl)-2-(4-trifluoromethylpyrimidin-5-yl)phenyl, 4-(trifluoromethyl)-2-(6-trifluoromethylpyrimidin-4-yl)phenyl, 4-(trifluoromethyl)-2-(6-cyano-5-methylpyrimidin-4-yl)phenyl, 4-(trifluoromethyl)-2-(2-cyanopyridin-4-yl)phenyl, 4-chloro-2-(6-methylthiopyridin-3-yl)phenyl, 4-chloro-2-(6-trifluoromethylpyridin-3-yl)phenyl, 4-chloro-2-(4-trifluoromethylpyrimidin-5-yl)phenyl, 4-chloro-2-(6-cyano-5-methylpyrimidin-4-yl)phenyl, 4-chloro-2-(6-trifluoromethylpyrimidin-4-yl)phenyl, or 4-chloro-2-(2-cyanopyridin-4-yl)phenyl.

27. A compound selected from:
(4aR)-1-[(2,3-difluorophenyl)methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrlo[1,2-b]pyridazine-3-carboxamide;
(4aR)—N-[2-(6-cyano-5-methylpyrimidin-4-yl)-4-(trifluoromethyl)phenyl]-1-[[2,3-difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxamide;
(4aR)—N-[2-(2-cyanopyridin-4-yl)-4(trifluoromethyl)phenyl]-1-[[2,3-difluoro-4-(2-morpholin-4-ylethoxy)phenyl]methyl]-4-hydroxy-4a-methyl-2-oxo-6,7-dihydro-5H-pyrrolo[1,2-b]pyridazine-3-carboxamide;
6-[4-[[(4aR)-4-hydroxy-4a-methyl-2-oxo-3-[[4-(trifluoromethyl)-2-[6-(trifluoromethyl)pyrimidin-4-yl]phenyl]carbamoyl]-6,7-dihydro-5H-pyrrolo[1,2-b]pyridazin-1-yl]methyl]-2,3-difluorophenyl]hex-5-ynoic acid;
(4aR)-1-[[2,3-difluoro-4-(3-morpholin-4-ylprop-1-ynyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;
(4aR)-1-[[4-[3-[(2R)-2,3-dihydroxypropoxy]propoxy]-2,3-difluorophenyl]methyl]-4-hydroxy-4a-methyl-2-oxo-N-[4-(trifluoromethyl)-2-[6(trifluoromethyl)pyridin-3-yl]phenyl]-6,7-dihydro-5H-pyrrolo[1,2b]pyridazine-3-carboxamide;
(4aR)-1-[[4-[4-[(2R)-2,3-dihydroxypropoxy]butoxy]-2,3-difluorophenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide;
(4aR)-1-[[4-[6-[(2R)-2,3-dihydroxypropoxy]hexoxy]-2,3-difluorophenyl]methyl]-4-hydroxy-4a-methyl-2-oxo-N-[2-(trifluoromethyl)-4-[6-(trifluoromethyl)pyridin-3-yl]pyrimidin-5-yl]-6,7-dihydro-5H-pyrrolo[1,2-b]pyridazine-3-carboxamide;
(4aR)-1-[[2,3-difluoro-4-(2-morpholin-4-ylethoxy)phenyl]methyl]-4-hydroxy-4a-methyl-2-oxo-N-[4-(trifluoromethyl)-2-[6-(trifluoromethyl)pyrimidin-4-yl]phenyl]-6,7-dihydro-5H-pyrrolo[1,2-b]pyridazine-3-carboxamide;
(4aR)-1-[[2,3-difluoro-4-(morpholin-4-ylmethyl)phenyl]methyl]-4-hydroxy-4a-methyl-2-oxo-N-[4-(trifluoromethyl)-2-[6-(trifluoromethyl)pyridin-3-yl]phenyl]-6,7-dihydro-5H-pyrrolo[1,2-b]pyridazine-3-carboxamide;
(4aR)—N-(4-bromo-3,5-difluorophenyl)-1-[(3-chloro-2-fluorophenyl)methyl]-4-hydroxy-4a-methyl-2-oxo-6,7-dihydro-5H-pyrrolo[1,2-b]pyridazine-3-carboxamide;
(3S)-3-tert-butyl-1-[[2,3-difluoro-4-(2-morpholin-4-ylethoxy)phenyl]methyl]-4-hydroxy-2-methyl-6-oxo-N-[4-(trifluoromethyl)-2-[6-(trifluoromethyl)pyrimidin-4-yl]phenyl]-3H-pyridazine-5-carboxamide;
(3S)-3-tert-butyl-N-[4-chloro-2-[6-(trifluoromethyl)pyrimidin-4-yl]phenyl]-1-[[2,3-difluoro-4-(2-morpholin-4-ylethoxy)phenyl]methyl]-4-hydroxy-2-methyl-6-oxo-3H-pyridazine-5-carboxamide;
(3S)-3-tert-butyl-N-[4-chloro-2-[6(trifluoromethyl)pyridin-3-yl]phenyl]-1-[[2,3-difluoro-4-(2-morpholin-4-ylethoxy)phenyl]methyl]-4-hydroxy-2-methyl-6-oxo-3H-pyridazine-5-carboxamide;
(3S)-3-tert-butyl-N-[4-chloro-2-(6-methylsulfanylpyridin-3-yl)phenyl]-1-[[2,3-difluoro-4-(2-morpholin-4-ylethoxy)phenyl]methyl]-4-hydroxy-2-methyl-6-oxo-3H-pyridazine-5-carboxamide;
(3S)-3-tert-butyl-N-[2-(6-cyano-5-methylpyrimidin-4-yl)-4-(trifluoromethyl)phenyl]-1-[[2,3-difluoro-4-(2-morpholin-4-ylethoxy)phenyl]methyl]-4-hydroxy-2-methyl-6-oxo-3H-pyridazine-5-carboxamide;
6-[[2,3-difluoro-4-(2-morpholin-4-ylethoxy)phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide;
7-[[2,3-difluoro-4-(2-morpholin-4-ylethoxy)phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;
6-[[2,3-difluoro-4-[2-[2-methoxyethyl(methyl)amino]ethoxy]phenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide;
7-[[2,3-difluoro-4-[2-[2-methoxyethyl(methyl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;
4-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]butanoic acid;
5-[2,3-[difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]pentanoic acid;
6-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]hexanoic acid;
7-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]heptanoic acid;
7-[[2,3-difluoro-4-[2-[(2S)-2-(methoxymethyl)pyrrolidin-1-yl]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;
(2S)-2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]butanedioic acid;

3-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]pentanedioic acid;

6-(2,3-difluoro-4-(2-(methyl(oxetan-3-yl)amino)ethoxy)benzyl)-9-hydroxy-5-methyl-7-oxo-N-(4-(trifluoromethyl)-2-(6-(trifluoromethyl)pyrimidin-4-yl)phenyl)-5,6-diazaspiro[3.5]non-8-ene-8-carboxamide;

7-[[2,3-difluoro-4-[2-[methyl(oxetan-3-yl)amino]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

7-(2,3-difluoro-4-(2-(methyl(oxetan-3-yl)amino)ethoxy)benzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide;

7-(4-(3-(dimethylamino)-2,2-dimethylpropoxy)-2,3-difluorobenzyl)-10-hydroxy-6-methyl-8-oxo-N-(4-(trifluoromethyl)-2-(6-(trifluoromethyl)pyrimidin-4-yl)phenyl)-6,7-diazaspiro[4.5]dec-9-ene-9-carboxamide;

6-[[2,3-difluoro-4-[1-(2-methoxyethyl)azetidin-3-yl]oxyphenyl]methyl]-9-hydroxy-5-methyl-7-oxo-N-[4-(trifluoromethyl)-2-[6-(trifluoromethyl)pyrimidin-4-yl]phenyl]-5,6-diazaspiro[3.5]non-8-ene-8-carboxamide;

7-[[2,3-difluoro-4-[4-[methyl-[(2S,3R,4R,5R)-2,3,4,5,6-pentahydroxyhexyl]amino]-4-oxobutoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

7-[[2,3-difluoro-4-[2-[2-[methyl-[(2S,3R,4R,5R)-2,3,4,5,6-pentahydroxyhexyl]amino]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

7-[[2,3-difluoro-4-[2-[2-[2-[2-methoxyethyl(methyl)amino]ethoxy]ethoxy]ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide;

2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]ethanesulfonic acid; and 2-[2-[2,3-difluoro-4-[[10-hydroxy-6-methyl-8-oxo-9-[[4-(trifluoromethyl)-2-[6-(trifluoromethyl)pyrimidin-4-yl]phenyl]carbamoyl]-6,7-diazaspiro[4.5]dec-9-en-7-yl]methyl]phenoxy]ethylamino]ethanesulfonic acid or a salt thereof, or a solvate of the compound or the salt.

28. A pharmaceutical composition comprising the compound according to claim 1 or a salt thereof, or a solvate of the compound or the salt.

29. A method for preventing or treating a disease selected from hyperphosphatemia, secondary hyperparathyroidism, chronic renal failure, chronic kidney disease, and arteriosclerosis associated with vascular calcification, or for preventing or suppressing ectopic calcification, comprising administering to a patient a therapeutically effective amount of a compound according to claim 1 or a salt thereof, or a solvate of the compound or the salt.

30. The method according to claim 29, wherein the disease is hyperphosphatemia.

31. The method according to claim 30, wherein the hyperphosphatemia is hyperphosphatemia in a patient with chronic kidney disease.

32. The method according to claim 29, wherein the disease is chronic renal failure or chronic kidney disease.

33. The method according to claim 32, wherein the chronic kidney disease is at stage 2 to 4 classified by GFR.

34. A method for inhibiting one or more transporters selected from NaPi-IIb, PiT-1, and PiT-2, comprising administering to a patient a therapeutically effective amount of a compound according to claim 1 or a salt thereof, or a solvate of the compound or the salt.

35. A method for preventing or treating a disease selected from hyperphosphatemia, secondary hyperparathyroidism, chronic renal failure, chronic kidney disease, and arteriosclerosis associated with vascular calcification, or for preventing or suppressing ectopic calcification, comprising administering to a patient a therapeutically effective amount of a substance that is a compound according to claim 1 or a salt thereof, or a solvate of the compound or the salt, which inhibits one or more transporters selected from PiT-1 and PiT-2.

36. The method according to claim 35, wherein the substance further inhibits NaPi-IIb.

37. The method according to claim 35, wherein the substance inhibits NaPi-IIb, PiT-1, and PiT-2.

38. A method for preventing or treating a disease selected from hyperphosphatemia, secondary hyperparathyroidism, chronic renal failure, chronic kidney disease, and arteriosclerosis associated with vascular calcification, or for preventing or suppressing ectopic calcification, comprising administering to the patient a therapeutically effective amount of a substance that is a compound according to claim 1 or a salt thereof, or a solvate of the compound or the salt, which inhibits one or more transporters selected from NaPi-IIb, PiT-1, and PiT-2, wherein the substance is administered in combination with a phosphorus adsorbent.

39. The method according to claim 38, wherein a combined drug comprising the substance that inhibits one or more transporters selected from NaPi-IIb, PiT-1, and PiT-2 and the phosphorus adsorbent is administered to the patient.

40. The method according to claim 38, wherein the phosphorus adsorbent is administered as a separate pharmaceutical composition.

41. The method according to claim 38, wherein the substance that inhibits the one or more transporters and the phosphorus adsorbent are administered simultaneously.

42. The method according to claim 38, wherein the substance that inhibits the one or more transporters and the phosphorus adsorbent are administered sequentially.

43. The method according to claim 38, wherein the substance that inhibits the one or more transporters is administered before or after administration of the phosphorus adsorbent.

44. The method according to claim 38, wherein the phosphorus adsorbent is a nonmetallic polymer adsorbent, a calcium salt preparation, or a metallic salt preparation.

45. The method of claim 38, wherein the phosphorus adsorbent is any one of medicaments selected from sevelamer carbonate, sevelamer hydrochloride, precipitated calcium carbonate, calcium acetate, calcium citrate, calcium alginate, calcium salt of keto-acid, lanthanum carbonate, aluminum hydroxide, ferric citrate hydrate, and polynuclear iron(III)-oxyhydroxide).

46. A compound of 7-[[2,3-difluoro-4-[2-[-2-methoxyethyl(methyl)amino]-ethoxy]phenyl]methyl]-10-hydroxy-6-methyl-8-oxo-N-[4-(trifluoromethyl)-2-[6-(trifluoromethyl)pyrimidin-4-yl]phenyl]-6,7-diazaspiro[4.5]dec-9-ene-9-carboxamide or a salt thereof, or a solvate of the compound or the salt.

47. A composition of claim 28, further comprising a phosphorous absorbent.

\* \* \* \* \*